US008707392B2

(12) United States Patent
Birtwhistle et al.

(10) Patent No.: US 8,707,392 B2
(45) Date of Patent: Apr. 22, 2014

(54) SYSTEMS AND METHODS FOR DISEASE MANAGEMENT

(75) Inventors: Daniel Birtwhistle, Fishers, IN (US);
Ulrich Porsch, Weinheim, DE (US);
John F. Price, McCordsville, IN (US);
Raymond Strickland, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/267,315

(22) Filed: Oct. 6, 2011

(65) Prior Publication Data
US 2012/0266251 A1    Oct. 18, 2012

Related U.S. Application Data

(60) Provisional application No. 61/393,567, filed on Oct. 15, 2010.

(51) Int. Cl.
*H04L 29/06*    (2006.01)

(52) U.S. Cl.
USPC ......... 726/3; 726/4; 726/26; 726/27; 600/365

(58) Field of Classification Search
None
See application file for complete search history.

(56) References Cited

U.S. PATENT DOCUMENTS 8,483,974 B2 *   7/2013   Connolly et al. ............... 702/32
2010/0218132 A1 *  8/2010   Soni et al. ..................... 715/771

OTHER PUBLICATIONS

Skevofilakas et al., A Communication and Information Technology Infrastructure for Real Time Monitoring and Management of Type 1 Diabetes Patients, IEEE, Aug. 2007.*
Mougiakakou et al., A Communication Platform for Tele-monitoring and Tele-management of Type 1 Diabetes, IEEE, Sep. 2005.*
Mougiakakou et al., SMARTDIAB: A Communication and Information Technology Approach for the Intelligent Monitoring, Management and Follow-up of Type 1 Diabetes Patients, IEEE, May 2010.*
Part 20601: Application Profile—Optimized Exchange Protocol, IEEE Std 11073-20601 Sep. 26, 2008.
Part 10417: Device Specialization-Glucose Meter, IEEE Std 11073-10417, May 8, 2009.
Continua Design Guidelines 2010, Oct. 1, 2010.

* cited by examiner

*Primary Examiner* — Minh Dinh
(74) *Attorney, Agent, or Firm* — Harness, Dickey

(57)    ABSTRACT

A computer-implemented diabetes management system is provided that supports enhanced security between a diabetes care manager in data communication with a medical device. The diabetes care manager includes: a first application that operates to request access to a first security role supported by the medical device, where the first security role is associated with a first set of commands for accessing data on the medical device that are defined as a private extension of the communication protocol; and a second application that operates to request access to a second security role supported by the medical device, where the second security role is associated with a second set of commands for accessing data on the medical device that are defined as a private extension of the communication protocol. The second set of commands has one or more commands that are mutually exclusive from the first set of commands.

20 Claims, 139 Drawing Sheets

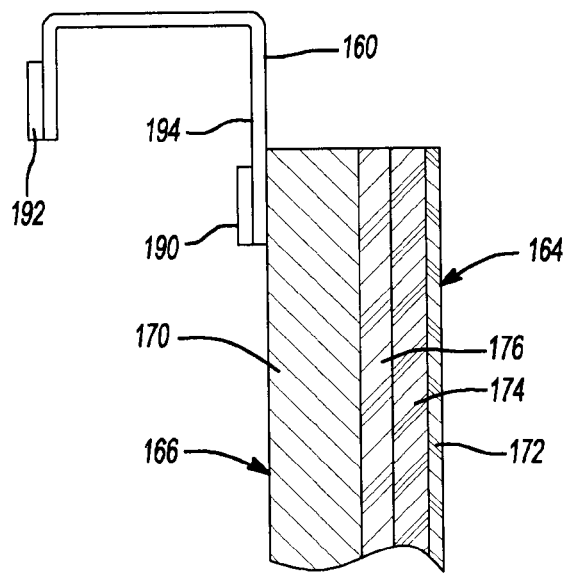
FIG. 12
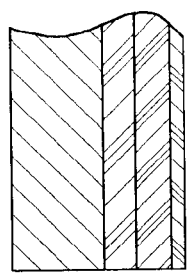
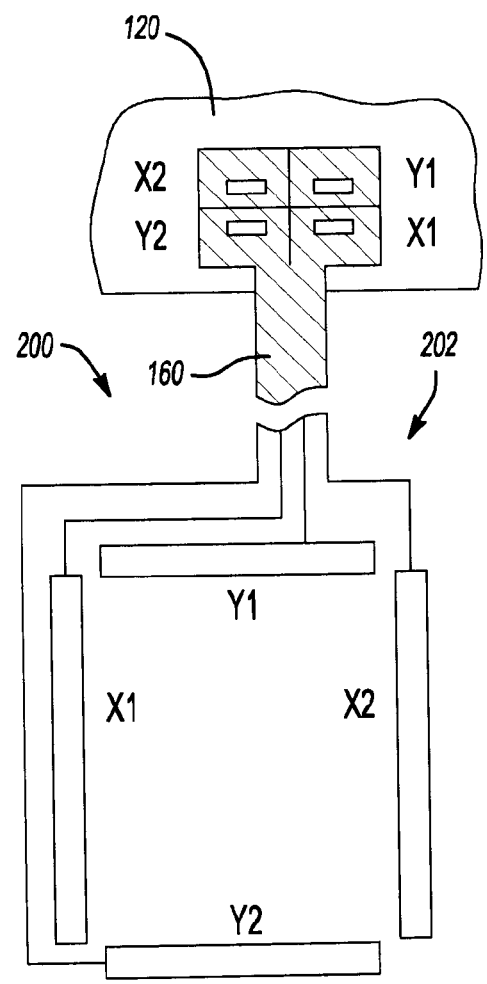
FIG. 13

| Event | Reminder | Event Qualifier/Trigger | After Event | Acceptance Window | Reminder |
|---|---|---|---|---|---|
| Breakfast | Brkfst typical time | In acceptance window, meal (+/- 2 h) | PostBreakfast | 1-4 h after meal start, +/- 30 min | 1-4 h after meal time |
| Breakfast | Brkfst typical time | In acceptance window, meal (+/- 2h) | PreLunch | 2 h before typical Lunch to 2 h after typical Lunch | Lunch typical time |
| Lunch | Lunch typical time | In acceptance window, meal (+/- 2h) | PostLunch | 1-4 h after meal start, +/- 30 min | 1-4 h after meal time |
| Lunch | Lunch typical time | In acceptance window, meal (typical lunch +/- 2h) | PreDinner | 2 h before typical Dinner to 2 h after typical Dinner | Dinner typical time |
| Dinner | Dinner typical time | In acceptance window, meal (typical dinner +/- 2 h) | PostDinner | 1-4 h after meal start, +/- 30 min | 1-4 h after meal time |
| Dinner | Dinner typical time | In acceptance window, meal | Bedtime | 2 h before typical Bedtime to 2 h after typical Bedtime | Typical Bedtime |
| Bedtime | Typical Bedtime | In acceptance window, no meal | PreBreakfast | 2 h before typical Brkfst to 2 h after typical Brkfst | Breakfast typical time |
| Exercise | None | Exercise with bG | User-set After Exercise time | 30 min to 6 h after event, +/- 30 min | After Exercise time |
| High bG | None | Above High bG | User-set After High time | 1-6 h after event, +/- 30 min | After High bG time |
| Low bG | None | Below Low bG | After Low Time | 5 to 30 min after event, +/- 15 min | After Low bG time |

FIG. 37

Prospective Data Structure for TIP's Data

| Structured Test # | Start Date | Procedure | Status |
|---|---|---|---|
| 001 | 10/01/2010 | TIPs Pre/Post Breakfast 3 Day Profile | In Progress |
| 002 | 10/02/2010 | | Completed |

FIG. 38

| Date/Time | ST # | Group | Sample | bG | ST Complete | bG Record # |
|---|---|---|---|---|---|---|
| 10/01/2010 7:45 | 001 | 1 | 1 | 85 | y | 102 |
| 10/01/2010 8:30 | 001 | 1 | 2 | 110 | y | 103 |
| 10/02/2010 7:40 | 001 | 2 | 1 | 76 | y | 107 |
| 10/02/2010 8:47 | 001 | 2 | 2 | 128 | y | 108 |

| Parameters | bG (Biosensor) Measurement | Meal Size (S, M, or L) | Energy Level (0-5) | Timing | Adherence Criteria | Guidance | Options |
|---|---|---|---|---|---|---|---|
| bG Level Trending | | | | | | | |
| Entry Criteria | | | | MM-DD-YYYY | Affirms Guidance, If Not Add 1 Day to Timing | Are You Willing to Conduct A Test Over 3 Consecutive Days? | 1 |
| Exit Criteria | | | | MM-DD-YYYY | Entry Timing + 3 Days | | |
| Before Breakfast | Y | | Y | HH:MM | | Please Indicate Energy Level | |
| n₁ Hours After Breakfast | Y | Y | Y | n₁ | ± 30 Minutes of n₁ | Please Indicate Meal Size & Energy Level | |
| Before Lunch | Y | | Y | | | Please Indicate Energy Level | |
| n₂ Hours After Lunch | Y | Y | Y | n₂ | ± 30 Minutes of n₁ | Please Indicate Meal Size & Energy Level | |
| Before Dinner | Y | | Y | | | Please Indicate Energy Level | |
| n₃ Hours After Dinner | Y | Y | Y | n₃ | ± 30 Minutes of n₁ | Please Indicate Meal Size & Energy Level | |
| Before Bed | Y | | Y | | | Please Indicate Energy Level | |

FIG. 83

| Table 1 - DM Result |
|---|
| <column><br>    Date-year: char(1)<br>    Date-month: char(1)<br>    Date-day: char(1)<br>    Time-hours: char(1)<br>    Time-minutes: char(1)<br>    Test Flags: char(1)<br>    bG Concentration: int<br>    Record Count: int<br>    DM Record Contents: char(1)<br>    Mealtime Selection: char(1)<br>    Health Event Selection: char(1)<br>    Recommended Carb Amount: int<br>    Modified Carb Amount: int<br>    Meal Name: text<br>    Food Item 1: text<br>    Food Item 2: text<br>    Food Item 3: text<br>    Food Item 4: text<br>    Food Item 5: text<br>    Food Item 6: text<br>    Food Item 7: text<br>    Food Item 8: text<br>    Food Item 9: text<br>    Food Item 10: text<br>    Food Item 11: text<br>    Food Item 12: text<br>    Recommended Bolus Insulin Amount for bG correction: int<br>    Recommended Bolus Insulin Amount for meal rise: int<br>    Confirmed Bolus Insulin Amount for bG correction: int<br>    Confirmed Bolus Insulin Amount for meal rise: int<br>    Bolus Insulin Amount for bG correction: int<br>    Basal Insulin Amount for meal rise: int<br>    Insulin Delivery Method: int<br>    Recommended Bolus based on carbs: int<br>    Recommended Bolus based on health: int<br>    Recommended Bolus based on bG: int<br>    Active Insulin: int<br>    Bolus Advice Minimum bG value (LTR): int<br>    Bolus Advice Maximum bG value (UTR): int<br>    Carb Ratio Insulin value: int<br>    Carb Ratio Carb value: int<br>    Insulin Sensitivity Insulin value: int<br>    Insulin Sensitivity bG value: int<br>    Bolus Advice Flags: int<br>    Health percentage: int<br>    Bolus Advice Meal Excursion: int<br>    Bolus Advice Active Time Out: int<br>    Bolus Advice Snack Limt (snack size): int<br>    Carb Calculated Amount: int<br>    Bolus Advice Offset Time Out: int<br>    Bolus Advice Upper bG Limit: int<br>    Carb Ratio Carbs Calculated Amount: int<br>    Offset Time: bigint<br>    16-Bit CRC: int |

Table 2 - Error

<column>
    Date-year: binary(8)
    Date-month: binary(8)
    Date-day: binary (8)
    Time-hours: binary(8)
    Time-minutes: binary(8)
    Error-Code: binary(16)
    Error-Description: text
    16-Bit CRC: binary(16)

4120

Table 3 - DM cG Result

<column>
    Date-year: (binary(8))
    Date-month: binary(8)
    Date-day: binary(8)
    Time-hours: binary(8)
    Time-minutes: binary(8)
    Test Flag: binary(8)
    Concentration: binary(16)
    Record Count: binary(16)
    16-Bit CRC: binary(16)

4130

Table 4 - Pump

<column>
    Date-year: binary(8)
    Date-month: binary(8)
    Date-day: binary(8)
    Time-hours: binary(8)
    Time-minutes: binary(8)
    Time-seconds: binary(8)
    Event Date: binary(32)
    Event ID: binary(16)
    Event Data Checksum: binary(16)
    Event Counter: binary(32)
    Event Counter Checksum: binary(32)
    Gap Event: binary(8)
    Synch Flag: binary(8)
    16-Bit CRC: binary(16)

| Table 5 - Bolus Advice Correction | |
|---|---|
| <column> | |
| Active Flag: binary(8) | |
| bG Result Date Year: binary(8) | |
| bG Result Date Month: binary(8) | |
| bG Result Date Day: binary(8) | |
| bG Result Date Hour: binary(8) | |
| bG Result Date Minute: binary(8) | |
| Correct Start Date Year: binary(8) | |
| Correct Start Date Month: binary(8) | |
| Correct Start Date Day: binary(8) | |
| Correct Start Date Hour: binary(8) | |
| Correct Start Date Minute: (binary(8) | |
| Correct End Date Year: binary(8) | |
| Correct End Date Month: binary(8) | |
| Correct End Date Day: binary(8) | |
| Correct End Date Minute: binary(8) | |
| Correction Offset Time: binary(16) | |
| Correction Active Time: binary(16) | |
| Correction Upper bG Limit: binary(16) | |
| Delta bG: binary(32) | |
| Correction Bolus: binary(32) | |
| bG Result Record Counter: binary(16) | |
| Meal Correction Active Flag: binary(8) | |
| Meal Increase: binary(16) | |
| DM Record Contents: binary(8) | |
| Mealtime Selection: binary(8) | |
| Test Flags: binary(8) | |
| Bolus Advice Flags: binary(8) | |
| Concentration: binary(16) | |
| Carb Amount: binary(16) | |
| Bolus Insulin Amount: binary(16) | |
| Spare: binary(8) | |
| 16-Bit CRC: binary(16) | |

4150

| Table 6 - Food | |
|---|---|
| <column> | |
| Description: text | |
| Category: text | |
| Food Flags: binary(8) | |
| carbs: binary(16) | |
| fats: binary(16) | |
| protein: binary(16) | |
| fiber: binary(16) | |
| calories: binary(16) | |
| Serving Size: binary(16) | |
| Spare: binary(16) | |
| 16-Bit CRC: binary(16) | |

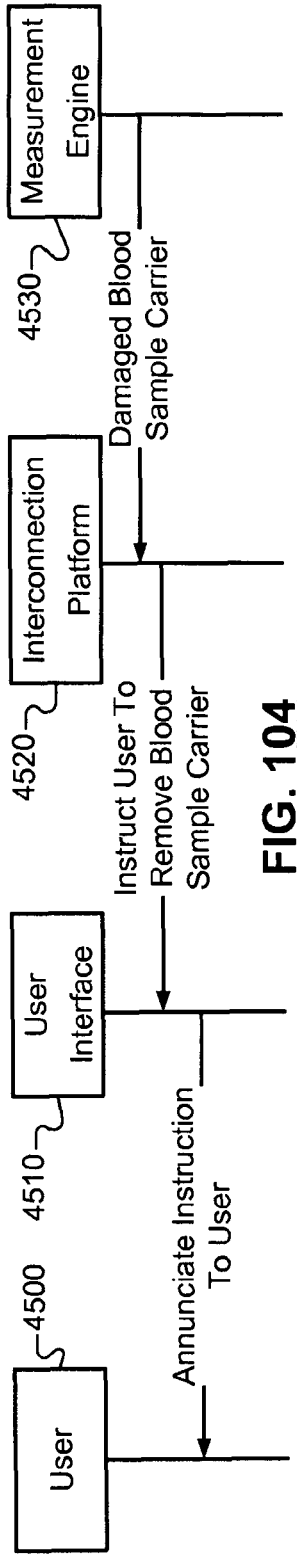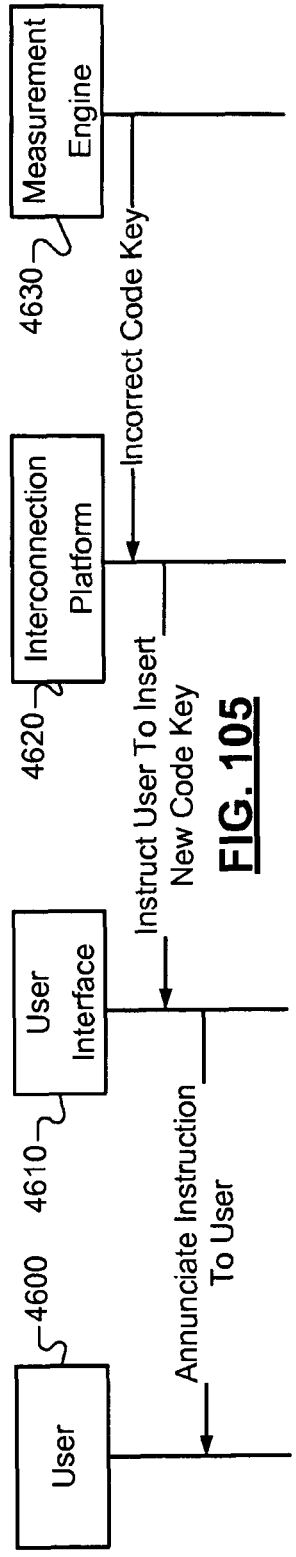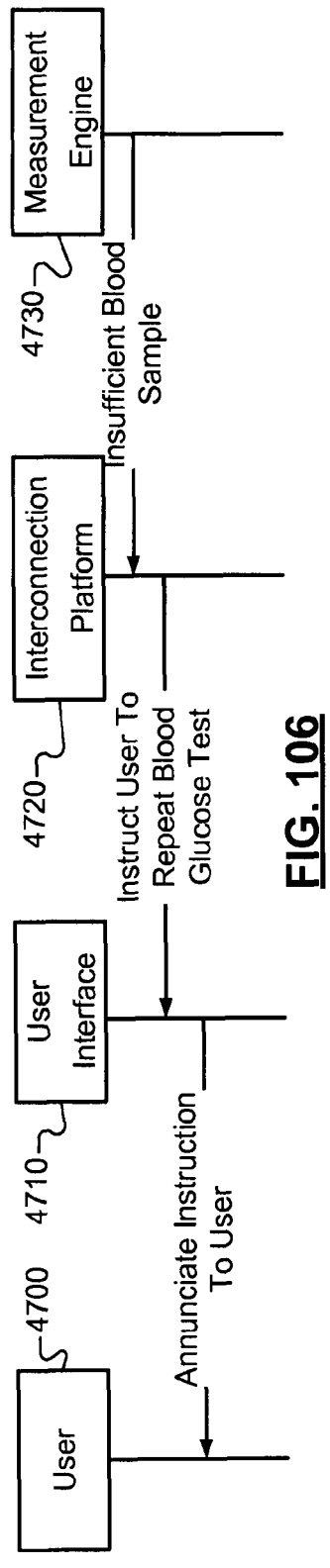

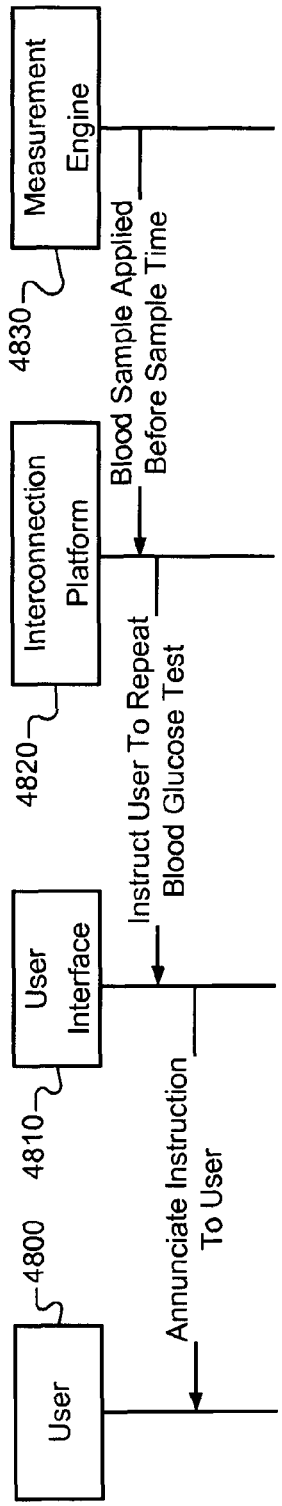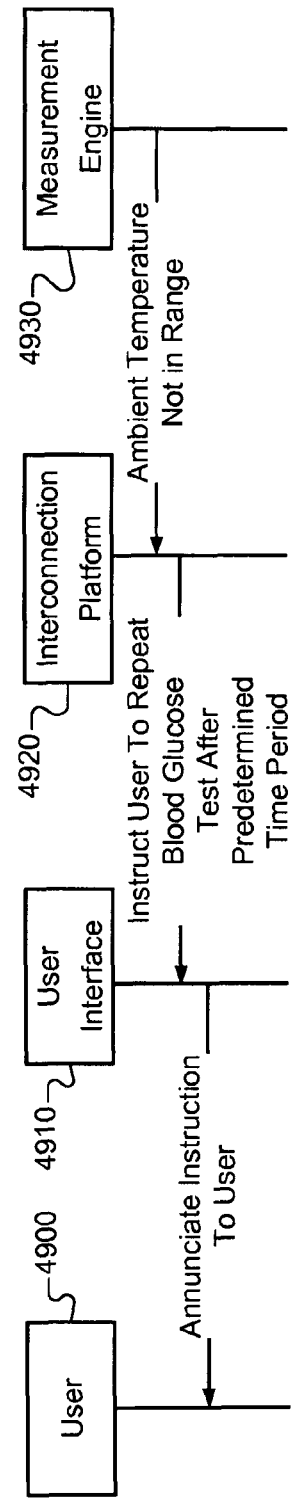

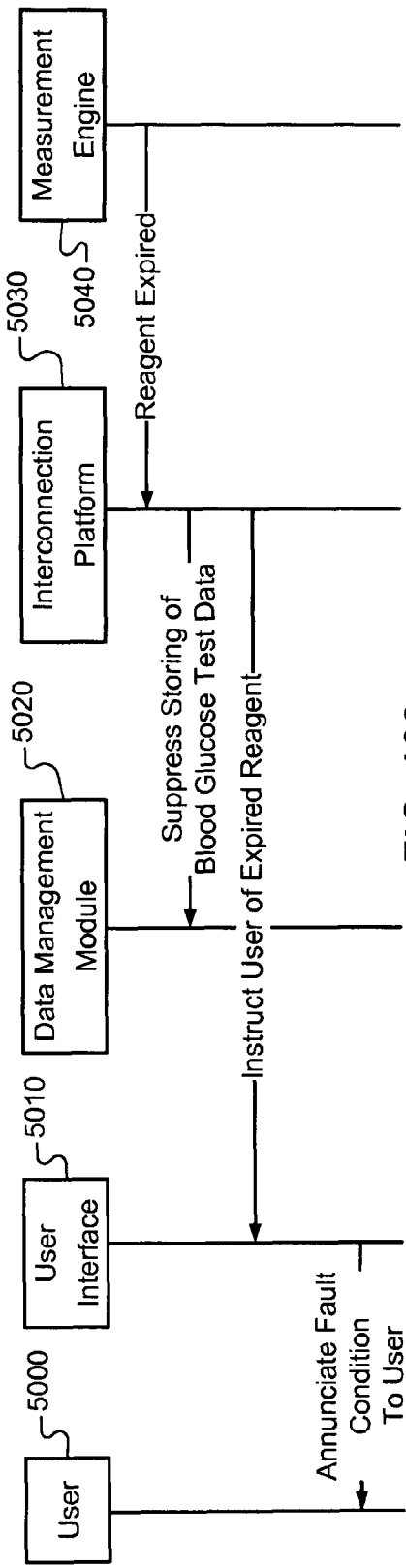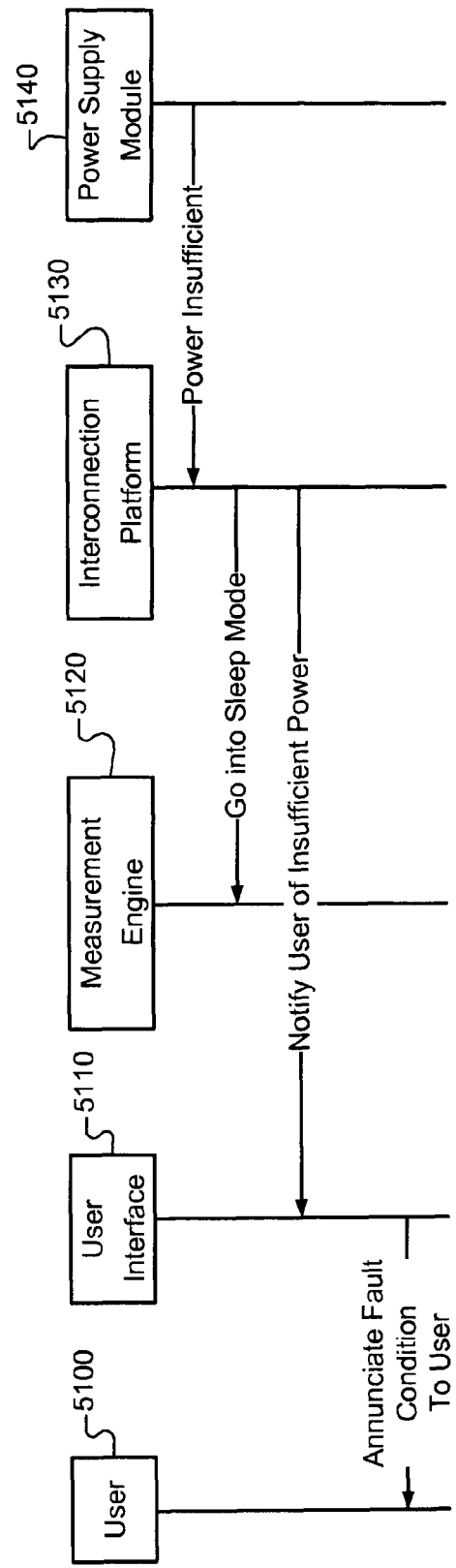
FIG. 109
FIG. 110

SYSTEMS AND METHODS FOR DISEASE MANAGEMENT

CROSS-REFERENCE TO RELATED APPLICATION

This application claims the benefit of U.S. Provisional Application No. 61/393,567, filed on Oct. 15, 2010. The entire disclosure of the above application is incorporated herein by reference.

FIELD

The present disclosure relates to disease management device systems and methods.

BACKGROUND

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and may be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. Its incidence is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Management of diabetes is complex as the level of blood glucose entering the bloodstream is dynamic. Variation of insulin in the bloodstream that controls the transport of glucose out of the bloodstream also complicates diabetes management. Blood glucose levels are sensitive to diet and exercise, but also can be affected by sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Management of diabetes is often highly intrusive because of the need to consistently obtain reliable diagnostic information, follow prescribed therapy, and manage lifestyle on a daily basis. Daily diagnostic information, such blood glucose, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data that are acquired from medical devices, personal healthcare devices, patient recorded information, healthcare professional tests results, prescribed medications and recorded information. Medical devices including self-monitoring blood glucose (bG) meters, continuous glucose monitors, ambulatory insulin infusion pumps, diabetes analysis software, and diabetes device configuration software each of which generates or manages or both large amounts of diagnostic and prescriptive data. Personal healthcare devices include weight scales, and blood pressure cuffs. Patient recorded information includes information relating to meals, exercise and lifestyle. Healthcare professional biomarker data includes glycated hemoglobin (HbA1C), cholesterol, triglycerides, and glucose tolerance. Healthcare professional recorded information includes therapy and other information relating to the patient's treatment.

There are times in which the diabetes patient may wish to perform personal glucose testing in low light conditions. For instance, the patient may want to perform the test in a dark or poorly lit room. Because the test requires a certain amount of precision (e.g., proper placement of a blood droplet on the dosing area of a test strip), it can be difficult to complete the test in such conditions. Thus, there is a need for a handheld diabetes management device for providing enhanced illumination in such situations.

There is a need for a handheld patient device to aggregate, manipulate, manage, present, and communicate diagnostic data and prescriptive data from medical devices, personal healthcare devices, patient recorded information, biomarker information and recorded information in an efficient manner to improve the care and health of a person with diabetes, so the person with diabetes can lead a full life and reduce the risk of complications from diabetes.

Additionally, there is a need to provide such a handheld patient device that can offer touch screen convenience while still meeting regulatory (such as Food and Drug Administration) cleaning requirements. Furthermore, there is a need to provide an internal component configuration that can optimize the internal space of the handheld device.

There is a need for a handheld patient device to aggregate, manipulate, manage, present, and communicate diagnostic data and prescriptive data from medical devices, personal healthcare devices, patient recorded information, biomarker information and recorded information in an efficient manner to improve the care and health of a person with diabetes, so the person with diabetes can lead a full life and reduce the risk of complications from diabetes.

It will also be appreciated that at the present time, patients with diabetes may be asked to periodically assess their daily glycemic control, for example by conducting a three day blood glucose (bG) test. This involves the patient checking his/her bG several times during consecutive twenty four hour periods and manually recording the data in a chart. Preferably, the three day bG test is done with the patient checking his/her bG levels at seven different times during the day: 1) pre-breakfast; 2) post-breakfast; 3) pre-lunch; 4) post-lunch; 5) pre-dinner; 6) post-dinner; and 7) bedtime. The results of each of the bG tests may be recorded manually by the patient. The bG tests need to be performed within the context for each of the above-described seven events (which may include a predetermined time window). As will be appreciated, this can be somewhat of a burdensome procedure for the patient. It is also important that the patient record all of the obtained bG information correctly on the three-day bG test chart. The information must be accurately and legibly recorded on the chart, typically using a writing implement such as a pencil or pen. Thus, while carrying out the three day bG profile the user is typically required to carry a pencil or pen with him or her as well as the bG testing supplies, which as will be appreciated may cause a degree of inconvenience to the user. Typically the user must carry, in a purse or pocket, the paper chart for recording the bG test values, which may also add some inconvenience to the user. Finally, it is important that the user not misplace or otherwise damage the paper chart while carrying out the test, lest important bG test information becomes unavailable or unreadable, thus requiring the test to be started over. Automating the three day bG profile through a handheld device that can be carried more easily on the person of a user would significantly reduce the possibility of a paper chart being lost, misplaced or otherwise damaged to the point where the data recorded thereon is unreadable.

Further to the above, individuals with diabetes often may need to perform a series of paired glucose tests to help understand particular issues with behavior or therapy. This test involves having an individual obtain pairs of bG values before and after various events. For example, an individual can obtain a bG value before a specific meal, for example before lunch, and another bG value within a specified time after the lunch meal. The "before" and "after" bG values form a related "pair" of bG values and can be used as data for a "Testing In Pairs" (TIPs) test. Collecting and reviewing a plurality of related pairs of before/after bG test data for various events throughout the day (e.g., breakfast, lunch, dinner), while considering the type of food that was consumed at each meal, may help give the individual a better idea of how his/her bG levels are affected by certain foods or events, and thus may help the individual to better manage her/his bG levels throughout the day.

The above described TIPs test, however, can be somewhat inconvenient for an individual to carry out manually. The paired bG values need to be manually recorded by the individual such as by writing down the results in a log. This must be done typically for each meal of the day, and then compiled in such a way that the recorded results are able to show the individual how the bG test values changed throughout the day in response to the meals that the individual consumed. Often an external computer may be needed to present the bG test results in a fashion that aids in understanding the test results. Moreover, the individual must be attentive to the time periods during which the "before" and "after" bG test values must be obtained. Missing a "before" meal bG test will prevent the use of an "after" meal bG test result, for the purpose of constructing a "pair" of bG values for the test.

Additionally, there is a need for a handheld diabetes management device that is able to provide an even more accurate bolus recommendation to the user based on various user inputs that take into account current activities and a current health of the user, and which is also highly customizable by the user to thus enhance the accuracy, convenience and efficiency of the device in generating a recommended bolus or a suggested carbohydrate amount for the user.

There is a need for a patient to be able to manage, manipulate and control the desired range of blood glucose levels over a period of time through a hand-held device in an efficient manner to improve the care and health of a person with diabetes, so the person with diabetes can lead a full life and reduce the risk of complications from diabetes.

Management of diabetes involves large amounts of diagnostic data and prescriptive data that are acquired from medical devices, personal healthcare devices, patient recorded information, healthcare professional tests results, prescribed medications and recorded information. Clinicians generally treat diabetic patients according to published therapeutic guidelines such as, for example, Joslin Diabetes Center & Joslin Clinic, *Clinical Guideline for Pharmacological Management of Type* 2 *Diabetes* (2007) and Joslin Diabetes Center & Joslin Clinic, *Clinical Guideline for Adults with Diabetes* (2008). The guidelines may specify a desired biomarker value, e.g., a fasting blood glucose value of less than 100 mg/dl, or the clinician can specify a desired biomarker value based on the clinician's training and experience in treating patients with diabetes. However, such guidelines do not specify biomarker collection procedures for parameter adjustments to support specific therapies used in optimizing a diabetic patient's therapy. Subsequently, diabetic patients often must measure their glucose levels with little structure for collection and with little regard to lifestyle factors. Such unstructured collection of glucose levels can result in some biomarker measurements lacking interpretative context, thereby reducing the value of such measurements to clinicians and other health care providers. Thus, there is a need to provide structured collection procedures for diagnostic or therapy support of a patient with diabetes or other chronic diseases.

Patients with diabetes and their healthcare professionals interact with a variety of medical devices and systems to help manage the disease, including performing structured collection procedures. For each of these differing types of medical devices, there is a need to aggregate, manipulate, manage, present, and communicate diagnostic data and prescriptive data from multiple data sources in an efficient manner to improve the care and health of a person with diabetes, so the person with diabetes can lead a full life and reduce the risk of complications from diabetes. There is also a need to aggregate, manipulate, manage, present, and communicate such diagnostic data and prescriptive data amongst the different types of medical devices using a standard communication protocol. IEEE 11073 is an exemplary communication standard that addresses interoperability and communication amongst medical devices such as blood pressure monitors, blood glucose monitors and the like. Within the context of such communication protocol, there is a further need to support the structured collection procedures implemented by the medical devices.

When designing an overall system for diabetes management or an application residing on a given medical device in the system, there is a further need to identify and implement extension points in the system to support future growth.

Additionally, since the handheld device is battery powered, there is a need to effectively manage power consumption of the handheld device to optimize operating times between battery recharges. Specifically, there is a need to control the power consumption by selectively disabling one or more components of the handheld device based on the usage and internal temperature of the handheld device. Further, the handheld device measures blood glucose levels by performing chemical analysis of samples deposited on a strip, which is inserted into a port of the handheld device. Since chemical processes used in the chemical analysis are sensitive to temperature, there is a need to monitor internal temperature of the handheld device, estimate an ambient temperature proximate to a reaction site on the strip based on the internal temperature, and selectively disable one or more components of the handheld device based on the ambient temperature.

Additionally, to effectively manage the care and health of the patient, there is a need for the handheld device to store the diagnostic and prescriptive data on a database on the handheld device. A technical problem arises, however, when the database is stored on a nonvolatile solid-state memory, as the risk of a database failing increases. Thus, there is a need to reliably store medically important data in a database on a handheld device.

The design and manufacture of such handheld devices may occur in multiple jurisdictions and different standards may apply for different components of the handheld device. For instance, regulatory agencies in Europe and the United States may impose different standards for radio communications, medical devices, and other areas. Thus, there is a need for well-defined interfaces in the core of the handheld device that allow for modularity when integrating different components in the handheld device, such that the core functionality of the handheld device does not need to be modified depending on the components of the device.

Consequently, there is a need for a handheld patient device that offers connectivity with a wide range of other devices, including healthcare devices, computers, consumer electronics, and accessories. There exists a need for a handheld patient device that serves as a hub for a patient's diabetes management, from glucose monitoring to insulin infusion to historical tracking. There exists a need for such a handheld patient device so that patients and clinicians will have more information to monitor and manage diabetes, thereby making diabetes management less intrusive and more appealing to the patient.

Consequently, there is a need for a handheld patient device that can be upgraded, both to add new features and improve patient interfaces, and to implement required improvements, such as regulatory requirements, business rule updates, and fixes. In order to reduce the burden on doctors' offices and to be more convenient for patients, there is a need for a handheld patient device that can be upgraded without requiring a clinic visit. However, there is a need for the upgrade process to require little or no computer expertise. Especially for upgrades that will not be performed at a clinic, there is a need for the upgrade process to be reliable so as to avoid compromising the function of the handheld patient device.

Additionally, to effectively manage the care and health of the patient, there is a need for the handheld device to communicate with other medical devices and systems. The other medical devices and systems, however, may use different communication protocols and interfaces (e.g., Bluetooth protocol, universal serial bus (USB) interface, etc.). Accordingly, there is a need for the handheld device to include multiple communication protocols and interfaces that enable the handheld device to communicate with the other medical devices and systems in a safe and secure manner. Additionally, to manage coexistence of multiple communication interfaces in the handheld device, there is a need for techniques to decrease probability of collisions and interference between communications performed by the multiple communication interfaces. Further, to minimize the size of the handheld device, two or more communication interfaces may be integrated into a single integrated circuit (IC) and may share an antenna so that additional communication interfaces and corresponding antennas can be added to the handheld device. Sharing an antenna also requires implementing prioritization and arbitration schemes to effectively communicate with the medical devices.

Additionally, to effectively manage the care and health of the patient, there is a need for the handheld device to communicate with other medical devices and systems, as well as for those other medical devices and systems to communicate. In order to communicate securely and reliably, the handheld device may need to establish a secure communication link between itself and the other medical devices and systems. Such a process may require a user (such as a patient with reduced visual acuity and/or technical skill) to follow a complex procedure that requires extensive user input. Additionally, in order for those other medical devices and systems to communicate between themselves securely and reliably, each device/system may need to establish a secure communication link between itself and the other medical devices and systems. To establish each such communication link, a user (such as a patient with reduced visual acuity and/or technical skill) may have to perform a complex procedure that requires extensive user input, which is inefficient subject to error. Accordingly, there is a need for a method of establishing a secure communication link between a handheld device and other medical devices/systems that is relatively simple and reduces the number and complexity of user inputs. Further, there is a need for a handheld device and/or diabetes management system that reduces the number and complexity of user inputs to utilize and establish secure communication links between a handheld device and various other devices that allows the various other devices to securely communicate without directly establishing a secure communication link between themselves.

Additionally, to effectively manage the care and health of the patient, there is a need for the handheld device to communicate with other medical devices and systems. In order to communicate securely and reliably, the handheld device may need to establish a secure communication link between itself and the other medical devices and systems. Such a process may require a user (such as a patient with reduced visual acuity and/or technical skill) to follow a complex procedure that requires extensive user input. Accordingly, there is a need for a method of establishing a secure communication link between the handheld device and other medical devices/systems that is relatively simple and reduces the number and complexity of user inputs. Further, there is a need for a diabetes management system that reduces the number and complexity of user inputs to utilize and establish a secure communication link between various devices.

Additionally, to effectively manage the care and health of the patient, there is a need for a means to reliably manage data records from the other medical devices. As the system of devices communicating with one another becomes more complex, a technical problem arises in trying to keep data records consistent, especially when patients are provided with the ability to enter and edit records manually. Accordingly, a system for tagging records with metadata that ensures unique metadata tags is described herein. Based on metadata tagging scheme, data records transmitted between the devices may remain consistent and confusion of data can be avoided.

Additionally, there is a need for a handheld diabetes management device that is able to provide an even more accurate bolus recommendation to the user based on various user inputs that take into account current activities and a current health of the user, and which is also highly customizable by the user to thus enhance the accuracy, convenience and efficiency of the device in generating a recommended bolus or a suggested carbohydrate amount for the user.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computer-implemented diabetes management system is provided that supports enhanced security between a diabetes care manager in data communication with a medical device. The diabetes care manager includes: a first application that operates to request access to a first security role supported by the medical device, where the first security role is associated with a first set of commands for accessing data on the medical device that are defined as a private extension of the communication protocol; and a second application that operates to request access to a second security role supported by the medical device, where the second security role is associated with a second set of commands for accessing data on the medical device that are defined as a private extension of the communication protocol. The second set of commands has one or more commands that are mutually exclusive from the first set of commands.

In another aspect of this disclosure, the diabetes care manager further includes: a meter that measures the concentration of glucose in blood; a collection application that executes a structured collection procedure for obtaining measurement data from the meter and provides access to the measurement data, where the structured collection procedure having parameters including a schedule of collection events; a configuration application that accesses and manipulates the parameters of the structured collection procedure using a set of action commands, where the set of action commands are defined in compliance with the communication protocol; and a collection interface that receives an action command from the configuration application, executes the received action command and issues a response command in response thereto, wherein the response command is defined in compliance with the communication protocol.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

FIG. 12 is a cross-sectional view of the touch window taken along line 12-12 of FIG. 11;

FIG. 13 shows an electrical schematic for a touch window sensor of the touch window of FIG. 11;

FIG. 37 is a table of exemplary times for the various events around which bG test pairs can be obtained using the device of FIG. 30;

FIG. 38 is a chart illustrating how a plurality of different structured tests may be recorded in the device of FIG. 30;

FIG. 39 is a chart showing a data structure which can be used to record the results of a TIPs test in the database of FIG. 31;

FIG. 47 is a drawing showing an exemplary layout of how various items of information may be presented to the user on the display of the device;

FIG. 83 is a chart that conceptually illustrates an exemplary structured collection procedure;

FIG. 100 shows a set of exemplary tables that are stored in an exemplary diabetes management device;

FIG. 104 shows a sequence diagram of the effecting of a first reliability protocol;

FIG. 105 shows a sequence diagram of the effecting of a second reliability protocol;

FIG. 106 shows a sequence diagram of the effecting of a third reliability protocol;

FIG. 107 shows a sequence diagram of the effecting of a fourth reliability protocol;

FIG. 108 shows a sequence diagram of the effecting of a fifth reliability protocol;

FIG. 109 shows a sequence diagram of the effecting of a sixth reliability protocol;

FIG. 110 shows a sequence diagram of the effecting of a seventh reliability protocol;

FIG. 124 shows a flow-chart illustrating a portion of an exemplary method of pairing a handheld diabetes managing device and an insulin pump according to the present disclosure;

FIG. 125 shows a flow-chart illustrating a portion of an exemplary method of pairing a handheld diabetes managing device and an insulin pump according to the present disclosure;

FIG. 126A shows a flow-chart illustrating a portion of an exemplary method of pairing a handheld diabetes managing device and an insulin pump according to the present disclosure;

FIG. 126B shows a flow-chart illustrating a portion of an exemplary method of pairing a handheld diabetes managing device and an insulin pump according to the present disclosure;

FIG. 127A shows a flow-chart illustrating a portion of an exemplary method of pairing a handheld diabetes managing device and an insulin pump according to the present disclosure;

FIG. 127B shows a flow-chart illustrating a portion of an exemplary method of pairing a handheld diabetes managing device and an insulin pump according to the present disclosure;

FIG. 128 shows a flow-chart illustrating an exemplary method of establishing a secure bidirectional communication link during pairing of a handheld diabetes managing device and an insulin pump according to the present disclosure;

FIG. 129 shows a flow-chart illustrating an exemplary method of confirming receipt of a communication message by a receiving device according to the present disclosure;

FIG. 130 shows a flow-chart illustrating an exemplary method of authenticating a communication message sent from a transmitting device to a receiving device according to the present disclosure;

FIG. 131 shows an exemplary diabetes care kit for providing diagnostics and therapy according to the present disclosure;

FIG. 132 shows a block diagram of an exemplary handheld diabetes managing device according to the present disclosure;

FIG. 133 shows a block diagram of an exemplary insulin pump according to the present disclosure;

Figure 3:
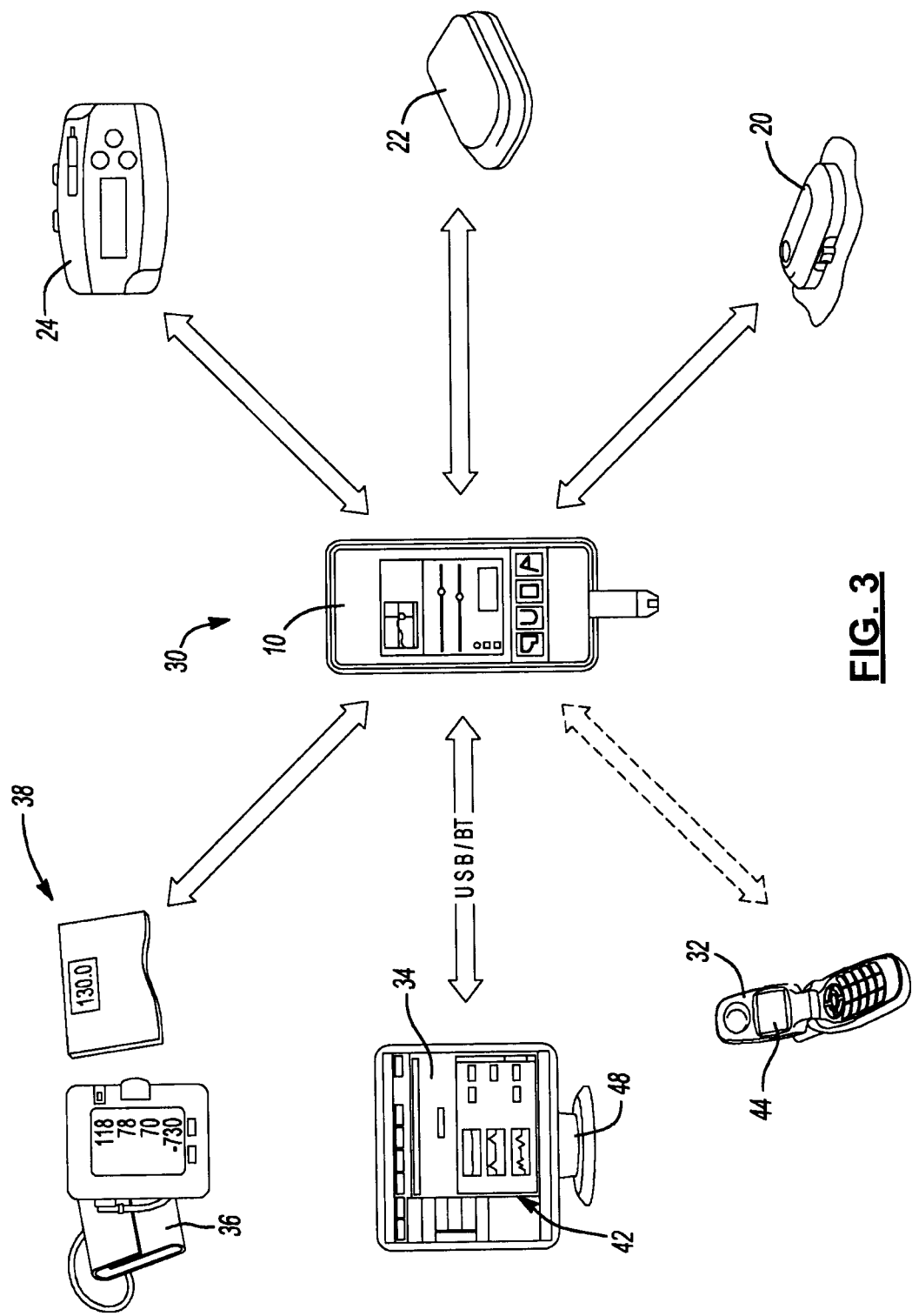
FIG. 3 shows an exemplary diabetes care system of devices used by patients and clinicians to manage diabetes.
Figure 4:
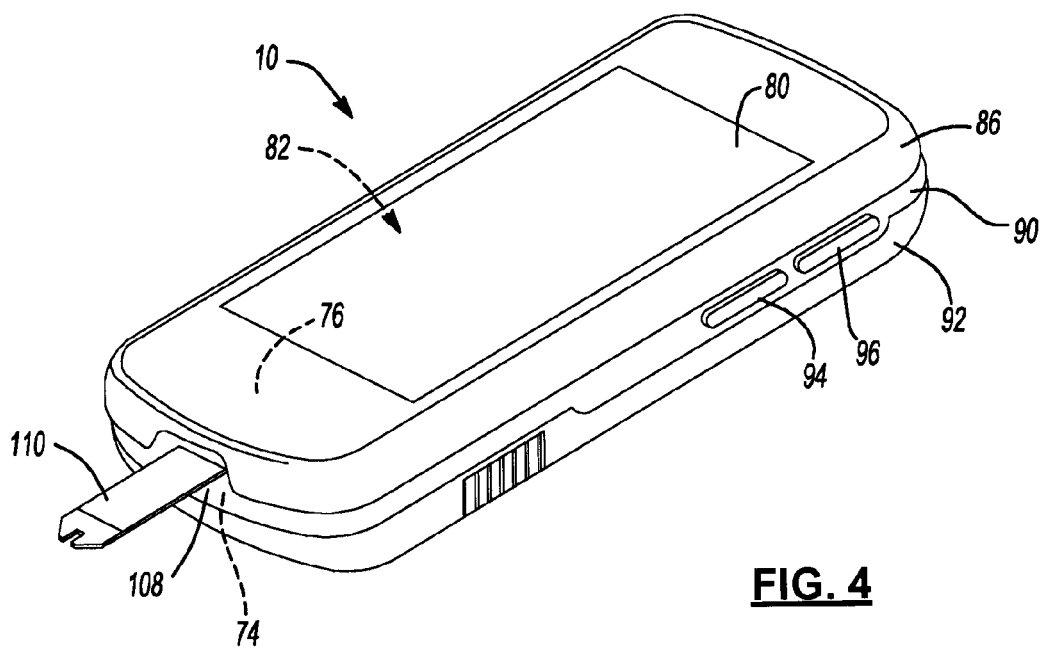
FIGS. 4-8 show various isometric views of the handheld diabetes manager of FIG. 1.
Figure 5:
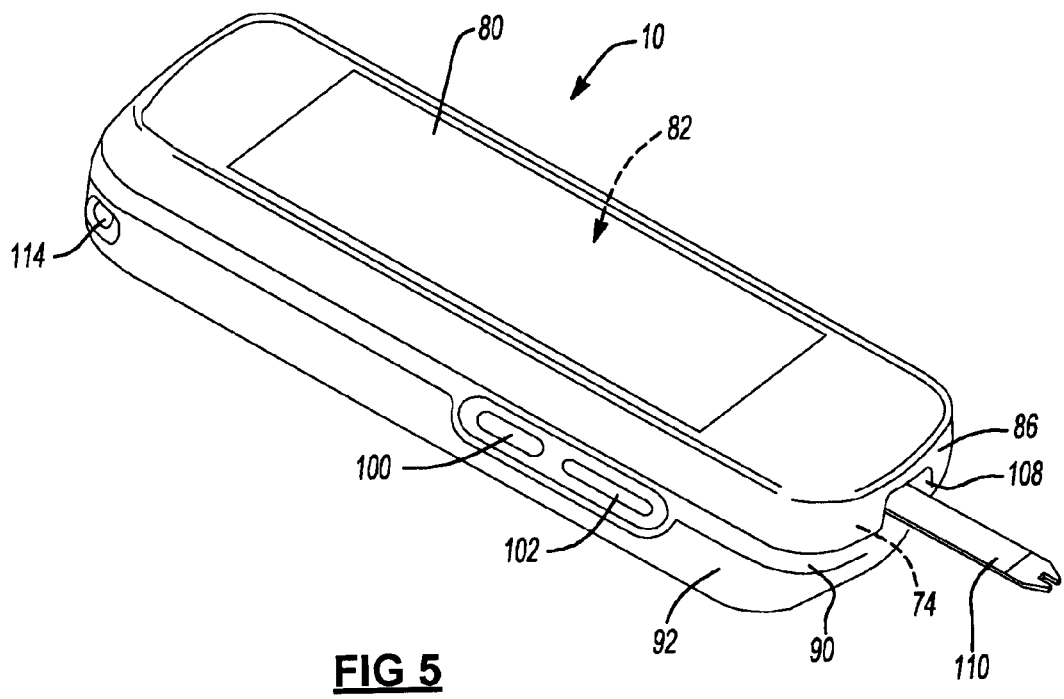
Figure 6:
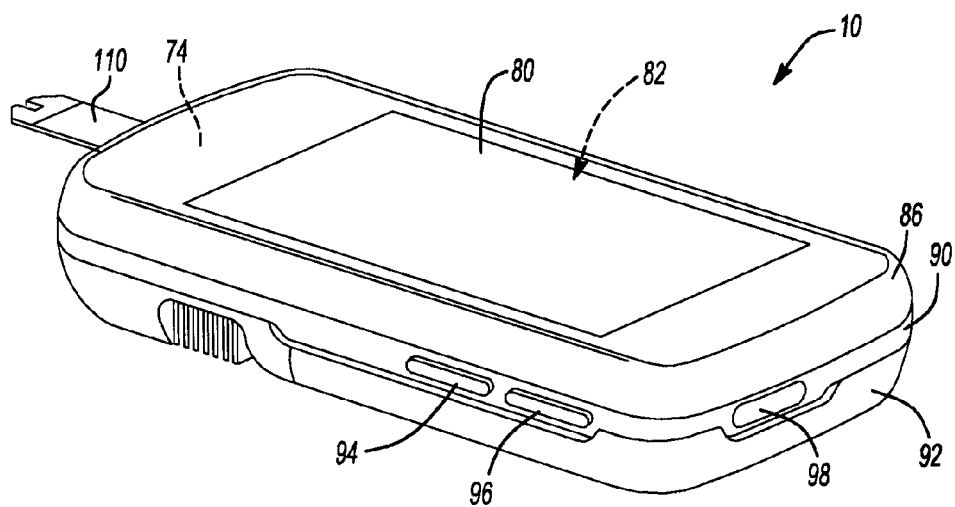
Figure 7:
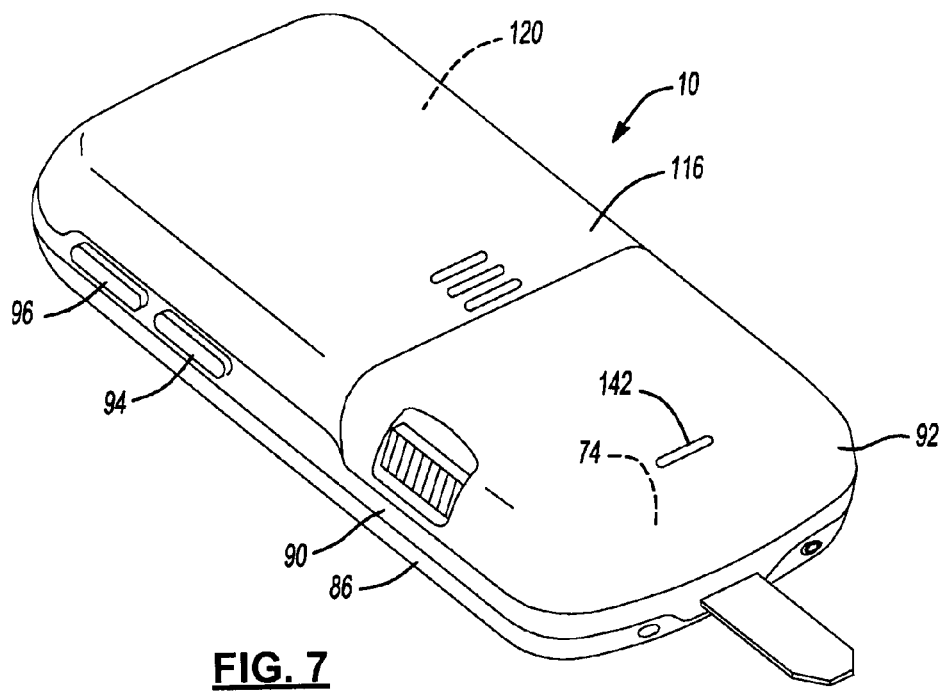
Figure 8:
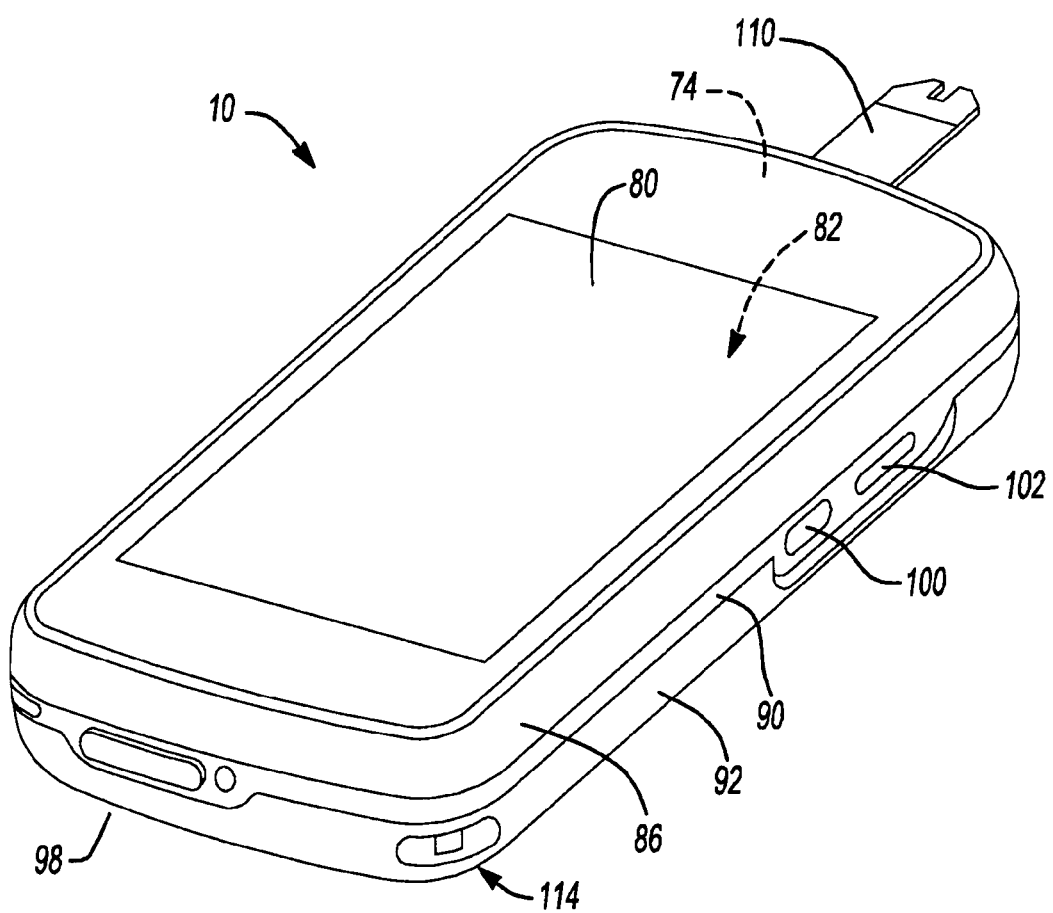
Figure 134:
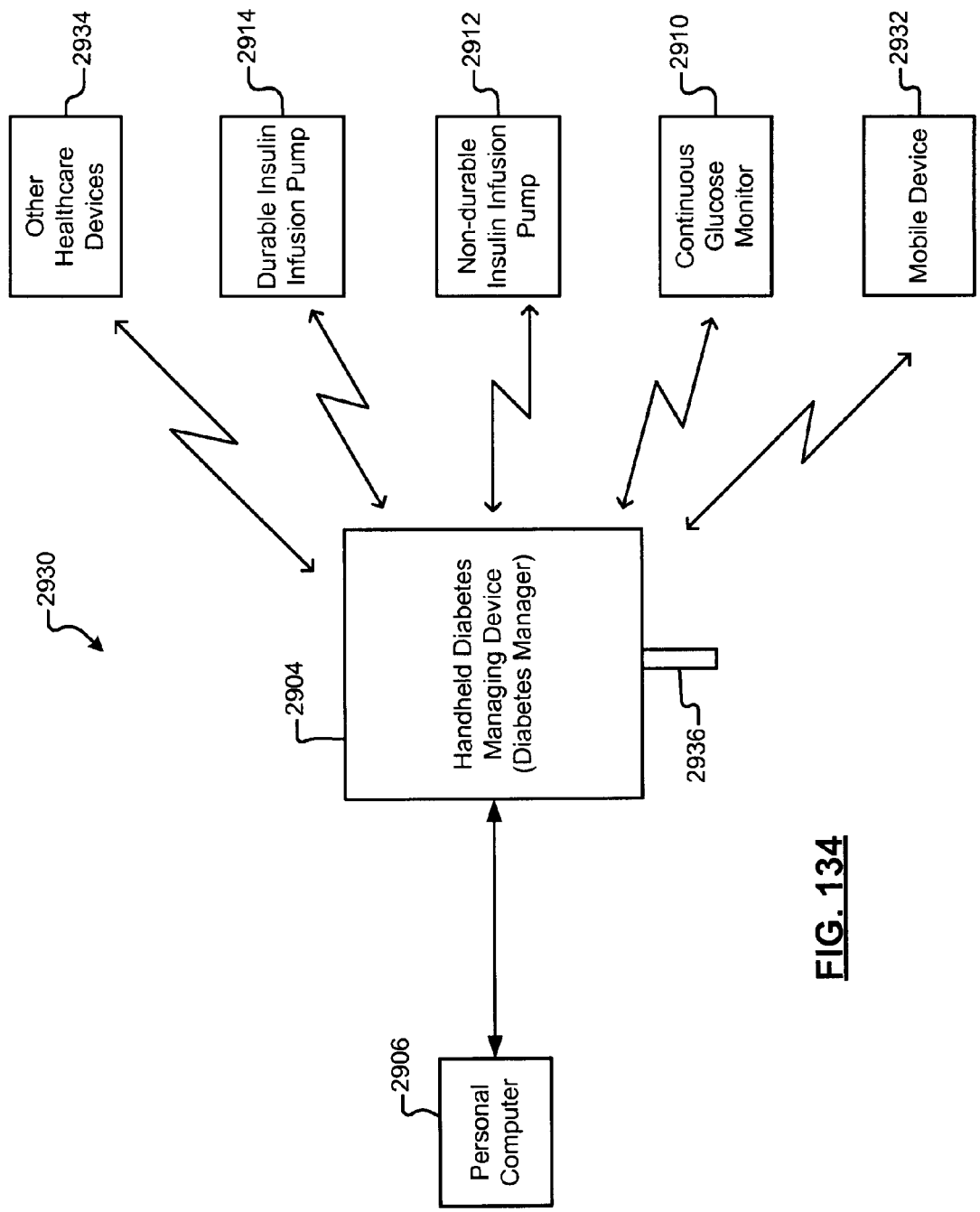
Figure 135:
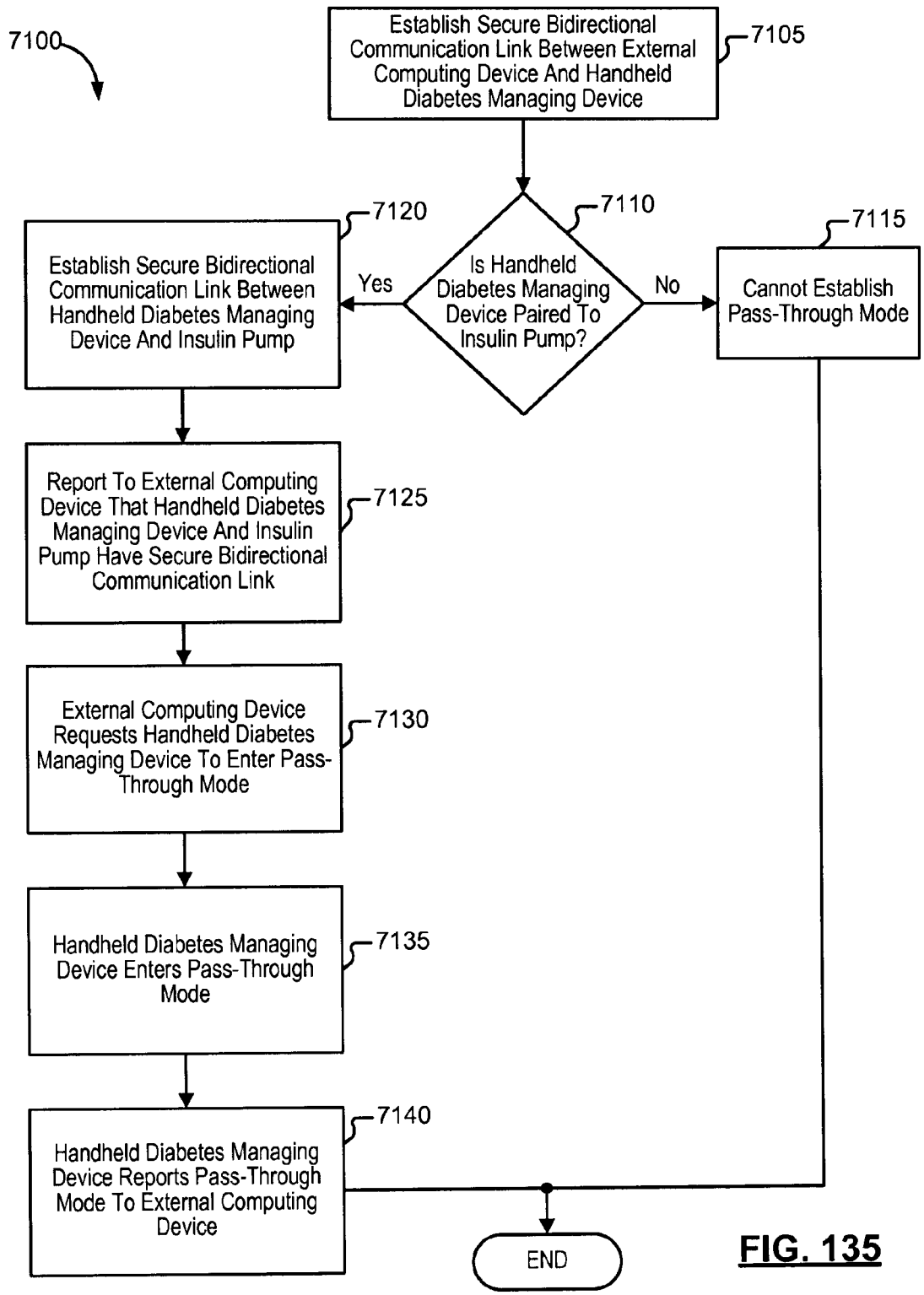
Figure 136:
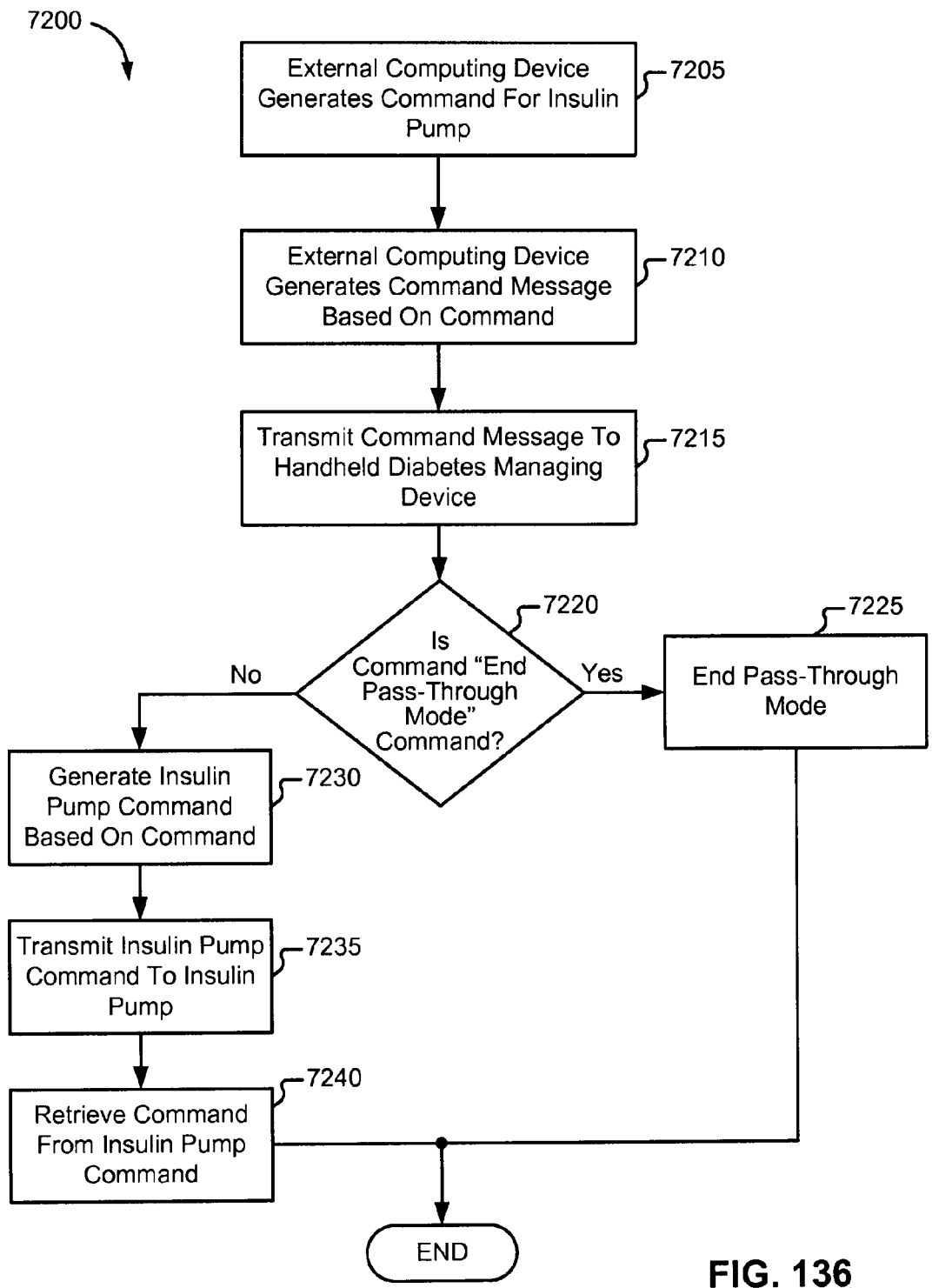
Figure 137:
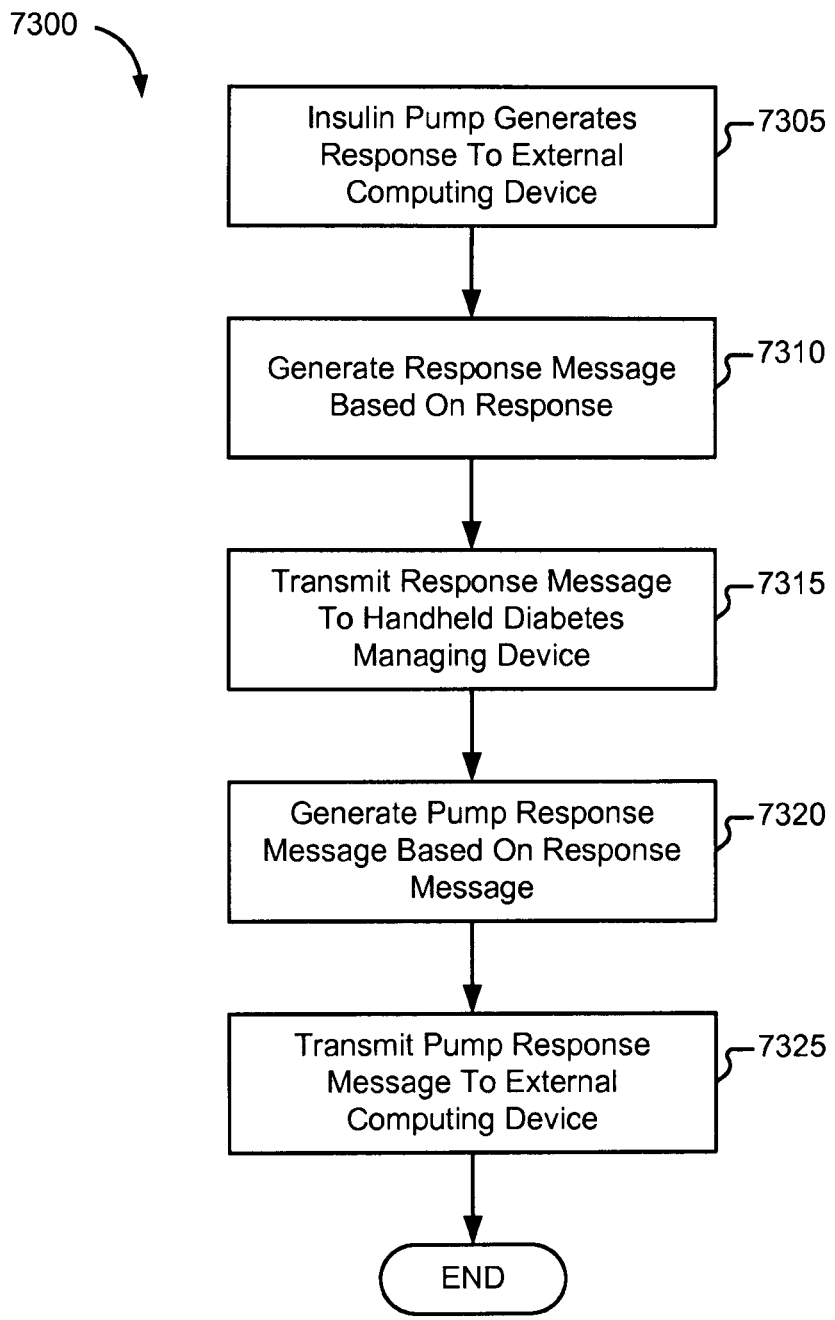
Figure 138:
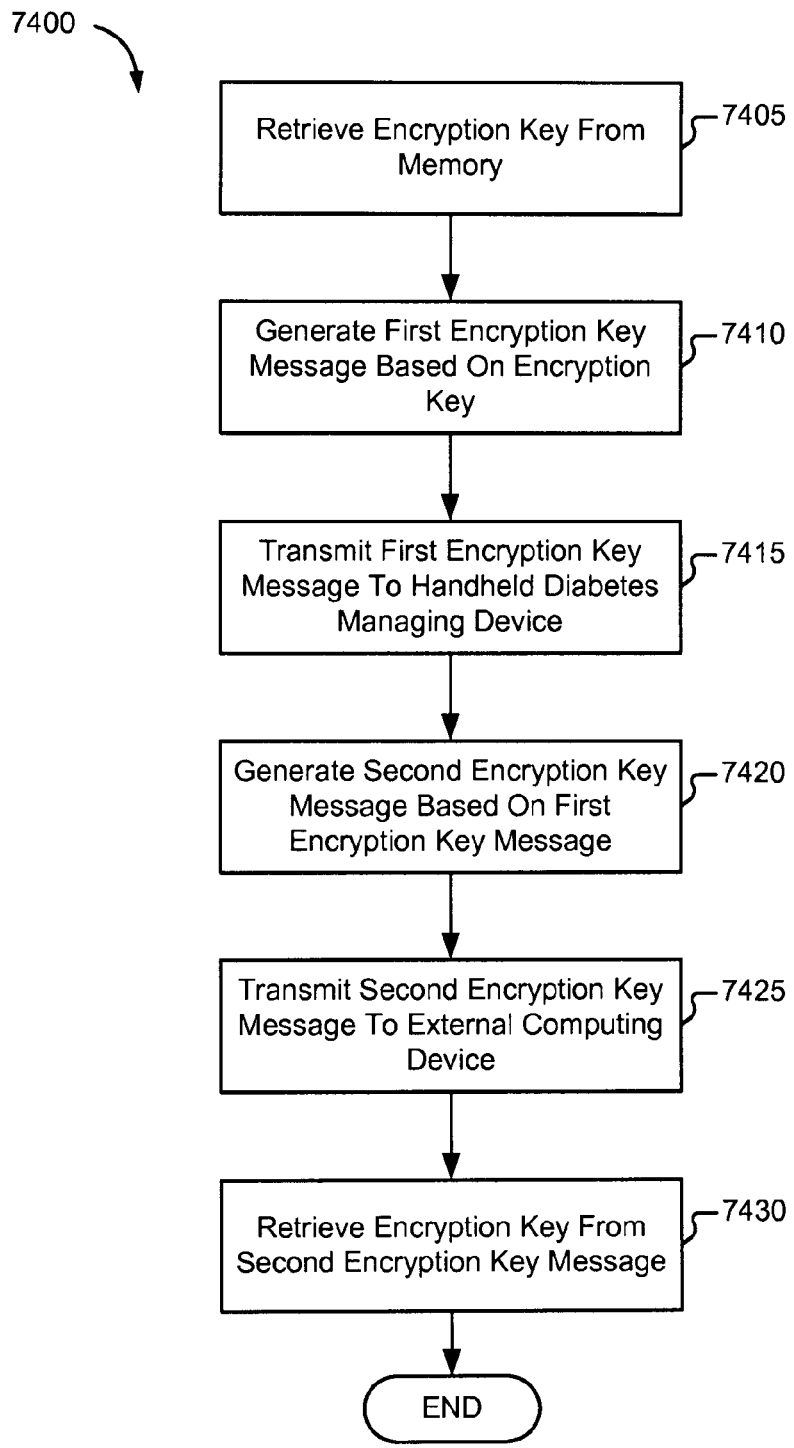
Figure 139:
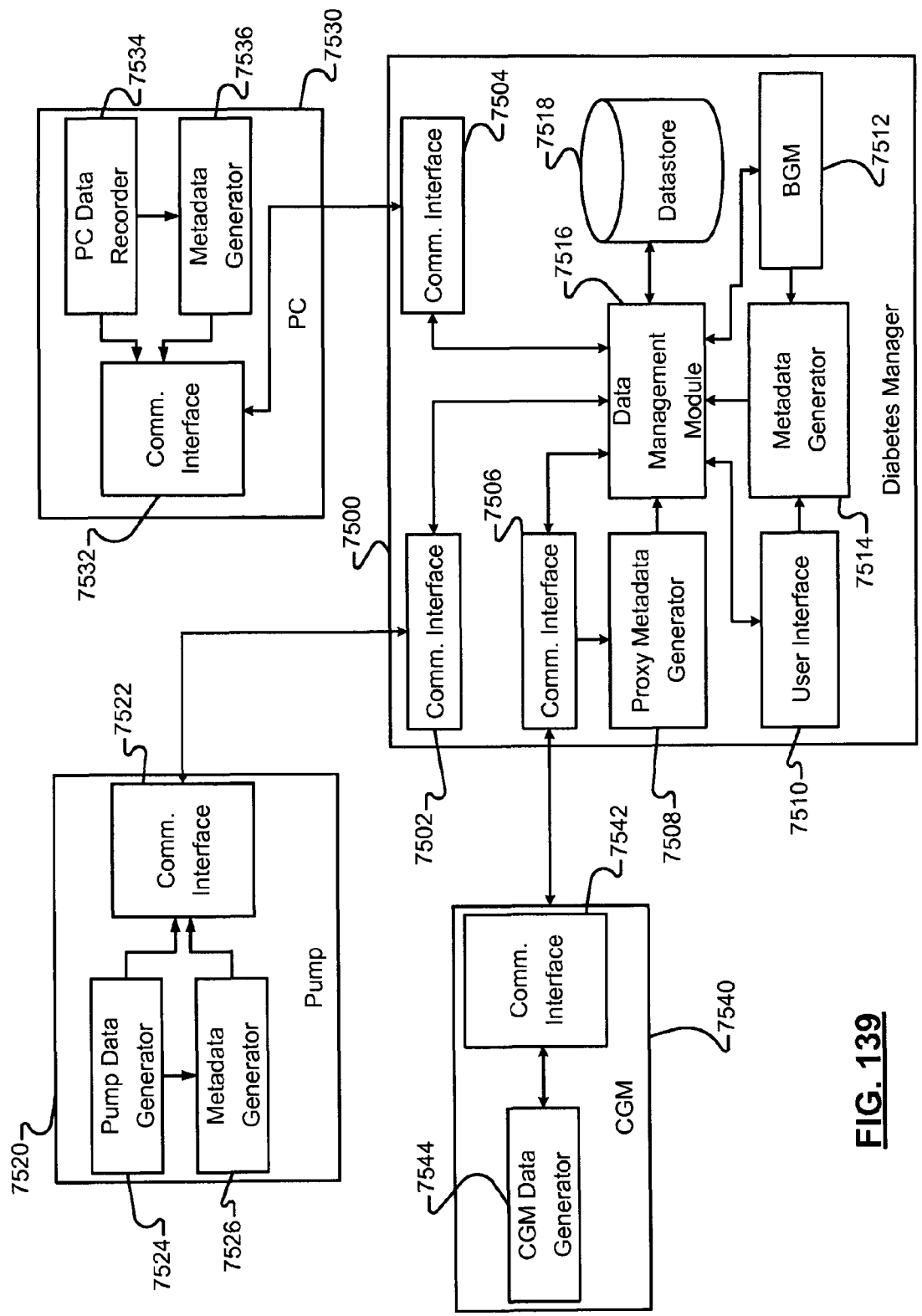
Figure 140:
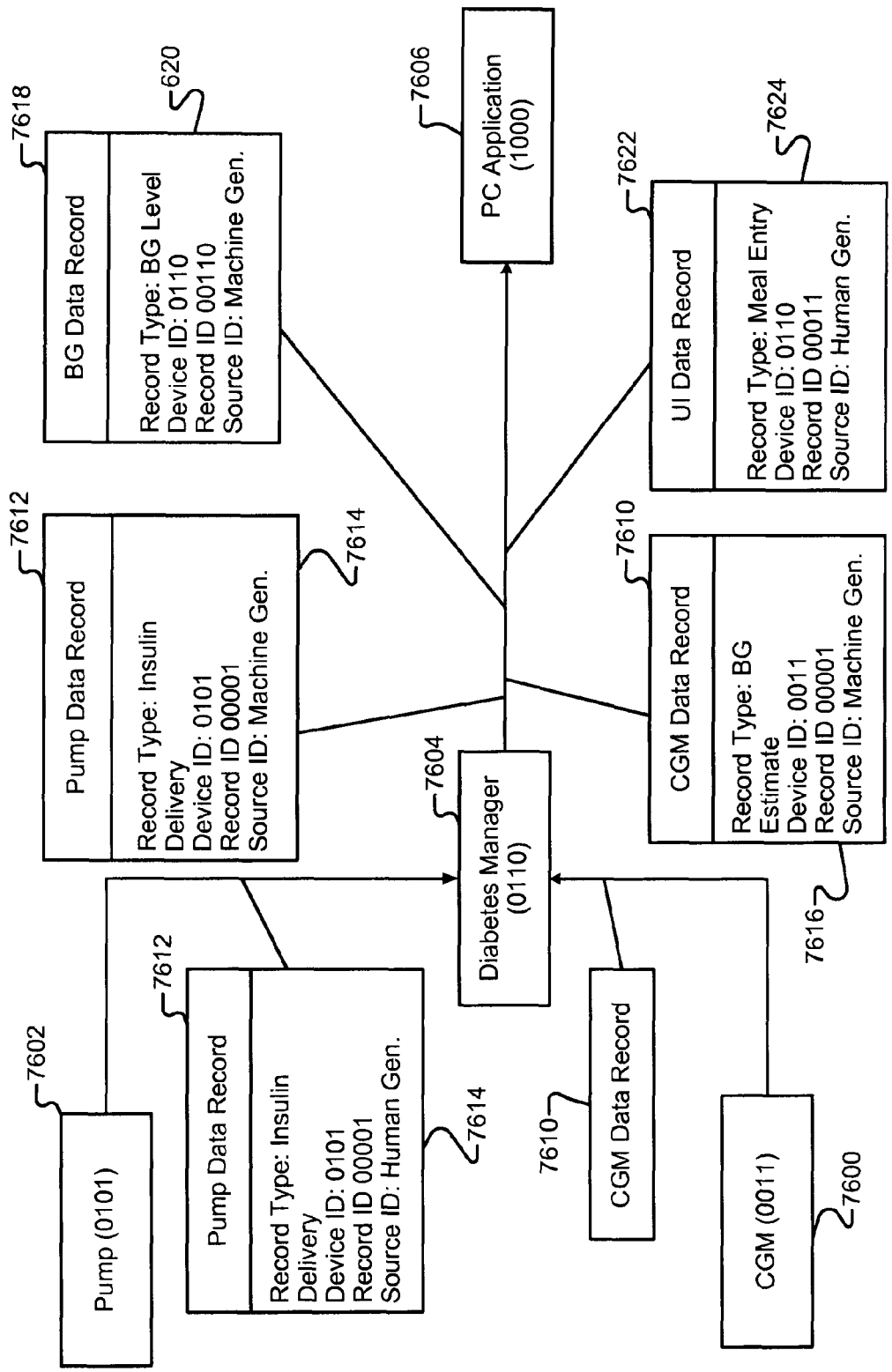
Figure 141:
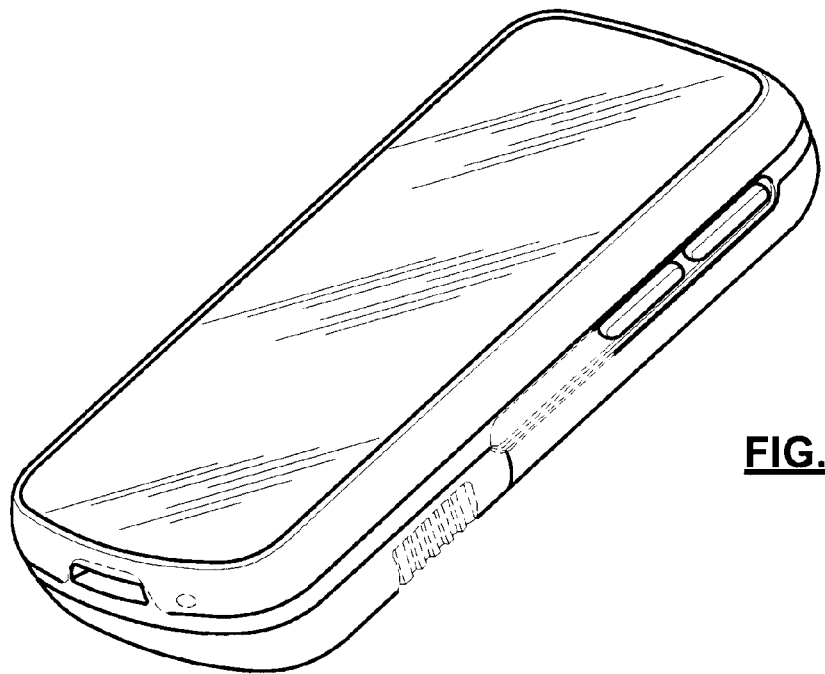
Figure 142:
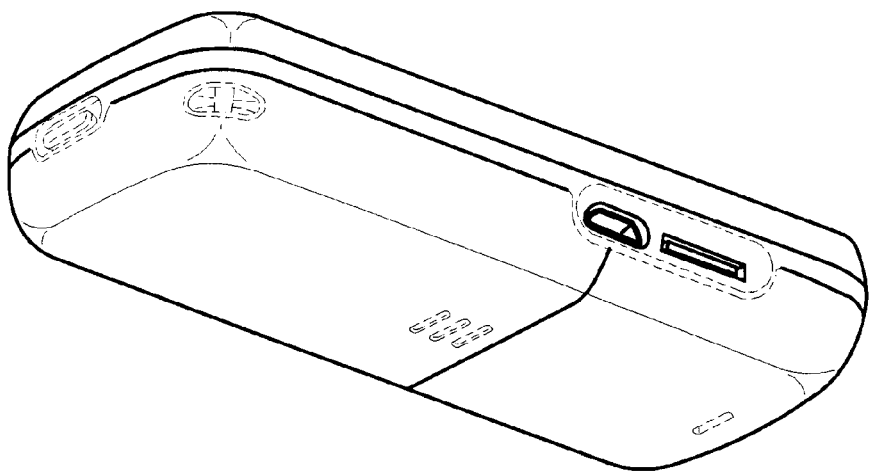
Figure 145:
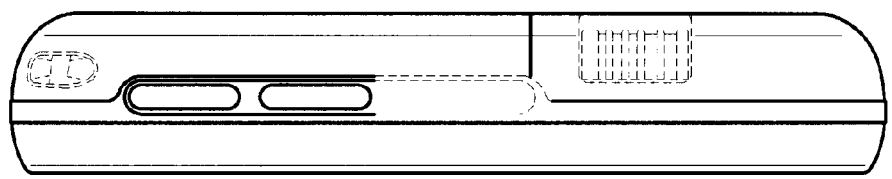
Figure 144:
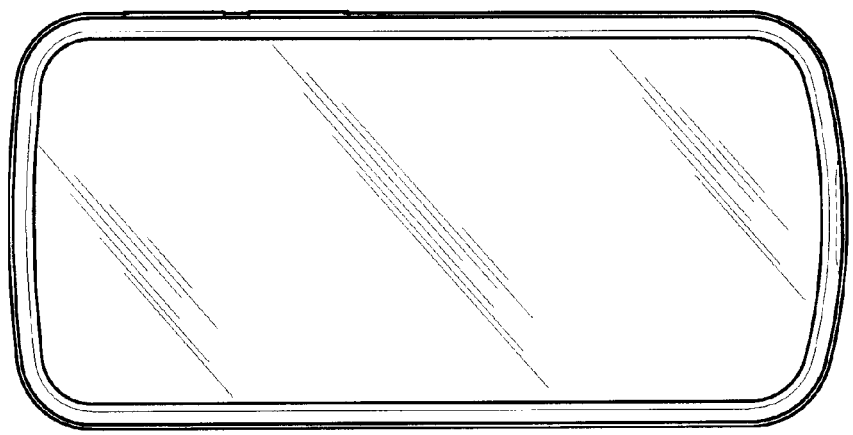
Figure 143:
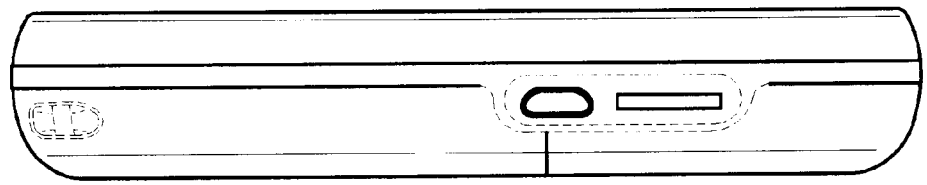
Figure 148:
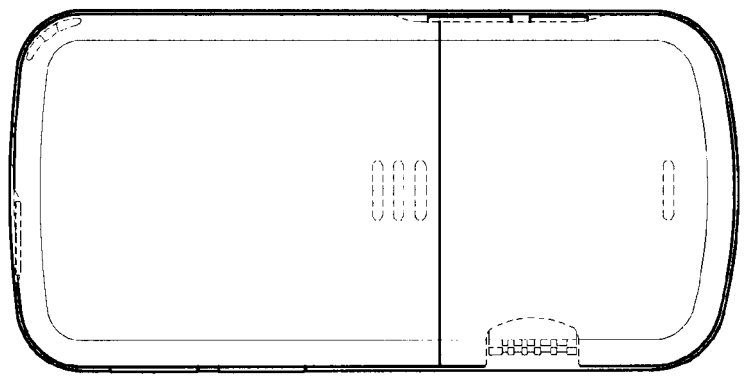
Figure 146:
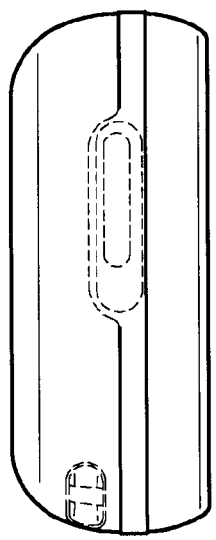
Figure 147:
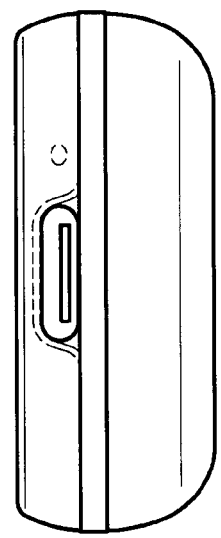

FIG. 134 shows a block diagram of an exemplary diabetes care system for providing diagnostics and therapy that includes a handheld diabetes managing device that provides a secure and efficient communication link between an insulin pump and an external computing device;

FIG. 135 shows a flow-chart illustrating an exemplary method of establishing a pass-through mode in a handheld diabetes managing device according to the present disclosure;

FIG. 136 shows a flow-chart illustrating an exemplary method of sending a command from an external computing device to an insulin pump through a handheld diabetes managing device in pass-through mode according to the present disclosure;

FIG. 137 shows a flow-chart illustrating an exemplary method of sending a response from an insulin pump to an external computing device through a handheld diabetes managing device in pass-through mode according to the present disclosure;

FIG. 138 shows a flow-chart illustrating an exemplary method of pairing an insulin pump to an external computing device through a handheld diabetes managing device in pass-through mode according to the present disclosure;

FIG. 139 shows components of a system of devices that are configured to communicate data records and corresponding metadata tags with one another;

FIG. 140 shows an example of data records and metadata tags being communicated throughout a system of diabetes treatment devices;

FIG. 141 is a front perspective view of a hand-held blood glucose meter showing a port and buttons therein in solid lines, and a display screen as shaded;

FIG. 142 is a rear perspective view of the hand-held blood glucose meter showing ports therein in solid lines;

FIG. 143 is a side elevational view of the hand-held blood glucose meter showing the ports therein in solid lines;

FIG. 144 is a front elevational view of the hand-held blood glucose meter showing the display screen as shaded;

FIG. 145 is a side elevational view of the hand-held blood glucose meter, viewed opposite that of FIG. 3, showing the buttons therein in solid lines;

FIG. 146 is an end elevational view of the hand-held blood glucose meter;

FIG. 147 is an end elevational view of the hand-held blood glucose meter, viewed opposite that of FIG. 6, showing the port in solid lines; and FIG. 148 is a rear elevational view of the hand-held blood glucose meter.

Corresponding reference numerals may indicate corresponding parts throughout the several views of the drawings.

DETAILED DESCRIPTION

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method can be executed in different order without altering the principles of the present disclosure.

As used herein, the term "module" can refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term "module" can include memory (shared, dedicated, or group) that stores code executed by the processor.

The term "code,", as used above, can include software, firmware, and/or microcode, and can refer to programs, routines, functions, classes, and/or objects. The term "shared," as used above, means that some or all code from multiple modules can be executed using a single (shared) processor. In addition, some or all code from multiple modules can be stored by a single (shared) memory. The term "group," as used above, means that some or all code from a single module can be executed using a group of processors. In addition, some or all code from a single module can be stored using a group of memories.

The apparatuses and methods described herein can be implemented by one or more computer programs executed by one or more processors. The computer programs include processor-executable instructions that are stored on a non-transitory, tangible, computer readable medium. The computer programs can also include stored data. Examples of the non-transitory, tangible, computer readable medium include, but are not limited to, nonvolatile memory, magnetic storage, and optical storage.

Example embodiments will now be described more fully with reference to the accompanying drawings.

Handheld Diabetes Management Device with Touchscreen Display

Figure 1:
FIG. 1 shows a patient and a treating clinician with a handheld diabetes manager according to the present teachings.
Figure 2:
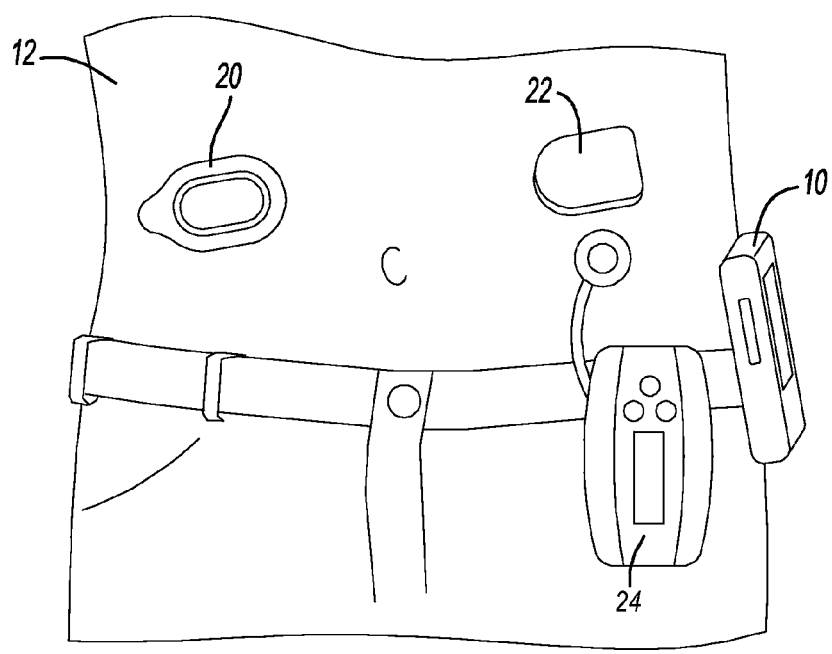
FIG. 2 shows a patient with an exemplary continuous glucose monitor (CGM), first ambulatory insulin infusion pump, second ambulatory insulin infusion pump, and handheld diabetes manager.

With initial reference to FIG. 1, a handheld diabetes manager constructed in accordance to one example of the present teachings is shown and generally identified at reference numeral 10. FIG. 1 also shows a patient 12 with diabetes and a clinician 14 in a clinic environment, the clinician 14 and patient 12 discussing various devices for managing diabetes including the handheld diabetes manager 10. For illustrative purposes, FIG. 2 shows the patient 12 with diabetes with the handheld diabetes manager 10, a continuous glucose monitor (CGM) 20, a first ambulatory insulin infusion pump 22, and a second ambulatory insulin infusion pump 24.

Persons with diabetes include persons with metabolic syndrome, pre-diabetes, type 1 diabetes, type 2 diabetes, gestational diabetes, and other types of diabetes and are collectively referred to as the patient 12 herein. Healthcare providers for diabetes are diverse and include nurses, nurse practitioners, physicians, and endocrinologists and are collectively referred to as the clinician 14 herein. During a healthcare consultation, a patient 12 typically shares with a clinician 14 a variety of patient data including blood glucose measurements, continuous glucose monitor data, insulin infused, food and beverages consumption, exercise, and other lifestyle information. This patient data can be recorded manually on a patient diary or other tools such as an Accu-Chek® 360 View Blood Glucose Analysis System form or electronically on a handheld diabetes manager, such as the handheld diabetes manager 10, or electronically on personal computer using diabetes analysis software, or electronically on a web-based diabetes analysis site, or a combination of these means. The clinician 14 will often obtain additional patient biomarker data such as measurements of HbA1C, cholesterol levels, triglycerides, blood pressure, and weight. The clinician 14 can analyze the patient data using manual techniques, electronically using diabetes analysis software, or a web-based diabetes analysis site, or a combination of these means. After analyzing the patient data along with the patient's adherence to the previously prescribed therapy, the clinician 14 can decide whether to modify the therapy for the patient 12. In considering whether to modify the therapy, the clinician 14 may need to balance the interests of the patient 12, the payer (not shown), and the clinician 14.

FIG. 3 shows a diabetes care system of devices 30 used by clinicians and patients with diabetes to manage diabetes according to the present teachings. The system of devices 30 can include one or more of the following devices: the handheld diabetes manager 10, the first ambulatory insulin infusion pump 22, the second ambulatory insulin infusion pump 24, the continuous glucose monitor (CGM) 20, the mobile phone 32, diabetes analysis software and pump configuration software 34, a health (such as blood pressure) monitor 36 and various health care devices 38. The handheld diabetes manager 10 is configured as the system hub in this embodiment. However, other devices such as the first ambulatory insulin infusion pump 22 or the mobile phone 32 can serve as the system hub according to other embodiments. Communications among the system of devices 30 can be performed using, for example, a wireless protocol such as Bluetooth or a proprietary protocol that operates IEEE 11073 as extended using guidelines provided by the Continual® Health Alliance Design Guidelines. Healthcare records systems such as Microsoft® HealthVault™ and Google™ Health can be used by the patient 12 and clinician 14 to exchange information. The CGM 20 uses a subcutaneous sensor to sense and monitor the amount of glucose in the blood of the patient 12 and communicates corresponding readings to the handheld diabetes manager 10.

The handheld diabetes manager 10 performs various tasks including measuring and recording blood glucose levels, determining an amount of insulin to be administered to the patient 12 via the insulin infusion pump 22 or 24, receiving patient data via a user interface, archiving the patient data, etc. The handheld diabetes manager 10 periodically receives readings from the CGM 20 indicating insulin level in the blood of the patient 12. The handheld diabetes manager 10 transmits instructions to the insulin infusion pump 22 or 24, which delivers insulin to the patient 12. Insulin can be delivered in a scheduled manner in the form of a basal dose, to maintain a predetermined insulin level in the blood of the patient 12. Additionally, insulin can be delivered in the form of a bolus dose, which raises the amount of insulin in the blood of the patient 12 by a predetermined amount.

The CGM patch 20 is a user-wearable continuous glucose monitoring patch. The CGM patch 20 collects CGM data and wirelessly transmits the CGM data to the handheld diabetes manager 10.

The mobile messenger 44 can be a mobile phone, pager, or other communications system. The mobile messenger 44 comprises a messenger subsystem that formats messages selected for transmission to an external communications network (not shown). The mobile messenger 44 accepts message requests from the handheld diabetes manager 10.

The health care devices 38 can include the health monitor 36, weight scale, pedometer, fingertip pulse oximeter, thermometer, or other device that obtains personal health information and is capable of communicating the health information to the handheld diabetes manager 10 through a data output channel such as a wireless or USB transport using a communications protocol such as ISO/IEEE 11073 extended using guidelines from Continual® Health Alliance.

The first insulin infusion pump 22 can have an insulin reservoir and can be configured to deliver insulin to the patient 12. The first insulin infusion pump 22 can also communicate data to the handheld diabetes manager 10. The data can include amounts of insulin delivered to the patient 12, corresponding times of delivery, and pump status. The handheld diabetes manager 10 and the first insulin infusion pump 22 can communicate using a wireless communication protocol such as Bluetooth. Other wireless or wireline communication protocols can also be used. It will be appreciated that the second insulin infusion pump 24 can be configured similarly.

The handheld diabetes manager 10 includes a blood glucose measurement engine 74. The blood glucose measurement engine 74 can determine a blood glucose value derived from a blood sample placed on a test strip as will be described herein.

With general reference now to FIGS. 4-8, additional features of the handheld diabetes manager 10 will be described. The handheld diabetes manager 10 is designed to have an appearance similar to a consumer electronics device and a popular Windows CE operating system, so persons with diabetes can manage their diabetes more discretely using a more familiar user interface. The handheld diabetes manager 10 can have a touch screen 80 that supports gesturing. The touch screen 80 overlays a thin film transistor (TFT) display 82. The TFT display 82 can display multiple colors for graphic displays for an improved user interface and the presentation of video. In one example, the TFT display 82 can be a liquid crystal diode (TFT-CD) display. The touch screen 80 can be a resistive touch screen. A top housing 86 can generally support the touch screen 80 at a position intermediate the touch screen 80 and the TFT display 82.

A center frame 90 can be positioned generally between the top housing 86 and a bottom housing 92. The center frame 90 can generally support buttons 94 and 96 on one side (FIG. 4) and provide access to a USB port 100 and SD port 102 on an opposite side. The buttons 94 and 96 can be indexing buttons. The center frame 90 can also define an access port 108 for insertion of a test strip 110 to perform blood glucose measurements using the blood glucose measurement engine 74. The bottom housing 92 can further comprise a lanyard 114. The lanyard 114 can be used to support a flexible member, such as a string or lace for attaching to the handheld diabetes manager 10. A battery cover 116 can be slidably coupled to the bottom housing 92 to securely retain a battery 118 relative to the bottom housing 92. The battery 118 can be a user-replaceable single lithium-ion battery with integrated safety circuit.

Figure 9:
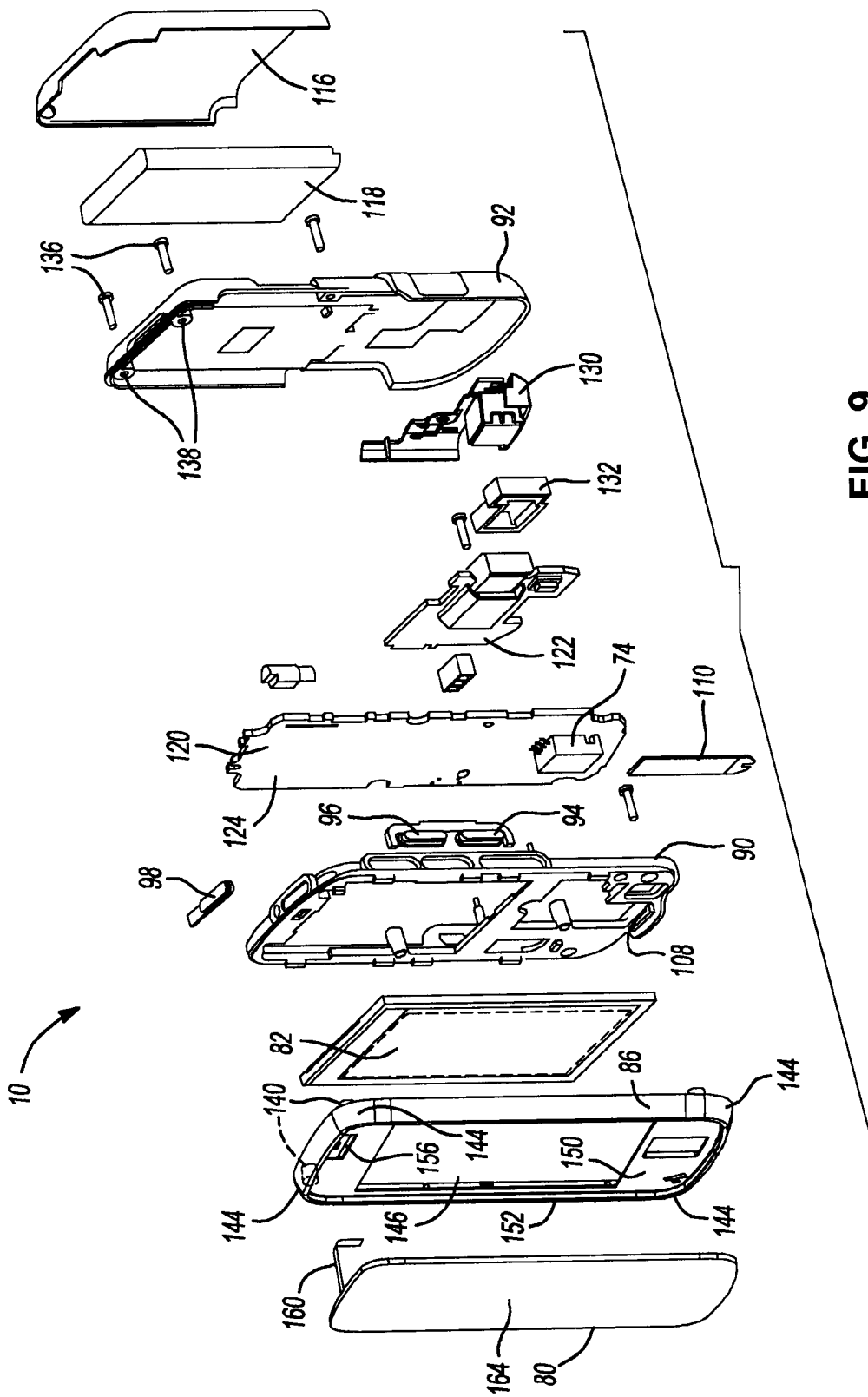
FIG. 9 shows an exploded view of an exemplary handheld diabetes manager according to the present teachings.

With specific reference now to FIG. 9, additional components of the handheld diabetes manager 10 will be described in greater detail. A printed circuit board (PCB) 120 can be positioned generally intermediate the center frame 90 and the bottom housing 92. A communications circuit 122 can be generally electrically connected to the PCB 120. The PCB 120 can incorporate a processor 124 that has integrated power management and system interfaces with internal nonvolatile memory. One suitable processor is a 32-bit ARM926SJ-E core processor. External memory can be flash memory for program and data storage and can be communicated such as through the SD port 102.

An antenna assembly 130 can be arranged generally between the communications circuit 122 and the bottom housing 92. A support member 132 can provide structural support for the antenna assembly 130 relative to the communications circuit 122. A series of fasteners 136 can be located through passages 138 defined through the bottom housing 92 and be threadably connected to complementary bosses 140 extending from the top housing 86. A speaker passage 142 (FIG. 7) can be provided through the bottom housing 92.

The blood glucose measurement engine 74 can be arranged against the PCB 120. The blood glucose measurement engine 74 can be of the type included in the Accu-Chek® Aviva Blood Glucose Meter, portions of which are disclosed in U.S.

Pat. No. 6,645,368 B1 entitled "Meter and method of using the meter for determining the concentration of a component of a fluid" assigned to Roche Diagnostics Operations, Inc., which is hereby incorporated by reference. The test strips 110, also known as disposable biosensors, are used with an integrated collection device to receive a sample of capillary blood which is exposed to an enzymatic reaction and measured by electrochemistry techniques, optical techniques, or both to measure blood glucose. An example of a test strip 110 and blood glucose measurement engine 74 is disclosed in U.S. Pat. No. 7,727,467 "Reagent stripe for test strip", assigned to Roche Diagnostic Operations, Inc., which is hereby incorporated by reference. The blood glucose measurement engine 74 provides a means to determine a blood glucose value derived from a blood sample placed on a test strip 110 and to send that data for viewing on the TFT display 82.

Figure 10:
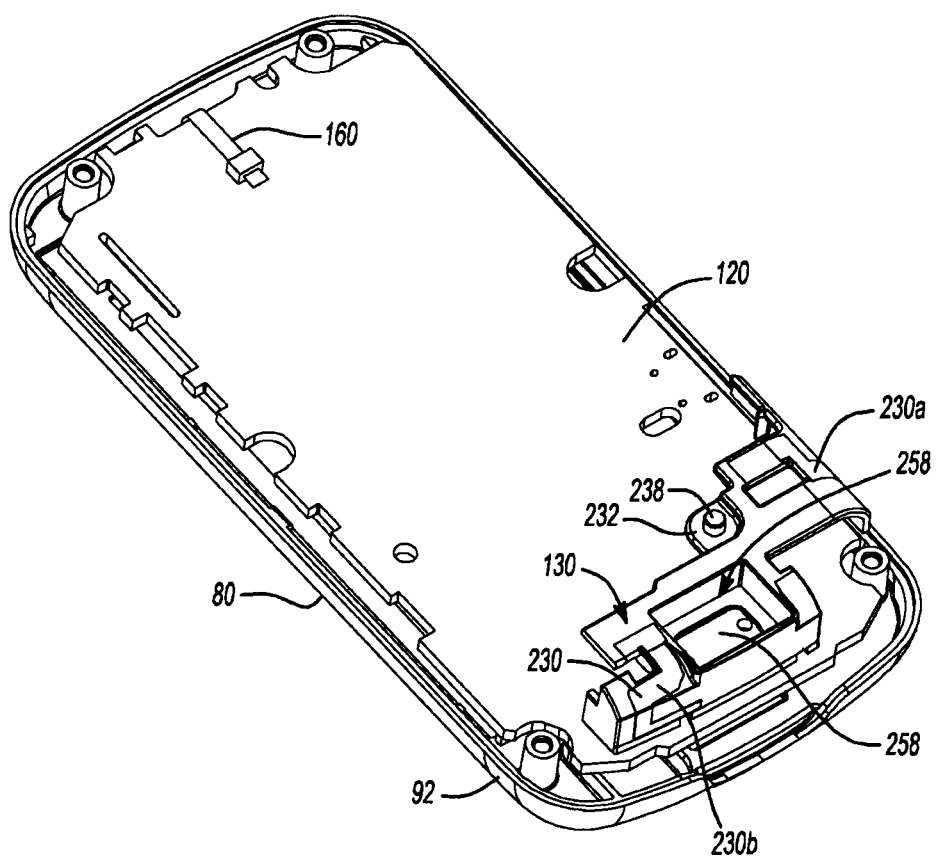
FIG. 10 is a rear perspective view of the handheld diabetes manager of FIG. 9 shown with the bottom housing, battery and battery cover removed.

With continued reference to FIG. 9 and additional reference now to FIGS. 10 and 11, the top housing 86 will be described in greater detail. The top housing 86 can generally have a rectangular profile that includes rounded corners 144. An opening 146 can be formed through the top housing 86 that generally provides a viewing area to observe the TFT display 82. A support surface 150 can be recessed a distance relative to a front edge 152. The support surface 150 can receive the touch screen 80 in a fluid-tight, sealed relationship as will be described herein. A passage 156 can be formed through the top housing 86 for receipt of a flexible connector 160 that is electrically connected between the touch screen 80 and the PCB 120.

Figure 11:
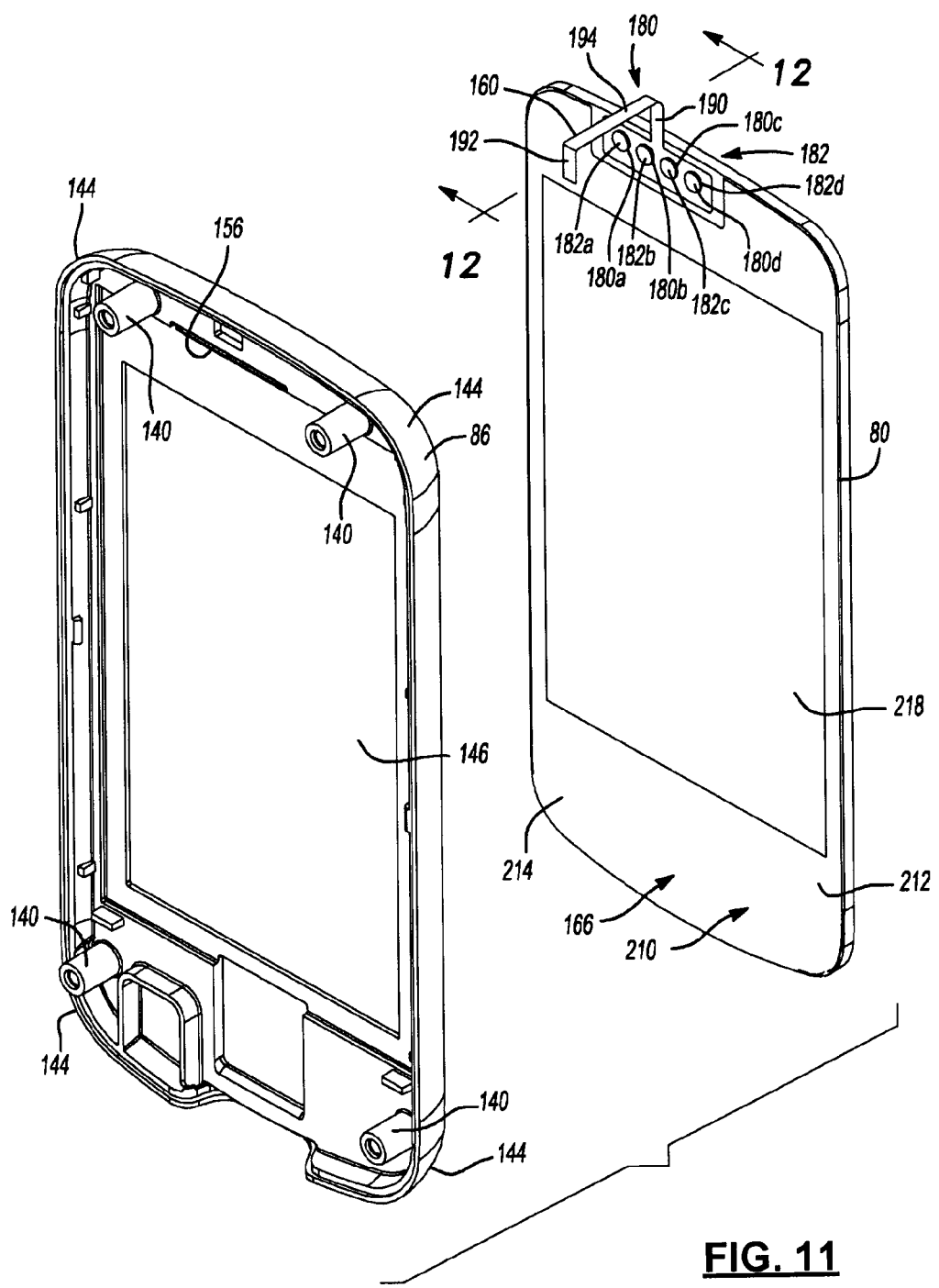
FIG. 11 is a rear exploded view of the touch window and top housing of FIG. 9.

The touch screen 80 generally includes a front touch surface 164 (FIG. 9) and a rear connection surface 166 (FIG. 11). The rear connection surface 166 can be securely connected to the support surface 150 of the top housing 86 by way of adhesive as will be described in greater detail.

With reference now to FIGS. 11 and 12, the touch screen 80 can generally include a substrate 170 that provides the rear connection surface 166, a first (lower) electrode film 172 disposed on the substrate 170, a second (upper) electrode film 174 disposed on the lower electrode film 172 and a graphic film 176 disposed on the upper electrode film 174. The upper electrode film 174 provides the front touch surface 164. In this regard, the touch screen 80 comprises a first electrode film 172 disposed on the substrate 170. The touch screen 80 further comprises a second electrode film, the first electrode film 172 disposed intermediate the second electrode film 174 and the substrate 170. The graphic film 176 can be disposed on the second electrode film 174. One suitable touch screen is manufactured by Nissha Printing Co., Ltd of Tokyo, Japan.

Referring again to FIG. 11, in the exemplary configuration, the flexible connector 160 can provide four distinct electrical leads collectively referred to at reference numeral 180 and individually identified at reference numerals 180a, 180b, 180c and 180d, respectively. Each of the electrical leads 180 can connect to the touch screen 80 by way of pins collectively referred to at reference numeral 182 and individually identified at reference numerals 182a, 182b, 182c and 182d, respectively. The flexible connector 160 can have a first segment 190 that connects to the electrical pins 182, a second segment 192 that connects to the PCB 120 and an intermediate segment 194 that connects between the first and the second segments 190 and 192, respectively. The flexible connector 160 flexes to achieve an orientation, such that the first and second segments 190 and 192 occupy planes that are generally parallel and offset relative to each other. The intermediate segment 194 can occupy a plane that is generally transverse to the planes occupied by the first and second segments 190 and 192. In general, the intermediate segment 194 can pass through the passage 156 in the top housing 86, such that the second segment 192 can electrically connect with the PCB 120.

FIG. 13 illustrates an exemplary electrical schematic 200 of a touch window sensor 202 that can be integrated into the touch screen 80. As is known in the art, the touch window sensor 202 can be configured to sense the touch of a user's finger on the front touch surface 164 of the touch screen 80. In this regard, circuitry on the PCB 120 can correlate a position that a user has touched the touch screen 80 with a location of an item presented on the TFT display 82.

Referring to FIG. 11, in one configuration, adhesive 210 is applied across a boundary 212 of the rear connection surface 166. The adhesive 210 can be pressure sensitive acrylic adhesive. The adhesive 210 can therefore be applied around the boundary 212 to create a generally non-transparent portion 214 that surrounds a transparent portion 218. As used herein, the term "non-transparent" is used to denote a portion of the touch screen 80 that has adhesive applied thereon. It will be appreciated that in some instances that the non-transparent portion 214 can be at least partially transparent.

The transparent portion 218 can have a generally transparent viewing area that corresponds to the opening 146 in the top housing 86 for viewing the TFT display 82. By applying adhesive 210 around the entire boundary 212, a liquid-tight seal can be made between the boundary 212 of the rear connection surface 166 on the touch screen 80 and the support surface 150 of the top housing 86. A liquid-tight seal can then be realized between the touch screen 80 and the top housing 86. In some examples, the liquid-tight seal can provide a hermetic seal. Since the touch screen 80 is the face of the handheld diabetes manager 10, the touch screen 80 is required to meet specific regulatory (such as Food and Drug Administration) guidelines that pertain to cleanliness. In this regard, the touch screen 80 must be designed, such that debris is not easily retained by the touch screen 80 and such that touch screen 80 can be cleaned with a liquid and cloth without liquid intrusion between the touch screen 80 and the top housing 86 of the handheld diabetes manager 10. The configuration of the touch screen 80, adhesive 210 and top housing 86 of the present disclosure meets these guidelines.

Figure 15:
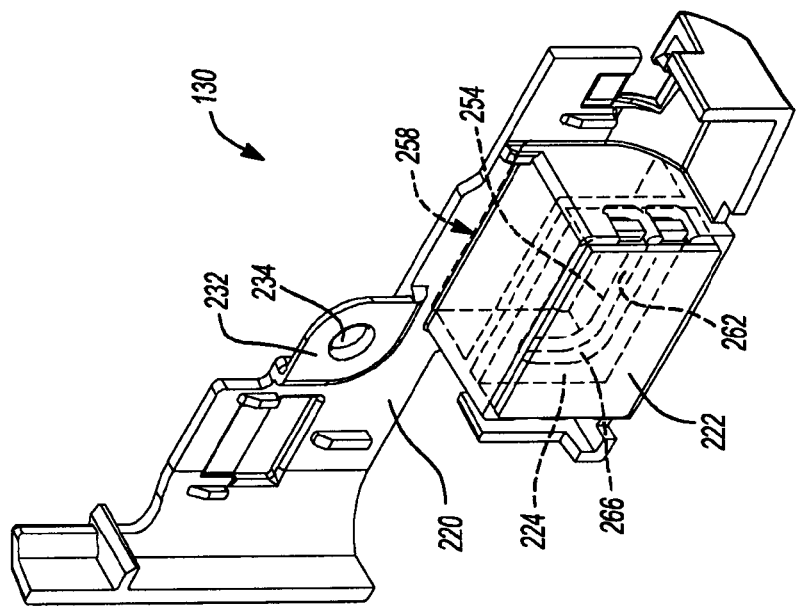
FIG. 15 is a rear perspective view of the antenna assembly of FIG. 14.
Figure 14:
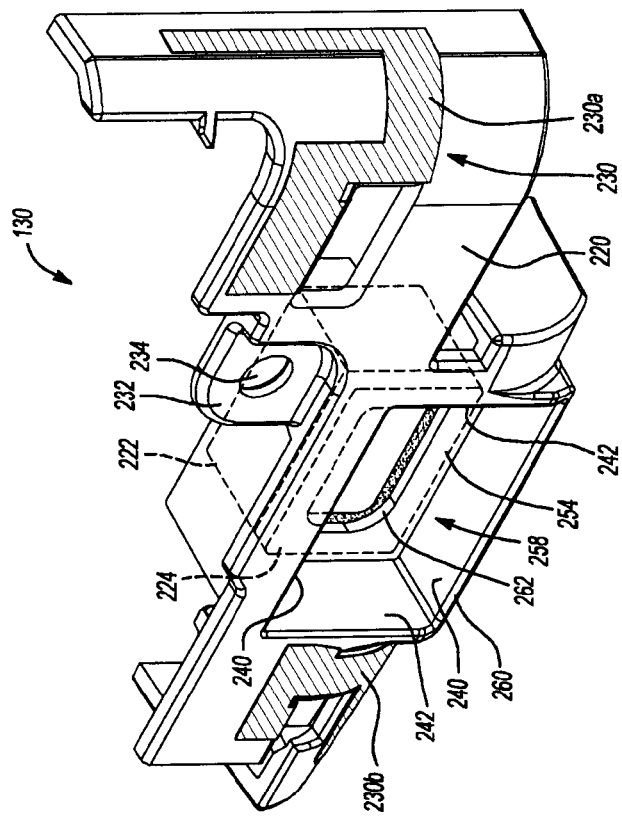
FIG. 14 is a front perspective view of an antenna assembly of the handheld diabetes manager.
Figure 16:
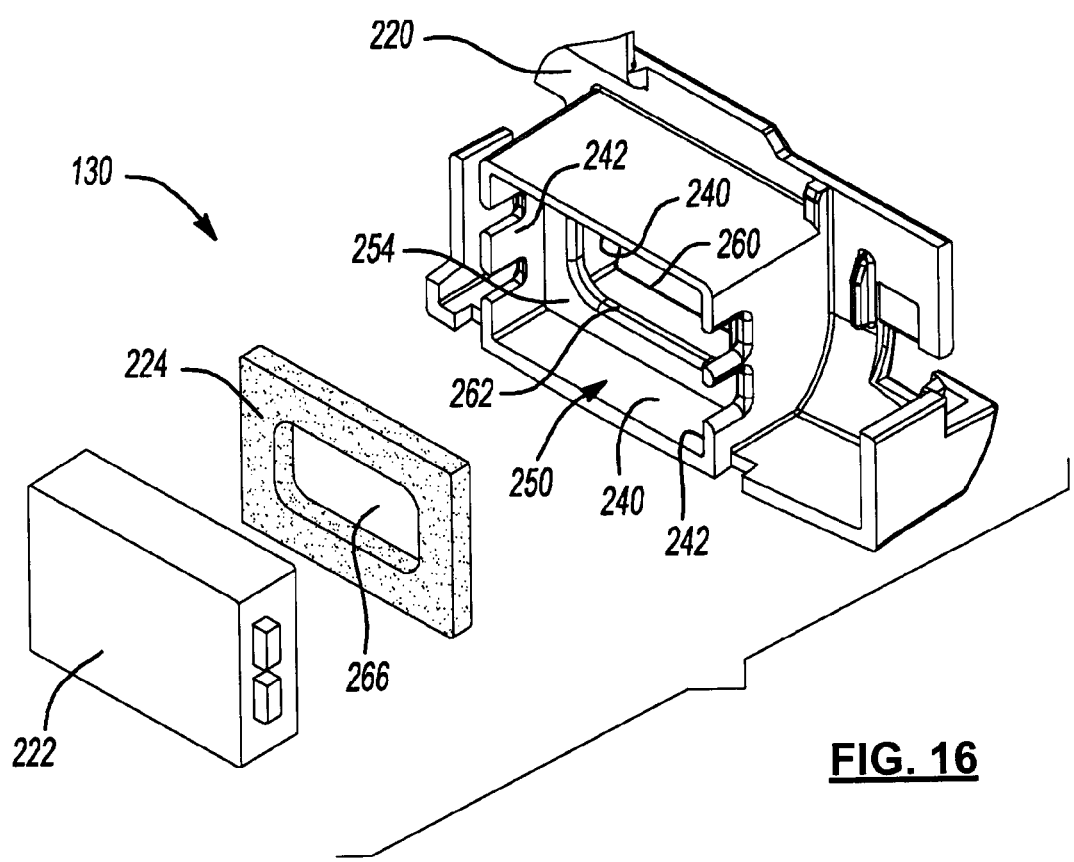
FIG. 16 is an exploded rear perspective view of the antenna assembly of FIG. 15.

With reference now to FIGS. 14-16, the antenna assembly 130 will be described in further detail. The antenna assembly 130 can generally include a molded carrier 220, a speaker 222 and a piece of foam 224. A conductive portion 230 can be arranged and supported on the molded carrier 220. In the example shown, two conductive portions 230a and 230b collectively comprise the conductive portion 230. A single conductive portion or multiple separate conductive portions can be incorporated as desired. According to one example, the conductive portion 230 can be manufactured by a laser direct structuring. In this regard, the molded carrier 220 can be processed using a laser to remove the base plastic resin in desired areas to expose and sinter copper particles in the resin. The exposed copper is then plated with more copper, nickel, and finally gold to form the conductive portion 230 in the desired shape.

The conductive portion 230 can be configured to receive a radio signal, such as any of the wireless signals discussed herein, and be electrically connected to the PCB 120. The molded carrier 220 can include a mounting tab 232 that defines an aperture 234. The aperture 234 can receive a fastener 238 (FIG. 10) that securely connects the molded carrier 220 to the center frame 90. The molded carrier 220 can generally comprise a first and a second pair of opposing sidewalls 240 and 242, respectively. In one example, the first pair of opposing sidewalls 240 can be parallel relative to each other and the second pair of opposing sidewalls 242 can be parallel relative to each other. In one example, the first and second pairs of opposing sidewalls 240 and 242 can cooperate to form a recess 250 that receives and supports the speaker 222 and the foam 224.

A support wall 254 can extend generally transversely between the respective first and second pairs of opposing sidewalls 240 and 242. In one example, the support wall 254 extends along a plane that is transverse to respective planes of each wall of the first and second pairs of opposing sidewalls 240 and 242. The foam 224 can be generally positioned against the support wall 254 to provide vibration damping between the speaker 222 and the molded carrier 220. A chute or chimney 258 can be formed by the recess 250 between an outlet 260 and the support wall 254. The chimney 258, and the recess 250 as a whole, can facilitate sound transmission from the speaker 222 to project sound emitted from the speaker 222. An opening 262 can be formed through the support wall 254 to pass sound emitted from the speaker 222 through the foam 224 and through the support wall 254. In one example, the foam 224 can also provide an opening 266 that coincides with the opening 262 in the support wall 254. The antenna assembly 130 of the present disclosure can provide an efficient packaging arrangement where valuable space within the handheld diabetes manager 10 can be used for both components of an antenna (the conductive portion 230) as well as providing support for the speaker 222.

Handheld Diabetes Managing Device with Light Pipe

Figure 17:
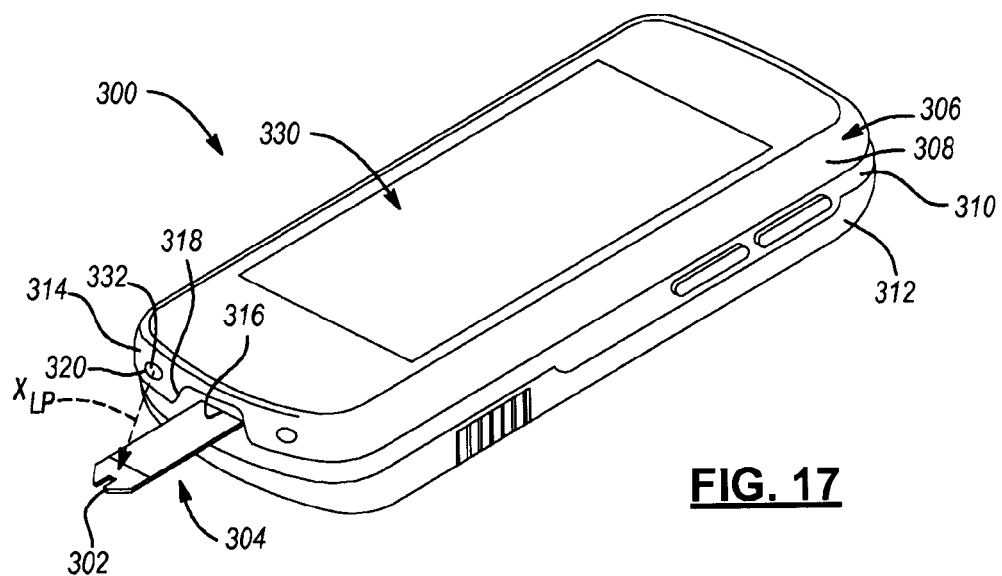
FIGS. 17 and 18 are exemplary perspective views of a handheld diabetes managing device according to the present teachings.
Figure 18:
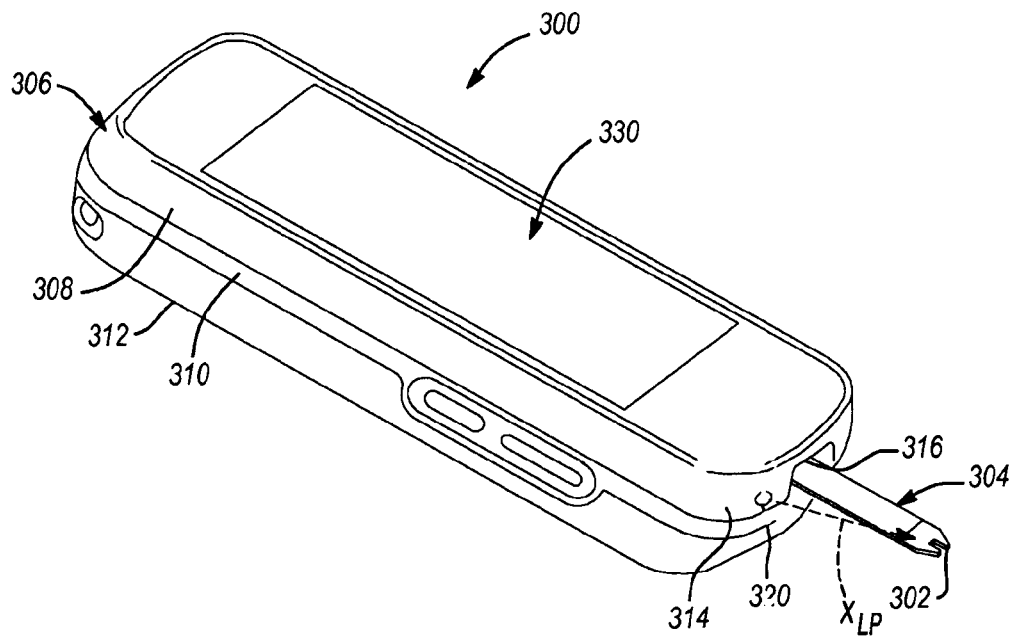

Referring initially to FIGS. 17 and 18, an exemplary embodiment of a portable, handheld diabetes management device 300 is illustrated according to the present teachings. The diabetes management device 300 can be used for analyzing a body fluid disposed on a dosing area 302 of a diabetes test element 304. For instance, as will be discussed, the test element 304 can be a disposable glucose test strip of a known type. A droplet of blood can be applied to the dosing area 302 while the test element 304 is inserted within the device 300, and the device 300 can analyze the droplet to detect the blood glucose level therein. It will be appreciated, however, that the device 300 could be used for analyzing any other suitable characteristic of any other body fluid without departing from the scope of the present disclosure.

The device 300 can include a housing 306. The housing 306 can include a first portion 308, an elongate second portion 312, and a center portion 310. The first, center, and second portions 308, 310, 312 can be removably coupled together such that the center portion 310 is disposed between the first and second portions 308, 312, to define an interior space therebetween, and to house various components therein, as will be discussed below.

Moreover, the housing 306 can include and can define an access port 316. The access port 316 can be a slot that is defined in the center portion 310. The access port 316 can removably receive the test element 304 as will be discussed below.

The housing 306 can include a light aperture 320. In some embodiments, the light aperture 320 can be a through hole with an ovate shape extending through a sidewall 314 of the first portion 308 of the housing 306. Furthermore, the light aperture 320 can be adjacent the access port 316; however, the light aperture 320 can be separated at a distance from the access port 316. Specifically, the light aperture 320 and the access port 316 can be separated by an intervening portion 318 of the sidewall 314 of the first portion 308 of the housing 306 such that the light aperture 320 and access port 316 are completely separate and distinct from each other.

Figure 19:
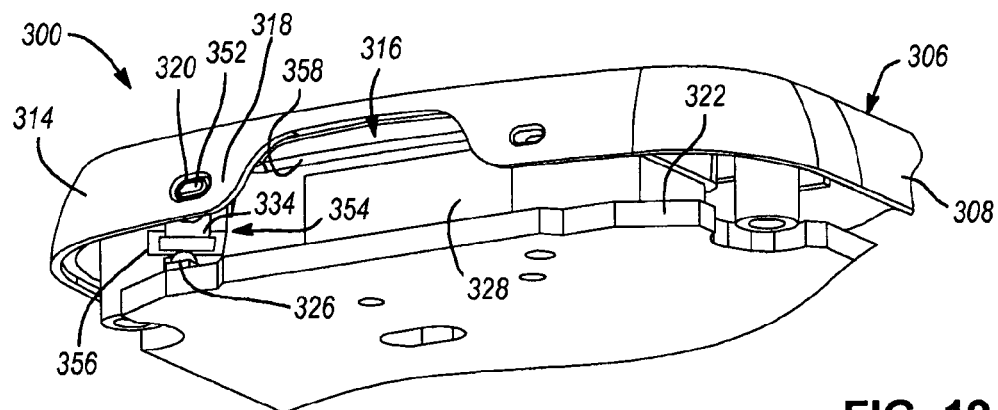
FIG. 19 is a perspective view of a portion of interior components of the handheld diabetes managing device of FIGS. 17 and 18 according to exemplary embodiments of the present teachings.
Figure 20:
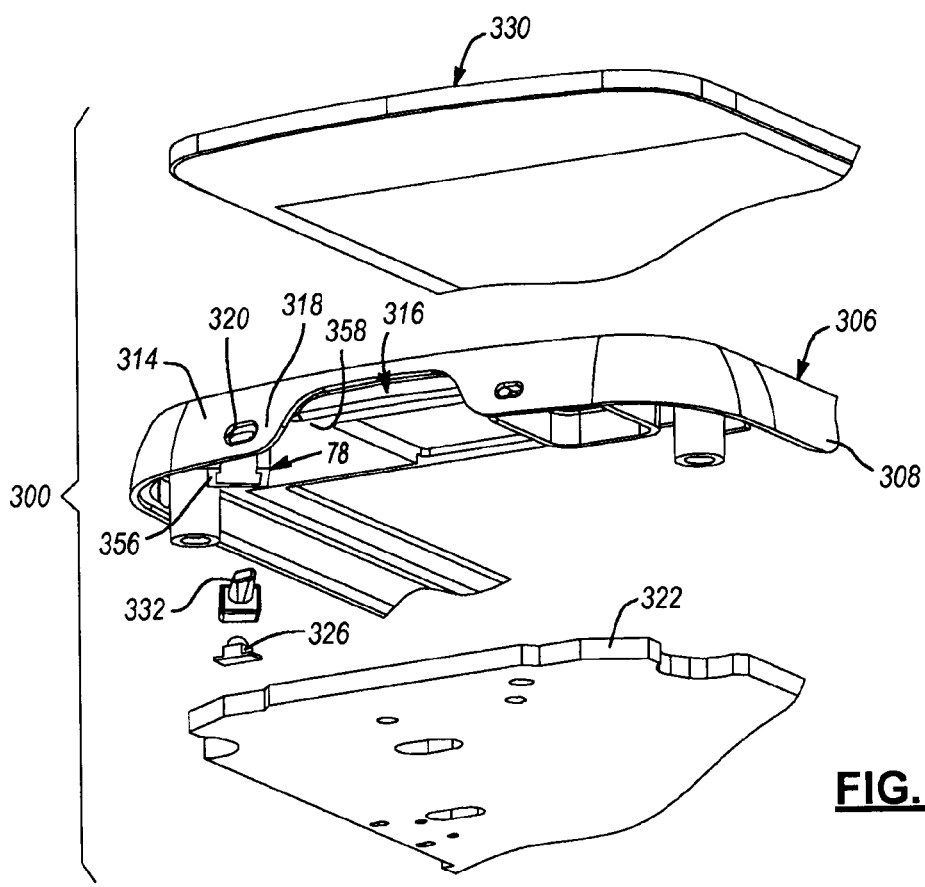
FIG. 20 is a perspective, exploded view of the interior components of FIG. 19.
Figure 23:
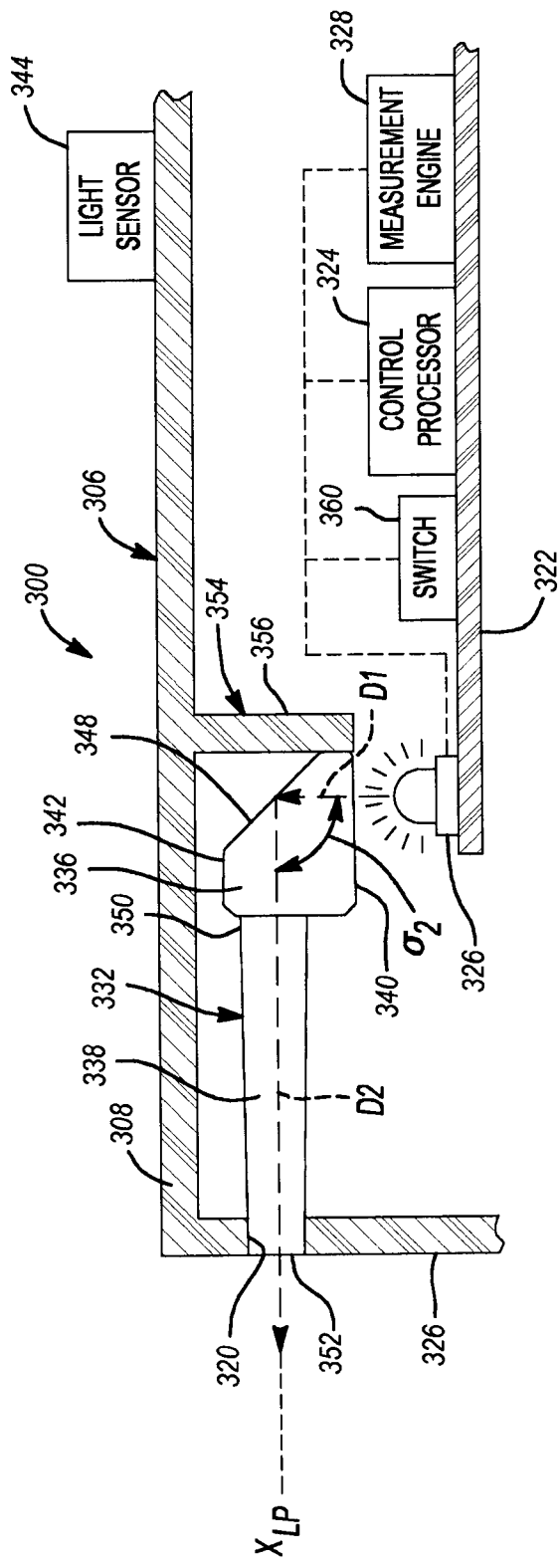
FIG. 23 is a section view of the light pipe shown in operation.

Referring now to FIGS. 19, 20, and 23, various internal components that are housed by the housing 306 will be discussed. For instance, the device 300 can include a circuit board 322. The circuit board 322 can be a printed circuit board with various circuits and circuit components included thereon. For instance, as shown in FIG. 23, a control processor 324 can be included on the circuit board 322 for controlling various functions of the device 300 as will be discussed. Furthermore, a light source 326 (FIGS. 19, 20, and 23) can be mounted to the circuit board 322. The light source 326 can be of any suitable type, such as a light emitting diode (LED). The circuit board 322, the control processor 324, and the light source 326 can each be housed within the housing 306.

The device 300 can additionally include a measurement engine 328 (FIGS. 19 and 23). The measurement engine 328 can be of a known type for analyzing the body fluid applied to the test element 304 as discussed above. The measurement engine 328 can be operably mounted to the circuit board 322 and can communicate with the access port 316. As such, when the test element 304 is inserted within the access port 316 and the body fluid is applied, the measurement engine 328 can perform the predetermined analysis. Moreover, the measurement engine 328 can include associated software and logic (e.g., within the control processor 324) for performing and controlling the analysis of the body fluid.

As shown in FIGS. 17, 18, and 20 the device 300 can include a display 330. The display 330 can be operably connected to the control processor 324 for displaying various information (e.g., text, graphics, icons, and other objects) relating to the operation of the device 300. The display 330 can be operably supported by the first portion 308 of the housing 306.

Referring now to FIGS. 19-23, the device 300 will be discussed in additional detail. As shown, the device 300 can additionally include a light pipe 332. The light pipe 332 can be made out of or include a light transmissive material. For instance, the light pipe 332 can be made out of or include a rigid, polymeric, light transmissive material. In other embodiments, the light pipe 332 can be made out of or include a flexible, light transmissive material.

Figure 21:
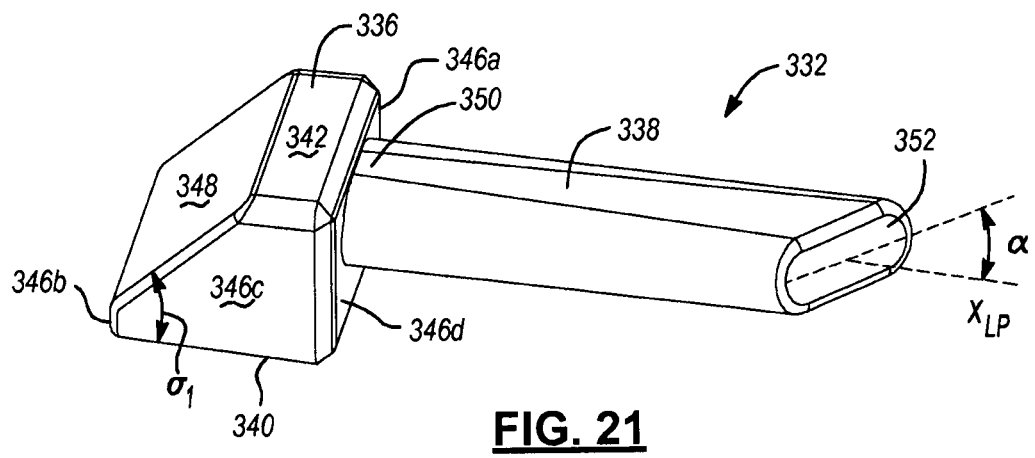
FIGS. 21 and 22 are various perspective views of a light pipe of the handheld diabetes managing device of FIGS. 17 and 18.
Figure 22:
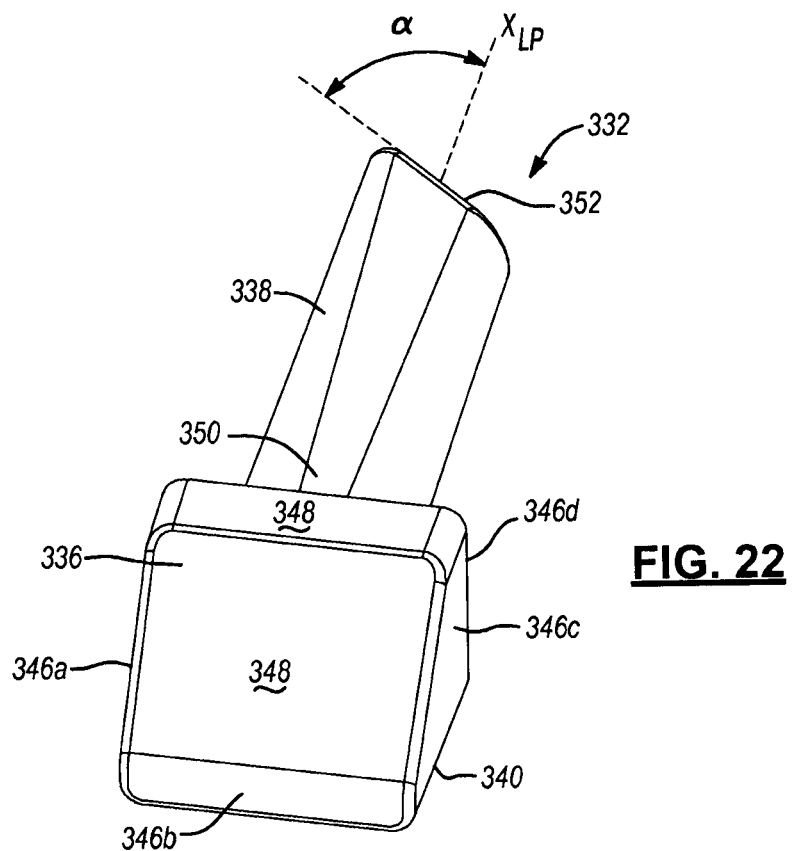

As shown in FIGS. 21-23, the light pipe 332 can generally include a first portion 336 and a second portion 338. The first and second portions 336, 338 can be integrally connected so as to be monolithic.

The first portion 336 can be a block with substantially flat surfaces and with chamfered edges. For instance, the first portion 336 can include a first surface 340 (FIG. 23) and a second surface 342 that are opposite and substantially parallel to each other. The first portion 336 can also include a plurality of side surfaces 346a-346d that each extend substantially perpendicular to the first and second surfaces 340, 342. The side surfaces 346a, 346c can be opposite and substantially parallel to each other. The side surfaces 346b, 346d can be opposite and substantially parallel to each other. Moreover, the first portion 336 can include a reflecting surface 348 that extends between the second surface 342 and the side surface 346b. The reflecting surface 348 can be substantially flat and disposed at an acute angle $\theta_1$ relative to the first surface 340. As will be discussed, the angle $\theta_1$ can be selected so that light transmitted through the first portion 336 can reflect off of the reflecting surface 348 toward the second portion 338 and along an axis $X_{LP}$ of the second portion 338.

The second portion 338 can be substantially elongate, tubular, and can have a substantially straight longitudinal (second) axis $X_{LP}$. The second portion 338 can have a rounded (e.g., circular or ovate) or rectangular cross section taken perpendicular to the longitudinal axis $X_{LP}$. The second portion 338 can also include a proximal end 350, which is connected directly to the side surface 346d of the first portion 336, and a distal end 352 that is opposite and spaced apart from the proximal end 350. As shown, the second portion 338 can be tapered between the proximal and distal end 350, 352. Also, the distal end 352 can be substantially flat and can be beveled so as to define a plane that is disposed at an acute angle α relative to the longitudinal axis $X_{LP}$ (FIGS. 21 and 22).

It will be appreciated that the first and second portions 336, 338 of the light pipe 332 can have any other suitable shape. For instance, the first portion 336 can have one or more rounded (convex or concave) outer surfaces. Moreover, the second portion 338 can have a non-linear longitudinal axis $X_{LP}$ and/or can any number of flat surfaces in cross section. Furthermore, the distal end 352 can have convex or concave curvature (e.g., to function as a lens for focusing light transmitted through the light pipe 332).

The light pipe 332 can be coupled to the housing 306 as shown in FIGS. 19 and 20. For instance, the housing 306 can include a coupling member 354 for retaining the light pipe 332. In some embodiments, the coupling member 354 can include a plurality of thin, integrally coupled walls 356 that extend from an inner surface 358 of the first portion 308 of the housing 306 toward the circuit board 322. As shown in FIG. 19, the light pipe 332 can be received between the walls 356 to be retained therebetween. The walls 356 can be shaped and sized so as to define a recess that closely matches the outer periphery of the light pipe 332. In some embodiments, the light pipe 332 can be retained between the walls 356 by friction, by an interference fit, by adhesives, by a fastener, or in any other manner.

When the light pipe 332 is mounted to the housing 306, the first surface 340 can be exposed from the walls 356 of the first portion 308 of the housing 306 (FIG. 19). Also, when the light pipe 332 is mounted, the first surface 340 can be disposed adjacent the light source 326 such that the first surface 340 directly faces the light source 326 (FIGS. 19 and 23).

Furthermore, when the light pipe 332 is mounted to the housing 306, the distal end 352 of the second portion 338 can be disposed adjacent the light aperture 320. For instance, the distal end 352 can be exposed from the housing 306 via the light aperture 320. Also, it will be appreciated that the distal end 352 can be angled with respect to the longitudinal axis $X_{LP}$ such that the distal end 352 is substantially flush with the area of the housing 306 surrounding the light aperture 320.

During operation, as shown in FIG. 23, light from the light source 326 can be emitted toward the light pipe 332 in a first direction D1 (e.g., substantially perpendicular to the first surface 340. The first surface 340 can receive the light traveling in the first direction D1 and transmit the light toward the reflecting surface 348. The light can reflect from the reflecting surface 348 and be redirected toward a second direction D2. The second direction D2 can be at a nonzero angle $\theta_2$ relative to the first direction D1. For instance, in some embodiments, the angle $\theta_2$ can be approximately ninety degrees (90°). Once the light is redirected toward the second direction D2, the light can travel along (e.g., substantially parallel to) the longitudinal axis $X_{LP}$ and out of the distal end 352 of the light pipe 332. Thus, the light pipe 332 can efficiently transmit the light generated by the light source 326 out of the housing 306 through the light aperture 320. In some embodiments, because the taper of the second portion 338 of the light pipe 332, the transmitted light can be concentrated as it travels through the second portion 338.

Also as shown in FIGS. 17 and 18, the light pipe 332 can be disposed such that the longitudinal axis $X_{LP}$ is substantially directed toward and aligned with the dosing area 302 of the test element 304. As such, the light transmitted from the light pipe 332 can illuminate the dosing area 302 as represented by an arrow in FIGS. 17 and 18. In some embodiments, the light pipe 332 can be focused on the dosing area 302 to distinguish the dosing area 302 from other portions of the test element 304 (e.g., only the dosing area 302 of the test element 304 is illuminated by the light pipe 332). As such, the user can more easily recognize where to apply a blood droplet for glucose analysis, and proper application of the blood droplet to the dosing area 302 is more likely.

It will also be appreciated that the device 300 can provide enhanced illumination efficiently and cost effectively. The light pipe 332 can be relatively inexpensive. The circuit board 322 can be manufactured independently with the light source 326 included thereon before being assembled within the housing 306. Then, during assembly of the device 300, the light pipe 332 can be easily mounted to the housing 306, and the circuit board 322 can be housed within the housing 306, such that the light pipe 332 is in its proper position for receiving light from the light source 326. The light pipe 332 is then ready for transmitting light out of the housing 306 toward the test element 304.

In some embodiments, the control processor 324 can control the light source 326 such that the light source 326 provides a visual feedback signal. The visual feedback signal (i.e., the light from the light source 326) can be transmitted through the light pipe 332.

The visual feedback signal can be of any suitable type. For instance, the light source 326 can be controlled such that the light emitted by the light source 326 changes colors (e.g., from blue light to red light, etc.). Also, the light source 326 can be controlled such that the light is emitted in a predetermined pattern, and the pattern can change to provide feedback. Specifically, the light source 326 can be illuminated for a predetermined amount of time, and then the light source 326 can begin blinking, and/or the blinking can speed up or slow down to provide visual feedback.

The feedback signal can be provided for any suitable purpose. For instance, the feedback signal can inform the user that the glucose analysis has been performed successfully, or that there has been an error in performing the glucose analysis. Also, the feedback signal can inform the user that the test element 304 is faulty and/or is not communicating properly with the measurement engine 328. Still further, the feedback signal can inform the user of the results of the analysis (e.g., high glucose level, low glucose level, and/or satisfactory glucose level). It will be appreciated that this visual feedback can be provided in addition to or as an alternative to audible feedback provided by the speaker of the device 300 and/or by messages or other objects displayed on the display 330.

Additionally, as shown schematically in FIG. 23, the device 300 can include a switch 360 that selectively turns the light source 326 on and off. The switch 360 can be of any suitable type, such as a mechanical switch (e.g., displaceable button, slider, etc.), an electronic switch, and the like. Furthermore, the switch 360 can automatically turn the light source 326 on and off in response to other events. For instance, the light source 326 can turn on automatically when the device 300 is powered up. Also, the light source 326 can be operably coupled to an ambient light sensor 344, such as a photocell or other similar device, and when ambient light levels are below a predetermined limit, the switch 360 can automatically illuminate the light source 326. In still other embodiments, the light source 326 can automatically illuminate upon insertion of the test element 304 into the access port 316. The switch 360 can be designed such that the device 300 can conserve energy.

Figure 24:
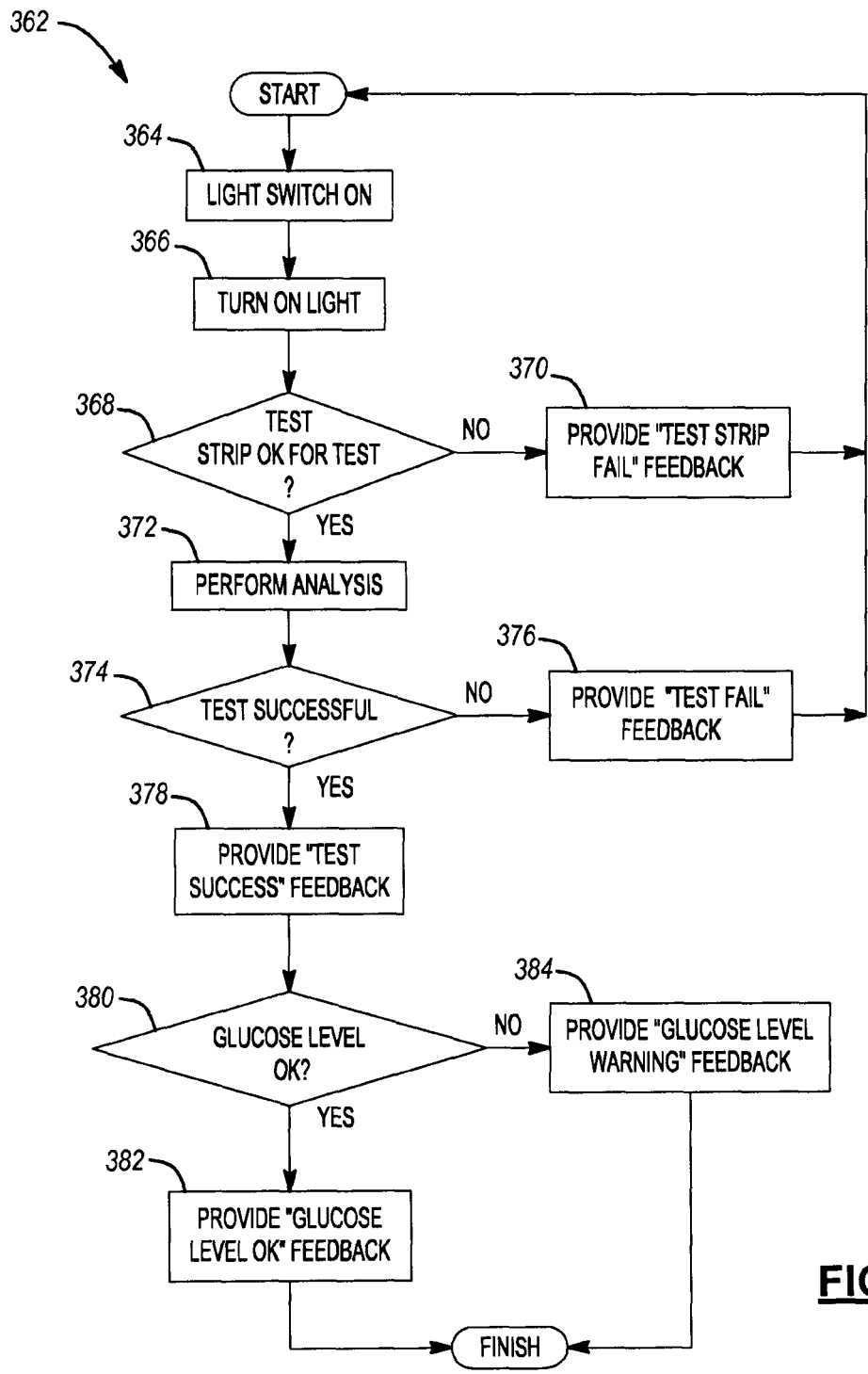
FIG. 24 is a flow chart illustrating a method of operation of the handheld diabetes managing device according to various exemplary embodiments.

Referring now to FIG. 24, a method 362 of operating the light pipe 332 of the device 300 is illustrated according to various exemplary embodiments. As shown, the method 362 can begin at block 364, wherein the switch 360 is changed from OFF to ON. As discussed above, the switch 360 can automatically and/or manually turn ON. The method 362 continues in block 366, wherein the light source 326 begins to illuminate.

Then, in decision block 368, it is determined whether the test element 304 is satisfactory for performing the glucose analysis. For instance, if the test element 304 is inserted improperly, if the test element 304 is defective, etc. (decision block 368 answered negatively), then block 370 follows. In block 370, the control processor 324 causes the light source 326 to provide a "test strip fail" feedback signal. As mentioned above, this feedback signal can be a change in color, illumination pattern, etc., informing the user that the test element 304 needs to be replaced before the analysis can be performed. Subsequently, the method 362 can restart until a new test element 304 is replaced and is satisfactory for performing the analysis.

If there is no problem with the test element 304 (decision block 368 answered affirmatively), then the glucose analysis can be performed in block 372. As mentioned above, the light from the light pipe can illuminate and distinguish the dosing area 302 of the test element 304 to help guide the user, even in low ambient light conditions.

Next, in decision block 374, it is determined whether the measurement engine 328 has successfully analyzed the blood on the test element 304. If not (decision block 374 answered negatively), then block 376 follows, and the control processor 324 causes the light source 326 to provide a "test fail" feedback signal. This signal can be different (e.g., in light color, light pattern, etc.) from the signal provided in block 370. Subsequently, the method 362 can restart until the test is performed successfully.

However, if the test is successful (decision block 374 answered affirmatively), then the control processor 324 can cause the light source 326 to provide a "test success" feedback signal in block 378. Again, this signal can be different than the other feedback signals discussed above.

Subsequently, in decision block 380, it can be determined whether the detected glucose level is within a satisfactory range. If the glucose level is within this range (decision block 380 answered affirmatively), then a "satisfactory" feedback signal can be output in block 382. This feedback signal can be different than each of the feedback signals discussed above in blocks 370 and 376. Moreover, if the detected glucose is either above or below this satisfactory range (decision block 380 answered negatively) one or more feedback signals can be provided at block 384. It will be appreciated that a "high detected glucose level" feedback signal can provided if the detected glucose level is above the satisfactory range, and a "low detected glucose level" feedback signal can be provided if the detected level is below the satisfactory range. The "high" and "low" feedback signals can be different from each other and can be different from each of the other feedback signals of blocks 370, 376, and 382.

Thus, the light pipe 332 and associated components of the device 300 can assist the user in performing analyses, especially in low ambient light conditions. Furthermore, the device 300 can provide various types of feedback to further assist the user.

Figure 25:
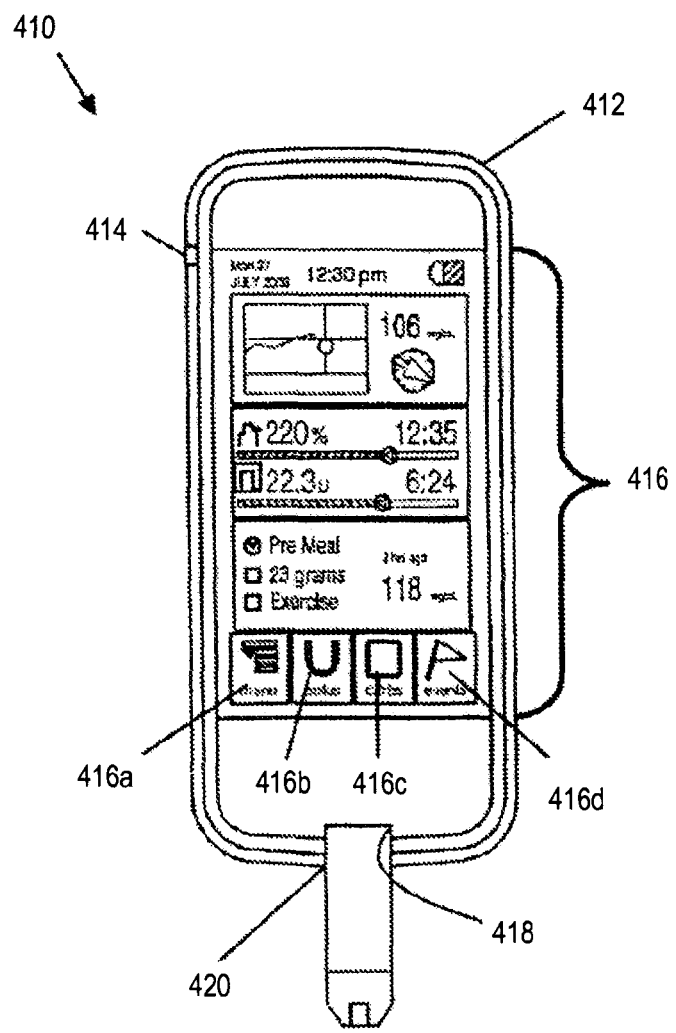
FIG. 25 is a perspective view of one embodiment of a handheld diabetes bG management device in accordance with the present disclosure.

Handheld Diabetes Management Device for Obtaining Three Day Blood Glucose Profile Referring to FIG. 25, there is shown a high level drawing of one embodiment of a handheld, portable blood glucose (bG) monitoring device 410 that may be used by a user in obtaining a three day bG profile. The device 410 can include a housing 412 that may contain one or more user actuatable unit control switches 414 (e.g., ON/OFF), a color (or black and white) touchscreen display 416, and a port 418 into which a bG test strip 420 may be inserted. The display 416 may display user selectable options for allowing the user to access a software driven menu 416a of a software module stored in the device 410 so that the user can make various selections while initiating, carrying out or concluding the 3 day bG profile. A menu selection 416b allows the user to enter bolus information, while a selection 416c enables the user to enter carbohydrate information for snacks or meals. A selection 416d allows the user to enter information pertaining to events (e.g., meals, exercise, periods of stress, etc.) that may affect the user's bG measurement being read by the device 410. Although the display 416 will be described herein as a color touchscreen display, it will be appreciated that any other suitable form of display may be incorporated (e.g., LED, LCD, etc.). If a touchscreen display is not used, the user control switches 414 may need to include specific buttons or controls by which the user is able to select various options and input markers needed to carry out the three day bG profile test. It will be appreciated that the above is a high level description of the device 410, and in practice the device may include additional controls, input ports, output ports, etc., as may be desired to even further enhance the utility of the device 410 or its use with other components and devices (e.g., laptop computers, infusion pumps, etc.). Accordingly, the above description of the device 410 should not be taken as limiting its construction or features in any way.

Figure 26:
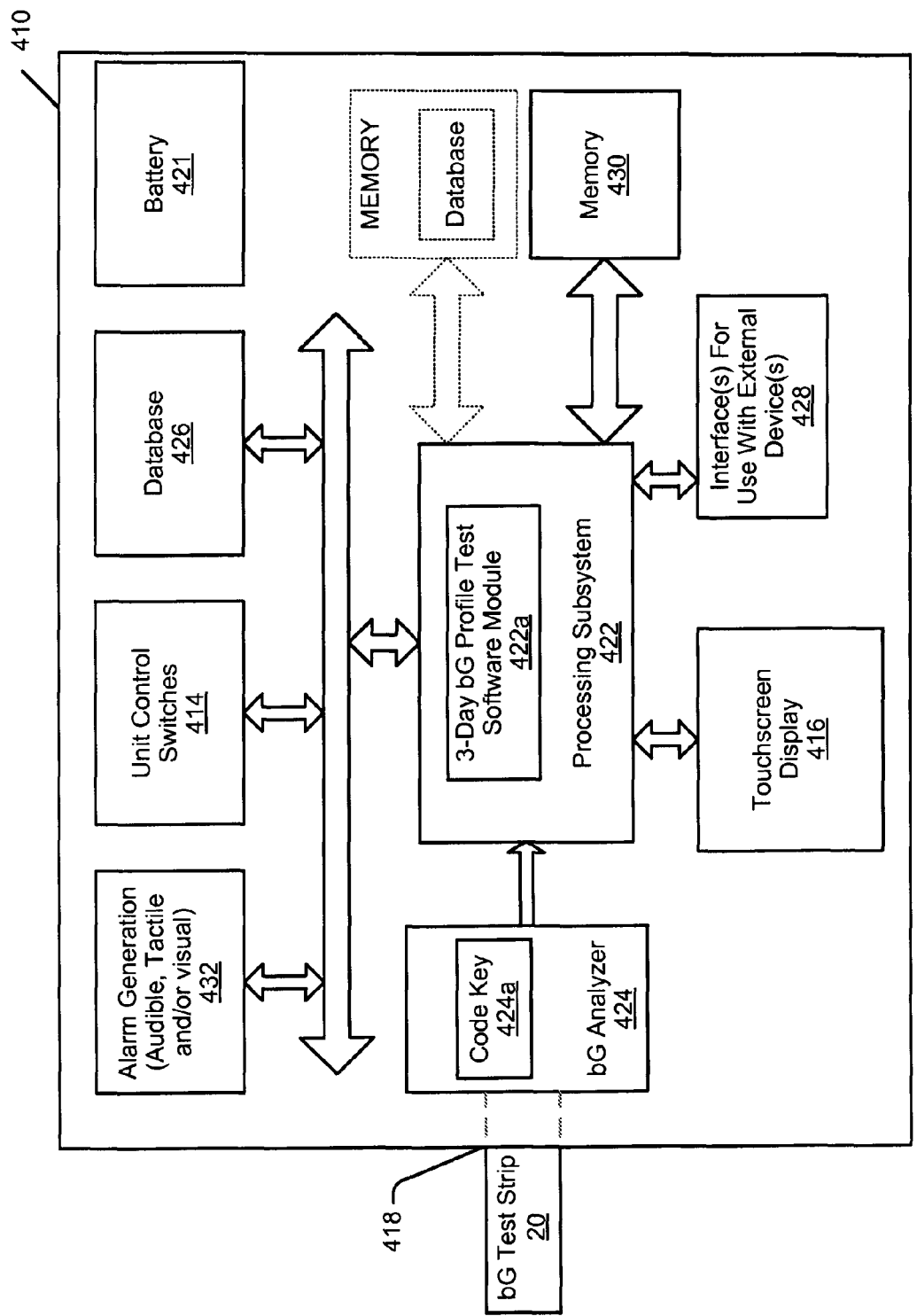
FIG. 26 is a high level block diagram of various components and subsystems that may be incorporated in the device shown in FIG. 25.

Referring to FIG. 26, a high level block diagram of the device 410 is shown. The device 410 may include a suitable rechargeable battery 421 for powering all the electronic components of the device 410. A processing subsystem 422 (e.g., a microprocessor based subsystem) receives information from a bG analyzer 424. The bG analyzer 424 is located adjacent the port 418 of the housing 412 to permit the bG analyzer 424 to read the bG test strip 420. The bG analyzer 424 may include a code key 424a that includes calibration for the bG test strip 420 being read. The processing subsystem 422 may also be in communication with a database 426, which may form a relational database, which is used to store bG test values obtained from the bG analyzer 424. The processing subsystem 422 may also be in contact with the display 416, the user control switches 414, and one or interfaces 428 for interfacing the device 410 to other external devices. The processing subsystem 422 may also be in communication with a memory 430 for storing various types of information (e.g., meal times) that are input by the user, as well as any other information requiring temporary or permanent storage. However, it will be appreciated that the database 426 and the memory 430 could be implemented in a single memory device (e.g., RAM) if desired, as indicated in phantom in FIG. 26. Finally the processing subsystem 422 may be in communication with an alarm generation subsystem 432 that may be used to generate an alarm consisting of audible signals, tactile signals (e.g., a vibration signal) or even possibly visual signals such as illuminated lights (e.g., LEDs) on the device 410.

The device 410 may be used to implement a non-transitory machine readable code, for example a software module 422a, that is run by the processing subsystem 422. The processing subsystem 422, working in connection with the software module 422a, initiates and controls the operation of a three day bG profile test, and may present the collected bG test value data obtained during the test in various forms on the display 416. The device 410 significantly enhances the convenience and ease to the user in carrying out a three day bG profile test, which hereinbefore has been required to be performed by the user by manually recording bG test information before and after meals on a paper chart with a suitable writing implement, such as a pen or pencil. By using the device 410, the three day bG profile may be automated to eliminate the need for the user to use a paper chart to manually record the bG test data. Automating the operations required to construct a three day bG profile also enables a significant number of highly desirable features to be implemented, such as reminding the user at the appropriate times of the day of the need to obtain and enter bG test information, as well as to organize and segregate the bG test results so that only those bG tests that are obtained at predetermined times throughout a three day window, and marked accordingly by the user, are used in compiling and presenting the results of the test. The device 410 may reduce the likelihood that a user forgets to obtain a bG reading at a required time or does not obtain a required number of bG test values in a given day to enable successful completion of a valid three day bG profile test.

To set up a three day bG profile test the user may select this option by navigating through various menu items that are displayed and selected through the "Menu" control 416a on touchscreen display 416. The user may select a typical breakfast time, a typical lunch time, a typical dinner time, and a typical bed time, and input these times into the device 410 via the touchscreen display 416. These times may be stored in the memory 430 or alternatively in the database 426. The user may also input a snack "threshold" (e.g., carbohydrate threshold) using the touchscreen display 416, which is also stored in the memory 430 (or possibly the database 426), to distinguish snacks from meals. A bG test result that accompanies a carbohydrate entry that is below the set snack threshold is marked and stored by the processing subsystem 422 as a "snack" rather than as a "meal". A carbohydrate entry above the set snack threshold may be marked by the device 410 as a meal. The touchscreen display 416 may also be used to allow the user to enter bG markers that designate whether an obtained bG test value is preprandial (i.e., pre-meal), postprandial (i.e., post-meal), or bedtime.

The software module 422a provides predetermined "acceptance" time windows of varying lengths during which bG test values must be entered by the user for the bG values to be included in the three day bG profile. In one embodiment the software module 422a implements acceptance time windows for user provided preprandial bG test values within two hours of the user typical breakfast, lunch and dinner meal times. The bedtime acceptance time window may be set to within two hours of the user typical bedtime. The postprandial acceptance time windows may be set to begin ninety minutes after each of the actual breakfast, lunch and dinner times. While the above described acceptance time windows may be varied through programming modifications to the software module 422a, it is preferred that the user not be able to directly edit or alter the preprandial, bedtime and postprandial acceptance time windows during the course of an active three day profile test. Maintaining these predetermined acceptance time windows at the above described durations helps to ensure consistency for pattern recognition Identification, especially of postprandial excursions, should demonstrate lower glucose variability when the relative measurement time (e.g., 90 to 150 min) is enforced. Likewise, long-acting insulin is expected to be delivered at about the same time every day. Helping to support a more uniform basal insulin dosing time should reduce fasting blood glucose variability.

When the user inserts a bG test trip into the port 418 of the device 410, the bG analyzer 424 reads the test strip and provides a bG test value and an associated time stamp to the processing subsystem 422 that identifies precisely when the bG test value was obtained. If only a single acceptance time window is open at this time, and the acceptance window is one relating to a preprandial, postprandial, or bedtime acceptance time window, then the bG test value qualifies for inclusion in the three day bG profile test and may be automatically stored in the database 426 by the processing subsystem 422. If more than one acceptance time window is open at this time, the processing subsystem 422 will provide a query on the display 416 asking the user to specify the label for the bG value. The display 416 may show selection boxes for the specific preprandial, postprandial, or bedtime event that the user may select simply by touching the appropriate selection on the display 416. This is a significant feature of the device 410 as it automatically detects the occurrence of two or more overlapping acceptance time windows and automatically provides the required message to the user to positively identify which type of event that the just-obtained bG test value is associated with. It will also be appreciated that it is a significant advantage of the device 410 that the user is able to select among overlapping time windows. This provides significant flexibility to the user in the event that the user has one or more meal times that may occasionally overlap. For example, if the user has a job that requires traveling between multiple locations and meetings before or after lunch, there may be times when the user needs to take an early lunch or a late lunch. Allowing the user to configure the device so that two acceptance windows (e.g., post-breakfast and pre-lunch) overlap slightly permits the user to accommodate those situations where the user needs to take an early or late meal because of her/his work schedule. Importantly, since the device 410 is able to recognize this situation, the user will automatically be alerted when two overlapping acceptance time windows happen to be open simultaneously, and the user provided with an opportunity to label a specific bG test value in accordance with its proper event.

Another important feature of the device 410 is that if the user obtains a bG test value outside of one of the predefined acceptance time windows (i.e., while no acceptance time window is open) or the user chooses to associate no label, then the device 410 will store the bG test value in the database 426 but will not include it in the three day bG profile results file(s). Thus, this bG test value will still be available to the user or a clinician in evaluating the user's bG history. But importantly the device 410 prevents the bG test value from being used to form a portion of the three day bG profile.

To assist the user in carrying out the three day bG profile, the device 410 may be configured by the user to provide reminders to carry out a bG test for each acceptance time window. The user can optionally be provided with the option to select one of at least three responses to a just-given reminder: "Accept"; "Dismiss"; and "Snooze". It will be understood that the "Accept" and "Dismiss" options could be replaced by a single "OK" or "Close" option with subsequent behavior dependent on the successful completion of a bG test within an acceptance window. In any event, these optional selections may be provided on the display 416 with a check box that the user may select via a touch selection. An "Accept" selection may indicate to the device 410 the user's acknowledgement of the reminder and that the user intends to enter a bG test value within a predetermined number of minutes (e.g., within five minutes). The "Dismiss" selection may allow the user to immediately dismiss the reminder, and all potential follow up reminders, for that particular acceptance time window. The user selecting the "Snooze" option in response to a generated reminder may signal to the processing subsystem 422 to repeat the reminder if the user does not respond to the reminder. The reminder may be repeated within a predetermined time interval, for example within five minutes, for up to a maximum predetermined number of times (e.g., four times maximum), after which the reminder can be automatically dismissed by the processing subsystem 422 if the user has not responded to any of the generated reminders. If an acceptance time window closes before the maximum number of Snooze reminders are generated, then the Snooze reminders may be automatically discontinued by the processing subsystem 422. If the Snooze reminder feature is incorporated in the device 410, then it is preferred that Snooze reminders for postprandial acceptance time windows be shorter than those presented for preprandial acceptance time windows. For example, postprandial Snooze reminders may occur every five minutes until the acceptance window is no longer available. Preprandial Snooze reminders may be spaced apart longer, for example every fifteen minutes, until a predetermined maximum number (e.g., four) such reminders have been presented. If the user accepts a given Snooze reminder but then does not enter a bG test value before the next Snooze reminder is scheduled to occur, then the next Snooze reminder may automatically be provided by the processing subsystem 422 as long as the current acceptance time window is open. If the currently open acceptance time window closes before the user has labeled a bG test value that matches the reminder for the acceptance window, then any remaining scheduled reminders are automatically cancelled by the processing subsystem 422.

If two acceptance time windows are open and overlapping one another, such as might be the case with a post-breakfast acceptance time window and a pre-lunch acceptance time window, and the user enters a bG test value which he/she has not marked with a specific label (i.e., either "Post-Breakfast" or "Pre-Lunch"), the processing subsystem 422 will prompt the user with a message on the display 416 to identify which one of the acceptance time windows the just-obtained bG test value is for. The user may then select on the touchscreen display 416, a label to be applied to the just-obtained bG test value from the displayed selection options.

It is also preferred that for the duration of a three day bG profile, the postprandial reminders should take precedence over any pre-existing postprandial reminders that the user has previously programmed in the device 410. After the three day bG profile has completed, any previously programmed postprandial bG time reminders may be reinstated by the processing subsystem 422. Also, if a three day bG profile is currently underway, the processing subsystem 422 preferably prevents the user from initiating another three day bG profile. If the user has initiated a three day bG profile and then one or two days later a scheduled subsequent three day bG test comes due to begin, the processing subsystem 422 may notify the user with a message on the display 416 that the current test is about to be terminated and the new, scheduled three day bG profile will be beginning. The software module 422a may include an option that enables the user to reschedule the scheduled three day bG test to a later date. The software module 422a also preferably notifies the user with a message on the touchscreen display 416 that when the 3 day bG profile has been successfully completed or has been terminated before completion.

The processing subsystem 422 and the software module 422a may also provide reminders to the user of user set upcoming medical visits, as well as prompts to conduct/schedule a three day bG profile before the user's next medical visit with a health care professional. The processing subsystem 422 may show a reminder on the display 416 to remind the user within, for example, two weeks of the next scheduled medical visit to conduct a three day bG profile. The processing subsystem 422 may clear the reminder if the user completes a three day bG profile prior to (e.g., three weeks prior to) the next scheduled medical visit. The software module 422a may also be configured with a default rescheduled test date if the user cancels a scheduled three day bG profile, which may, for example, occur on the next calendar day.

The software module 422a may also be configured to store at least one of a preprandial, postprandial, and bedtime bG target ranges specifically for use with the three day bG profile device 410. Such information may be used by the processing subsystem 422 and the software module 422a when showing (e.g., graphing) results of a three day bG profile on the display 416 after a test is completed. Stored default upper and lower limits for each target range may be modified by a user by selecting suitable options from the touchscreen display 416. Also, a postprandial bG excursion of more than a default value, for example more than 50 mg/dL, may be stored and used by the processing subsystem 422 when analyzing the results of a three day bG profile. The software module 422a may also include a default hypoglycemic bG threshold value at or below which any bG value would be recognized as being hypoglycemic. In this instance the hypoglycemic bG value should be below the lower target of any of the bG target ranges.

Figure 27:
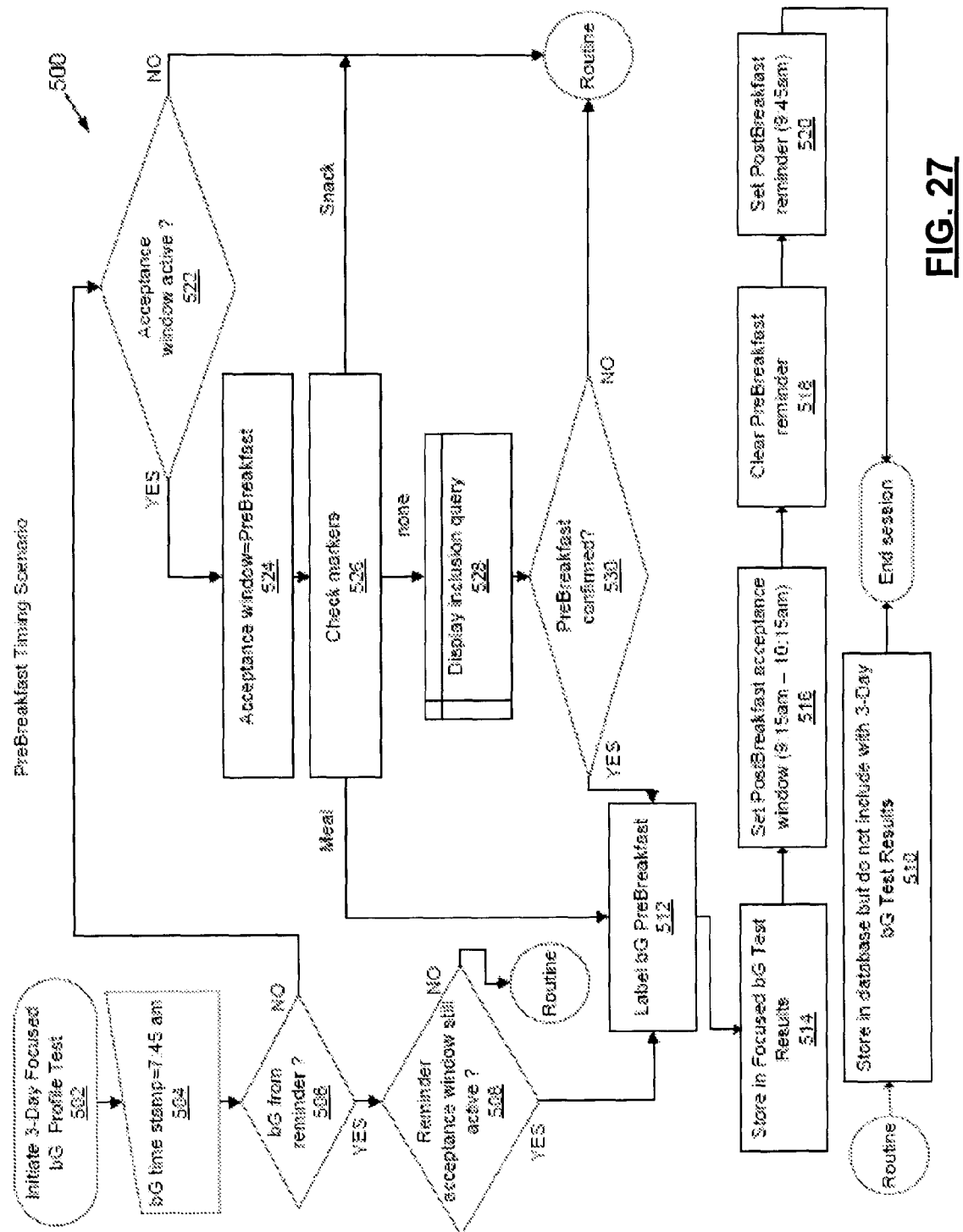
FIG. 27 is a flowchart illustrating an exemplary pre-breakfast (preprandial) timing scenario that may be performed in collecting bG test values pertaining to a pre-breakfast acceptance time window pursuant to obtaining a three day bG profile.

Referring now to FIG. 27, a high level flowchart 500 is shown that illustrates exemplary operations that may be implemented by the software module 422a as it runs on the processing subsystem 422. It will be appreciated that the flowchart of FIG. 27 is merely exemplary and that other operations could be included as well, besides those expressly shown, and that some operations shown in FIG. 27 may be omitted without departing from the general scope of operation described for FIG. 27. Also the order of operations of the flowchart 500 of FIG. 27, as well as the other flowcharts discussed herein, could potentially be altered while still achieving the same end result as that described herein.

At operation 502 a three day bG profile is initiated pursuant to a scheduled start date. At operation 504 the user obtains a bG test sample which is time stamped by the bG analyzer 424 with a time of 7:45 am. At operation 506 the processing subsystem 422 checks if the bG test value with the 7:45 am time stamp was generated in response to a pre-breakfast (i.e., preprandial) reminder. If so, then the processing subsystem 422 may optionally check to see if the reminder acceptance window is still active (i.e., open) at operation 508. If not, the processing subsystem 422 may store the bG test value in the database 426 (or memory 430), as indicated at operation 510, but will not include it in the three day bG profile results. If the answer to the inquiry at operation 508 is "Yes", then the bG test value may be accepted and labeled as a "Pre-breakfast" bG test value at operation 512, and stored in the database 426 (or memory 430) at operation 524 for inclusion in the three day bG profile results.

At operation 526 the Post-breakfast acceptance time window is set and at operation 518 the Pre-breakfast acceptance time window is cleared. The Post-breakfast time reminder is set to be provided at a predetermined time (in this example 9:45 am), as indicated at operation 520, in relation to the user input typical breakfast time.

If the inquiry at operation 506 indicates that a bG test value was not provided pursuant to a reminder then a check is made if any acceptance time window is still active (i.e., open), as indicated at operation 522. If not, then the just-obtained bG test value may be stored in the database 426 (or memory 430), as indicated at operation 510, but will not be included as part of the three day bG profile results. If the inquiry at operation 522 indicates that the current acceptance time window is still open, then at operation 524 the processing subsystem 422 confirms that the Pre-breakfast acceptance time window is still open and then checks to see if the user has entered a marker for the just-obtained bG test value, as indicated at operation 526. If the check at operation 526 indicates that a bG test value has been entered by the user with a marker identifying it as a "meal", then operations 512-520 are repeated. If the check at operation 526 reveals that a marker has been entered by the user for a snack, then operation 510 is repeated so that the bG test value is stored in the database 426 but not used in the results that form the 3 day bG profile. If the check at operation 526 reveals that a bG test value has been entered by the user but without a label, then the processing subsystem 422 displays a query in the display 416 prompting the user to select whether the bG test value entered is a preprandial or postprandial bG test value, as indicated at operation 528. If the bG test value turns out to be a Pre-breakfast bG test value (i.e., preprandial bG value), as determined at operation 530, then operations 512-520 are carried out. If the check at operation 530 indicates that the bG was not labeled as Pre-Breakfast, then operation 510 is carried out to store the bG test value, but it will not be included in the three day bG profile results. It will be appreciated that for simplicity, the instance of having two or more overlapping acceptance time windows has not been included in the example of FIG. 27.

Figure 28:
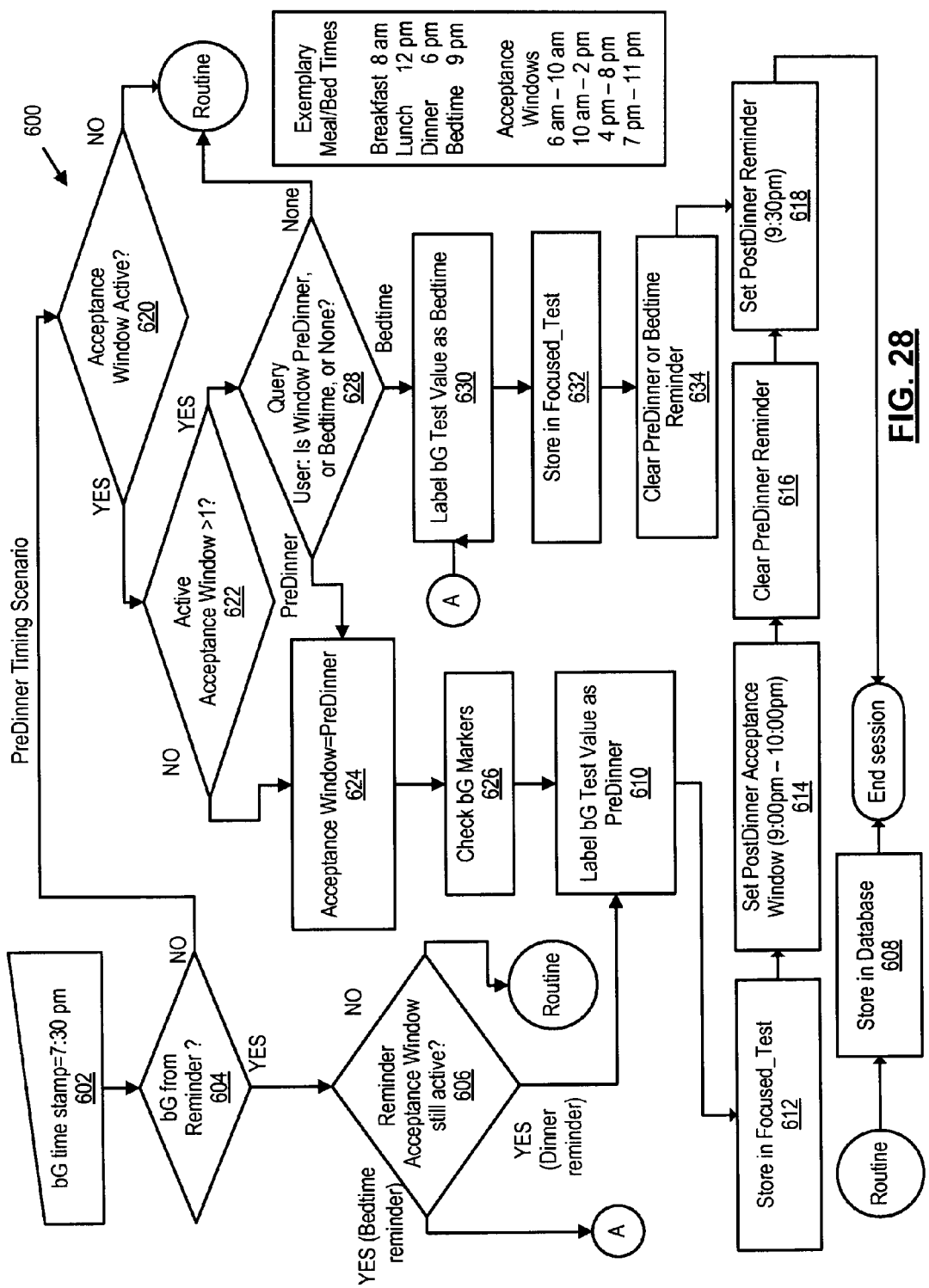
FIG. 28 is a flowchart illustrating an exemplary pre-dinner timing scenario that may be performed in collecting bG test values pertaining to a pre-dinner acceptance time window, pursuant to obtaining a three day bG profile.

Referring to FIG. 28, a flowchart 600 is shown of an exemplary Pre-dinner timing scenario that may be implemented using the device 410. Again, flowchart 600 represents a high level flowchart and additional operations could easily be incorporated as desired, while potentially one or more operations could be eliminated or merged with other operations. The order of operations could also potentially be changed while still achieving the same result as that described before for FIG. 28.

At operation 602 the user provides a bG test sample having a time stamp of 7:30 pm. At operation 604 a check is made to determine if the bG test value has been entered pursuant to a reminder. If so, then at operation 606 a check is made to see if the reminder acceptance window is still open and what type of reminder was given. If no reminder window is still open, then the bG test value may be stored in the relational database 426 at operation 608 but will not be used as part of the test results for the three day bG profile. If the check at operation 606 indicates that the reminder acceptance window for a Pre-dinner reminder is still active, then the bG test value may be automatically labeled as a "Pre-dinner" bG test value at operation 610 and stored in the database 426 at operation 612 as part of the three day bG profile results. If the check at operation 606 reveals that the reminder was associated with a "Bedtime" event, then operations 630-634 may be performed to automatically label the bG test value as a "Bedtime" bG test value, then store the bG test value in the relational database 426, and then clear the previously given reminder. By "reminder acceptance window" it is meant a short time interval, for example five minutes, after a reminder is generated.

At operation 614 the Post-dinner acceptance time window is set. At operation 616 the Pre-dinner reminder is cleared and at operation 618 the Post-dinner reminder is then set to provide the first Post-dinner reminder at 9:30 pm.

Operations 604 and 606, described above, may be optional. But if they are included it means that when the processing subsystem 422 detects that the bG test value is entered within a specific number of minutes of the Pre-dinner reminder being given (e.g., five minutes), then the processing subsystem 422 will simply recognize the bG test value as a Pre-dinner bG test value. This logic will require that the processing subsystem 422 set an additional reminder timer acceptance window when the Pre-dinner acceptance time window is opened, with the additional reminder timer acceptance window being a much shorter duration timer than the timer that is used for the Pre-dinner acceptance time window.

Returning to the flowchart 600 of FIG. 28, if the check at operation 604 indicates that the bG test value was not made during a reminder acceptance window, then a check is made to see if the Pre-dinner acceptance time window is still active, as indicated at operation 620. If not, then the bG test value may be stored at operation 608 but will not be used as part of the test results that form the three day bG profile.

If the check at operation 620 indicates that the Pre-dinner acceptance time window is still active, then a check is made at operation 622 to determine if more than one acceptance time window is currently active. If not, then the processing subsystem 422 determines that the Pre-dinner acceptance time window is the only window currently still active, as indicated at operation 624. A check is then made to determine what label, if any, has been applied by the user to the just-obtained bG test value, as indicated at operation 626. Operation 626 may essentially be the same framework of checks as described above for operations 526, 528 and 530 of FIG. 27. Assuming that operation 626 identifies the bG test value as having a preprandial marker, then operations 610-618 are repeated. If operation 622 indicates that more than one acceptance time window is currently open, then the processing subsystem 422 generates a query on the display 416 at operation 628 requesting the user to identify if the bG test value is a Pre-dinner or bedtime bG test value. This may be a pair of radio selection boxes labeled "Pre-dinner" and "Bedtime" that the user may select using the touchscreen display 416. If the user marks the bG test value as a Pre-dinner bG test value, then operations 624, 626 and 610-618 are repeated. If the user indicates the bG test value is associated with a Bedtime, then the processing subsystem 422 labels the bG test value as a "Bedtime" bG test value, as indicated at operation 630, and then stores it in the database 426, as indicated at operation 632. The Bedtime reminder is then cleared at operation 634.

Figure 29:
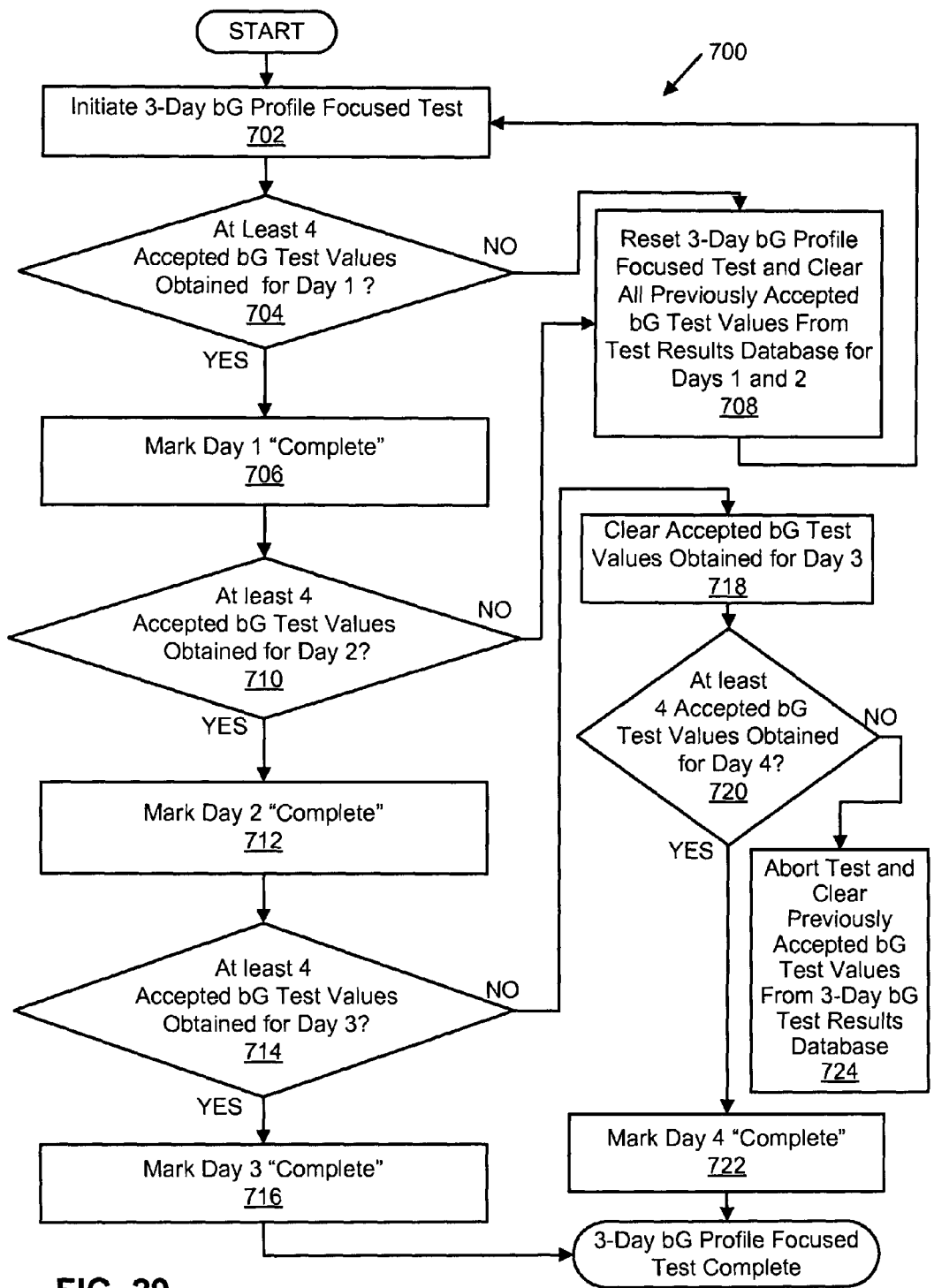
FIG. 29 is a flowchart illustrating exemplary operations that may be implemented by the device in collecting bG test values from a user during a three day bG profile period.

Referring now to FIG. 29, an exemplary high level flowchart 700 is shown that sets forth various operations that may be taken by the processing subsystem 422 in managing the three day bG profile. By "managing" it is meant checking the accumulated bG test values stored in the database 426 at the end of each day to ensure that sufficient bG test samples have been accepted to warrant continuing with the test, clearing previously accepted bG test values if an adequate number of bG values is not obtained on a given day, and potentially restarting the test if needed. At operation 702 the three day bG profile is initiated. At the end of day one the processing subsystem 422 checks to determine if at least four bG test values have been accepted during the preceding twenty four hour period, as indicated at operation 704. If so, then the day one bG test results in the relational database is marked "Complete", as indicated at operation 706. If the check at operation 704 reveals that less than four accepted bG test values were obtained during day one, then the processing subsystem 422 may automatically reset the three day bG profile and clear the previously stored, accepted bG test values from the collection of results being used for the test, as indicated at operation 708. It will be appreciated, however, that the recorded bG test values are not completely erased from the database 426 but rather only that they are deleted from within the database 426 where test results are compiled for the three day bG profile. The three day bG profile is then restarted at operation 702. The processing subsystem 422 preferably provides messages on the touchscreen display 416 that the present test has been cancelled and that a new test is being initiated.

If at least four accepted bG test values are obtained on day one, as indicated at operation 704, then a check is made at the end of day two to determine if at least four accepted bG test values were obtained during the twenty four hour period comprising day two, as indicated at operation 710. If the check at operation 710 indicates that at least four accepted bG test values were recorded during day two, then the database entries for the accepted day two bG test values is marked "Complete" by the processing subsystem 422, as indicated at operation 712. If the check at operation 710 indicates that fewer than four accepted bG test values were recorded during the twenty four hour period for day two, then operation 708 is repeated to clear all of the previously accepted bG test values recorded for days one and two, and the currently underway test is aborted and restarted at operation 702. Again, the bG test values recorded in the database 426 for days one and two are not completely erased from the database 426, but rather only erased from the specific file (or files) that are holding bG test values for use in the three day bG profile.

If at least four accepted bG test values are obtained during day two, then the accepted day two bG test values are marked "Complete" (operation 712), and the processing subsystem 422 will check at the end of the next day (i.e., day three) to see if at least four accepted bG test values have been recorded, as indicated at operation 714. If so, then the day three recorded bG test values in the database 426 are marked "Complete", as indicated at operation 716, and the three day bG profile is concluded. A message informing the user of the successful completion of the test may be displayed on the touchscreen display 416. If the check at operation 714 indicates that fewer than four accepted bG test values were obtained during the twenty four hour period comprising day three, then at operation 718 the processing subsystem 422 clears the previously recorded, accepted bG test values obtained for day three only from the database 426 where these values are being recorded for the three day bG profile. The processing subsystem 422 then continues carrying out the three day bG profile during the subsequent day (i.e., day four), as indicated at operation 720. At the end of day four a check is made to determine if at least four accepted bG test samples have been obtained, as indicated at operation 720. If so, then the day four database entries are marked "Complete", as indicated at operation 722, and the three day bG profile is concluded. If the check at operation 720 indicates that fewer than four accepted bG test samples were obtained during the twenty four hour period comprising day four, then all of the previously accepted bG test samples are cleared from the database 426 where the three day bG profile results have been recorded, and the test is aborted, as indicated at operation 724. A message informing the user of this action may be provided on the touchscreen display 416 along with an option for the user to restart the test on the following day or to reschedule the test for a later date. Again, the stored bG values are not deleted entirely from the database 426, but only from the test results recorded for purposes of collecting test data for the three day bG profile.

It will be appreciated that the results of a given three day bG profile may be stored indefinitely in the device 410, or stored for a fixed number of three day profile tests, or stored for a predetermined time period before being automatically erased by the processing subsystem 422. The test results may be presented in a graphical format along with the predefined bG target ranges. If the touchscreen display 416 is a color touchscreen display, this enables various colors to be used to highlight the bG target ranges. Any bG excursions for a given one of the accepted bG test values plotted on a graph may also be identified with a different color. The interface 428 (FIG. 25) enables the stored test results to be downloaded by a health care professional onto a different medium (e.g., laptop or desktop computer) for use by the professional and/or made a part of a permanent electronic health record for the user.

In one aspect the present disclosure relates to a method for managing three day profile blood glucose (bG) measurements provided by a user on a handheld diabetes management device. The method can comprise configuring a database of the device to store a plurality of bG test values input by a user for each day of a three day test period, wherein bG test values are required to be provided by the user in accordance with a predetermined plurality of differing acceptance time windows during each day of the three day test period. A processing subsystem of the device can be used to receive bG test values provided by the user and to store the bG test values in the database of the device. The method allows two acceptance time windows to be opened at the same time, and if a given bG test value is obtained during such a condition, then the user is allowed to select which one of the open acceptance time windows to associate the given bG test value with. The processing subsystem can be used to determine if at least a predetermined minimum plurality of the stored bG test values has been provided by the user during the predetermined plurality of differing acceptance time windows for each day of the three day test period. If so, the processing subsystem can accept the bG test values for the purpose of compiling results for a three day bG profile. The method can further comprise using a display of the device to display the results of the three day bG profile. Furthermore, the three day test period during which the bG test values are provided to the processing subsystem can require at least the predetermined minimum plurality of the bG test values to have been provided by the user during the predetermined plurality of differing acceptance time windows during both of first and second successive days that form the three day test period. Still further, the processing subsystem can be configured to abort a collection of the bG test values and restart the three day test period if at least the predetermined minimum plurality of bG test values is not provided during a first day of the three day test period. Still further, the processing subsystem can remove a collection of the bG test values, from a file of the database, that were obtained during the first and second days of the three day test period, if the predetermined minimum plurality of bG test values is provided during a first day of the three day test period but not during the second day of the three day test period. Moreover, the predetermined plurality of differing time acceptance windows can comprise seven different acceptance time windows each having a predetermined duration. Furthermore, the seven different acceptance time windows can comprise: a pre-breakfast meal acceptance time window with a user selected breakfast time input to the processing subsystem by the user; a post-breakfast meal acceptance time window; a pre-lunch meal acceptance time window; with a user selected lunch time input to the processing subsystem by the user; a post-lunch meal acceptance time window; a pre-dinner meal acceptance time window with a user selected dinner time input to the processing subsystem by the user; a post-dinner meal time acceptance window; and a pre-bedtime meal acceptance time window with a user selected bed time input to the processing subsystem. Furthermore, the processing subsystem can be used to cause the device to generate one of a tactile and audible reminder, at each one of the predetermined plurality of differing acceptance time windows, to alert the user to conduct a bG test in accordance with a specific one of the acceptance time windows. Still further, the processing subsystem can be used to receive information from the user designating a bG test value being input to the device, wherein the bG test value relates to a snack or a meal, and wherein the device only uses bG test values that correspond to a meal. Moreover, the processing subsystem can recognize that at least two of the predetermined plurality of differing acceptance time windows overlap relative to a user set meal time, and the processing system can prompt the device to query the user to define whether a given bG test value input by the user corresponds is a preprandial bG test value or a postprandial test value, and the processing subsystem can generate a plurality of selection choices on a display of the device that allows the user to specify whether the given bG test value is a preprandial bG test value or a postprandial bG test value. Still further, the display can be implemented as a touchscreen display, and the selection choices can comprise choices that are presented on the touchscreen for selection by the user.

In another aspect the present disclosure relates to a non-transitory, computer readable medium. The computer readable medium is adapted to run on a processing subsystem of a handheld diabetes device for managing three day profile blood glucose (bG) measurements input by a user to the device. The computer readable medium can comprise a database that stores a plurality of bG test values input to the device by a user for each day of a three day test period. The bG test values can be provided by the user in accordance with a predetermined plurality of differing acceptance time windows during each day of the three day test period. The computer readable medium is adapted to determine if at least a predetermined minimum plurality of the stored bG test values has been accepted during the predetermined plurality of differing acceptance time windows for each day of the three day test period. If so, the accepted bG test values are used as test results for a three day bG profile. The computer readable medium is also able to determine if the first two days of the three day test period each have the minimum plurality of the stored bG test values obtained therefore, and that the third day does not, and then enables the test to continue on a successive fourth day following the third day in an attempt to successfully complete the three day test period. The test results are sent to a display of the device for display to the user. The non-transitory, computer readable medium can be adapted to determine if the bG test values input to the device by the user have been provided during the predetermined plurality of differing acceptance time windows during both of first and second successive days that form the three day test period. Still further, the predetermined plurality of differing acceptance time windows can be implemented in accordance with seven different acceptance time windows over a twenty four hour period, with each one of the seven different acceptance time windows having a predetermined time duration. The processing subsystem can also be used to analyze a marker for each of the bG test values that is provided by the user, and further can allow only specific ones of those bG test values to be used for the three day profile that: have been marked by the user as corresponding to a meal; and that have been input by the user during ones of the predetermined plurality of differing acceptance time windows.

In another aspect the present disclosure relates to a system for managing three day profile blood glucose (bG) measurements provided by a user. The system can comprise a handheld diabetes management device. The device can include a database for storing bG values input to the device by a user for each day of a three day test period. The device can also include a processing subsystem in communication with the database. The processing system can be configured to perform several operations: to generate a plurality of acceptance time windows for a twenty four hour period; to analyze the bG test values stored in the database during each twenty four hour period for each day over a three day period; to determine whether each of the stored bG test values corresponds to a meal; to accept only ones of the bG test values input by the user that correspond to a meal, and that have been input during specific ones of the plurality of acceptance time windows over the three day period; and to use the accepted bG values in generating information relating to test results for a three day bG profile. The system can also determine if a sufficient number of accepted bG test values has been obtained for each of the first and second days of the three day test, but the third day of the test did not, then allowing the user to attempt to complete the test by entering bG test values on a fourth day following the third day of the test. The handheld diabetes management device may further include a display that displays the results of the three day bG profile. The processing subsystem can further be configured to abort the three day test period, and to start a new three day test period, if: at the end of the first day of the three day time test period at least four accepted bG test values have not obtained for the first day; or at the end of the second day of the three day test period at least four accepted bG test values have not been obtained for the second day. If at least four accepted bG test values are obtained during each of the first and second days, and only three or fewer accepted ones of the bG test values are obtained during the third day, the processing subsystem can also be configured to clear the previously accepted bG test values obtained during the third day from a collection of the test results, and to enable bG test values to be input to the device by the user during the fourth day immediately following the third day, and if at least four accepted bG test values are obtained during the fourth day, then the processing subsystem can use the accepted bG test values obtained during the first, second and fourth days to form the three day bG profile results. The predetermined acceptance time windows are implemented by the processing subsystem as seven acceptance time windows throughout a twenty four hour period, and wherein six of the seven acceptance time windows are set in relation to specific meal times input to the device by the user, and a seventh time window is set in relation to a bed time input to the device by the user.

Handheld Diabetes Management Device having Testing in Pairs Blood Glucose Test

Figure 30:
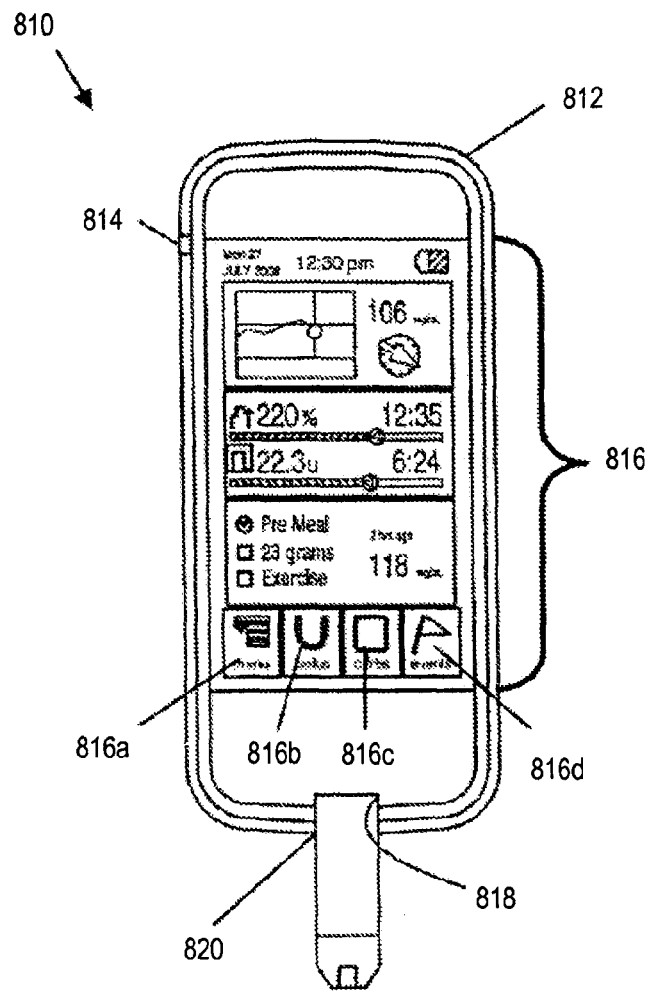
FIG. 30 is a perspective view of one embodiment of a handheld diabetes bG management device in accordance with the present disclosure.

Referring to FIG. 30, there is shown a high level drawing of one embodiment of a handheld, portable blood glucose (bG) monitoring device 810 that can be used in implementing a Testing In Pairs (TIPs) test. Typically the device 810 includes a housing 812 that can contain one or more unit control switches 814 (e.g., ON/OFF), a touchscreen display 816, and a port 818 into which a bG test strip 820 can be inserted. The display 816 can be used in connection with a menu-driven software program that enables a user to access a menu 816a of various selections, such as a selection 816b for allowing the user to enter bolus information, a selection 816c for enabling the user to enter carbohydrate information for snacks or meals, and a selection 816d for allowing the user to enter information pertaining to markers or events (e.g., meals, exercise, periods of stress, etc.) that can affect the user's bG measurement being read by the device 810. Although the display 816 will be described herein as a touchscreen display, it will be appreciated that any other suitable form of display can be incorporated (e.g., LED, etc.). If a touchscreen display is not used, the user control switches 814 may need to include specific buttons or controls by which the user is able to select various options and input markers needed to carry out the TIPs test. It will be appreciated that the above is a high level description of the device 810, and in practice the device can include additional controls, input ports, output ports, etc., as may be desired to even further enhance the utility of the device 810 or its use with other components and devices (e.g., laptop computers, infusion pumps, etc.). Accordingly, the above description of the device 810 should not be taken as limiting its construction or features in any way.

Figure 31:
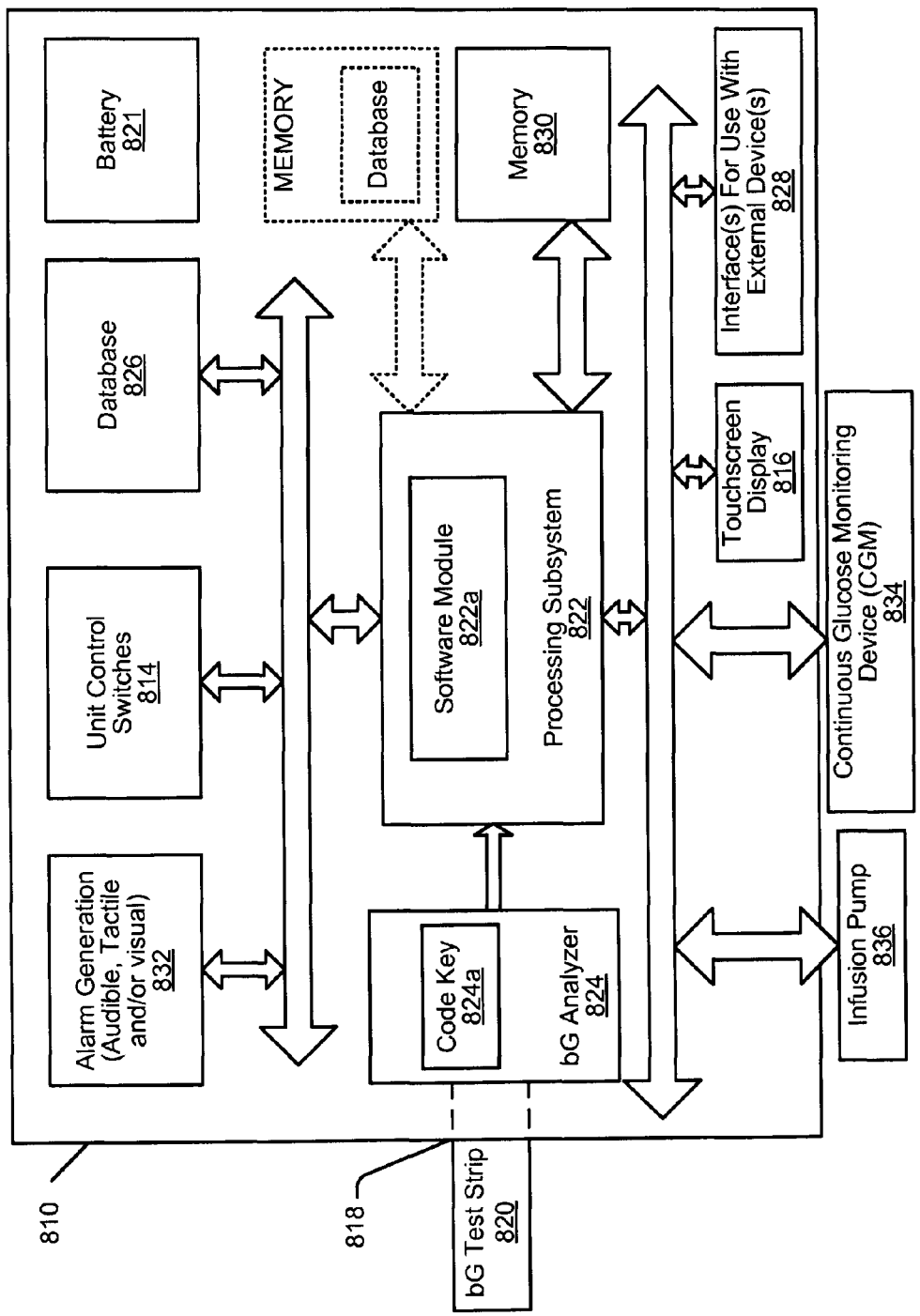
FIG. 31 is a high level block diagram of various components and subsystems that can be incorporated in the device shown in FIG. 30.

Referring to FIG. 31, a high level block diagram of the device 810 is shown. The device 810 can include a rechargeable or non-rechargeable battery 821 for power all the electronic components of the device 810. The device 810 can also include a processing subsystem 822 (e.g., a microprocessor based subsystem) that receives information from a bG analyzer 824. The bG analyzer 824 is in communication with the port 818 of the housing 812 to permit the bG analyzer 824 to read the bG test strip 820. The bG analyzer 824 can include a code key 824a that includes calibration information for the bG test strip 820 being read. The processing subsystem 822 can also be in communication with a database 826, which can be a relational database, that is used to store bG test values obtained from the bG analyzer 824. The processing subsystem 822 can also be in communication with the display 816, the user control switches 814, and one or more interfaces 828 for interfacing the device 810 to other external devices. The processing subsystem 822 can also be in communication with a memory 830 for storing various types of information (e.g., meal times) that are input by the user, as well as any other information requiring temporary or permanent storage. However, it will be appreciated that the database 826 and the memory 830 could be implemented in a single memory device (e.g., RAM) if desired, as indicated in phantom in FIG. 30. The processing subsystem 822 can be in communication with an alarm generation subsystem 832 that can be used to generate reminders to the user consisting of audible signals, tactile signals (e.g., a vibration signal) or even possibly visual signals such as illuminated lights (e.g., LEDs) on the device 810. The processing subsystem 822 can also be in communication with a continuous blood glucose monitoring (CGM) system 834 worn by the user, as well as an insulin infusion pump 836 worn by the user. It will be appreciated that the CGM system 834 and the infusion pump 836 are located remotely from the device 810 and therefore do not form a portion of the device 810.

The device 810 can be used to implement a non-transitory machine readable code, for example a software module 822a, that is run by the processing subsystem 822. The processing subsystem 822, working in connection with the software module 822a, initiates and controls the operation of the TIPs test, and can present the collected TIPs test data obtained in various forms (e.g., charts, graphs, etc.) on the display 816 using one or more colors. The device 810 significantly enhances the convenience and ease to the user in carrying out a TIPs test. Previously, performing a TIPs test has required the user to manually record on a paper chart the bG test information that is obtained before and after meals, and within predetermined acceptance times. By using the device 810, a significant number of highly desirable features can be implemented to remind the user at the appropriate times of the day of the need to obtain and enter bG test values, as well as to organize and segregate the bG test results so that only those bG test results that form the predefined pairs of bG test values are used as related bG pair data for the TIPs results. The device 810 may reduce the likelihood that a user forgets to obtain a bG reading at a required time or otherwise incorrectly manually records bG test data on the paper chart pursuant to performing a TIPs test. The device also eliminates the possibility that the user may forget to carry the paper chart with her/him while travelling during the day, or may not have a writing implement with her/him at the time a bG test result needs to be recorded.

To set up a TIPs test the user can select this option by navigating through various menu items that are displayed and selected through the "Menu" control 816a on touchscreen display 816. The user can select a typical breakfast time, a typical lunch time, a typical dinner time, and a typical bed time, and input these times into the device 810 via the touchscreen display 816. These times can be stored in the memory 830 or alternatively in the database 826. The user can also input a snack "threshold" (e.g., carbohydrate threshold) using the touchscreen display 816, which is also stored in the memory 830 (or possibly the database 826), to distinguish snacks from meals. A bG test result that accompanies a carbohydrate entry that is below the set snack threshold is marked and stored by the processing subsystem 822 as a "Snack" rather than as a "Meal". A carbohydrate entry above the set snack threshold can be marked by the device 810 as a meal. The touchscreen display 816 can also be used to allow the user to enter bG markers (i.e., labels) that designate whether an obtained bG test value is preprandial (i.e., pre-meal) or postprandial (i.e., post-meal).

The software module 822a provides predetermined "acceptance" time windows of varying lengths during which bG test values must be entered by the user for the bG values to be included in the TIPs results. In one embodiment the software module 822a implements acceptance time windows for user provided preprandial bG test values within two hours of the user set meal breakfast, lunch and dinner meal times. The bedtime acceptance time window can be set to within two hours of the user input bedtime. The postprandial acceptance time window can be set to 90-150 minutes after each of the user selected actual meal times. While the above described time windows can be varied through programming modifications to the software module 822a, it is preferred that the user not be able to directly edit or alter the preprandial, bedtime and postprandial acceptance time windows while a test is in progress. Maintaining these predetermined acceptance time windows at the above described durations helps to ensure consistency for pattern recognition. Identification, especially of postprandial excursions, should demonstrate lower glucose variability when the relative measurement time (e.g., 90 to 150 minutes) is enforced. Likewise long-acting insulin is expected to be delivered about the same time every day. Helping to support a more uniform basal insulin dosing time should reduce fasting blood glucose variability.

When the user inserts a bG test trip into the port 818 of the device 810, the bG analyzer 824 reads the test strip and provides a bG test value to the processing subsystem 822. The bG analyzer 824 attaches a bG "time stamp" to the just-obtained bG test value which indicates the time of day that the bG test value was obtained. To assist the user in carrying out the TIPs test, the device 810 can be configured by the user to provide reminders to carry out a bG test during each acceptance time window. The user can optionally be provided with the option to select one of at least three responses to a just-given reminder: "Accept"; "Dismiss"; and "Snooze". It will be understood that the "Accept" and "Dismiss" options could be replaced by a single "OK" or "Close" option with subsequent behavior dependent on the successful completion of a bG test within an acceptance window. In any event, these optional selections may be provided on the display 816 with a check box that the user may select via a touch selection. An "Accept" selection may indicate to the device 810 the user's acknowledgement of the reminder and that the user intends to enter a bG test value within a predetermined number of minutes (e.g., within five minutes). The "Dismiss" selection may allow the user to immediately dismiss the reminder, and all potential follow up reminders, for that particular acceptance time window. The user selecting the "Snooze" option in response to a generated reminder may signal to the processing subsystem 822 to repeat the reminder if the user does not respond to the reminder. The reminder may be repeated within a predetermined time interval, for example within five minutes, for up to a maximum predetermined number of times (e.g., four times maximum), after which the reminder can be automatically dismissed by the processing subsystem 822. If an acceptance time window closes before the maximum number of snooze reminders are generated, then the snooze reminders can be automatically discontinued by the processing subsystem 822 if the user has not responded to any of the reminders. If an acceptance time window closes before the maximum number of Snooze reminders are generated, then the Snooze reminders may be automatically discontinued by the processing subsystem 822. If the Snooze reminder feature is incorporated in the device 810, then it is preferred that Snooze reminders for postprandial acceptance time windows be shorter than those presented for preprandial acceptance time windows. For example, postprandial Snooze reminders may occur every five minutes until the acceptance window is no longer available. Preprandial Snooze reminders may be spaced apart longer, for example every fifteen minutes, until a predetermined maximum number (e.g., four) such reminders have been presented. If the user accepts a given Snooze reminder but then does not enter a bG test value before the next Snooze reminder is scheduled to occur, then the next Snooze reminder may automatically be provided by the processing subsystem 822 as long as the current acceptance time window is open. If the currently open acceptance time window closes before the user has labeled a bG test value that matches the reminder for the acceptance window, then any remaining scheduled reminders are automatically cancelled by the processing subsystem 822.

Figure 32:
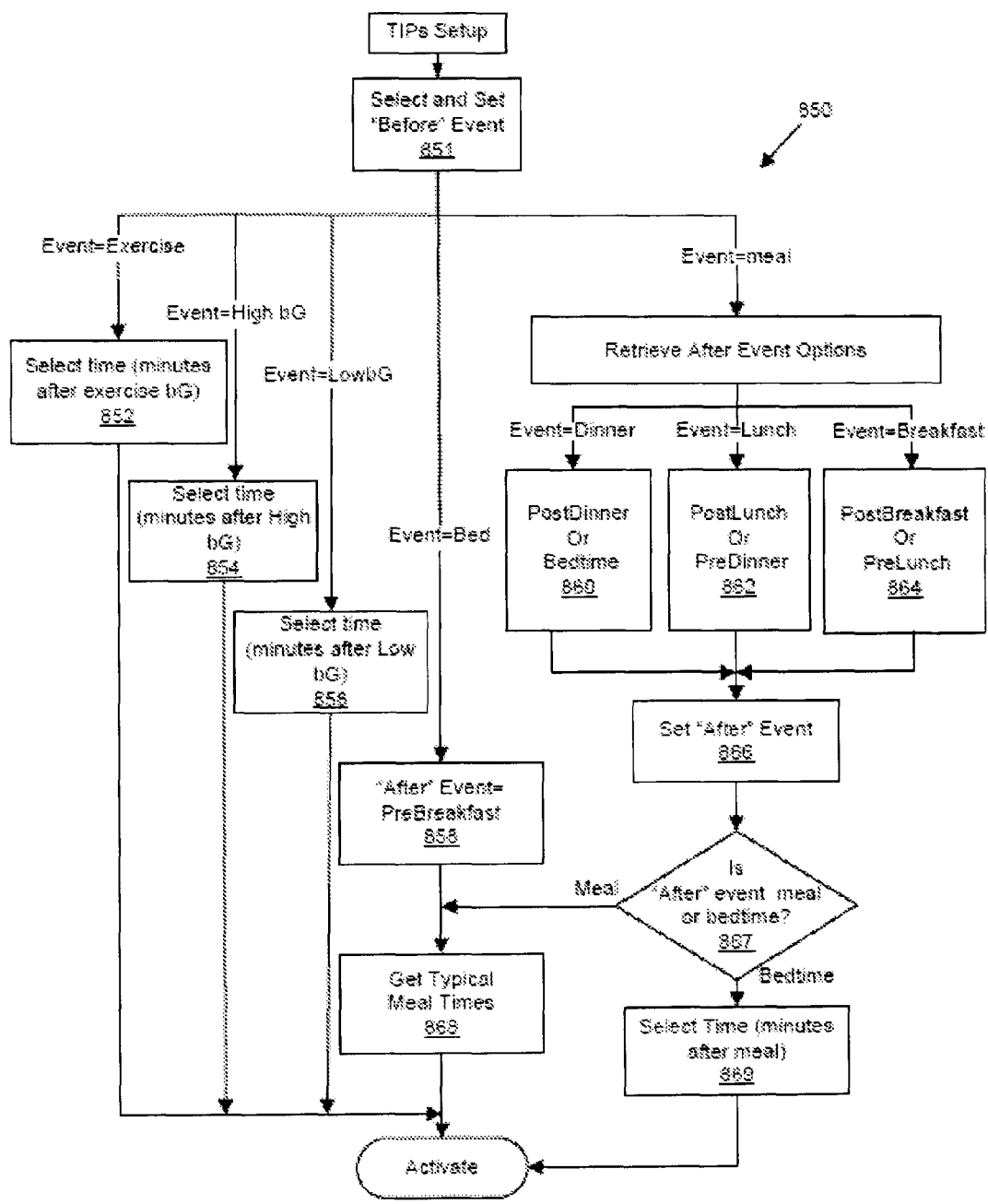
FIG. 32 is an exemplary flowchart of operations that can be performed in setting up a software module of the device to execute a TIPS test.

Referring now to FIG. 32, a flowchart 850 is shown of exemplary operations that can be implemented using the device 810 in configuring the software module 822a of the device to carry out a TIPs test. At operation 851 the user may first select and set a "Before" event. If the Before event is Exercise, initially at operation 852 the user is prompted with a query on the display 816 of the device 810 to select an "After Exercise" time (in minutes) from the exercise bG at which he/she will be prompted to enter an "After Exercise" bG test value during the TIPs test. In one implementation the "After Exercise" time set by the user can vary from thirty minutes to six hours after the user labels the Before Exercise bG test value. The acceptance time window for the user to enter the "After Exercise" bG test value can open thirty minutes before the user selected "After Exercise" time and closes preferably thirty minutes after the user selected "After Exercise" time. However, this acceptance time window could be modified as needed by the system designer, or possibly by even providing additional options to the user in configuring this time window.

If the Before event is High bG, at operation 854 the user also enters on the display 816 a "High bG" time at which an "After" event bG test value can be entered for a "High bG" event. The "High bG" time can be selectable by the user from the display 816 preferably from one hour to six hours after the time stamp for the High bG test value. However, as with the "After Exercise" bG option, this time window could be modified by the system designer. The acceptance window for entering an "After" event bG test value for a "High bG" test result is preferably thirty minutes before the user set "High bG" time to thirty minutes after the user set "High bG" time, although this window could be modified by the system designer to lengthen or shorten it.

If the Before event is Low bG, at operation 856 the user also enters a "Low bG" time at which the user is to be prompted by the device 810 to enter an "After" event bG test value when the user obtains a low bG test value. The "Low bG" time can be five minutes to about thirty minutes after the timestamp for a Low bG test value. The acceptance time window during which the "After" event Low bG test value can be entered can be up to fifteen minutes before the user set "Low bG" time to about fifteen minutes after the user set "Low bG" time. Again, this acceptance time window could be modified by the system designer.

Referring further to FIG. 32, if the event is bedtime, then the "After" event will be a "Pre-breakfast" time (i.e., preprandial time) selected by the user, as indicated at operation 858. This time can be the same as the "Breakfast" time that the user would normally program into the device 810, and can include the same acceptance time window as that provided for the "Breakfast" window. This acceptance time window could be two hours before to two hours after the typical breakfast time.

For a "Dinner" Before event, the "After" event can be selected by the user to be "Post-Dinner" or Bedtime, as indicated at operation 860. The Post-dinner time can preferably be one hour to four hours after the Dinner meal start timestamp, and the acceptance time window can be user set to preferably thirty minutes before the user set Post-meal time to thirty minutes after the user set Post-meal. If the user selects Bedtime as the "After" event, then the acceptance time window will be set according to the user set Bedtime, and will vary, for example, from two hours before the user set Bedtime to two hours after the user set Bedtime.

For a "Lunch Event", the user can select "Post-lunch" or "Pre-dinner as the "After" event, as indicated at operation 862. If the "Post-lunch" option is selected, the acceptance time window and reminders are set in accordance with the postprandial acceptance window, which is preferably centered one to four hours after the Lunch meal timestamp. If the Pre-Dinner option is chosen, then the acceptance window and reminders are chosen according to the time for the next Pre-Dinner acceptance window configured by the user.

For a "Breakfast Event", the user can select either a "Post-Breakfast" or "Pre-Lunch" as the "After" event option, as indicated at operation 864. The acceptance time window for a "Post-breakfast" selection can be, for example, thirty minutes before the user selected Post-meal time to thirty minutes after the user selected Post-meal time. If "Pre-lunch" is selected as the "After" event, then an acceptance time window can be two hours before the user set Pre-lunch time until two hours after the set Pre-lunch time.

The software module 822a then sets the user selected "After" event at operation 866 and then checks to whether the "After" event is a meal or bedtime, or whether the "After" event is a post-meal, as indicated at operation 867. If the "After" event is a meal or bedtime, then the processing subsystem 822 obtains the typical user set meal times, at operation 868. If the "After" event check at operation 867 results in the "After" event being determined to be post-meal, then at operation 869 the user selected time after meal (e.g., one to four hours) is obtained. The software module 822a can then activate the TIPs test when the test is subsequently commanded by the user to start.

Figure 33:
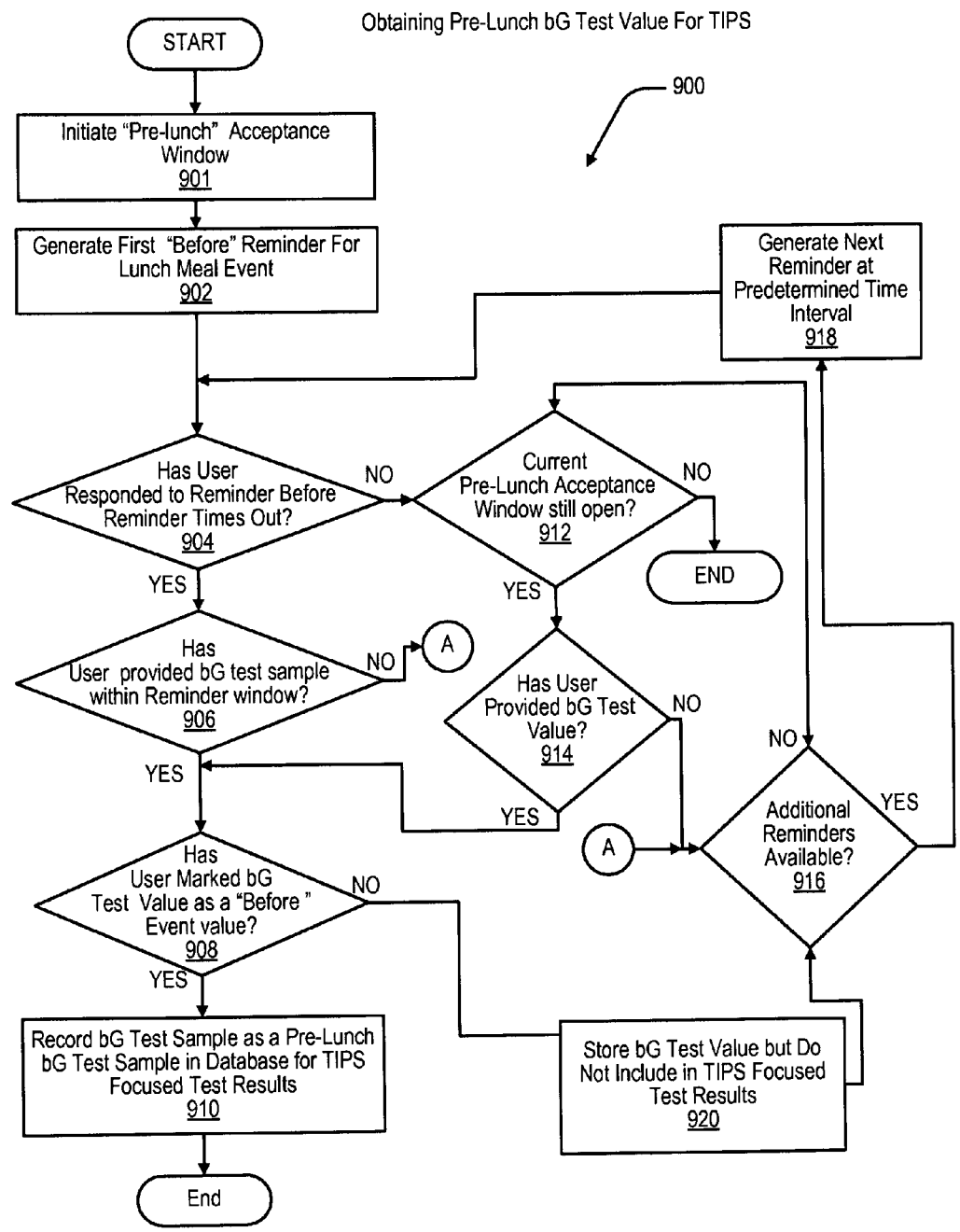
FIG. 33 is an exemplary flowchart of operations that can be performed with the device of FIG. 30 in obtaining a Pre-lunch bG test value from the user.

Referring now to FIG. 33, a flowchart 900 is shown of operations that can be performed using the device 810 and the software module 822a to obtain a Pre-lunch bG test value for the TIPs test. The Pre-lunch meal event acceptance time window is initially opened by the processing subsystem 822, as indicated at operation 901. At operation 902 the device 810 generates the first "Before" reminder for the Lunch meal event. At operation 904 the processing subsystem 822 can check to determine if the user has responded to the reminder before the reminder times out. In this implementation, it will be appreciated that the software module 822a implements a second timer that gives the user a short predetermined time period (e.g., three-five minutes) in which to respond to and accept the reminder, and to perform the requested bG test. If the user accepts the reminder within the short predetermined time period, then at operation 906 the processing subsystem 822 checks to see if the user has entered a time stamped bG test value within the reminder time window. If so, the processing subsystem 822 checks to see if the user has marked (i.e., labeled) the entry as a "Before" event bG entry on the display 816, as indicated at operation 908. If so, then at operation 910 the processing subsystem 822 records the bG test value in the database 826 as a "Before-lunch" bG test value and the Pre-Lunch acceptance window and any pending lunch reminders are closed. If the optional reminder timer is not used, then operations 904 and 906 can be eliminated, and operation 912 would be performed immediately after operation 902. It will also be appreciated that at each opportunity for the user to mark a just-obtained bG test value, the display 816 will display a field where the user may also enter specific notes about the event (e.g., amount of carbohydrates consumed at a given meal). This information will be stored by the processing subsystem 822 together with the related bG test value.

At operation 904, if the user does not accept the reminder before the reminder times out, then at operation 912 the processing subsystem 822 checks to see if the current Pre-lunch acceptance time window is still open. If not, then the user is not permitted to enter a Pre-lunch bG test value for purposes of forming a Lunch Event pair of related bG values for the TIPs test. If the check at operation 912 produces a "Yes" answer, then the processing subsystem 822 checks to determine if the user has provided a time stamped bG test value, as indicated at operation 914. If so, then operation 908 is repeated. If not, then a check is made at operation 916 if additional reminders are available. If so, then the next reminder is generated in accordance with the predetermined time interval (e.g., thirty minutes as in the case of a snoozed reminder), as indicated at operation 918, and operation 904 is repeated. If the check at operation 916 produces a "No" answer, meaning no additional reminders are available, then operation 912 will be repeated.

If the check at operation 908 reveals that the user has not selected the "Before" event (Pre-Lunch) option from the display 816, then at operation 920 the bG test value is stored in the database 826 but is not used for purposes of constructing a related pair of bG test values for the TIPs test.

Figure 34:
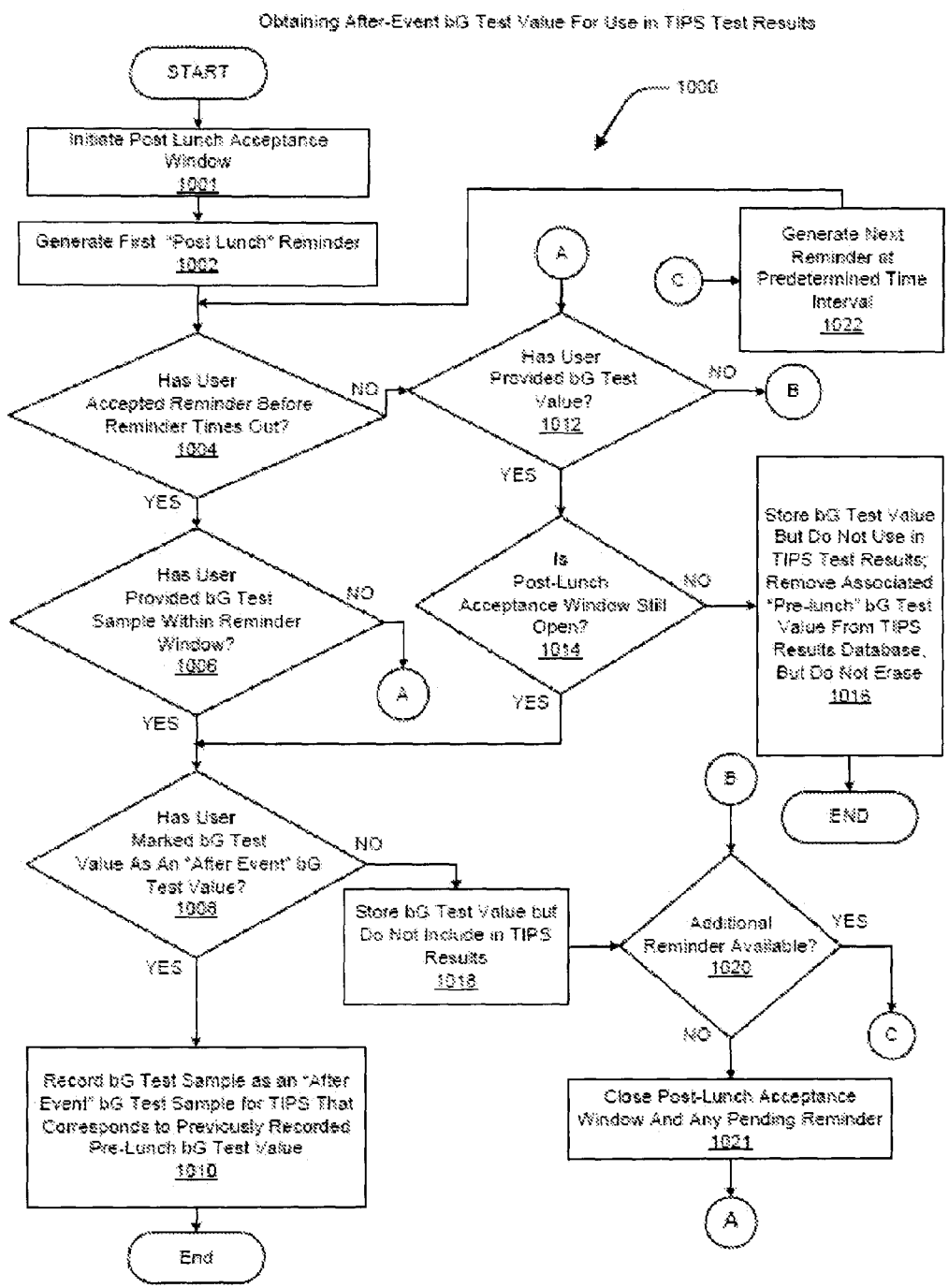
FIG. 34 is an exemplary flowchart of operations that can be performed with the device of FIG. 30 in obtaining a Post-lunch bG test value.

Referring now to FIG. 34, a flowchart 1000 is shown for operations that can be performed in obtaining a Post-lunch bG value. It will be noted that flowchart 1000 is similar in its sequence of operations to flowchart 900 of FIG. 33. At operation 1002 the "Post Lunch" acceptance time window is opened and the first "Post-lunch" reminder is generated. At operation 1004 a check is made by the processing subsystem 822 to determine if the user has responded to the reminder before it times out. If the user has responded, then a check is made at operation 1006 to determine if the user has obtained a time stamped bG test value within the reminder window. If the user has obtained such a bG test value, then a check is made at operation 1008 to determine if the user has marked the bG test value as an "After" event bG test value. If so, the bG test value is stored and used in the TIPs test to form the second one of a pair of bG test values for the Lunch event, as indicated at operation 1010. The Post-Lunch acceptance window and any pending Post-Lunch reminders are closed.

If the check at operation 1004 reveals that the current reminder window has timed out, then a check is made at operation 1012 to determine if the user has provided a bG test value.

If so, then a check is made at operation 1014 to determine if the current acceptance time window is still open. If so, then operation 1008 is repeated. If the check at operation 1014 reveals that the current acceptance window has closed, then the previously recorded bG test value (corresponding to the Pre-Lunch bG test) is deleted from the database 826 where the TIPs results are being collected, as indicated at operation 1016, but the just-recorded bG test value otherwise remains stored in the database 826. If the check at operation 1008 reveals that the user has obtained a bG test value but has not marked it as an "After" event bG test value, then it can be stored in the database 826, as indicated at operation 1018, but it will not be used for the TIPS results. A check will then be made at operation 1020 to see if any additional reminders are available to be presented to the user and, if so, then the next reminder is generated at operation 1022. If no additional reminder is available, then at operation 1021 the Post-lunch acceptance window and any pending reminder are closed, and operation 1012 is then repeated. If the check at operation 1012 reveals that the user has not provided a bG test value after accepting a reminder, then operation 1020 can be repeated.

Figure 35A:
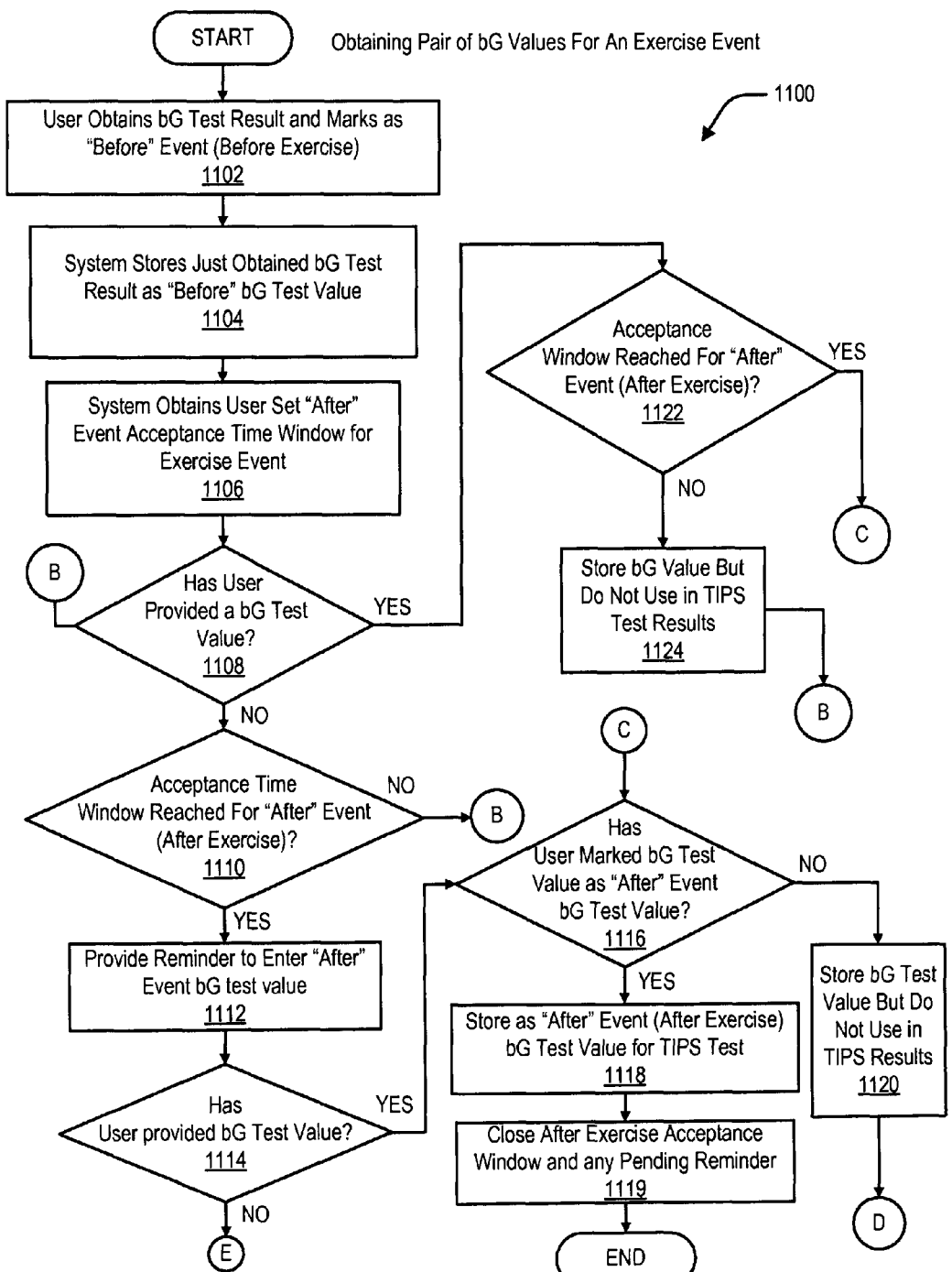
FIGS. 35A and 35B show an exemplary flowchart of operations that can be performed with the device of FIG. 30 in obtaining an "Exercise" bG test value and a Post-exercise bG test value, for the purpose of collecting data for the TIPs test.
Figure 35B:
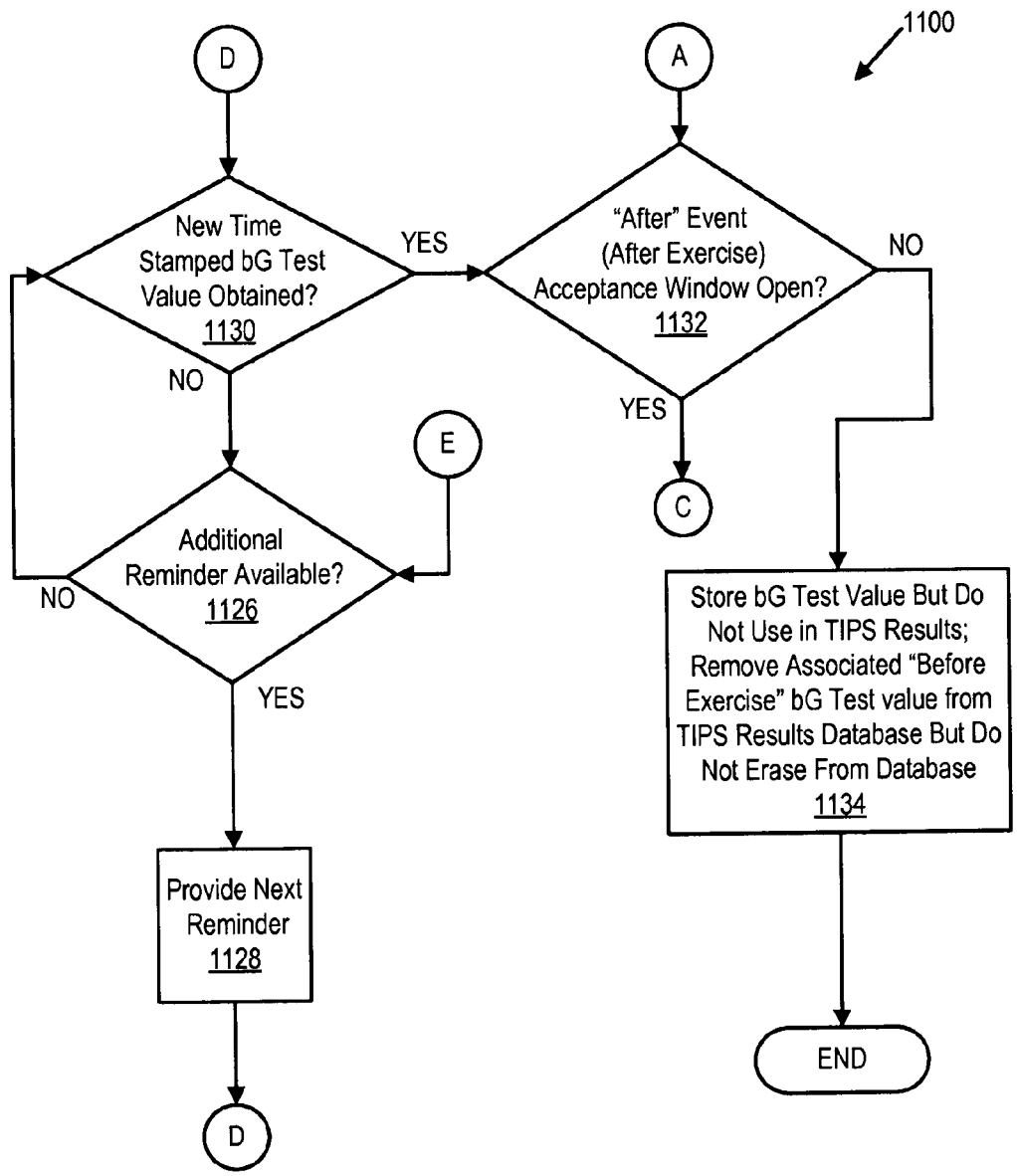

Referring now to FIGS. 35A and 35B, an exemplary flowchart 1100 for obtaining an Exercise bG pair for the TIPs test is shown. At operation 1102 the user can obtain a bG test value before an exercise event, and labels the test value as a "Before Exercise" event. At operation 1104 the device 810 stores the just-obtained bG test value as a Before Event value. At operation 1106 the processing subsystem 822 obtains the user set acceptance time window for an "After Exercise" event. The processing subsystem 822 then checks if the user has provided a bG test value, as indicated at operation 1108. If not, then a check is made if the acceptance time for the Exercise "After" event is now open, as indicated at operation 1110. If the check at operation 1110 returns a "Yes" answer, then the first reminder is provided to the user to enter the "After" event bG test value, as indicated at operation 1112. A check is then made to determine if the user has provided a bG test value, as indicated at operation 1114. If the answer is "Yes", then a check is made to determine if the user has marked the bG test value as an "After" event bG test value, as indicated at operation 1116. If the answer is "Yes", then the bG test value is stored in the database 826 as the "After" event bG test value, as indicated at operation 1118, and used in the TIPs test results. The After exercise acceptance time window and any pending reminder are then closed, as indicated at operation 1119. If the check at operation 1116 returns a "No" answer, then the bG test value is stored in the database 826, as indicated at operation 1120, but it will not be included in the TIPs test results.

If the check at operation 1114 reveals that the user did not provide a response to the first reminder, then a check is made if an additional reminder is available to be provided, as indicated at operation 1126 (FIG. 35B). If the check at operation 1126 indicates that another reminder is available, then at operation 1128 the next reminder is provided to the user at the predetermined reminder time interval.

If the check at operation 1126 indicates that no additional reminders are available to be provided, then a check is made at operation 1130 to determine if the user has entered a new time stamped bG test value. If not, then operation 1126 is repeated. If so, then a check is made to see if the "After" event acceptance time window is still open, as indicated at operation 1132. If the "After" event acceptance time window is no longer open, then the bG test value can be stored in the database but will not be included in the TIPS results, as indicated at operation 1134. The associated "Before" event bG test value will also be removed from the TIPS results but will not be erased from the database 826. If the check at operation 1132 reveals that the acceptance time window is still open, then operation 1116 (FIG. 35A) can be repeated.

Figure 36A:
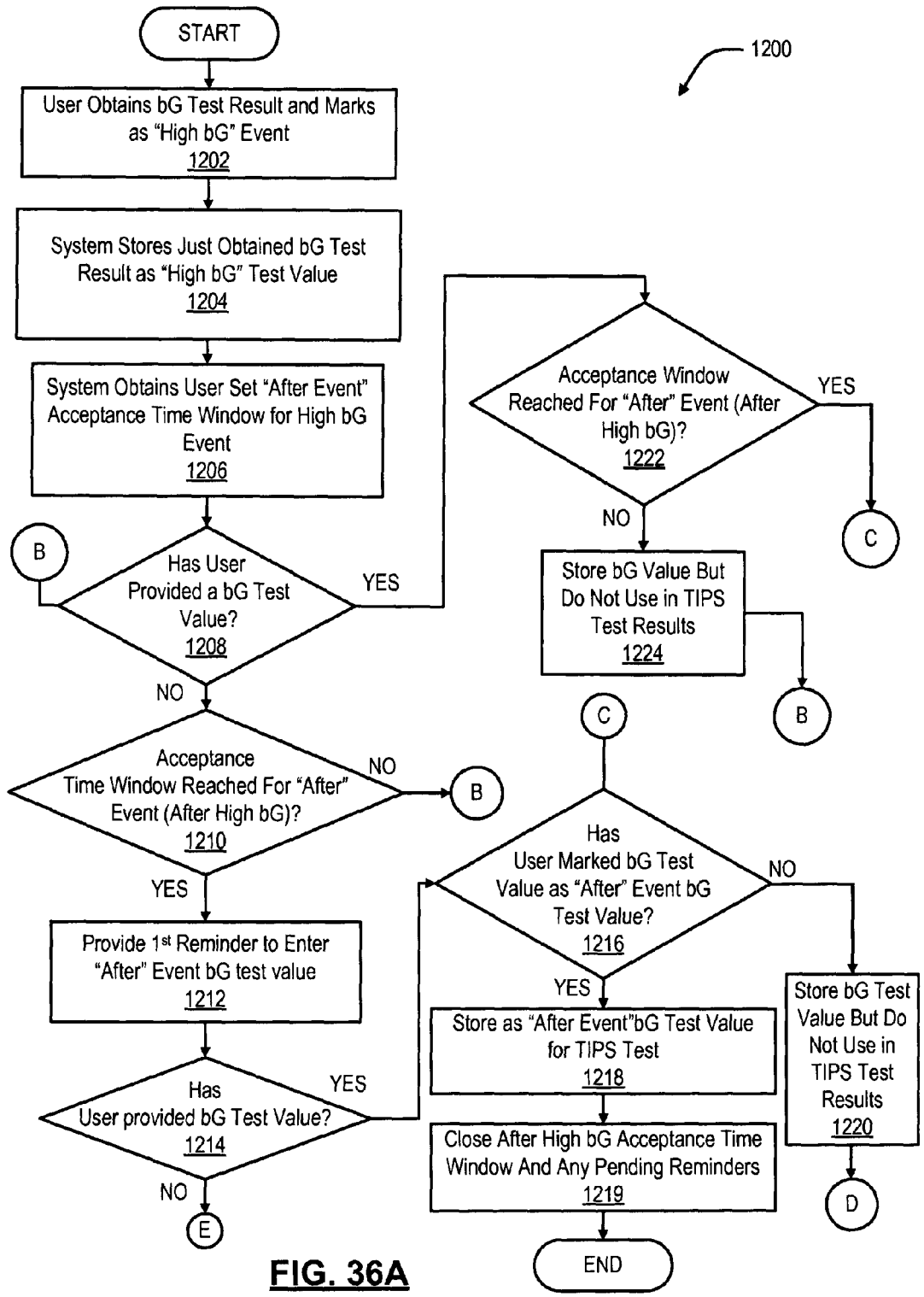
FIGS. 36A and 36B show an exemplary flowchart of operations that can be performed with the device of FIG. 30 in obtaining a High bG pair of test values for the TIPs test.
Figure 36B:
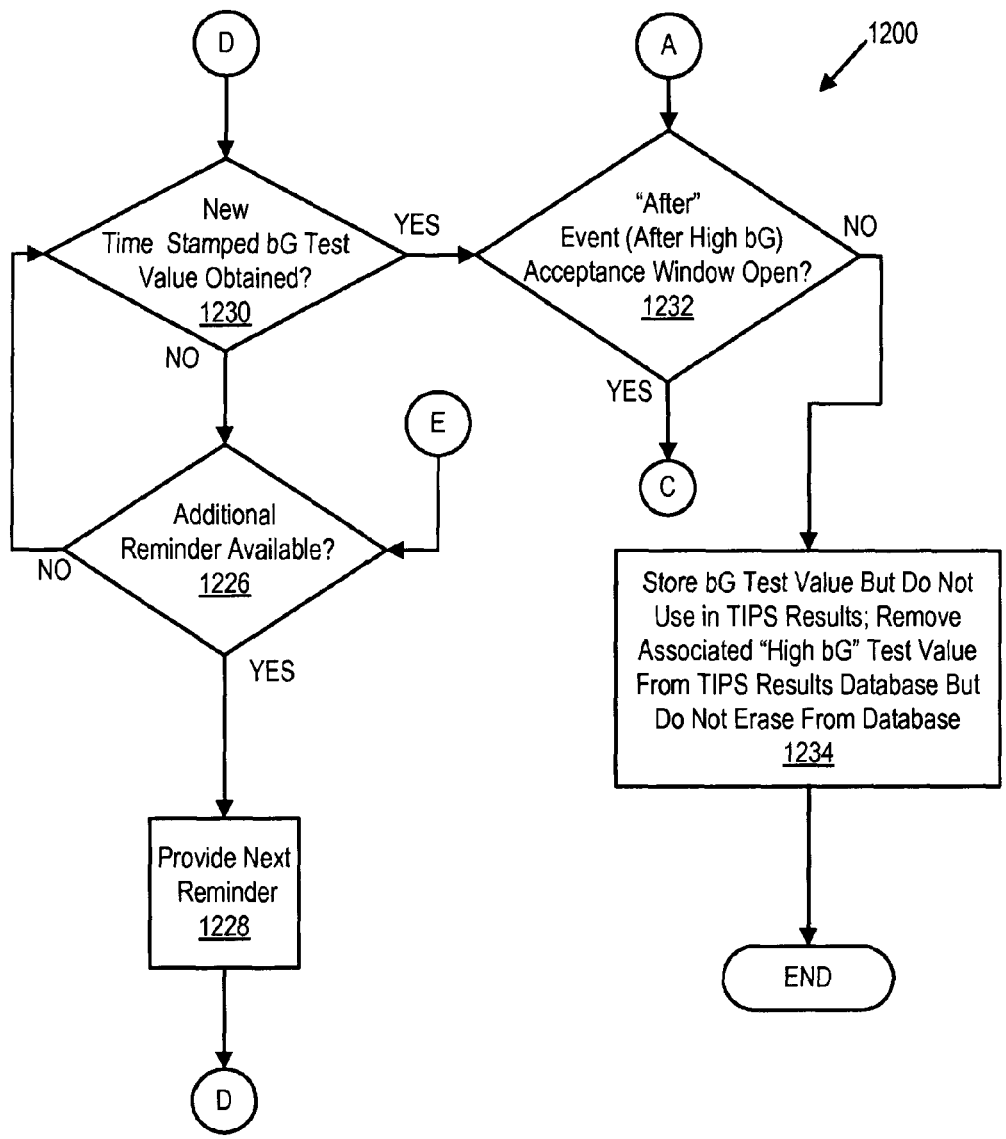

At FIGS. 36A and 36B a flowchart 1200 is shown for the operations that can be implemented in recording a pair of bG test values for a "High bG" event. It will be noted that operations 1202-1234 of this flowchart are similar to those for the "Exercise" event described in connection with FIGS. 35A and 35B. At operation 1202 the user obtains a "High bG" test result, which can be automatically recognized by the processing subsystem 822 when reading a time stamped bG test value from the bG analyzer 824. By "automatically recognized" it is meant that once the TIPs test is initiated by the user, the software module 822a will automatically be monitoring for a "High bG" event as well as a "Low bG" event. When the user obtains a time stamped bG value that falls above or below the pertinent bG threshold for triggering either the "High bG" event or the "Low bG" event, this will be detected by the software module 822a. In this example the "High bG" TIPs test is initiated and the corresponding event is detected. The processing subsystem 822 will then store the just-obtained bG test value in the database 826 as the first one of a related pair of bG test values for the "High bG" event, as indicated at operation 1204. At operation 1206 the "After" event acceptance time window for the "High bG" event is obtained. The remaining operations 1208-1234 parallel those explained above for FIGS. 35A and 35B, and therefore the description of these operations will not be repeated. If a Low bG TIPs test is initiated, obtaining a pair of bG test values for a "Low bG" event involves essentially the same sequence of operations as that described above for a "High bG" event, with the exception being that the processing subsystem 822 automatically detects a Low bG time stamped value instead of a high bG time stamped value.

Various exemplary set up times and acceptance reminder windows for different Events are illustrated in the chart of FIG. 37. FIG. 38 illustrates a data structure showing how multiple different types of structured tests can be recorded/monitored by the device 810. In this example "ST#" indicates two structured tests are recorded, with the first one (001) being still in progress, while the second one (002) has completed. The "Status" field may indicate, in addition to "IN PROGRESS" and "COMPLETE", a notation for "SCHEDULED", which indicates that a structured test has been scheduled into the device 810 but not yet initiated. The notation "CANCELLED" may also appear, which means that the structured test was cancelled by the user before its completion.

FIG. 39 illustrates how the accumulated data for a single structured test may be stored in a record in the database 826. In this example the "SAMPLE" column contains numbers "1" and "2" that both correspond to "GROUP" "1", meaning that these samples form the first pair of the TIPS results. The "NOTES" field contains any notes entered by the user when the user marked the related bG test value with a marker.

A TIPs test can be considered completed after a predetermined number of related pairs of bG test values have been obtained. It is expected that for most users obtaining seven related pairs of bG test values can suffice to complete a TIPs test, although optimum results would likely involve obtaining seven related pairs of bG test values for seven consecutive days. When initially configuring the variables for the TIPs test, the user could be provided with an option to select how many pairs of bG test values are to be obtained for the TIPs test and then the processing subsystem 822 can signal the user when the required number of related pairs of bG test values has been obtained. If the user skips entering an "After" event bG test value (e.g., Post-lunch) that corresponds to a previously entered bG test value, and instead enters a another subsequent "Before" event bG test value (e.g., Pre-Dinner), the previously marked "Before" event bG test value should be marked "Incomplete" for purposes of the TIPs results, and ignored in presenting the test results to the user. It is also preferred that the software module 822a display a field where the user can select from different options involving one or more of "Medication", "Food", "Exercise", "Health", "Insulin". By selecting one or more of these options, the user can correlate additional information to the event for which he/she is marking a bG test sample. For example, by selecting "Food", the user can be presented with various carbohydrate quantity options to select from that identify the level of carbohydrates that were consumed at a given meal event that the user is marking a time stamped bG test value during the TIPs test.

The system and method of the present disclosure provides a highly desirable device 810 and method of operation by, which related pairs of bG test values can be collected and recorded for future use by the user or a health care professional in studying events (including diet and lifestyle) affecting the user, and how such events impact the user's bG levels. The device 810 can enable the TIPs results to be displayed on the display 816 in chart form, in graphical form, or in any other manner that is helpful to the user in understanding the changes in bG levels for different events and/or in response to different types (or quantities) of foods consumed at given meals. If the display 816 is a color touchscreen display, then various colors could be used to highlight various ones of the bG test values, such as those corresponding to High bG or Low bG events. The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same can also be varied in many ways. Such variations are not to be regarded as a departure from the disclosure, and all such modifications are intended to be included within the scope of the disclosure.

In one aspect the present disclosure relates to a method for conducting a Testing In Pairs (TIPs) blood glucose (bG) test using a handheld diabetes management device carried by a user. The method can comprise using a processing subsystem to implement a software module for managing the TIPs test. The software module can control the generation of a plurality of predetermined acceptance time windows corresponding to different user defined events. The processing subsystem can be used to identify specific ones of a plurality of bG test values read by the device which are obtained during the predetermined bG acceptance time windows, and which are identified as being related pairs of accepted bG test values that correspond to specific ones of the user defined events. The processing subsystem can be used to store the related pairs of accepted bG test values in a database. The processing subsystem can conclude the TIPs test when a predetermined number of pairs of accepted bG test values has been stored in the database and can use the stored bG test values in providing results of the TIPs test to the user. The results of the TIPs test can be provided on a touchscreen display of the device. Furthermore, the bG acceptance time windows can be defined by the user using a touchscreen display of the device. Furthermore, the user defined events comprise at least two of the following group of events: a breakfast meal; a lunch meal; a dinner meal; a bedtime; a low bG test result; a high bG test result; and an exercise event. Moreover, the predetermined bG acceptance windows can include at least two or more of the following bG acceptance time windows: a Breakfast bG acceptance time window; an After-breakfast bG acceptance time window; a Lunch bG acceptance time window; an After-lunch bG acceptance time window; a Dinner bG acceptance time window; an After-dinner bG acceptance time window; a Bedtime bG acceptance window; an After-exercise bG acceptance time window; a Low-bG acceptance time window; and a High-bG acceptance time window. Still further, the predetermined bG acceptance time window can be provided in accordance with user set Post Meal times, where the user set Post Meal times occur after each of user set breakfast, lunch and dinner times. Furthermore, the predetermined bG acceptance time windows can include an After Exercise bG acceptance time window that is provided in accordance with a user set After Exercise time, and where the After Exercise bG acceptance time window begins thirty minutes before the user set After Exercise time and ends thirty minutes after the user set After Exercise time. Moreover, the predetermined bG acceptance time windows can include an After High bG acceptance time window that is provided in accordance with a user set After High bG time, and where the After High bG acceptance time window begins thirty minutes before the user set After High bG time and ends thirty minutes after the user set After High bG time. Furthermore, the predetermined bG acceptance time windows can include an After Low bG acceptance time window that is provided in accordance with a user set After Low bG time, and where the After Low bG acceptance time window begins fifteen minutes before the user set After Low bG time and ends fifteen minutes after the user set After Low bG time. Still further, the processing subsystem can detect the beginning of each one of the bG acceptance time windows and generate a reminder to the user of the device to announce a beginning of each one of the bG acceptance time windows. Still further, the processing subsystem can detect that two ones of the bG acceptance windows are open simultaneously and overlapping, and can signal the user to mark a just obtained bG test result as being preprandial or postprandial.

In another aspect the present disclosure relates to a method for conducting a TIPs test using a handheld diabetes management device carried by a user. The method can comprise using a processing subsystem to implement a software module for managing the TIPS test, the software module controlling the generation of a plurality of predetermined bG acceptance time windows corresponding to different user defined events. A color touchscreen display of the device, which is in communication with the processing subsystem, can be used to enable a user to configure the device to implement the predetermined bG acceptance time windows, to mark bG test values read by the device as preprandial or postprandial bG test values, and to display results of the TIPs test. The processing subsystem can also be used to provide a reminder to the user during each one of the predetermined bG acceptance time windows to perform a bG test and to provide a bG test value for the purpose of carrying out the TIPs test. The processing subsystem can also be used to identify specific ones of a plurality of bG test values read by the device, which are obtained during the predetermined bG acceptance time windows, as being related pairs of accepted bG test values that correspond to specific ones of the user defined events. The user defined events can include a Breakfast event, a Lunch event, a Dinner event, a Low bG event; a High bG event and an Exercise event. The processing subsystem can also store the related pairs of accepted bG test values in a database and can conclude the TIPs test when a predetermined number of pairs of accepted bG test values have been stored in the database. The processing subsystem can also be used to retrieve and use the accepted bG test values stored in the database and to display the results of the TIPs test to the user. Still further, the predetermined bG acceptance windows can include at least two of the following bG acceptance time windows: a Breakfast bG acceptance time window; an After-breakfast bG acceptance time window; a Lunch bG acceptance time window; an After-lunch bG acceptance time window; a Dinner bG acceptance time window; an After-dinner bG acceptance time window; a Bedtime bG acceptance window; an After-exercise bG acceptance time window; a Low-bG acceptance time window; and a High-bG acceptance time window. Furthermore, the predetermined bG acceptance time windows can include an After High bG acceptance time window that is provided in accordance with a user set After High bG time, and where the After High bG acceptance time window begins thirty minutes before the user set After High bG time and ends thirty minutes after the user set After High bG time. Moreover, the processing subsystem can detect that two ones of the bG acceptance windows are open simultaneously and overlapping, and can signal the user to mark a just obtained bG test result as being preprandial or postprandial.

In still another aspect the present disclosure relates to a handheld diabetes management device for monitoring and recording bG levels of a user. The device can comprise a port for receiving a bG test strip input by a user and a bG analyzer for reading the bG test strip. A software module can be included for conducting a TIPs test using the device. A processing subsystem can be included which is responsive to an output from the bG analyzer and which uses the bG test value provided by the bG analyzer. The processing subsystem can run the software module, with the software module controlling the generation of a plurality of predetermined acceptance time windows corresponding to different user defined events programmed into the software module by the user. The processing system can further be adapted to identify specific ones of a plurality of bG test values read by the device, which are obtained during the predetermined bG acceptance time windows, as being related pairs of accepted bG test values that correspond to specific ones of the user defined events. A database can be in communication with the processing subsystem for storing the related pairs of accepted bG test values. Furthermore, the device can comprise a touchscreen display in communication with the processing subsystem for enabling the user to program the different user defined events into the device. Still further, the touchscreen display can comprise a color touchscreen display, and the user defined events can comprise a breakfast meal, a lunch meal, a dinner meal, a bedtime, a low bG test result, a high bG test result and an exercise event. Furthermore, the predetermined bG acceptance time windows can comprise two or more of: a Breakfast bG acceptance time window; an After-breakfast bG acceptance time window; a Lunch bG acceptance time window; an After-lunch bG acceptance time window; a Dinner bG acceptance time window; an After-dinner bG acceptance time window; a Bedtime bG acceptance window; an After-exercise bG acceptance time window; a Low-bG acceptance time window; and a High-bG acceptance time window. Still further, the processing subsystem can detect the beginning of each one of the bG acceptance time windows and can generate a reminder to the user of the device to announce a beginning of each one of the bG acceptance time windows.

A method for conducting a Testing In Pairs (TIPs) blood glucose (bG) test using a handheld diabetes management device carried by a user is also disclosed. The method can comprise using a processing subsystem to implement a software module for managing the TIPs test, the software module controlling the generation of a plurality of predetermined acceptance time windows corresponding to different user defined events. The processing system can be used to identify specific ones of a plurality of bG test values read by the device, which are obtained during said predetermined bG acceptance time windows, as being related pairs of accepted bG test values that correspond to specific ones of the user defined events, the user defined events including: a breakfast meal; a lunch meal; a dinner meal; a bedtime; a low bG test result; and a high bG test result; an exercise event. The predetermined bG acceptance time windows can include: a Breakfast bG acceptance time window; an After-breakfast bG acceptance time window; a Lunch bG acceptance time window; an After-lunch bG acceptance time window; a Dinner bG acceptance time window; an After-dinner bG acceptance time window; a Bedtime bG acceptance window; an After-exercise bG acceptance time window; a Low-bG acceptance time window; and a High-bG acceptance time window.

Handheld Diabetes Management Device with Bolus Calculator

Figure 40:
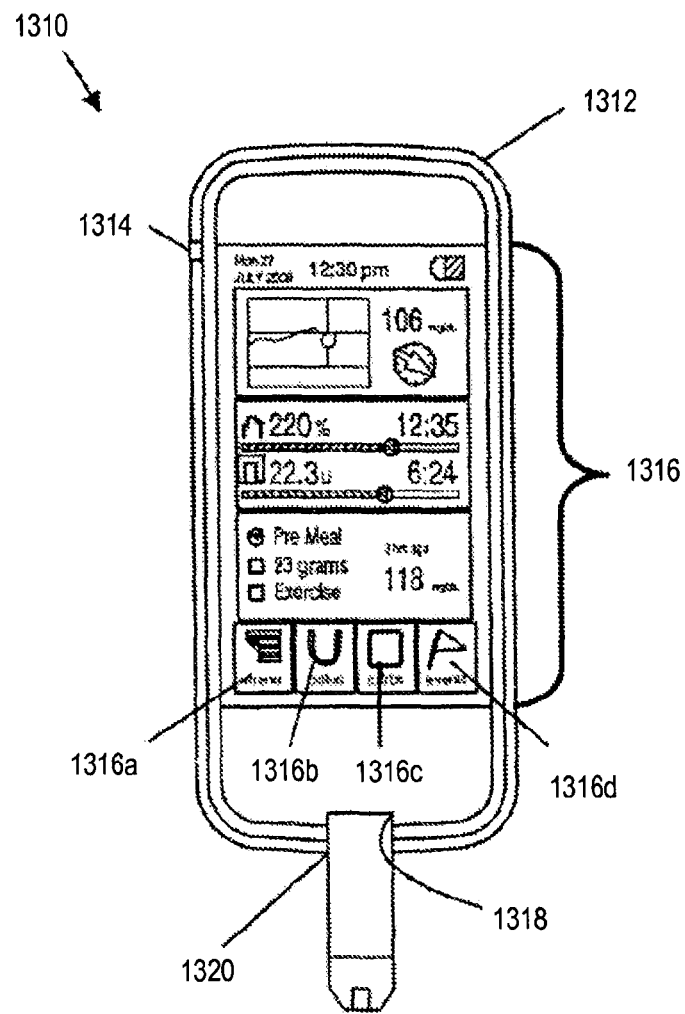
FIG. 40 is a perspective view of one embodiment of a handheld diabetes bG management device in accordance with the present disclosure.

Referring to FIG. 40, there is shown a high level drawing of one embodiment of a handheld, portable blood glucose (bG) monitoring device 1310 that may be used in implementing a bolus calculation or carbohydrate suggestion. Typically the device 1310 includes a housing 1312 that may contain a user unit control 1314 (e.g., ON/OFF), a touchscreen display 1316, and a port 1318 into which a bG test strip 1320 may be inserted. The display 1316 may display user selectable options for allowing the user to access a software driven menu 1316a of various selections, a selection 1316b for allowing the user to enter bolus information, a selection 1316c for enabling the user to enter carbohydrate information for snacks or meals, and a selection 1316d for allowing the user to enter information pertaining to events (e.g., meals, exercise, periods of stress, periodic physiological events such as a menstrual cycle, etc.) that may affect the user's bG measurement being read by the device 1310. Although the display 1316 will be described herein as a touchscreen display, it will be appreciated that any other suitable form of display may be incorporated (e.g., LED, etc.). If a touchscreen display is not used, the user control switches 1314 may need to include specific buttons or controls by which the user is able to select various options and input markers needed to carry out the bolus calculation or carbohydrate suggestion. It will be appreciated that the above is a high level description of the device 1310, and in practice the device may include additional controls, input ports, output ports, etc., as may be desired to even further enhance the utility of the device 1310 or its use with other components and devices (e.g., laptop computers, infusion pumps, etc.). Accordingly, the above description of the device 1310 should not be taken as limiting its construction or features in any way.

Figure 41:
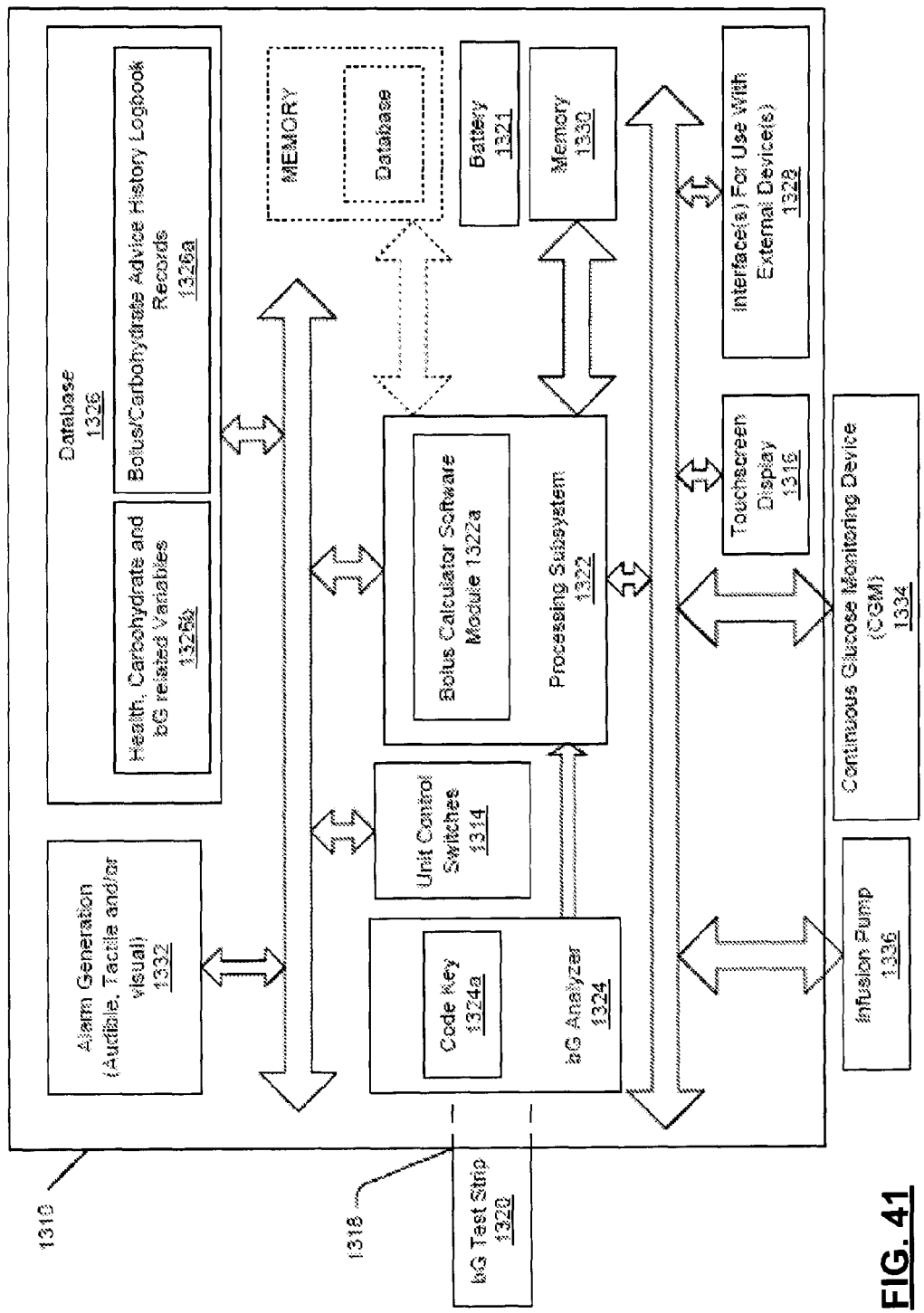
FIG. 41 is a high level block diagram of various components and subsystems that may be incorporated in the device shown in FIG. 40.

Referring to FIG. 41, a high level block diagram of the device 1310 is shown. The device 1310 can include a rechargeable or non-rechargeable battery 1321 for powering the various electronic components of the device 1310. A processing subsystem 1322 (e.g., a microprocessor based subsystem) is included that receives information from a bG analyzer 1324. The bG analyzer 1324 is located adjacent the port 1318 of the housing 1312 to permit the bG analyzer 1324 to read the bG test strip 1320. The bG analyzer 1324 can include a code key 1324a that includes calibration information for the bG test strip 1320 being read. The processing subsystem 1322 can also be in communication with a database 1326 that is used to store bG test values obtained from the bG analyzer 1324 and other important health related information for the user. In particular, the database 1326 can include a subsection 1326a for storing recommended bolus and carbohydrate advice history records, and a section 1326b for storing health, carbohydrate and bG related variables (e.g., insulin sensitivities of the user for various time segments of the day) pertinent to the user. It will be appreciated that the database 1326 will be formed by a non-volatile memory.

The processing subsystem 1322 can also be in communication with the display 1316, the user control panel 1314, and one or more interfaces 1328 for interfacing the device 1310 to other external devices. The processing subsystem 1322 can also be in communication with a memory (such as a RAM) 1330 for storing various types of information (e.g., meal and bed times) that are input by the user, as well as any other information requiring temporary or permanent storage. However, it will be appreciated that the database 1326 and the memory 1330 could be implemented in a single memory device (e.g., RAM) if desired, as indicated in phantom in FIG. 41. The processing subsystem 1322 can be in communication with an alarm generation subsystem 1332 that is used to generate an alarm consisting of audible signals, tactile signals (e.g., a vibration signal) or possibly even visual signals such as illuminated lights (e.g., LEDs) on the device 1310. The processing subsystem 1322 can also receive inputs from a remote continuous glucose monitoring ("CGM") device 1334 secured to the user's body such the device 1310 is continually updated with bG information for the user. Finally the processing subsystem 1322 can be in communication with a remote insulin infusion pump 1336 (either through a wired or wireless RF connection) being worn by the user so that the device 1310 is able to communicate bolus information to the infusion pump 1336. By "remote", it is meant that the CGM device 1334 and the infusion pump 1336 are each located outside of the device 1310 but otherwise still in communication with the device 1310.

The device 1310 can be used to implement a non-transitory machine readable code, for example a software module 1322a, that is run by the processing subsystem 1322. The software module 1322a can be formed as a single module or as a collection of independent modules that run concurrently on the processing subsystem 1322. The processing subsystem 1322, working in connection with the software module 1322a, receives a wide variety of user inputs applied by the user through the touchscreen display 1316 to generate a recommended meal bolus, a recommended correction bolus, a recommended total bolus, or when appropriate a suggested carbohydrate amount. The suggested carbohydrate amount may be provided in response to the detection by the device 1310 of a hypoglycemic bG test value. The operations and capabilities of the device 1310 will be explained in detail in the following paragraphs. The device 1310 significantly enhances the convenience and ease of use to the user through the implementation of a plurality of customizable inputs that enable the user to program the device 1310 with unique health information pertinent to the user. More specifically, the device 1310 allows the user to program the device 1310 with health information which even more completely enables the device 1310 to take into account unique health conditions affecting the user, as well regular occurring and non-regular occurring health events that could otherwise have an impact on the bolus and carbohydrate calculations made by the device 1310.

Figure 42:
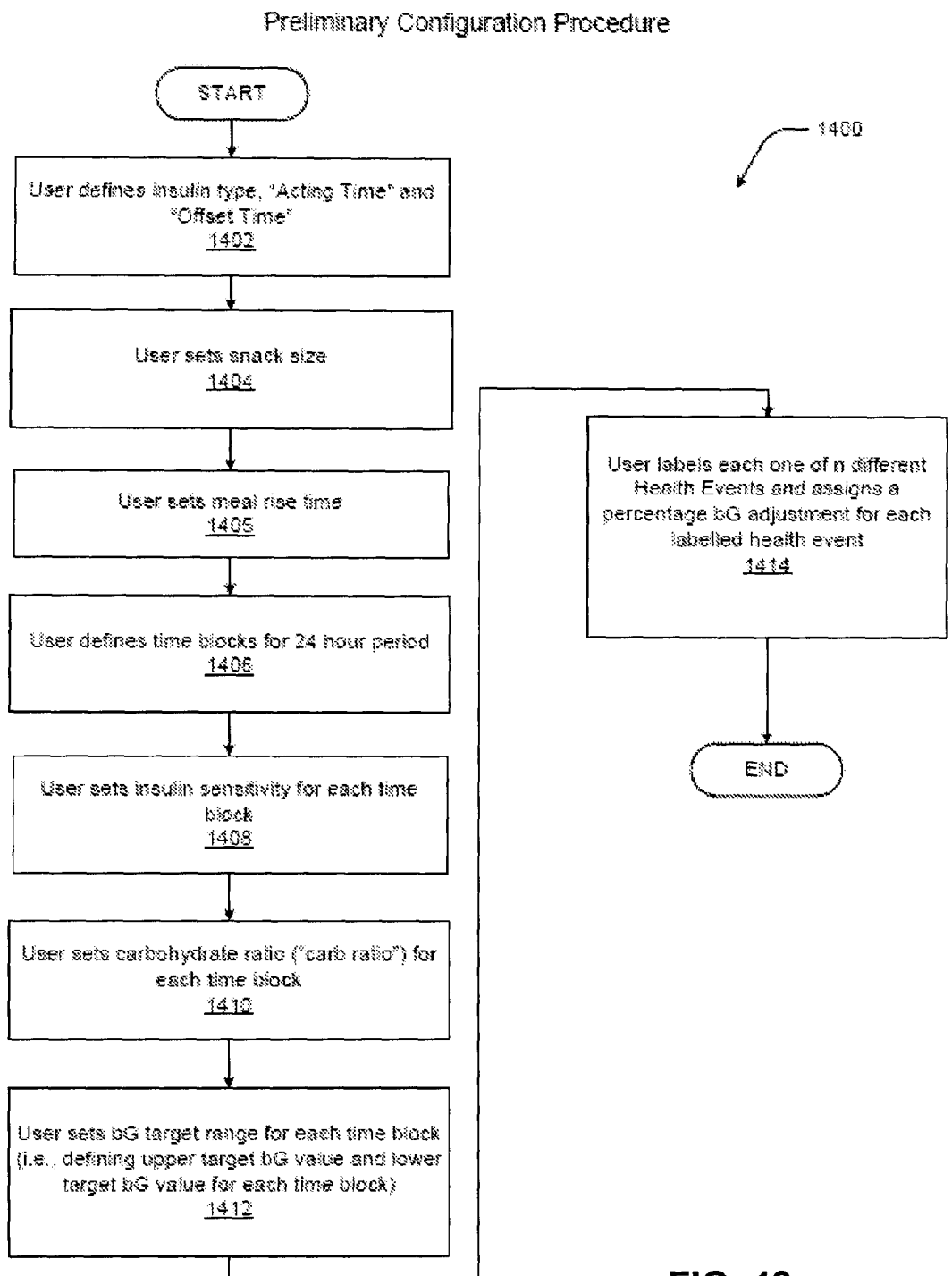
FIG. 42 is an exemplary flowchart illustrating a preliminary configuration procedure for configuring the device shown in FIG. 40.

Referring to FIG. 42, a flowchart 1400 illustrates an exemplary preliminary configuration procedure that the user can perform to configure the various inputs needed to tailor the device 1310 to the requirements of the user. At operation 1402 the user can define the insulin type that she/he is using, as well as the "acting time" and "offset time" associated with the specified insulin. The user also sets a snack size at operation 1404. Any carbohydrate amount greater than the snack size that the user enters into the device 1310 will be considered as a "meal" by the device 1310 if the amount exceeds the user defined snack size. A meal rise time is also defined by the user at operation 1405. At operation 1406 the user can define the various time blocks for a twenty four hour period. It one exemplary implementation the user may define up to eight contiguous or non-contiguous time blocks during a twenty four hour period. However, it will be appreciated that a greater or lesser number of time blocks could be provided for. Since the user's insulin sensitivity will be assumed to vary over the course of the day, the user can set a different insulin sensitivity value for each time block, as indicated at operation 1408. At operation 1410 the user can set a carbohydrate ratio ("carb ratio") for each time block as well, as this ratio can be assumed to vary slightly for different users throughout the course of a day. At operation 1412 the user can set a bG target range for each time block, as this range is also presumed to vary slightly over the course of a day. The bG target range is made up of an upper target bG value and a lower target bG value which define the upper and lower bounds, respectively, of the bG target range. It will also be appreciated that the processing subsystem 1322 operates to consider an action shape of a previously taken correction bolus, where the action shape is defined by a bG lowering potential of the previously taken correction bolus, as well as the offset time and the acting time of the insulin associated with the previously taken correction bolus. The action shape is considered by the processing subsystem 1322 when generating a new bolus recommendation.

At operation 1414 the user labels each one of up to n different health events with a label using the touchscreen display 1316 and assigns a percentage bG adjustment for each labeled health event. It is a valuable feature of the device 1310 that the user is able to program these various percentage adjustments for each of a plurality of user defined health events that the user knows in advance will affect her/his bG test values. For example, the user may program the device with different bG percentage adjustment values for health events such as "exercise", "illness", "stress", or even for recurring conditions such as a menstrual cycle. The precise percentages selected by the user for each user defined health event can be based on past history and experience of the user or based in part on the advice of a health care professional who is helping the user to manage her/his blood glucose levels. As one example, if the user knows from experience that an exercise event performed right after a meal will reduce a needed meal bolus by about 20%, then the user may enter "–20" in a displayed field on the display 1316. The processing subsystem 1322 will thereafter use this 20% reduction in calculating the meal bolus and the correction bolus when the exercise event has been selected. These features will be defined in greater detail in the following paragraphs.

Figure 43:
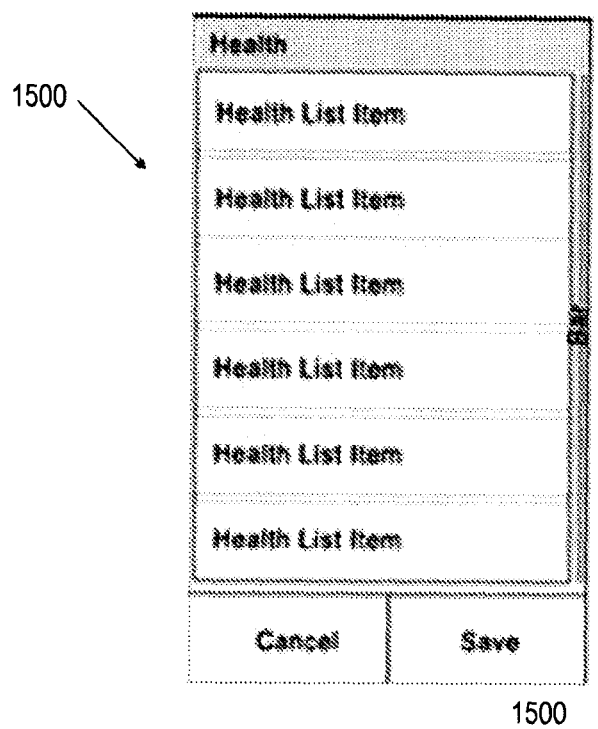
FIG. 43 is a drawing illustrating an example screen for enabling a user to program in various health events to be considered by the device when providing bolus recommendations.
Figure 44:
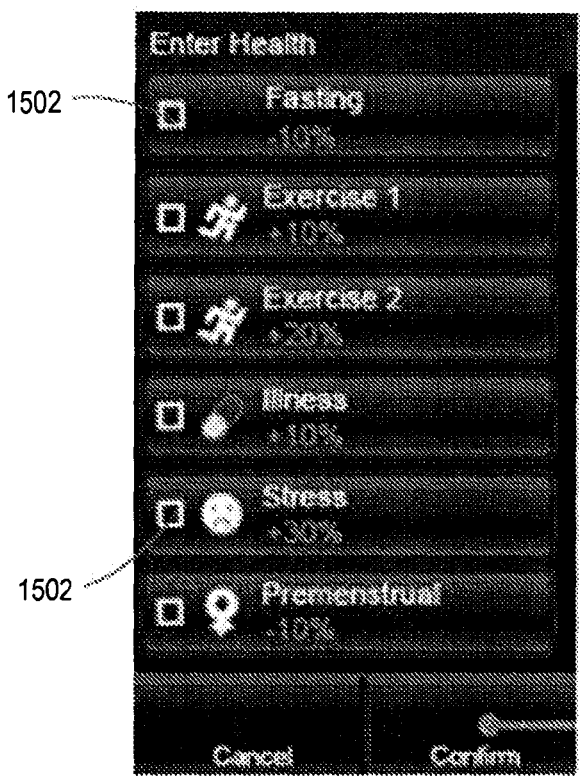
FIG. 44 is an illustration showing how the display of the device may display the various programmed health event options after same are programmed into the device.
Figure 45:
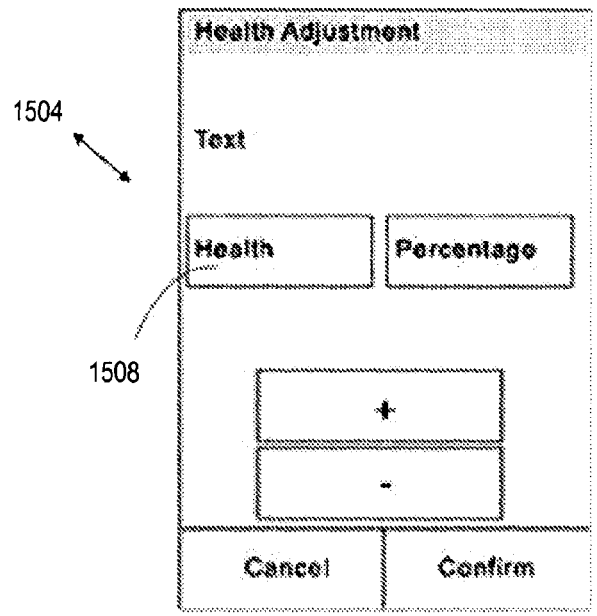
FIG. 45 is a drawing of an exemplary layout that may be presented on the display of the device for allowing the user to enter text that describes the health event being programmed, along with the percentage adjustment to be made to the health event.
Figure 46:
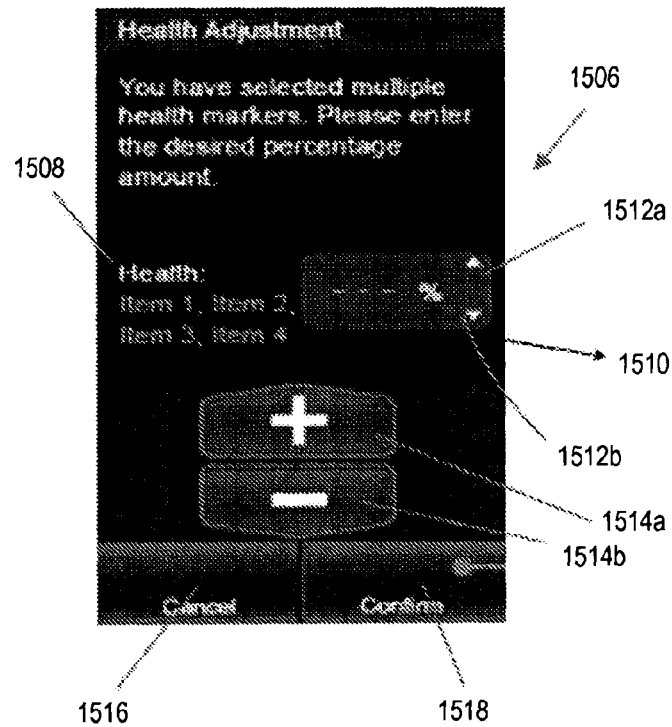
FIG. 46 is an illustration showing how the display of the device may display a message to the user if the user has selected more than one health event, and allows the user to enter a custom health adjustment percentage to be applied to a bolus calculation.
Figure 47:
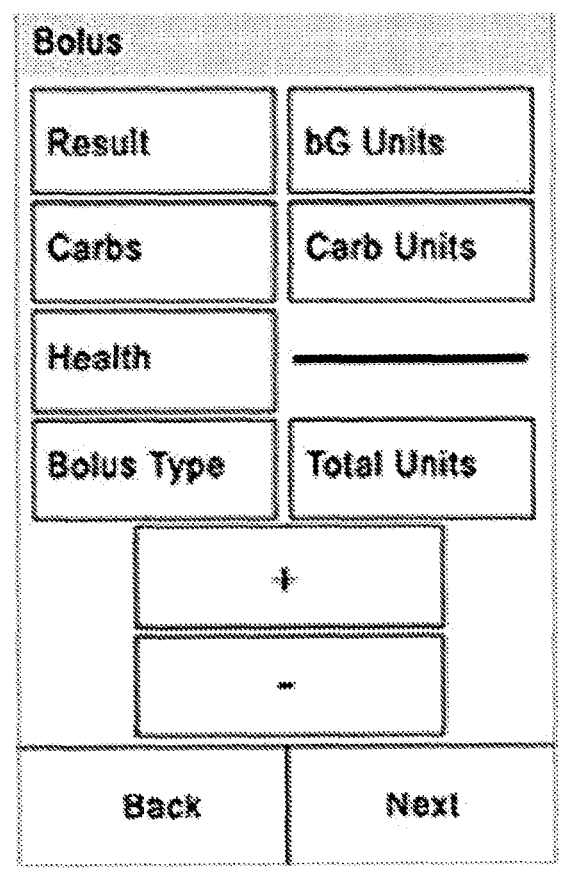

Referring to FIGS. 42-47, illustrations are presented of how the various forms of information can be displayed to the user on the display 1316 of the device 1310. FIG. 43 shows a screen 1500 that presents six "Health List Item" boxes that may be displayed in the display 1316 when the user has chosen to assign a specific health event to a bG test value that she/he has just obtained. FIG. 44 shows a screen display 1500a illustrating how this information can appear on the display 1316. The user can select one of the boxes 1502 in FIG. 44, which will mark the just-obtained bG test value with the user programmed specific health event, and thus apply the user programmed percentage adjustment to the just-obtained bG test value. If the user selects two or more health events for a single bG test value, then the device 1310 can display a different screen that forces the user to select a "custom" health event percentage that will be applied to the just-obtained bG test value. Such a screen layout 1504 is shown in FIG. 45. An actual exemplary screen display 1506 is shown in FIG. 46 that corresponds to the screen layout 1504. The "Health" field 1508 in FIG. 46 displays all the health events that the user has checked off in boxes 1502 of screen display 1500a of FIG. 44. In field 1510 the user can enter and/or adjust a custom health percentage adjustment using the arrows 1512a and 1512b. Arrows 1514a and 1514b may also be displayed, which are used to enable the user to increase or decrease a suggested bolus. User control 1516 enables the user to cancel the health event adjustment and control 1518 enables the user to confirm the selection (i.e., apply) the custom health percentage in field 1510. FIG. 47 illustrates how various items of information (e.g., bg test value; carbohydrate information; health adjustment percentage; and recommended bolus) can be displayed to the user on the display 1316.

Figure 48:
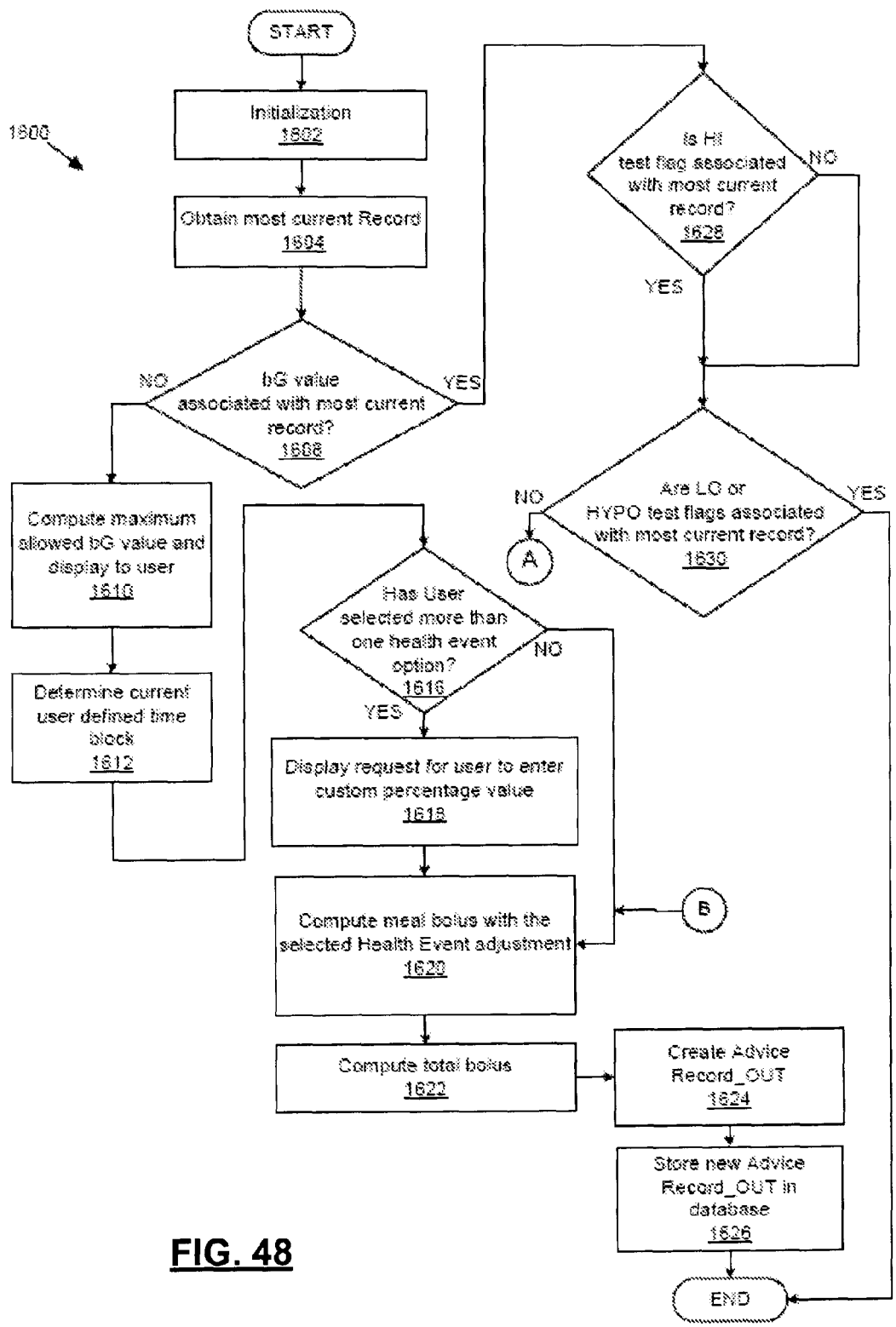
FIGS. 48 and 49 represent an exemplary flowchart illustrating operations that can be performed in computing a total bolus using user defined health adjustment percentages by which the computed meal bolus and computed correction bolus can be modified before calculating a recommended total bolus.
Figure 49:
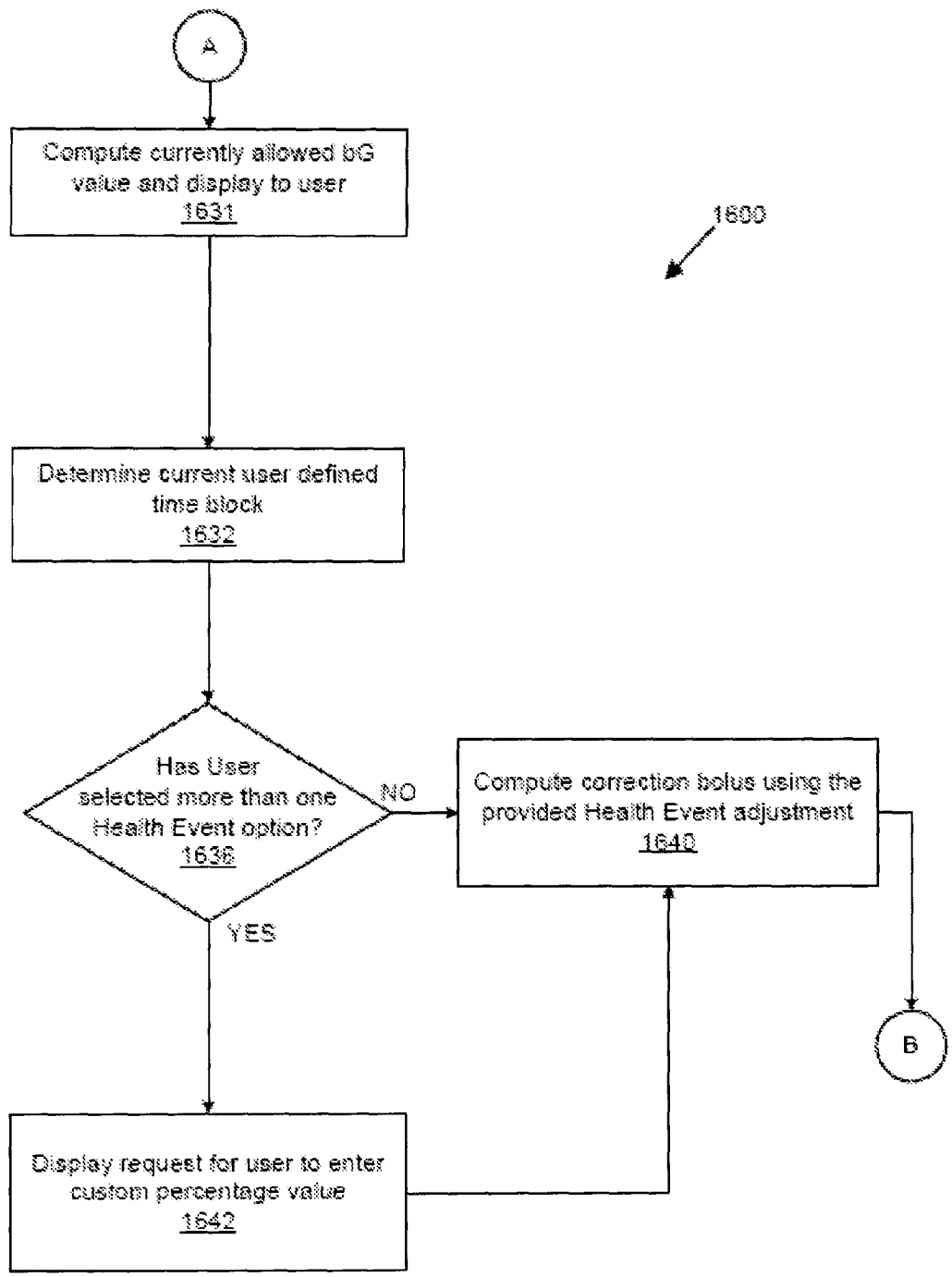

Referring now to FIGS. 48 and 49, a flowchart 1600 is shown of exemplary operations that can be performed by the device 1310 in determining a total bolus recommendation for the user that takes into account the configuration programmed into the device 1310 by the user. At operation 1602 an initialization operation is performed to set the record contents of the processing subsystem 1322 to "0". At operation 1604 the processing subsystem 1322 obtains the Advice Record_In (i.e., the most current record stored in the database 1326) and checks at operation 1608 to determine if it has an associated bG test value. If not, then at operation 1610 the maximum allowed bG is computed and displayed to the user. At operation 1612 the processing subsystem 1322 determines the current user defined time block (if any). At operation 1616 the processing subsystem 1322 checks to determine if the user has selected more than one health event option and, if the user has selected more than one option, a request is displayed on the display 1316 for the user to enter a custom percentage value, as indicated at operation 1618, that will be applied to subsequent meal bolus, correction bolus and suggested carbohydrate calculations. At operation 1620 the processing subsystem 1322 will compute the meal bolus and apply the selected health event adjustment defined by the user (if any such adjustment has been selected by the user). At operation 1622 the processing subsystem 1322 will compute the total bolus. At operation 1624 the processing subsystem 1322 will create a new Advice Record_OUT and store the new record in the database 1326 at operation 1626.

Referring to FIGS. 48 and 49, if the check at operation 1608 reveals that there is a bG value associated with the most current record, then a check is made at operation 1628 to see if the "HI" test flag of the record is set, indicating a bG reading that is above a display limit of the device 1310, and which therefore will not be used to calculate a recommended correction bolus. If this check provides a "Yes" answer, then operations 1610-1626 may be performed to obtain only a meal bolus. If the check at operation 1628 produces a "No" answer, then a check is made to determine if the "LO" or "HYPO" test flags are set for the most current record (Advice Record_IN), as indicated at operation 1630. This check indicates either a hypoglycemic condition or a bG reading below the display limit of the device 1310. In this event the routine of flowchart 1600 ends. If the check at operation 1630 produces a "No" answer, then in FIG. 49 the processing subsystem 1322 computes the maximum allowed bG value at operation 1631 and displays it to the user on the display 1316.

Continuing in FIG. 49, at operation 1632 the processing subsystem 1322 determines the current user defined time block (if any) and then displays to the user all the user defined health event adjustment options, and requests the user to select one or "None", as indicated at operation 1634. If "None" or only one health event is selected by the user, then the processing subsystem 1322 will compute the correction bolus in accordance with the user's selection (i.e., applying either no percentage adjustment or the percentage adjustment of the selected health event), as indicated at operation 1640. Operations 1620-1626 from FIG. 48 will then be repeated. If the check at operation 1636 reveals that the user has selected more than one health event option, then a request is displayed on the display 1316 for the user to select a custom percentage, as indicated at operation 1642, that will be used thereafter in calculating meal and correction boluses at operation 1640. If the check at operation 1636 products a "No" answer, then operation 1640 is performed to compute the correction bolus using the provided health event adjustment. Operations 1620-1626 will then be completed.

Figure 50:
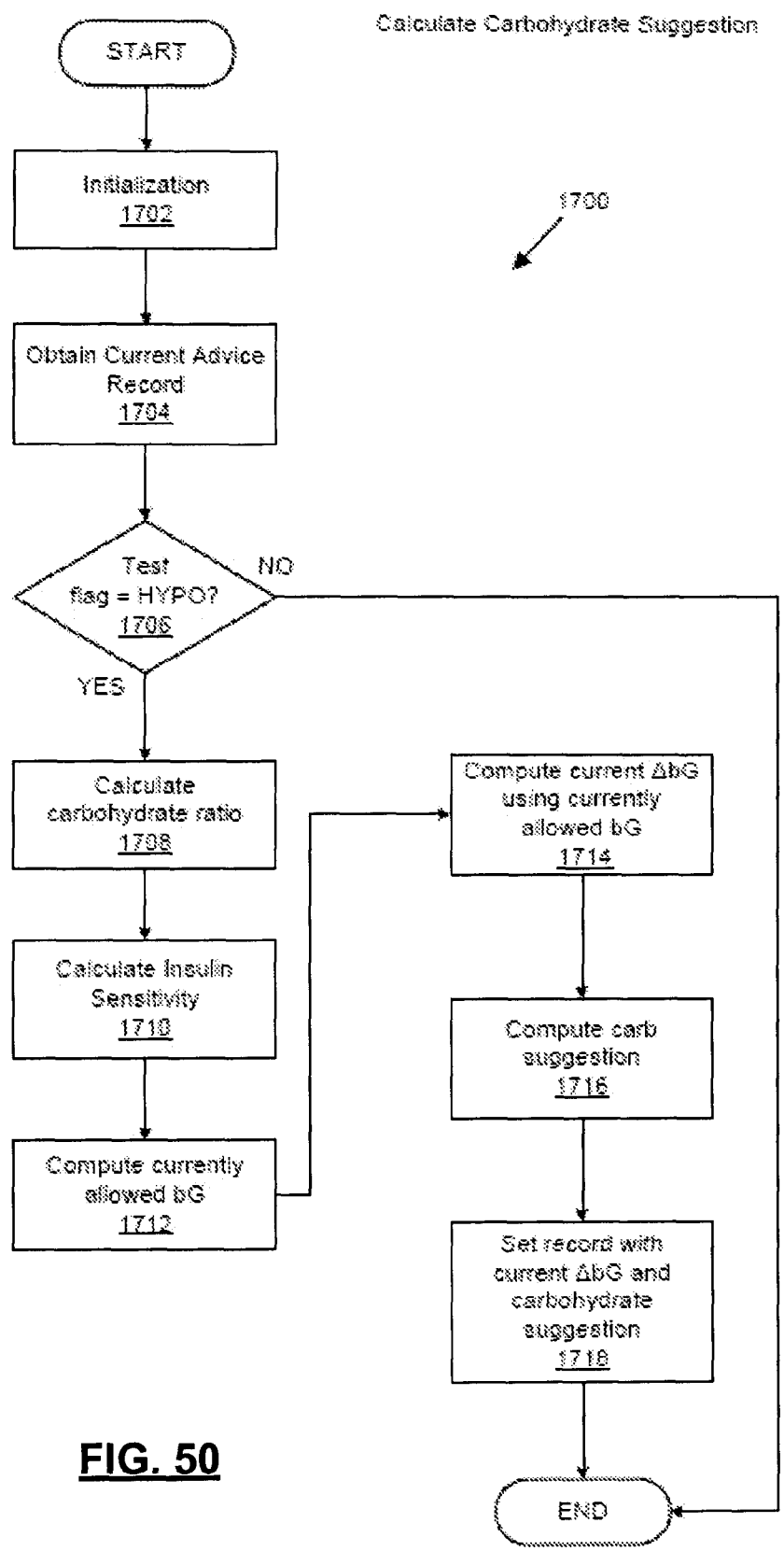
FIG. 50 is an exemplary flowchart illustrating operations that can be performed by the device of FIG. 40 in calculating a carbohydrate suggestion for the user.
Figure 51:
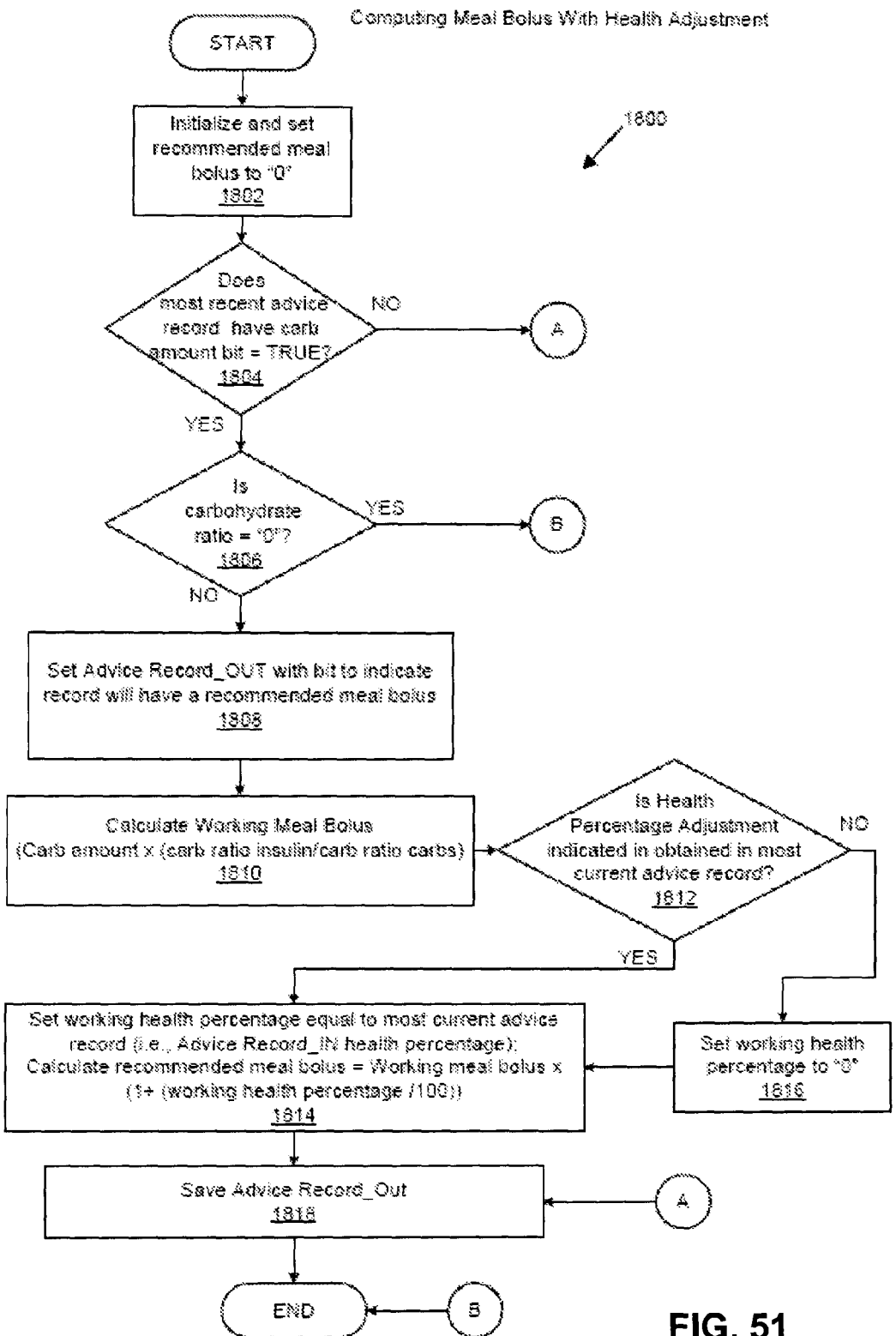
FIG. 51 is a flowchart illustrating exemplary operation performed by the device of FIG. 40 in computing the recommended meal bolus with a user programmed health adjustment applied thereto.

Turning to FIG. 50, a flowchart 1700 is shown illustrating exemplary operations to show a carbohydrate suggestion can be calculated using the device 1310. At operation 1702 an initialization procedure is performed to ensure that any pre-existing data that may be present in the Advice Record_Out contents of the processing subsystem 1322 is cleared. The most current advice record (Advice Record_In) is then obtained at operation 1704. At operation 1706 a check is made to determine if the HYPO test flag of the most current advice record is set, indicating a hypoglycemic condition for the current bG test value being analyzed. If so, the processing subsystem 1322 computes the carbohydrate ("carb") ratio at operation 1708 in the traditional manner. At operation 1710 the insulin sensitivity is calculated in the traditional manner. At operation 1712 the currently allowed bG is computed. At operation 1714 the current delta bG is computed by subtracting the currently allowed bG from the most current advice record bG concentration. This is different from previous operations, which involved subtracting the bG value at the center of the user set bG target range. So in effect, operation 1714 allows a previously eaten meal, which could operate to help raise the user's bG level, or a previously taken correction bolus, which would operate to lower the user's bG, to be factored into the equation for determining the current delta bG. At operation 1716 the Advice Record_Out carbohydrate suggestion is calculated by multiplying the current delta bG by the insulin sensitivity and by the carbohydrate ratio. At operation 1718 the Advice Record_Out contents is set to indicate that a carbohydrate suggestion was calculated with the current delta bG.

Figure 61:
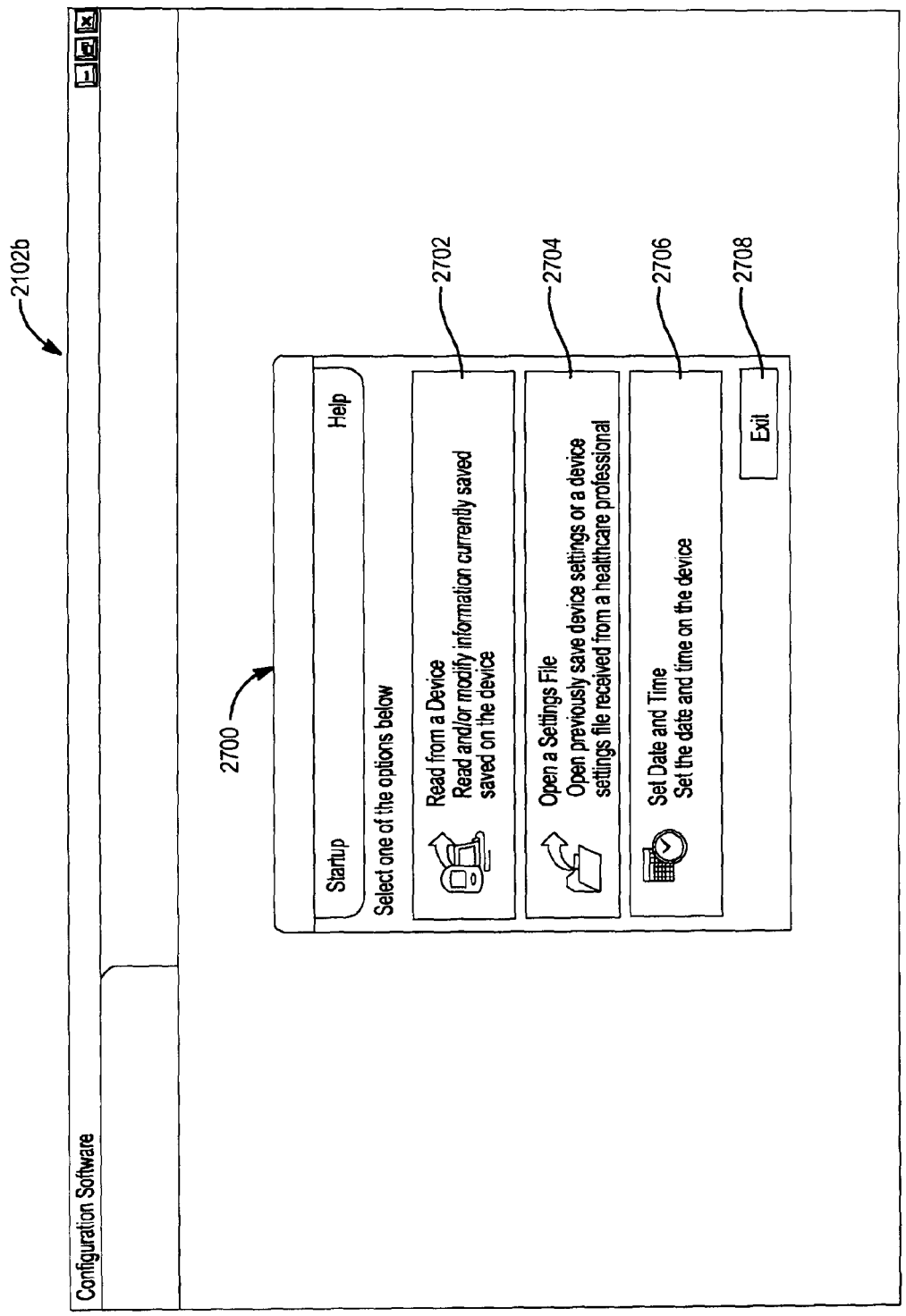
FIG. 61 illustrates an exemplary "Startup" user interface.

Referring now to FIG. 61, a flowchart 1800 is shown illustrating one exemplary manner of computing a meal bolus with a health event adjustment. At operation 1802 an initialization is performed to set the Advice Record_OUT record to zero. At operation 1804 a check is made to determine if the most current advice record (Advice Record_IN) retrieved by the processing subsystem 1322 from the database 1326 has a bit set to "True" (e.g., "1") for the carbohydrate amount, indicating that a carbohydrate amount is available for use in the following calculations. If the answer is "Yes", then at operation 1806 a check is made to ensure that the carbohydrate ratio is not "0". If it is not, then at operation 1808 a bit will be set for the Advice Record_OUT being created by the processing subsystem 1322 to indicate a recommended meal bolus is associated with it. At operation 1810 the working meal bolus is calculated. At operation 1812 a check is made if a health event adjustment percentage bit is set in the most current advice record (Advice Record_IN) record contents. If so, then at operation 1814 a working health percentage is set equal to the health percentage contained in the most current advice IN record, and the recommended meal bolus is calculated using this working health percentage. For example, if the user has indicated "−20" in her/his percentage adjustment for the associated health event, then operation 1814 uses this information to convert the "−20" to 80%, and the 80% figure is used to modify the working meal bolus to come up with the recommended meal bolus. Thus, in this example the recommended meal bolus would be reduced by 20%. At operation 1818 the Advice Record_OUT record just created by the processing subsystem 1322 is saved in the log records portion 1326a of the database 1326.

If the check at operation 1812 indicates that no health percentage adjustment is indicated in the most current advice record, then the working health adjustment percentage is set equal to zero at operation 1816 and then operations 1814 and 1818 are repeated. If a carbohydrate amount bit of the most current advice record is found to be set to "0" at operation 1804, then it is understood that there is no carbohydrate amount from which a recommended meal bolus can be calculated, and the Advice Record_OUT is simply saved at operation 1818. If the carbohydrate ratio of the most current advice record is found to be "0" at operation 1806, then the routine ends with an error condition.

Figure 52:
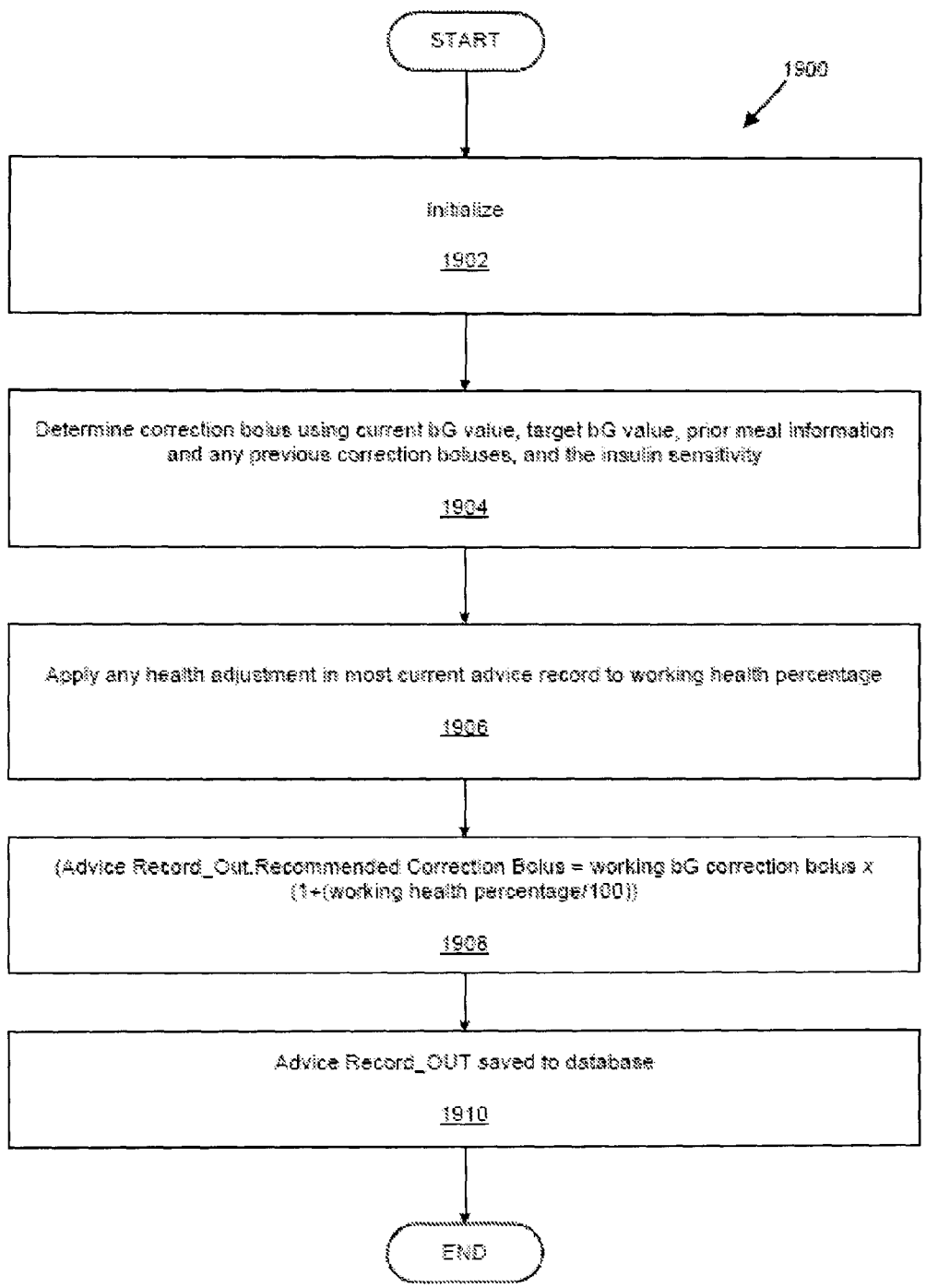
FIG. 52 is a flowchart illustrating exemplary operations that can be performed in computing a recommended correction bolus with a health adjustment percentage set by the user.

Referring to FIG. 52, there is shown an exemplary flowchart 1900 setting forth operations that can be performed in computing a correction bolus, taking into account a percentage health adjustment input by the user. At operation 1902 the Advice Record_OUT record contents are set to equal the recommended correction bolus for the current delta bG that has been determined by the processing subsystem 1322. At operation 1904 the working bG correction bolus is calculated from the Advice Record_OUT current delta bG, the most current advice record (Advice Record_IN) insulin sensitivity (insulin) and the most current advice record insulin sensitivity in bG. At operation 1906 any health adjustment percentage present in the most current advice record is applied to the working health percentage. Again, if the user has specified "None" when selecting a health adjustment percentage for the bG test value associated with the most current advice record, then the working health percentage will not be modified by any percentage value. At operation 1908 the Advice Record_OUT recommended correction bolus is obtained by modifying the working bG correction bolus by the health percentage adjustment. Thus, if the user had set the health adjustment percentage for the bG test value associated with the most current advice record to "−25", then the calculation at operation 1908 would multiply the working bG correction bolus by 75%. The Advice Record_OUT with the newly calculated recommended correction bolus is then saved to the database history logbook records 1326*a* at operation 1910.

In calculating the correction delta bG, an advantage of the device 1310 is that the working delta bG is allowed to be a negative value. This allows a portion of any correction to be removed from the newly calculated correction delta bG, such as if the user had previously taken some carbohydrates, to be factored into the newly calculated correction delta bG. Another advantage is that for computing a carbohydrate suggestion for the user, the recommendations can be calculated to the currently allowed bG value rather than to the center of the bG target range.

In one aspect the present disclosure relates to a method implemented on a non-transitory computer readable medium adapted to run on a processing subsystem. The processing subsystem can form a portion of a handheld diabetes management device for monitoring blood glucose (bG) levels of a diabetic user and determining a total bolus to be provided to the user. The method can comprise using a memory to store information that can include the following:

an upper target bG value for each one of a plurality of different time blocks, defined by the user, during a twenty four hour period;

a lower target bG value for each one of the different time blocks during the twenty four hour period;

a hyperglycemic warning value, defined by the user, representing a hyperglycemic bG value for the user;

a hypoglycemic warning value, defined by the user, representing a hypoglycemic bG value for the user;

a plurality of differing user defined health events that each include a predetermined associated percentage value set by the user by which a meal bolus calculation and a correction bolus calculation will each be modified to account for one of an increase or a decrease in insulin associated with each one of the differing health events; and a carbohydrate value input by the user in connection with a meal; and using the processing subsystem to communicate with the memory and to obtain the information and to calculate therefrom the meal bolus, the correction bolus, and a recommended total bolus that is a sum of the calculated meal bolus and the calculated correction bolus. The method may further comprise using the memory to store insulin sensitivity information pertaining to the user, and to use the insulin sensitivity in modifying each of the calculated meal bolus and the calculated correction bolus. The method may still further comprising enabling the user to define and store in the memory different insulin sensitivity percentage values for each one of the different time blocks. Still further, the calculated meal bolus can be modified by both the insulin sensitivity percentage value and the percentage value associated with one of the user defined health events. Still further, the processing subsystem can be used to use the information to generate a carbohydrate amount recommendation for the user when the user's bG level is below the hypoglycemic warning value. Furthermore, the method can include using the processing subsystem to consider an action shape of a previously taken correction bolus, the action shape being defined by a bG lowering potential of the previously taken correction bolus, an offset time of insulin associated with the previously taken correction bolus, and an acting time of the insulin associated with the previously taken correction bolus, and the action shape being considered by the processing subsystem when generating a new bolus recommendation. Still further, the method can comprise using the processing subsystem to consider an acting time, input by the user, for insulin being taken by the user, before generating a new bolus recommendation. Furthermore, the plurality of user defined differing health events can include at least one of an exercise event, a stress event, an illness event and a periodic physiological cycle event.

Still further, a method is disclosed that can be implemented on a non-transitory computer readable medium adapted to run on a processing subsystem, the processing subsystem forming a portion of a handheld diabetes management device for monitoring blood glucose (bG) levels of a diabetic user and determining a total bolus to be provided to the user. The method can comprise using a memory to store:

an upper target bG value for each one of eight different time blocks during a twenty four hour period;

a lower target bG value for each one of the eight different time blocks during the twenty four hour period;

a maximum allowed bG value representing a currently corrected for bG value of the user;

a plurality of user defined health events including an exercise event, a stress event and an illness event, with each one of the health events including a predetermined associated percentage value selected by the user by which a preliminary bolus calculation will be modified to account for one of an increase or a decrease in insulin associated with the health event;

a carbohydrate value input by the user in connection with a meal;

using the processing subsystem to communicate with the memory and obtain the upper target bG value, the lower target bG value, the maximum allowed bG value, one of the user defined health events, and the carbohydrate value input by the user; and to calculate therefrom:

a meal bolus calculated based on the carbohydrate value input by the user, the meal bolus representing an amount of insulin needed to compensate for the carbohydrate value representing the meal;

a correction bolus representing an additional amount of insulin needed beyond the insulin represented by the meal bolus, to bring a bG value exceeding the maximum bG value at least down to the maximum bG value; and a total bolus value obtained by summing the meal bolus and the correction bolus to obtained a summed bolus value, and then modifying the summed bolus value in accordance with the percentage value of a user selected one of the user defined health events; and displaying the total bolus value and the maximum allowed bG value to the user on a display of the device. The processing subsystem can further be adapted to consider an offset time, input by the user, for insulin previously taken by the user, before generating a new bolus recommendation; and an acting time, input by the user, for insulin previously taken by the user, before generating a new bolus recommendation. The processing subsystem can further be adapted to use the information to generate a carbohydrate amount recommendation for the user when the user's bG level is below the minimum allowed bG value.

In another aspect the present disclosure relates to a customizable, handheld diabetes management device for monitoring blood glucose (bG) levels of a diabetic user and determining a total bolus to be provided to the user. The device can comprise a housing adapted to be held in a hand of the user. A memory can be included that is contained in the housing and configured to store information including:

an upper target bG value for each one of eight different time blocks, defined by the user, during a twenty four hour period;

a lower target bG value for each one of the eight different time blocks during the twenty four hour period;

a maximum allowed bG value, defined by the user, representing a hyperglycemic bG value for the user;

a minimum allowed bG value, defined by the user, representing a hypoglycemic bG value for the user;

a plurality of differing user defined health events that each include a predetermined associated percentage value set by the user by which a meal bolus calculation and a correction bolus calculation will each be modified to account for one of an increase or a decrease in insulin associated with each one of the differing health events; and a carbohydrate value input by the user in connection with a meal. A processing subsystem contained in the housing and in communication with the memory is adapted to obtain the information from the memory and to calculate therefrom the meal bolus, the correction bolus, and a recommended total bolus. The recommended total bolus is a sum of the calculated meal bolus and the calculated correction bolus. A display system can also be contained in the housing for displaying a plurality of fields that the user is able to configure to include the information, and for displaying the recommended total bolus to the user. The information can further comprise insulin sensitivity information pertaining to the user, the insulin sensitivity information being input by the user and used by the processing subsystem to modify the calculated meal bolus and the calculated correction bolus prior to calculating the recommended total bolus. The insulin sensitivity information can comprise a plurality of differing insulin sensitivity percentage values input by the user for different ones of the eight different time blocks. Furthermore, the calculated meal bolus is modified by both the insulin sensitivity percentage value and the percentage value associated with one of the user defined health events. Still further, the processing subsystem can be adapted to use the information to generate a carbohydrate amount recommendation for the user when the user's bG level is below the minimum allowed bG value. Moreover, the processing subsystem can be further adapted to consider an offset time, input by the user, for insulin previously taken by the user, before generating a new bolus recommendation. Still further, the processing subsystem can be adapted to consider an acting time, input by the user, for insulin previously taken by the user, before generating a new bolus recommendation. Finally, the plurality of user defined differing health events can include at least one of an exercise event, a stress event, an illness event and a periodic physiological cycle event.

Time Block Manipulation for Insulin Infusion Delivery

It should be understood that although the concepts below are described as relating to diabetes management software systems for tracking and analyzing health data, such as, for example, the ACCU-CHEK® 360® product provided by Roche Diagnostics Corporation, the concepts apply to systems in other areas of healthcare. Moreover, the concepts described herein may also have applicability to apparatuses, methods, systems, and software in fields that are unrelated to healthcare. Furthermore, it should be understood that references in the present disclosure to devices, meters, monitors, or related items are intended to encompass any currently existing or later developed apparatus that includes some or all of the features attributed to the referred to apparatus, including but not limited to the ACCU-CHEK® Active, ACCU-CHEK® Aviva, ACCU-CHEK® Compact, ACCU-CHEK® Compact Plus, and ACCU-CHEK® Advantage, all commercially available from Roche Diagnostics Corporation or divisions thereof.

Figure 53:
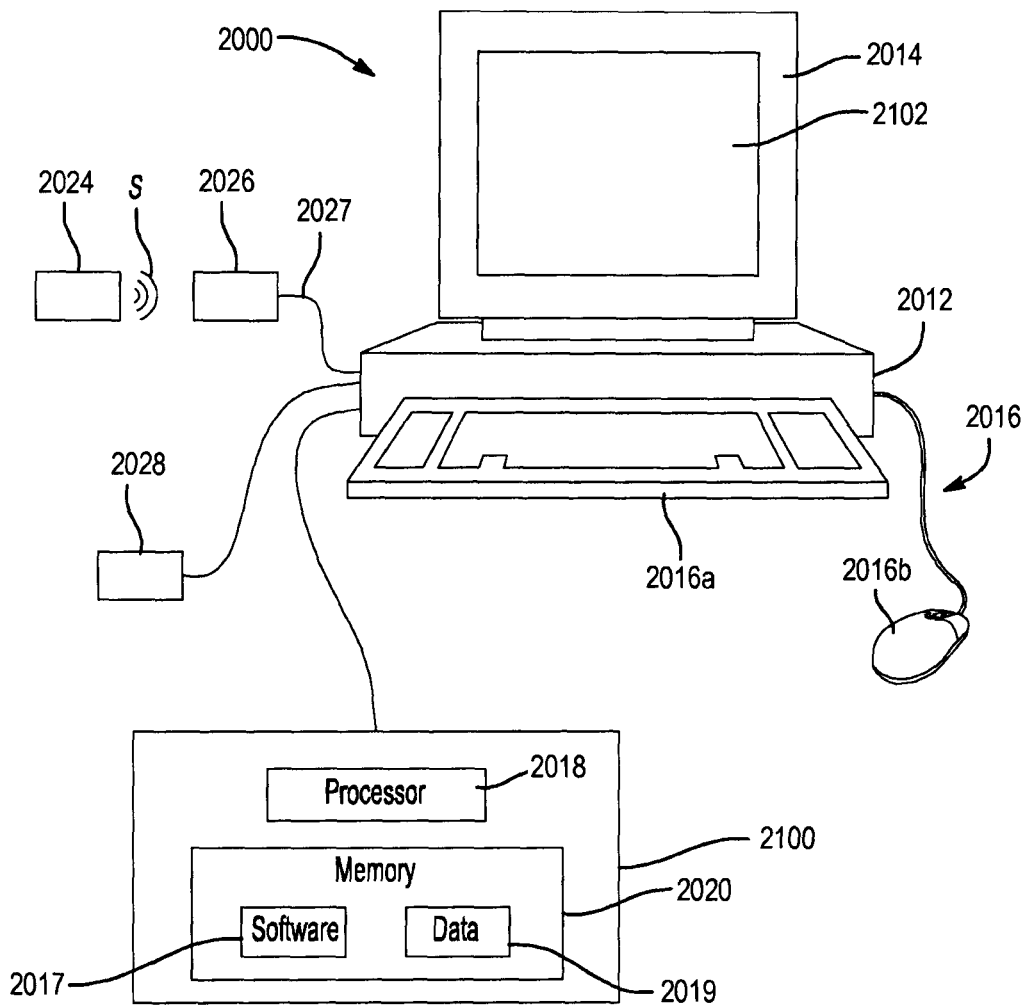
FIG. 53 is a schematic illustration of a computing system in communication with a hand-held diabetes device and a data storage device.

FIG. 53 is a diagram illustrating an exemplary embodiment of a computing system 2000, some or all of the components of which can be used in conjunction with the teachings of the present disclosure. The computing system 2000 can include a variety of computer-readable media. The computer-readable media can be any available media that can be accessed by the computing system 2000 and includes both volatile and non-volatile media, and removable and non-removable media. By way of example, and not limitation, the computer-readable media can comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 2000. The computer-readable media may be accessed directly or through a network such as the Internet.

In one example, the computing system 2000 comprises a system unit 2012 and a display device 2014. As illustrated, the display device 2014 can comprise a computer video screen or monitor. The computing system 2000 can also include at least one user input device 2016. The system unit 2012 includes, as shown in an exploded view at 100, a processor 2018, and memory 2020 that includes software 2017 and data 2019.

In this example, the at least one user input device 2016 comprises a keyboard 2016a and a pointing device 2016b. It should be understood, however, that the at least one user input device 2016 can comprise any suitable device to enable a user to interface with the computing system 2000, such as a touchpad, touch pen, touch screen, keyboard, mouse, joystick, trackball, wireless mouse, or a combination thereof. Furthermore, while the computing system 2000 is described and illustrated herein as comprising the system unit 2012 with the display device 2014, the computing system 2000 could comprise a touchpad or tablet computing device, and further, that the computing system 2000 could be integrated within or be part of a hand-held diabetes management device.

As will be discussed with regard to FIGS. 54 and 61-74, the computing system 2000 can generate a plurality of graphical user interfaces 2102 for display on the display 2014. An exemplary user interface 2102 can comprise at least one or a plurality of interactive screens that can be displayed on the display device 2014. The user interface 2102 can enable the user to manipulate or manage insulin therapy support parameters, such as time blocks and bolus advice settings, and save the parameters on a hand-held diabetes management device 2024.

In this regard, the computing system 2000 can provide information to, and receive information from, the hand-held diabetes management device 2024. In one example, the hand-held diabetes management device 2024 can comprise a hand-held glucose monitor; however, it should be understood that the teachings of the present disclosure also apply to devices such as a programmable insulin pump, or other such devices known or hereafter developed. In FIG. 53, the computing system 2000 can be coupled to a communication media or dongle 2026, which can be attached to the computing system 2000 using a cable 2027. The dongle 2026 is configured to establish logical communication with the hand-held diabetes management device 2024. For example, the dongle 2026 can be a modulated signal transceiver that communicates with the hand-held diabetes management device 2024 by transmitting and receiving a modulated radio-frequency (RF) signal S. In another exemplary embodiment, the computing system 2000 and the hand-held diabetes management device 2024 include ports configured to establish a physical connection. By way of example, the dongle 2026 may include wired media such as a wired network or direct wired connection, and wireless media such as acoustic, RF, infrared and other wireless media. For example, the dongle 2026 can include an infrared port for communication with a corresponding infrared port of the hand-held diabetes management device 2024.

In addition, with continued reference to FIG. 53, the computing system 2000 can include a data storage device 2028. The data storage device 2028 can comprise at least one of RAM, ROM, EEPROM, flash memory or other memory technology, CD-ROM, DVD or other optical disk storage, magnetic cassettes, magnetic tape, magnetic disk storage or other magnetic storage devices, or any other medium which can be used to store computer-readable instructions, software, data structures, program modules and other data and which can be accessed by and written to by the computing system 2000. Thus, the data storage device 2028 can be integral with the system unit 2012 or can be in communication with the computing system 2000 through a suitable connection. For example, the data storage device 2028 can be accessed via a physical connection or a wireless connection, such as a wired network or direct wired connection, and wireless media such as acoustic, RF, infrared, and other wireless media. In one example, as illustrated, the computing system 2000 and the data storage device 2028 may include ports configured to establish a physical connection.

Figure 54:
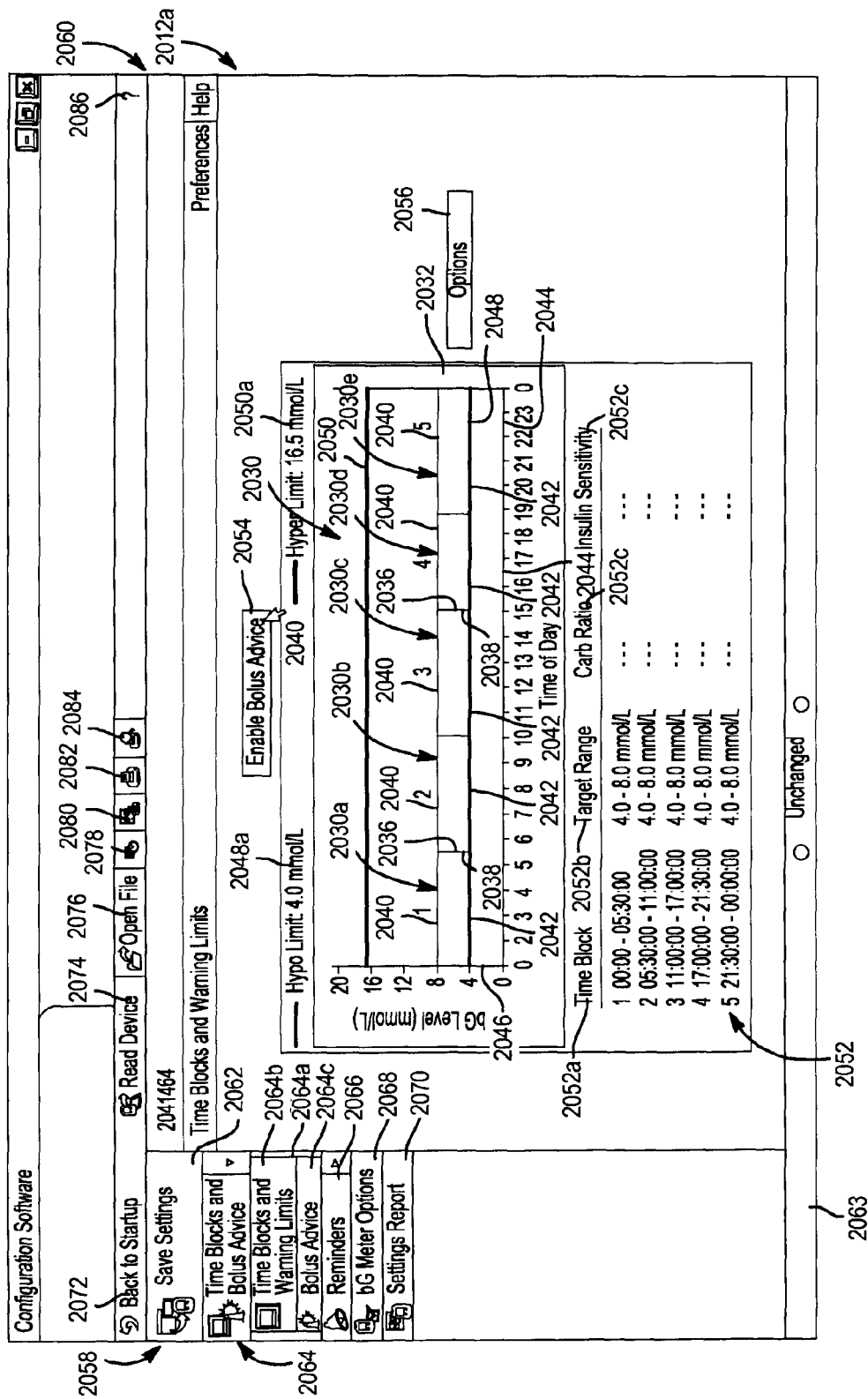
FIG. 54 illustrates an exemplary "Time Blocks and Warning Limits" user interface.

Briefly, with reference to FIG. 54, an exemplary user interface 2102a, "Time Blocks and Warning Limits", of the plurality of user interfaces 2102 is illustrated. The "Time Blocks and Warning Limits" user interface 2102a can include at least one or a plurality of bar structures 2030, which can be arranged as a bar chart 2032. Software components for creating bar charts are commercially available, such as from Dundas Data Visualization Services, Inc. of Toronto, Ontario, Canada. It should be noted that while the "Time Blocks and Warning Limits" user interface 2102a includes five bar structures 2030a-2030e, the "Time Blocks and Warning Limits" user interface 2102a can include any number of bar structures 2030, as will be discussed in greater detail herein.

Each of the plurality of bar structures 2030 can include a first or left side 2036 opposite a second or right side 2038, and a third or top side 2040 opposite a fourth or bottom side 2042. Each of the plurality of bar structures 2030 can graphically illustrate a range of values over a unique time window. In addition, the left side 2036, right side 2038, top side 2040, and bottom side 2042 can be manipulated by the user to select the range of values and unique time window, as will be discussed.

Generally, the "Time Blocks and Warning Limits" user interface 2102a can also include an x-axis 2044, a y-axis 2046, a first or lower boundary line 2048, and a second or upper boundary line 2050. In one example, the x-axis 2044 corresponds to a time of day in hours, and the y-axis 2046 corresponds to a blood glucose (bG) level in millimoles per liter (mmoL/liter). It should be noted that the illustrated scales for the x-axis 2044 and the y-axis 2046 are merely exemplary, and can use any suitable unit of measure for time and bG level, respectively. The location of the left side 2036 of each bar of the plurality of bar structures 2030a-2030e corresponds to a start time of the unique time window for the bar and the right side 2038 corresponds to an end time of the unique time window for the bar. The location of each bottom side 2042 can correspond to a start value or lower target value of a range of bG levels, while the top side 2040 can correspond to an end value or upper target value for the range of bG levels. Each of the plurality of bar structures 2030 can be positioned on or between the lower boundary line 2048 and the upper boundary line 2050. In other words, the lower target value for the range of bG levels (the bottom side 2042) need not be the same value as the lower boundary line 2048.

The lower boundary line 2048 can graphically represent a hypoglycemic warning limit for the user's bG level, and can comprise a horizontal line. As will be discussed, the user can use the at least one user input device 2016 to move or position the lower boundary line 2048 between the bottom side 2042 having the lowest value and the x-axis 2044 to enable the user to select a desired hypoglycemic warning limit based on the user's particular health needs. The particular bG level selected from the y-axis that corresponds to the lower boundary line 2048 can be displayed as a "Hypo Limit" 2048a on the "Time Blocks and Warning Limits" user interface 2102a.

The upper boundary line 2050 can graphically represent a hyperglycemic warning limit for the user's bG level, and can comprise a horizontal line. As will be discussed, the user can use the at least one user input device 2016 to move or position the upper boundary line 2050 above the lower boundary line 2048 to enable the user to select a desired hyperglycemic warning limit based on the user's particular health needs. The particular bG level selected from the y-axis that corresponds to the upper boundary line 2050 can be displayed as a "Hyper Limit" 2050a on the "Time Blocks and Warning Limits" user interface 2102a.

For purposes of illustration only, the bar structure 2030a covers a time period beginning at the left side 2036 of the bar structure 2030a and ending at the right side 2038 of the bar structure 2030a. The bar structure 2030a graphically illustrates upper and lower blood sugar limits applied during the time period. The upper limit is indicated by the top side 2040 and the lower limit is indicated by the bottom side 2042. In the depicted example, the lower limit (bottom side 2042) is at the same level as the overall hypoglycemic limit ("Hypo Limit") 48. In various implementations, the lower limit (bottom side 2042) can not be set lower than the overall hypoglycemic limit 2048. Meanwhile, the upper limit (top side 2040) is set below the overall hyperglycemic limit ("Hyper Limit") 2050. In various implementations, the upper limit (top side 2040) can not be set higher than the overall hyperglycemic limit 2050.

In various implementations, the upper limit (top side 2040) and the lower limit (bottom side 2042) can be set individually for each of the bar structures 2030. In addition, the beginning (left side 2036) and end (right side 2038) can be adjusted for each of the bar structures 2030. Further, the number of bar structures 2030 can be adjusted to change the number of time periods for which limit adjustments can be made.

The "Time Blocks and Warning Limits" user interface 2102a can also include a summary section 2052, a "Bolus Advice" button 2054 and an "Options" button 2056. The term "selector" and "button" as used herein can denote any appropriate user selection device that activates a feature on the user, interface, such as a scroll bar, radio button, checkbox, button, drop-down menu, link or combinations thereof. The summary section 2052 can be positioned adjacent to the bar chart 2032, and can list the data associated with each of the bar structures 2030a-2030e in a tabular format. Exemplary headings for the summary section 2052 include a "Time Block" heading 2052a, a "Target Range" heading 2052b, a "Carb Ratio" heading 2052c and an "Insulin Sensitivity" heading 2052d. As will be discussed in greater detail herein, the summary section 2052 can be populated by the control module 2100.

The "Time Block" heading 2052a can comprise the start time of day value and the end time of day value for the particular time window, based on the location of the first side 2036 and the third side 2038 of each bar structure 2030. The "Target Range" heading 2052b can comprise a start value or lower target value for the range of bG levels and an end value or upper target value for the range of bG values based on the location of the bottom side 2042 and the top side 2040 of each of the bar structures 2030.

Each of the "Carb Ratio" heading 2052c and the "Insulin Sensitivity" heading 2052d can be populated when the "Bolus Advice" button 2054 is selected, as will be discussed in greater detail herein. If populated, the "Carb Ratio" heading 2052c can comprise a user specific ratio of a number of units of insulin needed per a particular number of grams of carbohydrates for the time window and range of bG levels associated with each bar structure 2030. The "Insulin Sensitivity" heading 2052d can comprise a user-specific ratio of a number of units of insulin needed to affect a particular numeric change in the user's bG level for the period of time associated with the particular bar structure 2030.

The "Bolus Advice" button 2054 can enable the user to select whether to enable bolus advice data for each of the bar structures 2030. The "Bolus Advice" button 2054 can be positioned adjacent to or above the bar chart 2032. As will be discussed herein, bolus advice data can comprise recommendations for the user if the value of the user's bG level falls outside of the range of bG levels identified for the respective bar structure 2030 based on the carb ratio data and insulin sensitivity data associated with the particular bar structure 2030. If the "Bolus Advice" button 2054 is disabled, the "Bolus Advice" button 2054 can display "Enable Bolus Advice." If the "Bolus Advice" button 2054 is enabled, then the "Bolus Advice" button 2054 can instead display "Disable Bolus Advice." In addition, if the "Bolus Advice" button 2054 is enabled, then the control module 2100 can display various bolus advice set-up user interfaces, as will be discussed further herein with reference to FIGS. 66-70.

The selection of the "Options" button 2056 can cause the control module 2100 to generate a "Time Blocks" user interface 2102r that allows the user to manipulate each of the first side 2036, second side 2038, top side 2040 and bottom side 2042 of the bar structures 2030, add or remove bar structures 2030, and adjust the position of the lower boundary line 2048 and the upper boundary line 2050, as will be discussed further herein with regard to FIG. 73. The "Options" button 2056 can be positioned generally adjacent to or to the side of the bar chart 2032.

In addition, as will be discussed, various ones of the plurality of user interfaces 2102 can each include a first or main menu 2058, a second or sub menu 2060 and a status indicator 2061. Generally, the main menu 2058 can include a "Save Settings" selector 2062, a "Time Blocks and Bolus Advice" menu selector 2064, a "Reminders" menu selector 2066, a "bG Meter Options" selector 2068 and a "Settings Report" selector 2070. The main menu 2058 can be positioned or anchored substantially vertically on a left side of each user interface 2102, however, the main menu 2058 could be positioned or anchored at any desired location on the user interface 2102.

The "Save Settings" selector 2062 can enable the user to save the data input to the user interface 2102 to the hand-held diabetes management device 2024 or to the data storage device 2028. The user interface associated with the "Save Settings" selector 2062 will be discussed with regard to FIGS. 71-72.

The "Time Blocks and Bolus Advice" menu selector 2064 can provide a drop-down menu 2064a, which can include a "Time Blocks and Warning Limits" button 2064b and a "Bolus Advice" button 2064c. The selection of the "Time Blocks and Warning Limits" button 2064b can display the "Time Blocks and Warning Limits" user interface 2102a illustrated in FIG. 54. The "Bolus Advice" button 2064c can display a "Bolus Advice" user interface 2102s, as will be discussed with regard to FIG. 74.

The features of the "Reminders" menu selector 2066, the "bG Meter Options" selector 2068 and the "Settings Report" selector 2070 are beyond the scope of the present disclosure. Briefly, however, the "Reminders" menu selector 2066 can display a user interface, which can enable the user to enter specific reminders that are associated with the management of the user's diabetes, such as a bG check reminder, a date reminder for a doctor's appointment, and alarm clocks that can be set to remind the user to perform specific tasks. The "bG Meter Options" selector 2068 can display a user interface, which can enable the user to change or update settings specific to their hand-held diabetes management device 2024, such as the language, date and time format, Bluetooth setting, unit settings (grams, units), maximum bolus dosage recommendation, sound and vibrate settings, and whether to lock the keys on the hand-held diabetes management device 2024 (i.e. "keylock"). The "Settings Report" selector 2070 can display a user interface, which can enable the user to view the current settings on their hand-held diabetes management device 2024 and the changes made to the settings via user input to the user interface 2102.

The sub menu 2060 can be arranged generally horizontally on the user interface 2102, and can be positioned above the main menu 2058. It should be noted, however, that the sub menu 2060 could be positioned or anchored at any desired location on the user interfaces 2102. The sub menu 2060 can include a "Back to Startup" button 2072, a "Read Device" button 2074, an "Open File" button 2076, a "Set Date and Time" button 2078, a "Create Pump/Meter Report" button 2080, a "Print" button 2082 and a "Print Preview" button 2084. Additionally, the sub menu 2060 can include a "Help" button 2086.

The "Back to Startup" button 2072, if selected, can display a "Startup" user interface 2102b, as will be discussed with regard to FIG. 61. The "Read Device" button 2074, if selected, can display a "Read From Device" user interface 2102c, as will be discussed with regard to FIG. 62. The "Open File" button 2076, if selected, can display an "Open File" user interface 2102e, as will be discussed with regard to FIG. 64. The "Set Date and Time" button 2078, if selected, can display a "Set Date and Time" user interface 2102f, as will be discussed with regard to FIG. 65. The features of the "Create Pump/Meter Report" button 2080 are beyond the scope of the present disclosure. Briefly, however, if selected, the "Create Pump/Meter Report" button 2080 can generate a series of user interfaces that can enable the user to pair an insulin pump to the hand-held diabetes management device 2024 and generate a report.

The "Print" button 2082, if selected, can generate a user interface that can allow the user to print a configuration settings report, which can include at least information regarding the current configuration of the bar chart 2032. The "Print Preview" button 2084, if selected, can provide the user with a user interface, which can display a preview of the configuration settings report prior to printing.

The status indicator 2063 can provide the user with a graphical illustration as to the status of the time block and bolus advice settings displayed on the user interfaces 2102. In this regard, if the user has modified the user interfaces 2102 via the at least one user input device 2016, then the status indicator 2063 can indicate "When ALL changes are complete, click "Save Settings to Device and/or File." If changes have not been made to the time block or bolus advice settings, then the status indicator 2063 can display a suitable indicator such as "Unchanged." It should be noted that the statements displayed by the status indicator 2063 are merely exemplary, as the status indicator 2063 could display any other suitable phrase or instruction, and/or could display different colors, such as red and green, etc.

Figure 55:
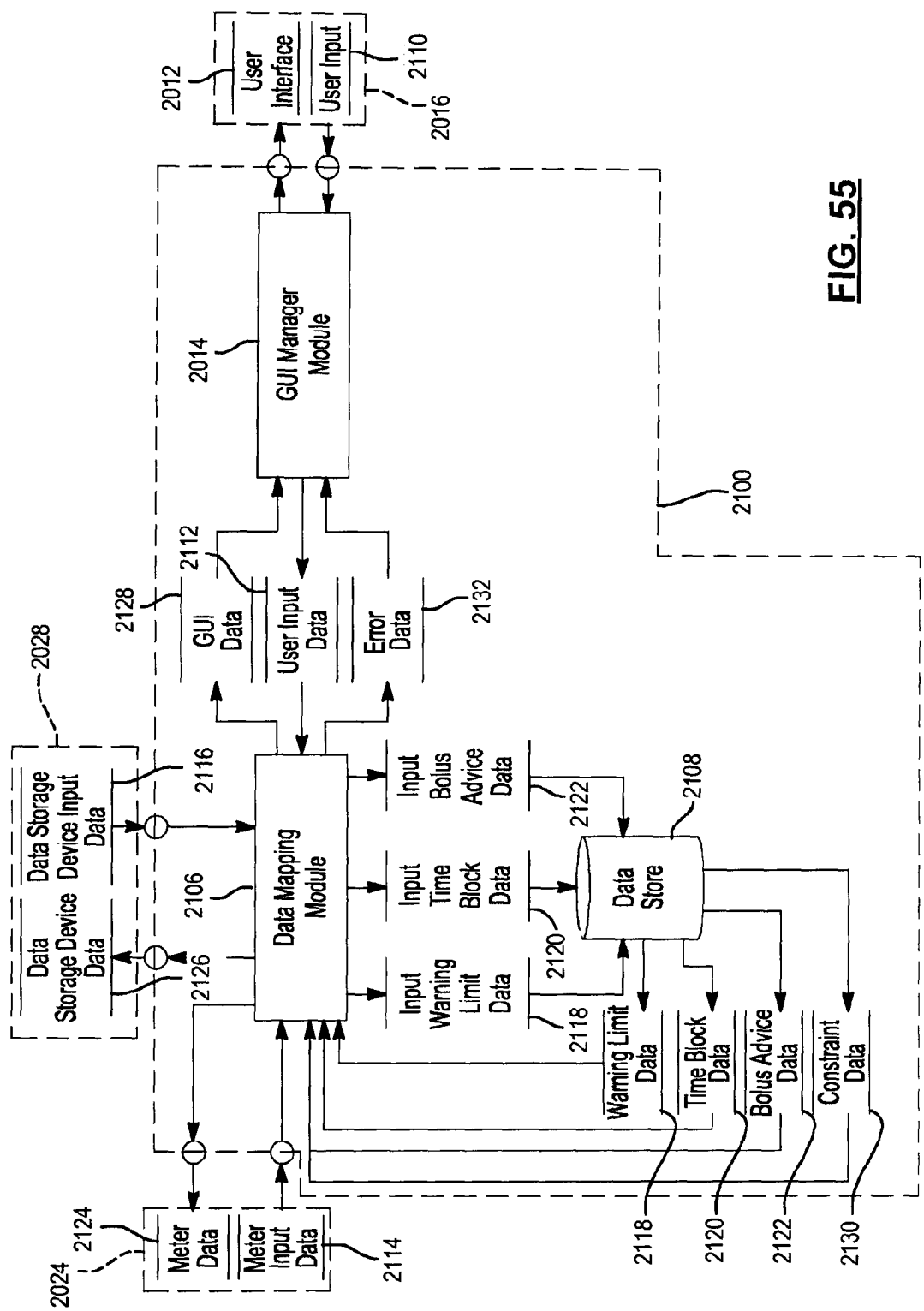
FIG. 55 is a dataflow diagram illustrating an exemplary control system performed by a control module.

Generally, with reference now to FIG. 55, a dataflow diagram illustrates various components of a user interface control system that can be embedded within the control module 2100. The control module 2100 can generate the plurality of user interfaces 2102 for display on the display device 2014. Various embodiments of the user interface control system according to the present disclosure can include any number of sub-modules embedded within the control module 2100. The sub-modules shown may be combined and/or further partitioned to similarly generate the user interfaces 2102. Further, the control module 2100 can comprise one or more software modules embodied in non-transitory, machine readable code that runs on the processor 2018. Inputs to the system can be received from the hand-held diabetes management device 2024, the data storage device 2028, the user input devices 2016, or even received from other control modules (not shown) within the computing system 2000, and/or determined by other sub-modules (not shown) within the control module 2100 (not shown).

With reference to FIG. 55, the control module 2100 can include a graphical user interface (GUI) manager module 2104, a data mapping module 2106 and a data store 2108. The graphical user interface manager module 2104 can generate the user interface 2102 to enable a user to manipulate various insulin therapy support parameters, such as those graphically associated with the bar structures 2030, lower boundary line 2048, upper boundary line 2050, along with the bolus advice data parameters, which can be saved to the hand-held diabetes management device 2024 or the data storage device 2028. The graphical user interface manager module 2104 can receive as input user input 2110, which can be received from the at least one user input device 2016. The user input 2110 can comprise an input to the user interface 2102 from the at least one user input device 2016 to adjust one or more of the left side 2036, right side 2038, top side 2040 and/or bottom side 2042 of the plurality of bar structures 2030, a location for the lower boundary line 2048, a location of the upper boundary line 2050, a request to add a new bar structure 2030, a carb ratio for a particular bar structure 2030, an insulin sensitivity value for a particular bar structure 2030, etc.

The graphical user interface manager module 2104 can also receive graphical user interface data 2128 and error data 2132 as input from the data mapping module 2106. The graphical user interface data 2128 and error data 2132 can each comprise instructions regarding the creation of the user interfaces 2102, as will be discussed. The graphical user interface manager module 2104 can set user input data 2112, which comprises the user input 2110, for the data mapping module 2106, and can output the user interfaces 2102 based on the graphical user interface data 2128 and error data 2132.

The data mapping module 2106 can receive as input the user input data 2112. The data mapping module 2106 can also receive as input meter input data 2114, data storage device input data 2116 and constraint data 2130. The meter input data 2114 can comprise data input by the user to the hand-held diabetes management device 2024, such as a hyperglycemic warning limit, a hypoglycemic warning limit, time blocks, carb ratios for a particular time block and/or insulin sensitivity for a particular time block. The meter input data 2114 can be read from the hand-held diabetes management device 2024, when the user selects to the "Read From Device" button 2074 (FIG. 54).

The data storage device input data 2116 can comprise data read from the data storage device 2028, which can include a hyperglycemic warning limit, a hypoglycemic warning limit, time blocks, carb ratios for a particular time block and/or insulin sensitivity for a particular time block. The data storage device input data 2116 can be read from the data storage device 2028 when the user selects to the "Open from File" button 2076 (FIG. 54).

The constraint data 2130 can be received as input from the data store 2108. The constraint data 2130 can include one or more rules regarding the data values for the hyperglycemic warning limit, the hypoglycemic warning limit and the time blocks, which can be applied to constrain or limit the manipulation of the upper boundary line 2048, lower boundary line 2050 and bar structures 2030 by the user input device 2016. Exemplary constraint data 2130 can include the limitation that each bar structure 2030 is confined to a unique time window, such that adjacent bar structures 2030 cannot overlap, that the upper boundary line 2050 cannot be positioned below the lower boundary line 2048, and that the bar structures 2030 are to be positioned between the upper boundary line 2050 and the lower boundary line 2048. Additional constraints can include particular data value minimums for the lower boundary line 2048 and the upper boundary line 2050, a maximum number of bar structures 2030, a minimum number of bar structures 2030, etc.

Based on the user input data 2112, the meter input data 2114, the data storage device input data 2116 and the constraint data 2130, the data mapping module 2106 can determine warning limit data 2118, time block data 2120, bolus advice data 2122 and error data 2132. The data mapping module 2106 can determine the warning limit data 2118 based on both the hypoglycemic warning limit and hyperglycemic warning limit received from the meter input data 2114 or the data storage device input data 2116. The warning limit data 2118 can also comprise the location of the lower boundary line 2048 and the upper boundary line 2050 received from the user input data 2112. For example, the data mapping module 2106 can map or assign a hypoglycemic warning limit to the location of the lower boundary line 2048 as received from the user input data 2112. As a further example, the data mapping module 2106 can map or assign the hyperglycemic warning limit to the location of the upper boundary line 2050 as received from the user input data 2112. The hyperglycemic warning limit and the hypoglycemic warning limit can be saved as warning limit data 2118 by the data mapping module 2106 in the data store 2108.

The data mapping module 2106 can determine the time block data 2120 based on both the time blocks received from the meter input data 2114 or the data storage device input data 2116. The time block data 2120 can also comprise the location of the plurality of bar structures 2030 received from the user input data 2112. For example, the data mapping module 2106 can map or assign the start time of day to the location of the left side 2036 of each of the bar structures 2030 as received from the user input data 2112. As a further example, the data mapping module 2106 can map or assign the end time of day to the location of the right side 2038 of each of the bar structures 2030 as received from the user input data 2112, and the data mapping module 2106 can map or assign the low bG level for a range of bG levels to the location of the bottom side 2042 of each of the bar structures 2030 as received from the user input data 2112: Further, the data mapping module 2106 can map or assign the high bG level for the range of bG levels to the location of the top side 2040 of each of the bar structures 2030 as received from the user input data 2112.

Thus, the data mapping module 2106 can generate time block data 2120 based on the locations of the bar structures 2030 on the user interface 2102. In general, the time block data 2120 can comprise a start time of day data value, an end time of day data value, a low bG level data value and a high bG level data value. In other words, the time block data 2120 can comprise a plurality of unique time windows, each of which can have a specified range of bG levels during the respective time window. The start time of day data value, the end time of day data value, the low bG level data value and the high bG level data value can be saved by the data mapping module 2106 as time block data 2120 in the data store 2108.

The data mapping module 2106 can determine the bolus advice data 2122 based on the bolus advice received from the meter input data 2114 or the data storage device input data 2116. The bolus advice data 2122 can also comprise the carb ratio data and the insulin sensitivity data for each of the bar structures 2030 as received by the user input data 2112. The carb ratio data and the insulin sensitivity data can be saved by the data mapping module 2106 as bolus advice data 2122 in the data store 2108.

The data mapping module 2106 can determine the error data 2132 based on the user input data 2112 received as input and the constraint data 2130. In this regard, if the user input data 2112 includes requests to manipulate the user interface 2102 that conflict with the constraint data 2130, then the data mapping module 2106 can set error data 2132 for the graphical user interface manager module 2104. The graphical user interface manager module 2104 can then display the error data 2132 on the user interface 2102.

The data mapping module 2106 can retrieve the stored warning limit data 2118, the time block data 2120 and the bolus advice data 2122 from the data store 2108 and can output the stored warning limit data 2118, the time block data 2120 and the bolus advice data 2122 as meter data 2124 for the hand-held diabetes management device 2024 based on the user input data 2112. In this regard, the data mapping module 2106 can output the meter data 2124 in request to the user selecting the "Save Settings" button 2062 from the sub menu 2060 (FIG. 54).

In addition, the data mapping module 2106 can retrieve the stored warning limit data 2118, the time block data 2120 and the bolus advice data 2122 from the data store 2108 and can output the stored warning limit data 2118, the time block data 2120 and the bolus advice data 2122 as data storage device data 2126 for the data storage device 2028 based on the user input data 2112. In this regard, the data mapping module 2106 can output the data storage device data 2126 in request to the user selecting the "Save Settings" button 2062 from the sub menu 2060 (FIG. 54).

The data mapping module 2106 can retrieve the stored warning limit data 2118, the time block data 2120 and the bolus advice data 2122 from the data store 2108 and can set the stored warning limit data 2118, the time block data 2120 and the bolus advice data 2122 as graphical user interface data 2128 for the graphical user interface module based on the user input data 2112. The graphical user interface data 2128 can be displayed as the summary data 2052, or could be displayed initially on the "Time Blocks and Warning Limits" screen 2102a (FIG. 54). In this regard, the data mapping module 2106 can set the graphical user interface data 2128 for the graphical user interface module 2102 in response to the user selecting the "Open File" button 2076 from the sub menu 2060 (FIG. 54).

The data store 2108 can comprise one or more data storage devices, which can be at least one of a RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules and other data associated with the control module 2100. The data store 2108 can store the warning limit data 2118, the time block data 2120 and the bolus advice data 2122 received from the data mapping module 2106, and can also set the stored warning limit data 2118, the time block data 2120 and the bolus advice data 2122 for retrieval by the data mapping module 2106. The data store 2108 can also store the constraint data 2130, which can be retrieved by the data mapping module 2106.

Figure 56:
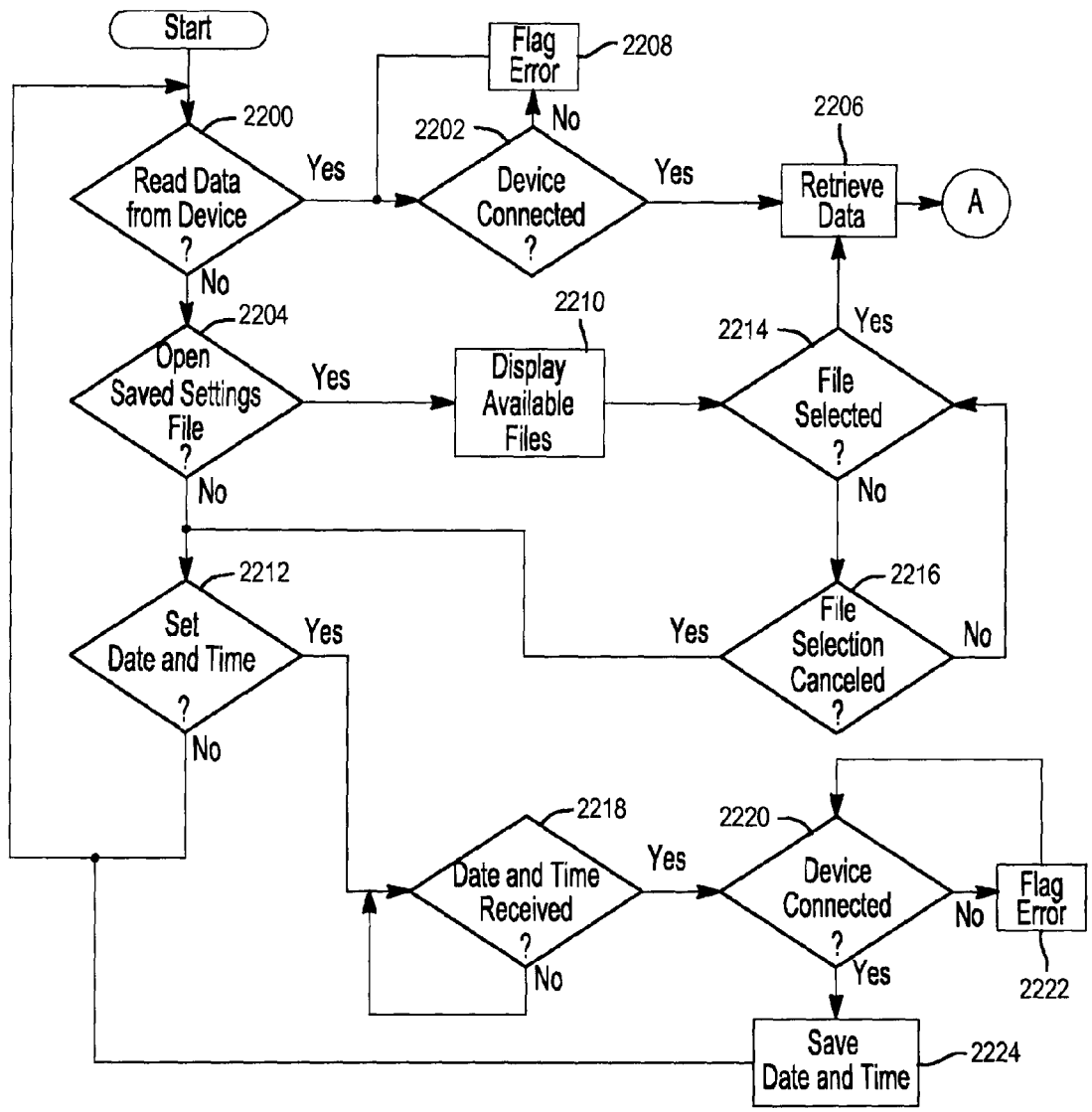
FIG. 56 is a flowchart illustrating a method performed by the control module.

With reference now to FIG. 56, a flowchart diagram illustrates an exemplary method performed by the control module 2100. It should be noted that the flowchart diagram described herein with regard to FIGS. 56-59 is merely exemplary, as the control module 2100 could generate the plurality of user interfaces 2102 in any desired or user requested sequence. With continued reference to FIG. 56, at decision block 2200 the method can determine if a request to retrieve data from the hand-held diabetes device 2024 has been received. If a request to retrieve data from the hand-held diabetes device 2024 has been received, then the method can go to decision block 2202. Otherwise, the method can go to decision block 2204.

At decision block 2202, the method can determine if the hand-held diabetes device 2024 is connected so as to be in communication with the computing system 2000. If the hand-held diabetes device 2024 is connected, then the method can go to block 2206. Otherwise, the method goes to block 2208 and flags an error. At block 2206 the method can retrieve the meter input data 2114. Then, the method can go to A on FIG. 57.

With continued reference to FIG. 56, at decision block 2204 the method can determine if a request has been received to open a saved data file, such as a data file stored on the data storage device 2028. If a request has been received to open a saved data file, the method can go to block 2210. Otherwise, the method can go to decision block 2212. At block 2210, the method can display an "Open a Settings File" user interface 2102e (FIG. 65), which can list available data files. Then, the method can go to decision block 2214.

At decision block 2214 the method can determine if a data file has been selected. If a data file has been selected, the method goes to block 2206. Otherwise, the method goes to decision block 2216. At decision block 2216, the method determines if the data file selection has been cancelled. If the file selection has been cancelled, then the method can go to decision block 2212. Otherwise, the method loops to decision block 2214.

At decision block 2212, the method can determine if a request has been received to set the date and time on the hand-held diabetes device 2024. If no request has been received, the method can loop to decision block 2200. Otherwise, the method can go to decision block 2218. At decision block 2218, the method can determine if the date and time have been entered via the at least one user input device 2016. Alternatively, the input from the at least one user input device 2016 can comprise a request to set the date and time to that of the computing system 2000. If the date and time have been received, then the method can go to decision block 2220. Otherwise, the method can loop until user input 2110 is received.

At decision block 2220, the method can determine if the hand-held diabetes device 2024 is connected so as to be in communication with the computing system 2000. If the hand-held diabetes device 2024 is not connected, the method can go to block 2222. At block 2222, the method can flag an error and then loop to decision block 2220. If the hand-held diabetes device 2024 is connected so as to be in communication with the computing system 2000, then the method can go to block 2224. At block 2224, the method can save the date and time to the hand-held diabetes device 2024. Then, the method can loop to decision block 2200.

Figure 57:
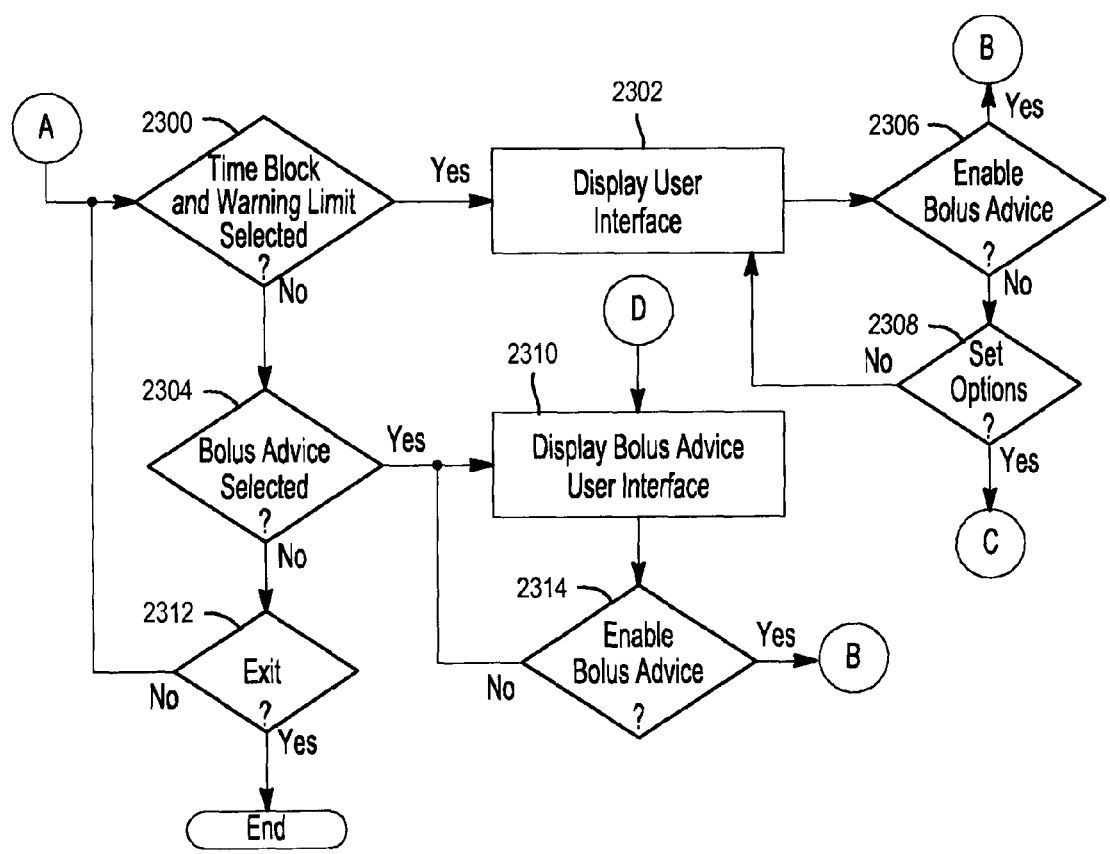
FIG. 57 is a continuation of the flowchart of FIG. 56 at A.

With reference to FIG. 57, starting at A, the method can go to decision block 2300. At decision block 2300, the method can determine if the "Time Blocks and Warning Limits" button 2064*b* has been selected. If the "Time Blocks and Warning Limits" button 2064*b* is selected, then the method can go to block 2302. Otherwise, the method can go to decision block 2304.

At block 2302, the method can display the "Time Blocks and Warning Limits" user interface 2102*a*. Then, the method can go to decision block 2306. At decision block 2306, the method can determine if the "Bolus Advice" button 2064*c* has been selected. If the "Bolus Advice" button 2064*c* has been selected, then the method can go to B on FIG. 58. Otherwise, the method can go to decision block 2308. At decision block 2308, the method can determine if the "Options" button 2056 has been selected. If the "Options" button 2056 has not been selected, then the method can loop to block 2302. Otherwise, the method goes to C on FIG. 58.

Figure 74:
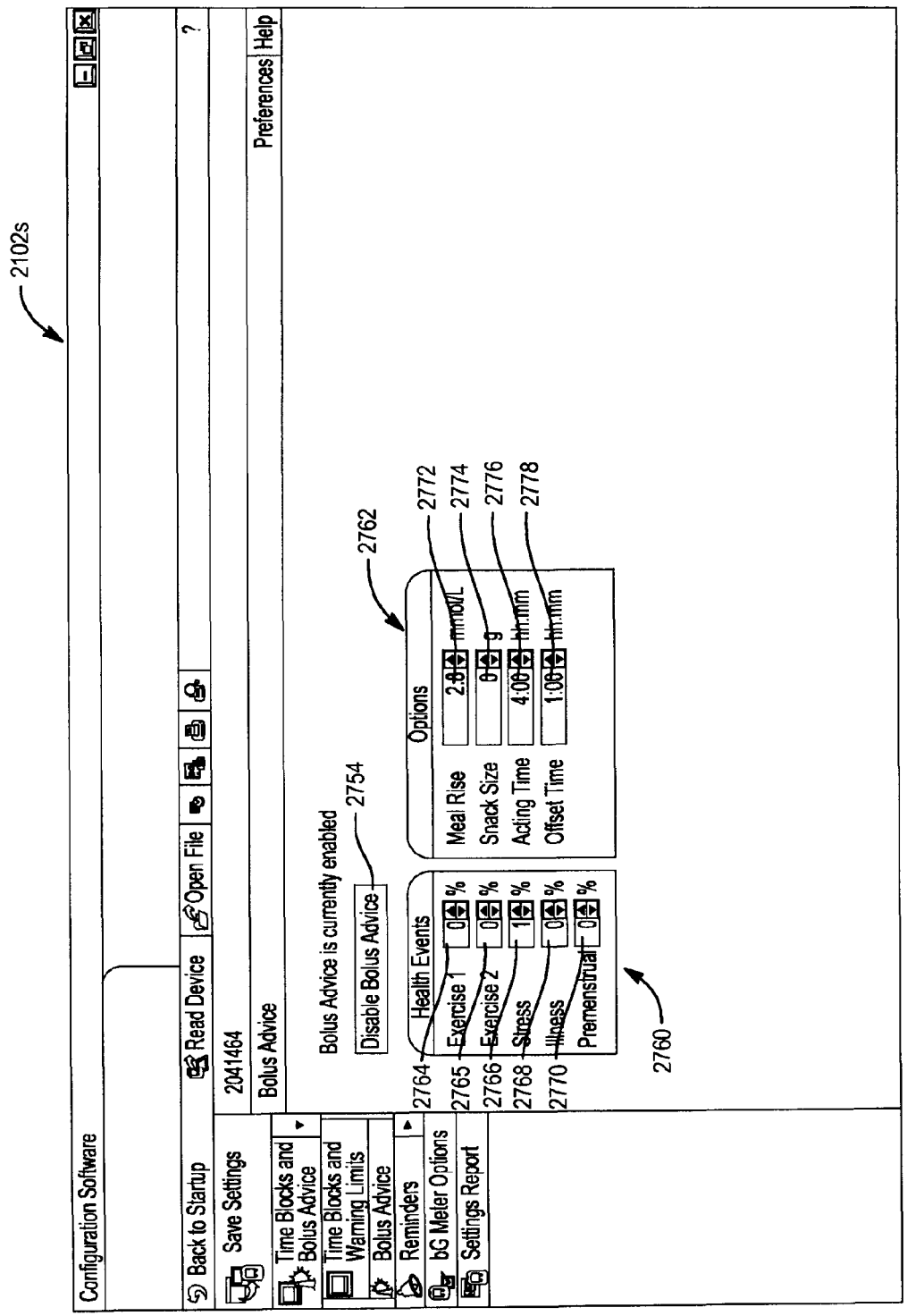
FIG. 74 illustrates an exemplary "Bolus Advice" user interface.

With reference to FIG. 57, at decision block 2304, the method can determine if the "Bolus Advice" button 2064*c* has been selected. If the "Bolus Advice" button 2064*c* has been selected, the method can go to block 2310. Otherwise, the method goes to block 2312. At block 2310, the method can display the "Bolus Advice" user interface 2102*s* (FIG. 74). Then, the method can go to decision block 2314.

At decision block 2314, the method can determine whether the "Bolus Advice" button 2054 has been selected. If the "Bolus Advice" button 2054 has been selected, then the method can go to B on FIG. 58. Otherwise, the method can loop to block 2310. At decision block 2312, the method can determine if an exit request has been received. If a request to exit has been received the method can end. Otherwise, the method can loop to decision block 2300.

Figure 58:
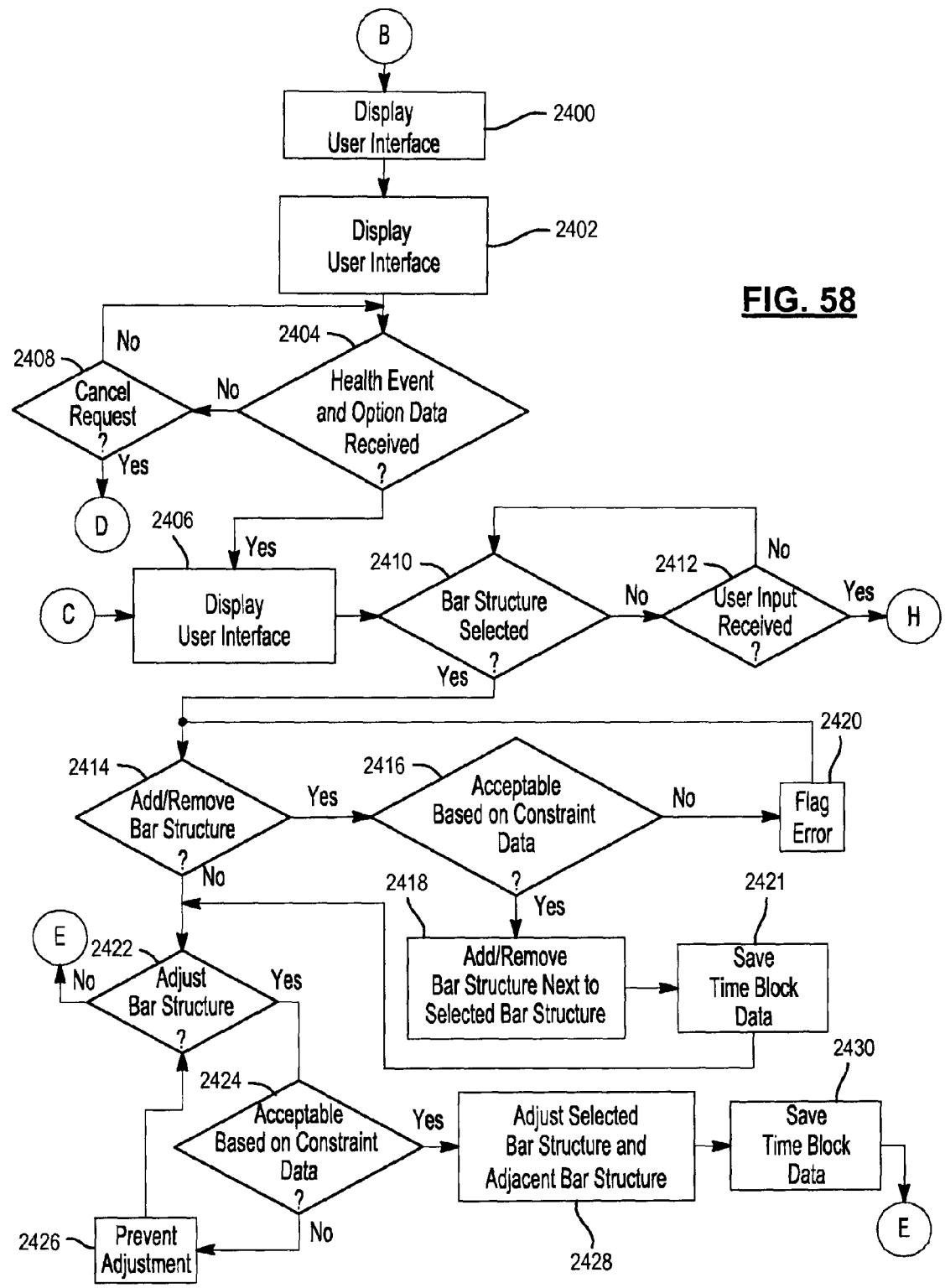
FIG. 58 is a continuation of the flowchart of FIG. 57 at B.
Figure 66:
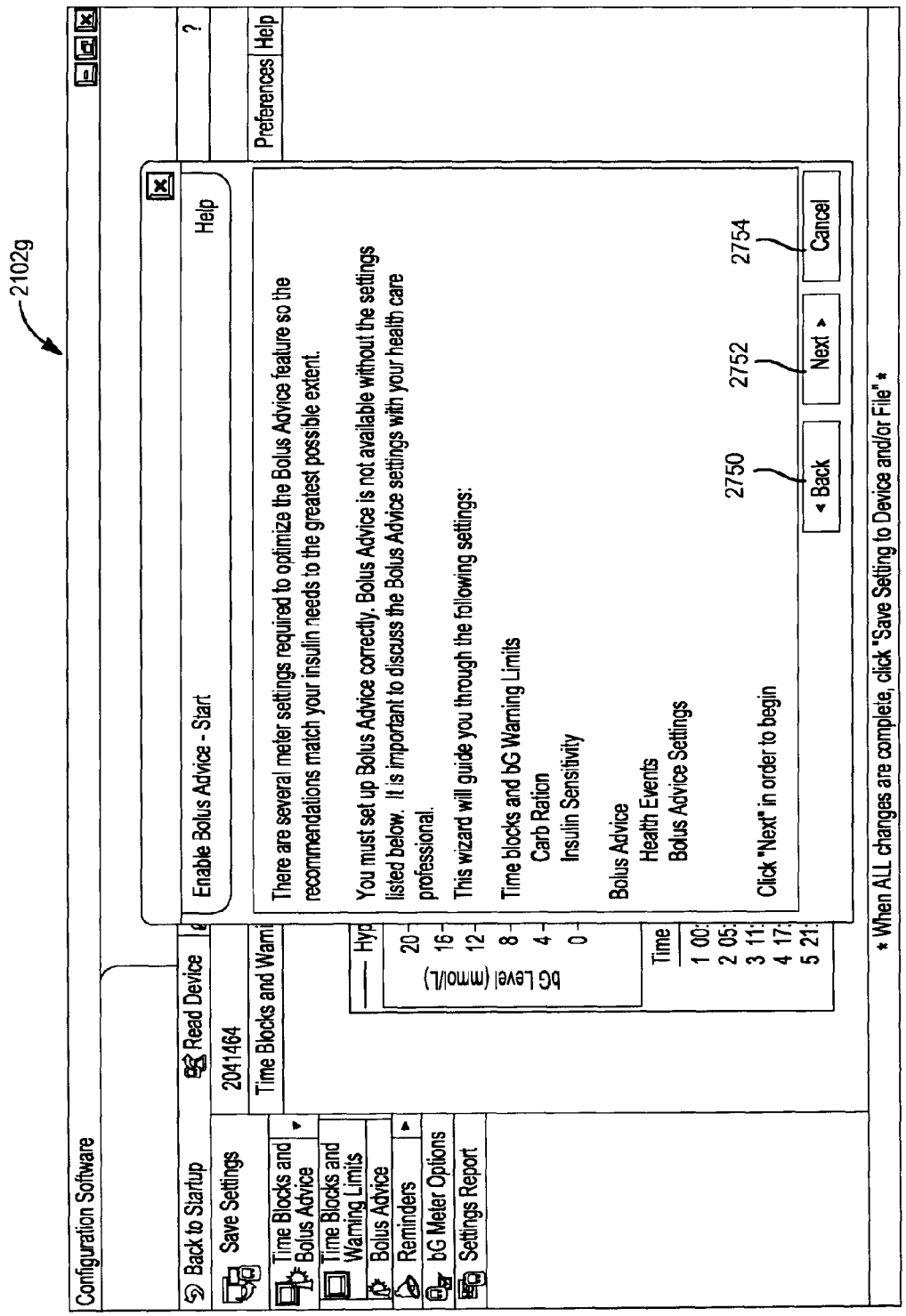
FIG. 66 illustrates an exemplary "Enable Bolus Advice-Start" user interface.
Figure 67:
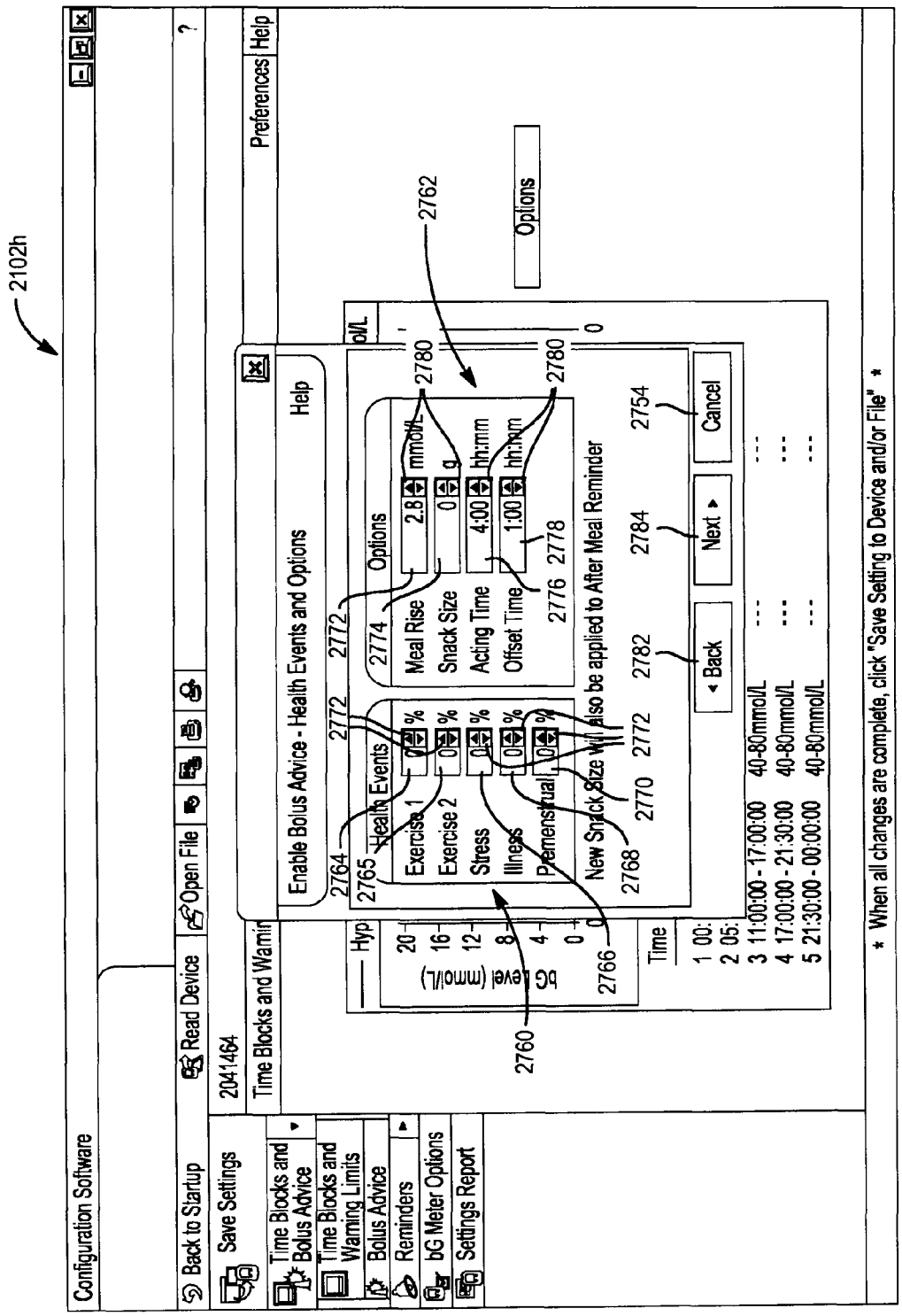
FIG. 67 illustrates an exemplary "Enable Bolus Advice-Health Events and Options" user interface.

With reference to FIG. 58, starting at B, the method can go to block 2400. At block 2400, the method can display an "Enable Bolus Advice-Start" user interface 2102*g* (FIG. 66). Then, at block 2402, the method can display a "Enable Bolus Advice-Health Events and Options" user interface 2102*h* (FIG. 67). At decision block 2404, the method can determine if health event and options data has been received via the at least one user input device 2016. If the health event and option data has been received, then the method can go to block 2406. Otherwise, the method goes to decision block 2408.

At decision block 2408, the method determines if a cancel request has been received through the at least one user input device 2016. If the cancel request has been received, then the method goes to D on FIG. 57. If the cancel request has not been received, then method loops to decision block 2404.

Figure 68A:
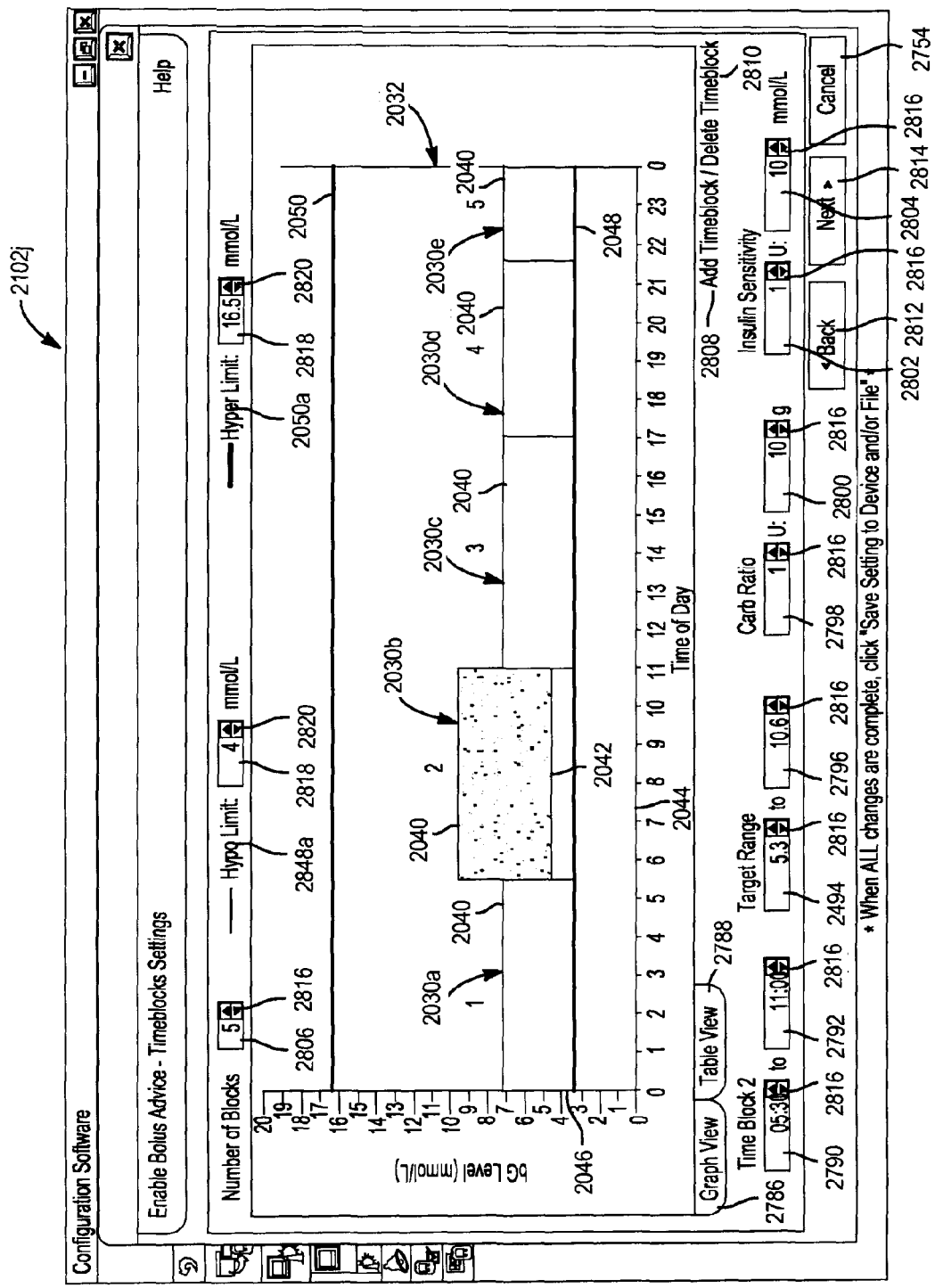
FIG. 68A illustrates an exemplary "Enable Bolus Advice-Timeblocks Settings" user interface.
Figure 68B:
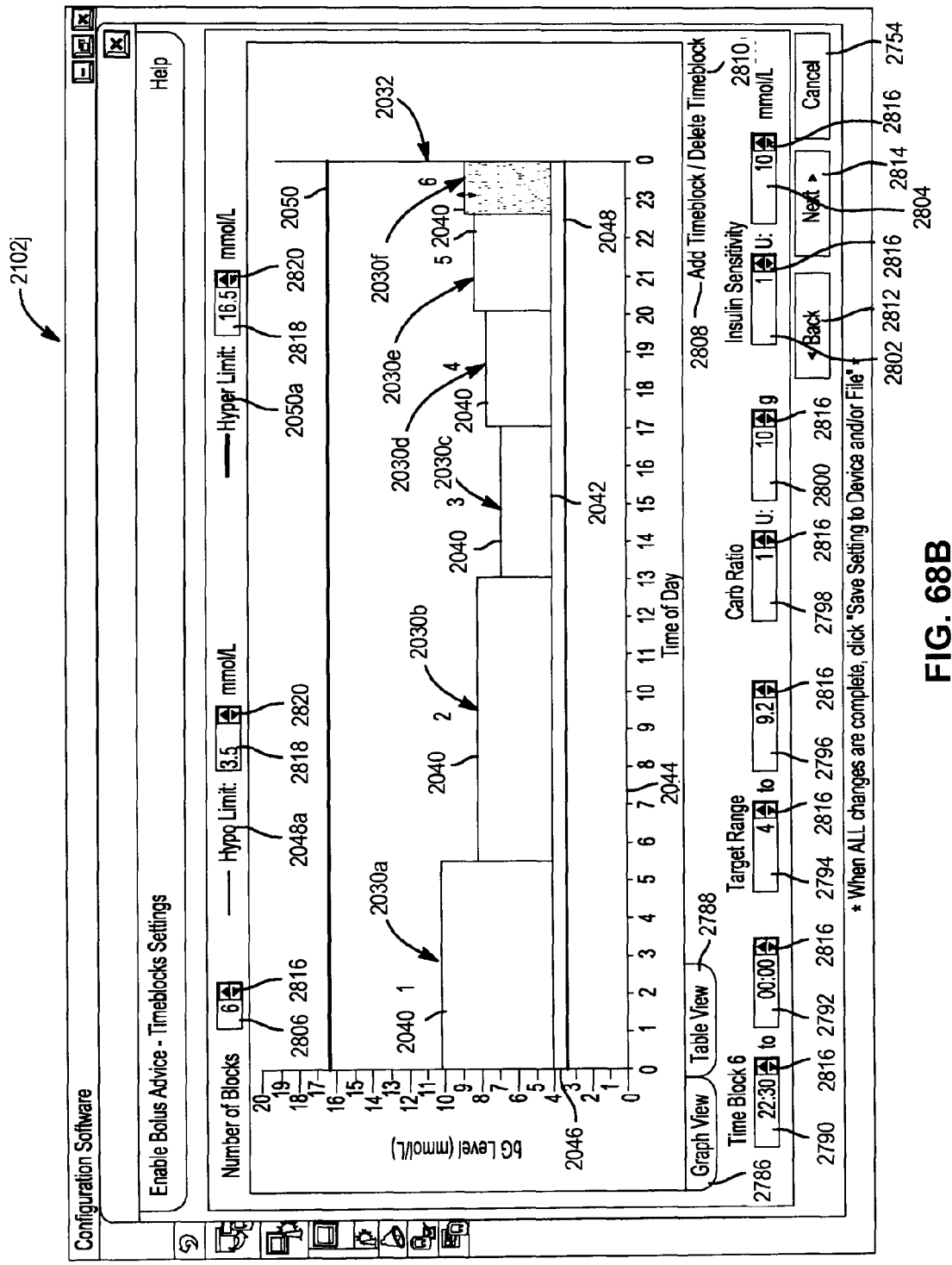
FIG. 68B illustrates the "Enable Bolus Advice-Timeblocks Settings" user interface of FIG. 68A in which the user interface illustrates an additional bar structure.
Figure 68C:
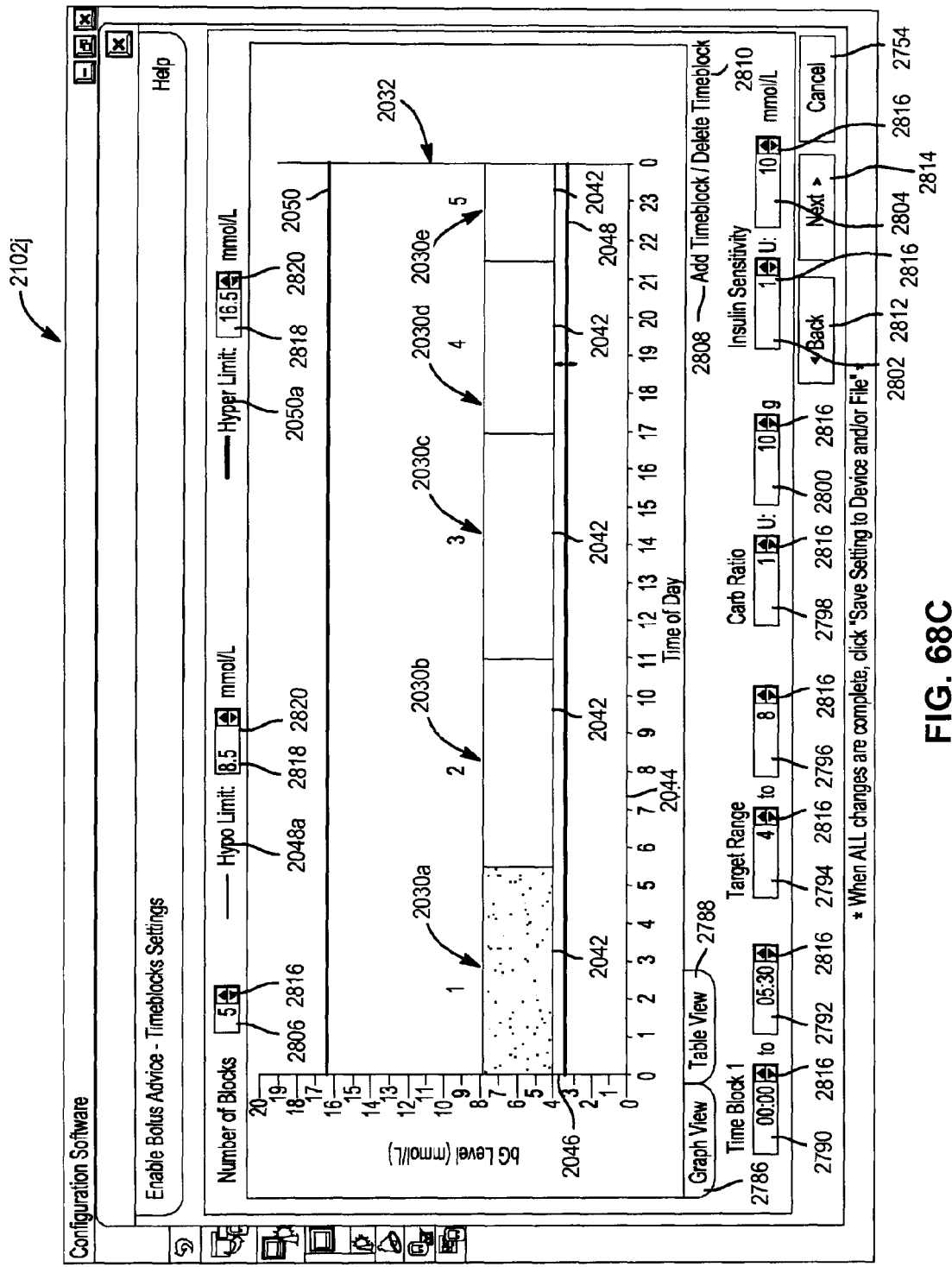
FIG. 68C illustrates the "Enable Bolus Advice-Timeblocks Settings" user interface of FIG. 68A in which the user interface illustrates moving a boundary line.

At block 2406, the method can display an "Enable Bolus Advice-Timeblocks Settings" user interface 2102*j* (FIGS. 68A-68C), then the method can go to decision block 2410. At decision block 2410, the method can determine if a particular bar structure 2030 has been selected with the at least one user input device 2016. If a bar structure has not been selected, then the method can go to decision block 2412. At decision block 2412, the method can determine if user input 2110 has been received on the "Enable Bolus Advice-Timeblocks Settings" user interface 2102*j* (FIGS. 68A-68C). If user input data 2112 has been received, then the method can go to H on FIG. 59. Otherwise, the method can loop to decision block 2410.

If a bar structure 2030 has been selected at decision block 2410, then the method can go to decision block 2414. At decision block 2414, the method can determine if the user input data 2112 includes a request to add or remove the bar structure. If, at decision block 2414, the user input data 2112 includes a request to add or remove a bar structure 2030, then the method can go to decision block 2416. At decision block 2416, the method can determine if the requested change in the number of bar structures 2030 is acceptable based on the constraint data 2130. If the requested change in the number of bar structures 2030 is unacceptable based on the constraint data 2130, then the method can go to block 2418. Otherwise, the method can go to block 2420. At block 2420, the method can flag an error, and then loop to decision block 2414.

If the change in the number of bar structures 2030 is acceptable based on the constraint data 2130, then at block 2418 the method can either add a new bar structure 2030 next to the selected bar structure 2030 or can remove the selected bar structure 2030 based on the user input data 2112. Then, the method can go to block 2421. At block 2421, the method can save the locations of bar structures 2030 as time block data 2120. Then, the method can go to decision block 2422.

At decision block 2422, the method can determine if one of the left side 2036, right side 2038, top side 2040 or bottom side 2042 of the bar structures 2030 has been adjusted via the at least one user input device 2016. If one of the left side 2036, right side 2038, top side 2040, or bottom side 2042 has changed locations, then the method can go to decision block 2424. At decision block 2424, the method can determine if the adjustment to the side of the selected bar structure 2030 is acceptable based on the constraint data 2130. If the adjustment is not acceptable based on the constraint data 2130, then at block 2426 the method can prevent the adjustment of the one of the left side 2036, right side 2038, top side 2040 or bottom side 2042 of the selected bar structure 2030. Then, the method can go to decision block 2422. Otherwise, if the adjustment is acceptable, then the method can go to block 2428.

At block 2428, the method can adjust the selected bar structure 2030 and the adjacent bar structure 2030 if applicable. Then, the method can go to block 2430. At block 2430, the method can save the bar structure locations as time block data 2120. Then, the method can go to E on FIG. 59. If at decision block 2422, one of the left side 2036, right side 2038, top side 2040 or bottom side 2042 of the selected bar structure 2030 the user has not been adjusted, then the method can also go to E on FIG. 59.

Figure 59:
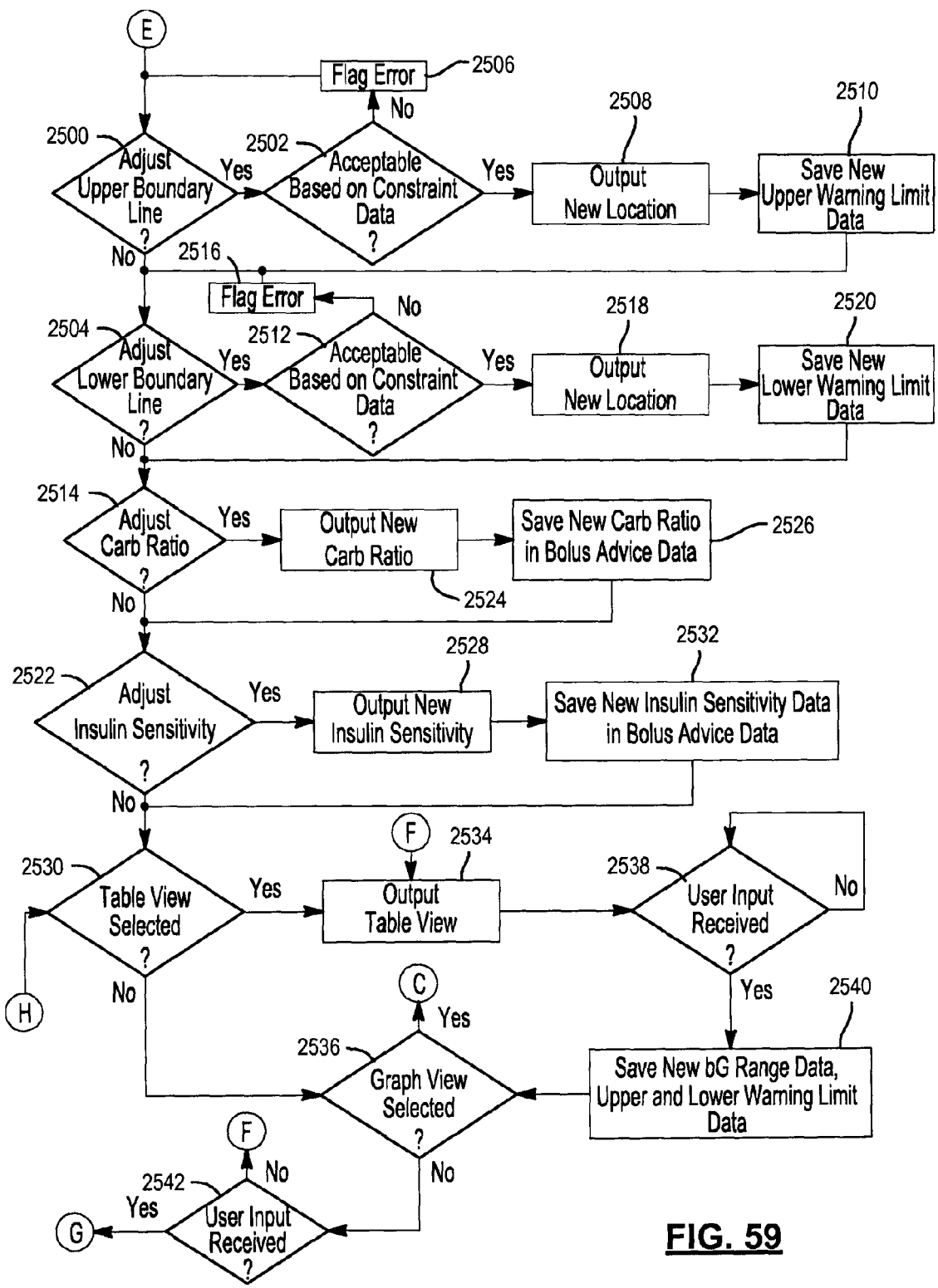
FIG. 59 is a continuation of the flowchart of FIG. 58 at E.

With reference to FIG. 59, starting at E, the method can go to decision block 2500. At decision block 2500, the method can determine if the upper boundary line 2050 has been adjusted. If the upper boundary line 2050 has been adjusted, then method can go to decision block 2502. Otherwise, the method can go to decision block 2504.

At decision block 2502, the method can determine if the new location for the upper boundary line 2050 is acceptable based on the constraint data 2130. If the new location of the upper boundary line 2050 is not acceptable, then the method can go to block 2506. At block 2506, the method can flag an error and then loop to decision block 2500. If the new location for the upper boundary line 2050 is acceptable, then at block 2508 the method can display the new location for the upper boundary line 2050 on the user interface along with the new "Hyper limit" data 2050*a*. Then, the method can go to block 2510. At block 2510, the method can save the new location of the upper boundary line 2050 as warning limit data 2118. Then, the method can go to decision block 2504.

At decision block 2504, the method can determine if the location of the lower boundary line 2048 has been adjusted. If the location of the lower boundary line 2048 has been adjusted, then the method can go to decision block 2512. Otherwise, the method can go to decision block 2514. At decision block 2512, the method can determine if the new location for the lower boundary line 2048 is acceptable based on the constraint data 2130. If the new location of the lower boundary line 2048 is not acceptable, then at block 2516 the method can flag an error before looping to decision block 2504. If the new location for the lower boundary line 2048 is acceptable, then the method can go to block 2518.

At block 2518, the method can display the lower boundary line 2048 at the new location and can also display the new "Hypo Limit" data 2048*a* associated with the new location of the lower boundary line 2048. At block 2520, the method can save the new location of the lower boundary line 2048 as warning limit data 2118. Then, the method can go to decision block 2514.

At decision block 2514, the method can determine if the carb ratio has been adjusted. If the carb ratio has not been adjusted, then the method can go to decision block 2522. Otherwise, at block 2524 the method can display a new carb ratio and can save the new carb ratio as bolus advice data 2122 in the data store 2108. Then, the method can go to decision block 2522. At decision block 2522, the method can determine if the insulin sensitivity has been adjusted. If the insulin sensitivity has been adjusted, then the method can go to block 2528. Otherwise, the method can go to decision block 2530. At block 2528, the method can display the new insulin sensitivity. Then, the method can go to block 2532. At block 2532, the method can save the new insulin sensitivity data as bolus advice data 2122.

Figure 69:
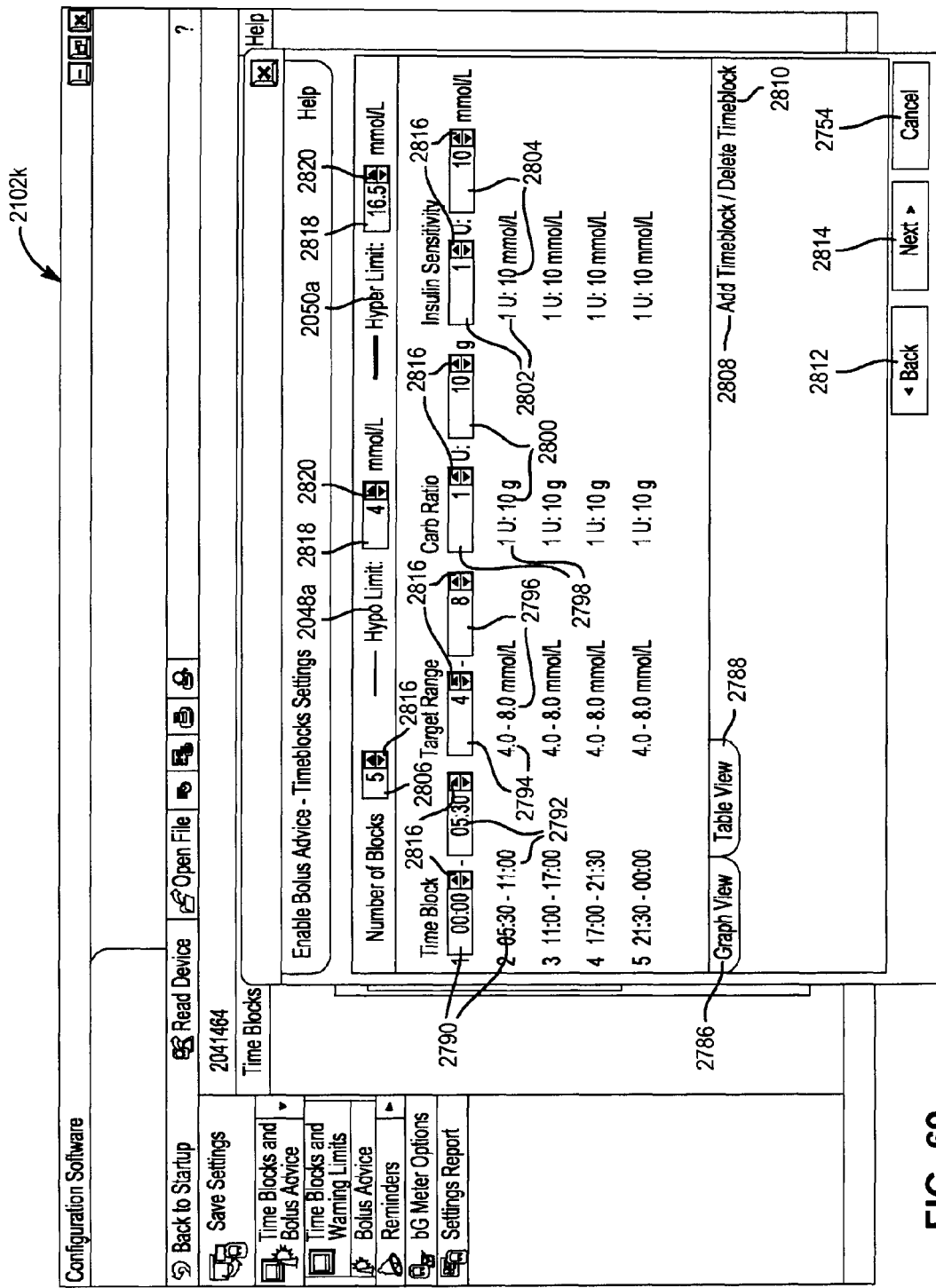
FIG. 69 illustrates an exemplary "Enable Bolus Advice-Table View" user interface.

At decision block 2530, the method can determine if a "Table View" tab 2788 has been selected (FIG. 68A). If the "Table View" tab 2788 has been selected, then the method can go to block 2534. Otherwise, the method can go to decision block 2536. At block 2534, the method can output the "Enable Bolus Advice-Table View" user interface 2102*k* (FIG. 69). Then, the method can go to decision block 2538. At decision block 2538, the method can determine if user input has been received from the at least one user input device 2016. If user input data 2112 has been received, then the method can go to block 2540. Otherwise, the method can loop until user input data 2112 is received. At block 2540, the method can save the user input data 2112 as warning limit data 2118, time block data 2120 and bolus advice data 2122. Then, the method can go to decision block 2536.

At decision block 2536, the method can determine if a "Graph View" tab 2786 (FIG. 68A) has been selected. If the "Graph View" tab 2786 was selected, then the method can go to C on FIG. 58. Otherwise, the method can go to decision block 2542. At decision block 2542, the method can determine if additional user input data 2112 was received. If additional user input data 2112 was received, then the method can go to G on FIG. 60. Otherwise, the method can go to F on FIG. 59.

Figure 60:
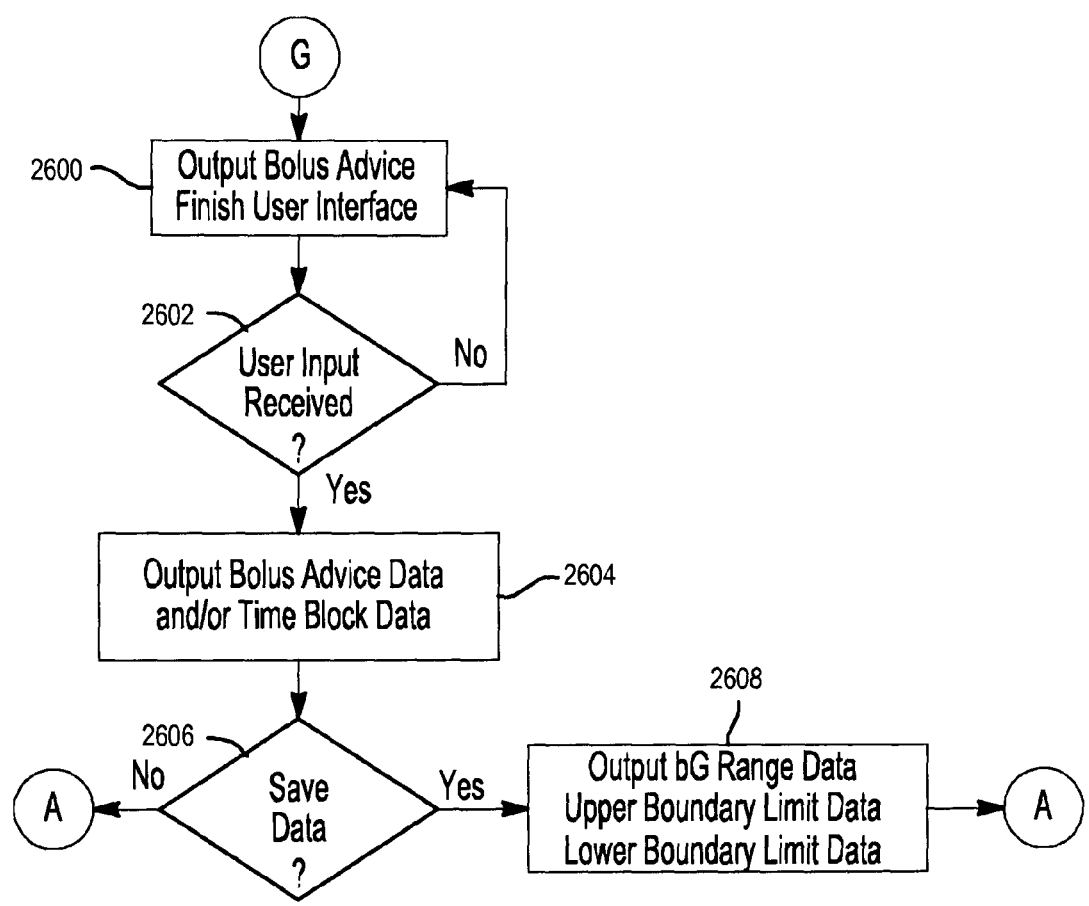
FIG. 60 is a continuation of the flowchart of FIG. 59 at G.
Figure 70:
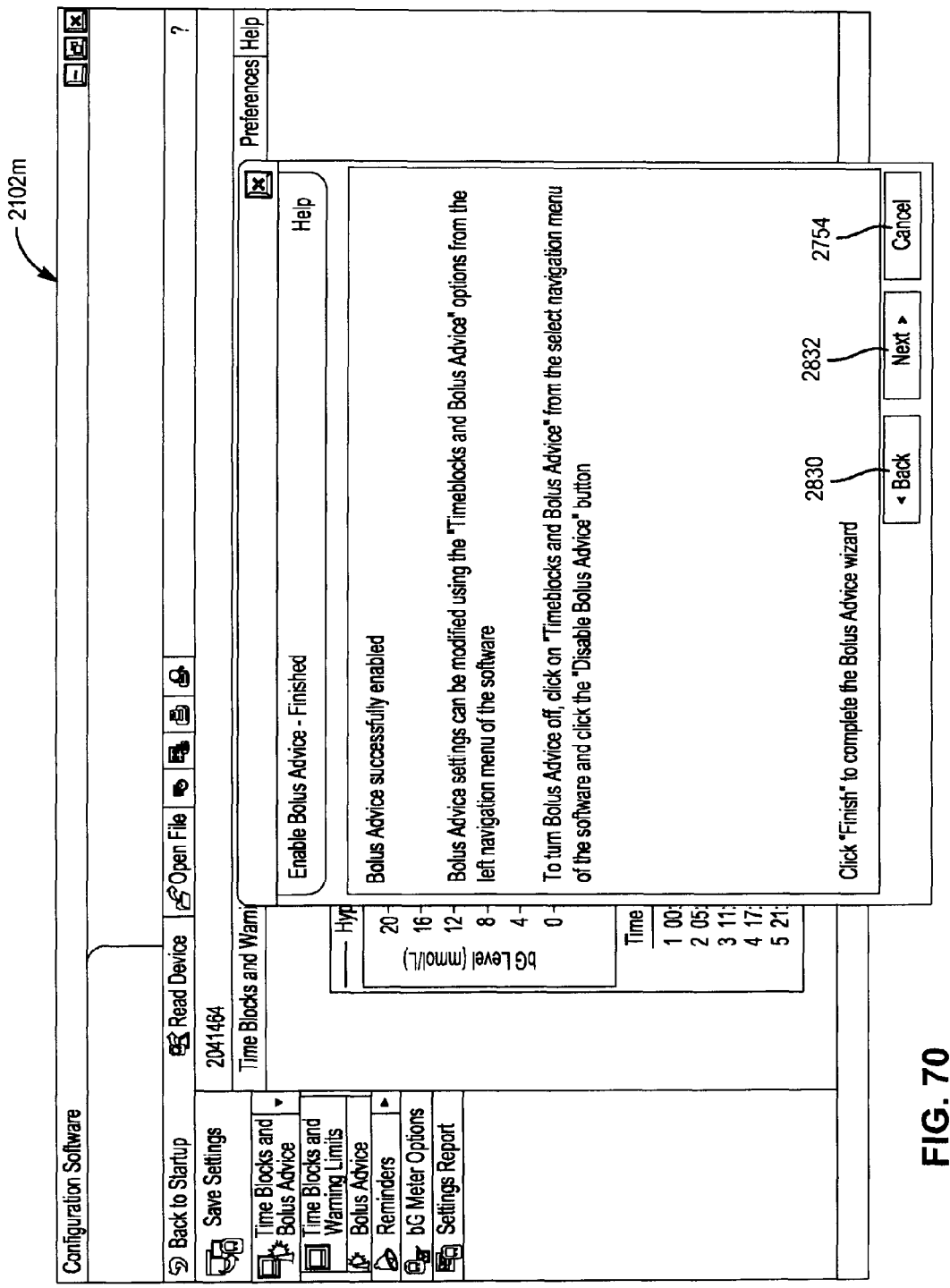
FIG. 70 illustrates an exemplary "Enable Bolus Advice-Finished" user interface.

With reference to FIG. 60, starting at G, the method can go to block 2600. At block 2600, the method can display the "Enable Bolus Advice-Finished" user interface 2102*m* (FIG. 70). Then, the method can go to decision block 2602. At decision block 2602, the method can determine if user input data 2112 has been received. If user input data 2112 has been received, then the method can go to block 2604. Otherwise, the method can loop to block 2600. At block 2604, the method can output bolus advice data 2122 and/or time block data 2120 on the user interface 2102. At decision block 2606, the method can determine if user input data 2112 has been received to save the warning limit data 2118, time block data 2120 and bolus advice data 2122. If a save data request has been received, then the method can output the warning limit data 2118, time block data 2120 and bolus advice data 2122 saved in the data store 2108 to the desired device, such as the hand-held diabetes device 2024 or data storage device 2028. Then, the method can go to A on FIG. 57. If a request to save data has not been received, then method can go to A on FIG. 57.

With reference to FIGS. 61-74, additional exemplary user interfaces 2102 generated by the graphical user interface module 2104 are illustrated. The user interface 2102 can be formed of various user interfaces, such as, the "Time Blocks and Warning Limits" user interface 2102*a* (FIG. 54), the "Startup" user interface 2102*b* (FIG. 61), the "Read From Device-Prepare Device" user interface 2102*c* (FIG. 62), a "Read From Device-Finished" user interface 2102*d* (FIG. 63), the "Open a Settings File" user interface 2102*e* (FIG. 64), the "Set Date and Time" user interface 2102*f* (FIG. 65), the "Enable Bolus Advice-Start" user interface 2102*g* (FIG. 66), the "Enable Bolus Advice-Health Events and Options" user interface 2102*h* (FIG. 67), the "Enable Bolus Advice-Timeblocks Settings" user interface 2102*j* (FIGS. 68A-68C), an "Enable Bolus Advice-Table View" user interface 2102*k* (FIG. 69), an "Enable Bolus Advice-Finished" user interface 2102*m* (FIG. 70), a "Save to a Device" user interface 2102*p* (FIG. 71), a "Save to Device-Finished" user interface 2102*q* (FIG. 72), the "Time Blocks" user interface 2102*r* (FIG. 73) and the "Bolus Advice" user interface 2102*s* (FIG. 74). The user interfaces 2102*g*-2102*m* (FIGS. 66-70) can generally comprise a bolus advice "wizard," which can guide the user through the act of inputting the warning limit data 2118, time block data 2120 and bolus advice data 2122.

With reference to FIG. 61, the "Startup" user interface 2102*b* can comprise an initial start-up screen for the computing system 2000. The "Startup" user interface 2102*b* can include a menu 2700, which can include various options for the user to initialize the computing system 2000. In one example, the menu 2700 can include a "Read from Device" button 2702, a "Open a Settings File" button 2704 and a "Set Date and Time" button 2706. The menu 2700 can also include an "Exit" button 2708, which can enable the user to exit the user interface 2102.

Figure 62:
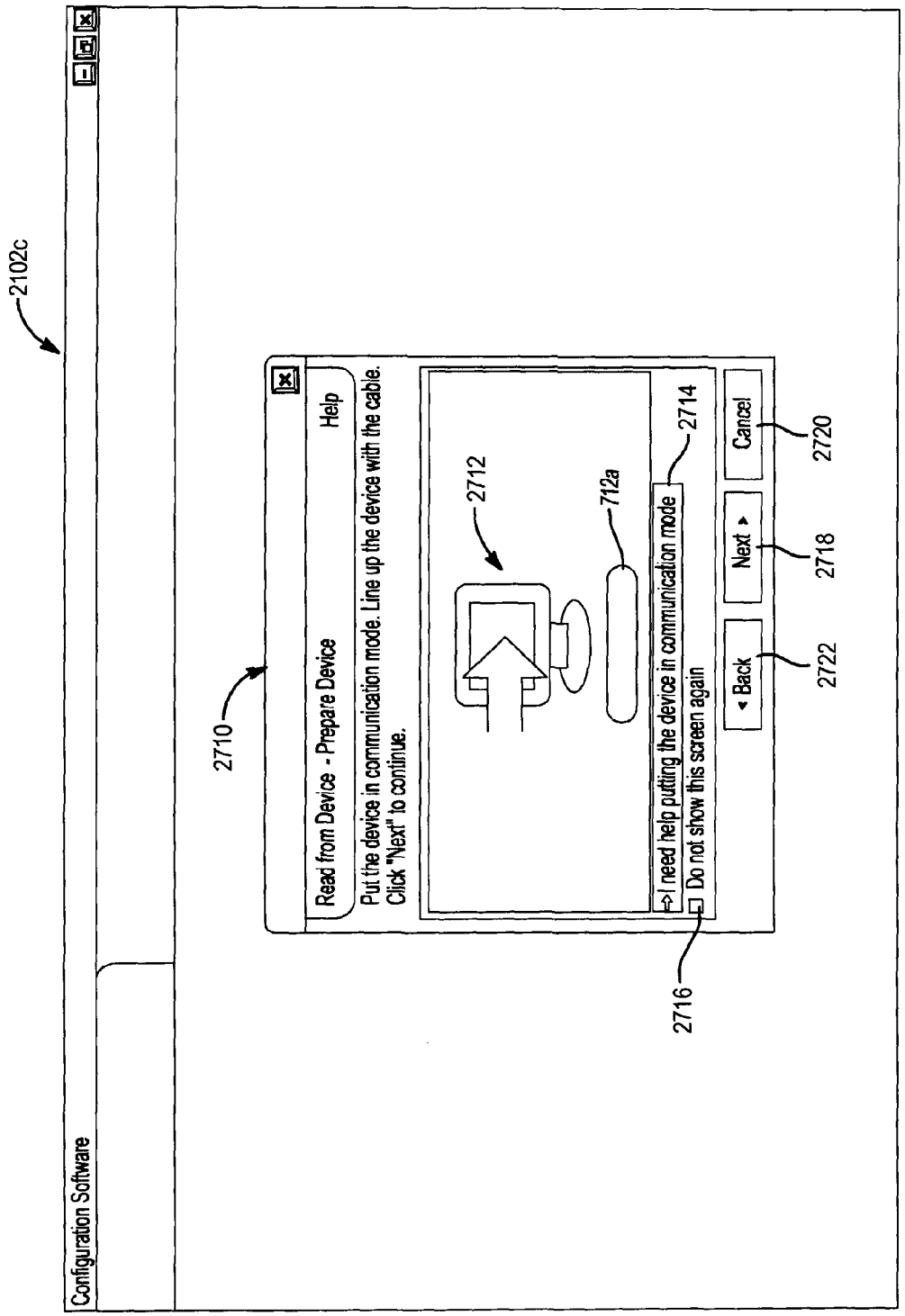
FIG. 62 illustrates an exemplary "Read From Device-Prepare Device" user interface.
Figure 64:
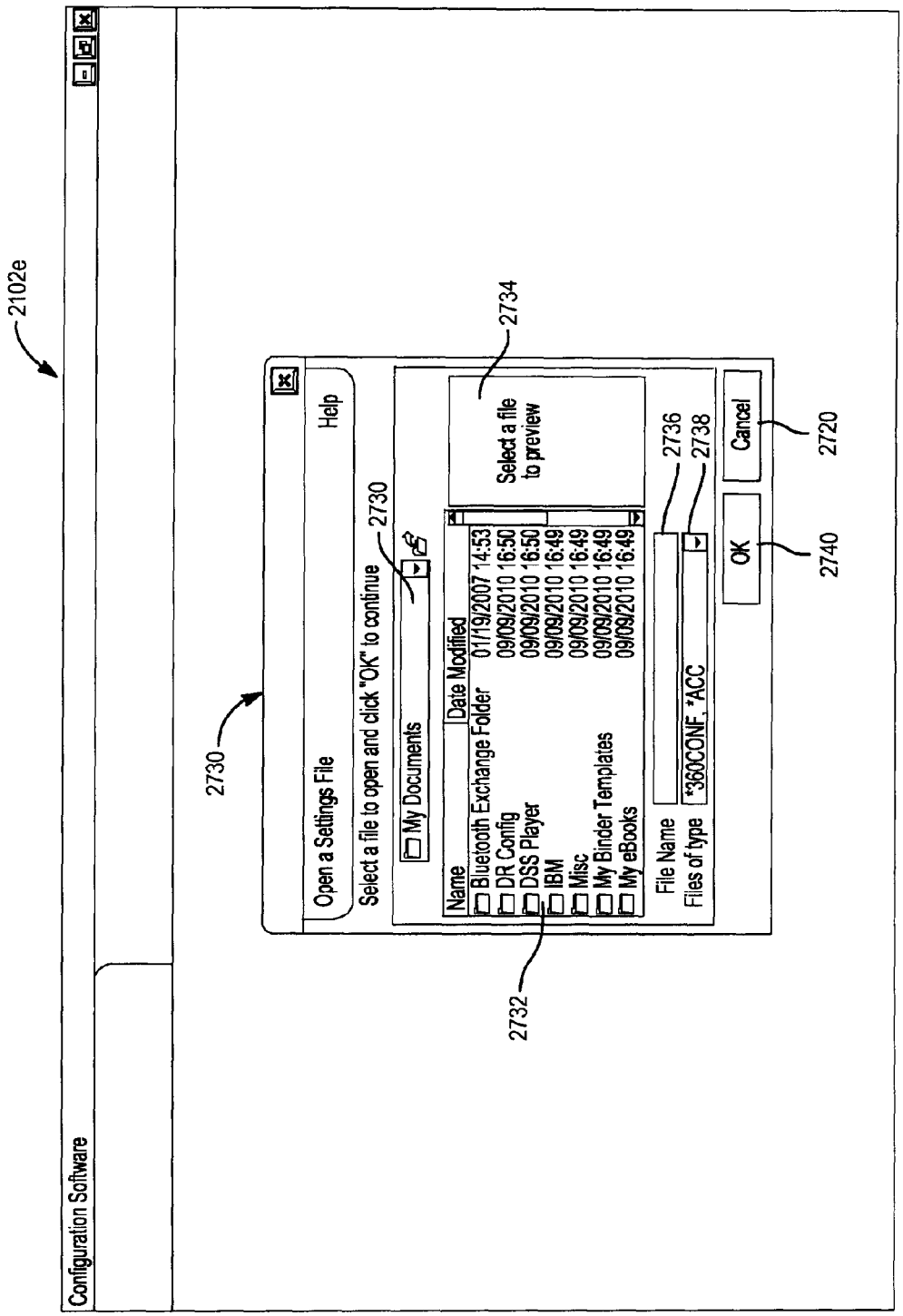
FIG. 64 illustrates an exemplary "Open a Settings File" user interface.

The "Read from Device" button 2702, if selected, can begin a series of user interfaces 2102 designed to retrieve the meter input data 2128 from the hand-held diabetes device 2024. In one example, the selection of the "Read from Device" button 2702 can direct the user to the "Read From Device-Prepare Device" user interface 2102*c* (FIG. 62). The "Open a Settings File" button 2704 can allow the user to open a data file from the computing system 2000 or the data storage device 2028, for example. If the data is obtained from the data storage device 2028, the data can comprise the data storage device input data 2122. In one example, selecting the "Open a Settings File" button 2704 can direct the user to the "Open a Settings File" user interface 2102e (FIG. 64). The "Set Date and Time" button 2706, if selected, can display the "Set Date and Time" user interface 2102f (FIG. 65) to enable the user to set the date and time on the hand-held diabetes device 2024.

Referring to FIG. 62, the "Read From Device-Prepare Device" user interface 2102c can prompt the user to connect the hand-held diabetes device 2024 to the computing system 2000. In one example, the "Read From Device-Prepare Device" user interface 2102c can include a display box 2710, which can provide the user with textual instructions for placing the hand-held diabetes device 2024 into communication with the computing system 2000. The display box 2710 can include a status indicator 2712, a help link 2714, a screen display selector 2716, a "Next" button 2718, a "Cancel" button 2720 and a "Back" button 2722.

The status indicator 2712 can display a status of the connection between the hand-held diabetes device 2024 and the computing system 2000. For example, the status indicator 2712 can include an indicator bar 2712a, which can indicate the progress of the connection. The help link 2714 can direct the user to a help screen user interface, which can further describe the process of placing the hand-held diabetes device 2024 into communication with the computing system 2000. The screen display selector 2716 can enable the user to instruct the control module 2100 to stop displaying the "Read From Device-Prepare Device" user interface 2102c upon the selection of the "Read from Device" button 2702. The "Next" button 2718, if selected, can display the "Read From Device-Finished" user interface 2102d. In other words, the selection of the "Next" button 2718 can enable the user to continue in the process of obtaining the meter input data 2118. The "Cancel" button 2720 can enable the user to cancel reading from the hand-held diabetes device 2014, and can redirect the user back to the "Startup" user interface 2102b (FIG. 61). The "Back" button 2722 can enable the user to go back to the "Startup" user interface 2102b (FIG. 61).

Figure 63:
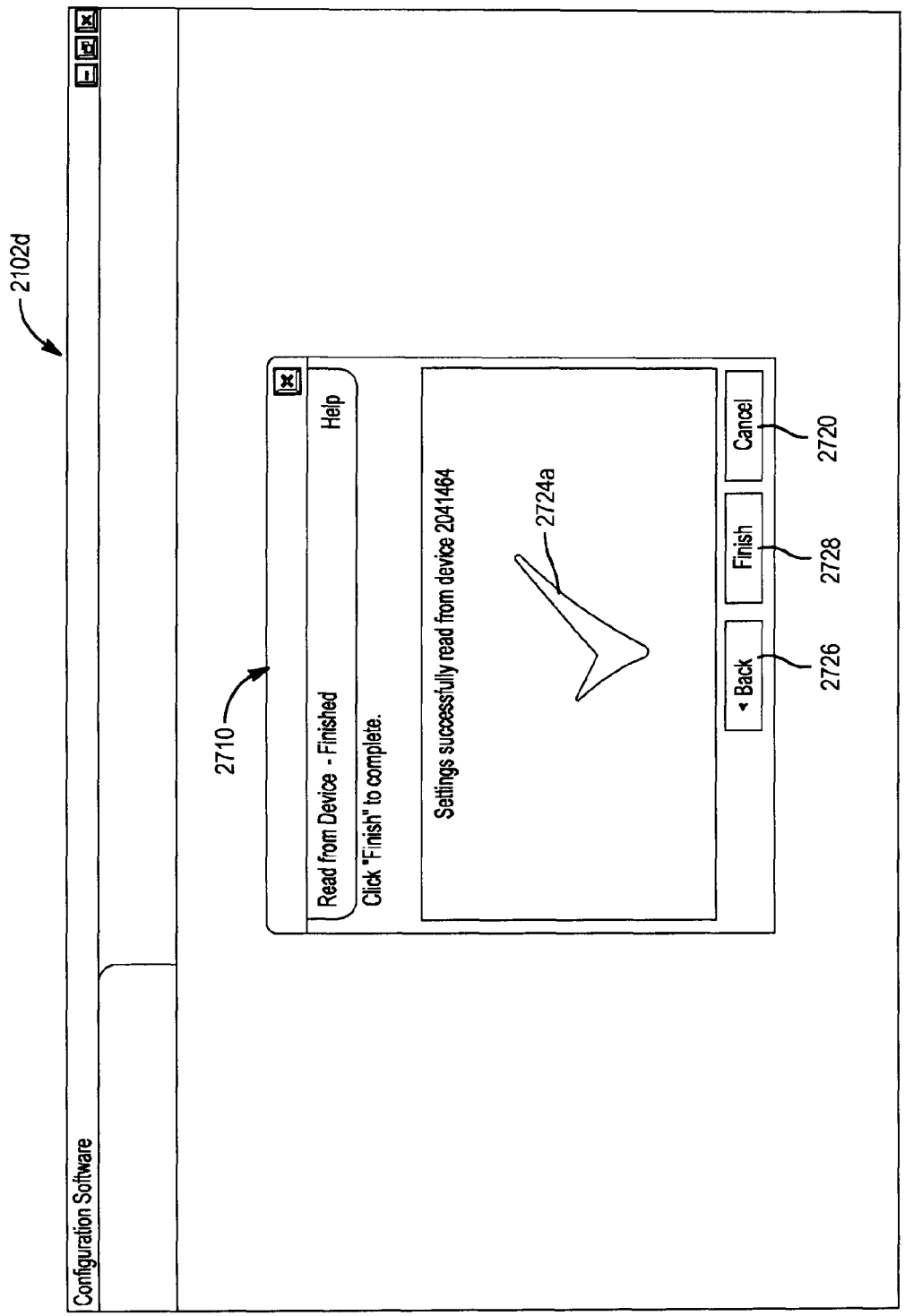
FIG. 63 illustrates an exemplary "Read From Device-Finished" user interface.

With regard to FIG. 63, the "Read From Device-Finished" user interface 2102d can include a display box 2724, which can graphically indicate to the user that the meter input data 2118 has been successfully obtained from the hand-held diabetes device 2024. In one example, the display box 2724 can include an icon 2724a, which can indicate that the meter input data 2118 has been successfully received by the control module 2100. The display box 2724 can also include a "Back" button 2726, a "Finish" button 2728 and the "Cancel" button 2720.

The "Back" button 2726, if selected, can allow the user to go back to the "Read From Device-Prepare Device" user interface 2102c. The "Finish" button 2728 can allow the user to finish the process of obtaining the meter input data 2118 from the hand-held diabetes device 2024. The user can be prompted to select the "Finish" button 2728 by instructions in the display box 2724. If the "Finish" button 2728 is selected, the control module 2100 can display the "Time Blocks and Warning Limits" user interface 2102a (FIG. 54).

With reference to FIG. 64, the "Open a Settings File" user interface 2102e can allow the user to select a data file from the computing system 2000 or the data storage device 2028. The "Open a Settings File" user interface 2102e can include a drop-down menu 2730, a file information box 2732, a file preview box 2734, a "File Name" input box 2736, a "Files of Type" drop-down menu 2738, an "OK" button 2740 and the "Cancel" button 2720.

The drop-down menu 2730 can provide a list of available sources on the computing system 2000 for obtaining the data file, such as the data storage device 2028. The file information box 2732 can provide detailed information regarding the data files. The file preview box 2734 can display an image of the data within the file. The "File Name" input box 2736 can display the name of the data file, while the "Files of Type" drop-down menu 2738 can enable the user to select the types of files to look for. The "OK" button 2740, if selected, can prompt the control module 2100 to load the data file as data storage input data 2118.

Figure 65:
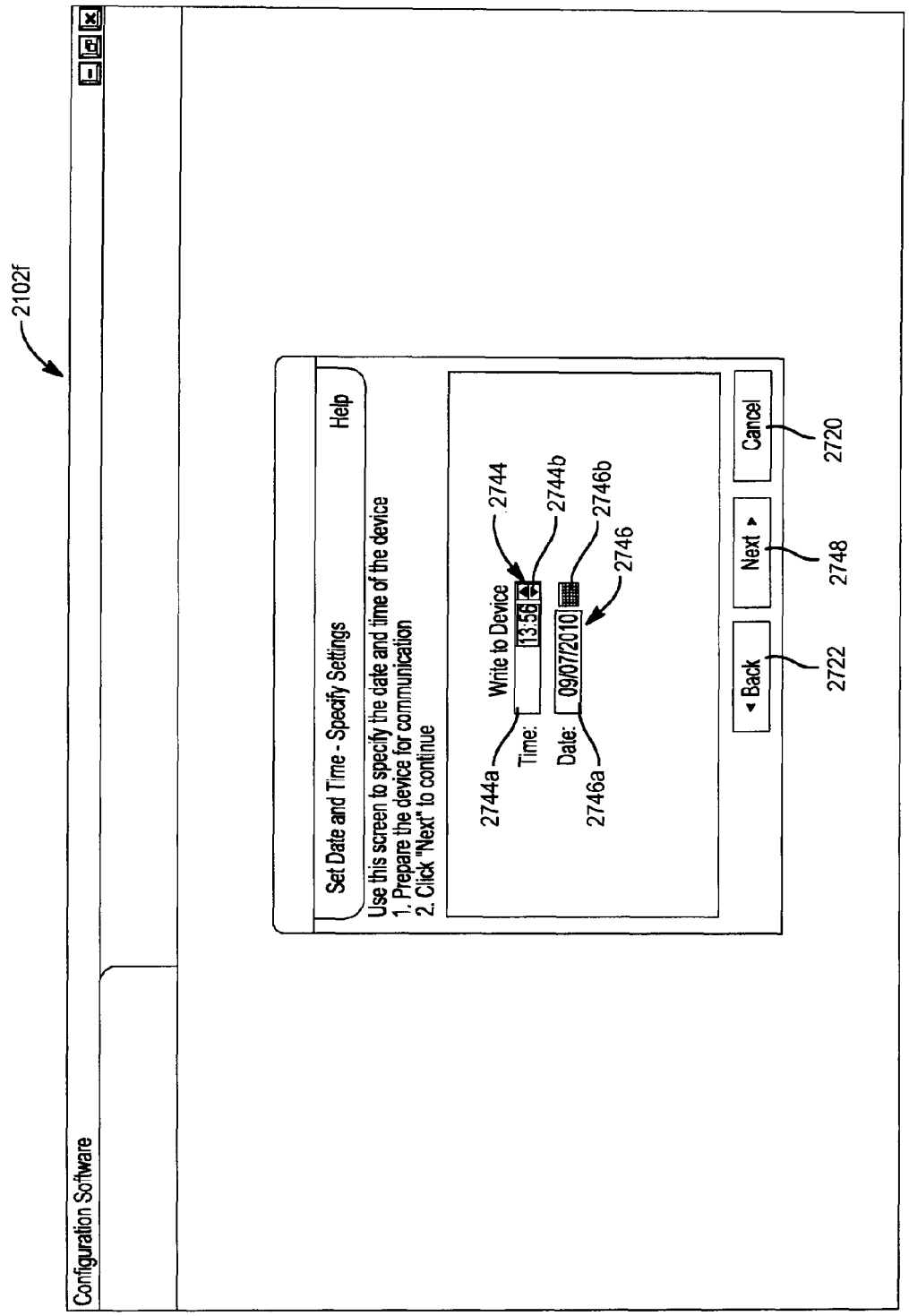
FIG. 65 illustrates an exemplary "Set Date and Time" user interface.

Referring to FIG. 65, the "Set Date and Time" user interface 2102f can enable the user to set the date and time for the hand-held diabetes device 2024. The "Set Date and Time" user interface 2102f can include a time input box 2744 and a date input box 2746. The "Set Date and Time" user interface 2102f can also include textual instructions to direct the user in placing the hand-held diabetes device 2024 in communication with the computing system 2000.

The time input box 2744 can provide a text box 2744a to enable a user to enter the text using the keyboard 2016a, for example. The time input box 2744 can also include one or more scroll selectors 2744b, which can enable the user to use the pointing device 2016b to incrementally adjust the time. The date input box 2746 can include a text box 2746a to enable a user to enter the text using the keyboard 2016a, for example. The date input box 2746 can also include a calendar button 2746b, which can prompt a calendar user interface to enable the user to select a specific date from a given month or months.

The "Set Date and Time" user interface 2102f can also include the "Back" button 2722, a "Next" button 2748 and the "Cancel" button 2720. The "Next" button 2748, if selected, can cause the control module 2100 to save the date and time to the hand-held diabetes device 2024. The selection of the "Next" button 2748 can also prompt the control module 2100 to display a user interface that indicates that the hand-held device 2024 has been updated or the control module 2100 could display the "Startup" user interface 2102b.

In FIG. 66, the "Enable Bolus Advice-Start" user interface 2102g can provide the user with textual information with regard to using the control module 2100 to set the warning limit data 2118, time block data 2120 and bolus advice data 2122. The "Enable Bolus Advice-Start" user interface 2102g can include a "Back" button 2750, a "Next" button 2752 and a "Cancel" button 2754. The "Back" button 2750, if selected, can display the "Time Blocks and Warning Limits" user interface 2102a (FIG. 54). The "Next" button 2752, if selected, can display the "Enable Bolus Advice-Health Events and Options" user interface 2102h (FIG. 67).

The "Cancel" button 2754, if selected, can display the "Time Blocks and Warning Limits" user interface 2102a (FIG. 54).

With regard to FIG. 67, the "Enable Bolus Advice-Health Events and Options" user interface 2102h can allow the user to input their specific health events and desired options with regard to bolus insulin advice. In one example, the "Enable Bolus Advice-Health Events and Options" user interface 2102h can include a "Health Events" input menu 2760 and an "Options" input menu 2762.

The "Health Events" input menu 2760 can include a first "Exercise" input box 2764, a second "Exercise" box 2765, a "Stress" input box 2766, an "Illness" input box 2768 and a "Premenstrual" input box 2770. The user can input values that specify a percentage that each of these events may impact their bG level. Each of the input boxes 2764, 2765, 2766, 2768, 2770 can include a scroll selector 2772, which can enable the user to use the pointing device 2016b to incrementally adjust the percentages for each of the first "Exercise" input box 2764, second "Exercise" box 2765, "Stress" input box 2766, "Illness" input box 2768 and "Premenstrual" input box 2770.

The "Options" input menu 2762 can include various options that the user can use to adjust the bolus advice data 2122. In one example, the "Options" input menu 2762 can include a "Meal Rise" input box 2772, a "Snack Size" input box 2774, an "Acting Time" input box 2776 and an "Offset Time" input box 2778. Each of the input boxes 2772, 2774, 2776, 2778 can include a scroll selector 2780, which can enable the user to use the pointing device 2016b to incrementally adjust the percentages for each of the "Meal Rise" input box 2772, "Snack Size" input box 2774, "Acting Time" input box 2776 and "Offset Time" input box 2778.

The "Enable Bolus Advice-Health Events and Options" user interface 2102h can also include a "Back" button 2782, a "Next" button 2784 and the "Cancel" button 2754. The "Back" button 2782, if selected, can display the "Enable Bolus Advice-Start" user interface 2102g (FIG. 66). The "Next" button 2784, if selected, can display the "Enable Bolus Advice-Timeblocks Settings" user interface 2102j (FIGS. 68A-68C).

With reference to FIGS. 68A-68C, the "Enable Bolus Advice-Timeblocks Settings" user interface 2102j (FIGS. 68A-68C) is illustrated. The "Enable Bolus Advice-Timeblocks Settings" user interface 2102j can include the bar chart 2032 including the plurality of bar structures 2030, the x-axis 2044, the y-axis 2046, the lower boundary line 2048 and upper boundary line 2050. In this example, the second bar structure 2030b can be selected, and can be graphically illustrated in a different color, for example, to indicate to the user that the second bar structure 2030b has been selected.

The "Enable Bolus Advice-Timeblocks Settings" user interface 2102j can also include a "Graph View" tab 2786, a "Table View" tab 2788, a "Time Block" start input box 2790, a "Time Block" end input box 2792; a "Target Range" start input box 2794, a "Target Range" end input box 2796, a "Carb Ratio" unit input box 2798, a "Carb Ratio" gram input box 2800, an "Insulin Sensitivity" unit box 2802 and an "Insulin Sensitivity" adjustment level input box 2804. The "Enable Bolus Advice-Timeblocks Settings" user interface 2102j can also include a "Number of Blocks" input box 2806, an "Add Time Block" link 2808, a "Delete Time Block" link 2810, a "Back" button 2812, a "Next" button 2814 and the "Cancel" button 2754.

The "Graph View" tab 2786 can cause the display of the bar chart 2032, as illustrated in FIG. 68A. The "Table View" tab 2788 can cause the display of the "Enable Bolus Advice-Table View" user interface 2102k (FIG. 69). Each of the input boxes 2790, 2792, 2796, 2798, 2800, 2802, 2804, 2806 can include a scroll selector 2816, which can enable the user to use the pointing device 2016b to incrementally adjust the data values for each of the "Time Block" start input box 2790, Time Block" end input box 2792, "Target Range" start input box 2794, "Target Range" end input box 2796, "Carb Ratio" unit input box 2798, "Carb Ratio" gram input box 2800, "Insulin Sensitivity" unit input box 2802, "Insulin Sensitivity" adjustment level input box 2804 and "Number of Blocks" input box 2806.

The "Time Block" start input box 2790 can allow the user to manually enter the start time for the selected bar structure 2030b through the keyboard 2016a. The "Time Block" end input box 2792 can allow the user to manually enter the end time for the selected bar structure 2030b through the keyboard 2016a. The "Target Range" start input box 2794 can allow the user to manually enter the starting bG level for the range of bG level associated with the selected bar structure 2030b through the keyboard 2016a. The "Target Range" end input box 2796 can allow the user to manually enter the ending bG level for the range of bG level associated with the selected bar structure 2030b through the keyboard 2016a. The data entered into the "Time Block" start input box 2790, "Time Block" end input box 2792, "Target Range" start input box 2794 and "Target Range" end input box 2796 can be saved as time block data 2120.

It should be noted that although the "Enable Bolus Advice-Timeblocks Settings" user interface 2102j includes the Time Block" start input box 2790, "Time Block" end input box 2792, "Target Range" start input box 2794 and "Target Range" end input box 2796, the user need not input data into these input boxes 2790, 2792, 2794, 2796 in order to modify or manipulate the time block data 2120. Rather, the user can use the pointing device 2016b, for example, to adjust one or more of the left side 2036, right side 2038, top side 2040 and bottom side 2042 of the selected bar structure 2030. For example, with reference to FIG. 68B, the pointing device 2016b can be used to adjust the top side 2040 of the sixth bar structure 2030f.

Additionally, while the "Hypo Limit" 2048a and "Hyper Limit" 2050a are illustrated herein as including a text input box 2818 for allowing the user to input the hypoglycemic and hyperglycemic warning limits, the "Hypo Limit" 2048a and the "Hyper Limit" 2050a can also include a scroll selector 2820 to enable the user to use the pointing device 2016b to incrementally adjust the locations of the upper boundary line 2050 and lower boundary line 2048. Furthermore, with reference to FIG. 68C, the pointing device 2016b could be used to manipulate or move the location of the lower boundary line 2048 and upper boundary line 2050 to the desired hypoglycemic warning limit and hyperglycemic warning limit. The locations of the lower boundary line 2048 and the upper boundary line 2050 can be saved as warning limit data 2118.

The "Carb Ratio" unit input box 2798 can allow the user to adjust the units of insulin required for a particular number of carbohydrates. The "Carb Ratio" gram input box 2800 can cooperate with the "Carb Ratio" unit input box 2798 to enable the user to set the number of carbohydrates that correspond to a particular unit of insulin. The "Carb Ratio" unit input box 2798 and the "Carb Ratio" gram input box 2800 can be saved as a portion of the bolus advice data 2122.

The "Insulin Sensitivity" unit input box 2802 can allow the user to select a number of units of insulin required to adjust their bG level a particular increment. The "Insulin Sensitivity" adjustment level input box 2804 can cooperate with the "Insulin Sensitivity" unit input box 2802 to enable the user to set the particular increment of bG level change for the number of units of insulin. The "Insulin Sensitivity" unit input box 2802 and the "Insulin Sensitivity" adjustment level input box 2804 can be saved as a portion of the bolus advice data 2122.

The "Number of Blocks" input box 2806 can enable the user to input a desired number of bar structures 2030 for display on the bar chart 2032, subject to the constraint data 2130. The "Add Time Block" link 2808, if selected, can cause the display of an additional bar structure 2030, which in one example can be added adjacent to the fifth bar structure 2030e. For example, with reference to FIG. 68B, a sixth bar structure 2030f can be inserted adjacent to the fifth bar structure 2030e. It should be noted that the example of FIG. 68B is merely exemplary, as the "Add Time Block" link 2808 could cause the insertion of a bar structure 2030 adjacent to the selected bar structure 2030, or could display a user interface to enable the user to select the location on the bar chart 2032 for the new bar structure 2030. The "Delete Time Block" link 2810, if selected, can cause the removal of the selected bar structure 2030 from the bar chart 2032.

The "Back" button 2812, if selected, can cause the display of the "Enable Bolus Advice-Health Events and Options" user interface 2102*h* (FIG. 67). The "Next" button 2814, if selected, can cause the display of the "Enable Bolus Advice-Finished" user interface 2102*m* (FIG. 70).

With reference to FIG. 69, the "Enable Bolus Advice-Table View" user interface 2102*k* is illustrated. The "Enable Bolus Advice-Table View" user interface 2102*k* can provide an alternative user interface for the population of the warning limit data 2118, time block data 2120 and bolus advice data 2122. In other words, the "Enable Bolus Advice-Table View" user interface 2102*k* can provide a tabular or chart-like representation of the data displayed on the "Enable Bolus Advice-Timeblocks Settings" user interface 2102*j*. Thus, the "Enable Bolus Advice-Table View" user interface 2102*k* can include the text input box 2818 and scroll selector 2820 for the "Hypo Limit" 2048*a* and "Hyper Limit" 2050*a*, the "Graph View" tab 2786, the "Table View" tab 2788, a plurality of "Time Block" start input boxes 2790, a plurality of "Time Block" end input boxes 2792, a plurality of "Target Range" start input boxes 2794, a plurality of "Target Range" end input boxes 2796, a plurality of "Carb Ratio" unit input boxes 2798, a plurality of "Carb Ratio" gram input boxes 2800, a plurality of "Insulin Sensitivity" unit boxes 2802 and a plurality of "Insulin Sensitivity" adjustment level input boxes 2804. The "Enable Bolus Advice-Table View" user interface 2102*k* can also include the "Number of Blocks" input box 2806, the "Add Time Block" link 2808, the "Delete Time Block" link 2810, the "Back" button 2812, the "Next" button 2814 and the "Cancel" button 2754.

With regard to FIG. 70, the "Enable Bolus Advice-Finished" user interface 2102*m* can provide the user with textual information with regard to performing additional modifications to the warning limit data 2118, time block data 2120 and bolus advice data 2122. The "Enable Bolus Advice-Finished" user interface 2102*m* can also provide the user with textual information with regard to disabling the bolus advice data 2122. The "Enable Bolus Advice-Finished" user interface 2102*m* can include a "Back" button 2830, a "Finish" button 2832 and the "Cancel" button 2754. The "Back" button 2830, if selected, can display the "Enable Bolus Advice-Timeblocks Settings" user interface 2102*j*. The "Finish" button 2832, if selected, can display the "Time Blocks and Warning Limits" user interface 2102*a* (FIG. 54). The "Cancel" button 2754, if selected, can display the "Time Blocks and Warning Limits" user interface 2102*a* (FIG. 54).

Figure 71:
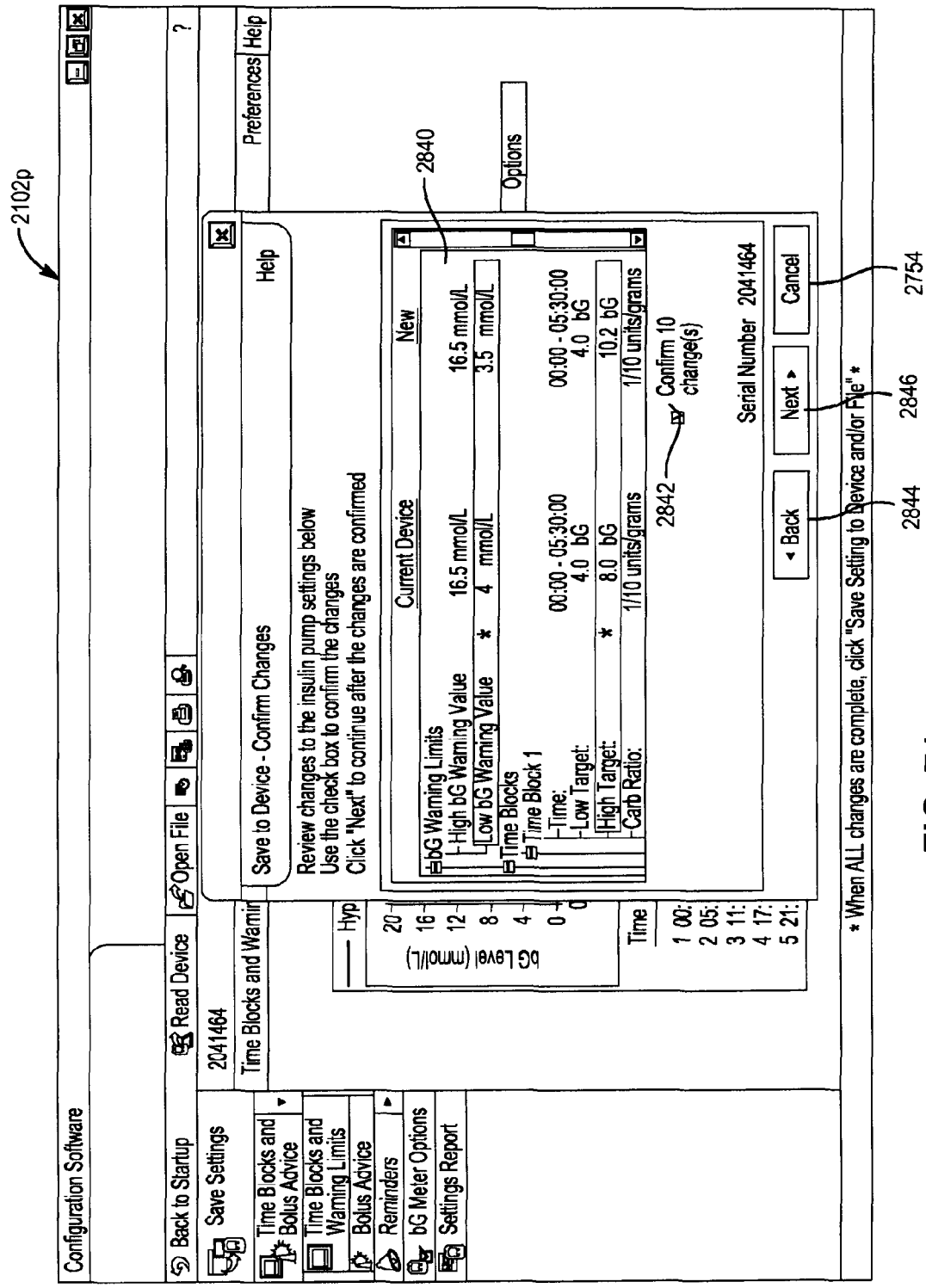
FIG. 71 illustrates an exemplary "Save to a Device" user interface.

Referring to FIG. 71, the "Save to a Device" user interface 2102*p* can be displayed upon selection of the "Save Settings" selector 2062. The "Save to a Device" user interface 2102*p* can allow the user to confirm the changes to the warning limit data 2118, time block data 2120 and bolus advice data 2122 prior to saving these data values to the hand-held diabetes device 2024. In one example, the "Save to a Device" user interface 2102*p* can include a summary chart 2840, which can display in a list form the warning limit data 2118, time block data 2120 and bolus advice data 2122 currently on the hand-held diabetes device 2024 and the warning limit data 2118, time block data 2120 and bolus advice data 2122 that has been input into the user interfaces 2102 via the at least one user input device 2016. The "Save to a Device" user interface 2102*p* can also include a "Confirm Changes" selector 2842, a "Back" button 2844, a "Next" button 2846 and the "Cancel" button 2754. The "Back" button 2844, if selected, can display the "Time Blocks and Warning Limits" user interface 2102*a* (FIG. 54). The "Next" button 2846, if selected, can display the "Save to Device-Finished" user interface 2102*q* (FIG. 72).

Figure 72:
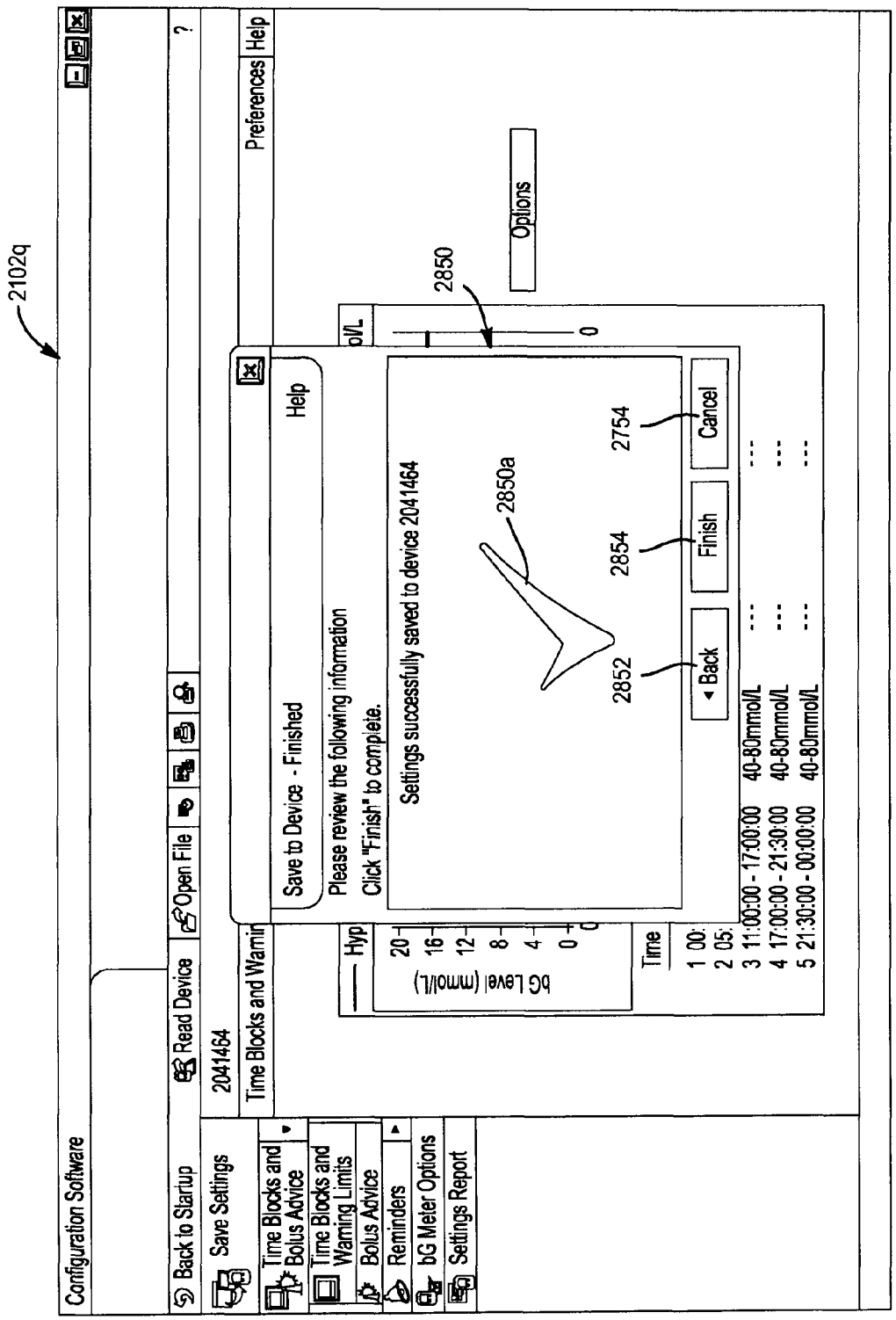
FIG. 72 illustrates an exemplary "Save to Device-Finished" user interface.

With regard to FIG. 72, the "Save to Device-Finished" user interface 2102*q* can include a display box 2850, which can graphically indicate to the user that the meter data 2124 has been successfully saved to the hand-held diabetes device 2024. In one example, the display box 2850 can include an icon 2850*a*, which can indicate that the meter data 2124 has been successfully output. The display box 2850 can also include a "Back" button 2852, a "Finish" button 2854 and a "Cancel" button 2754. The "Back" button 2852, if selected, can display the "Save to a Device" user interface 2102*p* (FIG. 71). The "Finish" button 2854, if selected, can display the "Time Blocks and Warning Limits" user interface 2102*a* (FIG. 54).

Figure 73:
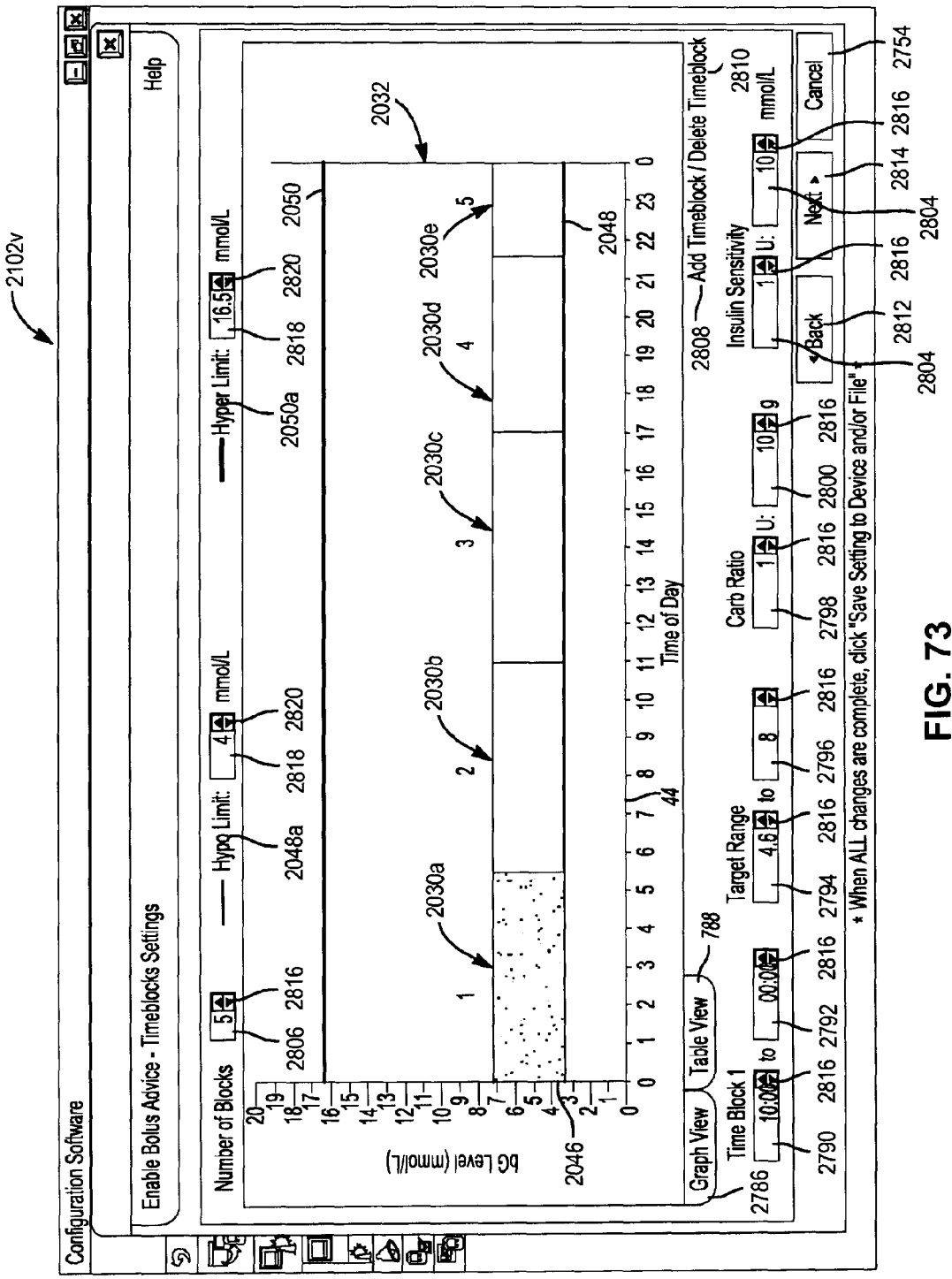
FIG. 73 illustrates an exemplary "Time Blocks" user interface.

In FIG. 73, the "Time Blocks" user interface 2102*r* can graphically illustrate substantially the same data as the "Enable Bolus Advice-Timeblocks Settings" user interface 2102*j*, and thus, the "Time Blocks" user interface 2102*r* will not be discussed in great detail herein. Briefly, however, the "Time Blocks" user interface 2102*r* can also include an "OK" button 2860 and the "Cancel" button 2754. The "OK" button 2860, if selected, can display the "Time Blocks and Warning Limits" user interface 2102*a* (FIG. 54).

With reference to FIG. 74, the "Bolus Advice" user interface 2102*s* is illustrated. The "Bolus Advice" user interface 2102*s* can be substantially similar to the "Enable Bolus Advice-Health Events and Options" user interface 2102*h* (FIG. 67), and thus, the "Bolus Advice" user interface 2102*s* will not be discussed in great detail herein. Briefly, however, the "Bolus Advice" user interface 2102*s* can include the "Bolus Advice" button 2054, which can enable or disable the bolus advice data 2122.

Thus, the user interfaces 2102 generated by the control module 2100 can provide the user with an efficient and easy manner to modify or view the warning limit data 2118, time-block data 2120 and bolus advice data 2122 and save those modifications to the hand-held diabetes device 2024. In other words, the computing system 2000 can enable modification of insulin therapy support parameters such as a start time of day data value, an end time of day data value, a lower blood glucose target data value, an upper blood glucose target data value, a high blood glucose warning data value and a low blood glucose warning data value on a hand-held diabetes management device. The system can include a graphical user interface module that creates a graphical user interface having a plurality of bar structures positionable on or between a first line that graphically illustrates an upper boundary limit and a second line that graphically indicates a lower boundary limit.

Each of the plurality of bar structures can have a first side that graphically indicates a start time of a time window opposite a second side that graphically indicates an end time of the time window and a third side that graphically indicates a start value for a range of values opposite a fourth side that graphically indicates an end value for the range of values. The first side, the second side, the third side and the fourth side of each of the plurality of bar structures, the first line and the second line can be adjustable by a user input. The plurality of bar structures can be governed by a set of constraints that confine each of the plurality of bar structures to an area defined by the first line and the second line and to a unique time window.

The system can also include a data store for storing at least the start time of day data value, the end time of day data value, the lower blood glucose target data value, the upper blood glucose target data value, the high blood glucose warning data value and the low blood glucose warning data value. The system can further include a data mapping module that maps for each of the plurality of bar structures on the graphical user interface the start time of day data value to a location of the first side, the end time of day data value to a location of the second side, the lower blood glucose target data value to a location of the third side and the upper blood glucose target data value to a location of the fourth side and stores the start time of day data value, end time of day data value, lower blood glucose target data value and upper blood glucose target data value in the data store. The data mapping module can also map the high blood glucose warning data value to a location of the first line and map the low blood glucose warning data value to a location of the second line. The data mapping module can store the high blood glucose warning data value and the low blood glucose warning data value in the data store.

In addition, the set of constraints can confine the second line to an area below the first line. The system can also include that the graphical user interface comprises a graphical illustration of a bar chart, which includes a time of day in hours on an x-axis and a blood glucose measurement on a y-axis. The plurality of bar structures can be graphically illustrated on the bar chart. Further, the third side of at least one of the plurality of bar structures is located above the x-axis so as to not be in contact with the x-axis. The graphical user interface can also comprise at least one input box for receipt of data relating to a carb ratio, insulin sensitivity and combinations thereof.

The system can further comprise the hand-held diabetes management device, and the data mapping module can output the start time of day data value, the end time of day data value, the lower blood glucose target data value, the upper blood glucose target data value, the high blood glucose warning data value and the low blood glucose warning data value to the hand-held diabetes management device.

Additionally, the graphical user interface module, data store and data mapping module of the system can be implemented on a computer readable medium on a computing device, and the hand-held diabetes management device can be in communication with the computing device through a wireless connection, a wired connection or combinations thereof.

The system can also include a user input device selected from the group comprising: touchpad, touch pen, touch screen, keyboard, mouse, joystick, trackball, wireless mouse, pointing device and combinations thereof.

Further provided is a system for modifying insulin therapy support parameters such as a start time of day data value, an end time of day data value, a lower blood glucose target data value, an upper blood glucose target data value, a high blood glucose warning data value and a low blood glucose warning data value on a hand-held diabetes management device. The system can include a graphical user interface module that creates a graphical user interface illustrating a bar chart having a plurality of bar structures, an x-axis graphically illustrating a time of day and a y-axis graphically illustrating a blood glucose level. The plurality of bar structures can be positionable on the bar chart, and each of the plurality of bar structures can have a first side that graphically indicates a start time of day opposite a second side that graphically indicates an end time of day and a third side that graphically indicates a lower target value for a blood glucose level opposite a fourth side that graphically indicates an upper target value for the blood glucose level. The first side, the second side, the third side and the fourth side of each of the plurality of bar structures can be adjustable by a user input. The third side of at least one of the plurality of bar structures can be spaced apart from the x-axis.

The system can also include a data store for storing at least the start time of day data value, the end time of day data value, the lower blood glucose target data value and the upper blood glucose target data value. The system can include a data mapping module that maps for each of the plurality of bar structures on the graphical user interface the start time of day data value to a location of the first side, the end time of day data value to a location of the second side, the lower blood glucose target data value to a location of the third side and the upper blood glucose target data value to a location of the fourth side and stores the start time of day data value, end time of day data value, lower blood glucose target data value and upper blood glucose target data value in the data store. The data mapping module can output the start time of day data value, end time of day data value, lower blood glucose target data value and upper blood glucose target data value to the hand-held diabetes management device.

In addition, the graphical user interface can further comprise a first line that graphically illustrates an upper boundary limit and a second line that graphically illustrates a lower boundary limit, the first line and second line each being graphically illustrated on the bar chart as horizontal lines. The first line and the second line can be adjustable by a user input. The second line can be positioned on the bar chart above the x-axis, such that the second line graphically represents a blood glucose level value greater than zero. The graphical user interface can further comprise at least one input box for receipt of data relating to a carb ratio, insulin sensitivity and combinations thereof.

Additionally, the data store further can store a high blood glucose warning data value and a low blood glucose warning data value, and the data mapping module can map the high blood glucose warning data value to a location of the first line and can map the low blood glucose warning data value to a location of the second line.

Furthermore, the plurality of bar structures can be governed by a set of constraints that confine each of the plurality of bar structures to an area defined by the first line and the second line. The first side and the second side of each of the plurality of bar structures cooperate to form a time window, and the set of constraints further confines the time window defined by the first side and the second side of each of the plurality of bar structures to a unique time window. The number of the plurality of bar structures displayed on the graphical user interface can be adjustable by user input.

The system can also include the graphical user interface module, data store and data mapping module being implemented on a computer readable medium on a computing device, and the hand-held diabetes management device being in communication with the computing device through a wireless connection, a wired connection or combinations thereof.

Improving Updatability of Structured Blood Glucose Tests Performed on Handheld Diabetes Management Devices A handheld blood glucose (bG) management device includes a processor that executes firmware for operating the diabetes management device. The firmware is stored in a firmware module that is implemented in a non-modifiable portion of memory of the diabetes management device. The firmware can be thought of as a routine executed by the processor to operate the diabetes management device.

One or more approvals of the firmware are typically necessary before the diabetes management device (executing the firmware) can be made publicly available. For example only, approval from one or more regulatory bodies (e.g., a Food and Drug Administration) can be required before the diabetes management device is made available in a region of the world that is subject to the regulations of the regulatory body. Before approving the firmware, a given regulatory body can require submission of a copy of the firmware, performance of one or more clinical tests to establish the operability of the firmware, and/or fulfillment of one or more other requirements.

Among other things, the firmware includes a subroutine for each different type of structured bG test that the diabetes management device is capable of performing. Each of the subroutines can be considered a submodule of the firmware module. One or more groups of bG samples are expected to be input for each structured bG test. One or more individual bG samples are expected to be input for each group of bG samples.

Entry criteria, adherence criteria, and exit criteria are associated with each structured bG test. Test configuration data is also associated with each structured bG test. Entry criteria, adherence criteria, and exit criteria are also associated with each expected bG sample group and each expected bG sample. The test configuration data may include how many data samples are expected to be input, how many data samples are expected for each group of data samples, spacing (e.g., period) between successive data samples, acceptance ranges or windows for each data sample, and/or other suitable data used in performing the structured bG test. Data collection for a structured bG test, for a group of bG samples, or for an individual bG sample can begin when the associated entry criteria are satisfied. A structured bG test, a group of bG samples, or a bG sample can be accepted as adhering to predetermined characteristics of the structured bG test, bG sample group, or bG sample when the associated adherence criteria are satisfied. Data collection for a structured bG test, a bG sample group, or a bG sample can end when the associated exit criteria are satisfied. Data collection for a structured bG test, a bG sample group, or a bG sample can alternatively end when the associated adherence criteria are satisfied.

All of the entry, adherence, and exit criteria could be written (coded) in the firmware in the firmware module (in the non-modifiable portion of memory). However, the requirement of regulatory approval of the firmware can limit the ability to modify/update one or more entry, adherence, and/or exit criteria if such modifications/updates are desired.

In the exemplary diabetes management device of the present disclosure, the entry, adherence, and exit criteria and the test configuration data can be stored in a modifiable portion of memory. In this manner, the test configuration data and/or entry, adherence, and/or exit criteria can be modified independently of the firmware. The firmware subroutines stored in the non-modifiable portion of memory point to where the associated test configuration data and the associated entry, adherence, and exit criteria are stored.

The separation in storage of the test configuration data and the entry, adherence, and entry criteria from the firmware module allows changes to the test configuration data and/or to the entry, adherence, and/or exit criteria to be made independently of the firmware. Therefore, because the firmware will not change when the test configuration data and/or entry, adherence, and/or exit criteria are changed/updated, another approval of the firmware can be unnecessary. Not having to obtain another approval can provide significant and measurable cost savings (e.g., from not having to conduct another round of clinical testing). This can also enable changes/updates to test configuration data and/or to entry, adherence, and/or exit criteria to be made publicly available sooner. Additionally, the same firmware can be distributed on diabetes management devices throughout the world while the test configuration data and/or the entry, adherence, and exit criteria can be updated remotely, for example, based on local standards.

Figure 75:
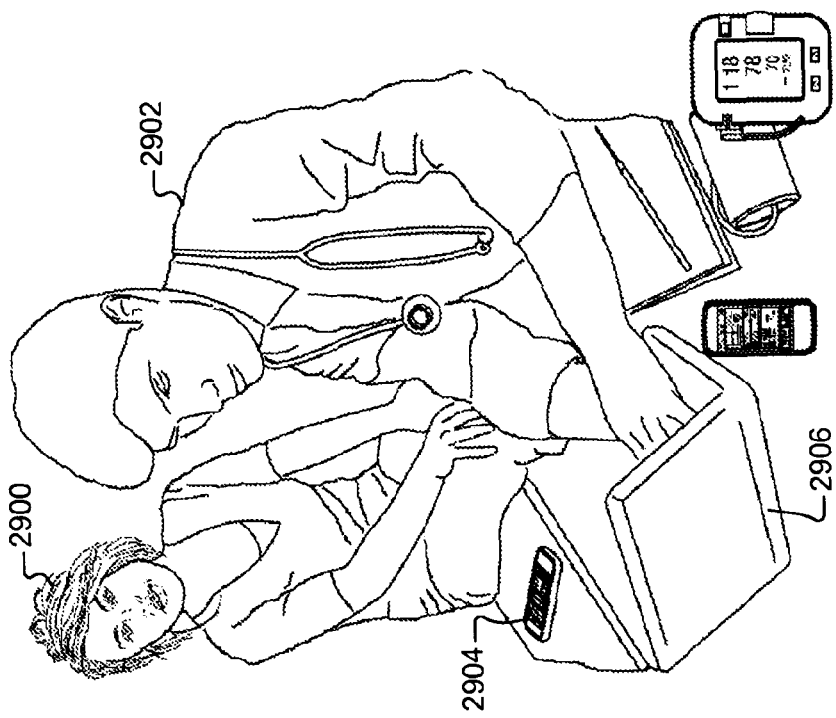
FIG. 75 shows a patient and a health care professional along with various devices that can be used to help the patient monitor and control health.

Referring now to FIG. 75, a patient 2900 with diabetes and a health care professional 2902 are shown in a clinical environment. A person with diabetes can have a metabolic syndrome, pre-diabetes, type 1 diabetes, type 2 diabetes, gestational diabetes, etc. Healthcare providers for diabetes are diverse and include nurses, nurse practitioners, physicians, endocrinologists, and others and are collectively referred to as health care professionals.

During a health care consultation, the patient 2900 typically shares with the health care professional 2902 a variety of data including blood glucose (bG) measurements, continuous glucose monitor data, amounts and type of insulin administered, amounts of food and beverages consumed, exercise schedules, health status, and other lifestyle information. The health care professional 2902 can obtain additional data for the patient 2900, such as measurements of HbA1C, cholesterol levels, triglycerides, blood pressure, and weight. The data can be recorded manually or electronically on a handheld diabetes management device 2904 (e.g., a handheld bG monitor device), a diabetes analysis software executed on a personal computer (PC) 2906, and/or a web-based diabetes analysis site. The health care professional 2902 can analyze the patient data manually or electronically using the diabetes analysis software and/or the web-based diabetes analysis site. After analyzing the data and reviewing how well the patient 2900 followed a previously prescribed therapy, the health care professional 2902 can decide whether to modify a therapy prescribed for the patient 2900.

Figure 76:
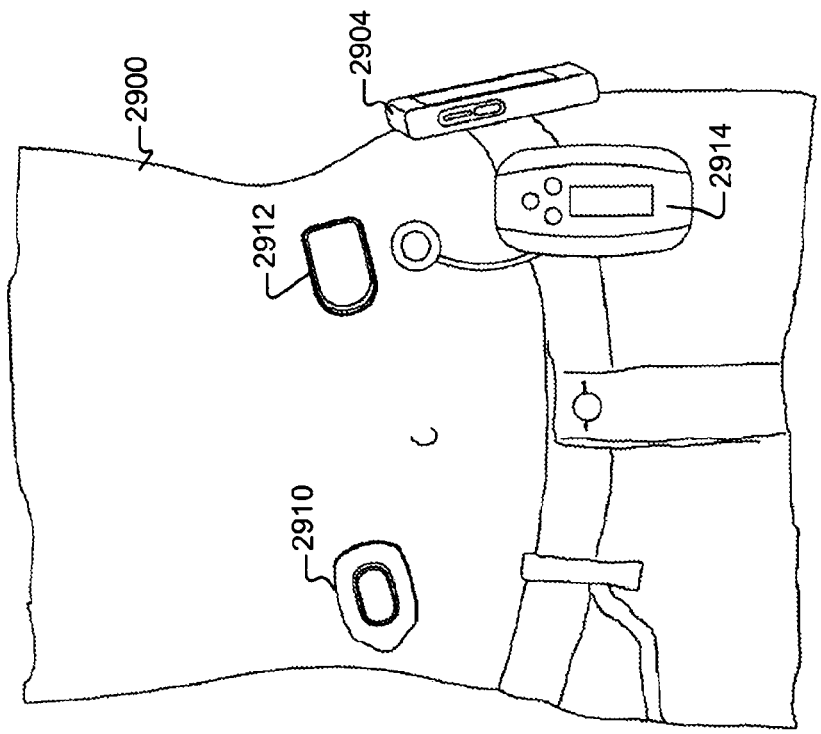
FIG. 76 shows a patient with a continuous glucose monitor (CGM), an ambulatory durable insulin infusion pump, an ambulatory non-durable insulin infusion pump, and a blood glucose (bG) management device.

Referring now to FIG. 76, the patient 2900 can use a continuous glucose monitor (CGM) 2910, an ambulatory durable insulin infusion pump 2912 or an ambulatory non-durable insulin infusion pump 2914 (collectively insulin pump 2912 or 2914), and the diabetes management device 2904. The CGM 2910 can use a subcutaneous sensor to sense and monitor the amount of glucose in the blood of the patient 2900. The CGM 2910 communicates bG measurements to the diabetes management device 2904. The CGM 2910 can also measure and communicate measurements to the diabetes management device 2904 regarding insulin level in the blood of the patient 2900.

The diabetes management device 2904 performs various tasks including measuring and recording bG measurements, determining an amount of insulin to be administered to the patient 2900 via the insulin pump 2912 or 2914, receiving user input via a user interface, archiving data, performing structured bG tests, etc. The diabetes management device 2904 can transmit instructions to the insulin pump 2912 or 2914, and the insulin pump 2912 or 2914 selectively delivers insulin to the patient 2900. Insulin can be delivered in the form of a meal bolus dose, a correction bolus dose, a basal dose, etc.

Figure 77:
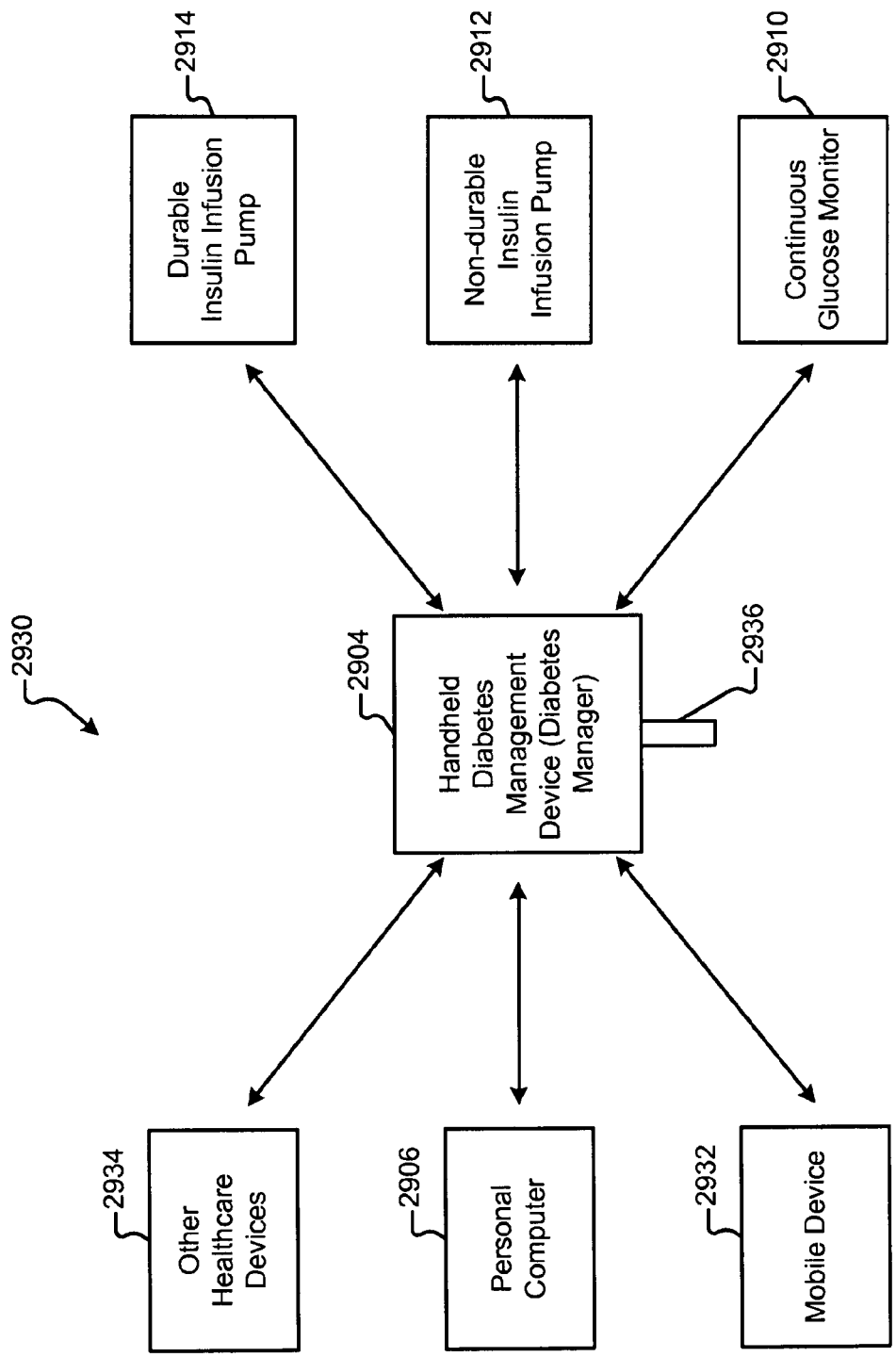
FIG. 77 shows a diabetes care system of systems that can be used to manage diabetes.

Referring now to FIG. 77, a diabetes management system 2930 is shown which can be used by the patient 2900 and/or the health care professional 2902. The system 2930 can include one or more of the following devices: the diabetes management device 2904, the CGM 2910, the insulin pump 2912 or 2914, a mobile device 2932, the diabetes management software executed on the computer 2906, and one or more other health care devices 2934. The diabetes management device 2904 can be configured as a system "hub" and communicate with one or more of the other devices of the system 2930. The insulin pump 2914, the mobile device 2932, or another suitable device can alternatively serve as the system hub. Communication between various devices in the system 2930 can be performed using wireless interfaces (e.g., Bluetooth) and/or wired interfaces (e.g., USB). Communication protocols used by these devices can include protocols compliant with the IEEE 11073 standard as extended using guidelines provided by Continua Health Alliance Design Guidelines. Further, health care records systems such as Microsoft HealthVault™ and Google Health™ can be used by the patient 2900 and health care professional 2902 to exchange information.

The diabetes management software running on the computer 2906 can include an analyzer-configurator that stores configuration information for devices of the system 2930. For example only, the configurator has a database to store configuration information for the diabetes management device 2904 and the other devices. A user can interface the configurator through standard web based or computer graphical user interfaces (GUIs). The configurator selectively transmits user-approved configurations to the devices of the system 2930. The analyzer selectively retrieves data from the devices of the system 2930, stores the data in a database, selectively analyzes the data, and outputs analysis results through standard web based or computer GUIs.

Figure 78:
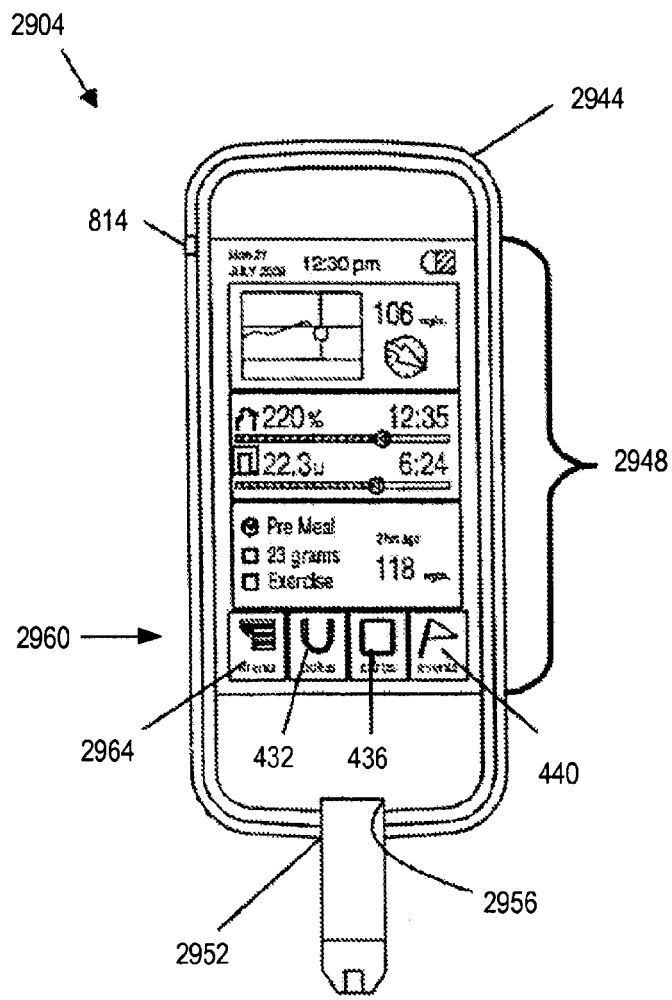
FIG. 78 is a high level diagram of an example implementation of a handheld diabetes management device.

Referring now to FIG. 78, a high level illustration of an example embodiment of the diabetes management device 2904 is presented. The diabetes management device 2904 includes, among other things, a housing 2944, user unit control switches (not shown in FIG. 78), a touchscreen display 2948, and a bG test strip port 2956. The user unit control switches, for example, can include ON/OFF switches, volume switches, alarm switches for bG testing and/or insulin administration, and/or one or more other switches or other types of control devices that a user can use to control functions/operations of the diabetes management device 2904.

A bG test strip 2952 can be inserted into the bG test strip port 2956. The bG test strip 2952 can be inserted into the bG test strip port 2956 by a user, from a test strip drum (not shown) located within the diabetes management device 2904, or in another suitable manner. The bG test strip 2952 is shown as being inserted into the bG test strip port 2956 in the example of FIG. 78 and as separate from the bG test strip port 2956 in the example of FIG. 79.

User selectable options 2960 can be displayed on a portion of the display 2948. The selectable options 2960 can include a menu option 2964, a bolus insulin option 2968, a carbohydrate option 2972, and an event option 2980. One or more other user selectable options can additionally or alternatively be available. The user can access a device menu for the diabetes management device 2904 by selecting the menu option 2964. The user can input various insulin (and/or other medication) information (e.g., amount, insulin type, etc.) by selecting the bolus insulin option 2968. The user can input various carbohydrate intake information (e.g., amount) by selecting the carbohydrate option 2972. The user can also input other food intake information (e.g., protein content, fat content, etc.) by selecting the carbohydrate option 2972. The user can input various event related information (e.g., meals, exercise, periods of stress, etc.) that can affect the user's bG measurements by selecting the event option 2980.

Although the display 2948 is described herein as a touchscreen display, the diabetes management device 2904 can include another suitable form of display (e.g., LED, etc.). If a touchscreen display is not used, the user control switches can include specific buttons or controls by which the user is able to select various options and input markers needed to select, input, and perform "structured bG tests." "Structured bG tests" can also be referred to as "focused tests."

The above description is a broad description of the diabetes management device 2904. In practice, the diabetes management device 2904 can include additional controls, input ports, output ports, etc., as can be desired to further enhance its utility or its use with other components and devices (e.g., computers, infusion pumps, cellular phones, etc.). The description of the diabetes management device 2904 should not be taken as limiting as to the construction of the diabetes management device 2904 or as to the features and capabilities of the diabetes management device 2904.

Figure 79:
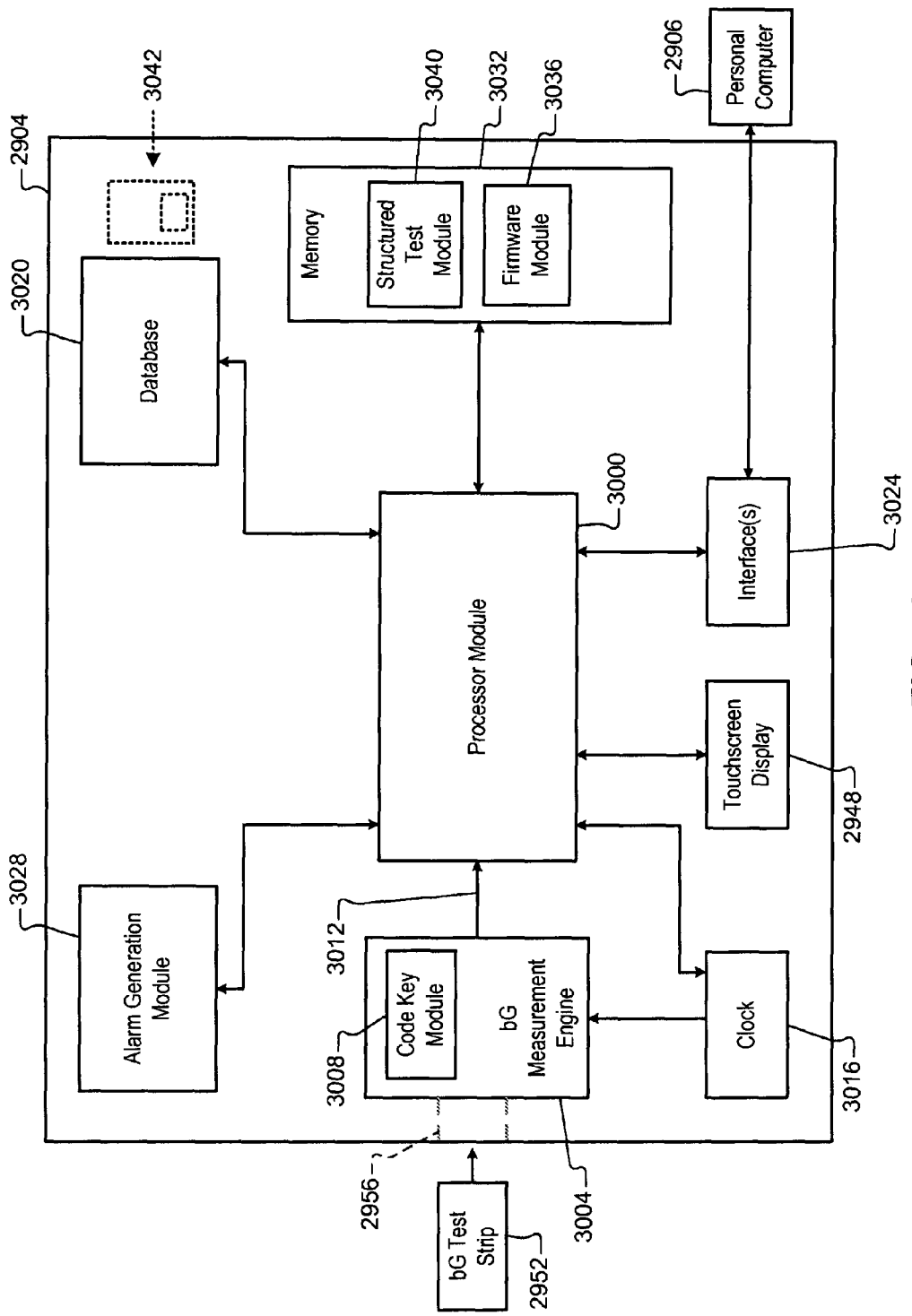
FIG. 79 includes a functional block diagram of an example implementation of the handheld diabetes management device.

Referring now to FIG. 79, a functional block diagram of the diabetes management device 2904 is presented. The diabetes management device 2904 can include a processor module (e.g., a microprocessor based subsystem) 504 that can receive information from a bG measurement engine 3004. The bG measurement engine 3004 can be located adjacent the bG test strip port 2956.

The bG measurement engine 3004 reads (measures) the bG test strip 2952. The bG measurement engine 3004 can include a code key module 3008 that includes pre-calibrated data for determining a bG level from the bG test strip 2952. The bG measurement engine 3004 generates bG sample data 3012 based on its reading of the bG test strip 2952. Among other things, the bG sample data 3012 includes data indicative of the bG level of a blood sample on the bG test strip 2952. The processor module 3000 can also receive bG sample data from other sources, such as via the CGM 2910, the display 2948, and/or another suitable source. The processor module 3000 can receive user input data via, for example, the display 2948 and/or one or more other suitable sources.

The bG measurement engine 3004 can also generate the bG sample data 3012 to indicate the date and time when the bG test strip 2952 was read. In other words, the bG measurement engine 3004 can include a time stamp with the bG sample data 3012. In various implementations, the processor module 3000 can selectively time stamp the bG sample data 3012 and can time stamp user input data and other data when it is received.

A clock 3016 can provide the date and time. The user can configure the present date and time, and the clock 3016 thereafter tracks the present date and time. In various implementations, the present date and time can be acquired from (e.g., synchronized with) the computer 2906. The bG measurement engine 3004 communicates the bG sample data 3012 to the processor module 3000.

The processor module 3000 is in communication with a database 3020 used to store bG sample data, user input data, and other data. For example only, the processor module 3000 can store each piece of bG sample data received in the database 3020. The processor module 3000 is also in communication with the display 2948 and one or more interfaces 3024. Each of the interfaces 3024 can provide an interface between the diabetes management device 2904 and an external device, such as the computer 2906, the insulin pump 2912 or 2914, the CGM 2910, the mobile device 2932, the other health care devices 2934, and/or one or more other suitable external devices.

The processor module 3000 is also in communication with an alarm generation module 3028. The alarm generation module 3028 can generate one or more alarms when prompted by the processor module 3000. For example only, the alarm generation module 3028 can generate audible, tactile (e.g., vibratory), and/or visual alarms. The alarms can be used, for example, in prompting a user to input data for a structured bG test during a window of time around an acceptance time. The acceptance time may be a default time or set, for example, by the user.

The processor module 3000 is also in communication with memory 3032. For example only, the memory 3032 can be NAND type flash memory or another suitable type of memory. While not shown in the example of FIG. 79, the database 3020 can be implemented within the memory 3032 in various implementations.

In an example embodiment, the structure of the memory 3032 can be thought of as being modular, where the modules of the memory 3032 each include a specific type of data. For example only, the memory 3032 can include a firmware module 3036 and a structured bG test module 3040 as shown in the example of FIG. 79. The memory 3032 can also include one or more other modules.

Firmware for the diabetes management device 2904 is stored in the firmware module 3036. In the case of the memory 3032 being NAND type flash or another type of re-writable memory, the firmware module 3036 is partitioned from other portions of the memory 3032 and otherwise made non-modifiable (e.g., read only). In this manner, the firmware cannot be updated, re-written, or otherwise modified, via user input to the diabetes management device 2904 or otherwise. In various implementations, the firmware module 3036 can be implemented independently of the memory 3032, such as within read only memory (ROM) or another suitable type of memory as shown in dashed lines at 3042. In all implementations, however, the firmware module 3036 is or is made non-modifiable.

The processor module 3000 selectively executes one or more portions of the firmware to perform various functions of the diabetes management device 2904. For example only, the processor module 3000 can execute a portion of the firmware corresponding to a structured bG test when performance of the structured bG test is initiated. For example only, the user, a health care professional, or the device itself can initiate performance of the structured bG test. While not specifically stated, the actions performed by the processor module 3000 described below can be performed in executing the firmware for the structured bG test.

The processor module 3000 can create a table in the database 3020 with one or more entries for each bG sample and group of bG samples that is expected to be input for the structured bG test. The processor module 3000 can selectively trigger generation of one or more alarms and/or cause one or more reminders indicating that user input or a bG sample is expected for the structured bG test to be displayed on the display 2948. The processor module 3000 may limit the number of structured bG tests that are being performed on the diabetes management device 2904 at a given time to one.

All of the entry, adherence, and exit criteria used in executing the structured bG tests are stored in the structured bG test module 3040. Test configuration data used in executing the structured bG tests is also stored in the structured bG test module 3040. Importantly, unlike the firmware stored in the firmware module 3036, the structured bG test module 3040 is modifiable and remotely updatable. For example only, one or more entry, adherence, and/or exit criteria and/or test configuration data can be remotely updated or otherwise modified via the software executed on the computer 2906 or in another suitable manner. This is advantageous as it allows the ready modification of such criteria and/or test configuration data in the future should such modification be necessary, preferable, etc. An additional significant advantage is that since the firmware module 3036 is non-modifiable, a future modification of entry, adherence, and/or exit criteria and/or the test configuration data will not trigger the need for another process of regulatory approval by the manufacturer of the diabetes management device 2904.

The portion of the firmware that the processor module 3000 executes to perform a given structured bG test points to associated test configuration data, entry, adherence, and exit criteria stored in the structured bG test module 3040. The processor module 3000 selectively retrieves the associated test configuration data and the associated entry, adherence, and exit criteria from the structured bG test module 3040. The processor module 3000 can retrieve all of the test configuration data and the entry, adherence, and exit criteria associated with the structured bG test when performance of the structured bG test is initiated, as necessary during execution of the structured bG test, or in another suitable manner. The processor module 3000 can retrieve entry, adherence, and exit criteria for each expected bG sample, for each expected group of bG samples (i.e., sample groups), and for the structured bG test. For example only, the test configuration data may include data regarding a number of data samples expected to be input for the structured bG test, a number of data sample groups for the bG structured test, an expected spacing (e.g., period) between successive data samples, a period (e.g., number of days) over which the structured bG test is to be conducted, an acceptance range or window of time for each data sample, and/or other suitable data.

The entry criteria for an expected (individual) bG sample include one or more criterion used in determining whether to begin expecting receipt of bG sample data. For example only, the entry criteria can include a time (of a date) after which the bG sample is expected to be input. For example only, if a given bG sample is expected on a given date between time X and time Y, the entry criteria for the bG sample can include the date and time X. The entry criteria for a bG sample can additionally or alternatively include one or more other suitable criteria, such as user input data, whether user input data has been received, whether the user input data exhibits predetermined characteristics, whether an earlier input satisfied its associated adherence criteria, etc.

The adherence criteria for a received bG sample include one or more criterion used in determining whether to accept or reject the bG sample. In other words, the adherence criteria for a received bG sample include criteria used in determining whether the bG sample data is acceptable for consideration in making a medical determination. For example only, if a bG sample is expected on a given date between time X and time Y, the adherence criteria for the bG sample can include the date and a window of time defined by time X and time Y. Accepted bG samples can be marked for consideration in making the medical determination. Rejected bG samples can be determining whether exit criteria for a bG sample group and/or the structured bG test are satisfied.

The processor module 3000 selectively accepts or rejects received bG samples based on comparisons of one or more characteristics of the bG sample data with the associated adherence criteria. For example only, the processor module 3000 can mark a received bG sample as accepted when the associated adherence criteria are satisfied. Conversely, the processor module 3000 can mark the bG sample as rejected when a received bG sample does not satisfy the associated adherence criteria.

The exit criteria for an expected bG sample include one or more criterion used in determining whether to stop expecting the input of an expected bG sample. For example only, the exit criteria for a bG sample can include satisfaction of the adherence criteria associated with the bG sample, satisfaction of the exit criteria for a bG sample group of which the expected bG sample is a part, and/or satisfaction of the exit criteria for the structured bG test. The exit criteria for an expected bG sample can additionally or alternatively include an ending time and date. For example only, if a bG sample is expected on a given date between time X and time Y, the exit criteria for the bG sample can include the date and time Y. The exit criteria can also include whether a previous bG sample satisfied its adherence criteria, and/or one or more other suitable exit criteria.

The processor module 3000 can selectively mark an expected bG sample of the structured bG test as having been missed (or otherwise not received) in the database 3020 when the exit criteria for the bG sample are satisfied and the satisfaction is not due to the associated adherence criteria being satisfied. For example only, if a bG sample is expected on a given date between time X and time Y, the processor module 3000 can mark the bG sample as having been missed in the database 3020 when a bG sample is not received and time Y passes.

The entry criteria for an expected bG sample group includes one or more criterion used in determining whether to begin expecting that bG samples of the bG sample group will be input. For example only, the entry criteria can include a time (of a date) after which the one or more bG samples of the bG sample group are expected to be input. For example only, if the bG sample(s) of a bG sample group are expected to be input beginning on a given date, the entry criteria for the given sample group can include the date. The entry criteria for an expected sample group can additionally or alternatively include one or more other suitable criteria.

The adherence criteria for an expected bG sample group include one or more criterion used in determining whether to accept or reject the bG sample group (including accepted bG samples of the bG sample group). In other words, the adherence criteria for a bG sample group includes criteria used in determining whether the bG samples of the bG sample group as a whole are acceptable for consideration in making the medical determination. For example only, the adherence criteria for an expected sample group can include a threshold number of accepted bG samples. For example only, if X bG samples are expected to be input for a given bG sample group and Y of the X bG samples are expected to be accepted, Y can be adherence criteria for the bG sample group. X and Y are integers, and Y is greater than zero and less than or equal to X. The adherence criteria for an expected bG sample group can additionally or alternatively include one or more other suitable criteria.

The processor module 3000 selectively accepts or rejects bG sample groups based on comparisons of one or more characteristics of the bG sample groups with the associated adherence criteria. For example only, the processor module 3000 can mark a bG sample group as accepted when the associated adherence criteria are satisfied.

The exit criteria for a bG sample group includes one or more criterion used in determining the expectation of receipt of expected bG samples for the bG sample group should end. For example only, the exit criteria for a bG sample group can include satisfaction of the adherence criteria associated with the bG sample group and/or satisfaction of exit criteria for the structured bG test. The exit criteria for a bG sample group can additionally or alternatively include an ending date and time for the sample group. For example only, if all of the bG samples of a bG sample group are expected to be input before a given date, the exit criteria for the bG sample group can include the given date. The exit criteria for a bG sample group can additionally or alternatively include a threshold number of missed or rejected bG samples. For example only, if X bG samples are expected for a bG sample group and Y of the X bG samples is a maximum number of the expected bG samples that can be missed or rejected, Y can be exit criteria for the bG sample group. X and Y are integers, and Y is greater than or equal to zero and less than or equal to X. The exit criteria for a bG sample group can additionally or alternatively include one or more other suitable criteria.

The entry criteria for the structured bG test include one or more criterion used in determining whether to begin performing the structured bG test. For example only, the entry criteria for the structured bG test can include a time (of a date) after which the structured bG test is to begin. The entry criteria for the structured bG test can additionally or alternatively include a threshold age of the user, a threshold range for HbA1c of the user, a threshold length of time that the user has had diabetes, a specified type of diabetes diagnosed to the user, a threshold body mass index (BMI) of the user, and/or a threshold fasting plasma glucose level. The entry criteria for the structured bG test can additionally or alternatively include one or more other suitable criteria.

The adherence criteria for the structured bG test includes one or more criterion used in determining whether to accept or reject all of the bG data received for the structured bG test. In other words, the adherence criteria for the structured bG test includes criteria used in determining whether accepted groups of bG samples, taken as a whole, are acceptable for consideration in making the medical determination. For example only, the adherence criteria for the structured bG test can include a threshold number of accepted bG sample groups. For example only, if X bG sample groups are expected for the structured bG test and Y of the X bG sample groups is a minimum number of the bG sample groups to be accepted, Y can be adherence criteria for the structured bG test. X and Y are integers, and Y is greater than zero and less than or equal to X. The adherence criteria for the structured bG test can additionally or alternatively include one or more other suitable criteria.

The processor module 3000 selectively accepts or rejects the sample data input for the structured bG test based on one or more characteristics of the bG sample groups or the bG samples and the associated adherence criteria. For example only, the processor module 3000 can mark the structured bG test as accepted when the associated adherence criteria are satisfied.

The exit criteria for the structured bG test include one or more criterion used in determining the expectation of receipt of bG samples for the structured bG test should end. For example only, the exit criteria for the structured bG test can include satisfaction of the adherence criteria associated with the structured bG test. The exit criteria for the structured bG test can additionally or alternatively include an ending date (and possibly time) for the structured bG test. For example only, if all of the samples of the structured bG test are expected to be input before a given date, the exit criteria for the structured bG test can include the date. The exit criteria for the structured bG test can additionally or alternatively include a threshold number of missed and rejected bG samples and/or a threshold number of rejected bG sample groups. For example only, if X bG samples are expected for a sample group, and if Y of the X bG samples is a maximum number of the expected bG samples that can be missed or rejected, Y can be exit criteria for the structured bG test. X and Y are integers, and Y is greater than or equal to zero and less than or equal to X. For another example only, if X bG sample groups are expected for the structured bG test and Y of the X bG sample groups is a maximum number of the bG sample groups that can be rejected, Y can be exit criteria for the structured bG test. X and Y are integers, and Y is greater than or equal to zero and less than or equal to X. The exit criteria for a bG sample group can additionally or alternatively include one or more other suitable criteria.

Further information on adherence, exit, and entry criteria can be found in paragraphs [0048] and [0092]-[0116] of commonly assigned U.S. patent application Ser. No. 12/643,338, filed Dec. 21, 2009, and titled "Structured Testing Method for Diagnostic or Therapy Support of a Patient with a Chronic Disease and Devices Thereof." Additional information on adherence, exit, and entry criteria can also be found in paragraphs [0087]-[0112] of commonly assigned U.S. patent application Ser. No. 12/643,415, filed on Dec. 21, 2009, and titled "Management Method and System for Implementation, Execution, Data Collection, and Data Analysis of a Structured Collection Procedure Which Runs on a Collection Device." The above patent applications, including the above mentioned paragraphs, are incorporated by reference.

Figure 80:
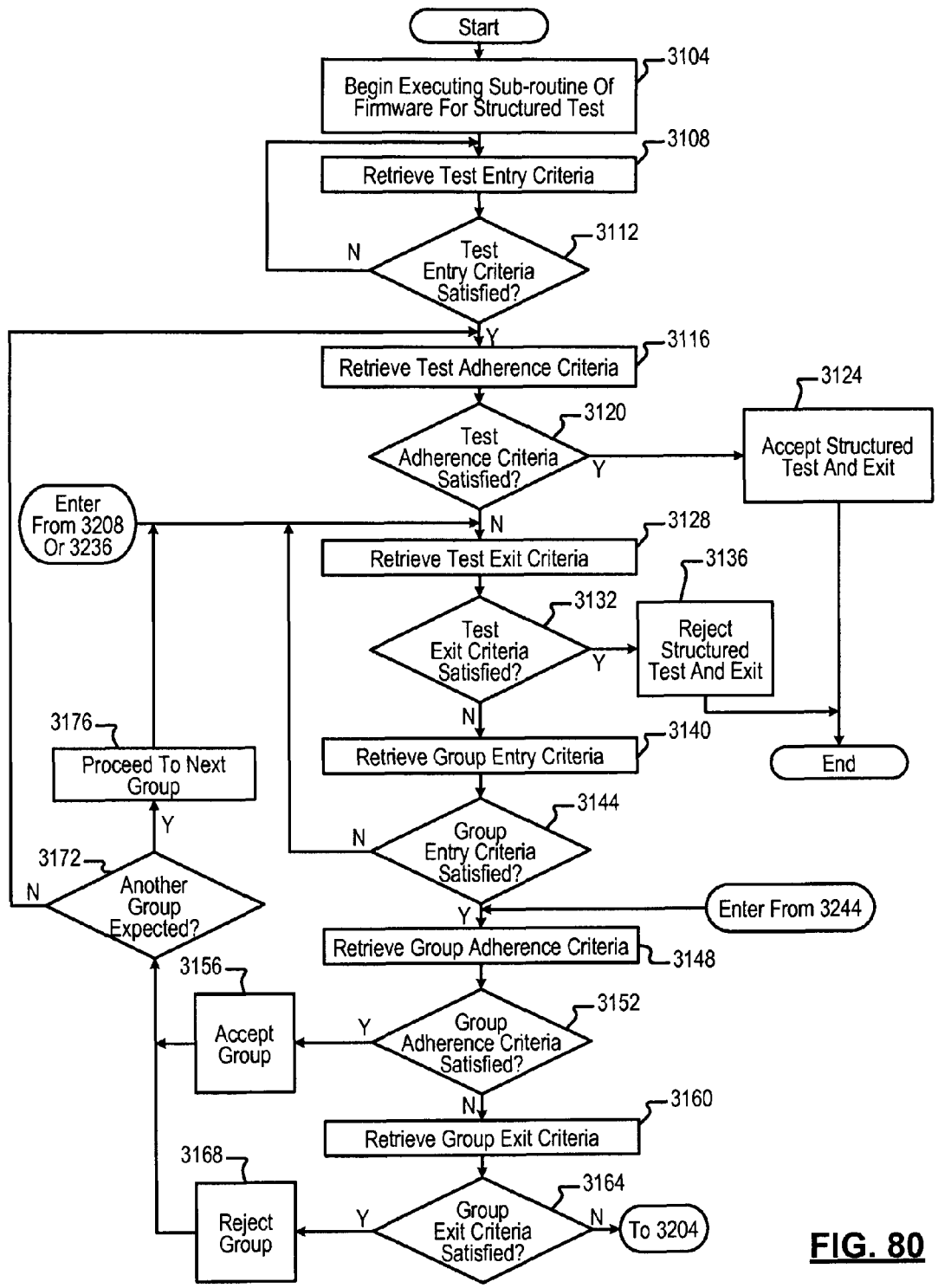
FIGS. 80-81 include a flowchart depicting an example method of performing a structured bG test on the handheld diabetes management device.
Figure 81:
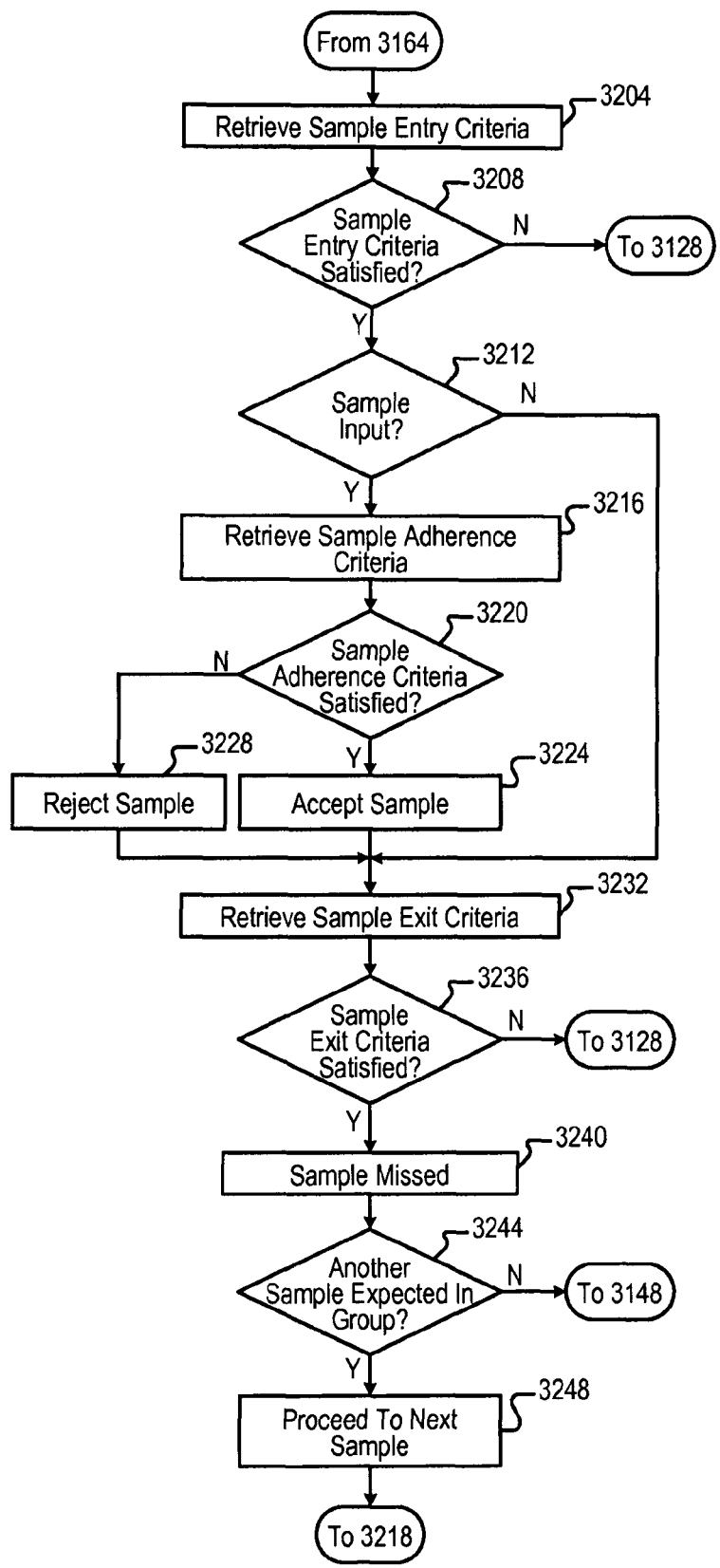

Referring now to FIGS. 80-81, an example method that the processor module 3000 can execute in carrying out the firmware for a given structured bG test is presented. Control can begin with operation 3104 where execution of the sub-routine of the firmware for the structured bG test can begin. The sub-routine and the firmware are stored in a non-modifiable portion of memory of the diabetes management device 2904.

At operation 3108, the entry criteria for the structured bG test can be retrieved from a modifiable portion of memory of the diabetes management device 2904. A determination can be made as to whether the entry criteria for the structured bG test are satisfied at operation 3112. If true, operation 3116 can be performed; if false, operation 3108 can be returned to. At operation 3116, the adherence criteria for the structured bG test can be retrieved from the modifiable portion of memory.

At 620, a determination can be made as to whether the adherence criteria for the structured bG test are satisfied. If true, the structured bG test can be accepted and performance of the structured bG test can be exited at operation 3124. If false, operation 3128 can be performed. The exit criteria for the structured bG test can be retrieved from the modifiable portion of memory at operation 3128. A determination can be made at operation 3132 as to whether the exit criteria for the structured bG test are satisfied. If true, the structured bG test can be rejected and performance of the structured bG test can be exited at operation 3136. If false, operation 3140 can be performed.

The entry criteria for a bG sample group can be retrieved from the modifiable portion of memory at operation 3140. A determination can be made as to whether the entry criteria for the bG sample group are satisfied at operation 3144. If true, operation 3148 can be performed; if false, operation 3128 can be returned to. At operation 3148, the adherence criteria for the bG sample group can be retrieved from the modifiable portion of memory. A determination can be made as to whether the adherence criteria for the bG sample group are satisfied at operation 3152. If true, the bG sample group can be accepted at operation 3156 and operation 3172 can be performed, which is discussed in detail below. If false, operation 3160 can be performed.

At operation 3160, the exit criteria for the bG sample group can be retrieved from the modifiable portion of memory. A determination can be made as to whether the exit criteria for the bG sample group are satisfied at operation 3164. If true, the bG sample group can be rejected at 3168 and operation 3172 can be performed. If false, operation 3204 of FIG. 81 can be performed. At operation 3172, a determination can be made as to whether another bG sample group is expected for the structured bG test. If true, the next bG sample group can be proceeded to at operation 3176 and operation 3128 can be returned to. If false, operation 3116 can be returned to.

Referring now to FIG. 81, the entry criteria for an expected bG sample can be retrieved from the modifiable portion of memory at operation 3204. A determination can be made as to whether the entry criteria for the bG sample are satisfied at operation 3208. If true, operation 3212 can be performed; if false, operation 3128 can be returned to. A determination can be made as to whether the expected bG sample has been input at operation 3212. If true, operation 3216 can be performed; if false, operation 3232 can be performed, which is discussed further below.

The adherence criteria for the bG sample can be retrieved from the modifiable portion of memory at operation 3216. A determination can be made as to whether the adherence criteria for the bG sample are satisfied at operation 3220. If true, the bG sample can be accepted at operation 3224 and operation 3232 can be performed; if false, the bG sample can be accepted at operation 3228 and operation 3232 can be performed. At operation 3232, the exit criteria for the bG sample can be retrieved from the modifiable portion of memory.

A determination can be made as to whether the exit criteria for the bG sample are satisfied at operation 3236. If true, the bG sample can be marked as having been missed at operation 3240 and operation 3244 can be performed; if false, operation 3128 can be returned to. At operation 3244, a determination can be made as to whether another bG sample is expected for the bG sample group. If true, the next bG sample can be proceeded to at operation 3248 and operation 3128 can be returned to; if false, operation 3148 can be returned to.

A handheld diabetes management device having improved updatability of entry, adherence, and exit criteria, comprises: a blood glucose (bG) management engine, memory, a display, and a processor module. The bG measurement engine that measures a bG level in a sample of blood of a user and that generates sample data indicative of the bG level. The processor module is in communication with the bG measurement engine, the display, and the memory. The processor module selectively executes firmware stored in a non-modifiable portion of the memory for performing operations to carry out a structured bG test; selectively retrieves entry, adherence, and exit criteria stored in a modifiable portion of the memory for individual bG samples expected to be input for the structured bG test; selectively retrieves entry, adherence, and exit criteria stored in the modifiable portion of the memory for bG sample groups expected for the structured bG test; and retrieves entry, adherence criteria, and exit criteria from the modifiable portion of the memory for the structured bG test.

In other features, the processor module of the handheld diabetes management device begins collection of data for the structured bG test when the entry criteria for the structured bG test are satisfied.

In still other features the processor module of the handheld diabetes management device ends data collection for the structured bG test when the adherence criteria or the exit criteria for the structured bG test are satisfied.

In further features, the processor module of the handheld diabetes management device marks data stored for the structured bG test as accepted when the adherence criteria for the structured bG test are satisfied.

In still further features, the processor module of the handheld diabetes management device begins collection of data for a bG sample group when the entry criteria for the bG sample group are satisfied.

In other features, the processor module of the handheld diabetes management device ends data collection for a bG sample group of the structured bG test when one of the adherence criteria and the exit criteria for the bG sample group are satisfied.

In still other features, the non-modifiable portion of the firmware is partitioned from other portions of the memory and marked as being non-modifiable.

In further features, the non-modifiable portion of memory is implemented in a first memory module, the modifiable portion of memory is implemented in a second memory module, and the first and second memory modules are separate memory modules.

In still further features, a diabetes management system includes the handheld diabetes management device of claim 1; and a computer that is remote to the handheld diabetes management device. The computer selectively updates at least one of the entry, adherence, and exit criteria.

Another handheld diabetes management device having improved updatability of entry, adherence, and exit criteria, comprises a blood glucose (bG) management engine, memory, a display, and a processor module. The bG measurement engine that measures a bG level in a sample of blood of a user and that generates sample data indicative of the bG level. The processor module is in communication with the bG measurement engine, the display, and the memory. The processor module selectively executes firmware for performing operations to carry out a structured bG test stored in a non-modifiable portion of the memory and selectively retrieves entry, adherence, and exit criteria for the structured bG test stored a modifiable portion of the memory.

In other features, the processor module begins collection of data for the structured bG test when the entry criteria are satisfied.

In still other features, the processor module ends data collection for the structured bG test when the adherence criteria or the exit criteria for the structured bG test are satisfied.

In further features, the non-modifiable portion of the firmware is partitioned from other portions of the memory and marked as being non-modifiable.

In still further features, the non-modifiable portion of memory is implemented in a first memory module, the modifiable portion of memory is implemented in a second memory module, and the first and second memory modules are separate memory modules.

A computer readable storage medium for a handheld blood glucose (bG) management device that measures a user's bG level and that includes a touchscreen display, the computer readable storage medium comprising a modifiable portion and a non-modifiable portion. The modifiable portion includes adherence, exit, and entry criteria for performing a structured bG test are stored. The non-modifiable portion includes firmware that, when executed by a processor of the handheld diabetes management device, causes the processor to perform the structured bG test involving obtaining measurements of the user's bG level according to a predefined schedule and selectively retrieving the adherence, exit, and entry criteria from the modifiable portion.

A method of improving updatability of entry, adherence, and exit criteria stored in memory of a handheld diabetes management device, the method comprises: providing the handheld diabetes management device with a blood glucose (bG) measurement engine that measures a bG level in a sample of blood of a user and that generates sample data indicative of the bG level; providing the handheld diabetes management device with the memory and a touchscreen display; providing the handheld diabetes management device with a processor module that is in communication with the bG measurement engine, the touchscreen display, and the memory; storing firmware that is executable by the processor module for performing operations to carry out a structured bG test in a non-modifiable portion of the memory; and storing the entry, adherence, and exit criteria in a modifiable portion of the memory.

In other features, the storing the entry, adherence, and exit criteria comprises: storing entry, adherence, and exit criteria stored for individual bG samples expected to be input in the carrying out of the structured bG test in the modifiable portion of the memory; storing entry, adherence, and exit criteria for groups of the individual bG samples expected in the carrying out of the structured bG test; and storing entry, adherence criteria, and exit criteria for the structured bG test in the modifiable portion of the memory.

In still other features, the method further comprises partitioning the non-modifiable portion of the firmware from other portions of the memory and marking the firmware as being non-modifiable.

Communication Protocol that Supports Structured Collection Procedures used in Diabetes Care Referring to FIG. 75, a person 2900 with diabetes and a healthcare professional 2902 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 2900 typically shares with the clinician 2902 a variety of patient data including blood glucose measurements, continuous glucose monitor data, amounts of insulin infused, amounts of food and beverages consumed, exercise schedules, and other lifestyle information. The clinician 2902 may obtain additional patient data that includes measurements of HbA1C, cholesterol levels, triglycerides, blood pressure, and weight of the patient 2900. The patient data can be recorded manually or electronically on a handheld diabetes management device 2904, a diabetes analysis software executed on a personal computer (PC) 2906, and/or a web-based diabetes analysis site (not shown). The clinician 2902 can analyze the patient data manually or electronically using the diabetes analysis software and/or the web-based diabetes analysis site. After analyzing the patient data and reviewing adherence of the patient 2900 to previously prescribed therapy, the clinician 2902 can decide whether to modify the therapy for the patient 2900.

Referring to FIG. 76, the patient 2900 can use a continuous glucose monitor (CGM) 2910, an ambulatory non-durable insulin infusion pump 2912 or an ambulatory durable insulin infusion pump 2914 (hereinafter insulin pump 2912 or 2914), and the handheld diabetes management device 2904 (hereinafter the diabetes manager 2904). The CGM 2910 uses a subcutaneous sensor to sense and monitor the amount of glucose in the blood of the patient 2900 and communicates corresponding readings to the diabetes manager 2904.

The diabetes manager 2904 performs various tasks including measuring and recording blood glucose levels, determining an amount of insulin to be administered to the patient 2900 via the insulin pump 2912 or 2914, receiving patient data via a user interface, archiving the patient data, etc. The diabetes manager 2904 periodically receives readings from the CGM 2910 indicating insulin level in the blood of the patient 2900. The diabetes manager 2904 transmits instructions to the insulin pump 2912 or 2914, which delivers insulin to the patient 2900. Insulin can be delivered in a scheduled manner in the form of a basal dose, which maintains a predetermined insulin level in the blood of the patient 2900. Additionally, insulin can be delivered in the form of a bolus dose, which raises the amount of insulin in the blood of the patient 2900 by a predetermined amount.

Referring to FIG. 77, a diabetes management system 2930 used by the patient 2900 and the clinician 2902 includes one or more of the following devices: the diabetes manager 2904, the continuous glucose monitor (CGM) 2910, the insulin pump 2912 or 2914, a mobile device 2932, the PC 2906 with the diabetes analysis software, and other healthcare devices 2934. The diabetes manager 2904 is configured as a system hub and communicates with the devices of the diabetes management system 2930. Alternatively, the insulin pump 2914 or the mobile device 2932 can serve as the system hub. Communication between the devices in the diabetes management system 2930 can be performed using wireless interfaces (e.g., Bluetooth) and/or wireline interfaces (e.g., USB). Communication protocols used by, these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 2900 and clinician 2902 to exchange information.

The diabetes manager 2904 can receive blood glucose readings from one or more sources (e.g., from the CGM 2910). The CGM 2910 continuously measures the blood glucose level of the patient 2900. The CGM 2910 periodically communicates the blood glucose level to the diabetes manager 2904. The diabetes manager 2904 and the CGM 2910 communicate wirelessly using a proprietary Gazell wireless protocol developed by Nordic Semiconductor, Inc.

Additionally, the diabetes manager 2904 includes a blood glucose meter (BGM) and a port that communicates with the BGM (not shown). The port can receive a blood glucose measurement strip 2936. The patient 2900 deposits a sample of blood or other bodily fluid on the blood glucose measurement strip 2936. The BGM analyzes the sample and measures the blood glucose level in the sample. The blood glucose level measured from the sample and/or the blood glucose level read by the CGM 2910 can be used to determine the amount of insulin to be administered to the patient 2900. To facilitate collection of blood glucose measures, the diabetes manager 2904 may executes one or more structured collection procedures as further described below.

The diabetes manager 2904 communicates with the insulin pump 2912 or 2914. The insulin pump 2912 or 2914 can be configured to receive instructions from the diabetes manager 2904 to deliver a predetermined amount of insulin to the patient 2900. Additionally, the insulin pump 2912 or 2914 can receive other information including meal and/or exercise schedules of the patient 2900. The insulin pump 2912 or 2914 can determine the amount of insulin to administer based on the additional information.

The insulin pump 2912 or 2914 can also communicate data to the diabetes manager 2904. The data can include amounts of insulin delivered to the patient 2900, corresponding times of delivery, and pump status. The diabetes manager 2904 and the insulin pump 2912 or 2914 can communicate using a wireless communication protocol such as Bluetooth. Other wireless or wireline communication protocols can also be used.

In addition, the diabetes manager 2904 can communicate with the other healthcare devices 2934. For example, the other healthcare devices 2934 can include a blood pressure meter, a weight scale, a pedometer, a fingertip pulse oximeter, a thermometer, etc. The other healthcare devices 2934 obtain and communicate personal health information of the patient 2900 to the diabetes manager 2904 through wireless, USB, or other interfaces. The other healthcare devices 2934 may use communication protocols compliant with ISO/IEEE 11073. The diabetes manager 2904 can communicate with the other healthcare devices 2934 using interfaces including Bluetooth, USB, etc. Further, the devices of the diabetes management system 2930 can communicate with each other via the diabetes manager 2904.

The diabetes manager 2904 can communicate with the PC 2906 using Bluetooth, USB, or other interfaces. A diabetes management software running on the PC 2906 includes an analyzer-configurator that stores configuration information of the devices of the diabetes management system 2930. The configurator has a database to store configuration information of the diabetes manager 2904 and the other devices. The configurator can communicate with users through standard web or computer screens in non-web applications. The configurator transmits user-approved configurations to the devices of the diabetes management system 2930. The analyzer retrieves data from the diabetes manager 2904, stores the data in a database, and outputs analysis results through standard web pages or computer screens in non-web based applications.

The diabetes manager 2904 can communicate with the mobile device 2932 using Bluetooth. The mobile device 2932 may include a cellular phone, a pager, or a personal digital assistant (PDA). The diabetes manager 2904 can send messages to an external network through the mobile device 2932. The mobile device 2932 can transmit messages to the external network upon receiving requests from the diabetes manager 2904.

Figure 82:
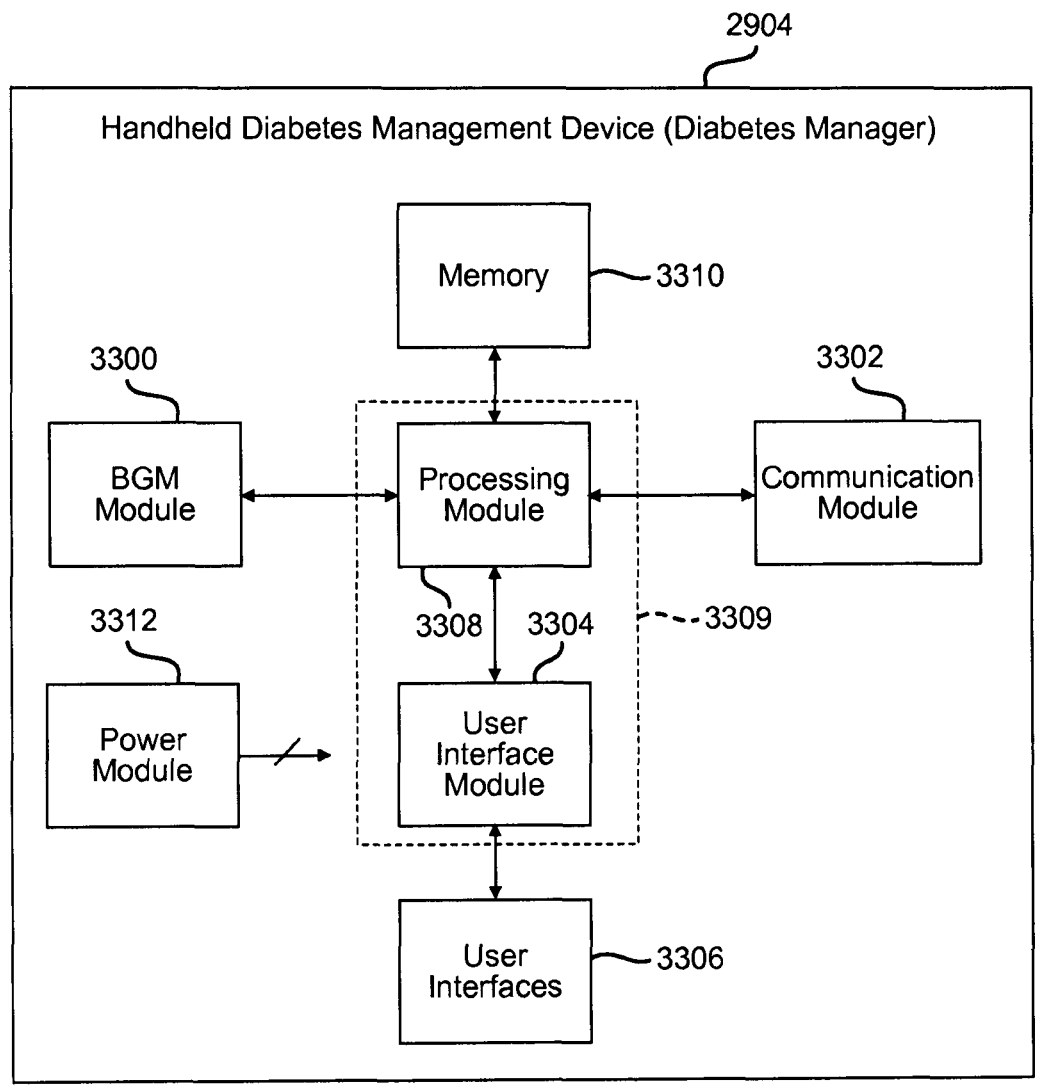
FIG. 82 is a functional block diagram of a diabetes manager.

An exemplary diabetes manager 2904 is further described in relation to FIG. 82. The diabetes manager 2904 comprises a blood glucose measuring (BGM) module 3300, a communication module 3302, a user interface module 3304, user interfaces 3306, a processing module 3308, memory 3310, and a power module 3312. The user interface module 3304 and the processing module 3308 can be implemented by an application processing module 3309. The BGM module 3300 includes a blood glucose measuring engine that analyzes samples provided by the patient 2900 on the blood glucose measurement strip 2936 and that measures the amount of blood glucose in the samples. The communication module 3302 includes multiple radios that communicate with different devices of the diabetes management system 2930. The user interface module 3304 interfaces the diabetes manager 2904 to various user interfaces 3306 that the patient 2900 can use to interact with the diabetes manager 2904. For example, the user interfaces 3306 can include keys, switches, a display, a speaker, a microphone, a secure digital (SD) card port, a USB port, etc. (not shown).

The processing module 3308 processes data received from the BGM module 3300, the communication module 3302, and the user interface module 3304. The processing module 3308 uses memory 3310 for processing and storing data. The memory 3310 can include volatile and nonvolatile memory. The processing module 3308 outputs data to and receives data from the user interfaces 3306 via the user interface module 3304. The processing module 3308 outputs data to and receives data from the devices of the diabetes management system 2930 via the communication module 3302. The power module 3312 supplies power to the components of the diabetes manager 2904. The power module 3312 includes a rechargeable battery. The battery can be recharged using an adapter that plugs into a wall outlet. The battery can also be charged via the USB port of the diabetes manager 2904.

For purposes of this disclosure, the diabetes manager 2904 serves as a collection device. However, the collection device can be any portable electronic device that can provide an acquisition mechanism for determining and storing physiological measures of a person. For example, self-monitoring blood glucose meters and continuous glucose monitor devices are examples of collection devices used in diabetes care. While this disclosure makes reference to diabetes care, it is readily understood that the concepts disclosed herein can be applied to other types of chronic diseases and/or collection devices.

In the diabetes care domain, a structured test or structure collection procedure is a particular type of treatment plan. FIG. 83 conceptually illustrates an exemplary structured collection procedure 3400 comprised of a plurality of parameters that define the procedure. A structured collection procedure is primarily comprised of a series of planned actions or collection events 3410 for obtaining measurement data using the collection device. Each collection event is a request for a physiological measure obtained using the collection device or other input by the patient into the collection device. In the illustrated procedure, the requests are for a bG measurement. A given collection event may require additional input such as an indication of meal size or an indication of the patient's energy level.

In addition to a series of collection events, the structured collection procedure 3400 may include other types of parameters such as a medical use case 3412, an entry criterion 3414, an adherence criterion 3416 and an exit criterion 3418. Medical use case 3412 provides an indication of when the particular procedure may be applicable. In this case, the collection procedure is helpful for determining trends in blood glucose (bG) levels of a patient and/or relationships between blood glucose and other parameters, such as time of day, meal size, energy level, etc. Entry criterion 3414 establishes the conditions needed to be met prior to obtaining a physiological measure from the patient. Adherence criterion 3416 is used to assess qualitatively whether a given collection event was performed. Exit criterion 3418 establishes the conditions needed to be met prior to exiting the structured collection procedure. It is readily understood that other types of parameters may be used to define a structured collection procedure. Further information regarding structure collection procedures may be found in U.S. patent application Ser. No. 12/643,338 entitled "Structured Testing Method for Diagnostic or Therapy Support of a Patient with a Chronic Disease and Devices Thereof" which is incorporated by reference herein.

Figure 85:
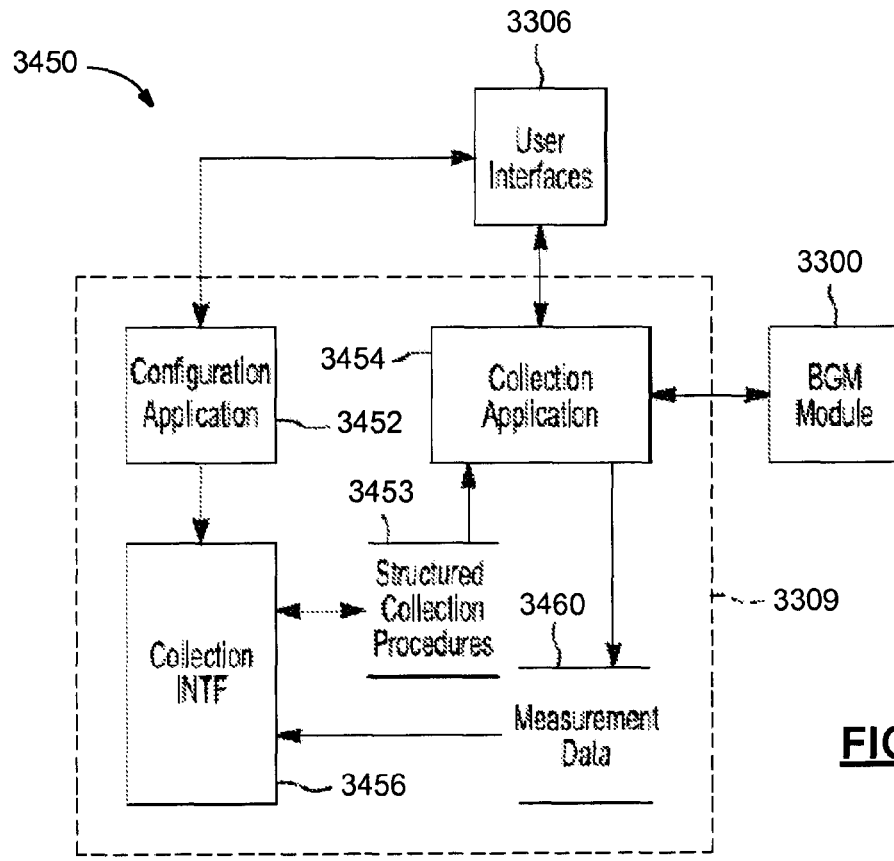
FIG. 85 is a diagram depicting an exemplary system that supports remote configuration of such structure collection procedures.

Structured collection procedures are typically implemented on a collection device, such as diabetes manager 2904. FIG. 85 depicts an exemplary system 3450 that supports remote configuration of such structure collection procedures by a configuration application 3452. In an exemplary embodiment, the application processing module 3309 of the diabetes manager 2904 is further defined to support configuration. The application processing module 3309 include a configuration application 3452, a collection application 3454 and a collection interface 3456; each of these components may be implemented as computer executable instructions in a data store of the collection device. One or more structured collection procedures may also reside in a data store 3458 accessible to the collection application 3454.

During operation, the collection application 3454 executes a structured collection procedure to obtain measurement data from the patient. In a simplified example, the collection application 3454 may interact with a user interface 3306 to prompt a patient to take a glucose measure. The patient may be prompted at a particular time of day as specified by the structured collection procedure. The collection application 3454 is interfaced with the BGM module 3300 to receive blood glucose measures obtained from the patient and store such measures in a data store residing on the collection device. The collection application 3454 may also interact with the user interface 3306 to obtain other input from the patient in accordance with the structured collection procedure.

The collection interface 3456 in turn provides access to the blood glucose measures and other related measurement data. In the exemplary embodiment, measurement data is accessed via the collection interface 3456 using a communication protocol defined in accordance with IEEE standard 11073-20601. In the case of blood glucose measures, the collection interface 3456 may implement a device specialized communication protocol as defined by IEEE standard 11073-10417. For other types of measures, it is understood that the collection interface 3456 may implement the applicable specialized communication protocol.

Over time, the parameters associated with a structured collection procedure residing on the collection device may need to be configured or otherwise modified by a tending healthcare provider. The configuration application 3452 provides the mechanism by which the parameters of a structured collection procedure may be accessed and manipulated by the healthcare provider. For example, the configuration application 3452, interacting with suitable user interfaces, enables the healthcare provider to select a structured collection procedure associated with a given patient. Parameters associated with the select collection procedure are then displayed to the healthcare provider. The healthcare provider may modify and save one or more of the parameters associated with the selected collection procedure. In one exemplary embodiment, the configuration application 3452 may reside on the collection device. In this embodiment, the configuration application 3452 interacts with the user interfaces 3306 residing on the collection device as shown in FIG. 85.

Figure 86:
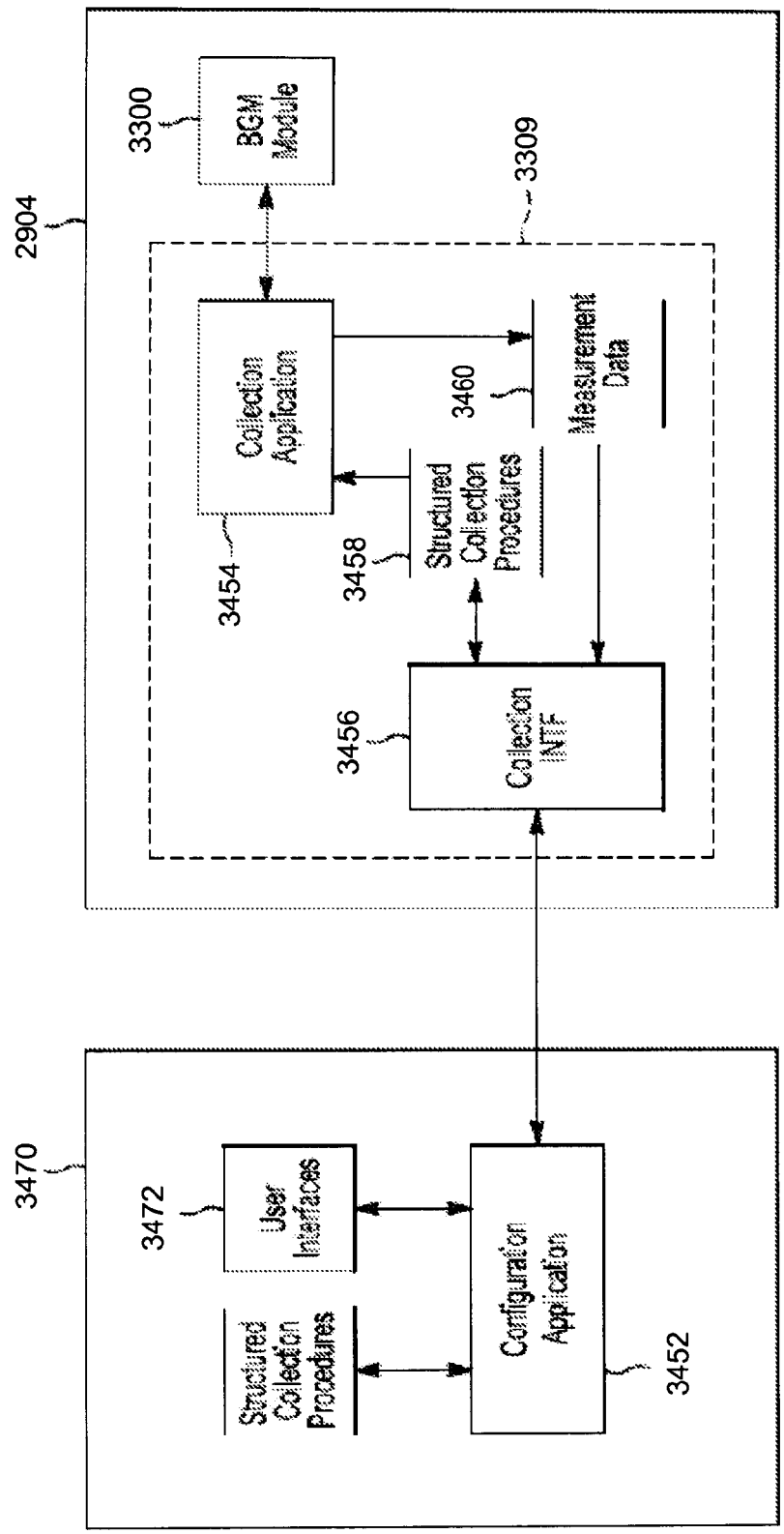
FIG. 86 is a diagram depicting another exemplary system that supports remote configuration of such structure collection procedures.

In another exemplary embodiment, the configuration application 3452 may reside on a device 3470 distinct and remote from the collection device as shown in FIG. 86. For example, the device 3470 may be a personal computer that resides with the healthcare provider. In this embodiment, the configuration application 3452 interacts with user interfaces 3472 residing on the device 3470 to access and manipulate the structured collection procedure, where the structured collection procedures are stored in a data store on the device 3470. Once healthcare provider has updated a given structure collection procedure locally, the configuration application 3452 will then interact with the collection interface to update the corresponding structured collection procedure on the collection device.

To do so, the configuration application 3452 interfaces with the collection interface 3456 using a set of action commands to update parameters of a structured collection procedure residing at the collection device. Of note, the set of action commands are defined in compliance with the communication protocol used to access the measurement data. In the exemplary embodiment, the collection interface 3456 accesses the blood glucose measures using the IEEE standard 11073-10417. Thus, the set of action commands used to access and manipulate the parameters of a structured collection procedure are defined as a private extension of the IEEE standard 11073-10417 as will be further described below.

ISO/IEEE 11073 standard enables communication amongst medical devices and other computer systems. By way of background, ISO/IEEE 11073 standard is based on an object oriented systems management paradigm. The overall system model is divided into three principal components: the domain information model (DIM), the service model, and the communication model. These three components work together to represent data, define data access and command methodologies and communicate the data from an agent to a manager. ISO/IEEE 11073-20601 may be referenced for a detailed description of the modeling constructs although each is described briefly below.

Figure 87:
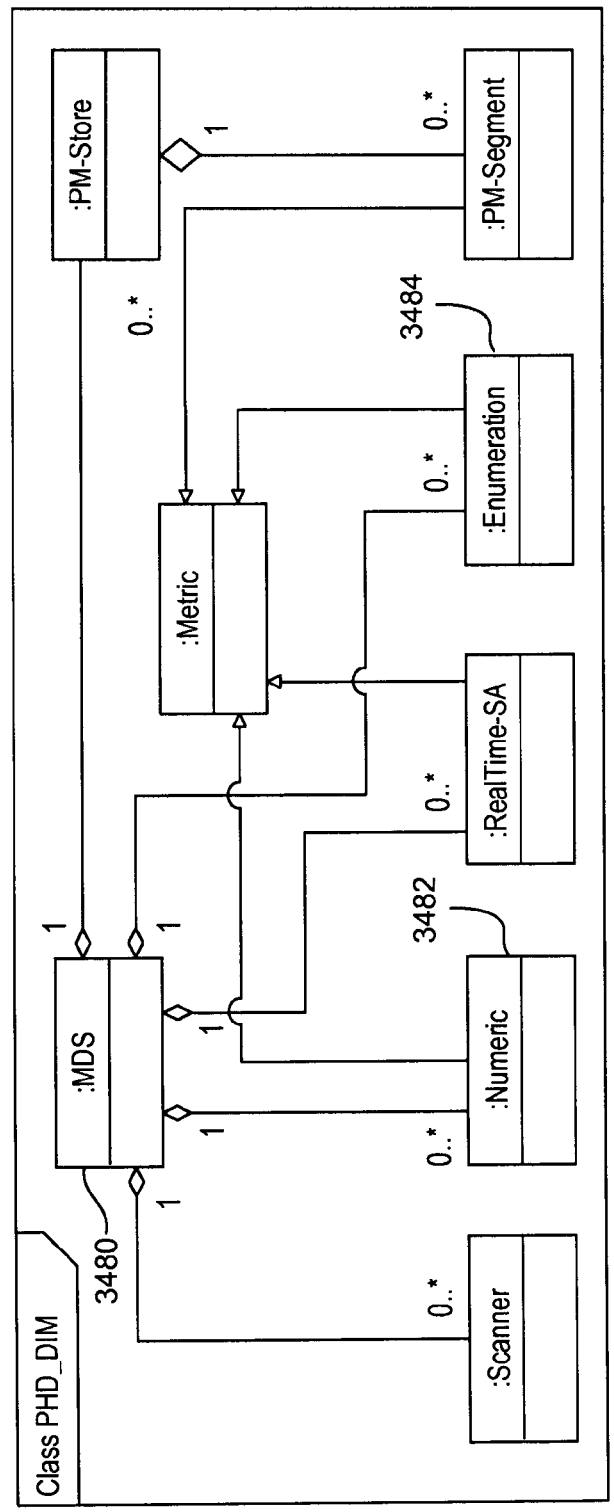
FIG. 87 is a class diagram for a personal health device defined in accordance with ISO/IEEE 11073-20601.

The domain information model is a hierarchical model that describes an agent as a set of objects. These objects and their attributes represent the elements that control behavior and report on the status of the agent and the data that an agent can communicate to a manager. With reference to FIG. 87, a class diagram for a personal health device is defined in accordance with ISO/IEEE 11073-20601. The Medical Device System class 3480 is the root class of the device and contains attributes defining the device itself. Exemplary attributes include the type of device, i.e., glucose meter or insulin pump, manufacturer and model information and registered certification information. All other object classes are derived from the MDS class. For example, the Numeric class represents numeric measurements such as bG, carbohydrates, bolus amount, etc; whereas, the enumeration class represents status information and/or annotation information. For brevity purposes, a description is not provided for all of the classes shown in the figure.

Communication between the agent and the manager is defined by the application protocol in ISO/IEEE 11073-20601. The service model defines the conceptual mechanisms for the data exchange services. Object access services, such as Get, Set, Action and Event Reports, are mapped to messages that are exchanged between the agent and the manager. Protocol messages within the ISO/IEEE 11072 series of standards are defined in ASN.1. The messages defined in ISO/IEEE 11073-20601 can coexist with messages defined in other standard application profiles defined in the ISO/IEEE 11072 series of standards.

In general, the communication model supports the topology of one or more agents communicating over logical point-to-point connections to a single manager. More specifically, the communication model defines the construct of an application protocol data unit (APDU). ADPUs are data packets exchanged between agents and managers. For each logical point-to-point connection, the dynamic system behavior is defined by a connection state machine as specified in ISO/IEEE 11073-20601.

Two styles of configuration are defined in ISO/IEEE 11073-20601: standard and extended. Standard configurations are defined in the ISO/IEEE 11073-104zz specializations (such as the ISO/IEEE 11073-10417 Glucose Device specialization) and are assigned a well-known identifier (Dev-Configuration-Id). The usage of a standard configuration is negotiated at association time between the agent and the manager. If the manager acknowledges that it understands and wants to operate using the configuration, then the agent can begin sending measurements immediately. If the manager does not understand the configuration, the agent provides the configuration prior to transmitting measurement information.

In extended configurations, the agent's configuration is not predefined in a standard. The agent determines which objects, attributes, and values will be used in a configuration and assigns a configuration identifier. When the agent associates with a manager, it negotiates an acceptable configuration. Typically, the manager does not recognize the agent's configuration on the first connection, so the manager responds that the agent needs to send the configuration information as a configuration event report. If, however, the manager already understands the configuration, either because it was pre-loaded in some way or the agent had previously associated with the manager, then the manager responds that the configuration is known and no further configuration information needs to be sent.

Figure 84:
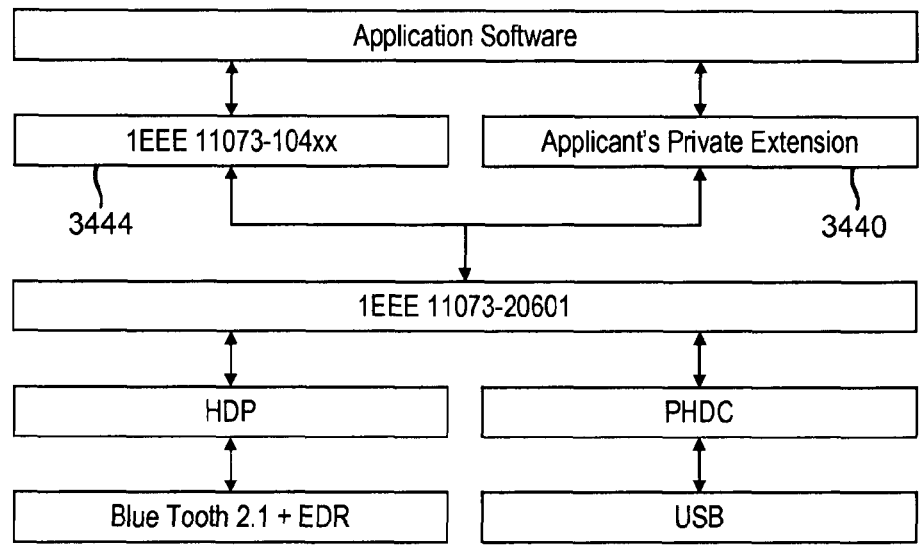
FIG. 84 is a block diagram depicting how applicant's private extension relates to the standardized communication protocols.

With reference to FIG. 84, this disclosure defines an extension 3440 to these configurations, i.e., applicant's private extension, which is not published in any of the ISO/IEEE 11073-104xx device specializations 3444. Applicant's private extension 3440 relationship to the standardized communication protocols is shown in FIG. 84. Generally speaking, implementation of this private extension 3440 defines the attributes and services to support the transfer and execution of specific commands and data. A basic framework for the private extension is first described below. Within this framework, a set of action commands that support structured collection procedures are then presented by this disclosure. The set of action commands are used by the configuration application 3452 and the collection interface 3456 to access and manipulate the parameters of structured collection procedures. It is readily understood that other types of commands sets can also fall within the framework for the private extension.

In an exemplary embodiment of applicant's private extension, each agent device has one MDS object. This top-level MDS object is instantiated from the MDS class. The MDS object represents the identification and status of the agent through its attributes. Beyond the class definition provided by the IEEE standards, additional standardized classes may be supported by the agents and managers in accordance with applicant's private extension. The additional standardized classes are referred to herein as RPC classes. RPC private nomenclature codes are assigned from the manufacturer-specific range of private term codes (0xF000-0xFBFF) within the object oriented partition category (MDC_PART-OBJ). The partition number for object oriented classes and objects is 1.

The attributes for each RPC class are defined in tables that specify the name of the attribute, its value and its qualifier. The qualifiers mean M—attribute is mandatory, C—attribute is conditional and depends on the condition stated in the remark or value column, R—attribute is recommended, NR—attribute is not recommended, and O—attribute is optional. Mandatory attributes shall be implemented by an agent. Conditional attributes shall be implemented if the condition applies and may be implemented otherwise. Recommended attributes should be implemented by the agent. Not recommend attributes should not be implemented by the agent. Optional attributes may be implemented on an agent.

RPC classes that instantiate numeric type objects are created as they exist in the device. These numeric type objects represent additional result data that can be obtained from the device in the same manner they are obtained from the device specialization. These objects shall be added to the device attribute value map for authenticated managers. Attributes common across all of the RPC numeric objects are set forth in Appendix A. Furthermore, applicant's private extension has defined a few RPC numeric objects available to system designers. Likewise, definitions for these common RPC numeric objects are set forth in Appendix A. Applicant's private extension also defines a few RPC enumeration objects as set forth in Appendix B.

Applicant's private extension further defines an application protocol data unit as set forth below. An APDU represents the top-level message frame of the personal health device protocol. The extended APDU is added as an extension to the standard list of APDUs defined in the ISO/IEEE 11073-20601 specification.

```
Apdu Type ::=CHOICE {
    aarq [57856]AarqApdu, -- Association Request [0xE200]
    aare [58112]AareApdu, -- Association Response [0xE300]
    rlrq [58368] RlrqApdu, -- Association Release Request [0xE400]
    rlre [58624] RlreApdu, -- Association Release Response [0xE500]
    abrt [58880] AbrtApdu, -- Association Abort [0xE600]
    prst [59136] PrstApdu, -- Presentation APDU [0xE700]
    prrp [61440] PrrpApdu - applicant's extended APDU [0xF000]
}
```

A presentation APDU as defined in ISO/IEEE 11073-20601 is simply an octet string. Applicant's extended APDU adds a 16-bit CRC in order to ensure data integrity beyond the level provided by the transport and the ISO/IEEE 11073-20601 concept of reliable data channels. With this CRC, corrupted data can be detected by the application. This CRC covers the entire "RPC" part of the command invoke and command response APDUs.

```
PrrpApdup ::= SEQUENCE {
    data  OCTET STRING, (ENCODED VERSION OF DataApdu)
    crc   INT-U16 (checksum over the entire data field)
}
```

Applicant's extended APDU shall encapsulate unconfirmed Action Argument and confirmed Event Report Data APDUs defined by the ISO/IEEE 11073-20601 standard as follows:

```
ActionArgumentSimple ::= SEQUENCE {
    obj-handle   HANDLE
    action-type  OID-Type,     --From the nom-part-obj partition
                               --Subpartition ACT (MDC_ACT_*)
    Action-info-args ANY DEFINED BY action-type
}
```

```
EventReportArgumentSimple ::=SEQUENCE {
    obj-handle  HANDLE
    event-time  Relative Time,
    event-type  OID-Type    --From the nom-part-obj partition
                            --Subpartition NOTI (MDC_NOTI_*)
    event-info  ANY DEFINED BY event-type
}
```

The approach used to invoke applicant's defined commands is to extend the MDS object methods with applicant defined actions. The ISO/IEEE 11073-20601 unconfirmed action service uses the ActionArgumentSimple structure previously discussed in this disclosure.

For the purposes of this specification, the fields would have the following values:

| | |
|---|---|
| handle | 0 (for the MDS object) |
| action-type | manufacturer specific code for applicant defined actions |
| action-info-args | manufacturer specific structure for each applicant defined action |

In order to invoke an applicant defined command, a manager would populate the action-type and action-info-arts of the ActionArgumentSimple object as follows:

| | |
|---|---|
| action-type | MDC_ACT_RPC_COMMAND_INVOKE |
| action-info-args | RpcCommandArguments |

The data objects used for command invocation action-info-args are defined as follows:

```
RpcCommandArguments ::= SEQUENCE {
    cmd-subcmd  INT-U16;       //Command/subcommand combined
    arguments   RpcDataArguments [ ];
}
RpcDataArguments ::= SEQUENCE {
    type  INT-U16;
    data  ANY DEFINED BY type
}
```

The encoding of ANY DEFINED BY is defined in ISO/IEEE 11073-20601 as follows: The ANY DEFINED BY type (ASN.1 1988/90) or the instance-of type (ASN.1 1994) is encoded by a header of a length field to specify the number of octets in the encoding of the selected value that follows. The length element shall be expressed as the number of bytes (octets) contained in the value element. An empty argument shall be indicated with the type element set to RPC_ARG_TYPE_EMPTY, the length element set to 2 and the value element set to zero as an INT-U16. An RpbCommandArguments structure which contains a cmd-subcmd value that requires no arguments will include a single RpcDataArguments element indicating an empty argument.

The approach used to return data as a result of an applicant defined command invocation is to extend the MDS event reports with applicant defined events. The ISO/IEEE 11073-20601 confirmed notification service uses the EventReportArgumentSimple structure previously discussed in this disclosure. For the purposes of the specification, the fields would have the following values:

| | |
|---|---|
| Handle | 0 (for the MDS object) |
| event-time | 0 (event time is not used for applicant actions) |

| | |
|---|---|
| event-type | manufacturer specific code for applicant defined command responses. |
| event-info | manufacturer specific structure for each applicant defined response. |

In order to respond to an applicant defined command, an agent would populate the event-type and event-info of the EventReportArgumentSimple object as follows:

| | |
|---|---|
| Event-type | MDC_NOTI_RPC_COMMAND_RESPONSE |
| event-info | RpcDataArguments [ ] |

The RpcDataArguments object is the same as is defined for applicant defined actions.

Methods (actions) available for the MDS object are defined in the table below. These methods are invoked using the ACTION service. In the table, the Method/Action column defines the name of the method. The Mode column defines whether the method is invoked as an unconfirmed action (i.e., roiv-cmip-action) or a confirmed action (i.e., roiv-cmip-confirmed-action). The Action-type column defines the nomenclature ID to use in the action-type field of an action request and response. The action-info-args column defines the associated data structure to use in the action message for the action-info-args field of the request. The Resulting action-info-args column define the structure to use in the action-info-args of the response.

| Method/Action | Mode | Action-type | Action-info-args | Resulting action-info-args |
|---|---|---|---|---|
| RPC-Command-Invoke | Unconfirmed | MDC_ACT_RPC_COMMAND_INVOKE | RpcCommandArguments | n/a |

This method allows the manager to invoke an applicant defined system command.

Potential events sent by the RPC object are defined in the table below. A manager shall support all methods defined in the table.

| Method/Action | Mode | Event-type | Event-info Parameter | Event-reply-info |
|---|---|---|---|---|
| RPC-Data-Event | Confirmed | MDC_NOTI_rpc_COMMAND_RESPONSE | RpcDataArguments | RpcDataArguments |
| RPC-Error-Event | Confirmed | MDC_NOTI_RPC_ERROR_RESPONSE | RpcDataArguments | RpcDataArguments |

For the command response event, after the execution of an applicant defined command has been requested via the ACTION service, the agent will process the command, subcommand and parameter objects. If there are no command parameter errors, the result will be an agent-initiated event report reflecting the result of successful command processing. In the case of command success, the event report will contain a command-specific result string of data as defined by this specification.

For the error response event, after the execution of an applicant defined command has been requested via the ACTION service, the agent will process the command, subcommand and parameter objects. If there are parameter errors, the result will be an agent-initiated event report specifying the parameter error. If a manager receives an RPC_ERR_HARDWARE or RPC_ERR_APPLICATION response, the manager should invoke the RPC Read and Clear Status command to retrieve further error information available from the device.

Within this framework, a set of action commands that support structured collection procedures is further described below. For example, a structured collection procedure is readable by using a Read ST Configuration command in conjunction with the subcommands listed in this section. The command for reading ST configuration is RPC_CMD_READ_ST_CONFIGURATION and has a value of 0x8000. It must be "OR-ed" with one of the read ST configuration subcommand values to form a complete command-subcommand value. Five exemplary subcommands are set forth below.

First, the Read 3-Day Reminders is a command that return an array of ST Reminder structures, the number of ST Reminder structures returned is device dependent. The ID values for the returned structures shall be one of Before Breakfast, Before Lunch, Before Dinner or Before Bedtime. An exemplary command definition is as follows.

```
Command/Subcommand = 0x8001
Input parameters:
    None
Output parameters:
    Reminder Array[ ]              RpcStReminder (section 6.1.2.8)
RPC Command Invocation:
cmd-subcmd                         RPC_CMD_READ_ST_CONFIGURATION|
                                   RPC_SUBCMD_READ_3D_REMINDERS
RpcDataArguments[0].type           RPC_ARG_TYPE_EMPTY
RpcDataArguments[0].length         0x0002
RpcDataArguments[0].value          0x0000
RPC Command Response:
obj-handle                         0x0000
event-time                         0x0000
event-type                         MDC_NOTI_RPC_COMMAND_RESPONSE
RpcDataArguments[0].type           RPC_ARG_TYPE_ST_REMINDER
RpcDataArguments[0].length         Length of RpcStReminder structure in bytes
RpcDataArguments[0].value          RpcStReminder structure
o                                  o
o                                  o
o                                  o
RpcDataArguments[n].type           RPC_ARG_TYPE_ST_REMINDER
RpcDataArguments[n].length         Length of RpcStReminder structure in bytes
RpcDataArguments[n].value          RpcStReminder structure
```

Second, the Read 3-Day Status is a command shall return an unsigned integer value which indicates whether the activation status is enabled or disabled. An exemplary command definition is as follows.

```
Command/Subcommand = 0x8002
Input parameters:
    None
Output parameters:
    Activation Status              OperationalState (See ISO/IEEE 11073-20601)
RPC Command Invocation:
cmd-subcmd                         RPC_CMD_READ_ST_CONFIGURATION|
                                   RPC_SUBCMD_READ_3D_STATUS
RpcDataArguments[0].type           RPC_ARG_TYPE_EMPTY
RpcDataArguments[0].length         0x0002
RpcDataArguments[0].value          0x0000
RPC Command Response:
obj-handle                         0x0000
event-time                         0x0000
event-type                         MDC_NOTI_RPC_COMMAND_RESPONSE
RpcDataArguments[0].type           RPC_ARG_TYPE_OPERATIONAL_STATE
RpcDataArguments[0].length         0.0002
RpcDataArguments[0].value          0x0001 = disabled
                                   0x0002 = enabled
```

Third, the Read 3-Day Protocol is a command that returns: the Start Date value of the protocol as an RPC Date structure; the Pre-Meal Target Range value of the protocol as an RPC Target Range structure; the Post-Meal Target Range value of the protocol as an RPC Target Range structure; the Bedtime Target Range value of the protocol as an RPC Target Range structure. An exemplary command definition is as follows.

```
Command/Subcommand = 0x8003
Input parameters:
    None
Output parameters:
    Start Date                     RpcTime
    Pre-meal Target Range          RpcTargetRange
    Post-meal Target Range         RpcTargetRange
    Bedtime Target Range           RpcTargetRange
RPC Command Invocation:
cmd-subcmd                         RPC_CMD_READ_ST_CONFIGURATION|
                                   RPC_SUBCMD_READ_3D_PROTOCOL
RpcDataArguments[0].type           RPC_ARG_TYPE_EMPTY
```

-continued

| | |
|---|---|
| RpcDataArguments[0].length | 0x0002 |
| RpcDataArguments[0].value | 0x0000 |
| RPC Command response: | |
| obj-handle | 0x0000 |
| event-time | 0x0000 |
| event-type | MDC_NOTI_RPC_COMMAND_RESPONSE |
| RpcDataArguments[0].type | RPC_ARG_TYPE_DATE |
| RpcDataArguments[0].length | Length of RpcDate structure in bytes |
| RpcDataArguments[0].value | RpcDate = start date value |
| RpcDataArguments[1].type | RPC_ARG_TYPE_TARGET_RANGE |
| RpcDataArguments[1].length | Length of RpcTargetRange structure in bytes |
| RpcDataArguments[1].value | RpcTargetRange = Pre-meal target range |
| RpcDataArguments[2].type | RPC_ARG_TYPE_TARGET_RANGE |
| RpcDataArguments[2].length | Length of RpcTargetRange structure in bytes |
| RpcDataArguments[2].value | RpcTargetRange = Post-meal target range |
| RpcDataArguments[3].type | RPC_ARG_TYPE_TARGET_RANGE |
| RpcDataArguments[3].length | Length of RpcTargetRange structure in bytes |
| RpcDataArguments[3].value | RpcTargetRange = Bedtime target range |

Fourth, the Read BIT Reminders is a command that shall return an array of ST Reminder structures. The number of ST Reminder structures returned is device dependent. The ID values for the returned structures shall be one of Administration or Acquisition. An exemplary command definition is as follows.

| | |
|---|---|
| Command/Subcommand = 0x8004 | |
| Input parameters: | |
|     None | |
| Output parameters: | |
|     Reminder Array[ ] | RpcStReminder (section 6.1.2.8) |
| RPC Command Invocation: | |
| cmd-subcmd | RPC_CMD_READ_ST_CONFIGURATION\| RPC_SUBCMD_READ_BIT_REMINDERS |
| RpcDataArguments[0].type | RPC_ARG_TYPE_EMPTY |
| RpcDataArguments[0].length | 0x0002 |
| RpcDataArguments[0].value | 0x0000 |
| RPC Command Response: | |
| obj-handle | 0x0000 |
| event-time | 0x0000 |
| event-type | MDC_NOTI_RPC_COMMAND_RESPONSE |
| RpcDataArguments[0].type | RPC_ARG_TYPE_ST_REMINDER |
| RpcDataArguments[0].length | Length of RpcStReminder structure in bytes |
| RpcDataArguments[0].value | RpcStReminder structure |
| o | o |
| o | o |
| o | o |
| RpcDataArguments[n].type | RPC_ARG_TYPE_ST_REMINDER |
| RpcDataArguments[n].length | Length of RpcStReminder structure in bytes |
| RpcDataArguments[n].value | RpcStReminder structure |

Fifth, the Read BIT Status is a command that returns an unsigned integer value which indicates whether the activation status is enabled or disabled; and the Exit Reason value as a 16 bit enumeration. An exemplary command definition is as follows.

| | |
|---|---|
| Command/Subcommand = 0x8005 | |
| Input parameters: | |
|     None | |
| Output parameters: | |
|     Activation Status | OperationalState (See ISO/IEEE 11073-20601) |
|     Exit Reason | UINT-16 |
| RPC Command Invocation: | |
| cmd-subcmd | RPC_CMD_READ_ST_CONFIGURATION\| RPC_SUBCMD_READ_BIT_STATUS |
| RpcDataArguments[0].type | RPC_ARG_TYPE_EMPTY |
| RpcDataArguments[0].length | 0x0002 |
| RpcDataArguments[0].value | 0x0000 |
| RPC Command Response: | |
| obj-handle | 0x0000 |
| event-time | 0x0000 |
| event-type | MDC_NOTI_RPC_COMMAND_RESPONSE |

-continued

| | |
|---|---|
| RpcDataArguments[0].type | RPC_ARG_TYPE_OPERATIONAL_STATE |
| RpcDataArguments[0].length | 0.0002 |
| RpcDataArguments[0].value | 0x0001 = disabled |
| | 0x0002 = enabled |
| RpcDataArguments[1].type | RPC_ARG_TYPE_UINT16 |
| RpcDataArguments[1].length | 0.0002 |
| RpcDataArguments[1].value | Exit reason value |

This command shall return an array of RpcStParameter structures, comprised of the following parameters:

1. The Start Date value of the protocol as an RPC Date structure.
2. The Start Dosage value (IU) of the protocol as an 8 bit unsigned integer.
3. The Maximum Dosage value (IU) of the protocol as an 8 bit unsigned integer.
4. The Minimum Fasting Time value (number of hours) as an 8 bit unsigned integer.
5. The Maximum Use Time value (number of days) as an 8 bit unsigned integer.
6. The Completion Threshold value (mg/dL) of the protocol as a 16 bit unsigned integer.
7. The Severe Hypo Threshold value (mg/dL) of the protocol as a 16 bit unsigned integer.
8. The Hypo Threshold value (mg/dL) of the protocol as a 16 bit unsigned integer.
9. The Maximum Severe Hypo Events value of the protocol as an 8 bit unsigned integer.
10. The Maximum Hypo Events value of the protocol as an 8 bit unsigned integer.
11. The Maximum Violation Events value of the protocol as an 8 bit unsigned integer.
12. The Maximum Adherence Events value of the protocol as an 8 bit unsigned integer.
13. The Doctor Phone Number value of the protocol as an Octet String of even length.
14. The Daylight Saving Time status value of the protocol as a 16 bit enumeration value (gee section 6.1.1.18 for enumeration values).
15. The Minimum Period Length value (days) of the protocol as an 8 bit unsigned integer.
16. The Number of Primary Samples as an 8 bit unsigned integer.

An exemplary command definition is as follows.

| | |
|---|---|
| Command/Subcommand = 0x8006 | |
| Input parameters: | |
|     None | |
| Output parameters: | |
|     Parameter Array[ ] | RpcStParameter |
| RPC Command Invocation: | |
| cmd-subcmd | RPC_CMD_READ_ST_CONFIGURATION\| |
| | RPC_SUBCMD_READ_BIT_PROTOCOL |
| RpcDataArguments[0].type | RPC_ARG_TYPE_EMPTY |
| RpcDataArguments[0].length | 0x0002 |
| RpcDataArguments[0].value | 0x0000 |
| RPC Command Response: | |
| obj-handle | 0x0000 |
| event-time | 0x0000 |
| event-type | MDC_NOTI_RPC_COMMAND_RESPONSE |
| RpcDataArguments[0].type | RPC_ARG_TYPE_ST_PARAMETER |
| RpcDataArguments[0].length | Length of RpcStParameter structure in bytes |
| RpcDataArguments[0].value | RpcStParameter = parameter ID and value |
| o | o |
| o | o |
| o | o |
| RpcDataArguments[n].type | RPC_ARG_TYPE_ST_PARAMETER |
| RpcDataArguments[0].length | Length of RpcStParameter structure in bytes |
| RpcDataArguments[0].value | RpcStParameter = parameter ID and value |

The parameters of a structure collection procedure can be changed by using the Set ST Configuration command in conjunction with the subcommands listed in this section. The command for setting ST configuration is RPC_CMD_SET_ST_CONFIGURATION and has a value of 0x8100. It must be "OR-ed" with one of the change setup subcommand values to form a complete command-subcommand value. Six exemplary subcommands are set forth below.

First, the Set 3-Day Reminders command shall set 3-Day time reminder values of the device to the values specified. The input parameter is an array of Structured Test time reminder structures. An agent device shall ignore any structures for which it has no corresponding ID. The ID values for the structures shall be one of Before Breakfast, Before Lunch, Before Dinner or Before Bedtime. The command returns an error code indicating success (RPC_ERR_NO_ERRORS) or failure. An exemplary command definition is as follows.

```
Command/Subcommand = 0x8101
Input parameters:
    Reminder Array [ ]         RpcStReminder (section 6.1.2.8)
Output parameters:
    Error Code                 Number
RPC Command Invocation:
cmd-subcmd                     RPC_CMD_SET_ST_CONFIGURATION|
                               RPC_SUBCMD_SET_3D_REMINDERS
RpcDataArguments[0].type       RPC_ARG_TYPE_ST_REMINDER
RpcDataArguments[0].length     Length of RpcStReminder structure in bytes
RpcDataArguments[0].value      RpcStReminder structure
    o                              o
    o                              o
    o                              o
RpcDataArguments[n].type       RPC_ARG_TYPE_ST_REMINDER
RpcDataArguments[n].length     Length fo RpcStReminder structure in bytes
RpcDataArguments[n].value      RpcStReminder structure
RPC Command Response:
obj-handle                     0x0000
event-time                     0x0000
event-type                     MDC_NOTI_RPC_COMMAND_RESPONSE
```

Second, the Set 3-Day Status command shall set the 3-Day Activation status value of the device to the value specified. The input parameters is a 16 bit OperationalState value. The command returns an error code indicating success (RPC_ERR_NO_ERRORS) or failure. An exemplary command definition is as follows.

```
Command/Subcommand = 0x8102
Input parameters:
    Activation Status          OperationalState
    (See ISO/IEEE 11073-20601)
Output parameters:
    Error Code                 Number
RPC Command Invocation:
cmd-subcmd                     RPC_CMD_SET_ST_CONFIGURATION|
                               RPC_SUBCMD_SET_3D_STATUS
RpcDataArguments[0].type       RPC_ARG_TYPE_OPERATIONAL_STATE
RpcDataArguments[0].length     0x0002
RpcDataArguments[0].value      0x0001 = disabled
                               0x0002 = enabled
RPC Command Response:
obj-handle                     0x0000
event-time                     0x0000
event-type                     MDC_NOTI_RPC_COMMAND_RESPONSE
RpcDataArguments[0].type       RPC_ARG_TYPE_UINT16
RpcDataArguments[0].length     0x0002
RpcDataArguments[0].value      Error code enumeration value
```

Third, the Set 3-Day Protocol command shall set the following protocol values of the device to the values specified:
1. The Start Date value of the protocol as an RPC Date structure.
2. The Pre-Meal Target Range value of the protocol as an RPC Target Range structure.
3. The Post-Meal Target Range value of the protocol as an RPC Target Range structure.
4. The Bedtime Target Range value of the protocol as an RPC Target Range structure.
An exemplary command definition is as follows.

```
Command/Subcommand = 0x8103
Input parameters:
    Start Date                 Rpc Time
    Pre-meal Target Range      Rpc Target Range
    Post-meal Target Range     Rpc Target Range
    Bedtime Target Range       Rpc Target Range
Output parameters:
    Error Code                 Number
```

-continued

| | |
|---|---|
| RPC Command Invocation: | |
| cmd-subcmd | RPC_CMD_SET_ST_CONFIGURATION\|<br>RPC_SUBCMD_SET_3D_PROTOCOL |
| RpcDataArguments[0].type | RPC_ARG_TYPE_DATE |
| RpcDataArguments[0].length | Length of RpcDate structure in bytes |
| RpcDataArguments[0].value | RpcDate = start date value |
| RpcDataArguments[1].type | RPC_ARG_TYPE_TARGET_RANGE |
| RpcDataArguments[1].length | Length of RpcTargetRange structure in bytes |
| RpcDataArguments[1].value | RpcTargetRange = Pre-meal target range |
| RpcDataArguments[2].type | RPC_ARG_TYPE_TARGET_RANGE |
| RpcDataArguments[2].length | Length of RpcTargetRange structure in bytes |
| RpcDataArguments[2].value | RpcTargetRange = Post-Meal target range |
| RpcDataArguments[3].type | RPC_ARG_TYPE_TARGET_RANGE |
| RpcDataArguments[3].length | Length of RpcTargetRange structure in bytes |
| RpcDataArguments[3].value | RpcTargetRange = Bedtime target range |
| RPC Command Response: | |
| obj-handle | 0x0000 |
| event-time | 0x0000 |
| event-type | MDC_NOTI_RPC_COMMAND_RESPONSE |
| RpcDataArguments[0].type | RPC_ARG_TYPE_UINT16 |
| RpcDataArguments[0].length | 0x0002 |
| RpcDataArguments[0].value | Error code enumeration value |

Fourth, the Set BIT Reminders command shall set BIT time reminder values of the device to the values specified. The input parameter is an array of Structured Test time reminder structures. An agent device shall ignore any structures for which it has no corresponding ID. The ID values for the structures shall be one of Administration or Acquisition. The command returns an error code indicating success (RPC_ERR_NO_ERRORS) or failure. An exemplary command definition is as follows.

| | |
|---|---|
| Command/Subcommand = 0x8104 | |
| Input parameters: | |
|     Reminder Array [ ] | RpcStReminder (section 6.1.2.8) |
| Output parameters: | |
|     Error Code | Number |
| RPC Command Invocation: | |
| cmd-subcmd | RPC_CMD_SET_ST_CONFIGURATION\|<br>RPC_SUBCMD_SET_BIT_REMINDERS |
| RpcDataArguments[0].type | RPC_ARG_TYPE_ST_REMINDER |
| RpcDataArguments[0].length | Length of RpcStReminder structure in bytes |
| RpcDataArguments[0].value | RpcStReminder structure |
| ○ | ○ |
| ○ | ○ |
| ○ | ○ |
| RpcDataArguments[n].type | RPC_ARG_TYPE_ST_REMINDER |
| RpcDataArguments[n].length | Length of RpcStReminder structure in bytes |
| RpcDataArguments[0].value | RpcStReminder structure |
| RPC Command Response: | |
| obj-handle | 0x0000 |
| event-time | 0x0000 |
| event-type | MDC_NOTI_RPC_COMMAND_RESPONSE |
| RpcDataArguments[0].type | RPC_ARG_TYPE_UINT16 |
| RpcDataArguments[0].length | 0x0002 |
| RpcDataArguments[0].value | Error code enumeration value |

Fifth, the Set BIT Status command shall set the following BIT status values of the device: the Activation Status value as a 16 bit OperationalState; and the Exit Reason value as a 16 bit enumeration. The command returns an error code indicating success (RPC_ERR_NO_ERRORS) or failure. An exemplary command definition is as follows.

| | |
|---|---|
| Command/Subcommand = 0x8105 | |
| Input parameters: | |
|     Activation Status | OperationalState |
|     (See ISO/IEEE 11073-20601) | |
|     Exit Reason | UINT-16 |
| Output parameters: | |
|     Error Code | Number |

```
RPC Command Invocation:
cmd-subcmd                      RPC_CMD_SET_ST_CONFIGURATION|
                                RPC_SUBCMD_SET_BIT_STATUS
RpcDataArguments[0].type        RPC_ARG_TYPE_OPERATIONAL_STATE
RpcDataArguments[0].length      0x0002
RpcDataArguments[0].value       0x0001 = disabled
                                0x0002 = enabled
RpcDataArguments[1].type        RPC_ARG_TYPE_UINT16
RPC Command Response:
obj-handle                      0x0000
event-time                      0x0000
event-type                      MDC_NOTI_RPC_COMMAND_RESPONSE
RpcDataArguments[0].type        RPC_ARG_TYPE_UINT16
RpcDataArguments[0].length      0x0002
RpcDataArguments[0].value       Error code enumeration value
```

Sixth, the Set BIT Protocol command shall set BIT protocol values of the device to the values specified. The input parameter is an array of Structured Test parameter structures. An agent device shall ignore any structures for which it has no corresponding parameter ID. The command returns an error code indicating success (PRC_ERR_NO_ERRORS) or failure. An exemplary command definition is as follows.

```
Command/Subcommand = 0x8106
Input parameters:
        Reminder Array [ ]       RpcStParameter (section 6.1.2.9)
Output parameters:
        Error Code               Number
RPC Command Invocation:
cmd-subcmd                      RPC_CMD_READ_ST_CONFIGURATION|
                                RPC_SUBCMD_SET_BIT_PROTOCOL
RpcDataArguments[0].type        RPC_ARG_TYPE_ST_PARAMETER
RpcDataArguments[0].length      Length of RpcStParameter structure in bytes
RpcDataArguments[0].value       RpcStParameter structure
o                               o
o                               o
o                               o
RpcDataArguments[n].type        RPC_ARG_TYPE_ST_PARAMETER
RpcDataArguments[n].length      Length of RpcStParameter structure in bytes
RpcDataArguments[n].value       RpcStParameter structure
RPC Command Response:
obj-handle                      0x0000
event-time                      0x0000
event-type                      MDC_NOTI_RPC_COMMAND_RESPONSE
RpcDataArguments[0].type        RPC_ARG_TYPE_UINT16
RpcDataArguments[0].length      0.0002
RpcDataArguments[0].value       Error code enumeration value
```

Medical Devices that Support Enhanced System Extensibility for Diabetes Care

Referring now to FIG. 75, a person 2900 with diabetes and a healthcare professional 2902 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 2900 typically shares with the clinician 2902 a variety of patient data including blood glucose measurements, continuous glucose monitor data, amounts of insulin infused, amounts of food and beverages consumed, exercise schedules, and other lifestyle information. The clinician 2902 may obtain additional patient data that includes measurements of HbA1C, cholesterol levels, triglycerides, blood pressure, and weight of the patient 2900. The patient data can be recorded manually or electronically on a handheld diabetes management device 2904, a diabetes analysis software executed on a personal computer (PC) 2906, and/or a web-based diabetes analysis site (not shown). The clinician 2902 can analyze the patient data manually or electronically using the diabetes analysis software and/or the web-based diabetes analysis site. After analyzing the patient data and reviewing adherence of the patient 2900 to previously prescribed therapy, the clinician 2902 can decide whether to modify the therapy for the patient 2900.

Referring now to FIG. 76, the patient 2900 can use a continuous glucose monitor (CGM) 2910, an ambulatory non-durable insulin infusion pump 2912 or an ambulatory durable insulin infusion pump 2914 (hereinafter insulin pump 2912 or 2914), and the handheld diabetes management device 2904 (hereinafter the diabetes manager 2904). The CGM 2910 uses a subcutaneous sensor to sense and monitor the amount of glucose in the interstitial fluid of the patient 2900 and communicates corresponding readings to the diabetes manager 2904.

The diabetes manager 2904 performs various tasks including measuring and recording blood glucose levels, determining an amount of insulin to be administered to the patient 2900 via the insulin pump 2912 or 2914, receiving patient data via a user interface, archiving the patient data, etc. The diabetes manager 2904 periodically receives readings from the CGM 2910 indicating glucose level in the interstitial fluid of the patient 2900. The diabetes manager 2904 transmits instructions to the insulin pump 2912 or 2914, which delivers insulin to the patient 2900. Insulin can be delivered in a scheduled manner in the form of basal (background) doses, which consists of multiple small doses of insulin to the patient 2900 over an extended period (e.g., a day). Additionally, insulin can be delivered in the form of a bolus dose, which delivers a single larger quantity of insulin to the patient 2900 to adjust for a particular situation (e.g., eating a meal).

Referring now to FIG. 77, a diabetes management system 2930 used by the patient 2900 and the clinician 2902 includes one or more of the following devices: the diabetes manager 2904, the continuous glucose monitor (CGM) 2910, the insulin pump 2912 or 2914, a mobile device 2932, the PC 2906 with the diabetes analysis software, and other healthcare devices 2934. The diabetes manager 2904 is configured as a system hub and communicates with the devices of the diabetes management system 2930. Alternatively, the insulin pump 2914 or the mobile device 2932 can serve as the system hub. Communication between the devices in the diabetes management system 2930 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 2900 and clinician 2902 to exchange information.

The diabetes manager 2904 can receive glucose readings from one or more sources (e.g., from the CGM 2910). The CGM 2910 continuously measures the glucose level in the abdominal interstitial fluid of the patient 2900. The CGM 2910 periodically communicates the readings to the diabetes manager 2904. The diabetes manager 2904 and the CGM 2910 communicate wirelessly using a proprietary Gazell wireless protocol developed by Nordic Semiconductor, Inc.

Additionally, the diabetes manager 2904 includes a blood glucose meter (BGM) and a port that communicates with the BGM (not shown). The port can receive a blood glucose measurement strip 2936. The patient 2900 deposits a sample of blood on the blood glucose measurement strip 2936. The BGM analyzes the sample and measures the blood glucose level in the sample. The blood glucose level measured from the sample can be used to calibrate the interstitial glucose level from the CGM 2910 in order to estimate a BG value from a CGM value. BG values can be used to determine the amount of insulin to be administered to the patient 2900.

The diabetes manager 2904 communicates with the insulin pump 2912 or 2914. The insulin pump 2912 or 2914 can be configured to receive instructions from the diabetes manager 2904 to deliver a user-determined amount of insulin to the patient 2900. Additionally, the diabetes manager 2904 can receive other information including meal and/or exercise schedules of the patient 2900 and use these to determine the amount of insulin to administer using insulin pump 2912 or 2914 based on the additional information.

The insulin pump 2912 or 2914 can also communicate data to the diabetes manager 2904. The data can include amounts of insulin delivered to the patient 2900, corresponding times of delivery, and pump status. The diabetes manager 2904 and the insulin pump 2912 or 2914 can communicate using a wireless communication protocol such as Bluetooth. Other wireless or wireline communication protocols can also be used.

In addition, the diabetes manager 2904 can communicate with the other healthcare devices 2934. For example, the other healthcare devices 2934 can include a blood pressure meter, a weight scale, a pedometer, a fingertip pulse oximeter, a thermometer, etc. The other healthcare devices 2934 obtain and communicate personal health information of the patient 2900 to the diabetes manager 2904 through wireless, USB, or other interfaces. The other healthcare devices 2934 may use communication protocols compliant with ISO/IEEE 11073 extended using guidelines from Continual® Health Alliance. The diabetes manager 2904 can communicate with the other healthcare devices 2934 using interfaces including Bluetooth, USB, etc. Further, the devices of the diabetes management system 2930 can communicate with each other via the diabetes manager 2904.

The diabetes manager 2904 can communicate with the PC 2906 using Bluetooth, USB, or other interfaces. A diabetes management software running on the PC 2906 includes an analyzer-configurator that stores configuration information of the devices of the diabetes management system 2930. The configurator has a database to store configuration information of the diabetes manager 2904 and the other devices. The configurator can communicate with users through standard web or computer screens in non-web applications. The configurator transmits user-approved configurations to the devices of the diabetes management system 2930. The analyzer retrieves data from the diabetes manager 2904, stores the data in a database, and outputs analysis results through standard web pages or computer screens in non-web based applications.

The diabetes manager 2904 can communicate with the mobile device 2932 using Bluetooth. The mobile device 2932 may include a cellular phone, a pager, or a personal digital assistant (PDA). The diabetes manager 2904 can send messages to an external network through the mobile device 2932. The mobile device 2932 can transmit messages to the external network upon receiving requests from the diabetes manager 2904.

Referring now to FIG. 82, the diabetes manager 2904 comprises a blood glucose measuring (BGM) module 3300, a communication module 3302, a user interface module 3304, user interfaces 3306, a processing module 3308, memory 3310, and a power module 3312. The BGM module 3300 includes a blood glucose measuring engine that analyzes samples provided by the patient 2900 on the blood glucose measurement strip 2936 and that measures the amount of blood glucose in the samples. The communication module 3302 includes multiple radios that communicate with different devices of the diabetes management system 2930, as well as communication processors to implement the communication protocols. The user interface module 3304 interfaces the diabetes manager 2904 to various user interfaces 3306 that the patient 2900 can use to interact with the diabetes manager 2904. For example, the user interfaces 3306 can include keys, switches, a display, a speaker, a microphone, a secure digital (SD) card port, a USB port, etc. (not shown).

The processing module 3308 processes data received from the BGM module 3300, the communication module 3302, and the user interface module 3304. The processing module 3308 uses memory 3310 for processing and storing data. The memory 3310 can include volatile and nonvolatile memory. The processing module 3308 outputs data to and receives data from the user interfaces 3306 via the user interface module 3304. The processing module 3308 outputs data to and receives data from the devices of the diabetes management system 2930 via the communication module 3302. The power module 3312 supplies power to the components of the diabetes manager 2904. The power module 3312 includes a rechargeable battery. The battery can be recharged using an adapter that plugs into a wall outlet. The battery can also be charged via the USB port of the diabetes manager 2904.

Figure 88:
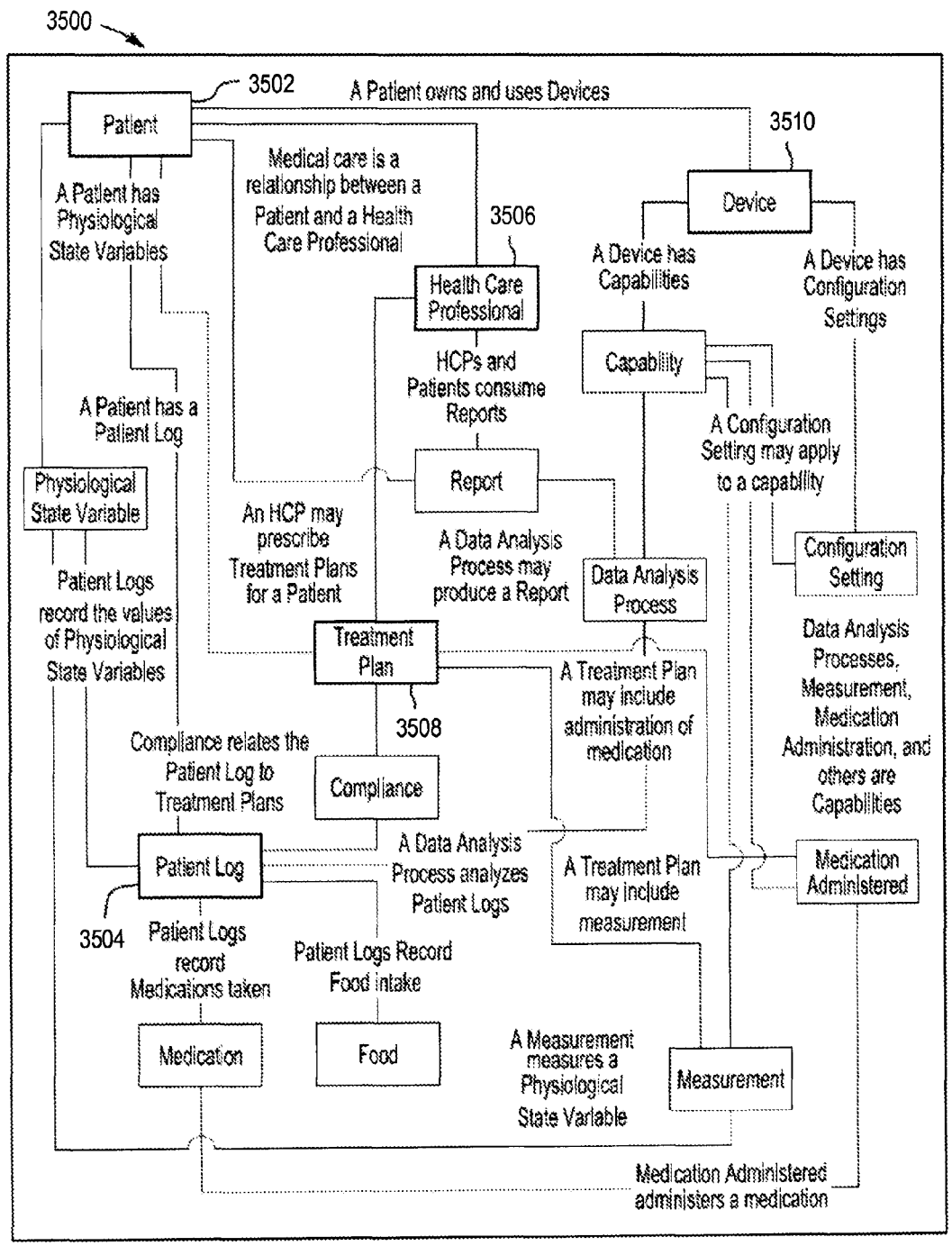
FIG. 88 is a diagram of a domain model for the diabetes care information management domain.

FIG. 88 depicts a domain model 3500 for the diabetes care information management domain. A domain model is a conceptual model of a system's domain of application (in this case diabetes care) which describes the entities in the domain and their relationships. In the area of diabetes care, the domain model 3500 is built around a patient 3502 who is receiving medical care for diabetes. Each patient 3502 has an associated patient log 3504 for recording actions taken by or in relation to the patient. Exemplary actions may include recording medication intake, food intake, or values of a patient's physiological state variable such as a blood glucose measure. Medical care is provided to the patient under the direction of one more health care professionals 3506. More specifically, a health care professional 3506 may prescribe a treatment plan 3508 comprised of a series of actions for administering medical treatment to the patient. Administering medical care typically involves one or more medical devices 3510 having different capabilities and configuration settings. It is readily understood that the domain model may include other entities and relationships related to diabetes care.

A domain model has two primary uses. First, a shared domain model insures that stakeholders and developers are thinking about the problem at hand in the same way and using the same terminology. Second, a domain model is used for identifying variability for architecture and design. Since a domain model is expressed in terms of the application area, variability points identified in the model are more likely to have business value. When technical architects and designers are aware of this predicted variability, they are better able to produce designs that will evolve in ways useful to the business. In this disclosure, the diabetes care information management domain model 3500 is used to identify business-relevant extension points for a computer-implemented diabetes care system.

First, a discussion is provided to clarify what is meant by extensibility and extension points. There are several meaningful ways to define extensibility. For the purpose of this disclosure, four types of extensibility are specifically defined for software and firmware: design extensible, compile-time extensible, run-time extensible and dynamically extensible.

A particular architecture or design is design extensible relative to a domain concept X if a new variant or member of X can be added to the system without requiring any re-design, where "re-design" is any change that requires a revision any of the system's architecture or high-level design documents. Design extensibility is the simplest version of extensibility. Note that under this definition, requiring a complete system re-build or even substantial code changes is permitted, as is added detailed design documentation for new elements.

A particular architecture or design is compile-time extensible relative to a domain concept X if it is design extensible relative to X and if adding a new variant or member for X can be done by a) adding code for the new member/variant and b) adding code in one place to include the new member/variant and c) recompiling all or part of the system.

A particular architecture or design is run-time extensible relative to a domain concept X if it is design extensible relative to X and if adding a new variant or member for X can be done by building a new module, locating it in a design-specified place, and modifying a manifest or other (non-code) configuration information. Run-time extensibility may require that the system be re-started before the new concept is visible in the system. Note that run-time extensibility does not require compile-time extensibility; these two extensibility methods are mutually exclusive.

For completeness, a definition for dynamic extensibility is included, which is characteristic of service-oriented architectures with service discovery. A particular architecture or design is dynamically extensible relative to a domain concept X if it is design extensible relative to X and if adding a new variant or member for X can be done dynamically while the system remains running.

Extensibility typically requires an explicit representation of the identified concept. In an exemplary embodiment, the diabetes management system 2930 is implemented using an object-oriented programming paradigm. In an object-oriented system, the explicit representation will be a class. Such abstractions should be isolated to a component intended for abstractions (i.e., not mixed with implementations). In this disclosure, the class diagrams are defined in accordance with the Unified Modeling Language (UML).

While this disclosure makes reference primarily to an object-oriented programming paradigm, it is readily understood that other types of implementations fall within the scope of this disclosure. For example, the diabetes management system 2930 may be implemented using functional designs. In functional designs, the explicit representation will typically be as a structure (record) type, with functions that work on that type isolated to a single module or component. If code that knows about a type is scattered across multiple modules, this is a sign that the given structure is not extensible. In a functional implementation, the header files declaring the structure type and externally-visible functions operating on that type should be isolated. Other types of implementations of the system are also contemplated.

Figure 89:
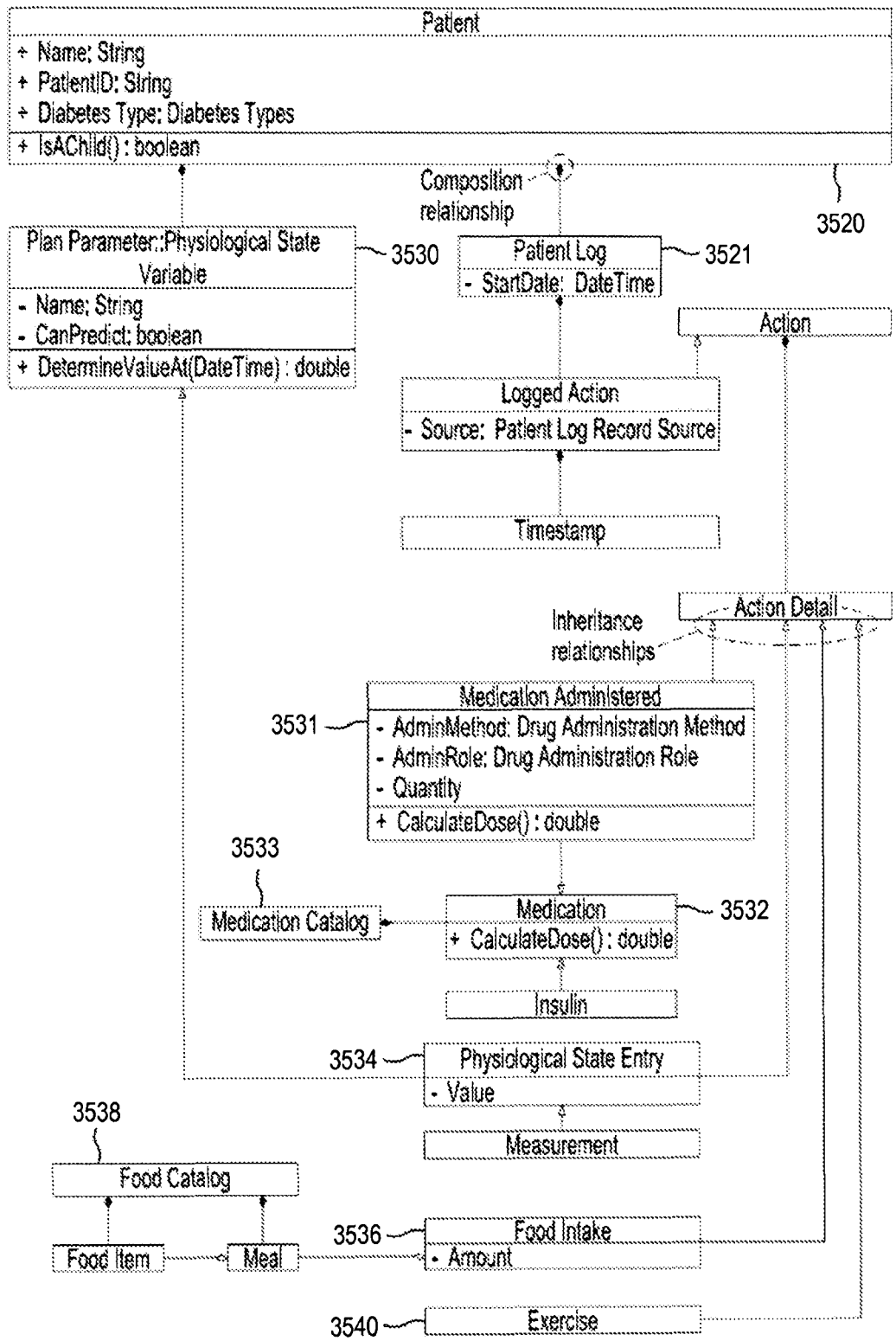
FIG. 89 is a class diagram for a portion of the diabetes care domain model that relates to a patient's log.

FIG. 89 is a class diagram for a portion of the diabetes care domain model that relates to a patient's log. Each patient has associated patient logs for recording a series of actions taken by or in relation to the patient as noted above. Patient logs are an identified extension point. Accordingly, the patient log class 3521 has a composition relationship with the patient class 3520; the patient class 3520 does not know anything about the contents of this composition except that they embody the patient log concept. Attributes of the patient log class 3521 include (but are not limited to) the date of the first entry in the log. Entries in the log are represented by the objects of the "logged action" class, which include (but are not limited to) an identifier for the origin of an action (e.g., a manual entry or a device) and a timestamp when the action occurred. Logged actions are an identified extension point. The patient log class 3521 is composed of logged actions; the patient log 3521 does not know anything about the contents of this composition except that they embody the logged action concept. In the exemplary embodiment, the logged actions are one of four different types: medication administration 3531, physiological state entry 3534, food intake 3536 or exercise 3540. Each of these action types is a subclass to a superclass that is associated with the logged action class as shown in the figure. Other types of actions are also contemplated by this disclosure.

The medication administered class 3531 records the administration of medicine to the patient. The medication class 3532 is associated with the medication administration class (i.e., each medication administration object has a relationship to a medication object for the medication that was taken by the patient). Supporting new types of medication is an identified extension point. Accordingly, the medication catalog class 3533 has a composition relationship with the medication class 3532; the medication catalog class 3533 does not know anything about the contents of this composition except that they embody the medication concept. Supporting new ways to calculate dosages for a given medication is another identified extension point. Thus, the medication class further includes a method that calculates a dosage of the medication to be administered to the patient (e.g., a bolus insulin dosage calculation).

The physiological state variable entry class 3534 refers to an input of a value of a physiological state variable such as blood glucose or a patient's wake/sleep state. Supporting new types of physiological state variables in the system is another identified extension point. Accordingly, the patient class 3520 has a composition relationship with the physiological state variable class 3530; the patient class 3520 does not know anything about the contents of this composition except that they embody the physiological state variable concept. For example, the glycemic index is a measure of how much your blood glucose level swings up and down. Supporting such physiological variables and methods for calculating the same are anticipated in future developments. Extensibility for these types of new variables is supported by defining a new subclass or instance of physiological state variable class 3530. Determining the value of a physiological state variable from date in the patient log 3521 is a defined extension point. Thus the physiological state variable class 3530 further has a method for determining its value at a particular date and time.

The food intake class 3536 represents food the patient has consumed. Food intake is associated with a meal object, which aggregates food items. Supporting new types of food in the system is another identified extension point. Accordingly, the food catalog class 3538 has a composition relationship with food items; the food catalog class 3538 does not know anything about the contents of this composition except that they embody the food item concept. New calculation logic associated with food items is also an identified extension point. For example, the rate at which foods introduce glucose into the bloodstream depends in part on the fat content of the food; new calculation logic for food items could include (but is not limited to) the duration over which the carbohydrate content should be distributed when making predictions.

Figure 90:
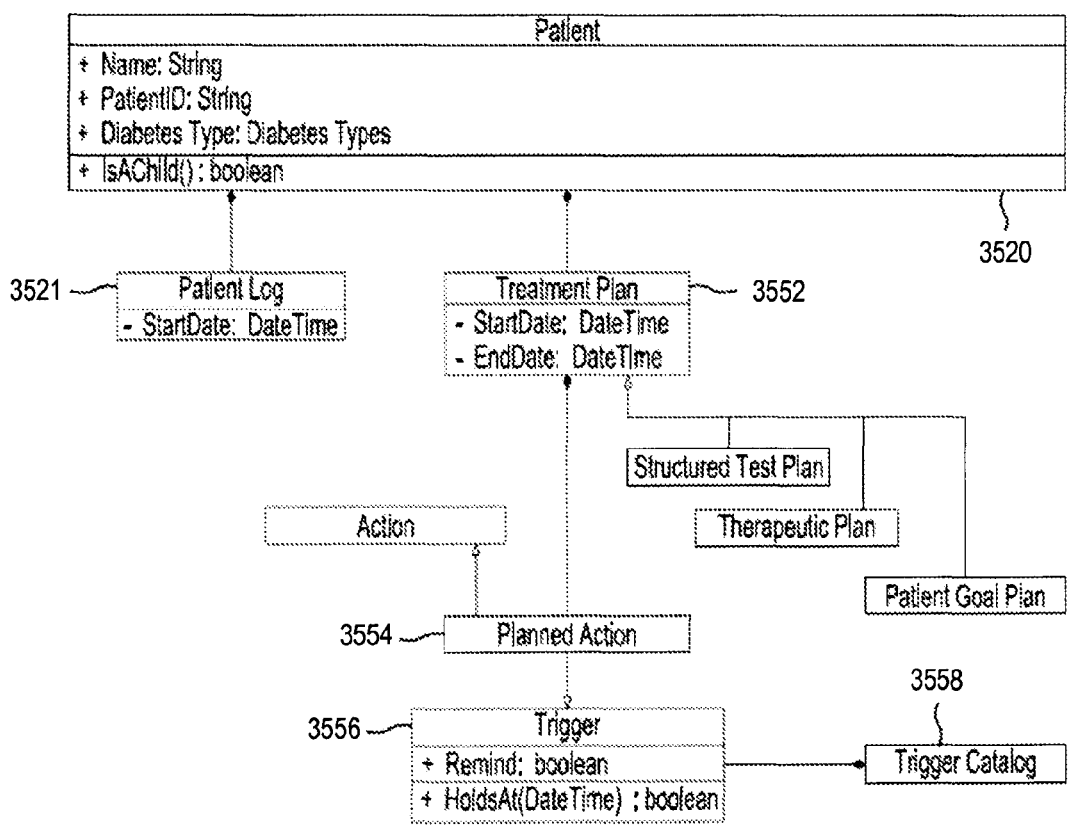
FIG. 90 is a class diagram for a portion of the diabetes care domain model that relates to a treatment plans.

FIG. 90 depicts a portion of the diabetes care domain model that relates to a treatment plans. A treatment plan is a general concept that covers a wide variety of planned actions on the part of the patient. In the context of diabetes care, a treatment plan is understood to be a series of planned action related to the medical treatment of the patient. Treatment plans may be a structured testing plan like a 3-day profile, and therapeutic plan like a pump's basal profile, a user goal plan like a target weight, or other types of plans not yet envisioned. Supporting new types of treatment plan is an identified extension point. Accordingly, the patient class 3520 has a composition relationship with treatment plans 3552; the patient class 3520 does not know anything about the contents of this composition except that they embody the treatment plan concept. Attributes of the treatment plan class include (but are not limited to) a starting date, an ending date and a series of planned actions which comprise the treatment plan.

An important aspect of a treatment plan is the capability to define the conditions that trigger one of the planned actions. A reminder to take a given medication based on the time of day or a reminder to perform a test based on a time interval since a given meal are examples of triggers. Supporting new types of triggers is an identified extension point. Accordingly, the trigger catalog class 3558 has a composition relationship with the treatment plan trigger class 3556; the trigger catalog class 3558 does not know anything about the contents of this composition except that they embody the treatment plan concept.

Actions in a treatment plan are instances of the planned action class 3554; each such action is associated with a trigger from the trigger catalog. In an exemplary embodiment, the diabetes management system 2930 provides run-time extensibility for ne types of triggers in the manger set forth below. New ways to compute trigger conditions are an identified extension point. Thus the trigger class 3556 further has a method for determining whether the trigger holds at a particular date and time.

A structured test plan is a particular type of treatment plan defined in the diabetes care domain. For example, a structured test plan may be a series of planned actions for obtaining measurement data from a glucose meter. In addition to a series of planned actions, the structured test plan includes attributes such as an entry criterion, an adherence criterion and an exit criterion. Entry criteria establish the conditions that need to be met prior to obtaining a physiological variable measure from the patient; this corresponds to the trigger class 3556. Adherence criteria are used to assess qualitatively whether a planned action was performed. Exit criterion establish the conditions needed to be met prior to exiting the structured test plan.

Figure 91:
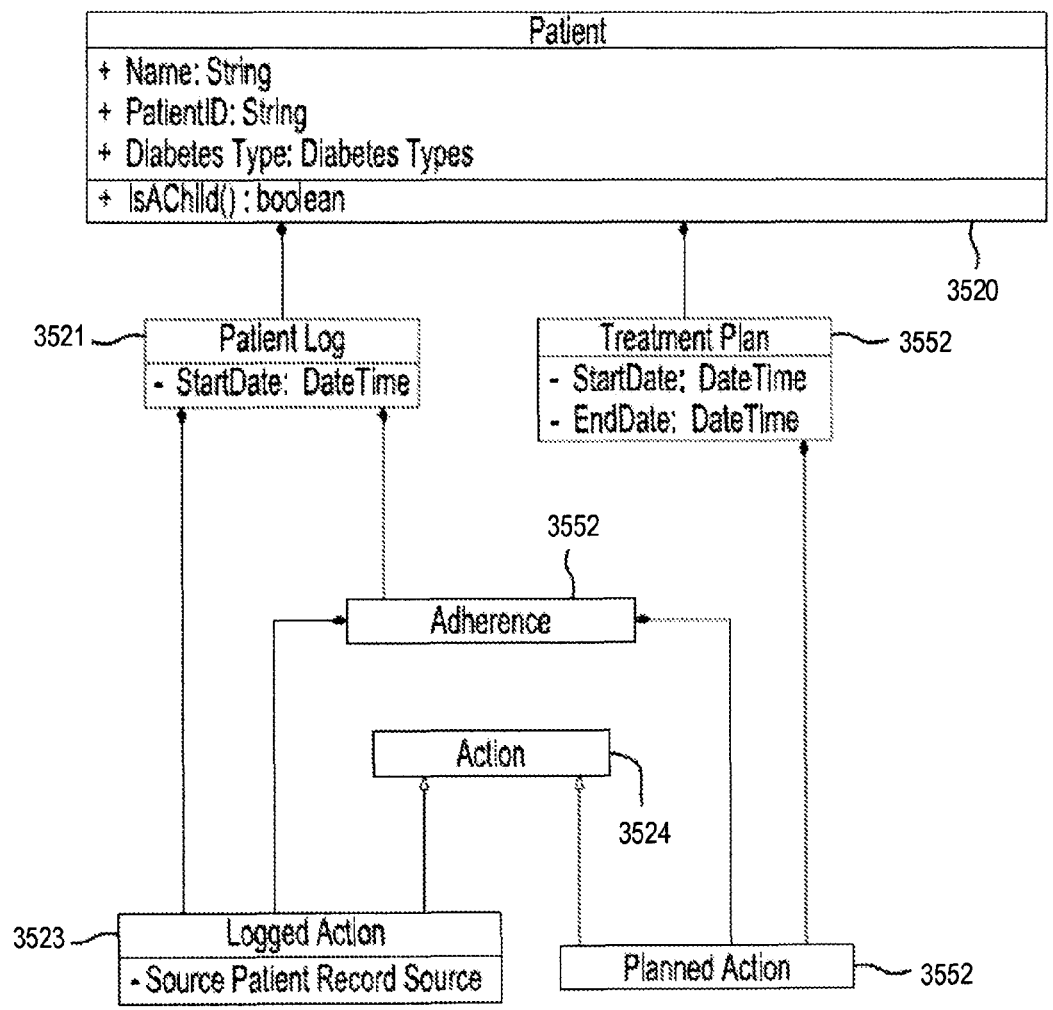
FIG. 91 is a class diagram for a portion of the diabetes care domain model that relates to adherence.

Adherence information for the patient may be managed using an adherence class 3552 as shown in FIG. 91. More specifically, the adherence class 3552 creates a relationship between planned actions for the patient defined by a treatment plan and the actions taken by the patient as recorded in the patient log. In an exemplary embodiment, the adherence class 3552 may define an indicator having values, such as compliant or non-compliant, as well as adherence criteria or methods for deriving a value for the indicator. In this example, the indicator may be assigned a 'compliant' value when an action planned for a particular time is performed within a prescribed range (as defined by the adherence criteria). Supporting new types of adherence is an identified extension point. Accordingly, the patient log class 3521 has a composition relationship with the adherence class 3552; the patient log class 3521 does not know anything about the contents of this composition except that they embody the adherence concept.

Figure 92:
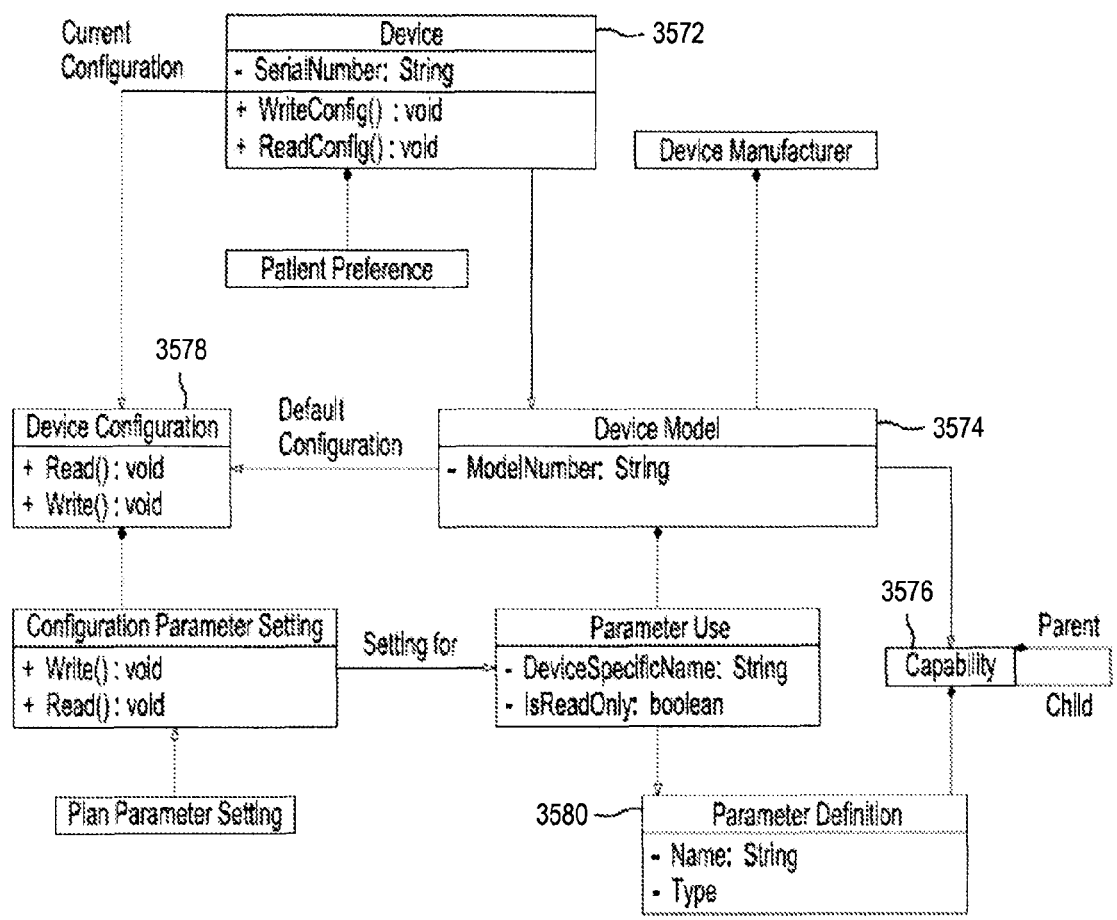
FIG. 92 is a class diagram for a portion of the diabetes care domain model that relates to medical devices.

FIG. 92 depicts a portion of the diabetes care domain model that relates to medical devices. Managing diabetes typically involves one or more medical devices. Over time, devices having new capabilities and/or configuration settings will emerge. Supporting new types of device capabilities and configuration parameters are identified extension points. Accordingly, the capability class 3576 forms a hierarchical (parent-child) structure using composition; the parent capability does not know anything about the contents of this composition except that they embody the capability. A particular device model implements some set of capabilities, as shown by the many-to-many relationship between the device model class 3574 and the capability class 3576. Similarly, the capability class 3576 has a composition relationship with the parameter definition class 3580; the capability does not know anything about the contents of this composition except that they embody the parameter definition concept. The relationships from device 3572 to device model 3574 and from device model 3572 to device configuration 3578 promote extensibility by insuring that configurations for individual devices are expressed in terms of the extensible concepts capability 3576 and parameter definition 3580.

Extensibility requires that an explicit representation of the extensible concept can be modified in some way that does not impact the design. In object-oriented systems, this is typically done with inheritance or with a container class referencing an interface. In functional systems, this can be done with a union structure or function pointers, or at worst with untyped pointers. Other techniques for changing the explicit representation are also contemplated by this disclosure.

Figure 93:
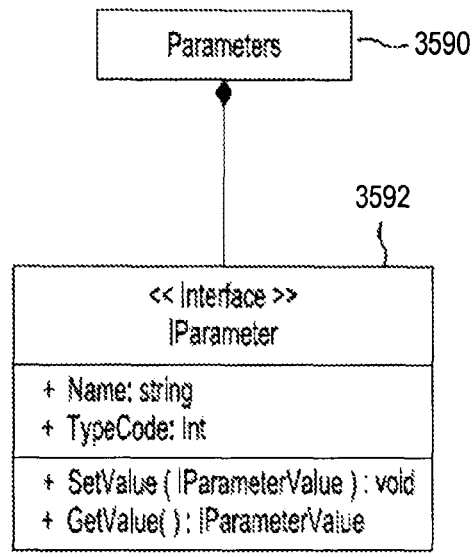
FIG. 93 is a diagram that illustrates a container class referencing an interface.

FIG. 93 illustrates a partial example of a detailed design using a container class 3590 referencing an interface 3592. For illustration purposes, supporting new parameters, such as device parameters, is the identified extensibility point. The design includes a 'Parameters' container (or containment) class having a composition relationship with an 'IParameter' interface. The 'Parameter' container class contains all of the system defined device parameters. An interface is an abstract class that specifies the elements, such as attributes and methods, common to all parameters of a device. In this simplified example of the 'IParameter' interface, each of the device parameters must have a name attribute and a typecode attribute. In addition, each of the device parameters must provide a method for setting the parameter value and a method for retrieving the parameter value. Additional attributes and/or method may be needed for an actual system design. Whether the members of this containment relationship are established at compile-time or run-time determines whether this design implements compile-time extensibility or run-time extensibility. In any case, it is understood that this principle can be extended to other data types.

For run-time extensibility, the system needs to be able to access software modules that were not implemented when the system was initially built. In the exemplary embodiment, the system has been implemented on devices which utilize the Microsoft Windows CE operating system. Thus, dynamic link loading is used by the system to access new software modules or libraries. In other computing environments, an interpreter or some other form of remote call may be used to access new software modules at run-time.

Figure 94:
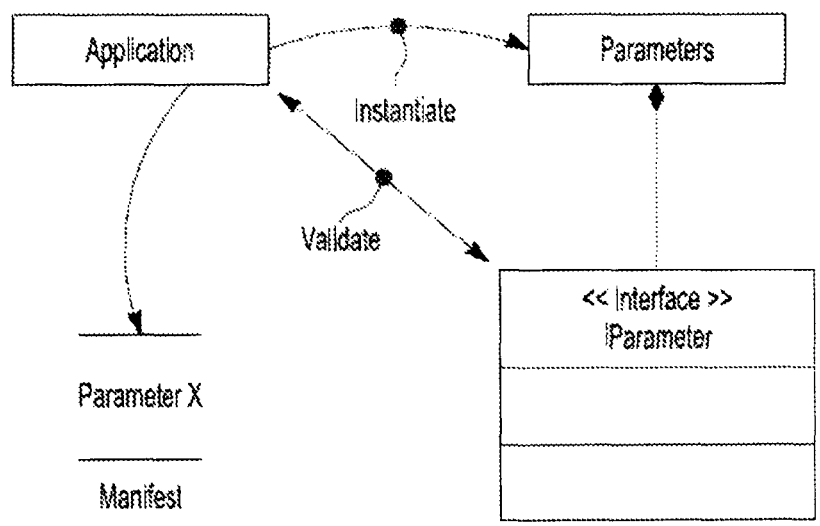
FIG. 94 is diagram that illustrates an application that instantiates an object of the container class by referencing the interface.

With reference to FIG. 94, an application may also want to make use of a new data types, such as a new device parameter. In this case, run-time extensibility requires that the application have some external source of knowledge about the new device parameter. In an exemplary embodiment, the new device parameter, such as Parameter X, is defined in a manifest. The manifest may be represented in a variety of ways, including binary file, text file, database, registry entry, etc. XML is a preferred format for the manifest representation.

At system start up, the application will instantiate one or more objects in the Parameter container class by referencing the 'IParameter' interface. For example, the application may make use of Parameter X. This new device parameter as defined in the manifest will be validated against the 'IParameter' interface. The new device parameter is instantiated as an object in the Parameter container class only if the new device parameter meets the criteria set forth by the interface. In this way, extensibility of new data types may be supported in the system. Instantiating new objects in this manner is one exemplary means of instantiating objects using a single coded list, such as a manifest, in a computer memory. Other means for instantiating objects using a single coded list also fall within the scope of this disclosure.

In an exemplary embodiment, a handheld medical device that supports extensibility for diabetes care would be set up as follows. First, an instance of the patient class with collections (compositions) for patient logs, physiological state variables, and treatment plans is created. Similarly, an instance of the medication catalog, trigger catalog and root capability will be created with collections for medications, treatment plan triggers, and child capabilities, respectively. Base classes for logged actions and adherence would also exist in the default configuration, but may not have instances in the initial (default) setup. Constructs for and the relationships amongst these classes are set forth above. In one implementation, extensibility requirements are enforced through inheritance. For example, all members of the patient object's physiological state variables collection would be derived from a common physiological state variable base class. In addition to those discussed above, it is readily understood that the device may be configured with other classes needed to support the functionality of the device.

The medical device is preferably configured with a meter that measures concentration of glucose in blood or some other type of measurement component (which may be no more than a way for users to manually enter a measurement value). The medical device further includes at least one application that utilizes the class structure. More specifically, the application instantiates an object from at least one of the patient class, the patient log class, the treatment plan class and the adherence class and performs a function using the instantiated objects. In the exemplary embodiment, the application is comprised of computer executable instructions executed by a computer processor in the device. While the extensibility configuration has been described in the context of a single medical device, it is understood that these principles apply to a diabetes management system distributed across multiple devices and/or having multiple software applications.

In another implementation, extensibility requirements are enforced by implementing select classes as container classes referencing an interface as described above. For example, the patient class would have containers for treatment plans and physiological state variables. In this example, a treatment plan interface a physiological state variable interface are also defined in the memory of the device. The treatment plan interface is an abstraction class that specifies the methods and properties that any member of the treatment plans collection must support. As shown in FIG. 90, this would include (but is not limited to) supporting properties for start date and end date. Similarly, the physiological state variable interface that specifies the methods and properties that any member of the physiological state variables collection must support. As shown in FIG. 89, this would include (but is not limited to) support properties for the variable's name and whether the variable's value can be predicted in the future, plus a method for calculating the value based on data in the patient logs. In this implementation, the application instantiates an object from some concrete class that supports the interface, for example by using a manifest as discussed above. Other classes in the domain model may also be implemented as container classes referencing an interface.

Power Management for a Handheld Medical Device

Referring now to FIG. 75, a person 2900 with diabetes and a healthcare professional 2902 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 2900 typically shares with the clinician 2902 a variety of patient data including blood glucose measurements, continuous glucose monitor data, amounts of insulin infused, amounts of food and beverages consumed, exercise schedules, and other lifestyle information. The clinician 2902 may obtain additional patient data that includes measurements of HbA1C, cholesterol levels, triglycerides, blood pressure, and weight of the patient 2900. The patient data can be recorded manually or electronically on a handheld diabetes management device

2904, a diabetes analysis software executed on a personal computer (PC) 2906, and/or a web-based diabetes analysis site (not shown). The clinician 2902 can analyze the patient data manually or electronically using the diabetes analysis software and/or the web-based diabetes analysis site. After analyzing the patient data and reviewing adherence of the patient 2900 to previously prescribed therapy, the clinician 2902 can decide whether to modify the therapy for the patient 2900.

Referring now to FIG. 76, the patient 2900 can use a continuous glucose monitor (CGM) 2910, an ambulatory non-durable insulin infusion pump 2912 or an ambulatory durable insulin infusion pump 2914 (hereinafter insulin pump 2912 or 2914), and the handheld diabetes management device 2904 (hereinafter the diabetes manager 2904). The CGM 2910 uses a subcutaneous sensor to sense and monitor the amount of glucose in interstitial fluid of the patient 2900 and communicates corresponding data to the diabetes manager 2904.

The diabetes manager 2904 performs various tasks including measuring and recording blood glucose levels, determining an amount of insulin to be administered to the patient 2900 via the insulin pump 2912 or 2914, receiving patient data via a user interface, archiving the patient data, etc. The diabetes manager 2904 periodically receives data from the CGM 2910 from which glucose levels of the patient 2900 are computed. The diabetes manager 2904 transmits instructions to the insulin pump 2912 or 2914, which delivers insulin to the patient 2900. Insulin can be delivered in a scheduled manner in the form of a basal dose, which maintains a predetermined insulin dose to the patient 2900. Additionally, insulin can be delivered in the form of a bolus dose, which raises the amount of insulin delivered to the patient 2900 by a predetermined amount.

Referring now to FIG. 77, a diabetes management system 2930 used by the patient 2900 and the clinician 2902 includes one or more of the following devices: the diabetes manager 2904, the continuous glucose monitor (CGM) 2910, the insulin pump 2912 or 2914, a mobile device 2932, the PC 2906 with the diabetes analysis software, and other healthcare devices 2934. The diabetes manager 2904 is configured as a system hub and communicates with the devices of the diabetes management system 2930. Alternatively, the mobile device 2932 can serve as the system hub. Communication between the devices in the diabetes management system 2930 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 2900 and clinician 2902 to exchange information.

The diabetes manager 2904 can receive glucose readings from one or more sources (e.g., from the CGM 2910). The CGM 2910 continuously monitors the glucose level of the patient 2900. The CGM 2910 periodically communicates data to the diabetes manager 2904 from which the diabetes manager 2904 computes glucose levels of the patient. The diabetes manager 2904 and the CGM 2910 communicate wirelessly using a proprietary wireless protocol. Throughout the present disclosure, Gazell wireless protocol developed by Nordic Semiconductor, Inc. is used as an example only. Any other suitable wireless protocol can be used instead. The Gazell wireless protocol is described in nRF24LE1 Ultra-low Power Wireless System On-Chip Solution, Product Specification v1.4, which is incorporated herein by reference in its entirety.

Additionally, the diabetes manager 2904 includes a blood glucose meter (BGM) and a port that communicates with the BGM (not shown). The port can receive a blood glucose measurement strip 2936. The patient 2900 deposits a sample of blood on the blood glucose measurement strip 2936. The BGM analyzes the sample and measures the blood glucose level in the sample. The blood glucose measured from the sample and/or the blood glucose level read by the CGM 2910 can be used to determine the amount of insulin to be administered to the patient 2900.

The diabetes manager 2904 communicates with the insulin pump 2912 or 2914. The insulin pump 2912 or 2914 can be configured to receive instructions from the diabetes manager 2904 to deliver a predetermined amount of insulin to the patient 2900. Additionally, the insulin pump 2912 or 2914 can receive other, information including meal and/or exercise schedules of the patient 2900. The insulin pump 2912 or 2914 can determine the amount of insulin to administer based on the additional information.

The insulin pump 2912 or 2914 can also communicate data to the diabetes manager 2904. The data can include amounts of insulin delivered to the patient 2900, corresponding times of delivery, and pump status. The diabetes manager 2904 and the insulin pump 2912 or 2914 can communicate using a wireless communication protocol such as Bluetooth. Other wireless or wireline communication protocols can also be used.

In addition, the diabetes manager 2904 can communicate with the other healthcare devices 2934. For example, the other healthcare devices 2934 can include a blood pressure meter, a weight scale, a pedometer, a fingertip pulse oximeter, a thermometer, etc. The other healthcare devices 2934 obtain and communicate personal health information of the patient 2900 to the diabetes manager 2904 through wireless, USB, or other interfaces. The other healthcare devices 2934 may use communication protocols compliant with ISO/IEEE 11073 extended using guidelines from Continual® Health Alliance. The diabetes manager 2904 can communicate with the other healthcare devices 2934 using interfaces including Bluetooth, USB, etc. Further, the devices of the diabetes management system 2930 can communicate with each other via the diabetes manager 2904.

The diabetes manager 2904 can communicate with the PC 2906 using Bluetooth, USB, or other interfaces. A diabetes management software running on the PC 2906 includes an analyzer-configurator that stores configuration information of the devices of the diabetes management system 2930. The configurator has a database to store configuration information of the diabetes manager 2904 and the other devices. The configurator can communicate with users through standard web or computer screens in non-web applications. The configurator transmits user-approved configurations to the devices of the diabetes management system 2930. The analyzer retrieves data from the diabetes manager 2904, stores the data in a database, and outputs analysis results through standard web pages or computer screens in non-web based applications.

The diabetes manager 2904 can communicate with the mobile device 2932 using Bluetooth. The mobile device 2932 may include a cellular phone, a pager, or a personal digital assistant (PDA). The diabetes manager 2904 can send messages to an external network through the mobile device 2932.

The mobile device 2932 can transmit messages to the external network upon receiving requests from the diabetes manager 2904.

Referring now to FIG. 82, the diabetes manager 2904 comprises a blood glucose measuring (BGM) module 3300, a communication module 3302, a user interface module 3304, user interfaces 3306, a processing module 3308, memory 3310, and a power module 3312. The user interface module 3304 and the processing module 3308 can be implemented by an application processing module 3309. The BGM module 3300 includes a blood glucose measuring engine that analyzes samples provided by the patient 2900 on the blood glucose measurement strip 2936 and that measures the amount of blood glucose in the samples. The communication module 3302 includes multiple radios that communicate with different devices the diabetes management system 2930. The user interface module 3304 interfaces the diabetes manager 2904 to various user interfaces 3306 that the patient 2900 can use to interact with the diabetes manager 2904. For example, the user interfaces 3306 can include keys, switches, a display, a speaker, a microphone, a secure digital (SD) card port, a USB port, etc. (not shown).

The processing module 3308 processes data received from the BGM module 3300, the communication module 3302, and the user interface module 3304. The processing module 3308 uses memory 3310 for processing and storing data. The memory 3310 can include volatile and nonvolatile memory. The processing module 3308 outputs data to and receives data from the user interfaces 3306 via the user interface module 3304. The processing module 3308 outputs data to and receives data from the devices of the diabetes management system 2930 via the communication module 3302. The power module 3312 supplies power to the components of the diabetes manager 2904. The power module 3312 includes a rechargeable battery. The battery can be recharged using an adapter that plugs into a wall outlet. The battery can also be charged via the USB port of the diabetes manager 2904.

Figure 95:
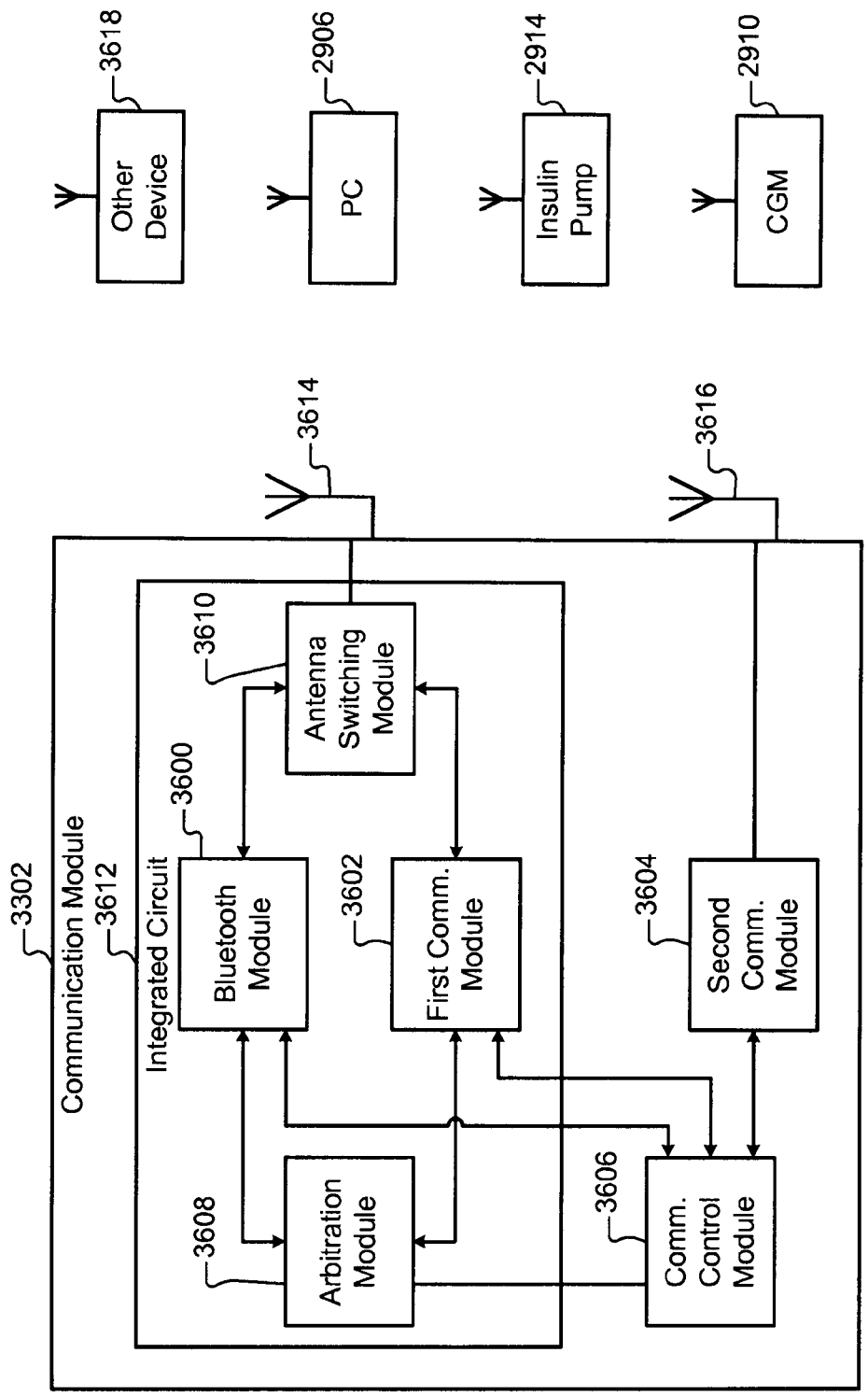
FIG. 95 is a functional block diagram of a communication module used by the diabetes manager of FIG. 82.

Referring now to FIG. 95, the communication module 3302 comprises a Bluetooth module 3600, a first communication module 3602, a second communication module 3604, a communication control module 3606, an arbitration module 3608, and an antenna switching module 3610. The Bluetooth module 3600 and the first communication module 3602 are integrated into an integrated circuit (IC) 3612. The Bluetooth module 3600 and the first communication module 3602 communicate in a 2.4 GHz frequency band (industrial, scientific, and medical or ISM band). The Bluetooth module 3600 and the first communication module 3602 share a first antenna 3614. The second communication module 3604 may operate in the ISM band or in a different frequency band and uses a second antenna 3616.

Specifically, the Bluetooth module 3600 communicates in the ISM band with the insulin pump 2914 or the PC 2906 via the first antenna 3614 using the Bluetooth protocol. The first communication module 3602 communicates in the ISM band with the CGM 2910 via the first antenna 3614 using the Gazell protocol. The second communication module 3604 communicates with other device 3618 using a wireless communication protocol different than Bluetooth and Gazell protocols. Throughout the present disclosure, the insulin pump 2914, the PC 2906, the CGM 2910, and related priorities are used as examples only. Additionally or alternatively, the Bluetooth module 3600 and the first and second communication modules 3602 and 3604 can communicate with other devices, and the other devices can have different priorities.

The communication control module 3606 controls communication of the diabetes manager 2904 with the other devices in the diabetes management system 2930 via the Bluetooth module 3600 and the first and second communication modules 3602 and 3604. The arbitration module 3608 arbitrates priority between the Bluetooth module 3600 and the first communication module 3602 when communication via the Bluetooth module 3600 and the first communication module 3602 is attempted concurrently. The antenna switching module 3610 switches the connection of the first antenna 3614 between the Bluetooth module 3600 and the first communication module 3602 depending on whether the Bluetooth module 3600 or the first communication module 3602 is granted priority.

Figure 96:
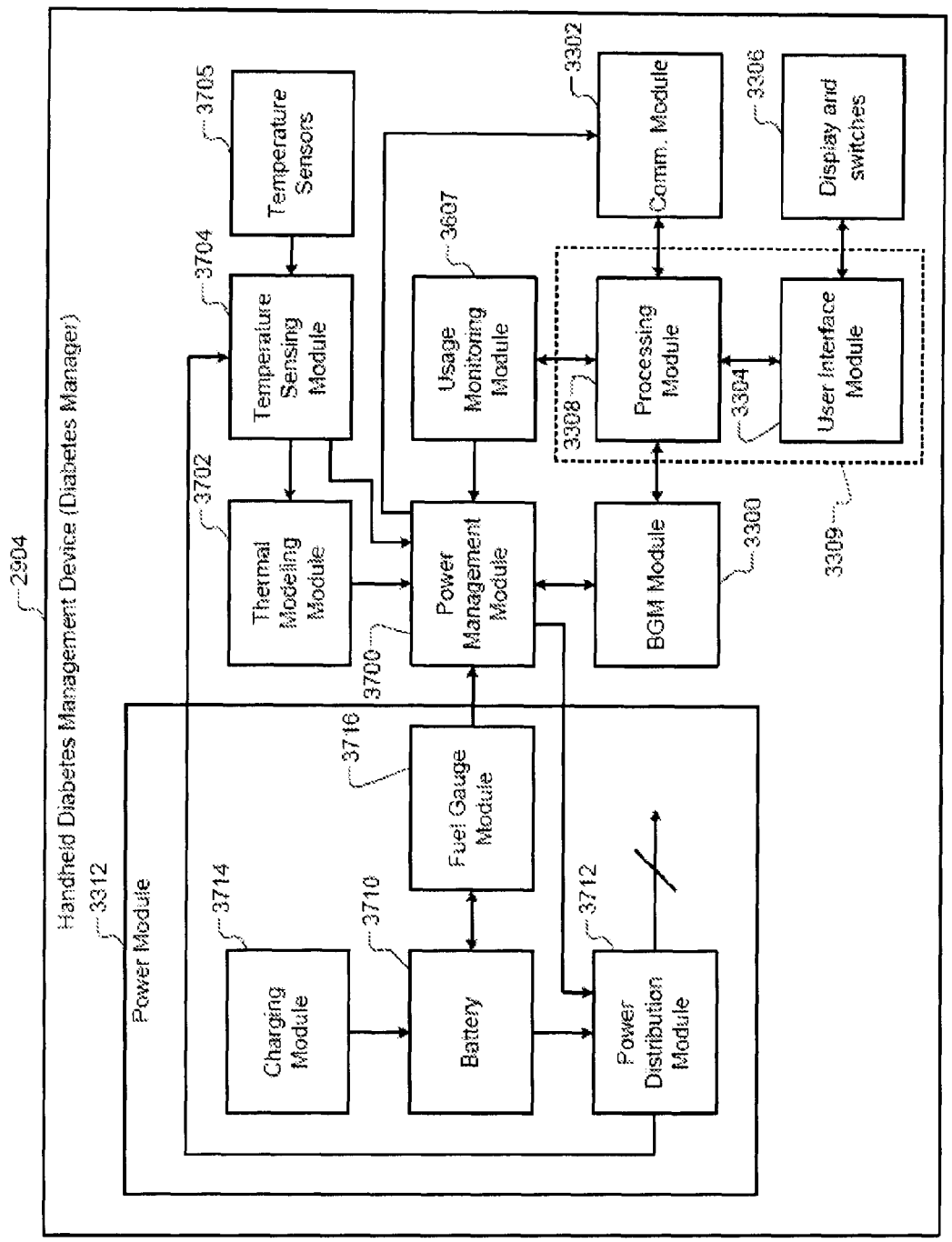
FIG. 96 is a detailed functional block diagram of the diabetes manager of FIG. 82.

Referring now to FIG. 96, a detailed functional block diagram of the diabetes manager 2904 is shown. Elements of the diabetes manager 2904 that are described above are not described again. In addition to these elements, the diabetes manager 2904 includes a power management module 3700, a thermal modeling module 3702, a temperature sensing module 3704, a plurality of temperature sensors 3705, and a usage monitoring module 3706. Further, the power module 3312 includes a rechargeable battery 3710, a power distribution module 3712, a charging module 3714, and a fuel gauge module 3716. The power distribution module 3712 selectively converts and distributes the power from the battery 3710 to the components of the diabetes manager 2904. The fuel gauge module 3716 determines the remaining capacity of the battery 3710. The charging module 3714 charges the battery 3710.

The power management module 3700 controls power consumption of the diabetes manager 2904 based on inputs received from the thermal modeling module 3702, the temperature sensing module 3704, the temperature sensors 3705, the usage monitoring module 3706, and the power module 3312. Based on these inputs, the power management module 3700 outputs power control signals to the power distribution module 3712. The power distribution module 3712 supplies power to the components of the diabetes manager 2904 based on the power control signals.

More specifically, the power distribution module 3712 receives power from the battery 3710 and generates different voltages and currents suitable for the different components of the diabetes manager 2904. The power distribution module 3712 outputs the voltages and currents (collectively power) to the components according to the power control signals received from the power management module 3700. Depending on the power control signals, the power distribution module 3712 can supply full power, no power, or standby power to one or more components. The components are activated when full power is supplied and deactivated when no power or standby power is supplied. For a plurality of standby modes, a plurality of intersecting sets of components may be activated to satisfy a plurality of device use cases.

Additionally, depending on the power control signals, the power distribution module 3712 can control frequencies of clock signals supplied to the components to conserve power. For example, a frequency of a clock signal supplied to a component when standby power is supplied to the component is less than the frequency when full power is supplied to the component. Use of clock signals having lower than normal frequencies requires less power than use of clock signals having normal clock frequencies, and this relationship scales linearly.

The temperature sensors 3705 are located at different locations in the diabetes manager 2904. The temperature sensors 3705 sense and output temperatures at the different locations to the temperature sensing module 3704. The temperature sensing module 3704 outputs the temperatures to the thermal modeling module 3702. The thermal modeling module 3702 processes the temperatures using a thermal model. Based on the processing, the thermal modeling module 3702 estimates an internal temperature of the diabetes manager 2904, a rate of change of the internal temperature, and an ambient temperature proximate to the blood glucose measurement strip 2936. The thermal model is described in U.S. patent application Ser. No. 12/479,212, filed Jun. 5, 2009, which is incorporated herein by reference in its entirety. The thermal model is also described below.

The temperature sensing module 3704 can also estimate the internal temperature and the rate of change of the internal temperature based on the amount of power supplied by the power distribution module 3712 to one or more components of the diabetes manager 2904. Specifically, the internal temperature of the diabetes manager 2904 and the rate of change of the internal temperature are directly proportional to the amount of power consumed by the components of the diabetes manager 2904. The power distribution module 3712 can provide data to the temperature sensing module 3704 indicating when and how long a component is activated and deactivated. Accordingly, the temperature sensing module 3704 can estimate the amount of heat generated by the component. Based on the estimates of heat generated by the components, the temperature sensing module 3704 can estimate the internal temperature and the rate of change of the internal temperature of the diabetes manager 2904.

The usage monitoring module 3706 monitors the usage of the diabetes manager 2904. For example, the usage can include, but is not limited to, one or more of these operations of the diabetes manager 2904: blood glucose measurement, interactions with the patient 2900 (e.g., receiving inputs, displaying data, generating alerts/alarms, etc.), communications with one or more devices external to the diabetes manager 2904 (e.g., receiving diagnostic data from the CGM 2910 or updates from the PC 2906, transmitting instructions to the insulin pump 2914, etc.), and so on. The usage monitoring module 3706 outputs the usage data to the power management module 3700. The usage data can also include data regarding planned or scheduled usage of one or more components of the diabetes manager 2904 (e.g., blood glucose measurement).

The power management module 3700 uses the usage data and the remaining capacity of the battery 3710 generated by the fuel gauge module 3716 to determine whether to activate or deactivate one or more components of the diabetes manager 2904. For example, when the remaining capacity of the battery is less than a predetermined threshold, the power management module 3700 generates the power control signals to deactivate components that consume large amount of power (e.g., the communication module 3302). Additionally, based on the usage data, the power management module 3700 can deactivate components that are idle (e.g., display) and/or that are not scheduled to be used for a predetermined period of time (e.g., the BGM module 3300).

The blood glucose measurements performed by the BGM module 3300 involve chemical analysis of the sample provided by the patient 2900 on a reaction site of the blood glucose measurement strip 2936. The chemical processes are sensitive to temperature. Since the port that receives the blood glucose measurement strip 2936 is proximate to the components of the diabetes manager 2904, the chemical processes at the reaction site can be affected by the internal temperature of the diabetes manager 2904. Accordingly, the blood glucose levels measured by the BGM module 3300 can be skewed by the internal temperature of the diabetes manager 2904.

In some blood glucose measurement strips, the chemical processes at the reaction site may be relatively insensitive to the internal temperature of the diabetes manager 2904. However, the accuracy of the blood glucose levels measured by the BGM module 3300 is characterized over a specified temperature range (e.g., 6° C. to 44° C.). The ambient temperature at the reaction site can be different than the internal temperature of the diabetes manager 2904 due to low thermal conductivity of the blood glucose measurement strip 2936. Accordingly, if the internal temperature of the diabetes manager 2904 is near 44° C. and is greater than the ambient temperature at the blood glucose measurement strip 2936, the BGM module 3300 may be prevented from measuring the blood glucose level (false positive). Conversely, if the ambient temperature at the blood glucose measurement strip 2936 is near 6° C. and is less than the internal temperature of the diabetes manager 2904, the BGM module 3300 may be permitted to measure the blood glucose level (false negative). These problems can be alleviated as follows.

The thermal modeling module 3702 estimates the ambient temperature proximate to the reaction site based on the internal temperature of the diabetes manager 2904. The power management module 3700 deactivates one or more components of the diabetes manager 2904 when the ambient temperature, the internal temperature, and/or the rate of change of internal temperature are greater than a predetermined threshold. The BGM module 3300 generates a status signal indicating whether a measurement is scheduled in a predetermined time or whether a measurement is in progress. For example, the status signal can indicate whether a measurement is scheduled at a particular time of the day. The status signal can also indicate a present status of the BGM module 3300 (e.g., whether the BGM module 3300 is performing a measurement or is idle). Based on the information conveyed by the status signal, the power management module 3700 can deactivate one or more components of the diabetes manager 2904 before or while the BGM module 3300 measures blood glucose levels. For example, the power management module 3700 can deactivate at least one or all of the communication modules 3600, 3602, and 3604 before or while the BGM module 3300 measures blood glucose levels.

Further, the diabetes manager 2904 can be configured to partially operate during charging of the battery 3710 depending on the state of charge of the battery 3710. For example, when the state of charge is greater than a first predetermined threshold, one or more of the communication modules 3600, 3602, and 3604 may be used to communicate with corresponding external devices (e.g., the insulin pump 2914, the PC 2906, and/or the CGM 2910). When the state of charge is greater than a second predetermined threshold, one or more of the user interfaces can be operated. For example, the display can operate at full brightness; the speaker can operate at full volume; and so on. When the state of charge is greater than a third predetermined threshold, the BGM module 3300 can be operated, and so on. These are only examples of sequences in which components of the diabetes manager 2904 can be operated during charging. Other sequences can be used.

The internal temperature of the diabetes manager 2904 can rise during charging of the battery 3710 and can remain high for a period of time after charging is complete. This could ordinarily skew and therefore prevent blood glucose measurements of the BGM module 3300. The power management module 3700, however, deactivates one or more components of the diabetes manager 2904 based on inputs received from the thermal modeling module 3702, temperature sensing module 3704, the temperature sensors 3705, and the usage monitoring module 3706 during charging of the battery 3710.

Accordingly, the internal temperature of the diabetes manager 2904 does not rise to a value that can skew the blood glucose measurements of the BGM module 3300. Further, the thermal modeling module 3702 estimates the ambient temperature proximate to the reaction site based on the internal temperature, and the BGM module 3300 adjusts blood glucose measurements based on the estimated ambient temperature. Alternatively, based on the estimated ambient temperature, the power management module 3700 can determine whether to permit the BGM module 3300 to measure blood glucose. Thus, the BGM module 3300 can reliably measure blood glucose levels during charging of the battery 3710 despite a rise in the internal temperature of the diabetes manager 2904.

The power management module 3700 can also forecast remaining operating time of the diabetes manager 2904 based on the remaining capacity of the battery 3710 received from the fuel gauge module 3716 and usage data received from the usage monitoring module 3706. The power management module 3700 can use the forecast to select components of the diabetes manager 2904 to deactivate. Further, the power management module 3700 can determine when and how long to deactivate the selected components. In some implementations, the power management module 3700 can also determine an order in which the selected components can be deactivated and reactivated. Thus, the power management module 3700 can use the forecast to prioritize and schedule power that can be supplied to one or more components of the diabetes manager 2904.

For example, based on the forecast, the power management module 3700 can output control signals to the arbitration module 3608, which can arbitrate priority between the Bluetooth module 3600 and the first communication module 3602 based on the control signals. When the control signals indicate that the remaining capacity of the battery 3710 is less than a predetermined threshold, the arbitration module 3608 can deny permission to one or more of the communication modules 3600, 3602, and 3604 that consume more power and grant priority to one of the communication modules 3600, 3602, and 3604 that consumes less power.

For example, the CGM 2910 monitors blood glucose more frequently than the insulin pump 2914 delivers insulin. Further, the first communication module 3602 communicates with the CGM 2910 more frequently than the frequency at which the Bluetooth module 3600 communicates with the insulin pump 2914. Further, the Bluetooth module 3600 may not communicate frequently with other devices such as the PC 2906. Consequently, the first communication module 3602 consumes more power than the Bluetooth module 3600. Accordingly, the power management module 3700 can deactivate the first communication module 3602 before deactivating the Bluetooth module 3600.

Further, when the control signals indicate that the remaining capacity of the battery 3710 is less than a predetermined threshold and an operation such as blood glucose measurement is scheduled to be performed, the power management module 3700 can reduce output levels of one or more of the user interfaces 3306 to conserve power until the battery 3710 is recharged. For example, brightness of the display and/or volume of the speaker can be limited to less than a predetermined threshold until the battery 3710 is recharged.

Figure 97A:
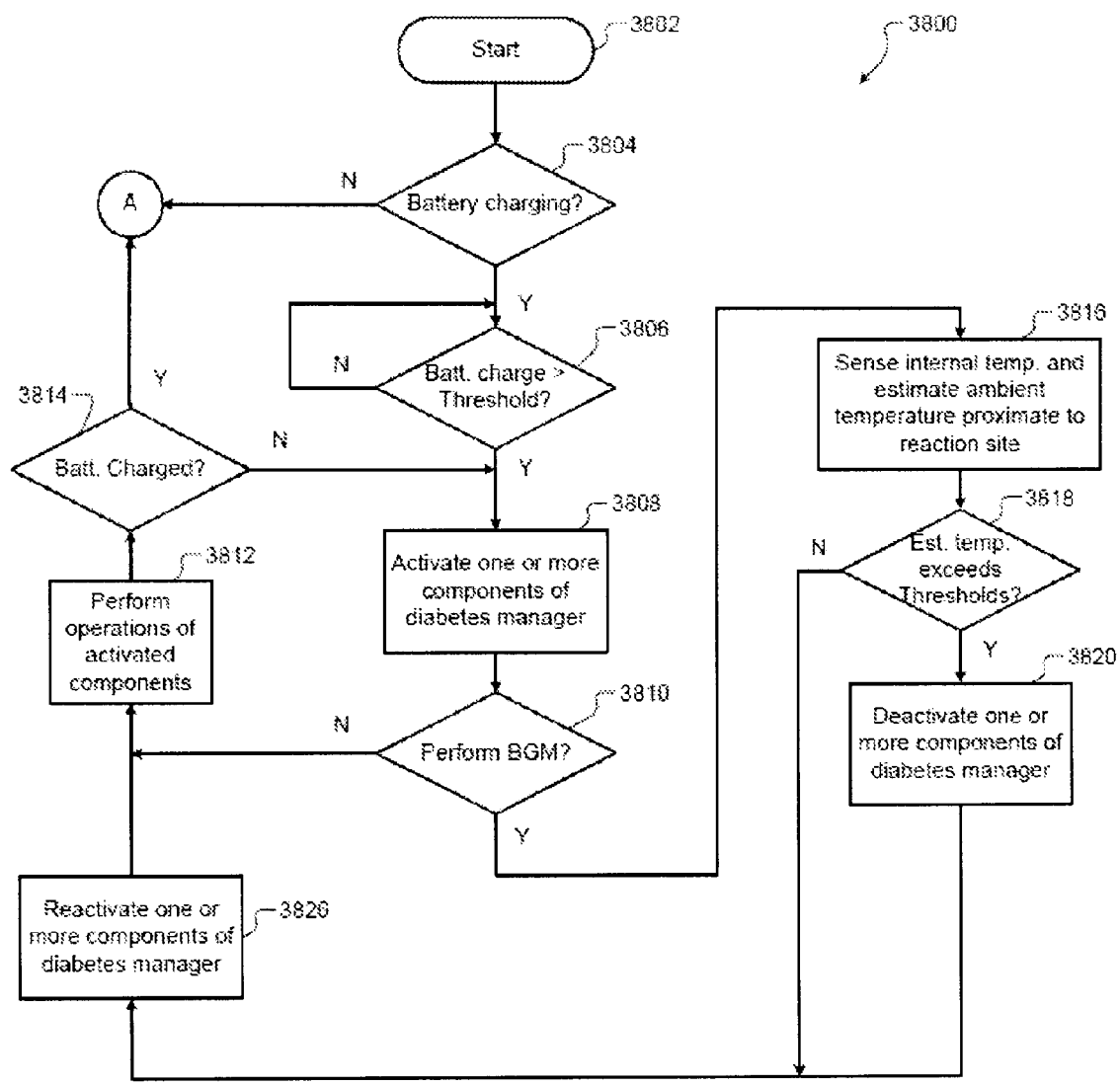
FIGS. 97A and 97B depict a flowchart of a method for managing power consumption of the diabetes manager and limiting effects of temperature on operations performed by the diabetes manager of FIG. 82.
Figure 97B:
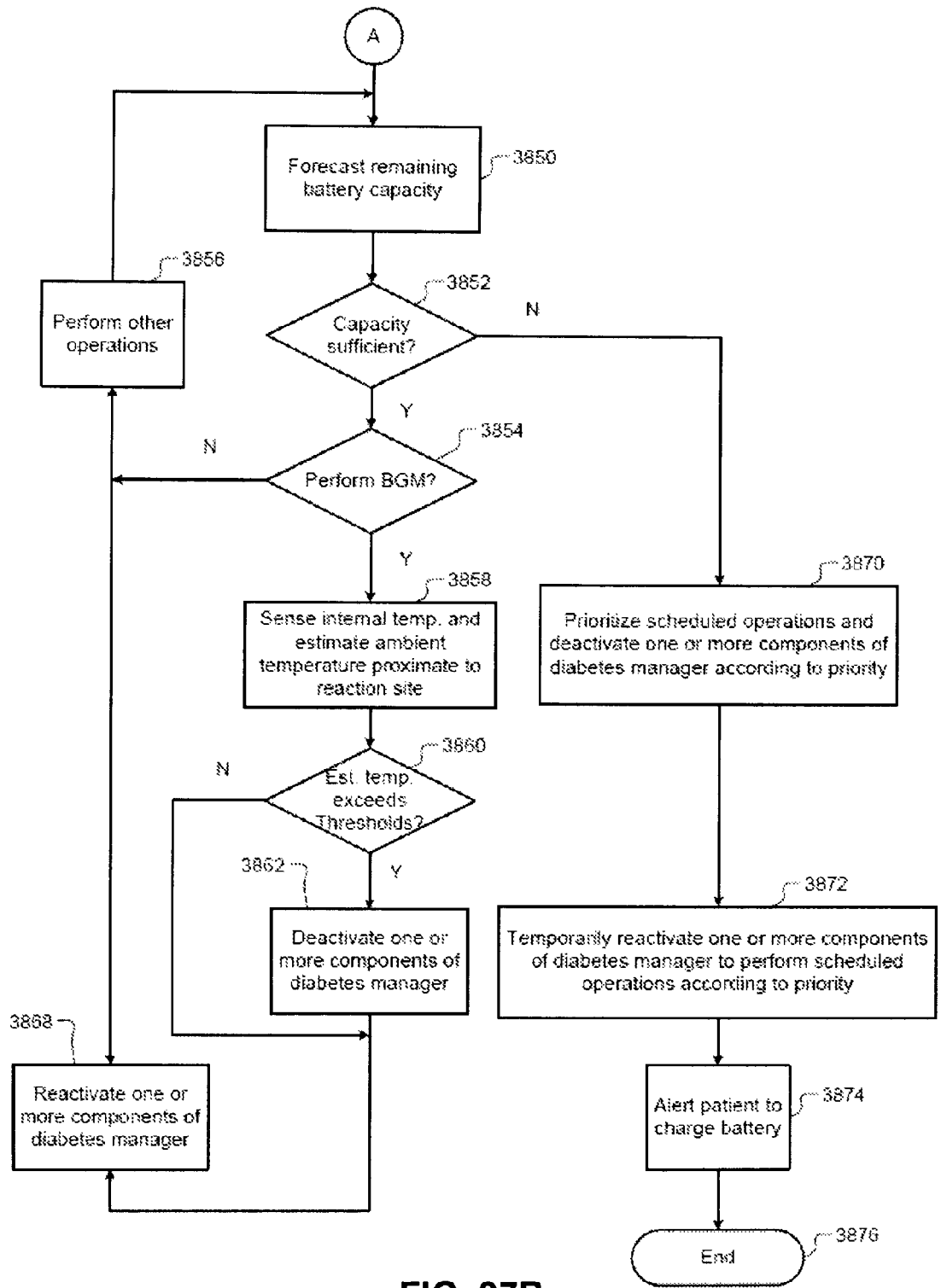

Referring now to FIGS. 97A and 97B, in an exemplary implementation, the power management module 3700 performs a method 3800. In FIG. 97A, control begins at 3802. At 3804, control determines if the battery 3710 is charging. If the battery 3710 is not charging, control goes to 3850 (see FIG. 97B). If the battery 3710 is charging, at 3806, control determines if the state of charge of the battery 3710 is greater than a predetermined threshold, which indicates that the battery 3710 has sufficient charge to supply power to one or more components of the diabetes manager 2904. Control waits until the state of charge of the battery 3710 is greater than a predetermined threshold. When the state of charge of the battery 3710 is greater than a predetermined threshold, at 3808, control activates one or more components of the diabetes manager 2904.

At 3810, control determines if a blood glucose measurement (BGM) is to be performed. If a BGM is not to be performed, at 3812, control performs operations of activated components. At 3814, control determines if the battery 3710 is charged. If the battery 3710 is charged, control goes to 3850 (see FIG. 97B). If the battery 3710 is not charged, control returns to 3808.

At 3816, if a BGM is to be performed, control senses the internal temperature of the diabetes manager 2904 and uses the thermal model to estimate the external temperature. At 3818, control determines if the estimated external temperature is greater than a first predetermined threshold or less than a second predetermined threshold. If either case is true, at 3820, control deactivates one or more components of the diabetes manager 2904. Thereafter, or if the estimated external temperature does not exceed the predetermined thresholds, at 3826, control reactivates one or more deactivated components, and control returns to 3812. In some implementations, instead of waiting for the temperature to return to an acceptable temperature range, the processing module 3308 can output a message to the patient 2900 that the temperature is outside the acceptable temperature range, and testing is disallowed.

In FIG. 97B, at 3850, control forecasts the remaining battery capacity as described above. At 3852, control determines if the remaining battery capacity is sufficient to perform scheduled operations. If the remaining battery capacity is sufficient to perform scheduled operations, at 3854, control determines if a blood glucose measurement (BGM) is to be performed. If a BGM is not to be performed, at 3856, control performs other scheduled operations of the diabetes manager 2904, and control returns to 3850.

At 3858, if a BGM is to be performed, control senses the internal temperature of the diabetes manager 2904 and uses the thermal model to estimate the external temperature. At 3860, control determines if the estimated external temperature is greater than a first predetermined threshold or less than a second predetermined threshold. If either case is true, at 3862, control deactivates one or more components of the diabetes manager 2904. Thereafter, or if the estimated external temperature does not exceed the predetermined thresholds, at 3868, control reactivates one or more deactivated components, and control returns to 3856. In some implementations, instead of waiting for the temperature to return to an acceptable temperature range, the processing module 3308 can output a message to the patient 2900 that the temperature is outside the acceptable temperature range, and testing is disallowed.

At 3870, if the remaining battery capacity is insufficient (e.g., less than a predetermined threshold) to perform scheduled operations, control prioritizes scheduled operations of the diabetes manager 2904 and deactivates one or more components of the diabetes manager 2904 according to the priority. Control also limits capabilities of one or more user interfaces 3306 (e.g., display, speaker, etc.) of the diabetes manager 2904. At 3872, control temporarily reactivates one or more deactivated components to perform the scheduled operations according to the priority, and deactivates the components after the scheduled operations are completed. At 3874, control alerts the patient 2900 to charge the battery 3710, and control ends at 3876.

In summary, a system for managing the power consumption of diabetes manager 2904 and limiting effects of temperature on operations performed by the diabetes manager 2904 includes the BGM module 3300, the temperature sensing module 3704, and the power management module 3700. The BGM module 3300 selectively measures blood glucose in a blood sample and generates a status signal indicating a status of operation of the BGM module 3300. The temperature sensing module 3704 senses the internal temperature of the diabetes manager 2904. The power management module 3700 deactivates one or more components of the diabetes manager 2904 based on the status of operation of the BGM module 3300 when the internal temperature of the diabetes manager 2904 exceeds a threshold temperature.

In an alternative embodiment, the system includes a temperature sensor (e.g., 3705) that senses the internal temperature of the diabetes manager 2904 and a port that externally receives a removable measurement strip (e.g., 2936) having a reaction site for receiving a blood sample. The system further includes the thermal modeling module 3702 and the power management module 3700. The thermal modeling module 3702 uses a thermal model to estimate the ambient temperature proximate to the reaction site based on the internal temperature. The power management module 3700 deactivates one or more components of the diabetes manager 2904 when the ambient temperature proximate to the reaction site is greater than a first threshold temperature or is less than a second threshold temperature.

Stated generally, a system for managing power consumption of a handheld medical device (e.g., 2904) and limiting effects of temperature on operations performed by the handheld medical device includes a temperature sensor (e.g., 3705), a port, a thermal modeling module (e.g., 3702), and a power management module (e.g., 3700). The temperature sensor senses an internal temperature of the medical device. The port externally receives a removable measurement strip having a reaction site for receiving a sample of a substance for measuring a health parameter of a patient. The thermal modeling module uses a thermal model to estimate an ambient temperature proximate to the reaction site based on the internal temperature. The power management module deactivates one or more components of the medical device when the ambient temperature proximate to the reaction site is greater than a first threshold temperature or is less than a second threshold temperature.

The thermal model utilized by the thermal modeling module 3702 is now described. The thermal model provides a method for estimation of the temperature at a blood glucose (bG) test strip reaction site when the test strip (e.g., the glucose measurement strip 2936) may be at a different temperature than the bG measurement electronic circuitry (e.g., the BGM module 3300 or the diabetes manager 2904). The readings from the temperature sensor (e.g., the temperature sensors 3705) in the bG measurement circuitry are used by a temperature estimation algorithm to estimate the temperature at the bG test strip reaction site. It is important to know the temperature at the reaction site in order to avoid unwarranted over-temperature lockout conditions, or to ignore valid under-temperature lock-out conditions, that would prevent proper use of the bG meter. Since all but the base of the bG test strip is exposed to the ambient air, the reaction site temperature closely follows the ambient air temperature. Studies have confirmed that the test strip has low thermal conductivity, so the internal temperature of the BGM module may differ from the temperature of the reaction site on the test strip.

In its simplest form, the algorithm uses a reading from a temperature sensor as the estimate of the reaction site temperature. If the reading is changing at a rate that exceeds a specified threshold, the temperature estimation algorithm may obtain an improved estimate of the ambient air temperature, and hence the reaction site temperature, by amplifying those changes in the temperature sensor reading and formulating a new prediction based on a static thermal model of the bG measurement device.

The reading from the sensor can, however, change not due to changes in the ambient air, but rather due to the internal heating of electronic components inside the device containing the bG circuitry (e.g., the diabetes manager 2904). For example, consider the case of bG measurement circuitry installed in a cell phone. Due to the high operating temperature of circuitry inside the cell phone, the temperature readings from the temperature sensor may be unduly elevated. Furthermore, the internal heat generation may vary depending on how the cell phone is being used. Accurate temperature estimation must continue even when the thermal characteristics of the device change with specific usage.

The thermal model provides a method for estimating the temperature elevation due to any number of heat sources of arbitrary strength and arbitrary duration. Once the total expected temperature elevation has been determined, then this quantity can be subtracted from the temperature sensor reading to furnish a corrected temperature reading upon which an accurate ambient temperature prediction can be based. An advantage of this approach is that the thermal model can be dynamically adjusted depending on the specific usage of the device. As more functions are added to the device, it becomes increasingly important to estimate reaction site temperature based on how the device has been used prior to the bG test.

The mathematical method of the thermal mode relies upon the linear superposition of temperature responses to an applied heat source or sources. A time-varying heat source may be characterized as a series of heat "impulses" of varying magnitude. For the purposes of the present disclosure, an "impulse" is a period of heating lasting a short time as compared to the total duration of heating. Due to linear superposition, the temperature response of a heat source of extended duration can be found by adding up the temperature responses of a succession of impulses that represent that heat source.

Within a device there may be multiple sources of heat, generally caused by the internal heat generation of specific electronic components. Again by linear superposition, the total temperature response of all of these components may be found by summing their individual contributions. These heat sources may become active prior to or during a blood glucose measurement. Their effect on the temperature measurement must be accounted for.

A number of factors affect the temperature response to a given heat source. Within the device enclosure, the heat source may be located on the same circuit board as the temperature sensor or on another circuit board, and it may be near the sensor or far from it. The heat generation of a particular electronic component may vary greatly during its various modes of operation. This heating can be mathematically characterized. The corresponding temperature response at the temperature sensor can also be measured with reasonable accuracy. Depending on the location of the heat producing electronic component relative to the temperature sensor and the nature of the thermal pathways between them, the temperature response at the temperature sensor can vary a great deal. A heat source near the temperature sensor tends to produce a rapid rise in temperature after the heat is applied, followed by a rapid decline in temperature when the heat is removed. For a more distant heat source, the rise and fall in temperature are more gradual and more time elapses before the peak temperature is reached.

The method of linear superposition may be used to characterize the combined effect of multiple, time-varying heat sources in an electronic device, such as a hand-held device incorporating bG measurement circuitry (e.g., the diabetes manager 2904). Consider the case of a heat source "A" of strength Qa being applied for duration $(Na/2) \cdot \Delta t$, where Na is an even positive integer and $\Delta t$ is an increment of time. A temperature sensor is installed in the package at a different location than the heat source. Let the temperature elevation at the location of the temperature sensor at time $t_i = i \cdot \Delta t$ after the activation of the heat source be given by $Ea_i = (Ta_i - T_{ref})$ where $Ta_i$ is the temperature at the location of the temperature sensor at time $t_i$, and $T_{ref}$ is a suitable reference temperature.

Let the reference temperature be the ambient temperature of the electronic package: $T_{ref} = T_{amb}$. The temperature elevations $Ea_i$ for times $t_1$ through $t_{Na}$ can be expressed by the following matrix equation:

$$Qa \cdot \begin{bmatrix} 1 & 0 & \cdots & & 0 & 0 & \cdots & & 0 \\ 1 & 1 & 0 & \cdots & & 0 & 0 & \cdots & & 0 \\ 1 & 1 & 1 & 0 & \cdots & 0 & 0 & \cdots & & 0 \\ \cdots & & & & & \cdots & & & \\ 1 & \cdots & & & 1 & 0 & 0 & \cdots & & 0 \\ 1 & 1 & \cdots & & & 1 & 0 & \cdots & & 0 \\ 0 & 1 & \cdots & & & 1 & 1 & 0 & \cdots & 0 \\ 0 & 0 & 1 & \cdots & & 1 & 1 & 1 & 0 & \cdots & 0 \\ 0 & 0 & 0 & 1 & \cdots & 1 & 1 & 1 & 1 & 0 & \cdots & 0 \\ \cdots & & & & & \cdots & & & \\ 0 & \cdots & & & 0 & 1 & 1 & \cdots & & 1 & 0 \\ 0 & 0 & \cdots & & & 0 & 1 & 1 & \cdots & & 1 \end{bmatrix} \begin{bmatrix} A_1 \\ A_2 \\ \cdot \\ \cdot \\ \cdot \\ \cdot \\ \\ \\ \\ \\ \\ A_{Na} \end{bmatrix} = \begin{bmatrix} Ea_1 \\ Ea_2 \\ \cdot \\ \cdot \\ \cdot \\ \\ \\ \\ \\ \\ \\ Ea_{Na} \end{bmatrix}$$

or $Qa \cdot [U] \cdot [A] = [Ea]$, where Qa is the magnitude of the heat source at point "A", [U] is the matrix of unit impulses, [A] is the matrix of impulse responses, and [Ea] is the matrix of temperature elevations.

If the magnitude Qa of the heat source and the temperature elevations from times $t_1$ through $t_{Na}$ are known, then the impulse responses $[A_i]$, i=1 to Na, can be determined. Likewise for a heat source at point "B" of strength Qb applied for duration $(Nb/2) \cdot \Delta t$, the temperature elevations Ebi for times $t_1$ through $t_{Nb}$ can be expressed by the following matrix equation $Qb \cdot [U] \cdot [B] = [Eb]$, where, Qb is the magnitude of the heat source at point "B", [U] is the matrix of unit impulses, [B] is the matrix of impulse responses, and [Eb] is the matrix of temperature elevations. Similarly, if the magnitude Qb of the heat sources and the temperature elevations from times $t_1$ through $t_{Nb}$ are known, then the impulse responses $[B_i]$, i=1 to Nb, can be found.

To characterize any given heat source "X" among those being considered, the total time duration $Nx \cdot \Delta t$ should be sufficiently long that for time $t > Nx \cdot \Delta t$, the magnitude of the impulse response is approximately zero, i.e., $xi \approx 0$ for $i > Nx$. For the purposes of the thermal model, let Nx be an even number chosen such that either $XNx-1 > 0$ and $Xi=0$ for $i > Nx-1$ or $XNx > 0$ and $Xi=0$ for $i > Nx$. In other words, Xi is truncated to zero for $i > Nx$. The interval $\Delta t$ corresponds to the "impulse" interval, a suitably short interval of time over which a heat source of unit strength acts. The interval $\Delta t$ should be small compared to the total duration over which the temperature elevations resulting from the applied heat source persist in the body of the electronic device.

For all heat sources of interest, let N be a number equal to the maximum of the individual interval counts Na, Nb, etc.: $N \geq \max\{Na, Nb, \ldots\}$. Hence for any given heat source, the impulse response at time ti where $i \leq N$ may be zero:

$A_i \geq 0$ for $1 \leq i \leq Na$, $A_i = 0$ for $i > Na$, and $Na \leq N$;
$B_i \geq 0$ for $1 \leq i \leq Nb$, $B_i = 0$ for $i > Nb$, and $Nb \leq N$;

and so on for all heat sources. Thus chosen, the upper limit N on the interval counts will be sufficiently large that the matrix of impulse responses for each and every heat source may be characterized with minimal loss due to truncation.

To characterize the impulse responses of the various heat sources in an electronic device, a series of procedures may be performed, based on the process described above. For each heat source "X" (="A", "B", etc.), the following procedure may be followed:

1) Allow the device to come to equilibrium temperature with its environment. The ambient temperature is the reference temperature: $T_{ref} = T_{amb}$.
2) Activate heat source "X" at constant strength Qx for a duration of $(N/2) \cdot \Delta t$, where N and $\Delta t$ have been chosen in the manner described above (i.e., $N \geq \max\{Na, Nb, \ldots\}$ and $\Delta t$ is a suitable impulse interval. Record the initial temperature at the temperature sensor at the time that the heat source is activated and the temperature at each succeeding time $t_i = i \cdot \Delta t$, i=1 to N/2.
3) At time $t = (N/2) \cdot \Delta t$, deactivate the heat source "X" and continue recording the sensor temperature at times $t_i = i \cdot \Delta t$, i=(N/2)+1 to N.
4) Calculate the temperature elevation at each time step:

$Ex_i = (Tx_i - T_{ref}), 0 \leq i \leq N$

5) Using matrix methods, determine the matrix of impulse temperature responses, [Xi]:

$Qx \cdot [U] \cdot [X] = [Ex]$ $[X] = (1/Qx) \cdot [U]-1 \cdot [Ex]$

6) Repeat the above steps for each heat source of interest.

During the procedure, the ambient environment of the electronic device should be held to conditions representative of the environment in which the device is expected to be used. For example, if the device will spend most of its time in still air at room temperature, then these conditions should be maintained. If the operating environment is expected to be drafty, then a suitable airflow should be imposed. Once the impulse response matrices for all of the heat sources have been determined, then the principle of superposition can be applied to determine the expected temperature response of the device to the influence of any combination of these sources acting at arbitrary strengths and for arbitrary durations. The above discussion considered heat sources with constant magnitude.

Consider now a sequence of heat impulses from source k having duration $\Delta t$ and variable magnitude $[Q_k]$ beginning at time $N \cdot \Delta t$ before the present:

$[Q_k] = [Q_{k,1} Q_{k,2} \ldots Q_{k,N-1} Q_{k,N}]$ where the magnitudes of the heat impulses are given by
$Q_{k,1}$ is the magnitude at time $t = -N \cdot \Delta t$
$Q_{k,2}$ is the magnitude at time $t = -(N-1) \cdot \Delta t$
$\ldots$
$Q_{k,N-1}$ is the magnitude at time $t = -2 \cdot \Delta t$
$Q_{k,N}$ is the magnitude at time $t = -1 \cdot \Delta t$.

The temperature elevation $E_k$ due to this sequence of impulses from source k is given by:

$$E_k = \sum_{i=1}^{N} Q_{k,i} \cdot X_{k \cdot N-i+1}$$

or $$E_k = \sum_{i=1}^{N} Q_{k \cdot N-i+1} \cdot X_{k \cdot i}$$

where $[X_k]=[X_{k,1} X_{k,2} \ldots X_{k,N-1} X_{k,N}]$ is the impulse temperature response for source k.

The total temperature elevation due to M sources is given by $$E_{total} = \sum_{k=1}^{M} E_k = \sum_{k=1}^{M} \sum_{i=1}^{N} Q_{k \cdot N-i+1} \cdot X_{k \cdot i}$$

Note that the effect of any temperature impulse prior to time $-N \cdot \Delta t$ is considered negligible and so no corresponding source terms are included in the calculations. This total temperature elevation due to the internal heat sources of the device may now be subtracted from the temperature sensor reading to yield a corrected temperature:

$$T_{corr} = T_{sensor} - E_{total}$$

The customary temperature estimation method may now be applied to this corrected temperature in order to obtain a prediction of the ambient temperature and, hence, the effective test strip reaction site temperature.

To implement the thermal model in a bG measurement device, the control for the device should know which components are being activated and at what strength and for how long. This information plus the reading of the temperature sensor mounted on the circuit board for the bG measurement circuitry is used to determine the temperature response to heat released by each of the heat generating components. Any number of these components may be characterized by the thermal model. The impulse response matrix for each component is stored with the temperature estimation algorithm and may be retrieved to calculate a temperature response whenever that component is activated.

The thermal model contains a number of operating parameters that need to be quantified. The maximum period of time that the temperature response due to an input of heat from any of the components is tracked is given by $N \cdot \Delta t$, where N is the total number of samples and $\Delta t$ is the sampling interval. From the standpoint of the algorithm, N is the total number of elements in the impulse temperature response matrix (dimension N×1) and $\Delta t$ is the impulse duration. For a handheld electronic device (e.g., the diabetes manager 2904), this maximum period is on the order of one to two hours. By that time, virtually all of any generated heat will have been dissipated to the environment of the device. The sampling interval $\Delta t$, which is also the assumed impulse duration, should be small enough to resolve the time-varying temperature response from a transient heat release with a sufficient degree of precision that reasonably accurate estimates of the individual and total temperature elevations can be calculated.

For a handheld electronic device such as the diabetes manager 2904, a suitable sampling interval might be on the order of several seconds to a few minutes. The exact choice depends on the nature of the heat sources and the degree of precision desired. A sampling interval of one minute appears to provide adequate results for the devices that have been tested. For a maximum tracking period of one hour, a one minute sampling period would yield N=60 samples, and hence 60 elements in the impulse temperature response matrices for the various components. As a further refinement of the thermal model, if the heat being released by a particular component varies during a given sampling period, then the reported strength of that source (which is known by the electronic control) can be adjusted to give a representative average over the interval.

Handheld Diabetes Management Device having a Database Management System

Referring now to FIG. 75, a person 2900 with diabetes and a healthcare professional 2902 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 2900 typically shares with the clinician 2902 a variety of patient data including blood glucose measurements, continuous glucose monitor data, amounts of insulin infused, amounts of food and beverages consumed, exercise schedules, and other lifestyle information. The clinician 2902 may obtain additional patient data that includes measurements of HbA1C, cholesterol levels, triglycerides, blood pressure, and weight of the patient 2900. The patient data can be recorded manually or electronically on a handheld diabetes management device 2904, a diabetes analysis software executed on a personal computer (PC) 2906, and/or a web-based diabetes analysis site (not shown). The clinician 2902 can analyze the patient data manually or electronically using the diabetes analysis software and/or the web-based diabetes analysis site. After analyzing the patient data and reviewing adherence of the patient 2900 to previously prescribed therapy, the clinician 2902 can decide whether to modify the therapy for the patient 2900.

Referring now to FIG. 76, the patient 2900 can use a continuous glucose monitor (CGM) 2910, an ambulatory durable insulin infusion pump 2912 or an ambulatory non-durable insulin infusion pump 2914 (collectively insulin pump 2912 or 2914), and the handheld diabetes management device 2904 (hereinafter the diabetes manager 2904). The CGM 2910 uses a subcutaneous sensor to sense and monitor the amount of glucose in the blood of the patient 2900 and communicates corresponding readings to the handheld diabetes management device 2904.

The diabetes manager 2904 performs various tasks including measuring and recording blood glucose levels, determining an amount of insulin to be administered to the patient 2900 via the insulin pump 2912 or 2914, receiving patient data via a user interface, archiving the patient data, etc. The diabetes manager 2904 periodically receives readings from the CGM 2910 indicating insulin level in the blood of the patient 2900. The diabetes manager 2904 transmits instructions to the insulin pump 2912 or 2914, which delivers insulin to the patient 2900. Insulin can be delivered in the form of a bolus dose, which raises the amount of insulin in the blood of the patient 2900 by a predetermined amount. Additionally, insulin can be delivered in a scheduled manner in the form of a basal dose, which maintains a predetermined insulin level in the blood of the patient 2900.

Referring now to FIG. 77, a diabetes management system 2930 used by the patient 2900 and the clinician 2902 includes one or more of the following devices: the diabetes manager 2904, the continuous glucose monitor (CGM) 2910, the insulin pump 2912 or 2914, a mobile device 2932, the diabetes analysis software on the PC 2906, and other healthcare devices 2934. The diabetes manager 2904 is configured as a system hub and communicates with the devices of the diabetes management system 2930. Alternatively, the insulin pump 2914 or the mobile device 2932 can serve as the system hub. Communication between the various devices in the diabetes management system 2930 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 2900 and clinician 2902 to exchange information.

The diabetes manager 2904 can receive blood glucose readings from one or more sources (e.g., from the CGM 2910). The CGM 2910 continuously measures the blood glucose level of the patient 2900. The CGM 2910 periodically communicates the blood glucose level to the diabetes manager 2904. The diabetes manager 2904 and the CGM 2910 communicate wirelessly using a proprietary Gazell wireless protocol developed by Nordic Semiconductor, Inc.

Additionally, the diabetes manager 2904 includes a blood glucose meter (BGM) and a port that communicates with the BGM (both not shown). The port can receive a blood glucose measurement strip 2936. The patient 2900 deposits a sample of blood or other bodily fluid on the blood glucose measurement strip 2936. The BGM analyzes the sample and measures the blood glucose level in the sample. The blood glucose level measured from the sample can be used to determine the amount of insulin to be administered to the patient 2900.

The diabetes manager 2904 communicates with the insulin pump 2912 or 2914. The insulin pump 2912 or 2914 can be configured to receive instructions from the diabetes manager 2904 to deliver a predetermined amount of insulin to the patient 2900. Additionally, the insulin pump 2912 or 2914 can receive other information including meal and/or exercise schedules of the patient 2900. The insulin pump 2912 or 2914 can determine the amount of insulin to administer based on the additional information.

The insulin pump 2912 or 2914 can also communicate data to the diabetes manager 2904. The data can include amounts of insulin delivered to the patient 2900, corresponding times of delivery, and pump status. The diabetes manager 2904 and the insulin pump 2912 or 2914 can communicate using a wireless communication protocol such as Bluetooth. Other wireless or wireline communication protocols can also be used.

In addition, the diabetes manager 2904 can communicate with other healthcare devices 2934. For example, the other healthcare devices 2934 can include a blood pressure meter, a weight scale, a pedometer, a fingertip pulse oximeter, a thermometer, etc. The other healthcare devices 2934 obtain and communicate personal health information of the patient 2900 to the diabetes manager 2904 through wireless, USB, or other interfaces. The other healthcare devices 2934 use communication protocols compliant with ISO/IEEE 11073 extended using guidelines from Continual® Health Alliance. The diabetes manager 2904 can communicate with the other healthcare devices 2934 using interfaces including Bluetooth, USB, etc. Further, the devices of the diabetes management system 2930 can communicate with each other via the diabetes manager 2904.

The diabetes manager 2904 can communicate with the PC 2906 using Bluetooth, USB, or other interfaces. A diabetes management software running on the PC 2906 includes an analyzer-configurator that stores configuration information of the devices of the diabetes management system 2930. The configurator has a database to store configuration information of the diabetes manager 2904 and the other devices. The configurator can communicate with users through standard web or computer screens in non-web applications. The configurator transmits user-approved configurations to the devices of the diabetes management system 2930. The analyzer retrieves data from the diabetes manager 2904, stores the data in a database, and outputs analysis results through standard web pages or computer screens in non-web based applications.

The diabetes manager 2904 can communicate with the mobile device 2932 using Bluetooth. The mobile device 2932 may include a cellular phone, a PDA, or a pager. The diabetes manager 2904 can send messages to an external network through the mobile device 2932. The mobile device 2932 can transmit messages to the external network based on requests received from the diabetes manager 2904.

Referring now to FIG. 82, the diabetes manager 2904 comprises a blood glucose measuring (BGM) module 3300, a communication module 3302, a user interface module 3304, user interfaces 3306, a processing module 3308, memory 3310, and a power module 3312. The user interface module 3304 and the processing module 3308 can be implemented by an application processing module 3309. The BGM module 3300 includes a blood glucose measuring engine that analyzes samples provided by the patient 2900 on the blood glucose measurement strip 2936 and that measures the amount of blood glucose in the samples. The communication module 3302 includes multiple radios that communicate with different devices of the diabetes management system 2930. The user interface module 3304 interfaces the diabetes manager 2904 to various user interfaces 3306 that the patient 2900 can use to interact with the diabetes manager 2904. For example, the user interfaces 3306 can include keys, switches, a display, a speaker, a microphone, a secure digital (SD) card port, a USB port, etc. (not shown).

The processing module 3308 processes data received from the BGM module 3300, the communication module 3302, and the user interface module 3304. The processing module 3308 uses memory 3310 for processing and storing data. The memory 3310 can include volatile and nonvolatile memory. The nonvolatile memory may be a solid-state memory, such as flash memory. The processing module 3308 outputs data to and receives data from the user interfaces 3306 via the user interface module 3304. The processing module 3308 outputs data to and receives data from the devices of the diabetes management system 2930 via the communication module 3302. The power module 3312 supplies power to the components of the diabetes manager 2904. The power module 3312 includes a rechargeable battery. The battery can be recharged using an adapter that plugs into a wall outlet. The battery can also be charged via the USB port of the diabetes manager 2904.

Figure 98:
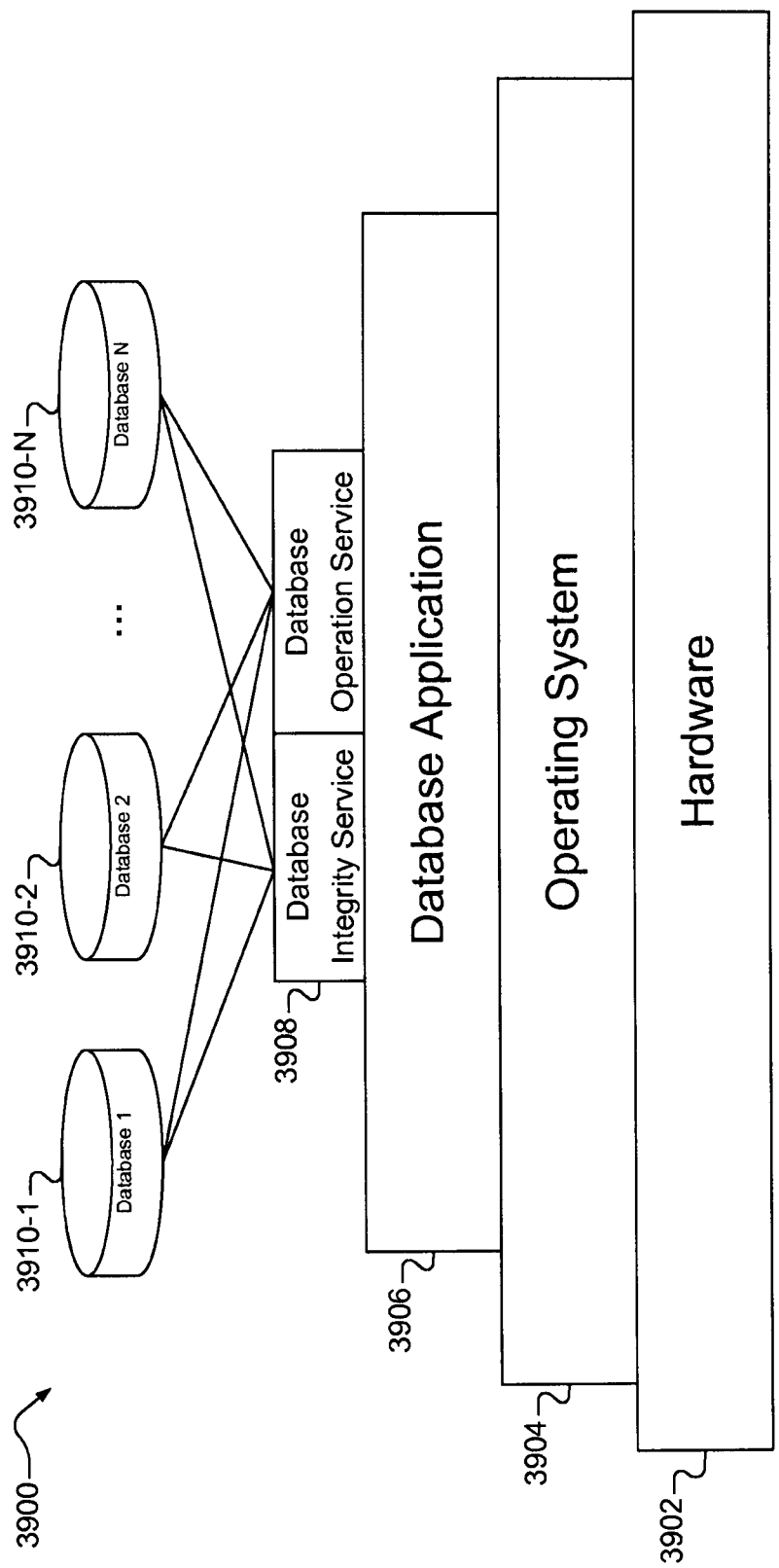
FIG. 98 shows a diagram of an exemplary hierarchy of a diabetes management device.

FIG. 98 shows an exemplary hierarchy 3900 of a data management system that is implemented on the diabetes manager 2904 (FIG. 75). A hardware level 3902 represents hardware components of the diabetes manager 2904. In an exemplary embodiment, the hardware components may include the components shown in FIG. 82. An operating system level 3904 represents the operating system (OS) running on the diabetes manager 2904. At the operating system level 3904, an OS is responsible for managing the hardware components of the diabetes manager and to support software applications running on the diabetes manager 2904. In an exemplary embodiment, the operating system of the diabetes manager can be Microsoft Windows CE®. It is envisioned, however, that another OS may be implemented at the OS level 3904.

The OS supports a data management system of the diabetes manager. As shown in FIGS. 76 and 77, the diabetes manager is configured to receive data from a plurality of different devices. For instance, the diabetes manager may receive data records from a bG reader, a CGM, and an insulin pump, all of which are stored in a system of databases stored, which reside on the memory of the diabetes manager. Thus, the next level in the exemplary hierarchy 3900 is a database application layer 3906. In an exemplary embodiment, the database application is Microsoft SQL CE®. It is envisioned, however, that other database applications may be implemented on the diabetes manager.

To support the database, a set of database services reside at the service level 3908 of the hierarchy. As will be discussed in greater detail below, the diabetes manager has a system of N databases 3910-1, 3910-2, ..., 3910-N. The database services can include a database integrity service, which verifies the integrity of one or more of the N databases, and a database operation service, which performs various operations on the database. Exemplary database operations include creating, deleting, updating, and indexing the various databases.

As discussed with respect to FIG. 82, a handheld diabetes manager 2904 may incorporate a non-volatile solid state memory, (e.g., a flash drive), as the primary storage device. A technical problem arises when a database is stored on a non-volatile solid state memory as opposed to hard disk memory. Namely, the probability that a record in the database will become corrupted, (i.e., the database will fail), increases when the database is stored on the non-volatile solid state memory. Moreover, as the frequency of updating and/or indexing the database increases, so does the probability that the database will fail. Given that the diabetes manager is used to assist a patient in his or her diabetes management, e.g., how much insulin to deliver to a patient, and the data used to support the diabetes management is stored in the databases, the risk associated with a database failure is magnified in this context, as opposed to risk associated with data in a mobile phone or mp3 player becoming corrupted. Thus, to reduce the risk that medically important data is not corrupted, the disclosed handheld diabetes manager includes a database management application that maintains a plurality of databases, wherein the databases are separated based upon (i) the frequency at which the database is updated and/or indexed and (ii) the criticality of the records stored therein.

For example, it is appreciated that the frequency at which CGM measurements are taken by the CGM, (e.g., every five minutes), can be much greater than the frequency at which a blood glucose measurement is obtained using the blood glucose reader, e.g., 4 or 5 times a day. Further, to enable a patient to better monitor his or her blood glucose between readings from the blood glucose reader, it is beneficial to store the CGM measurements in a database. As discussed, however, the CGM measurements are not used to make medical decisions, i.e., how much insulin to include in a bolus, while the blood glucose readings from the blood glucose reader are used to make medical decisions. Therefore, the blood glucose measurement records are more critical to the patient's diabetes management than the CGM records. To ensure that updating a database with a new CGM record does not cause the failure of the database storing the blood glucose measurement records, the CGM records are stored in a different database than the database storing the blood glucose measurement records.

As will be discussed, the database management application can be further configured to detect when a database has failed or a record stored therein has been corrupted.

Figure 99:
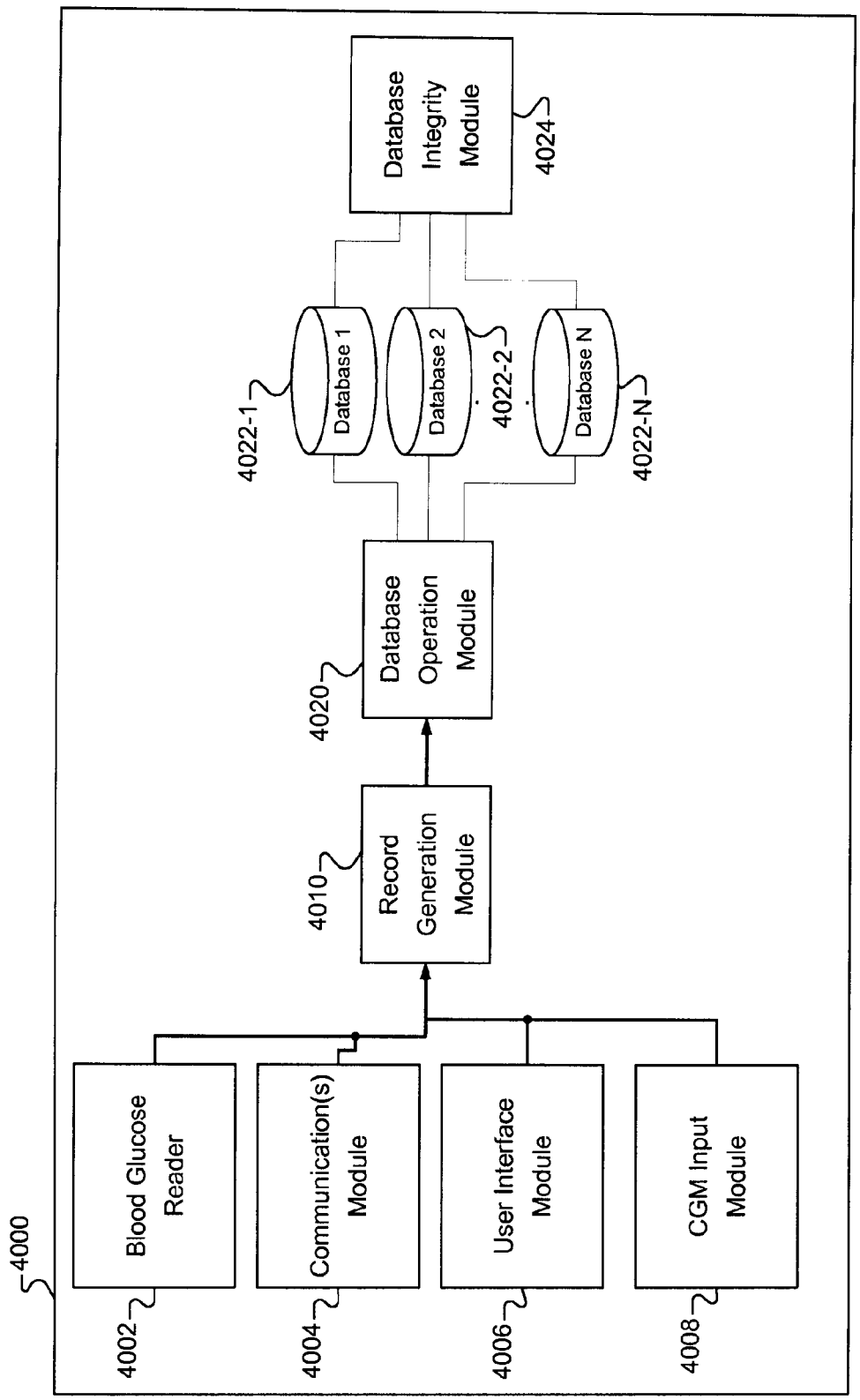
FIG. 99 shows a component level architecture of a database management system of a diabetes management device.

FIG. 99 illustrates exemplary components of a diabetes manager 4000 configured to solve the technical problem identified above. The diabetes manager 4000 includes a plurality of input modules. In an exemplary embodiment, the input modules of the diabetes manager 4000 may include but are not limited to a blood glucose reader 4002, one or more communications modules 4004, a user interface module 4006, and a CGM input module 4008. The various input modules can be configured to output data to a record generator 4010, that generates a new record for storage in at least one of a plurality of databases 4022-1, 4022-2, ... 4022-N. The new record will have a corresponding record type, e.g., a blood glucose measurement record or an error record. The new record is communicated to a database operation module 4020, which is configured to operate on the plurality of databases 4022-1-4022-N such that the database operation module 4020 updates one of the databases with the new record. A database integrity module 4024 analyzes the databases 4022-1-4022-N to ensure that the databases have not failed.

The diabetes manager 4000 includes a blood glucose reader 4002. The blood glucose reader 4002 receives a fluid sample from a patient and outputs a blood glucose measurement based on the fluid sample. For instance, the blood glucose reader 4002 can include a blood glucose measurement engine that receives a test strip containing a small amount of the patient's bodily fluid, e.g., a drop of blood, and that determines an amount of glucose in the blood therefrom. The blood glucose reader 4002 may be integrated into the housing of the diabetes manager such that the patient deposits the fluid sample on the strip and inserts the test strip into the blood glucose reader. The blood glucose reader 4002 outputs a blood glucose measurement which is used to generate a blood glucose measurement record. As will be discussed, the blood glucose measurement record is generated by the record generation module 4010 based on the blood glucose measurement and is communicated to the database operation module 4020.

The communication module(s) 604 can be any of the communication interfaces discussed above. An exemplary communication module may be a Bluetooth® receiver which is in wireless communication with an external device, e.g., an insulin pump. It is appreciated that the diabetes manager 4000 may include more than one communications modules 4004 depending on how many communications protocols are enabled on the device. In addition to supporting Bluetooth® communications, an exemplary communication module may support infra red (IR) communications, radio frequency (RF) communications, or any other wireless communications. Further, an exemplary communications module may support wireline communications, such as those received via a USB interface or a LAN interface. An exemplary communications module may receive data from the external device and metadata which provides information including but not limited to a time-stamp and/or a device identifier.

In an exemplary embodiment, the user interface 4006 is a touch screen adapted to receive a patient's input. The patient can use the user interface 4006 to enter patient data, such as meal information and personal information. While a touch screen is considered, it is appreciated that other user interfaces are contemplated. For example, a display and a small keyboard integrated on the diabetes manager 4000 can be used to enter patient data as well. The user interface 4006 receives user input and generates data indicating the same. The data is communicated to the record generation module 4010, which generates a new record based thereon.

The CGM input module 4008 is configured to receive CGM measurements from a CGM. In a preferred embodiment, the CGM input module 4008 utilizes a proprietary Gazell wireless protocol developed by Nordic Semiconductor, Inc. It is appreciated that in other embodiments, the CGM input module 4008 may be a wireless interface such as Bluetooth®, IR, or RF, or a wireline interface. The CGM measurements are received by the CGM input module 4008 and communicated to the record generation module 4010. It is appreciated that some CGMs may not generate metadata and may only provide CGM measurements. In this scenario, the CGM input module 4008 may generate metadata tags by applying a timestamp or other metadata to the raw CGM measurements.

The record generation module 4010 is configured to generate records for storage in the N databases 4022-1-4022-N. Based on the type of data received, the record generation module 4010 can generate a record having a record type. Depending on the record type being generated, the record generation module 4010 can fill in different fields of the record with data received from one or more of the input modules 4002-4008. For instance, if a new blood glucose measurement is received from the blood glucose reader 4002, the record generation module 4010 can generate a blood glucose measurement record. A blood glucose measurement record, however, may include meal information such as an amount of carbohydrates consumed in a recent meal or an amount of carbohydrates to be consumed in an upcoming meal, which is received via the user interface 4006.

Furthermore, the record generation module 4010 can also include a time stamp and a record identifier in the new record. Additionally, the record generation module 4010 calculates a cyclic redundancy check (CRC) and/or a checksum using predetermined functions. The calculated CRC and/or checksum values is/are inserted into a newly generated record.

An exemplary record entry is provided herein:

```
New Blood Glucose Measurement Record{
    Record_ID;
    Year_of_Measurement;
    Month_of_Measurement;
    Day_of_Measurement;
    Time_of_Measurement;
    bG_measurement;
    ...
    Amount_of_carbs_before_measurement;
    Food_item;
    ...
    CRC value;
}
```

It is appreciated that a separate record generation module 4010 may be integrated into each input module 4002-4008 such that when data is received from a data source, the respective input module generates the new record.

The database operation module 4020 is configured to perform database operations on the N databases 4022-1-4022-N. Database operations include but are not limited to creating, deleting, and/or updating a database. Updating a database includes inserting a new record generated by the record generation module 4010 into the appropriate table of an appropriate database. The database operations module 4020 can also perform indexing of the databases. Each database of the N databases 4022-1-4022-N may have a corresponding index. The size of the index for a particular database can be adjusted based on how frequently the database is searched or read from. The database operation module 4020 can be further configured to perform operations such as reads and searches.

The N databases 4022-1-4022-N are now described in greater detail. The N databases 4022-1-4022-N have a different frequency ranges associated thereto. A new record of a particular record type received from one of the blood glucose reader, the user interface, and the communication interface is stored in a particular database of the N databases based on the frequency range of the particular database and the frequency of the particular record type. Each database includes at least one table and at least one index for the database. A table is comprised of a set of records of the same record type. For instance, each time a patient's blood glucose levels are measured by the blood glucose reader, a blood glucose measurement can be stored in a blood glucose measurement table. An index is a database table attribute which can be used to decrease search times. Indexes can be created for any field within the table, primarily for fields which searches are frequently performed.

FIG. 100 illustrates exemplary tables that comprise the N databases. Table 4110 is an exemplary table for storing diabetes manager results. Included in the table are columns or fields for, inter alia, for: i) time stamp information include a year, month, day, hour, minute, and second of a result, ii) blood glucose measurement test results including a test flag, a blood glucose reading, and a record count, iii) meal information, iv) bolus information, and v) a cyclic redundancy check (CRC) value. Table 4120 stores error records relating to operational errors that may have been detected in the system of devices. Table 4130 stores records relating to the results of the CGM. Table 4140 stores pump records relating to the insulin pump in communication with the diabetes manager. Table 4150 stores bolus correction records relating to the bolus advice correction. Table 4160 stores meal records relating to a patient's food intake.

Each record entry can include a cyclic redundancy check (CRC) value. As will be discussed below, the CRC value is used to verify the integrity of the record, the table, or the database. Furthermore, some tables, such as table 4140, may include a checksum value as additional verification that the record is uncorrupted.

It is appreciated that the foregoing tables, and the contents stored therein, are exemplary and are only meant to demonstrate the types of data that may be stored in a table. It is noted that one or more of the tables are relational to one another. Furthermore, the relations may extend from a first database 4022-I to a second database 4022-M. For instance, the blood glucose measurement field in table 4110 may be related to a CGM measurement field in another table via the respective time stamp fields in the tables.

Referring to FIGS. 99 and 100 in combination, the N databases 4022-1-4022-N are separated based upon a frequency range and criticality of the records stored therein. Using the exemplary tables provided in FIG. 100, an example of the division of the databases 4022-1-4022-N is provided, where N is four. Database 4022-1 stores records that are recorded more than 25 times/day and are critical to a patient's diabetes management. Database 4022-2 stores records that are recorded more than 25 times/day but are not critical to the patient's diabetes management. Database 4022-3 stores records that are recorded 25 times/day or less and are critical to a patient's diabetes management. Database 4022-4 stores records that are recorded 25 times/day or less and are not critical to a patient's diabetes management.

As mentioned table 4130 stores the CGM records, which may be received every 5 minutes or 480 records/day. The CGM records can be used to provide a graphical display to the patient on a display associated with the diabetes manager 4000. The CGM records are not used, however, to make medical decisions such as how much insulin to deliver in the bolus. Thus, the CGM records are considered to be of lower criticality. In this example, table 4130 is stored in database 4022-2 because CGM records are received at a frequency which is greater than 25 times/day and are not critical to the patient's diabetes management. Thus, when a new CGM record is received via the CGM input module 4008, the database operation module 4020 updates database 4022-2 by adding the new CGM record to table 4130.

An insulin pump may deliver a bolus to the patient between 3 and 5 times a day. When a bolus is delivered, data relating to whether the bolus was successfully delivered may be received via the communications module 4004. Based thereon, a pump record may be generated. As pump records are critical to a patient's treatment and new pump records are received less than 25 times/day, table 4140 is stored in database 4022-3. When a new pump record is received via the communications module 4004, the database operation module 4020 updates database 4022-3 by adding the new pump record to table 4140.

Referring back to FIG. 99, the database application of the exemplary diabetes manager 4000 includes an integrity check module that performs an integrity check on a critical database of the N databases to determine if a critical record in the critical database has been corrupted. The database application is configured to ensure that each database have the following properties: atomicity, consistency, isolation, durability (ACID). In an exemplary embodiment, Microsoft Sequel CE® is configured to ensure that these properties are adhered to. As mentioned, however, the databases reside on a non-volatile solid-state memory. Thus, in the operational lifetime of the diabetes manager 4000, a portion of the memory may fail. In these instances, a failure may be as simple as a single bit value being flipped. To ensure that a record has not been corrupted, the integrity check module 4024 performs integrity checks on the records in each database by determining if a critical record has been corrupted by calculating a check value based on the critical record and comparing it to a stored check value that was previously calculated based on the critical record at a time that the critical record was stored in the critical database. As mentioned, the record generation module 4010 inserts at least one of a CRC value and a checksum value in a new record. The CRC value or the checksum is calculated by a predetermined function that receives values indicative of the data entered into the fields of the record. The integrity check module 4024 use the same formula and the same fields to generate a CRC check value or a checksum check value as the record generation module 4010 uses to generate the CRC value and or the checksum value. If the CRC check value or checksum check value matches the CRC value or the checksum value stored in the record, then the integrity module 4024 checks the next record. If, however, the check value does not match the stored value, the integrity check module 4024 will deem the record corrupted. A bit flag in the record may be switched to indicate that the record has been corrupted. A corrupted record can be removed from its respective database or the database itself can be deleted and rebuilt. Furthermore, in some embodiments where storage space and computational resources are not primary concerns, database mirroring may be performed such that a failed database can be recreated using the mirror copy of the database.

In an aspect of the disclosure, a handheld diabetes management device having a database management system is disclosed. The handheld diabetes management device includes a blood glucose reader that receives a fluid sample from a patient and that outputs a blood glucose measurement that is used to generate a first record having a first record type, a user interface that receives input from the patient via an input device associated with the handheld diabetes management device and that outputs patient data that is used to generate a second record having a second record type, a communication interface that receives data from an external device and that outputs device data that is used to generate a third record having a third record type. The first record type, the second record type, and the third record type are of a plurality of different record types. Each record type of the plurality of different record types has a corresponding frequency. The frequency of a record type indicates an average amount of records having the record type received during a predetermined period of time; N databases each having a different frequency range associated thereto. A new record of a particular record type based on data received from one of the blood glucose reader, the user interface, and the communication interface is stored in a particular database of the N databases based on the frequency range of the particular database and the frequency of the particular record type, where N is an integer greater than 1. The handheld diabetes management device further includes a database operation module that performs database operations on the N databases.

In another feature, the diabetes management device further includes a database integrity module that performs an integrity check on a critical database of the N databases to determine if a critical record in the critical database has been corrupted.

In another feature, the database integrity module determines if the critical record has been corrupted by calculating a check value based on the critical record and comparing it to a stored check value that was previously calculated based on the critical record at a time when the critical record was stored in the critical database. A predetermined function is used to calculate the check value and the stored check value.

In another feature, the database integrity module further includes a continuous blood glucose input module that receives a blood glucose reading from a continuous blood glucose meter and outputs a continuous blood glucose measurement used to generate a fourth record of a fourth record type. The fourth record is stored in a different database of the N databases than a database storing the first records.

In another feature, each of the N databases includes an index and at least one table. A table stores records of a corresponding record type.

In another feature, at least a first record in a first table of a first database has a relationship to a second record in a second table of a second database.

In another feature, the relationship between the first record and the second record is based on a time stamp of both the first record and the second record.

In another feature, the diabetes management device further includes a record generation module that receives data and that generates the new record having the particular record type based on the received data.

In another aspect of the disclosure, a handheld diabetes management device having a database management system is disclosed. The handheld diabetes management devices includes a plurality of input modules, the plurality of modules including i) a blood glucose reader that receives a fluid sample from a patient and that outputs a blood glucose measurement that is used to generate a first record having a first record type; ii) a user interface that receives input from the patient via an input device associated with the handheld diabetes management device and that outputs patient data that is used to generate a second record having a second record type; iii) a communication interface that receives data from an external device and that outputs device data that is used to generate a third record having a third record type; and iv) a continuous blood glucose input module that receives a blood glucose reading from a continuous blood glucose meter and that outputs a continuous blood glucose measurements used to generate a fourth record of a fourth record type. The first record type, the second record type, the third record type, and the fourth record type are of a plurality of different record types. Each record type of the plurality of different record types has a corresponding frequency. The frequency of a record type indicates an average amount of records having the record type received during a predetermined period of time. The diabetes management device further includes a record generation module that receives data from one or more of the input modules and that generates a new record of a particular record type based on the received data; N databases each having a different frequency range associated thereto, A new record is stored in a particular database of the N databases based on the frequency range of the particular database and the frequency of the particular record type, where N is an integer greater than 1. The diabetes management device further includes a database operation module that performs database operations on the N databases.

In another feature, the diabetes management device further includes a database integrity module that performs an integrity check on a critical database of the N databases to determine if a critical record in the critical database has been corrupted.

In another feature, the database integrity module determines if the critical record has been corrupted by calculating a check value based on the critical record and comparing it to a stored check value that was previously calculated based on the critical record at a time when the critical record was stored in the critical database. A predetermined function is used to calculate the check value and the stored check value.

In another feature, each of the N databases includes an index and at least one table. A table stores records of a corresponding record type.

In another feature, at least a first record in a first table of a first database has a relationship to a second record in a second table of a second database.

In another feature, the relationship between the first record and the second record is based on a time stamp of both the first record and the second record.

In another feature, the first records are stored in a first database and the fourth records are stored in a second database, whereby if the second database fails the first records are preserved.

Blood Glucose Test Instrument Kit having Modular Component Parts

Referring now to FIG. 75, a person 2900 with diabetes and a healthcare professional 2902 are shown in a clinical environment. Persons with diabetes include persons with metabolic syndrome, pre-diabetes, type 1 diabetes, type 2 diabetes, and gestational diabetes and are collectively referred to as a patient. Healthcare providers for diabetes are diverse and include nurses, nurse practitioners, physicians, and endocrinologists and are collectively referred to as a clinician.

During a healthcare consultation, the patient 2900 typically shares with the clinician 2902 a variety of patient data including blood glucose measurements, continuous glucose monitor data, amounts of insulin infused, amounts of food and beverages consumed, exercise schedules, and other lifestyle information. The clinician 2902 may obtain additional patient data that includes measurements of HbA1C, cholesterol levels, triglycerides, blood pressure, and weight of the patient 2900. The patient data can be recorded manually or electronically on a handheld diabetes management device 2904, a diabetes analysis software executed on a personal computer (PC) 2906, and/or a web-based diabetes analysis site (not shown). The clinician 2902 can analyze the patient data manually or electronically using the diabetes analysis software and/or the web-based diabetes analysis site. After analyzing the patient data and reviewing adherence of the patient 2900 to previously prescribed therapy, the clinician 2902 can decide whether to modify the therapy for the patient 2900.

Referring now to FIG. 76, the patient 2900 can use a continuous glucose monitor (CGM) 2910, an ambulatory durable insulin infusion pump 2912 or an ambulatory non-durable insulin infusion pump 2914 (collectively insulin pump 2912 or 2914), and the handheld diabetes management device 2904 (hereinafter the diabetes manager 2904). The CGM 2910 uses a subcutaneous sensor to sense and monitor the amount of glucose in the interstitial fluid of the patient 2900 and communicates corresponding data to the handheld diabetes management device 2904.

The diabetes manager 2904 performs various tasks including measuring and recording blood glucose levels, determining an amount of insulin to be administered to the patient 2900 via the insulin pump 2912 or 2914, receiving patient data via a user interface, archiving the patient data, etc. The diabetes manager 2904 periodically receives data from the CGM 2910 from which glucose levels of the patient 2900 are computed. The diabetes manager 2904 transmits instructions to the insulin pump 2912 or 2914, which delivers insulin to the patient 2900. Insulin can be delivered in the form of a bolus dose, which raises the amount of insulin delivered to the patient 2900 by a predetermined amount. Additionally, insulin can be delivered in a scheduled manner in the form of a basal dose, which maintains a predetermined insulin dose to the patient 2900.

Referring now to FIG. 77, a diabetes management system 2930 used by the patient 2900 and the clinician 2902 includes one or more of the following devices: the diabetes manager 2904, the continuous glucose monitor (CGM) 2910, the insulin pump 2912 or 2914, a mobile device 2932, the diabetes analysis software on the PC 2906, and other healthcare devices 2934. The diabetes manager 2904 is configured as a system hub and communicates with the devices of the diabetes management system 2930. Alternatively, the insulin pump 2914 or the mobile device 2932 can serve as components of the system hub. Communication between the various devices in the diabetes management system 2930 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 2900 and clinician 2902 to exchange information.

The diabetes manager 2904 can receive glucose readings from one or more sources (e.g., from the CGM 2910). The CGM 2910 continuously measures the glucose level of the patient 2900. The CGM 2910 periodically communicates the glucose level to the diabetes manager 2904. The diabetes manager 2904 and the CGM 2910 communicate wirelessly using a proprietary Gazell wireless protocol developed by Nordic Semiconductor, Inc.

Additionally, the diabetes manager 2904 includes a blood glucose meter (BGM) and a port that communicates with the BGM (both not shown). The port can receive a blood glucose measurement strip 2936. The patient 2900 deposits a sample of blood on the blood glucose measurement strip 2936. The BGM analyzes the sample and measures the blood glucose level in the sample. The blood glucose level measured from the sample and/or the blood glucose level read by the CGM 2910 can be used to determine the amount of insulin to be administered to the patient 2900.

The diabetes manager 2904 communicates with the insulin pump 2912 or 2914. The insulin pump 2912 or 2914 can be configured to receive instructions from the diabetes manager 2904 to deliver a predetermined amount of insulin to the patient 2900. Additionally, the insulin pump 2912 or 2914 can receive other information including meal and/or exercise schedules of the patient 2900. The insulin pump 2912 or 2914 can determine the amount of insulin to administer based on the additional information.

The insulin pump 2912 or 2914 can also communicate data to the diabetes manager 2904. The data can include amounts of insulin delivered to the patient 2900, corresponding times of delivery, and pump status. The diabetes manager 2904 and the insulin pump 2912 or 2914 can communicate using a wireless communication protocol such as Bluetooth. Other wireless or wireline communication protocols can also be used.

In addition, the diabetes manager 2904 can communicate with other healthcare devices 2934. For example, the other healthcare devices 2934 can include a blood pressure meter, a weight scale, a pedometer, a fingertip pulse oximeter, a thermometer, etc. The other healthcare devices 2934 obtain and communicate personal health information of the patient 2900 to the diabetes manager 2904 through wireless, USB, or other interfaces. The other healthcare devices 2934 use communication protocols compliant with ISO/IEEE 11073 extended using guidelines from Continual® Health Alliance. The diabetes manager 2904 can communicate with the other healthcare devices 2934 using interfaces including Bluetooth, USB, etc. Further, the devices of the diabetes management system 2930 can communicate with each other via the diabetes manager 2904.

The diabetes manager 2904 can communicate with the PC 2906 using Bluetooth, USB, or other interfaces. A diabetes management software running on the PC 2906 includes an analyzer-configurator that stores configuration information of the devices of the diabetes management system 2930. The configurator has a database to store configuration information of the diabetes manager 2904 and the other devices. The configurator can communicate with users through standard web or computer screens in non-web applications. The configurator transmits user-approved configurations to the devices of the diabetes management system 2930. The analyzer retrieves data from the diabetes manager 2904, stores the data in a database, and outputs analysis results through standard web pages or computer screens in non-web based applications.

The diabetes manager 2904 can communicate with the mobile device 2932 using Bluetooth. The mobile device 2932 may include a cellular phone, a PDA, or a pager. The diabetes manager 2904 can send messages to an external network through the mobile device 2932. The mobile device 2932 can transmit messages to the external network based on requests received from the diabetes manager 2904.

Referring now to FIG. 82, the diabetes manager 2904 comprises a blood glucose measuring (BGM) module 3300, a communication module 3302, a user interface module 3304, user interfaces 3306, a processing module 3308, memory 3310, and a power module 3312. The user interface module 3304 and the processing module 3308 can be implemented by an application processing module 3309. The BGM module 3300 includes a blood glucose measuring engine that analyzes samples provided by the patient 2900 on the blood glucose measurement strip 2936 and that measures the amount of blood glucose in the samples. The communication module 3302 includes multiple radios that communicate with different devices of the diabetes management system 2930. The user interface module 3304 interfaces the diabetes manager 2904 to various user interfaces 3306 that the patient 2900 can use to interact with the diabetes manager 2904. For example, the user interfaces 3306 can include keys, switches, a display, a speaker, a microphone, a secure digital (SD) card port, a USB port, etc. (not shown).

The processing module 3308 processes data received from the BGM module 3300, the communication module 3302, and the user interface module 3304. The processing module 3308 uses memory 3310 for processing and storing data. The memory 3310 can include volatile and nonvolatile memory. The nonvolatile memory may be a solid-state memory, such as flash memory. The processing module 3308 outputs data to and receives data from the user interfaces 3306 via the user interface module 3304. The processing module 3308 outputs data to and receives data from the devices of the diabetes management system 2930 via the communication module 3302. The power module 3312 supplies power to the components of the diabetes manager 2904. The power module 3312 includes a rechargeable battery. The battery can be recharged using an adapter that plugs into a wall outlet. The battery can also be charged via the USB port of the diabetes manager 2904.

Figure 101:
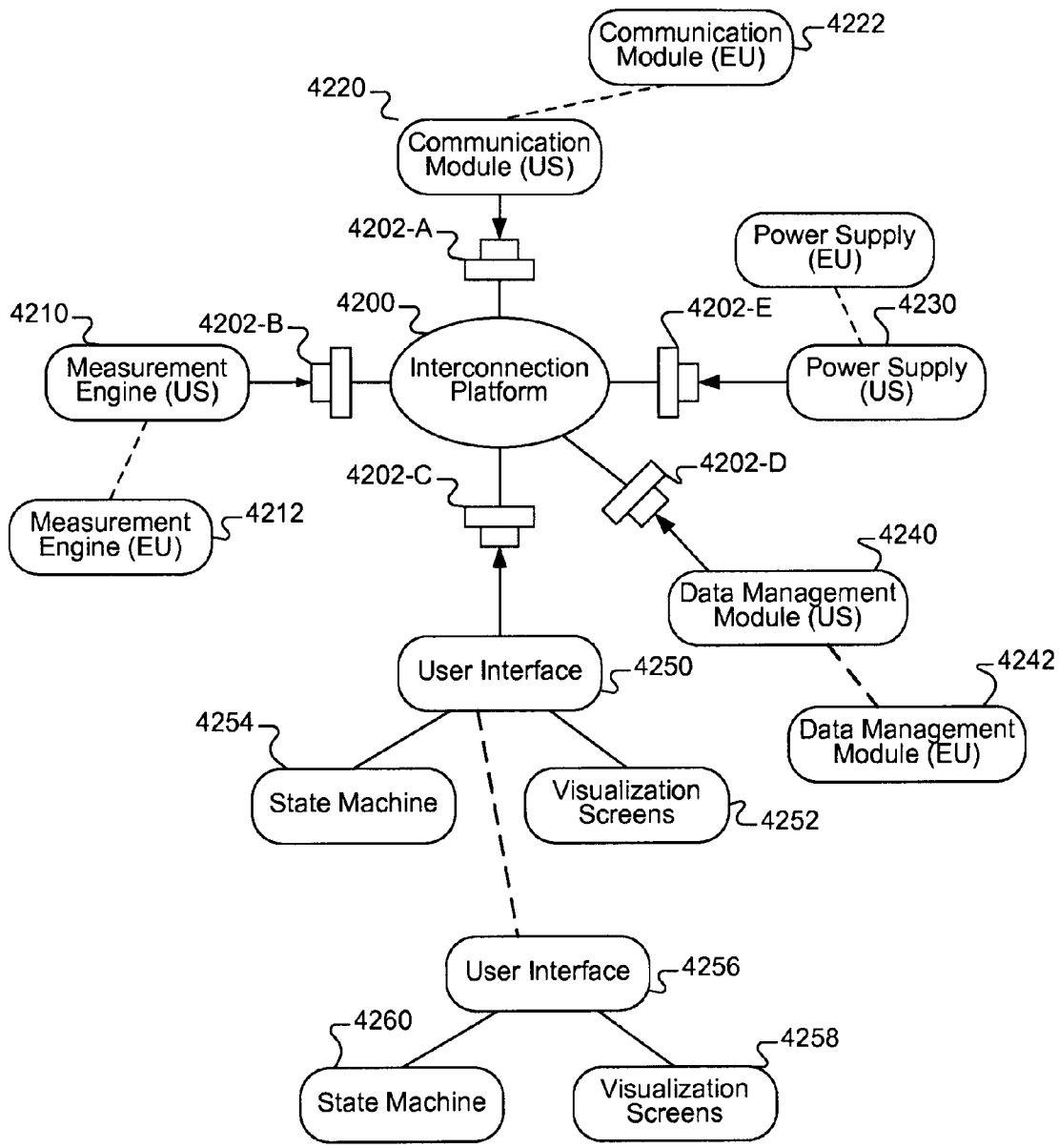
FIG. 101 shows a diagram of a modularized platform of a handheld diabetes manager.

FIG. 101 illustrates a platform that allows for modularization of the components of the diabetes manager. The processing module 3308 (FIG. 82) includes an interconnection platform 4200. The interconnection platform 4200 is adapted to connect to a collection of interoperable modules, each of the modules having an interface adapted for connection to the interconnection platform 4200, such that a first set of modules and a second set of modules are able to interface with the processing module 3308. The inter connection platform is adapted to fit within a portable housing that supports at least one display device. The first set of modules includes a measurement engine 4210, a communication module 4220, a power supply 4230, a data management module 4240, and a user interface module 4250, which are configured to electrically and physically couple to the interconnection platform 4200 via an interface 4202-A-4202-E, e.g. pins adapted to couple to the modules. In this example, the modules that are connected to the interconnection platform 4200 adhere to the standards, practices, and/or regulations of a first jurisdiction, e.g. the United States. The interface is standardized so as to receive a second set of components that comply with the standards, practices, and/or regulations of a second jurisdiction, e.g. the European Union. The second set of modules includes a second measurement engine 4212, a second communication module 4222, a second power supply 4232, the data management module 4240, and a second user interface module 4256. The modularity afforded by the interconnection platform reduces development time and cost by providing a shared platform that can support different types of components, such as different types of measurement engines.

Due to practices of a region or country, some of the modules will have different designs or architectures. For example, regulations regarding radio communications in two different jurisdictions may require that the antennas on a communication module transmit at different frequencies. Thus, the first communication module 4220 transmits at a first frequency or according to a first protocol and the second communication module 4222 transmits at a second frequency or according to a second protocol. To accomplish modularity, however, the interconnection platform 4200 is adapted to physically couple to both communication modules 4220 and 4222, via interface 4202-A. Furthermore, the communication between the interconnection platform 4200 and the communication modules 4220 and 4222, or any later developed communication modules, are standardized so as not to require modifications to be made to the physical interface 4202-A of the interconnection platform 4200.

Similarly, the interconnection platform 4200 is adapted to connect to plurality of different measurement engine modules 4210 and 4212, each measurement engine module having an input port to receive a blood sample carrier and producing blood test data. For instance, the first measurement engine module 4210 receives a test strip as a blood sample carrier and produces blood test data based on electrochemical sensing performed on the test strip. The second measurement engine module 4212 receives a blood sample carrier and produces blood test data based on optical sensing performed on the blood sample carrier. In general, a measurement engine modules 4210 or 4212, is configured to receive, via the interface 4202-B, a command from the interconnection platform 4200 to perform a blood glucose test. The measurement engine modules 4210 and 4212 are configured to respond to the interconnection platform 4200 with, for example, a status of the blood glucose test, the results of the blood glucose test, or feedback such as: what code key is used, when the measurement engine is ready for a blood strip carrier to be inserted, when a sample should be applied to the blood sample carrier. The process of a blood glucose test is described in greater detail below.

The interconnection platform 4200 is further adapted to connect to at least one user interface module 4250 adapted to couple to the display device and containing test logic for implementing at least one structured blood glucose test protocol. In this embodiment, the user interface module includes a visualization module 4252 that performs the display functionality of the user interface module and a state machine 4254, which contains the test logic for implementing the at least one structured blood glucose test protocol. The visualization module 4252 provides the screens that can be displayed to a user during a blood glucose test for the measurement engine module 4210. The state machine implements the test logic for implementing the blood glucose test protocol for the first measurement engine module 4210. When the second measurement engine module 4212 is used in the diabetes manager, however, the second user interface module 4256 can be connected to interface 4202-C the interconnection platform 4200, as a different blood glucose test protocol may be required, which would require a different state machine 4258 and a different visualization module 4252.

The interconnection platform 4200 is further adapted to connect to at least one data management module 4240 for storing data based upon said blood test data. The data management module 4240 receives the blood test data and stores the blood test data in a data store integrated into the diabetes manager. The data management module 4240 is connected to the interconnection platform 4200 by interface 4202-D. It is appreciated that communication between the data management module 4240 and the interconnection platform is achieved via interface 4202-D.

The interconnection platform 4200 is further adapted to connect to connect to at least one power supply module 4230 via interface 4202-E. The power supply module 4230 or 4232 is adapted, when connected to the interconnection platform, to provide operating power to other modules that are connected to said interconnection platform. It is noted, that based on the type of measurement engine module 4210 or 4212, the amount of power that is necessary to power the measurement engine module 4210 or 4212 can differ. Thus, if the first measurement engine module 4210 is used, then the first power supply module 4230 is connected to the interconnection platform 4200. If the second measurement engine module 4212 is used, then the second power supply module 4232 is connected to the interconnection platform 4200.

As mentioned, the interfaces 4202-A-4202-E are comprised of a series of interface pins. The pins communicate signals sent from one of the modules to the interconnection platform 4200 and from the interconnection platform 4200 to the intended module. Exemplary signals that are communicated to the measurement engine module 4210 through interface 4202-B include a power signal providing power to the interconnection platform 4200, a reset signal requesting that a module reset, an event signal indicating that an event of interest has occurred, a ready signal indicating that measurement engine module 4210 is ready to respond to requests, and an event interrupt signal requesting attention from the processing module 3308. It is appreciated that similar signals may be transmitted via interfaces 4202-A, 4202-C, 4202-D, and 4202-E.

A handheld blood glucose test instrument is assembled by the interconnection to the interconnection platform 4200 of at least one measurement engine module 4210, at least one user interface module 4250, and at least one power supply 4230 module and further by the optional interconnection to the interconnection platform of at least one data management module 4240, and by the optional interconnection to the interconnection platform 4200 of at least one communication module 4220. It is appreciated that the handheld glucose test instrument is integrated into the diabetes manager.

Once the various components are interconnected, the handheld blood glucose test instrument is realized. A patient can interact with the user interface module 4250 and the measurement engine module 4210 to obtain a blood glucose test measurement. As mentioned, the user interface module 4250 has a state machine 4254 and visualization screens 4252 associated therewith. The state machine 4254 maintains the state of the measurement engine 4210, such that when a patient's blood glucose is to be tested, the state machine 4254 provides test logic for implementing at least one blood glucose test protocol.

Figure 102:
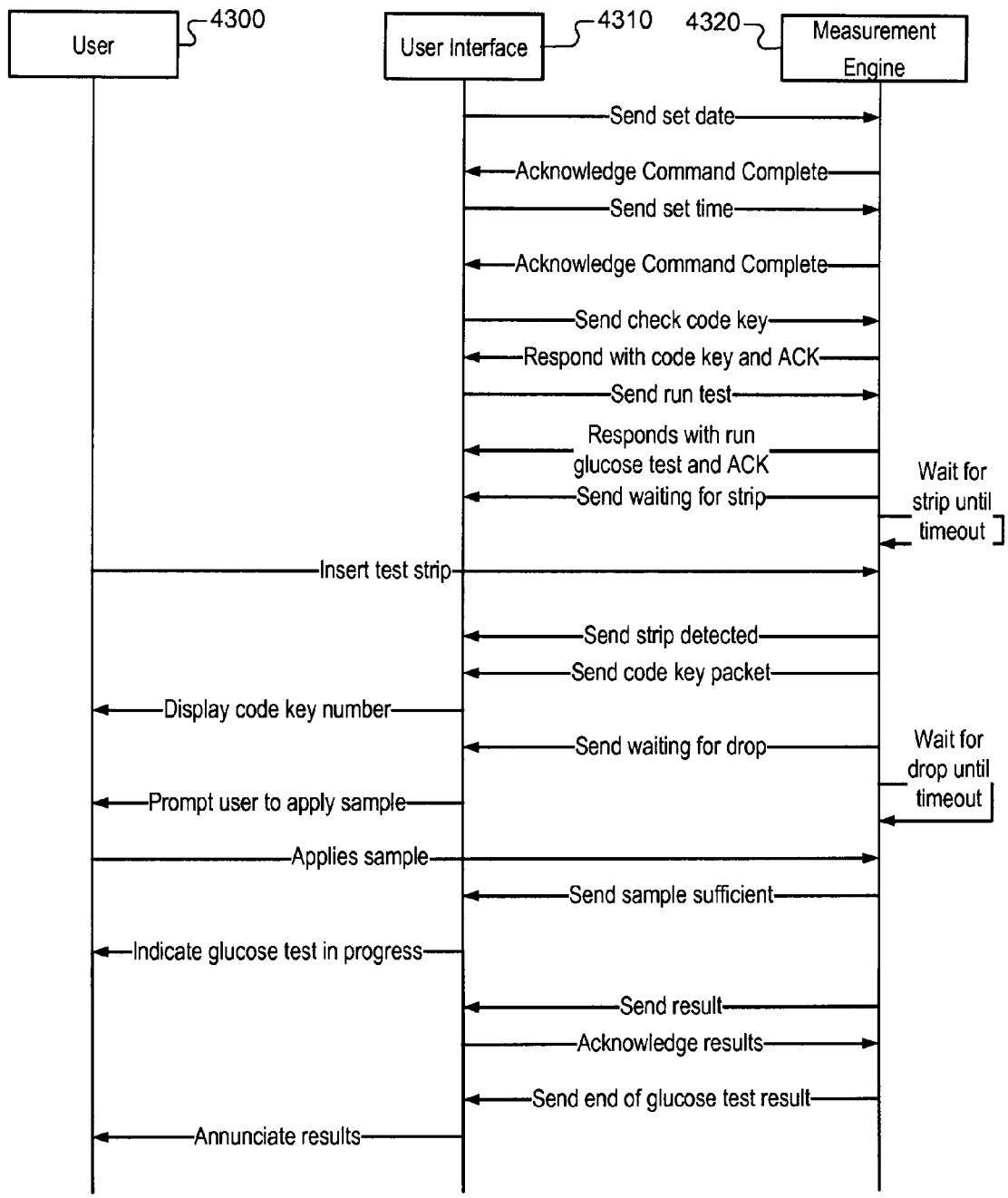
FIG. 102 shows a sequence diagram of a blood glucose test performed according to a blood glucose test protocol.

FIG. 102 illustrates a sequence diagram of a blood glucose test being performed according to an exemplary test protocol. The interconnection platform 4310 facilitates interaction between a patient 4300 and a measurement engine module 4320. In this example, the measurement engine module 4320 utilizes test strips as the blood sample carrier. Initially, upon removing the measurement engine module 4320 from an OFF state or a SLEEP state, the interconnection platform 4310 will transmit a set date command to the measurement engine module 4320, thereby instructing the measurement engine module 4320 to set a valid date. The measurement engine module 4320 sets its internal date and responds with an acknowledgment (ACK) indicating that the valid date has been set. In general, the measurement engine module 4320 utilizes ACKs to inform the interconnection platform 4310 that a command was received and performed. Upon receiving the ACK from the measurement engine module 4320, the interconnection platform 4310 sends a request to set the time. The measurement engine module 4320 sets a valid time and transmits an ACK to the interconnection platform 4200. At this juncture, a valid date and time have been sent and the management engine can begin preparing to execute a blood glucose test.

Before the blood glucose test can be executed, the interconnection platform 4310 executes a series of commands to verify that a code key provided to the measurement engine module 4320 is valid and available. The code key information is downloaded to the measurement engine module 4320 prior to the execution of the blood glucose test. A code key is used by the measurement engine 4320 to calibrate the test strips to the measurement engine module 4320. The code key can be embedded on a chip that is inserted into a port of the measurement engine module 4320 or can be entered manually by the user, via the user interface module. The interconnection platform 4310 sends a request to the measurement engine module 4320 to determine if a code key has been provided to the measurement engine module 4320 and, if so, whether the code key is valid. If the code key is valid, the measurement engine module 4320 responds with the code key status and an ACK. If no valid code is available or found, the measurement engine module 4320 will send a negative acknowledgement (NACK) to the interconnection platform, indicating an error. Recovery from test failures is discussed in greater detail below.

Once the ACK indicating a valid code key is received, the interconnection platform 4310 initiates a blood glucose test by sending a run test command to the measurement engine module 4320. The measurement engine module 4320 responds with an ACK once the measurement engine module 4320 is ready to execute a glucose test. The measurement engine module 4320 then sends a signal indicating that it is waiting for a strip to be inserted into the measurement engine module 4320. The measurement engine module 4320 then waits for the user to enter a strip. The interconnection platform 4310 then displays, via the user interface module, a screen to the user prompting the user to insert a strip. If a strip is not inserted within a timeout period, the blood glucose test is aborted.

Once a strip is detected in the measurement engine module 4320, the measurement engine module 4320 transmits a signal indicating that a strip has been detected to the interconnection platform 4310. The signal can be a bit string of predetermined length that indicates the current status of the strip, but may not indicate whether the strip is fully or correctly inserted. It is noted that the measurement engine module 4320 can perform a more exhaustive strip insertion confirmation, which indicates that the strip is present but not fully inserted. The measurement engine module 4320 also transmits a code key packet indicating a code key lot number of fixed length. The interconnection platform 4310 then displays, via the user interface module, a screen to the user indicating the code key number to the user, via the display device. In some embodiments, the last three digits of the code key lot number are displayed to the user for user confirmation of the correct code key.

Once the measurement engine module 4320 confirms that the strip is fully inserted, the measurement engine module 4320 transmits to the interconnection platform 4310, a signal indicating that the code key is OK and a signal indicating that the measurement engine module 4320 is waiting for a sample, e.g. a drop of blood. The interconnection platform 4310 then displays, via the user interface module, a screen to the user 4300 prompting the user 4300 to apply a sample to the test strip. The measurement engine module 4320 waits for the sample. If a sample is received before a timeout period has lapsed and the amount is sufficient to determine a result, the measurement engine module 4320 sends a signal indicating that the sample is sufficient to the interconnection platform 4310. Upon receiving an indication that the sample was sufficient, the user interface module displays a screen to the user 4300 indicating that the glucose test is in progress.

Once a result is determined by the measurement engine module 4320, the measurement engine module 4320 sends the result to the interconnection platform 4310. The interconnection platform 4310 then sends an ACK to the measurement engine module 4320. The measurement engine module 4320 then sends an end of test signal to the interconnection platform 4310. The user interface module then displays the result to the user 4300.

It is noted that if at any time an error occurs at the measurement engine module 4320, the measurement engine module 4320 will send a NACK with an error code to the interconnection platform 4310.

It is further noted that the foregoing sequence is exemplary and pertains to a measurement engine module 4320 that utilizes test strips. It is appreciated that the interconnection platform 4310 is configured to execute variations of the above described sequence when connected to different measurement engine modules, e.g. a measurement engine module that performs optical sensing. As the exact sequence of events will vary from measurement engine module to measurement engine module, the test logic for implementing the blood glucose test will change. Thus, when a different measurement engine module is connected to the interconnection platform 4310, a new user interface module containing different visualization screens and a different state machine providing the test logic will be connected to the interconnection platform as well. The set of commands and signals, however, will remain the same, thereby promoting modularity. Meaning that the interconnection platform 4310 will transmit these signals to a measurement engine module, independent on the type of measurement engine module, and the measurement engine module will be configured to interpret the commands and signals. For instance, commands such as set date, set time, and run test should be understood by any measurement engine module. Thus, the configuration of the interconnection platform 4310 will not need to be significantly altered, if at all, to support different measurement engine modules.

Figure 103:
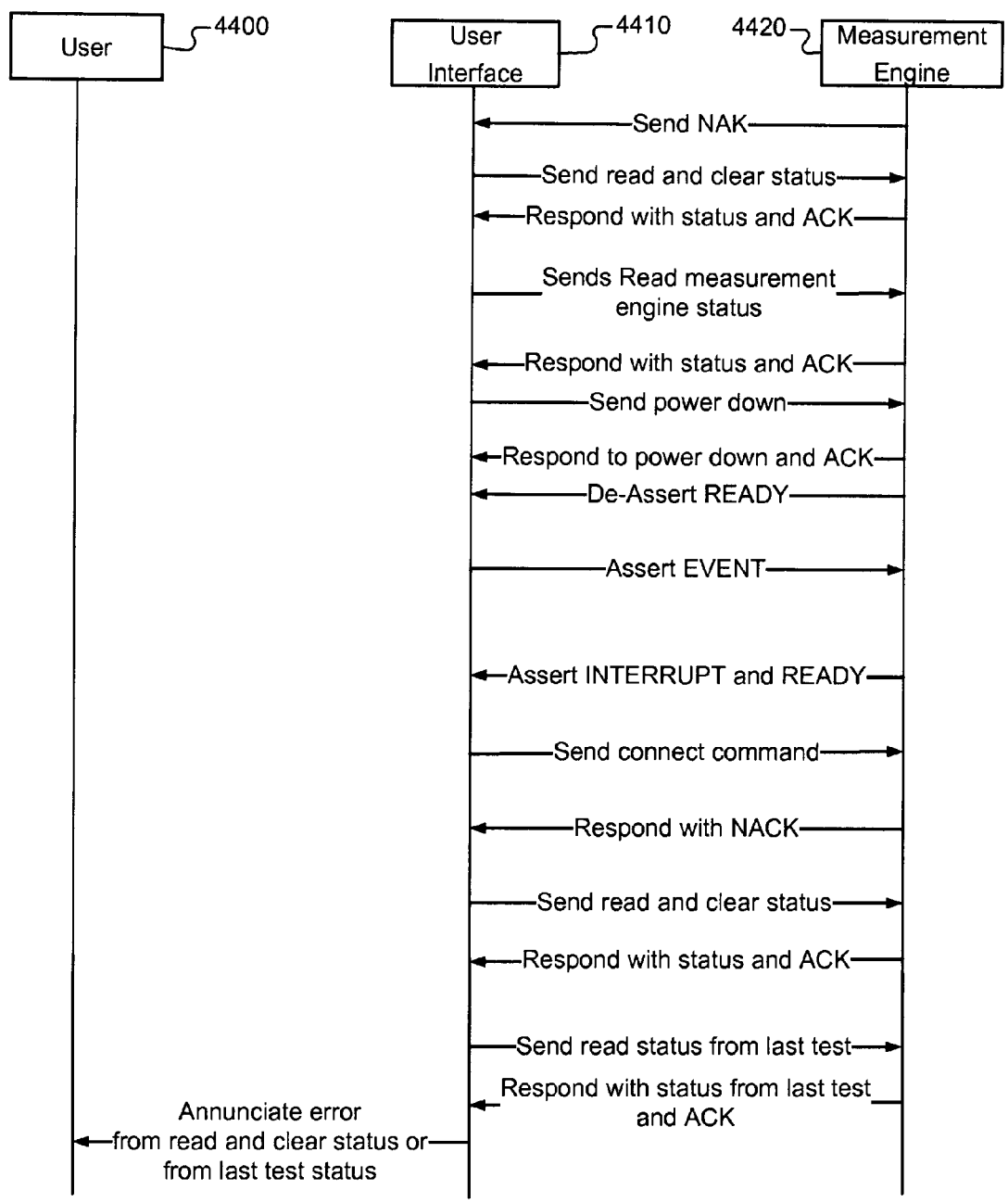
FIG. 103 shows a sequence diagram of a recovery from a blood glucose test failure according to a blood glucose test protocol.

FIG. 103 is a sequence diagram of a recovery from a glucose test failure. The following sequence occurs when the measurement engine module 4420 has received a request to run the test but an error condition has been detected during the execution of a blood glucose test. Once an error has been detected, the measurement engine module 4420 sends a NACK to the interconnection platform 4410. The interconnection platform 4410 responds with a read and clear status command to the measurement engine module 4420. The read and clear status command allows the interconnection platform 4410 read a serial status register of the measurement engine module 4420. Once the command initiates, the serial status register is cleared. The measurement engine module 4420 returns the status and resets the status of the measurement engine module 4420, and returns an ACK to the interconnection platform 4410. The interconnection platform can communicate the received status to the data management module for archiving in a database that records the operational status of the modules of the diabetes manager.

The interconnection platform 4410 then sends a read measurement engine status command. The read measurement engine status command allows the host to determine what events and states the measurement engine module 4420 has detected. The measurement engine module 4420 returns the status of the measurement engine module 4420 in a fixed length bit string, wherein predetermined bits are flags indicating status of the measurement engine module 4420. For instance, the flags can indicate whether a strip has been removed, whether a strip is present, whether the temperature of the measurement engine module 4420 is in a warning condition or in an error condition, whether the power supply module is in a warning condition or error condition, or whether there has been a clock error. If the status indicates that the strip has not been removed, then the interconnection platform waits until the strip is removed before initiating a new test.

If the interconnection platform 4410 does not receive a proper response to a request for the status, the interconnection platform 4410 sends a power down signal to the measurement engine module 4420. The measurement engine module 4420 powers down to a sleep mode and responds to the interconnection platform with an ACK. Once powered down, the measurement engine module 4420 de-asserts a ready signal that was asserted during the testing phase. The interconnection platform 4410 waits a predetermined amount of time, e.g. 10 ms, and then asserts an event signal to the measurement engine module 4420, thereby removing the measurement engine module 4420 from the sleep mode. In response, the measurement engine module 4420 asserts an event interrupt signal and a ready signal, thereby indicating that the measurement engine module 4420 has removed itself from the sleep mode.

In response to the ready signal, the interconnection platform 4410 sends a connect command to the measurement engine module 4420. If the serial status register has not been cleared, the measurement engine module 4420 responds with a NACK. If, however, the serial status register has been cleared, the interconnection platform 4410 responds with an ACK. Assuming a NACK is received by the interconnection platform 4410, the interconnection platform 4410 sends a read and clear status command to the measurement engine module 4420. The measurement engine module 4420 clears the serial status register and responds with the status and an ACK.

Once the ACK is received, the interconnection platform 4410 sends a read status from last test command. The read status from last test command allows the interconnection platform 4410 to read the last test result stored in a memory of the measurement engine module 4420. The last result will include a bG value, a time, a date, and result flags. The result flags is a fixed length bit string having flags indicating, inter alia, whether the bG value is less than a first reliability threshold, i.e. too low to be trusted, whether the bG value is greater than a second reliability threshold, i.e. too high to be trusted, and whether the measurement engine module 4420 issued a temperature warning.

Upon receiving the read status from last test command, the measurement engine module 4420 responds with the status of the last test and an ACK. Upon receiving the read status from last test command, the interconnection platform 4410 displays at least one of the read and clear status command result and the read status from last test command to the user 4400, via the user interface module.

The foregoing sequence is exemplary and pertains to a measurement engine module 4420 that utilizes test strips. It is appreciated that the interconnection platform 4410 is configured to execute a variation of this sequence when connected to different measurement engine modules, e.g. a measurement engine module that performs optical sensing. As the exact sequence of events will vary from measurement engine module to measurement engine module, the test logic for implementing the blood glucose test will change. Thus, when a different measurement engine module is connected to the interconnection platform 4410, a new user interface module containing different visualization screens and a different state machine providing the test logic will be connected to the interconnection platform as well. The set of commands and signals, however, will remain the same, thereby promoting modularity. The interconnection platform 4410 will transmit these signals to a measurement engine module, independent on the type of measurement engine module, and the measurement engine module will be configured to interpret the commands and signals. For instance, commands such as read and clear status, read measurement engine status, and connect, as well as signals such as, EVENT and READY, will be understood by different measurement engines. Thus, the configuration of the interconnection platform 4310 will not be need to be significantly altered, if at all, to support different measurement engine modules.

It is noted that the interconnection platform 4200 (FIG. 101) provides inter-module communication among the modules connected thereto to achieve enhanced glucose test instrument reliability by effecting at least one reliability protocol. The reliability protocols are defined by a set of actions that the modules can perform in combination with one another to increase the reliability of the blood glucose test instrument.

FIG. 104 illustrates an exemplary reliability protocol that ensures that the patient does not attempt to execute a blood glucose test with a damaged blood sample carrier. In this protocol a connected measurement engine module 4530 cooperates with the user interface module 4510 to instruct the user 4500 to remove the blood sample carrier when the measurement engine module detects the blood sample carrier is damaged. As discussed above, the measurement engine module 4530 will send a status thereof to the interconnection platform 4520. Upon receiving a status indicating that the blood sample carrier, e.g. the test strip, is damaged, the interconnection platform 4520 instructs the user interface module to display an instruction to the user to remove the damaged blood sample carrier. The user interface module 4510 presents the instruction to the user 4500 visually, e.g. displaying the instruction on a screen, and/or audibly, e.g. outputting the instruction on the speaker.

FIG. 105 illustrates an exemplary reliability protocol that ensures that the user has provided the proper code key. According to this protocol, the connected measurement engine module 4630 cooperates with the user interface module 4610 to instruct the user to insert a new code key when the measurement engine module 4630 detects that a previously entered code key is incorrect. As mentioned, the measurement engine module 4630 reports whether the correct code key has been entered by the user. Upon detecting that the code key is incorrect, the measurement engine module 4630 will notify the interconnection platform 4620 that the code key is incorrect. The interconnection platform then transmits a command to the user interface module 4610 to instruct the user 4600 to enter a new code key. The user interface module 4610 then presents the instruction to the user 4600 visually and/or audibly.

FIG. 106 illustrates an exemplary reliability protocol that ensures that the user has provided a sufficient blood sample and control sample. According to this protocol, the connected measurement engine module 4730 cooperates with the user interface module 4710 to instruct the user to repeat an attempted blood glucose test when the connected measurement engine 4730 detects that an insufficient amount of blood or control solution has been deposited on blood sample carrier. Upon detecting an insufficient amount of blood on the blood sample carrier or an insufficient amount of control solution, the blood measurement module 4730 will notify the interconnection platform 4720 of the insufficient sample. The interconnection platform 4720 then commands the user interface module 4710 to instruct the user 4700 to repeat the blood glucose test. The user interface module 4710 then presents the instruction to the user 4700 visually and/or audibly.

FIG. 107 illustrates an exemplary reliability protocol that ensures that the user 4800 follows the procedures indicated in the glucose test protocol. According to this protocol, the connected measurement engine cooperates with the user interface module to instruct the user to repeat an attempted blood glucose test when the connected measurement engine detects that the user failed to adhere to a sequence defined in the blood glucose test protocol. In the example of FIG. 107, the user 4800 applies a drop of blood to the blood sample carrier before the measurement engine module 4830 has transmitted a ready for blood sample signal to the interconnection platform 4820. Once this occurs, the measurement engine module 4830 notifies the interconnection platform 4820 of the failure to adhere to the sequence defined in the test protocol. The interconnection platform 4820 then commands the user interface module 4810 to instruct the user 4800 to repeat the blood glucose test. The user interface module 4810 then presents the instruction to the user 4800 visually and/or audibly.

FIG. 108 illustrates an exemplary reliability protocol that ensures that the blood glucose test is being conducted in an appropriate temperature. It is appreciated that a blood glucose test should be performed in an optimal temperature range. Thus, the measurement engine module 4930, in some embodiments, will have a temperature sensor, e.g. a thermistor, embedded therein. According to this protocol, the connected measurement engine module 4930 cooperates with the user interface module 4910 to instruct the user to repeat an attempted blood glucose test when the connected measurement engine module 4930 detects that an ambient temperature outside of the connected measurement engine module 4930 is not within a predefined temperature range. When the measurement engine module 4930 detects that the ambient temperature is either less than a first threshold, e.g. 6 C, or greater than a second threshold, e.g. 44 C, the measurement engine module 4930 will notify the interconnection platform 4920 of the error condition. The interconnection platform 4920 then command the user interface module 4910 to instruct the user 4900 to wait a predetermined amount of time, e.g. 5 minutes, and to repeat the blood glucose test. The user interface module 4910 then presents the instruction to the user 4900 visually and/or audibly.

FIG. 109 illustrates an exemplary reliability protocol that ensures that the blood glucose test was conducted with valid test strips. According to this protocol, the user interface module 5010 cooperates with the connected measurement engine module 5040 and the data management module 5020 to suppress generation of blood test data when an expiry date of a reagent used in the blood sample carrier has passed and to communicate a fault condition message to the user. When the measurement engine module 5040 detects that the expiration date of a strip has passed, i.e. the reagent found on the test strip has expired, the measurement engine module 5040 will notify the interconnection platform 5030 that a test was performed using an expired test strip. For example, the measurement engine module 5040 can be configured to compare the date set at the beginning of the blood glucose test, as discussed with respect to FIG. 102, and a expiration date contained in the key code or entered by the user. If the set date is passed the expiration date, then the measurement engine module 5040 notifies the interconnection platform 5030. The interconnection platform 5030 will instruct the data management module 5020 to suppress storing of the blood glucose test data and will command the user interface module 5010 to notify the user 5000 of the expired test strips. The user interface module 5010 then presents the notification to the user 5000 visually and/or audibly.

FIG. 110 illustrates an exemplary reliability protocol that ensures that the power supply module 5140 has sufficient power to power the measurement engine module 5120. According to this protocol, the power supply module 5140 cooperates with the connected measurement engine module 5120 and the user interface module 5110 to communicate a fault condition message to the user when power supply module resources are insufficient to reliably produce blood test data. When the power supply module 5140 determines that a battery or other power source has insufficient energy left to power the measurement engine module 5120, the power supply module 5140 notifies the interconnection platform 5130 that the power supply module resources are insufficient. The interconnection platform 5130 then commands the measurement engine module 5120 to enter a sleep mode. The interconnection platform 5130 will also command the user interface module 5110 to notify the user 5100 that the power supply resources are insufficient to power the measurement engine 5120. The user interface module 5010 then presents the notification to the user 5000 visually and/or audibly.

Figure 111:
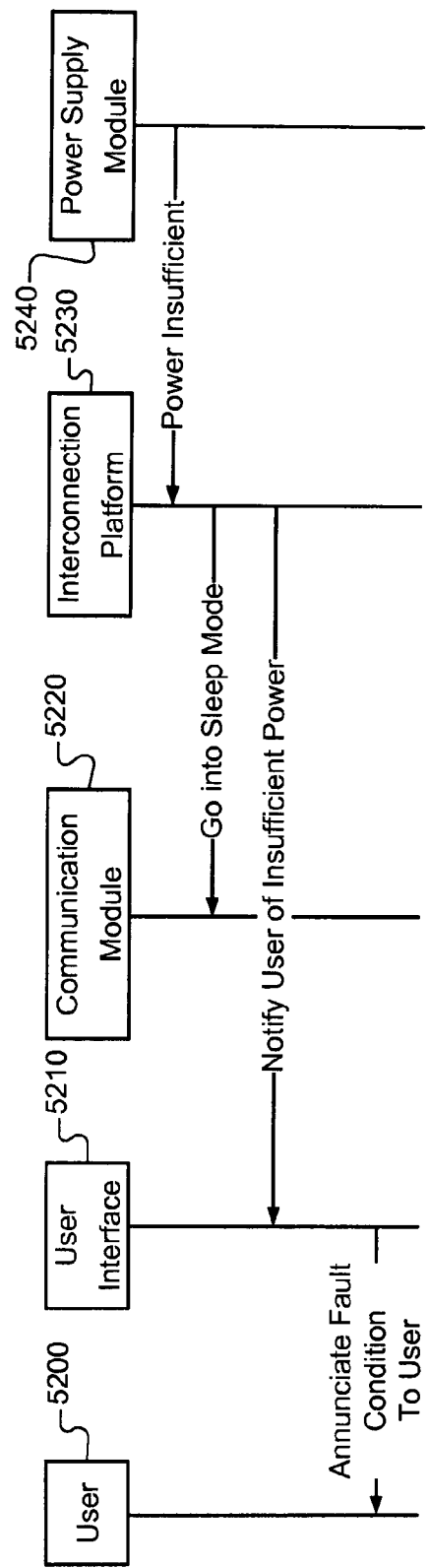
FIG. 111 shows a sequence diagram of the effecting of an eight reliability protocol.

FIG. 111 illustrates an exemplary reliability protocol that ensures that the power supply module 5240 has sufficient power to power the communication module 5220. According to this protocol, the power supply module 5240 cooperates with the communication module 5220 and the user interface module 5210 to communicate a fault condition message to the user interface module 5210 when power supply module resources are insufficient to reliably communicate with a separate therapy system. When the power supply module 5240 determines that a battery or other power resource has insufficient energy left to power the communication module 5220, the power supply module 5240 notifies the interconnection platform 5230 that the power supply module resources are insufficient. The interconnection platform 5230 then commands the communication module 5220 to enter a sleep mode. The interconnection platform 5230 will also command the user interface module 5210 to notify the user 5200 that the power supply resources are insufficient to power the communication module 5220. The user interface module 5010 then presents the notification to the user 5000 visually and/or audibly.

In an aspect of the disclosure, a blood glucose test instrument kit having modular component parts capable of being assembled into a plurality of different handheld blood glucose test instruments has been described. The kit includes the combination of an interconnection platform adapted to fit within a portable housing that supports at least one display device, and a collection of interoperable modules. Each of the modules having an interface adapted for connection to the interconnection platform. The collection of interoperable modules includes a plurality of different measurement engine modules each having an input port to receive a blood sample carrier and producing blood test data, at least one user interface module adapted to couple to the display device and containing test logic for implementing at least one blood glucose test protocol, at least one power supply module adapted, when connected to the interconnection platform, to provide operating power to other modules that are connected to the interconnection platform. A handheld blood glucose test instrument is assembled by the interconnection to the interconnection platform of at least one measurement engine module, at least one user interface module, and at least one power supply module. The interconnection platform provides inter-module communication among the modules connected thereto to achieve enhanced glucose test instrument reliability by effecting at least one reliability protocol selected from the group consisting of (a) a connected measurement engine module from the plurality of measurement engine modules cooperating with a user interface module to instruct the user to remove the blood sample carrier when the measurement engine module detects the blood sample carrier is damaged; (b) the connected measurement engine module cooperating with the user interface module to instruct the user to insert a new code key, when the measurement engine module detects that a previously entered code key is incorrect; and (c) the connected measurement engine module cooperating with the user interface module to instruct the user to repeat an attempted blood glucose test when the connected measurement engine module detects that an insufficient amount of blood or control solution has been deposited was deposited on blood sample carrier.

In another feature of the disclosure, the group of reliability protocols further includes the connected measurement engine module cooperating with the user interface module to instruct the user to repeat an attempted blood glucose test when the connected measurement engine module detects that the user failed to adhere to a sequence defined in the blood glucose test protocol.

In another feature of the disclosure, the group of reliability protocols further includes the connected measurement engine module cooperating with the user interface module to instruct the user to repeat an attempted blood glucose test when the connected measurement engine module detects that an ambient temperature outside of the connected measurement engine module is not within a predefined temperature.

In another feature of the disclosure, the collection of modules further include at least one data management module for storing data based upon the blood test data. The handheld blood glucose test instrument is further assembled by the interconnection to the interconnection platform of the data management module.

In another feature of the disclosure, the group of reliability protocols further includes the user interface module cooperating with the connected measurement engine module and the data management module to suppress generation of blood test data when an expiry date of a reagent used in the blood sample carrier has been passed and to communicate a fault condition message to the user.

In another feature of the disclosure, group of reliability protocols further includes the user interface module cooperating with the data management module and the measurement engine module to suppress the storing of data based upon the blood test data when the measurement engine module detects a fault condition at the blood sample carrier site.

In another feature of the disclosure, the group of reliability protocols further includes the power supply module cooperating with the connected measurement engine module and the user interface module to communicate a fault condition message to the user when power supply module resources are insufficient to reliably produce blood test data.

In another feature of the disclosure, the collection modules further include at least one communication module adapted to provide connectivity between the blood glucose test instrument and a separate therapy system. The handheld blood glucose test instrument is further assembled by the interconnection to the interconnection platform of the at least one communication module.

In another feature of the disclosure, the group of reliability protocols further includes the power supply module cooperating with the communication module and the user interface module to communicate a fault condition message to the user interface module when power supply module resources are insufficient to reliably communicate with a separate therapy system.

In another feature of the disclosure, the plurality of different measurement engine modules includes a first measurement engine module that performs electrochemical sensing and a second measurement engine module that performs optical sensing.

In another aspect of the disclosure, a blood glucose test instrument kit having modular component parts capable of being assembled into a plurality of different handheld blood glucose test instruments has been described. The kit includes the combination of an interconnection platform adapted to fit within a portable housing that supports at least one display device and a collection of interoperable modules. Each of the modules having an interface adapted for connection to the interconnection platform. The collection of interoperable modules include a plurality of different measurement engine modules each having an input port to receive a blood sample carrier and producing blood test data, at least one user interface module adapted to couple to the display device and containing test logic for implementing at least one blood glucose test protocol, at least one power supply module adapted, when connected to the interconnection platform, to provide operating power to other modules that are connected to the interconnection platform, at least one communication module adapted to provide connectivity between the blood glucose test instrument and a separate therapy system, and at least one data management module for storing data based upon the blood test data. A handheld blood glucose test instrument is assembled by the interconnection to the interconnection platform of at least one measurement engine module, at least one user interface module, at least one power supply module, at least one communication module and at least one data management module. The interconnection platform providing inter-module communication among the modules connected thereto to achieve enhanced glucose test instrument reliability by effecting at least one reliability protocol selected from the group consisting of (a) a connected measurement engine module from the plurality of measurement engine modules cooperating with a user interface module to instruct the user to remove the blood sample carrier when the measurement engine module detects the blood sample carrier is damaged; (b) the connected measurement engine module cooperating with the user interface module to instruct the user to insert a new code key, when the measurement engine module detects that a previously entered code key is incorrect; and (c) the connected measurement engine module cooperating with the user interface module to instruct the user to repeat an attempted blood glucose test when the connected measurement engine module detects that an insufficient amount of blood or control solution has been deposited was deposited on blood sample carrier.

In another feature of the disclosure, the group of reliability protocols further includes the connected measurement engine module cooperating with the user interface module to instruct the user to repeat an attempted blood glucose test when the connected measurement engine module detects that the user failed to adhere to a sequence defined in the blood glucose test protocol.

In another feature of the disclosure, the group of reliability protocols further includes the connected measurement engine module cooperating with the user interface module to instruct the user to repeat an attempted blood glucose test when the connected measurement engine module detects that an ambient temperature outside of the connected measurement engine module is not within a predefined temperature.

In another feature of the disclosure, the group of reliability protocols further includes the user interface module cooperating with the connected measurement engine module and the data management module to suppress generation of blood test data when an expiry date of a reagent used in the blood sample carrier has been passed and to communicate a fault condition message to the user.

In another feature of the disclosure, group of reliability protocols further includes the user interface module cooperating with the data management module and the measurement engine module to suppress the storing of data based upon the blood test data when the measurement engine module detects a fault condition at the blood sample carrier site.

In another feature of the disclosure, the group of reliability protocols further includes the power supply module cooperating with the connected measurement engine module and the user interface module to communicate a fault condition message to the user when power supply module resources are insufficient to reliably produce blood test data.

In another feature of the disclosure, the group of reliability protocols further includes the power supply module cooperating with the communication module and the user interface module to communicate a fault condition message to the user interface module when power supply module resources are insufficient to reliably communicate with a separate therapy system.

In another feature of the disclosure, the plurality of different measurement engine modules includes a first measurement engine module that performs electrochemical sensing and a second measurement engine module that performs optical sensing.

Configuration of Blood Glucose Meter Interfaces

Systems and devices according to the present disclosure allow for a wide variety of interconnection options while minimizing the number of physical ports. Increasing the number of physical ports can lead to confusion regarding which physical port is associated with any given cable. Additional physical ports can also increase the number of associated cables and adapters necessary when using a device. With respect to safety, physical ports present a site for intrusion of foreign material, such as fluids. Further, cleanliness standards, including those established by regulatory bodies such as the Food and Drug Administration (FDA), can require the ability to clean a medical device. Systems and devices according to the present disclosure avoid these problems by multiplexing at least one physical port so that the physical port can accommodate multiple interface protocols. In addition, the present disclosure describes, for at least one of the interface protocols, interfacing with multiple classes of device using the same interface protocol. The present disclosure also describes leveraging wireless interfaces to allow for further interconnection options.

Referring now to FIG. 75, a patient 2900 with diabetes and a clinician 2902 are shown in a clinic environment. The term 'patient' encompasses persons with metabolic syndrome, pre-diabetes, type 1 diabetics, type 2 diabetics, and gestational diabetics. The term 'clinician' is used broadly to include nurses, nurse practitioners, physicians, endocrinologists, etc.

During a healthcare consultation, the patient 2900 typically shares with the clinician 2902 a variety of patient data including blood glucose measurements, continuous glucose monitor data, amounts of insulin infused, amounts of food and beverages consumed, exercise schedules, and other lifestyle information. The clinician 2902 can obtain additional patient data that includes measurements of HbA1C, cholesterol levels, triglycerides, blood pressure, and weight. The patient data can be recorded manually and/or can be recorded electronically on a handheld diabetes management device 2904, diabetes analysis software executed on a computing device such as a personal computer (PC) 2906, and/or a web-based diabetes analysis site (not shown). The term PC, as used herein, includes computers using a Microsoft operating system as well as computers using an Apple operating system, Linux, OpenBSD, Ubuntu, etc.

The clinician 2902 can analyze the patient data manually and/or can analyze the patient data electronically using the diabetes analysis software and/or the web-based diabetes analysis site. After analyzing the patient data and reviewing adherence of the patient 2900 to previously prescribed therapy, the clinician 2902 can decide whether to modify the therapy for the patient 2900.

Referring now to FIG. 76, the patient 2900 can use a continuous glucose monitor (CGM) 2910, an ambulatory durable insulin pump 2912, an ambulatory non-durable insulin pump 2914, and the handheld diabetes management device 2904. In various implementations, the durable insulin pump 2912 and the non-durable insulin pump 2914 can be used interchangeably, and the handheld diabetes management device 2904 can be configured to interact with whichever of the insulin pumps 2912 or 2914 is currently in use. In various implementations, if both the insulin pumps 2912 and 2914 are worn by the patient 2900, the handheld diabetes management device 2904 can communicate with only one of the insulin pumps 2912 or 2914. In various other implementations, the handheld diabetes management device 2904 can communicate with both of the insulin pumps 2912 and 2914. The insulin pumps 2912 and 2914 will be referred to collectively as insulin pump 2912.

The CGM 2910 uses a subcutaneous sensor to sense and monitor the amount of glucose in the blood of the patient 2900 and communicates corresponding readings to the handheld diabetes management device 2904. The handheld diabetes management device 2904 performs various tasks including measuring and recording blood glucose levels, determining an amount of insulin to be administered to the patient 2900 via the insulin pump 2912, receiving patient data via a user interface, archiving the patient data, etc. When the CGM 2910 is in use, the handheld diabetes management device 2904 periodically receives readings from the CGM 2910 indicating glucose level in the blood of the patient 2900. When the insulin pump 2912 is in use, the handheld diabetes management device 2904 transmits instructions to the insulin pump 2912, which delivers insulin to the patient 2900. Insulin can be delivered in a scheduled manner at a basal rate, which attempts to maintain a predetermined insulin level in the blood of the patient 2900. Additionally, insulin can be delivered in the form of a bolus dose, which raises the amount of insulin in the blood of the patient 2900 by a predetermined amount.

Figure 112:
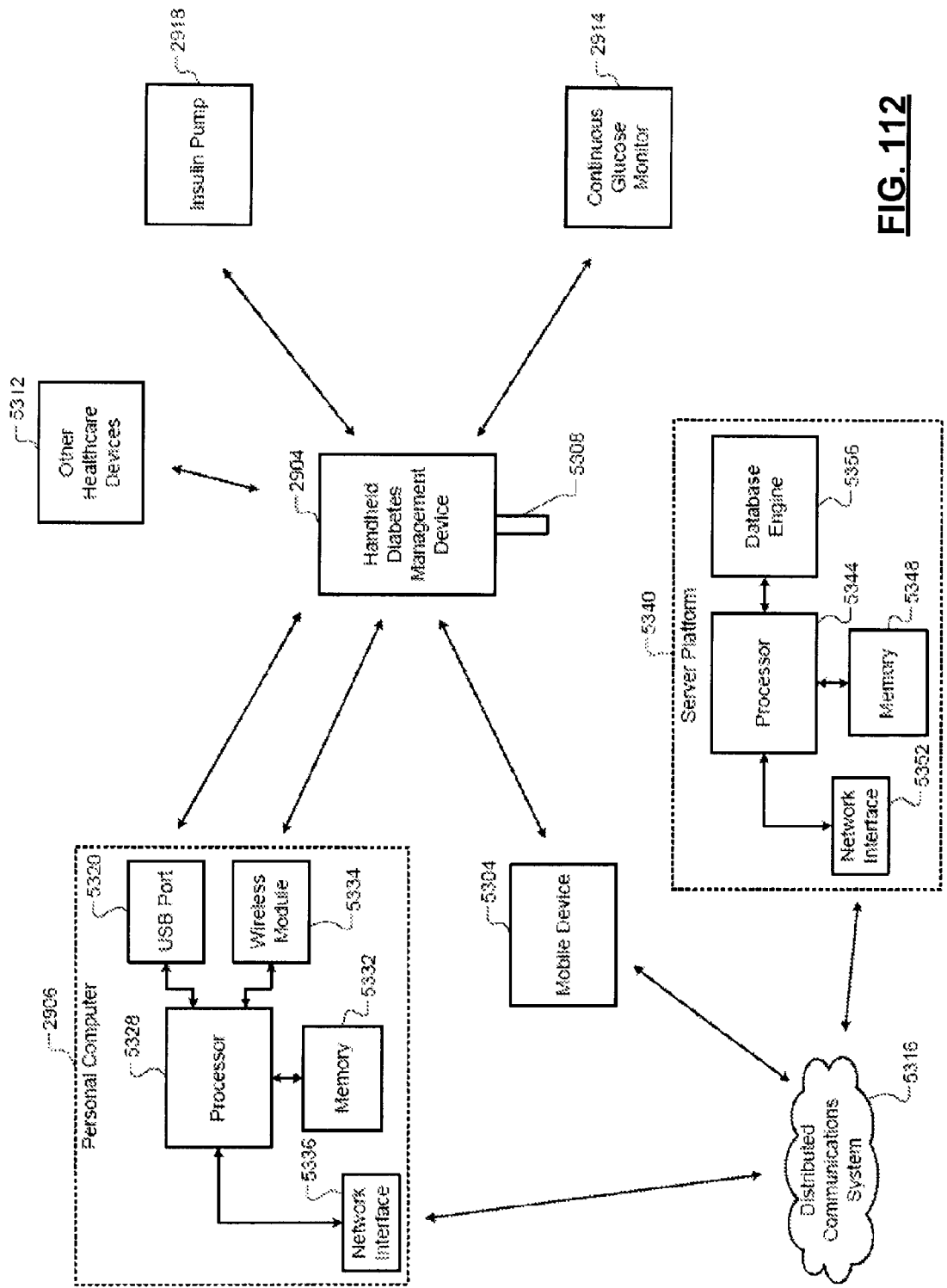
FIG. 112 shows a diabetes management system used by patients and clinicians to manage diabetes.

Referring now to FIG. 112, a diabetes management system used by the patient 2900 and the clinician 2902 includes one or more of the following devices: the handheld diabetes management device 2904, the CGM 2910, the insulin pump 2912, the PC 2906 with the diabetes analysis software, a mobile device 5304, and other healthcare devices represented collectively at 5312. The handheld diabetes management device 2904 is configured as a system hub and communicates with the devices of the diabetes management system. Alternatively, the insulin pump 2912 or the mobile device 5304 can be configured as the system hub. Communication between the devices in the diabetes management system can be performed using wireless interfaces (e.g., Bluetooth) and/or wireline interfaces (e.g., USB). For example, one of versions 1.1, 1.2, 2.0, 2.1, 3.0, and 4.0 of the Bluetooth standard can be used.

Communication protocols used by these devices can include protocols compliant with the IEEE 11073 standard, which can be extended using guidelines provided by Continua® Health Alliance Design Guidelines. For example, IEEE 11703-20601 Optimized Exchange Protocol with the IEEE 11073-10417 Blood Glucose Device Specialization standards can be used. In addition, the device specialization can be supplemented by predefined Roche proprietary communications protocols, which for example can include additional measurement objects. Further, healthcare records systems such as Microsoft® HealthVault™ and Google™ Health can be used by the patient 2900 and/or the clinician 2902 to exchange information.

The handheld diabetes management device 2904 can receive blood glucose readings from one or more sources, such as the CGM 2910. The CGM 2910 continuously measures the blood glucose level of the patient 2900. The CGM 2910 periodically communicates the blood glucose level to the handheld diabetes management device 2904. In various implementations, the handheld diabetes management device 2904 and the CGM 2910 communicate wirelessly.

Additionally, the handheld diabetes management device 2904 includes blood glucose meter (BGM) functionality. The handheld diabetes management device 2904 can measure glucose levels from a sample from the patient 2900. For example, in various implementations, the handheld diabetes management device 2904 can receive a blood glucose measurement strip 5308. The patient 2900 deposits a sample of blood or other bodily fluid on the blood glucose measurement strip 5308. The handheld diabetes management device 2904 analyzes the sample to determine the blood glucose level in the sample. The blood glucose level measured from the sample and/or the blood glucose level read by the CGM 2910 can be used in determining the amount of insulin to be administered to the patient 2900.

The handheld diabetes management device 2904 communicates with the insulin pump 2912. The insulin pump 2912 can be configured to receive instructions from the handheld diabetes management device 2904 to deliver a predetermined amount of insulin to the patient 2900. Additionally, the insulin pump 2912 can receive additional information including meal and/or exercise schedules of the patient 2900. In various implementations, the insulin pump 2912 can determine the amount of insulin to administer based on the additional information.

The insulin pump 2912 can also communicate data to the handheld diabetes management device 2904. The data can include amounts of insulin delivered to the patient 2900, corresponding times of delivery, and pump status. In various implementations, the handheld diabetes management device 2904 and the insulin pump 2912 can communicate wirelessly.

In addition, the handheld diabetes management device 2904 can communicate with the other healthcare devices 5312. For example, the other healthcare devices 5312 can include a blood pressure meter, a weight scale, a pedometer, a fingertip pulse oximeter, a thermometer, etc. The other healthcare devices 5312 obtain and communicate personal health information of the patient 2900 to the handheld diabetes management device 2904 through wireless, USB, or other interfaces. The other healthcare devices 5312 can use communication protocols compliant with ISO/IEEE 11073 extended using guidelines from Continual® Health Alliance. Further, the devices of the diabetes management system can communicate with each other via the handheld diabetes management device 2904.

The handheld diabetes management device 2904 can communicate with the PC 2906 using Bluetooth, USB, or other interfaces. Diabetes management software running on the PC 2906 includes an analyzer-configurator that stores configuration information of the devices of the diabetes management system. The configurator has a database to store configuration information of the handheld diabetes management device 2904 and the other devices. The configurator can communicate with users through web pages or computer screens in non-web applications. The configurator transmits user-approved configurations to the devices of the diabetes management system. The analyzer retrieves data from the handheld diabetes management device 2904, stores the data in a database, and outputs analysis results through standard web pages or computer screens in non-web based applications.

The handheld diabetes management device 2904 can communicate with the mobile device 5304 using wired or wireless protocols, such as Bluetooth. Examples of the mobile device 5304 include a cellular phone, a pager, a personal digital assistant (PDA), a tablet computing device, etc. The mobile device 5304 can communicate with a network, such as a distributed communications system 5316. In various implementations, the distributed communications system 5316 can be the Internet. The handheld diabetes management device 2904 can send and receive messages, including data and instructions, to the distributed communications system 5316 via the mobile device 5304.

The PC 2906 includes a USB port 5320 and/or a wireless module 5324. A processor 5328 controls communications over the USB port 5320 and/or the wireless module 5324. The processor 5328 can execute instructions from memory 5332. Further, the PC 2906 includes a network interface 5336, which can be wired, such as Ethernet, or wireless, such as WiFi (including 802.11a, b, g and/or n). The network interface 5336 can communicate with the distributed communications system 5316. The PC 2906 can therefore also serve as an intermediary between the distributed communications system 5316 and the handheld diabetes management device 2904. The PC 2906 and the handheld diabetes management device 2904 can communicate using USB and using a wireless protocol, such as Bluetooth. In various implementations, the wireless protocol can be a network protocol, such as WiFi. In such implementations, functionality of the wireless module 5324 and the network interface 5336 can be combined into a single module.

When the handheld diabetes management device 2904 is connected via USB to the PC 2906, the handheld diabetes management device 2904 can charge an internal power supply, such as a rechargeable battery. The PC 2906 can be replaced by any other device having sufficient processing capability, such as a laptop, a netbook, or a tablet computing device. The PC 2906 can execute software stored in nonvolatile storage of the PC 2906. For example only, some or all of the memory 5332 can be nonvolatile. Additionally or alternatively, other nonvolatile storage media can be present, such as flash memory, magnetic storage, and optical storage.

The PC 2906 can execute specialized software corresponding to the handheld diabetes management device 2904 and can execute general purpose software that can interact with the handheld diabetes management device 2904. The PC 2906 can also execute software provided by the handheld diabetes management device 2904. The software provided by the handheld diabetes management device 2904 can then be stored persistently on the PC 2906 or can be removed when the PC 2906 is no longer in communication with the handheld diabetes management device 2904. In various implementations, the software provided by the handheld diabetes management device 2904 can be low- or zero-footprint software such that when the handheld diabetes management device 2904 is no longer in communication with the PC 2906, traces of the software, such as files and settings, are not left behind on the PC 2906.

The PC 2906 can also acquire software via the distributed communications system 5316, such as from a server platform 5340. For example, the server platform 5340 can provide web server functionality. The PC 2906 can download and execute software from the server platform 5340. In various implementations, the downloaded software can be web-based, such as a Java or Flash application. The local applications can communicate data and instructions with the server platform 5340. In addition, the PC 2906 can interact with a server-side application executed by the server platform 5340. The remote and local applications may be known collectively as Accu-Chek 360°.

The applications can have varying functionality and access authorizations. For example, some applications can be authorized to access historical data from the handheld diabetes management device 2904, while other applications can be authorized to control operation of the handheld diabetes management device 2904, such as glucose measurement settings and insulin pump settings. In various implementations, the applications can also control other devices, such as the insulin pump 2912 and the CGM 2910, via the handheld diabetes management device 2904. For example, the applications can update firmware, retrieve configuration settings and error codes, and provide configuration settings. The applications can also control firmware updates of the handheld diabetes management device 2904 itself.

The server platform 5340 can include one or more physical servers having multiple processors, but logically includes at least a processor 5344 that executes instructions from memory 5348 and communicates with the distributed communications system 5316 via a network interface 5352. Further, the processor 5344 communicates with a database engine 5356, which can be executed by a separate processor and memory and/or by the processor 5344 itself, such as in a virtual machine.

The database engine 5356 stores one or more databases, which can track firmware versions of the handheld diabetes management device 2904 as well as associated devices, such as the CGM 2910 and the insulin pump 2912. The database engine 5356 can store contact information for the patient 2900 so that, for example, firmware updates and other alerts can be communicated to the patient 2900. The database engine 5356 can also store historical data from the handheld diabetes management device 2904. The stored data can be used for remote access by the patient 2900, the clinician 2902, or in the case of a failure or erasure of the handheld diabetes management device 2904.

The database engine 5356 can also store language settings and localizations for various regions, and can track which of these languages are installed in the handheld diabetes management device 2904. The database engine 5356 can also store food and exercise databases that indicate the corresponding effect on blood sugar of various foods and activities. These databases can be supplemented by data entered by the patient 2900 and/or the clinician 2902 via the handheld diabetes management device 2904 or via some other interface such as one presented by the PC 2906. The database engine 5356 can also store user preferences for the handheld diabetes management device 2904 as well as treatment parameters for the handheld diabetes management device 2904, such as equations and/or constants for calculating amounts of insulin.

A number of device classes are defined for use with the USB protocol. In various implementations, the handheld diabetes management device 2904 implements the mass storage device class (MSC) and the personal healthcare device class (PHDC). In various implementations, the handheld diabetes management device 2904 also implements the communications device class (CDC) and/or the remote network driver interface specification (RNDIS).

The MSC is used to access raw data, such as files and file systems. For example only, USB flash drives and memory card readers for digital cameras and video-cameras generally implement the MSC. The MSC is supported by a wide variety of operating systems, including Microsoft Windows, which has offered native support for MSC since Windows 2000. In various implementations, the handheld diabetes management device 2904 can also implement the media transfer protocol (MTP), which also allows file access.

In various implementations, the handheld diabetes management device 2904 stores blood glucose data, insulin data, exercise data, and food data as files that can be accessed via the MSC. The handheld diabetes management device 2904 can also store software for use by the PC 2906. In addition, the handheld diabetes management device 2904 can store documentation, such as health files, frequently asked questions files, and training videos and podcasts.

The handheld diabetes management device 2904 can store web pages and other interactive content. For example only, the handheld diabetes management device 2904 can store a start webpage, from which a user can access other information and options. The handheld diabetes management device 2904 can be configured so that the start webpage or a startup program is automatically executed when the handheld diabetes management device 2904 is connected to an appropriately configured computer. The startup program can provide the option of installing the necessary components for PHDC support. To allow access via the MSC, the handheld diabetes management device 2904 can implement a FAT32 file system or another file system, such as FAT, HFS Plus, and Ext2.

The PC 2906 may not natively support the PHDC. For example, drivers and/or configuration files may be required prior to the PC 2906 supporting communication with the handheld diabetes management device 2904 using the PHDC. The handheld diabetes management device 2904 can therefore store various drivers and configuration files to support the PHDC operation for one or more operating systems. The PHDC was designed to allow interoperability between medical devices, and can support IEEE 11073 operation. The PC 2906 can communicate with the handheld diabetes management device 2904 using the PHDC in order to obtain medical data, such as blood glucose readings and historical insulin injection records. The PC 2906 can also use the PHDC to read and command basal rate and bolus parameters.

The handheld diabetes management device 2904 can implement the CDC to allow direct communication between the PC 2906 and various components of the handheld diabetes management device 2904. The CDC allows a variety of pre-existing communication protocols, such as serial protocols and network protocols, to be carried over USB. For example only, the PC 2906 can communicate with an internal component of the handheld diabetes management device 2904 using the CDC. Additionally, the PC 2906 can use the CDC to communicate with other devices, such as the CGM 2910 and the insulin pump 2912, via the handheld diabetes management device 2904. In addition, the CDC can be used during manufacturing, testing, calibration, and repair. For example, the CDC can be used by a specialized test environment, such as a test stand, and/or by a computer having specialized software. In various implementations, end users are prevented from using the CDC. Additionally or alternatively to implementing the CDC, the Remote Network Driver Interface Specification (RNDIS) can be used. RNDIS is a specification for supporting network devices over USB, and is supported natively in some Microsoft operating systems.

As discussed above, the handheld diabetes management device 2904 can communicate with the PC using a wireless protocol such as Bluetooth. Although Bluetooth is described herein for purposes of illustration only, other protocols can be used, such as ZigBee or Bluetooth low energy. Similar to the classes of USB, profiles are defined for Bluetooth. For example, the handheld diabetes management device 2904 can implement a serial port profile (SPP) and/or a health device profile (HDP). The SPP defines protocols and procedures to allow devices to emulate a serial protocol, such as RS-232, using Bluetooth.

In various implementations, the SPP can be used in similar scenarios as the CDC of USB. For example, the SPP can be used by the PC 2906 to communicate with the CGM 2910 and/or the insulin pump 2912 via the handheld diabetes management device 2904. Further, the handheld diabetes management device 2904 can use the SPP to communicate with the CGM 2910 and the insulin pump 2912. For example only, the SPP can be used for configuration and updating of the CGM 2910 and the insulin pump 2912. The handheld diabetes management device 2904 can use the HDP for supplying and receiving medical data to and from the CGM 2910 and the insulin pump 2912, such as blood glucose readings and insulin doses.

The HDP can be used in conjunction with IEEE 11073. The HDP can be used when transmitting medical information from the handheld diabetes management device 2904 to the PC 2906. The medical information can include glucose readings, exercise data, and food data from handheld diabetes management device 2904 as well as glucose readings from the CGM 2910 and insulin dosing history from the insulin pump 2912.

Figure 113:
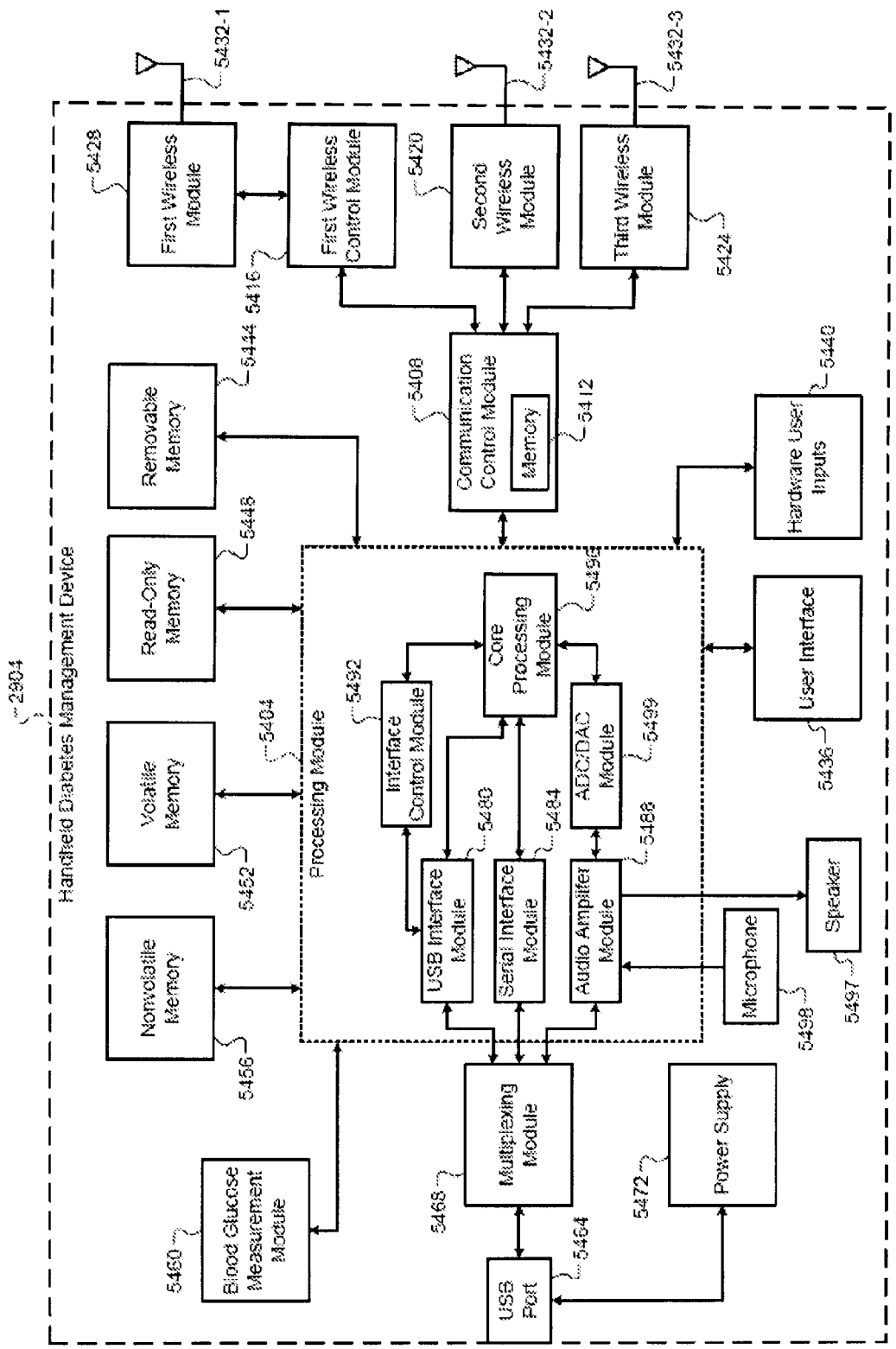
FIG. 113 is a functional block diagram of an example implementation of a handheld diabetes management device.

Referring now to FIG. 113, a functional block diagram of an example implementation of the handheld diabetes management device 2904 is presented. The handheld diabetes management device 2904 includes a processing module 5404, such as the i.MX233 applications processor from Freescale Semiconductor, Inc. The processing module 5404 communicates with a communication control module 5408, such as an STM32F103 32-bit ARM Cortex microcontroller unit from ST Microelectronics. For example only, the communication control module 5408 includes memory 5412 having volatile and nonvolatile components. For example only, the communication control module 5408 includes 512 KB of flash memory and 64 KB of random access memory (RAM).

The processing module 5404 and the communication control module 5408 can communicate using universal asynchronous receiver/transmitters (UARTs). In various implementations, a level shifter or a voltage transformer is interposed between the processing module 5404 and the communication control module 5408 to match signal levels of the respective UARTs. The communication control module 5408 controls wireless communication. In various implementations, the communication control module 5408 controls a first wireless control module 5416 and a second wireless module 5420. In various implementations, the communication control module 5408 also controls a third wireless module 5424.

The first wireless control module 5416 controls a first wireless module 5428, which can implement RF processing and/or baseband processing. Antennas 5432-1, 5432-2, and 5432-3 are illustrated as being connected to the first wireless module 5428, the second wireless module 5420, and the third wireless module 5424, respectively. However, more or fewer antennas can be used. When fewer antennas are used, access to the antenna can be multiplexed and/or different frequency operating ranges can allow antenna to be used by different modules simultaneously. Further, RF and/or baseband processing can be shared between modules. In various implementations, the first wireless control module 5416 can subsume the functionality of the first wireless module 5428.

The first wireless control module 5416 can implement encryption, such as the advanced encryption standard (AES), to prevent eavesdropping and other malicious activity from affecting the wireless communication. The first wireless control module 5416 can implement a proprietary wireless protocol operating in a specified frequency band, such as the 2.4 GHz industrial, scientific, and medical (ISM) band. For example, the first wireless control module 5416 can be an nRF24LE1™ ultra-low-power wireless system-on-chip solution from Nordic Semiconductor, Inc.

The second wireless module 5420 can implement a wireless personal area network (WPAN) protocol such as Bluetooth, Bluetooth low energy, or Zigbee. For example only, the second wireless module 5420 can be a BL6450 controller from Texas Instruments. When present, the third wireless module 5424 can implement another proprietary wireless protocol and/or a wireless local area network (WLAN) protocol, such as IEEE 802.11(a, b, g, and/or n).

The processing module 5404 communicates with a user interface 5436, which can include a liquid crystal display (LCD) touchscreen, which can be backlit by light-emitting diodes (LEDs). For example only, the touchscreen can be a WQVGA (400×240) 3-inch screen. The processing module 5404 can receive hardware user inputs 5440. For example only, the hardware user inputs can include buttons and switches, such as a microswitch for performing a hardware reset. The microswitch can be recessed to prevent accidental actuation.

The processing module 5404 can communicate with removable memory 5444, such as flash storage, including secure digital (SD), compact flash (CF), and other flash storage technologies. For example, the removable memory 5444 can be a microSD card. The removable memory 5444 can be used to store the software, instructional material, and drivers to be provided to the PC 2906 and/or the mobile device 5304.

The processing module 5404 also communicates with read-only memory 5448. The read-only memory 5448 can include an electrically erasable programmable read-only memory (EEPROM). The processing module 5404 communicates with volatile memory 5452, such as synchronous dynamic random access memory (SDRAM). The processing module 5404 communicates with nonvolatile memory 5456, such as NAND flash memory. In various implementations, some or all of the read-only memory 5448, the volatile memory 5452, and the nonvolatile memory 5456 can be incorporated on the same die or in the same package as the processing module 5404.

The processing module 5404 communicates with a blood glucose measurement module 5460, which analyzes a sample from the patient 2900 to determine a glucose level in the patient's blood. For example only, the blood glucose measurement module 5460 can dispense test strips to which a blood sample is applied. In various implementations, the blood glucose measurement module 5460 processes readings from the sample and provide a blood glucose number to the processing module 5404. Alternatively, the blood glucose measurement module 5460 can provide raw data to the processing module 5404, which determines a blood glucose level based on the raw data.

The handheld diabetes management device 2904 includes a USB port 5464. For example, the USB port 5464 can be a standard USB port, a micro USB port, or a mini USB port. Specifically, the USB port 5464 can be a micro-B female port. The small size of the micro-B port offers less area for potential fluid or other contaminant intrusion, and allows a physical size of the handheld diabetes management device 2904 to be minimized.

To reduce the number of physical ports required in the handheld diabetes management device 2904, a multiplexing module 5468, such as an MC34825 from Freescale Semiconductor, Inc., is connected to the USB port 5464. The multiplexing module 5468 can allow the USB port 5464 to be used for USB purposes, for a non-USB serial interface, and for an audio interface. In addition, a power supply 5472 can be connected to the USB port 5464. The power supply 5472 can include a battery, such as a lithium ion rechargeable battery, which provides power to components of the handheld diabetes management device 2904.

The power supply 5472 can be recharged via the USB port 5464. In various implementations, the power supply 5472 can be recharged when the USB port 5464 is connected to the PC 2906 and/or a powered USB hub. In addition, a separate adapter can be used to recharge the power supply 5472 via the USB port 5464. In various implementations, the current required by the power supply 5472 is greater than can be provided by a computer, and charging therefore requires the charging adapter. The charging adapter can be integrated with a stand that retains the handheld diabetes management device 2904 and also allows interaction with the user interface 5436 of the handheld diabetes management device 2904. Charging using the USB port 5464 allows a separate charging port to be eliminated.

In various implementations, the multiplexing module 5468 can analyze cables and/or devices connected to the USB port 5464. For example only, termination resistances, pull-up resistances, and pull-down resistances of cables and/or devices attached to the USB port 5464 can indicate to the multiplexing module 5468 the type of device connected to the USB port 5464. When the multiplexing module 5468 determines that a USB device is attached, the multiplexing module 5468 can connect the USB port 5464 to a USB interface module 5480 of the processing module 5404.

Similarly, the multiplexing module 5468 can connect the USB port 5464 to a serial interface module 5484 when a non-USB serial device is determined to be connected to the USB port 5464. The multiplexing module 5468 connects the USB port 5464 to an audio amplifier module 5488 when an audio device is determined to be connected to the USB port 5464.

The USB interface module 5480 is controlled by an interface control module 5492, which determines whether the USB interface module 5480 should be operating using the PHDC, the MSC, the CDC, or another class. The interface control module 5492 communicates with a core processing module 5496, which can coordinate operation of the processing module 5404 and also implement user interface features. In various implementations, the core processing module can run Windows CE from Microsoft Corp.

After manufacturing, the interface control module 5492 can initially instruct the USB interface module 5480 to operate using the CDC. This mode can be used for programming, configuration, calibration, and testing. The interface control module 5492 can then control the USB interface module 5480 to operate using the MSC prior to providing the handheld diabetes management device 2904 to the patient 2900. Repair and testing facilities can provide signals and/or commands to the interface control module 5492 to indicate that CDC is once again required, such as if the handheld diabetes management device 2904 is returned for servicing.

When the handheld diabetes management device 2904 is with the patient 2900, the interface control module 5492 can set the USB interface module 5480 to use the MSC by default. However, if it is determined that the device connected to the USB port 5464 has the necessary drivers and configuration to use the PHDC, the interface control module 5492 can set the USB interface module 5480 to use the PHDC. A user of the handheld diabetes management device 2904 and user of the connected device can override this operation and cause the interface control module 5492 to maintain the USB interface module 5480 using the MSC. The MSC can allow the USB interface module 5480 to provide access to the removable memory 5444. When operating using the CDC, the USB interface module 5480 can communicate with, for example, the blood glucose measurement module 5460 and/or with the communication control module 5408.

The serial interface module 5484 implements a non-USB protocol, such as the inter-integrated circuit ($I^2C$) protocol, General Purpose Input/Output (GPIO), and/or RS-232. The non-USB serial protocol can be used during manufacturing and testing by test equipment that has a serial interface. By multiplexing the non-USB pins onto the USB port 5464, the need for a separate serial port, such as a 9-pin DE-9, can be eliminated.

The audio amplifier module 5488 can include an audio amplifier for powering a speaker 5497 and an audio amplifier for amplifying signals from a microphone 5498. An ADC/DAC module 5499 converts analog microphone signals into digital and converts digital sound signals into analog signals for playback. The ADC/DAC module 5499 communicates with the core processing module 5496. For example only, the microphone 5498 can be used to record journal entries corresponding to insulin doses, exercise, meals, and blood glucose readings. The speaker 5497 can be used to play back journal entries and/or to play audio and video files, such as instructional videos. The audio and video files can be stored in the removable memory 5444.

The audio amplifier module 5488 is selectively connected to the USB port 5464 by the multiplexing module 5468. The pins of the USB port 5464 are thereby used as microphone and/or headphone conductors. By using the USB port 5464, the need for separate audio connectors, such as tip/ring/sleeve (TRS) connectors, can be eliminated. An adapter can be used that simply electrically connects one or two TRS connectors to the conductors on a USB plug. When the adapter is used, standard headphones and microphones can be used. When an audio device, such as a set of headphones, with or without a microphone, is connected to the USB port 5464, the audio amplifier module 5488 can disable amplification of the microphone 5498 and the speaker 5497.

Figure 114:
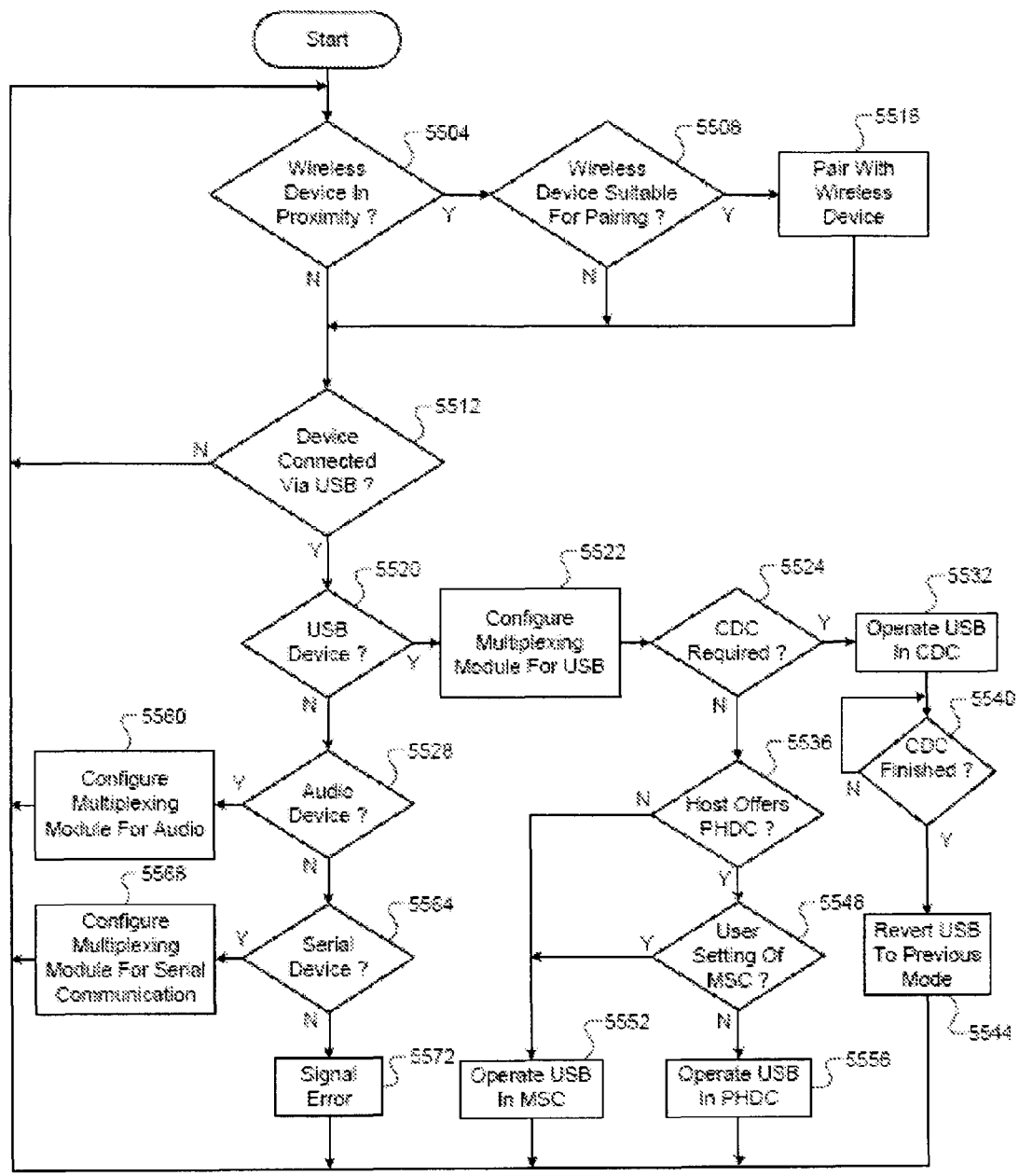
FIG. 114 is a flowchart of example operation of a handheld diabetes management device.
Figure 115:
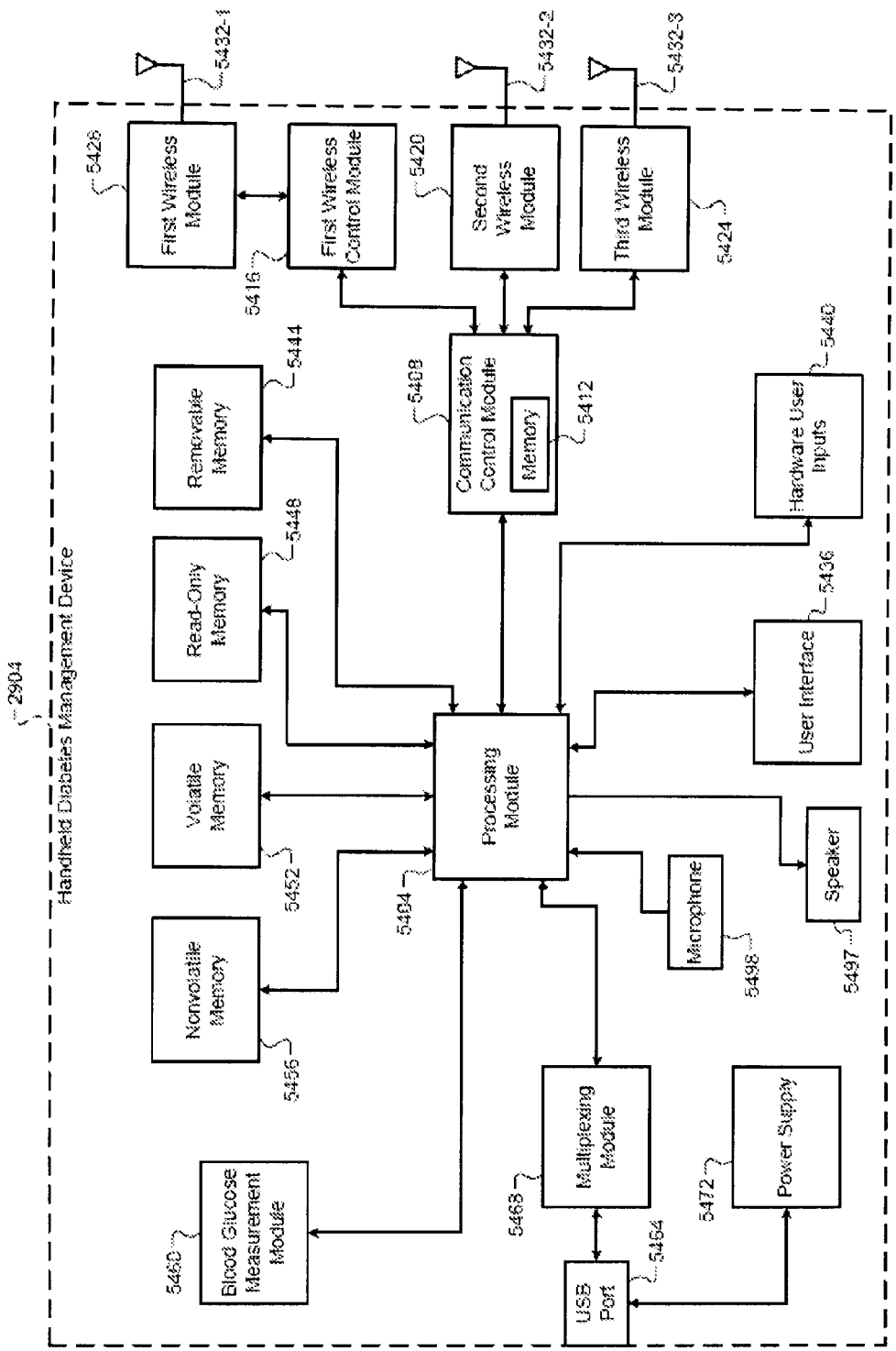
FIG. 115 is a functional block diagram of an example implementation of a handheld diabetes management device.

Referring now to FIG. 114, a flowchart of example operation of the handheld diabetes management device 2904 is presented. Control begins at 5504, where control determines whether a wireless device is in proximity to the handheld diabetes management device 2904. For example, this wireless device can be a Bluetooth device or a device implementing the same proprietary protocol as the first wireless control module 5416. If there is a wireless device in proximity, control transfers to 5508; otherwise, control transfers to 5512.

At 5508, control determines whether the wireless device is suitable for pairing or otherwise interfacing with. If so, control transfers to 5516; otherwise, control transfers to 5512. Wireless devices that are suitable for pairing/interfacing can be specified by manufacturer, device type, and/or authentication codes. For example, pairing with a Bluetooth headset can be disallowed while pairing with an insulin pump is allowed. Compatibility between the insulin pump and the handheld diabetes management device 2904 can be determined before or after pairing. If compatibility is determined after pairing, pairings with incompatible devices can later be terminated. At 5516, control pairs with the suitable wireless device, such as a continuous glucose monitor or an insulin pump. Additionally, pairing can be performed with the PC 2906 and/or the mobile device 5304. Control continues at 5512.

At 5512, control determines whether a device is connected via the USB port. If so, control transfers to 5520; otherwise, control returns to 5504. At 5520, control determines whether the connected device is a USB device. If so, control transfers to 5522; otherwise, control transfers to 5528. At 5522, control configures the multiplexing module for USB operation and continues at 5524. The connected USB device can be referred to as a host.

At 5524, control determines whether the CDC is required or requested. If so, control transfers to 5532; otherwise, control transfers to 5536. For example, the CDC can be required by a test or manufacturing interface and/or a diagnostic/troubleshooting application on a personal computer. At 5532, control switches operation of the USB to the CDC. Control continues at 5540. Control remains at 5540 until use of the CDC is finished, at which point control transfers to 5544. Control determines that use of the CDC is finished when a corresponding indication is received from the host, when a user of the handheld diabetes management device 2904 requests that the CDC operation end, or when the host is disconnected. At 5544, control reverts USB operation to the previous mode (such as the MSC or the PHDC) and returns to 5504.

At 5536, control determines whether the host offers PHDC. If so, control transfers to 5548; otherwise, control transfers to 5552. At 5552, control causes the USB to operate using the MSC. Control then returns to 5504. While operating in the MSC, the host can obtain firmware and/or configuration files that allow the host to offer PHDC. Once PHDC operation is enabled, when control again arrives at 5536, control would then transfer to 5548. At 5548, control determines whether a user setting has requested operation using the MSC. If so, control transfers to 5552; otherwise, control transfers to 5556. At 5556, control operates USB using the PHDC and returns to 5504.

At 5528, control determines whether the attached device is an audio device. If so, control transfers to 5560; otherwise, control transfers to 5564. At 5560, control configures the multiplexing module for audio and returns to 5504. At 5564, control determines whether a non-USB serial device is connected. If so, control transfers to 5568; otherwise, control transfers to 5572. At 5568, control configures the multiplexing module for non-USB serial communication and returns to 5504. At 5572, the type of the connected device does not appear to be one of the recognized devices, and therefore an error is signaled and control returns to 5504.

The present disclosure describes a handheld diabetes management device to provide interconnection options while minimizing a number of physical ports. The handheld diabetes management device includes a blood glucose measurement engine configured to measure blood glucose of a patient and a universal serial bus (USB) port including electrical conductors. The handheld diabetes management device also includes a USB control module, a serial control module that implements a second serial bus protocol, an audio amplifier module, and a multiplexing module electrically connected to the USB port.

The multiplexing module alternatively electrically connects ones of the electrical conductors of the USB port to one of the USB control module, the serial control module, and the audio amplifier. The USB control module is configured to selectively (i) operate using a personal healthcare device class (PHDC) based on information from a host connected to the USB port and (ii) operate using a mass storage class (MSC) based on the information. The handheld diabetes management device also includes a core processing module that communicates data based on the blood glucose measurement to the host via the USB port when the USB control module is operating using the PHDC.

In other features, the handheld diabetes management device further includes a processing module that includes the core processing module, the audio amplifier module, the serial control module, and the USB control module. The second serial bus protocol is based on a universal asynchronous receiver/transmitter (UART). The second serial bus protocol is RS-232. The multiplexing module selects one of the USB control module, the serial control module, and the audio amplifier based on characteristics of a cable connected to the USB port. The USB port is one of a female mini USB port, a female micro USB port, and a female standard USB port.

In further features, the USB control module is further configured to operate using a communication device class (CDC) based on a request from the host. The USB control module prevents operation using the CDC when the host is a computer of the patient. The USB control module operates using Remote Network Driver Interface Specification (RNDIS) based on a request from the host. The USB control module prevents operation using the RNDIS when the host is a computer of the patient.

In still other features, the handheld diabetes management device further includes a wireless communications module that selectively establishes communication with a continuous glucose monitor (CGM) using a proprietary industrial, scientific, and medical (ISM) band wireless interface. The handheld diabetes management device further includes a second wireless communications module that selectively establishes communication with an insulin pump using a Bluetooth wireless interface.

A handheld diabetes management device for providing communication options while minimizing a number of physical connectors includes a blood glucose measurement engine that measures a blood glucose level of a patient. The handheld diabetes management device includes a physical port that includes electrical conductors and that is exposed at an exterior of the handheld diabetes management device. The handheld diabetes management device includes a processing module that provides a user interface to the patient and that includes first, second, and third physical interfaces that are internal to the handheld diabetes management device.

The handheld diabetes management device further includes a multiplexing module that is electrically connected to the physical port and that alternatively electrically connects ones of the electrical conductors to one of the first, second, and third physical interfaces of the processing module. The processing module selectively operates the first physical interface using first and second modes. When an external host is connected to the physical port, the processing module selectively transfers information based on the blood glucose level to the external host using the first mode of the first physical interface. When the external host is connected to the physical port, the processing module selectively provides file access to the external host using the second mode of the first physical interface.

In other features, the physical port is a Universal Serial Bus (USB) port. The first physical interface is a USB interface. The first mode is a personal healthcare device class (PHDC). The second mode is a mass storage device class (MSC). The processing module operates using the second mode when the external host does not offer the first mode. The processing module also selectively operates the first physical interface using a third mode. The third mode is a communications device class (CDC).

In further features, the second and third physical interfaces are a non-USB serial interface and an audio interface, respectively. The handheld diabetes management device further includes first and second wireless interfaces that implement first and second wireless protocols, respectively; and a communication control module that is in communication with the processing module and that controls the first and second wireless interfaces. The communication control module operates the first wireless interface in first and second wireless modes.

In still other features, the first wireless protocol is Bluetooth. The first and second wireless modes are a health device profile (HDP) and a serial port profile (SPP), respectively. The second wireless protocol is a 2.4 GHz wireless interface. The handheld diabetes management device further includes a third wireless interface that implements a third wireless protocol.

Firmware Update in a Medical Device with Multiple Processors

Systems and methods according to the present disclosure offer a failsafe firmware upgrading protocol. The protocol retains previous versions of firmware so that if new versions fail to work correctly, operation can revert to the previous versions. In addition, the entire firmware of each processor or module is upgraded at once to avoid errors in integrating new upgrades with old software. Further, the present disclosure describes backing up user information from the device, and then adding the user information into newly created databases. This allows new and improved database structures to be defined without orphaning previous data. This also ensures that, at each upgrade, the databases are properly structured, and cumulative data and/or format corruption is avoided. One processor can serve as the central hub, and may write software to additional processors. In fact, the one processor can use one of the other processors as a pass-through to program one or more additional processors.

Referring now to FIG. 75, a patient 2900 with diabetes and a clinician 2902 are shown in a clinic environment. The term 'patient' encompasses persons with metabolic syndrome, pre-diabetes, type 1 diabetics, type 2 diabetics, and gestational diabetics. The term 'clinician' is used broadly to include nurses, nurse practitioners, physicians, endocrinologists, etc.

During a healthcare consultation, the patient 2900 typically shares with the clinician 2902 a variety of patient data including blood glucose measurements, continuous glucose monitor data, amounts of insulin infused, amounts of food and beverages consumed, exercise schedules, and other lifestyle information. The clinician 2902 can obtain additional patient data that includes measurements of HbA1C, cholesterol levels, triglycerides, blood pressure, and weight. The patient data can be recorded manually and/or can be recorded electronically on a handheld diabetes management device 2904, diabetes analysis software executed on a computing device such as a personal computer (PC) 2906, and/or a web-based diabetes analysis site (not shown). The term PC, as used herein, includes computers using a Microsoft operating system as well as computers using an Apple operating system, Linux, OpenBSD, Ubuntu, etc.

The clinician 2902 can analyze the patient data manually and/or can analyze the patient data electronically using the diabetes analysis software and/or the web-based diabetes analysis site. After analyzing the patient data and reviewing adherence of the patient 2900 to previously prescribed therapy, the clinician 2902 can decide whether to modify the therapy for the patient 2900.

Referring now to FIG. 76, the patient 2900 can use a continuous glucose monitor (CGM) 2910, an ambulatory durable insulin pump 2912, an ambulatory non-durable insulin pump 2914, and the handheld diabetes management device 2904. In various implementations, the durable insulin pump 2912 and the non-durable insulin pump 2914 can be used interchangeably, and the handheld diabetes management device 2904 can be configured to interact with whichever of the insulin pumps 2912 or 2914 is currently in use. In various implementations, if both the insulin pumps 2912 and 2914 are worn by the patient 2900, the handheld diabetes management device 2904 can communicate with only one of the insulin pumps 2912 or 2914. In various other implementations, the handheld diabetes management device 2904 can communicate with both of the insulin pumps 2912 and 2914. The insulin pumps 2912 and 2914 will be referred to collectively as insulin pump 2912.

The CGM 2910 uses a subcutaneous sensor to sense and monitor the amount of glucose in the blood of the patient 2900 and communicates corresponding readings to the handheld diabetes management device 2904. The handheld diabetes management device 2904 performs various tasks including measuring and recording blood glucose levels, determining an amount of insulin to be administered to the patient 2900 via the insulin pump 2912, receiving patient data via a user interface, archiving the patient data, etc. When the CGM 2910 is in use, the handheld diabetes management device 2904 periodically receives readings from the CGM 2910 indicating glucose level in the blood of the patient 2900. When the insulin pump 2912 is in use, the handheld diabetes management device 2904 transmits instructions to the insulin pump 2912, which delivers insulin to the patient 2900. Insulin can be delivered in a scheduled manner at a basal rate, which attempts to maintain a predetermined insulin level in the blood of the patient 2900. Additionally, insulin can be delivered in the form of a bolus dose, which raises the amount of insulin in the blood of the patient 2900 by a predetermined amount.

Referring now to FIG. 112, a diabetes management system used by the patient 2900 and the clinician 2902 includes one or more of the following devices: the handheld diabetes management device 2904, the CGM 2910, the insulin pump 2912, the PC 2906 with the diabetes analysis software, a mobile device 5304, and other healthcare devices represented collectively at 5312. The handheld diabetes management device 2904 is configured as a system hub and communicates with the devices of the diabetes management system. Alternatively, the insulin pump 2912 or the mobile device 5304 can be configured as the system hub. Communication between the devices in the diabetes management system can be performed using wireless interfaces (e.g., Bluetooth) and/or wireline interfaces (e.g., USB). For example, one of versions 1.1, 1.2, 2.0, 2.1, 3.0, and 4.0 of the Bluetooth standard can be used.

Communication protocols used by these devices can include protocols compliant with the IEEE 11073 standard, which can be extended using guidelines provided by Continua® Health Alliance Design Guidelines. For example, IEEE 11703-20601 Optimized Exchange Protocol with the IEEE 11073-10417 Blood Glucose Device Specialization standards can be used. In addition, the device specialization can be supplemented by predefined Roche proprietary communications protocols, which for example can include additional measurement objects. Further, healthcare records systems such as Microsoft® HealthVault™ and Google™ Health can be used by the patient 2900 and/or the clinician 2902 to exchange information.

The handheld diabetes management device 2904 can receive blood glucose readings from one or more sources, such as the CGM 2910. The CGM 2910 continuously measures the blood glucose level of the patient 2900. The CGM 2910 periodically communicates the blood glucose level to the handheld diabetes management device 2904. In various implementations, the handheld diabetes management device 2904 and the CGM 2910 communicate wirelessly.

Additionally, the handheld diabetes management device 2904 includes blood glucose meter (BGM) functionality. The handheld diabetes management device 2904 can measure glucose levels from a sample from the patient 2900. For example, in various implementations, the handheld diabetes management device 2904 can receive a blood glucose measurement strip 5308. The patient 2900 deposits a sample of blood or other bodily fluid on the blood glucose measurement strip 5308. The handheld diabetes management device 2904 analyzes the sample to determine the blood glucose level in the sample. The blood glucose level measured from the sample and/or the blood glucose level read by the CGM 2910 can be used in determining the amount of insulin to be administered to the patient 2900.

The handheld diabetes management device 2904 communicates with the insulin pump 2912. The insulin pump 2912 can be configured to receive instructions from the handheld diabetes management device 2904 to deliver a predetermined amount of insulin to the patient 2900. Additionally, the insulin pump 2912 can receive additional information including meal and/or exercise schedules of the patient 2900. In various implementations, the insulin pump 2912 can determine the amount of insulin to administer based on the additional information.

The insulin pump 2912 can also communicate data to the handheld diabetes management device 2904. The data can include amounts of insulin delivered to the patient 2900, corresponding times of delivery, and pump status. In various implementations, the handheld diabetes management device 2904 and the insulin pump 2912 can communicate wirelessly.

In addition, the handheld diabetes management device 2904 can communicate with the other healthcare devices 5312. For example, the other healthcare devices 5312 can include a blood pressure meter, a weight scale, a pedometer, a fingertip pulse oximeter, a thermometer, etc. The other healthcare devices 5312 obtain and communicate personal health information of the patient 2900 to the handheld diabetes management device 2904 through wireless, USB, or other interfaces. The other healthcare devices 5312 can use communication protocols compliant with ISO/IEEE 11073 extended using guidelines from Continual® Health Alliance. Further, the devices of the diabetes management system can communicate with each other via the handheld diabetes management device 2904.

The handheld diabetes management device 2904 can communicate with the PC 2906 using Bluetooth, USB, or other interfaces. Diabetes management software running on the PC 2906 includes an analyzer-configurator that stores configuration information of the devices of the diabetes management system. The configurator has a database to store configuration information of the handheld diabetes management device 2904 and the other devices. The configurator can communicate with users through web pages or computer screens in non-web applications. The configurator transmits user-approved configurations to the devices of the diabetes management system. The analyzer retrieves data from the handheld diabetes management device 2904, stores the data in a database, and outputs analysis results through standard web pages or computer screens in non-web based applications.

The handheld diabetes management device 2904 can communicate with the mobile device 5304 using wired or wireless protocols, such as Bluetooth. Examples of the mobile device 5304 include a cellular phone, a pager, a personal digital assistant (PDA), a tablet computing device, etc. The mobile device 5304 can communicate with a network, such as a distributed communications system 5316. In various implementations, the distributed communications system 5316 can be the Internet. The handheld diabetes management device 2904 can send and receive messages, including data and instructions, to the distributed communications system 5316 via the mobile device 5304.

The PC 2906 includes a USB port 5320 and/or a wireless module 5324. A processor 5328 controls communications over the USB port 5320 and/or the wireless module 5324. The processor 5328 can execute instructions from memory 5332. Further, the PC 2906 includes a network interface 5336, which can be wired, such as Ethernet, or wireless, such as WiFi (including 802.11a, b, g and/or n). The network interface 5336 can communicate with the distributed communications system 5316. The PC 2906 can therefore also serve as an intermediary between the distributed communications system 5316 and the handheld diabetes management device 2904. The PC 2906 and the handheld diabetes management device 2904 can communicate using USB and using a wireless protocol, such as Bluetooth. In various implementations, the wireless protocol can be a network protocol, such as WiFi. In such implementations, functionality of the wireless module 5324 and the network interface 5336 can be combined into a single module.

When the handheld diabetes management device 2904 is connected via USB to the PC 2906, the handheld diabetes management device 2904 can charge an internal power supply, such as a rechargeable battery. The PC 2906 can be replaced by any other device having sufficient processing capability, such as a laptop, a netbook, or a tablet computing device. The PC 2906 can execute software stored in nonvolatile storage of the PC 2906. For example only, some or all of the memory 5332 can be nonvolatile. Additionally or alternatively, other nonvolatile storage media can be present, such as flash memory, magnetic storage, and optical storage.

The PC 2906 can execute specialized software corresponding to the handheld diabetes management device 2904 and can execute general purpose software that can interact with the handheld diabetes management device 2904. The PC 2906 can also execute software provided by the handheld diabetes management device 2904. The software provided by the handheld diabetes management device 2904 can then be stored persistently on the PC 2906 or can be removed when the PC 2906 is no longer in communication with the handheld diabetes management device 2904. In various implementations, the software provided by the handheld diabetes management device 2904 can be low- or zero-footprint software such that when the handheld diabetes management device 2904 is no longer in communication with the PC 2906, traces of the software, such as files and settings, are not left behind on the PC 2906.

The PC 2906 can also acquire software via the distributed communications system 5316, such as from a server platform 5340. For example, the server platform 5340 can provide web server functionality. The PC 2906 can download and execute software from the server platform 5340. In various implementations, the downloaded software can be web-based, such as a Java or Flash application. The local applications can communicate data and instructions with the server platform 5340. In addition, the PC 2906 can interact with a server-side application executed by the server platform 5340. The remote and local applications may be known collectively as Accu-Chek 360°.

The applications can have varying functionality and access authorizations. For example, some applications can be authorized to access historical data from the handheld diabetes management device 2904, while other applications can be authorized to control operation of the handheld diabetes management device 2904, such as glucose measurement settings and insulin pump settings. In various implementations, the applications can also control other devices, such as the insulin pump 2912 and the CGM 2910, via the handheld diabetes management device 2904. For example, the applications can update firmware, retrieve configuration settings and error codes, and provide configuration settings. The applications can also control firmware updates of the handheld diabetes management device 2904 itself.

The server platform 5340 can include one or more physical servers having multiple processors, but logically includes at least a processor 5344 that executes instructions from memory 5348 and communicates with the distributed communications system 5316 via a network interface 5352. Further, the processor 5344 communicates with a database engine 5356, which can be executed by a separate processor and memory and/or by the processor 5344 itself, such as in a virtual machine.

The database engine 5356 stores one or more databases, which can track firmware versions of the handheld diabetes management device 2904 as well as associated devices, such as the CGM 2910 and the insulin pump 2912. The database engine 5356 can store contact information for the patient 2900 so that, for example, firmware updates and other alerts can be communicated to the patient 2900. The database engine 5356 can also store historical data from the handheld diabetes management device 2904. The stored data can be used for remote access by the patient 2900, the clinician 2902, or in the case of a failure or erasure of the handheld diabetes management device 2904.

The database engine 5356 can also store language settings and localizations for various regions, and can track which of these languages are installed in the handheld diabetes management device 2904. The database engine 5356 can also store food and exercise databases that indicate the corresponding effect on blood sugar of various foods and activities. These databases can be supplemented by data entered by the patient 2900 and/or the clinician 2902 via the handheld diabetes management device 2904 or via some other interface such as one presented by the PC 2906. The database engine 5356 can also store user preferences for the handheld diabetes management device 2904 as well as treatment parameters for the handheld diabetes management device 2904, such as equations and/or constants for calculating amounts of insulin.

A number of device classes are defined for use with the USB protocol. In various implementations, the handheld diabetes management device 2904 implements the mass storage device class (MSC) and the personal healthcare device class (PHDC). In various implementations, the handheld diabetes management device 2904 also implements the communications device class (CDC) and/or the remote network driver interface specification (RNDIS).

The MSC is used to access raw data, such as files and file systems. For example only, USB flash drives and memory card readers for digital cameras and video-cameras generally implement the MSC. The MSC is supported by a wide variety of operating systems, including Microsoft Windows, which has offered native support for MSC since Windows 2000. In various implementations, the handheld diabetes management device 2904 can also implement the media transfer protocol (MTP), which also allows file access.

In various implementations, the handheld diabetes management device 2904 stores blood glucose data, insulin data, exercise data, and food data as files that can be accessed via the MSC. The handheld diabetes management device 2904 can also store software for use by the PC 2906. In addition, the handheld diabetes management device 2904 can store documentation, such as health files, frequently asked questions files, and training videos and podcasts.

The handheld diabetes management device 2904 can store web pages and other interactive content. For example only, the handheld diabetes management device 2904 can store a start webpage, from which a user can access other information and options. The handheld diabetes management device 2904 can be configured so that the start webpage or a startup program is automatically executed when the handheld diabetes management device 2904 is connected to an appropriately configured computer. The startup program can provide the option of installing the necessary components for PHDC support. To allow access via the MSC, the handheld diabetes management device 2904 can implement a FAT32 file system or another file system, such as FAT, HFS Plus, and Ext2.

The PC 2906 may not natively support the PHDC. For example, drivers and/or configuration files may be required prior to the PC 2906 supporting communication with the handheld diabetes management device 2904 using the PHDC. The handheld diabetes management device 2904 can therefore store various drivers and configuration files to support the PHDC operation for one or more operating systems. The PHDC was designed to allow interoperability between medical devices, and can support IEEE 11073 operation. The PC 2906 can communicate with the handheld diabetes management device 2904 using the PHDC in order to obtain medical data, such as blood glucose readings and historical insulin injection records. The PC 2906 can also use the PHDC to read and command basal rate and bolus parameters.

The handheld diabetes management device 2904 can implement the CDC to allow direct communication between the PC 2906 and various components of the handheld diabetes management device 2904. The CDC allows a variety of pre-existing communication protocols, such as serial protocols and network protocols, to be carried over USB. For example only, the PC 2906 can communicate with an internal component of the handheld diabetes management device 2904 using the CDC. Additionally, the PC 2906 can use the CDC to communicate with other devices, such as the CGM 2910 and the insulin pump 2912, via the handheld diabetes management device 2904. In addition, the CDC can be used during manufacturing, testing, calibration, and repair. For example, the CDC can be used by a specialized test environment, such as a test stand, and/or by a computer having specialized software. In various implementations, end users are prevented from using the CDC. Additionally or alternatively to implementing the CDC, the Remote Network Driver Interface Specification (RNDIS) can be used. RNDIS is a specification for supporting network devices over USB, and is supported natively in some Microsoft operating systems.

As discussed above, the handheld diabetes management device 2904 can communicate with the PC using a wireless protocol such as Bluetooth. Although Bluetooth is described herein for purposes of illustration only, other protocols can be used, such as ZigBee or Bluetooth low energy. Similar to the classes of USB, profiles are defined for Bluetooth. For example, the handheld diabetes management device 2904 can implement a serial port profile (SPP) and/or a health device profile (HDP). The SPP defines protocols and procedures to allow devices to emulate a serial protocol, such as RS-232, using Bluetooth.

In various implementations, the SPP can be used in similar scenarios as the CDC of USB. For example, the SPP can be used by the PC 2906 to communicate with the CGM 2910 and/or the insulin pump 2912 via the handheld diabetes management device 2904. Further, the handheld diabetes management device 2904 can use the SPP to communicate with the CGM 2910 and the insulin pump 2912. For example only, the SPP can be used for configuration and updating of the CGM 2910 and the insulin pump 2912. The handheld diabetes management device 2904 can use the HDP for supplying and receiving medical data to and from the CGM 2910 and the insulin pump 2912, such as blood glucose readings and insulin doses.

The HDP can be used in conjunction with IEEE 11073. The HDP can be used when transmitting medical information from the handheld diabetes management device 2904 to the PC 2906. The medical information can include glucose readings, exercise data, and food data from handheld diabetes management device 2904 as well as glucose readings from the CGM 2910 and insulin dosing history from the insulin pump 2912.

Referring now to FIG. 113, a functional block diagram of an example implementation of the handheld diabetes management device 2904 is presented. The handheld diabetes management device 2904 includes a processing module 5404, such as the i.MX233 applications processor from Freescale Semiconductor, Inc. The processing module 5404 communicates with a communication control module 5408, such as an STM32F103 32-bit ARM Cortex microcontroller unit from ST Microelectronics. For example only, the communication control module 5408 includes memory 5412 having volatile and nonvolatile components. For example only, the communication control module 5408 includes 512 KB of flash memory and 64 KB of random access memory (RAM).

The processing module 5404 and the communication control module 5408 can communicate using universal asynchronous receiver/transmitters (UARTs). In various implementations, a level shifter or a voltage transformer is interposed between the processing module 5404 and the communication control module 5408 to match signal levels of the respective UARTs. The communication control module 5408 controls wireless communication. In various implementations, the communication control module 5408 controls a first wireless control module 5416 and a second wireless module 5420. In various implementations, the communication control module 5408 also controls a third wireless module 5424.

The first wireless control module 5416 controls a first wireless module 5428, which can implement RF processing and/or baseband processing. Antennas 5432-1, 5432-2, and 5432-3 are illustrated as being connected to the first wireless module 5428, the second wireless module 5420, and the third wireless module 5424, respectively. However, more or fewer antennas can be used. When fewer antennas are used, access to the antenna can be multiplexed and/or different frequency operating ranges can allow antenna to be used by different modules simultaneously. Further, RF and/or baseband processing can be shared between modules. In various implementations, the first wireless control module 5416 can subsume the functionality of the first wireless module 5428.

The first wireless control module 5416 can implement encryption, such as the advanced encryption standard (AES), to prevent eavesdropping and other malicious activity from affecting the wireless communication. The first wireless control module 5416 can implement a proprietary wireless protocol operating in a specified frequency band, such as the 2.4 GHz industrial, scientific, and medical (ISM) band. For example, the first wireless control module 5416 can be an nRF24LE1™ ultra-low-power wireless system-on-chip solution from Nordic Semiconductor, Inc.

The second wireless module 5420 can implement a wireless personal area network (WPAN) protocol such as Bluetooth, Bluetooth low energy, or Zigbee. For example only, the second wireless module 5420 can be a BL6450 controller from Texas Instruments. When present, the third wireless module 5424 can implement another proprietary wireless protocol and/or a wireless local area network (WLAN) protocol, such as IEEE 802.11(a, b, g, and/or n).

The processing module 5404 communicates with a user interface 5436, which can include a liquid crystal display (LCD) touchscreen, which can be backlit by light-emitting diodes (LEDs). For example only, the touchscreen can be a WQVGA (400×240) 3-inch screen. The processing module 5404 can receive hardware user inputs 5440. For example only, the hardware user inputs can include buttons and switches, such as a microswitch for performing a hardware reset. The microswitch can be recessed to prevent accidental actuation.

The processing module 5404 can communicate with removable memory 5444, such as flash storage, including secure digital (SD), compact flash (CF), and other flash storage technologies. For example, the removable memory 5444 can be a microSD card. The removable memory 5444 can be used to store the software, instructional material, and drivers to be provided to the PC 2906 and/or the mobile device 5304.

The processing module 5404 also communicates with read-only memory 5448. The read-only memory 5448 can include an electrically erasable programmable read-only memory (EEPROM). The processing module 5404 communicates with volatile memory 5452, such as synchronous dynamic random access memory (SDRAM). The processing module 5404 communicates with nonvolatile memory 5456, such as NAND flash memory. In various implementations, some or all of the read-only memory 5448, the volatile memory 5452, and the nonvolatile memory 5456 can be incorporated on the same die or in the same package as the processing module 5404.

The processing module 5404 communicates with a blood glucose measurement module 5460, which analyzes a sample from the patient 2900 to determine a glucose level in the patient's blood. For example only, the blood glucose measurement module 5460 can dispense test strips to which a blood sample is applied. In various implementations, the blood glucose measurement module 5460 processes readings from the sample and provide a blood glucose number to the processing module 5404. Alternatively, the blood glucose measurement module 5460 can provide raw data to the processing module 5404, which determines a blood glucose level based on the raw data.

The handheld diabetes management device 2904 includes a USB port 5464. For example, the USB port 5464 can be a standard USB port, a micro USB port, or a mini USB port. Specifically, the USB port 5464 can be a micro-B female port. The small size of the micro-B port offers less area for potential fluid or other contaminant intrusion, and allows a physical size of the handheld diabetes management device 2904 to be minimized.

To reduce the number of physical ports required in the handheld diabetes management device 2904, a multiplexing module 5468, such as an MC34825 from Freescale Semiconductor, Inc., is connected to the USB port 5464. The multiplexing module 5468 can allow the USB port 5464 to be used for USB purposes, for a non-USB serial interface, and for an audio interface. In addition, a power supply 5472 can be connected to the USB port 5464. The power supply 5472 can include a battery, such as a lithium ion rechargeable battery, which provides power to components of the handheld diabetes management device 2904.

The power supply 5472 can be recharged via the USB port 5464. In various implementations, the power supply 5472 can be recharged when the USB port 5464 is connected to the PC 2906 and/or a powered USB hub. In addition, a separate adapter can be used to recharge the power supply 5472 via the USB port 5464. In various implementations, the current required by the power supply 5472 is greater than can be provided by a computer, and charging therefore requires the charging adapter. The charging adapter can be integrated with a stand that retains the handheld diabetes management device 2904 and also allows interaction with the user interface 5436 of the handheld diabetes management device 2904. Charging using the USB port 5464 allows a separate charging port to be eliminated.

In various implementations, the multiplexing module 5468 can analyze cables and/or devices connected to the USB port 5464. For example only, termination resistances, pull-up resistances, and pull-down resistances of cables and/or devices attached to the USB port 5464 can indicate to the multiplexing module 5468 the type of device connected to the USB port 5464. When the multiplexing module 5468 determines that a USB device is attached, the multiplexing module 5468 can connect the USB port 5464 to a USB interface of the processing module 5404.

Similarly, the multiplexing module 5468 can connect the USB port 5464 to a serial interface when a non-USB serial device is determined to be connected to the USB port 5464. The multiplexing module 5468 connects the USB port 5464 to an audio interface when an audio device is determined to be connected to the USB port 5464.

The processing module 5404 determines whether the USB interface should be operating using the PHDC, the MSC, the CDC, or another class. After manufacturing, the processing module 5404 can initially control the USB interface to operate using the CDC. This mode can be used for programming, configuration, calibration, and testing. The processing module 5404 can then control the USB interface to operate using the MSC prior to providing the handheld diabetes management device 2904 to the patient 2900. Repair and testing facilities can provide signals and/or commands to the processing module 5404 to indicate that CDC is once again required, such as if the handheld diabetes management device 2904 is returned for servicing.

When the handheld diabetes management device 2904 is with the patient 2900, the processing module 5404 can set the USB interface to use the MSC by default. However, if it is determined that the device connected to the USB port 5464 has the necessary drivers and configuration to use the PHDC, the processing module 5404 can set the USB interface to use the PHDC. A user of the handheld diabetes management device 2904 and user of the connected device can override this operation and cause the processing module 5404 to maintain the USB interface using the MSC. The MSC can allow the USB interface to provide access to the removable memory 5444. When operating using the CDC, the USB interface can communicate with, for example, the blood glucose measurement module 5460 and/or with the communication control module 5408.

The serial interface implements a non-USB protocol, such as the inter-integrated circuit ($I^2C$) protocol, General Purpose Input/Output (GPIO), and/or RS-232. The non-USB serial protocol can be used during manufacturing and testing by test equipment that has a serial interface. By multiplexing the non-USB pins onto the USB port 5464, the need for a separate serial port, such as a 9-pin DE-9, can be eliminated.

The processing module 5404 can include an audio amplifier for powering a speaker 5497 and an audio amplifier for amplifying signals from a microphone 5498. The processing module 5404 can convert analog microphone signals into digital and converts digital sound signals into analog signals for playback. For example only, the microphone 5498 can be used to record journal entries corresponding to insulin doses, exercise, meals, and blood glucose readings. The speaker 5497 can be used to play back journal entries and/or to play audio and video files, such as instructional videos. The audio and video files can be stored in the removable memory 5444.

The audio interface is selectively connected to the USB port 5464 by the multiplexing module 5468. The pins of the USB port 5464 are thereby used as microphone and/or headphone conductors. By using the USB port 5464, the need for separate audio connectors, such as tip/ring/sleeve (TRS) connectors, can be eliminated. An adapter can be used that simply electrically connects one or two TRS connectors to the conductors on a USB plug. When the adapter is used, standard headphones and microphones can be used. When an audio device, such as a set of headphones, with or without a microphone, is connected to the USB port 5464, the processing module 5404 can disable amplification of the microphone 5498 and the speaker 5497.

Figure 116:
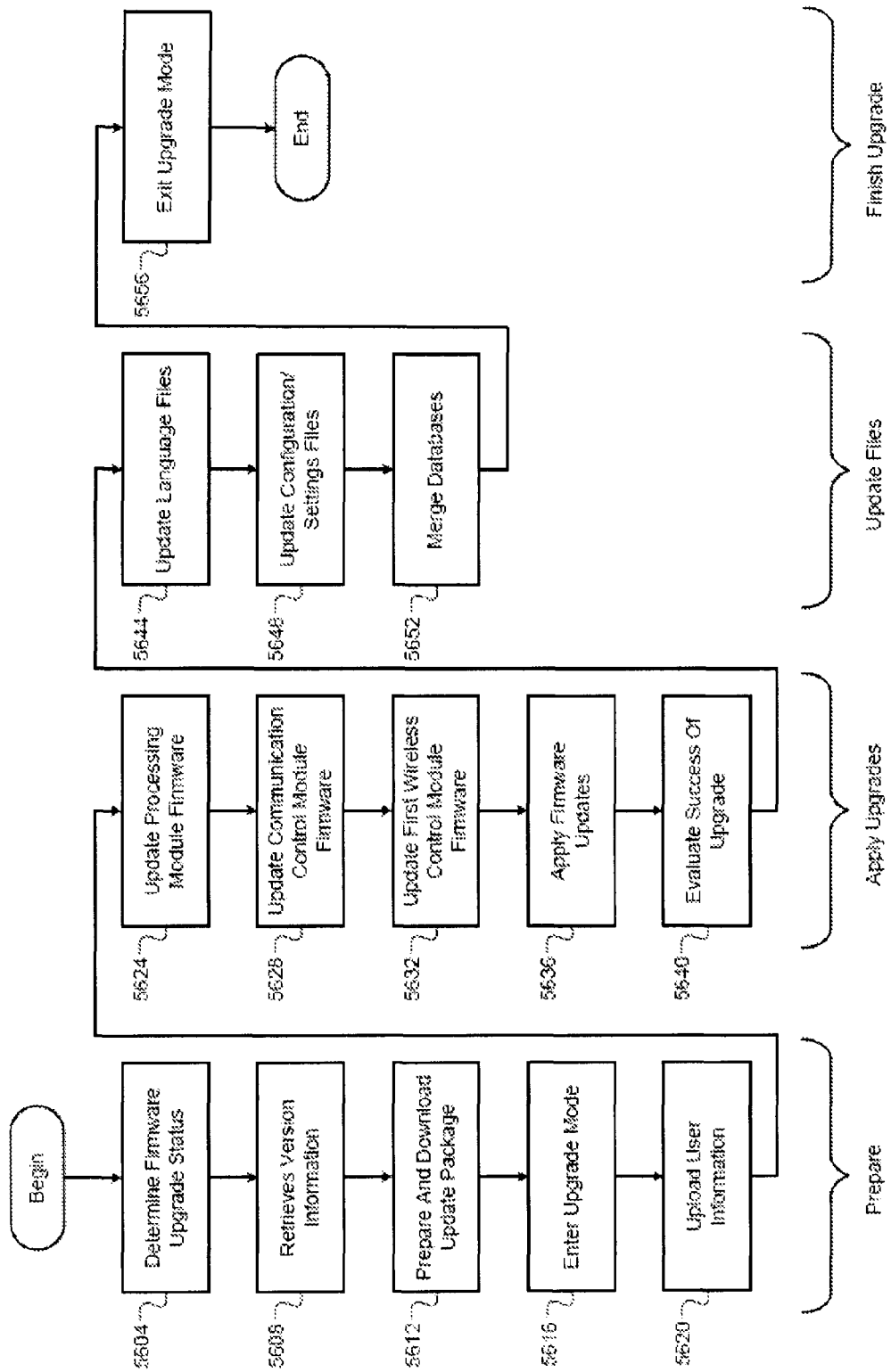
FIG. 116 is a flowchart depicting an overview of example firmware upgrading operation.

Referring now to FIG. 116, a flowchart depicts an overview of exemplary firmware upgrading operation. Control begins at 5604 when a firmware upgrade is requested. The firmware upgrade can be requested by the patient 2900, the clinician 2902, another user, and/or a periodic upgrade checking process. In addition, in various implementations, a firmware upgrade can be requested by software running on the PC 2906, the mobile device 5304, or the server platform 5316.

For example, a person, such as the patient 2900 or the clinician 2902, can request an upgrade in response to receiving a notification that the upgrade is available. The notification can be sent in the form of an email, a letter, a phone call, a text message, a notice on a website, and/or a notice generated by software running on the PC 2906. Control operations in FIGS. 116 and 6A-6E can be shared between the handheld diabetes management device 2904 and remote software, which can be executing on the PC 2906, the mobile device 5304, and/or the server platform 5316, or a combination thereof. Some operational tasks are performed only by one of these entities, while other tasks are shared between the entities. For purposes of illustration only, some operational tasks will be described as being assigned to only one of the entities. However, depending on implementation details, business rules, and regulatory requirements, tasks can be reassigned and/or reapportioned among the entities.

Figure 117A:
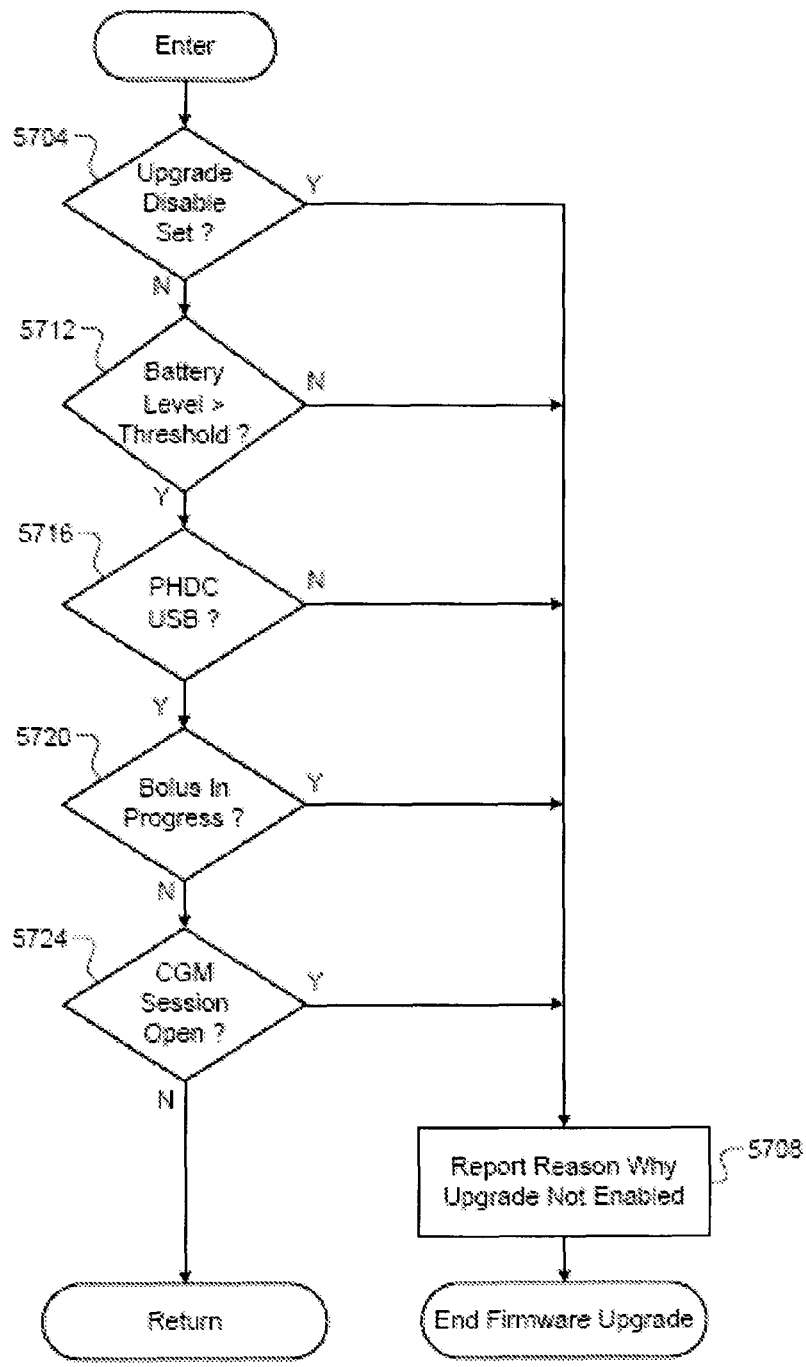
FIGS. 117A-117E are flowcharts depicting example operation of portions of the firmware upgrading of FIG. 116.

At 5604, control determines the current upgrade status. If the preconditions for performing an upgrade are met, a firmware upgrade is currently possible and control continues at 5608; otherwise, control indicates the reasons for why the upgrade is currently not allowed and ends the upgrade. Control can also provide an indication, such as to the patient 2900, clinician 2902, or remote software regarding what steps can be taken to reach a status where the firmware upgrade is allowed. An example implementation of 5604 is shown in FIG. 117A.

At 5608, control retrieves version information. The version information can include versions of software residing on components of the handheld diabetes management device 2904, versions of hardware components of the handheld diabetes management device 2904, and hardware and software versions of associated devices, such as the CGM 2910 and the insulin pump 2912. Version information can also include versions of communication interfaces, database files, language files, and configuration files. Version information can also include serial numbers and model numbers of the handheld diabetes management device 2904 and any recently associated devices. The version information can be used locally by the handheld diabetes management device 2904 or transmitted to the remote software.

Control continues at 5612, where control prepares and selectively downloads an update package. Control determines whether newer versions exist of any of the items indicated by the version information of 5608. In various implementations, some of the version information indicates versions of components, such as hardware components, read-only memories, and low-level software such as boot loaders, that cannot be upgraded. The version information of these components can be used to determine compatibility of available software upgrades.

In addition, upgrade dependencies can be present. For example, software on the CGM 2910 and/or the insulin pump 2912 may need to be updated prior to updating the handheld diabetes management device 2904. Control can require that any currently or recently associated (or, 'paired' in the context of Bluetooth) devices be upgraded to maintain compatibility with upgraded software in the handheld diabetes management device 2904. If the handheld diabetes management device 2904 has historically been paired or associated with devices for which upgrades would be necessary, but which have not bee used recently, control can report this potential incompatibility.

In cases where the patient 2900 is no longer making use of such device, control can proceed with the upgrade as the potential incompatibility of that device is irrelevant. Upgrades to attached devices can be performed at this time, prior to performing any further upgrade tasks on the handheld diabetes management device 2904. In various implementations, devices such as the CGM 2910 and the insulin pump 2912 can be upgraded via the handheld diabetes management device 2904. For example, USB passthrough can be used to communicate between the PC 2906 and the CGM 2910 and/or the insulin pump 2912. In various implementations, control can upgrade the CGM 2910 and the insulin pump 2912 even when no upgrades are present and/or applied to the handheld diabetes management device 2904.

If any upgrades are present for the handheld diabetes management device 2904, control acquires each portion of the upgrade and assembles them into an upgrade package. For example only, the individual portions can be verified using an integrity check, such as a cyclic redundancy check (CRC) and/or a hash, such as a cryptographic hash. The upgrade components can also be verified using a cryptographic signature, such as a hash of the component encrypted by a private key, the corresponding public key being known by control.

Figure 117B:
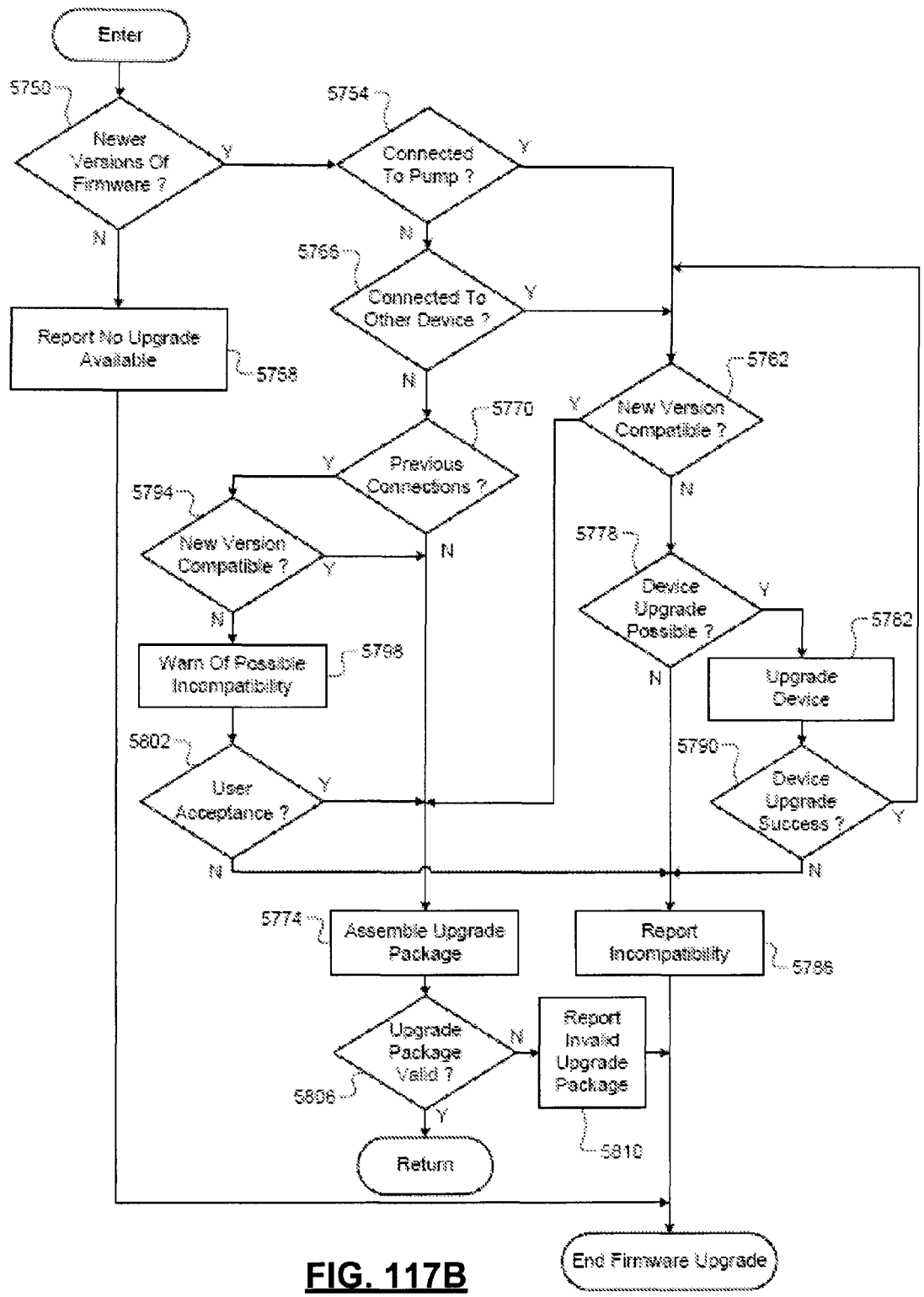

In various implementations, license agreements and/or warnings and/or instructions are presented prior to assembling the update package. In implementations where the handheld diabetes management device 2904 has not assembled the update package, control then initiates a transfer of the update package to the handheld diabetes management device 2904. An example implementation of 5612 is shown in FIG. 117B.

Control continues at 5616 and enters upgrade mode. In upgrade mode, the handheld diabetes management device 2904 automatically attempts to reestablish communication with the remote software if communication is lost, such as upon a reboot. In various implementations, upgrade mode suspends all non-upgrade functionality of the handheld diabetes management device 2904, including suspending blood glucose measurements, test strip dispensing, and user interface interaction. Control can also close all databases, which can include configuration and settings databases.

Figure 117C:
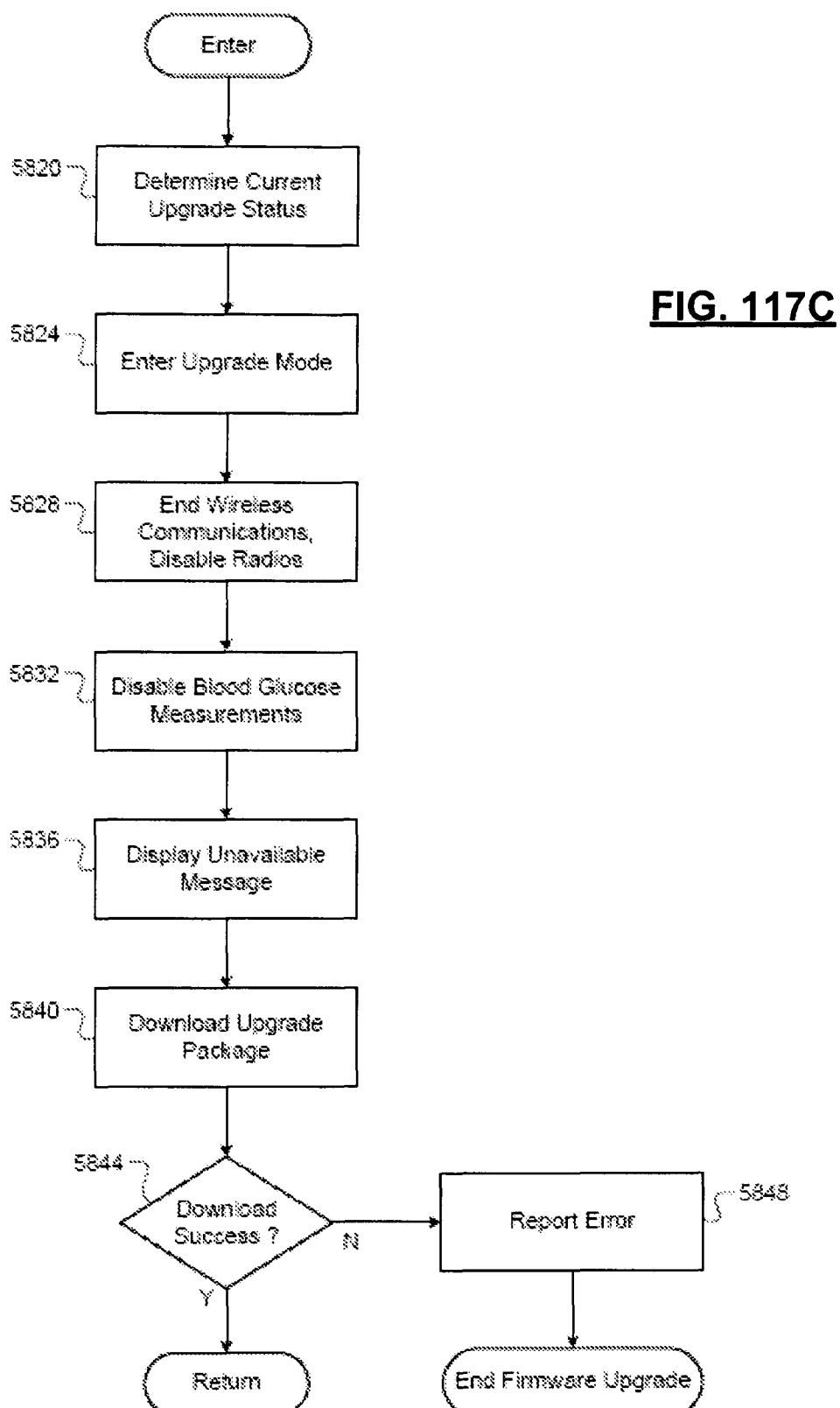

Control also ends wireless communications and disables all radios. In implementations where communication with the remote software is being performed over a wireless connection, the corresponding wireless radio remains enabled. The handheld diabetes management device 2904 remains in upgrade mode until instructed to leave upgrade mode by the remote software. In various implementations, while in upgrade mode, if a software or hardware reset occurs, the handheld diabetes management device 2904 can skip all normal checks and internal tests and attempt to reestablish communication with the remote software as quickly as possible and without user interaction. An example implementation of 5616 is shown in FIG. 117C.

Control continues at 5620, where user information is uploaded to the remote software. The user information can include confirmation and setting information, food, exercise, blood glucose, and insulin data. In various implementations, some or all of this data can be backed up to the server platform 5316. In various implementations, some or all of the user information is already backed up to mitigate the effects of loss or damage to the handheld diabetes management device 2904. The backup can be user-initiated or occur during clinic visits or on a periodic schedule. Operation at 5604, 5608, 5612, 5616, and 5620 can be considered to be part of a preparation phase.

Control then continues at 5624. At 5624, control updates, if necessary, firmware of the processing module 5404. Control can verify once again that the handheld diabetes management device 2904 is in upgrade mode. Then control also verifies the integrity and authenticity of the upgrade package on the handheld diabetes management device 2904.

Figure 117D:
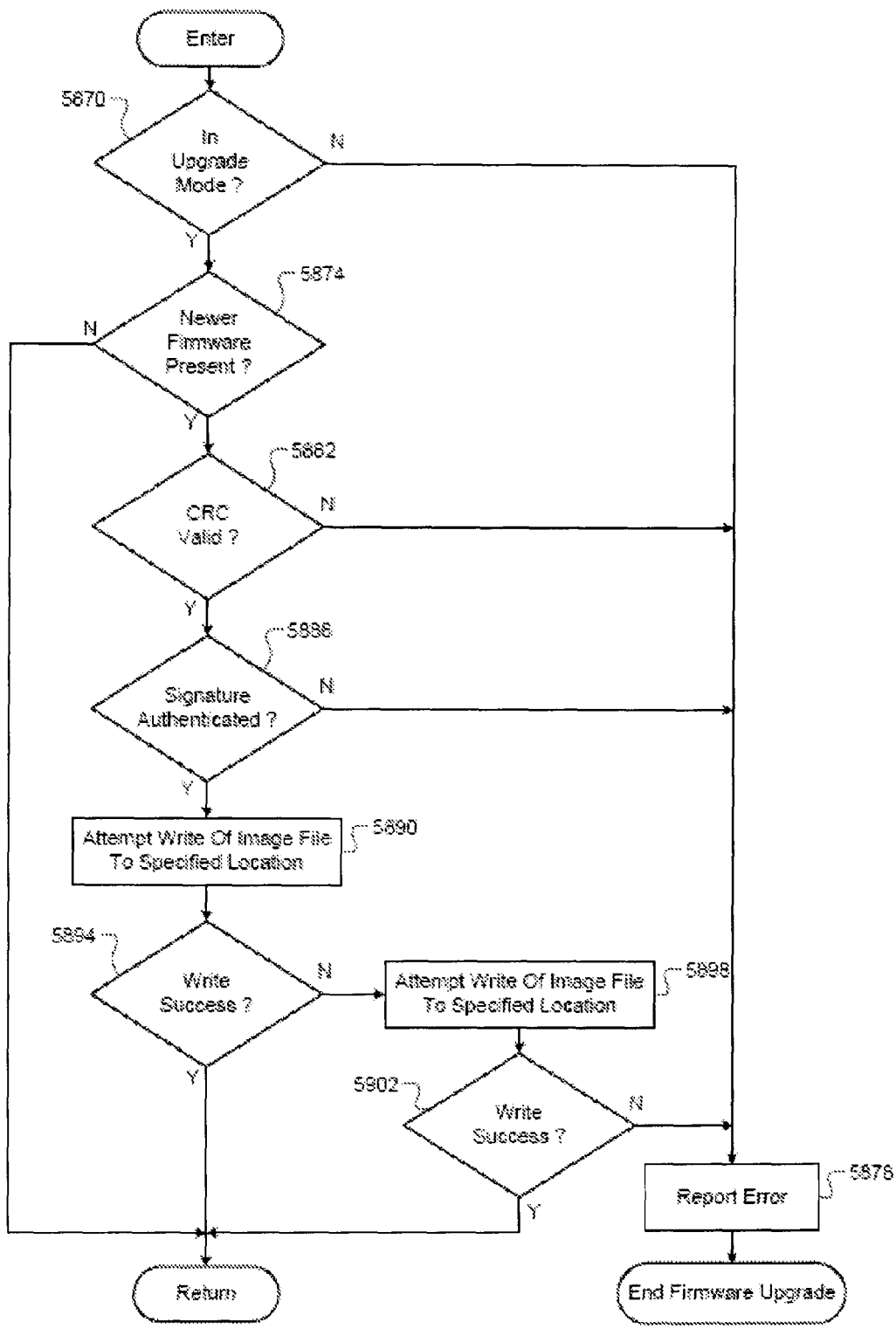

Control then attempts to write the firmware to a predetermined memory location. For example only, control attempts to write the firmware for the processing module 5404 to a predetermined memory location in the nonvolatile memory 5456. To allow the processing module 5404 to revert back to the previous software should the new software fail for any reason, the previous software is not overwritten in the nonvolatile memory 5456. If the write fails, control can attempt additional writes. In various implementations, the number of attempts is limited to two. Control reports the success or failure to the remote software, and can also indicate whether more than one attempt was necessary. An example implementation of 5624 is shown in FIG. 117D.

To improve reliability, the entire firmware of the processing module 5404 can be updated at once. This removes the possibility of new upgrades conflicting with old components. Essentially, each upgrade of the processing module is a new self-contained firmware image. Similarly, the firmware for the communication control module 5408 and for the first wireless control module 5416 can be upgraded as a single image.

Control continues at 5628, where if applicable, control updates firmware of the communication module 5408. Operation of 5628 may be similar to that of 5624. For example, the processing module 5404 can verify the integrity and authenticity of the upgrade. The processing module 5404 then transmits the upgrade to the memory 5412 of the communication control module 5408.

Control continues at 5632, where control updates, if applicable, the first wireless control module 5416. The processing module 5404 can verify the integrity and authenticity of the upgrade before sending the upgrade to the first wireless control module 5416 via the communication control module 5408. The communication control module 5408 can operate as a serial passthrough device during this process. In various implementations, the second wireless module 5420 and the third wireless module 5424 are not upgraded. However, configuration parameters and/or startup scripts can be stored by the communication control module 5408 and read by the second wireless control module 5420 and/or the third wireless module 5424 upon startup. These configuration parameters can be considered as part of the upgrade of the communication control module 5408.

In various implementations, the upgrade of the communication control module 5408 overwrites the previous software stored by the communication control module 5408. If operation of the communication control module 5408 fails when using the new software, the processing module 5404 can write the old software back to the communication control module 5408. In various implementations, the processing module 5404 can retrieve the old version of the software from the remote software. Alternatively, the processing module 5404 can maintain the previous version in memory, such as the nonvolatile memory 5456.

The software for the communication control module 5408 can be read from the communication control module 5408 and written into the nonvolatile memory 5456 prior to writing the new software. Alternatively, the nonvolatile memory 5456 can persistently store the most recent software installed in the communication control module 5408. Then if the new software fails, the most recent functioning software from the nonvolatile memory 5456 can be reinstalled. In various implementations, the nonvolatile memory 5456 can be populated at the time of manufacture with the version of software initially installed in the communication control module 5408. In this way, prior to the very first upgrade of the communication control module 5408, the nonvolatile memory 5456 will already have the most recent functioning version of the software stored. A similar, backup can be maintained for the software in the first wireless control module 5416. After new software has been installed on the communication control module 5408, and all integrity checks have been passed upon reboot, the nonvolatile memory 5456 can be similarly updated with the new functioning software that was installed in the communication control module 5408.

Control continues at 5636, where control applies the firmware upgrades. At 5636, control applies the firmware upgrades. When new software has been installed in the nonvolatile memory 5456 with the processing module 5404, the boot loader of the processing module 5404 is updated to point to the new software. For example only, a starting address of the new software is stored in the boot loader. Then a reset instruction is issued, which resets the processing module 5404 and can also reset the communication control module 5408 and the first wireless control module 5416.

The boot loader causes the processing module 5404 to execute the new software from the nonvolatile memory 5456. If booting the new software is not successful, the processing module 5404 is rebooted, and the boot loader reverts execution back to the previous software. For example only, the boot loader can store a flag indicating that a boot using the new software has been attempted. When booting using the new software succeeds, the new software can clear the flag in the boot loader. Therefore, if the boot loader sees that the flag is still set during a boot, the boot loader can recognize that booting using the new software failed and revert to the old software.

A software and/or hardware watchdog timer can be implemented to ensure that the processing module 5404 does not freeze. After a predetermined period of time, the watchdog timer can issue a reset command to the processing module 5404, which can then boot using the old software. Further, one of the hardware user inputs 5440, such as a recessed microswitch, can be used by a user to reset the handheld diabetes management device 2904 when the user recognizes that the handheld diabetes management device 2904 is unresponsive.

If booting of either the communication control module 5408 or the first wireless control module 5416 fails, the processing module 5404 can reinstall the previous software into the failing control module. If all boots prove successful, however, control can execute self-tests to ensure proper functioning. If any of the boots fail or if an integrity check fails, control reports this failure to the remote software. The remove software can attempt to troubleshoot the problem, which includes reinstalling software, installing an intermediary version of software, or reverting everything to the previous version. In various implementations, the remote software has the ability to disable all functionality of the handheld diabetes management device 2904 until new software can be properly installed. This capability can be used when installation of updates is required, which can be determined by the manufacturer and/or a regulatory agency.

Figure 117E:
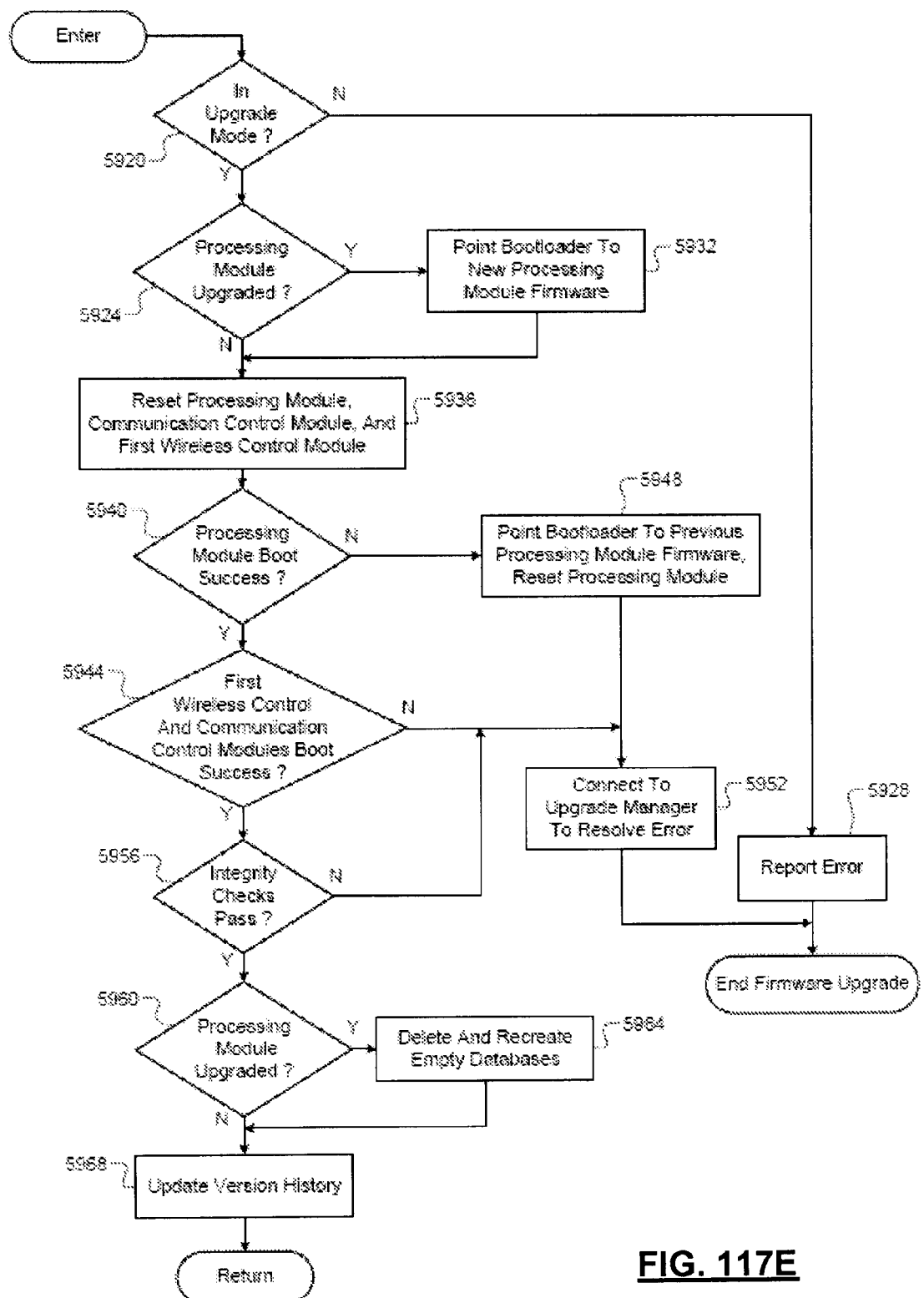

If all integrity checks are successful, control can update a version history stored in the handheld diabetes management device 2904. The version history can include everything described with respect to the version information of 5608. In addition, the version history can include records of all previous versions installed and can include the dates and times at which the versions were installed. When the processing module 5404 has been updated, databases used by the processing module 5404 can be deleted and recreated to ensure compatibility with the new version of the firmware of the processing module 5404. An example implementation of 5636 is shown in FIG. 117E.

Control continues at 5640, where the success of the upgrade is evaluated. This can include providing the version information to the remote software to allow the remote software to verify that the most up-to-date versions are now installed. The remote software can also store this data, which may be required in some jurisdictions for regulatory compliance. In various implementations, firmware versions are tracked by serial number and no information correlating serial number with patient information is maintained. This insures privacy while still allowing for reliable tracking of firmware versions across devices. For example, manufacturers can determine what compatibility issues could be present when various software components are upgraded and can be used to identify devices that are in need of critical updates and/or that have not been updated recently. Control operation at 5624, 5628, 5632, 5636, and 5640 can be considered an apply upgrade phase.

Control continues at 5644, where language files are updated. For example only, the default language of the software install is English. Additional languages can be added after a successful installation. In any given jurisdiction, regulatory agencies may require that certain languages are installed. The remote software can therefore provide these mandatory languages to the handheld diabetes management device 2904. In addition, the user may previously have installed one or more additional languages. These language files can also be provided to the handheld diabetes management device 2904. As with software updates, the processing module 5404 can verify the integrity and authenticity of received language files before installing and using language files. Versions of the installed language files can then be stored in the version history.

Control continues at 5648, where configuration and settings files are transferred to the handheld diabetes management device 2904. In various implementations, a user's previous configurations and settings can be merged into a new database version, which is then provided to the handheld diabetes management device 2904. Control continues at 5652, where control merges additional databases and installs those databases on the handheld diabetes management device 2904. For example only, a patient 2900 or clinician 2902 can add foods to the food database, which can include descriptions, comments, carbohydrate content, and other nutrition information. The patient 2900 or clinician 2902 can manually enter this information or acquire it from some other source, such as a third party or the manufacturer. This additional food database information, backed up 5620, can be added to an updated food database from the manufacturer. This merged food database is then provided to the handheld diabetes management device 2904. Similarly, custom exercise information can be present in an exercise database, which can indicate the effects on blood sugar of various exercise activities.

In cases where the remote software merges user-provided information into a database, the mode of authentication provided by the manufacturer no longer covers the updated database. For example, the remote software can itself authenticate the updated database using a private key known only to the remote software. The processing module 5404 can verify the authenticity of the updated database using a corresponding public key. Control operation at 5644, 5648, and 5652 can be considered as part of an update file phase.

Control continues at 5656, where control exits the upgrade mode. In various implementations, exiting the upgrade mode is only initiated by the remote software, so that a successful upgrade of the handheld diabetes management device 2904 is verified by and known by the remote software. Upon receiving the exit upgrade mode instruction, the handheld diabetes management device 2904 acknowledges the instruction to the remote software, exits upgrade mode, and reboots.

In other words, a reset instruction can be issued to the processing module 5404, the communication control module 5408, and the first wireless control module 5416. In addition, reset signals can also be applied to the second wireless module 5420 and the third wireless module 5424, as well as other components of the handheld diabetes management device 2904. During a standard boot process, the processing module 5404 verifies versions and integrity of installed software. Following the first normal boot after an upgrade, the handheld diabetes management device 2904 reconnects to the remote software and indicates whether the standard version and integrity checks, as well as any other self-tests, were successful. The upgrade process then ends.

Referring now to FIG. 117A, control enters at 5704. If an upgrade disable setting is set, such as in the handheld diabetes management device 2904 or the remote software, control transfers to 5708; otherwise, control transfers to 5712. At 5712, if a battery level of the handheld diabetes management device 2904 is greater than a threshold, control continues at 5716; otherwise, control transfers to 5708. At 5716, control verifies that a USB post is connected using the PHDC. If so, control transfers to 5720; otherwise, control transfers to 5708. In various implementations, upgrading can be allowed over other interfaces. In such implementations, 5716 can be updated to allow those interfaces as well.

At 5720, control determines whether a bolus is in progress. If so, control transfers to 5708; otherwise, control transfers to 5724. Alternatively, at 5720, control can wait until the bolus has completed and then transfer to 5724. At 5724, control determines whether a CGM session is open. If so, control transfers to 5708; otherwise, the handheld diabetes management device 2904 is ready for upgrading and control returns. At 5708, control reports the reason why the upgrade is not currently enabled and the firmware upgrade process is ended. The reason can be reported to the remote software and/or to the handheld diabetes management device 2904. The reason, as well as information on how to address the reason, can be displayed to a user, such as the patient 2900 or the clinician 2902.

Referring now to FIG. 117B, control enters at 5750. Control determines whether there are newer versions of firmware based on the version information retrieved at 5608 of FIG. 116. If so, control transfers to 5754; otherwise, control transfers to 5758. At 5758, control reports that no upgrade is available and ends the firmware upgrade process. At 5754, control determines whether a connection is open with an insulin pump. If so, control transfers to 5762; otherwise, control transfers to 5766.

At 5766, control determines whether a connection (or, a pairing in the context of Bluetooth) is open with another device. If so, control transfers to 5762; otherwise, control transfers to 5770. At 5762, control determines whether new versions of the firmware for the handheld diabetes management device 2904 are compatible with the pump or the other device. If so, control transfers to 5774; otherwise, control transfers to 5778. At 5778, control determines whether an upgrade of the potentially incompatible device is possible. If so, control transfers to 5782; otherwise, control transfers to 5786.

At 5782, control attempts to upgrade the device. At 5790, if the upgrade is successful, control returns to 5762 to recheck compatibility. Otherwise, control transfers to 5786. At 5786, control reports incompatibility between new versions of the firmware and connected devices and ends the firmware upgrade. At 5770, control determines whether previous connections have been made to devices, such as a pump or other device such as a CGM. If so, control transfers to 5794; otherwise, control transfers to 5774. In 5794, control determines whether the new versions of firmware are compatible with previously connected devices. If so, control transfers to 5774; otherwise, control transfers to 5798.

At 5798, control warns of possible incompatibility with previously connected devices. If a user, such as the patient 2900 or the clinician 2902, accepts this possible incompatibility at 5802, control transfers to 5774; otherwise, control transfers to 5786. At 5774, control assembles an upgrade package including the newer versions of the firmware(s). At 5806, control determines whether the upgrade package is valid, such as by checking integrity and authenticity. If valid, control returns; otherwise, control transfers to 5810. At 5810, control reports that the upgrade package is invalid and ends the firmware upgrade.

Referring now to FIG. 117C, control enters at 5820, where control re-verifies that the handheld diabetes management device 2904 is currently able to upgrade its firmware. Control continues at 5824, where upgrade mode is entered. As described above, upgrade mode treats connectivity with the remote software as the highest priority in order to allow the remote software to monitor progress of the upgrade and troubleshoot any problems. Control continues at 5828, where control ends wireless communications and disables radios. If communication with the remote software is performed via one of the radios, that radio is left enabled. However, no other connections besides the connection required for the connection with the remote software is allowed.

Control continues at 5832, where control disables blood glucose measurements, which can also include disabling dispensing of test strips. Control continues at 5836, where control displays a message indicating unavailability on user interface 5436 of the handheld diabetes management device 2904. Control continues at 5840, where control attempts to download the upgrade package from the remote software. If the handheld diabetes management device 2904 itself had prepared the upgrade package, the components of the upgrade package will already have been verified on the handheld diabetes management device 2904. Control continues at 5844, where if the download is successful, control returns; otherwise control transfers to 5848. At 5848, control reports an error and waits for instructions from the remote software. In various implementations, control then ends the firmware upgrade and exits from upgrade mode. If the reason that the download failed can be resolved, another upgrade process can then be initiated.

Referring now to FIG. 117D, control enters at 5870. Control verifies that the handheld diabetes management device 2904 is still operating in upgrade mode and continues at 5874; otherwise, control transfers to 5878. At 5874, control determines whether newer firmware is present. If so, control transfers to 5882; otherwise, control returns. Because FIG. 117D can describe high level operation of 5624, 5628, and 5632 of FIG. 116, one or more of the modules may not have newer firmware. At 5882, control uses a cyclic redundancy check or other mechanism for verifying integrity of the firmware. If the firmware appears uncorrupted, control transfers to 5886; otherwise, control transfers to 5878.

At 5886, control determines whether the firmware is authentic, such as by verifying a signature. If the firmware is authentic, control transfers to 5890; otherwise, control transfers to 5878. At 5890, control attempts to write the firmware image file to a specified location. For example only, the specified location for the processing module 5404 is the nonvolatile memory 5456, the specified location for the communication control module 5408 is the memory 5412, and the specified location for the first wireless control module 5416 is internal memory of the first wireless control module 5416. Control continues at 5894, where if the write is successful, control returns; otherwise, control transfers to 5898. At 5898, control reattempts a write of the image file to the specified location. If at 5902, the write is successful, control returns; otherwise, control transfers to 5878.

At 5878, control reports an error to the remote software. The remote software determines an appropriate response. For example, when writing new firmware for the processing module 5404, if the write fails, the previous software will continue to be used. However, in various implementations, writing new software to the communication control module 5408 or to the first wireless control module 5416 overwrites the previous software. The remote software can therefore instruct the processing module 5404 to overwrite the communication module 5408 and/or the first wireless control module 5416 with the previous version of the software.

Referring now to FIG. 117E, control enters at 5920. At 5920, if the upgrade mode is still enabled, control continues at 5924; otherwise, control transfers to 5928. At 5928, control can attempt to re-enter upgrade mode, and/or can attempt to establish communication with the remote software. Control reports the error to the remote software, and can replace the firmware in the communication control module 5408 and the first wireless control module 5416. The firmware upgrade process then ends.

At 5924, control determines whether the processing module 5404 has been upgraded. If so, control transfers to 5932; otherwise, control transfers to 5936. At 5936, control resets the processing module 5404, the communication module 5408, and the first wireless control module 5416. Control continues at 5940 where control determines whether the processing module 5404 successfully booted. If so, control transfers to 5944; otherwise, control transfers to 5948.

At 5948, control points the boot loader to the previous firmware for the processing module 5404 and resets the processing module 5404. Control then continues at 5952. At 5944, control determines whether the first wireless control module 5416 and the communication control module 5408 successfully booted. If so, control transfers to 5956; otherwise, control transfers to 5952. At 5956, control runs integrity checks. If the integrity checks all pass, control transfers to 5960; otherwise, control transfers to 5952. At 5952, control connects to the upgrade manager to resolve the error. At 5960, control determines whether the processing module 5404 has been upgraded. If so, control transfers to 5964; otherwise, control transfers to 5968. At 5964, control deletes current databases and recreates empty databases based on definitions in the new firmware. Control continues at 5968, where control updates the version history to reflect the upgraded versions of the firmware and databases. Control then returns.

The present disclosure describes a handheld diabetes management device that implements a failsafe firmware upgrading protocol to reduce risk of device downtime and to reduce required user interaction. The handheld diabetes management device includes a nonvolatile memory and a general processing module in electrical communication with the nonvolatile memory. The general processing module executes first software from the nonvolatile memory. An external port is in electrical communication with the general processing module. The general processing module receives second software from the external port and writes the second software to the nonvolatile memory.

Based on an upgrade signal, the general processing module switches execution from the first software to the second software, evaluates proper operation of the general processing module, and switches execution back to the first software from the second software when proper operation of the general processing module using the second software is not detected. A communications module, in electrical communication with the general processing module, stores third software and executes the third software. The general processing module receives fourth software from the external port and replaces the third software with the fourth software.

In other features, the handheld diabetes management device includes a wireless control module in electrical communication with the communications module. The general processing module selectively updates operating instructions of the wireless control module via the communications module. The general processing module replaces previous operating instructions of the wireless control module with updated operating instructions via the communications module.

In further features, when proper operation of the wireless control module using the updated operating instructions is not detected, the general processing module replaces the updated operating instructions of the wireless control module with the previous operating instructions via the communications module. When proper operation of the communications module using the fourth software is not detected, the general processing module replaces the fourth software with the third software. The general processing module uploads user information to a remote host via the external port prior to switching execution of the general processing module from the first software to the second software.

In still other features, the general processing module stores the user information in one or more databases. The general processing module deletes the one or more databases when proper operation of the general processing module using the second software is detected. The processing module receives updated databases including the user information from the remote host. The general processing module deletes the first software when proper operation of the general processing module using the second software is detected. The second software is self-contained such that the general processing module executes the second software independent of any portion of the first software.

A method is defined for operating a handheld diabetes management device to implement a failsafe firmware upgrading protocol to maximize availability. The method includes storing first software in a nonvolatile memory, receiving second software from an external port, writing the second software to the nonvolatile memory, and selectively receiving an upgrade signal. Based on the upgrade signal, the method switches execution from the first software to the second software, evaluates proper operation of the second software, and switches execution back to the first software from the second software when proper operation of second software is not detected. The method further includes receiving third software from the external port and replacing fourth software of a communications module with the third software.

In other features, the method includes selectively updating operating instructions of a wireless control module via the communications module. The method further includes replacing previous operating instructions of the wireless control module with updated operating instructions via the communications module. The method further includes evaluating proper operation of the wireless control module using the updated operating instructions. When proper operation of the wireless control module using the updated operating instructions is not detected, the method replaces the updated operating instructions of the wireless control module with the previous operating instructions via the communications module.

In further features, the method includes, when proper operation of the communications module using the third software is not detected, replacing the third software with the fourth software. The method further includes uploading user information to a remote host via the external port prior to switching execution from the first software to the second software. The method further includes storing the user information in one or more databases and deleting the one or more databases when proper operation of the second software is detected.

In still other features, the method further includes receiving updated databases including the user information from the remote host. The method further includes deleting the first software when proper operation of the second software is detected. The second software is self-contained such that execution of the second software is independent of any portion of the first software.

Coexistence of Multiple Radios in a Medical Device

Referring now to FIG. 75, a person 2900 with diabetes and a healthcare professional 2902 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 2900 typically shares with the clinician 2902 a variety of patient data including blood glucose measurements, continuous glucose monitor data, amounts of insulin infused, amounts of food and beverages consumed, exercise schedules, and other lifestyle information. The clinician 2902 may obtain additional patient data that includes measurements of HbA1C, cholesterol levels, triglycerides, blood pressure, and weight of the patient 2900. The patient data can be recorded manually or electronically on a handheld diabetes management device 2904, a diabetes analysis software executed on a personal computer (PC) 2906, and/or a web-based diabetes analysis site (not shown). The clinician 2902 can analyze the patient data manually or electronically using the diabetes analysis software and/or the web-based diabetes analysis site. After analyzing the patient data and reviewing adherence of the patient 2900 to previously prescribed therapy, the clinician 2902 can decide whether to modify the therapy for the patient 2900.

Referring now to FIG. 76, the patient 2900 can use a continuous glucose monitor (CGM) 2910, an ambulatory non-durable insulin infusion pump 2912 or an ambulatory durable insulin infusion pump 2914 (hereinafter insulin pump 2912 or 2914), and the handheld diabetes management device 2904 (hereinafter the diabetes manager 2904). The CGM 2910 uses a subcutaneous sensor to sense and monitor the amount of glucose in interstitial fluid of the patient 2900 and communicates corresponding data to the diabetes manager 2904.

The diabetes manager 2904 performs various tasks including measuring and recording blood glucose levels, determining an amount of insulin to be administered to the patient 2900 via the insulin pump 2912 or 2914, receiving patient data via a user interface, archiving the patient data, etc. The diabetes manager 2904 periodically receives data from the CGM 2910 from which glucose levels of the patient 2900 are computed. The diabetes manager 2904 transmits instructions to the insulin pump 2912 or 2914, which delivers insulin to the patient 2900. Insulin can be delivered in a scheduled manner in the form of a basal dose, which maintains a predetermined insulin dose to the patient 2900. Additionally, insulin can be delivered in the form of a bolus dose, which raises the amount of insulin delivered to the patient 2900 by a predetermined amount.

Referring now to FIG. 77, a diabetes management system 2390 used by the patient 2900 and the clinician 2902 includes one or more of the following devices: the diabetes manager 2904, the continuous glucose monitor (CGM) 2910, the insulin pump 2912 or 2914, a mobile device 2932, the PC 2906 with the diabetes analysis software, and other healthcare devices 2934. The diabetes manager 2904 is configured as a system hub and communicates with the devices of the diabetes management system 2390. Alternatively, the mobile device 2932 can serve as the system hub. Communication between the devices in the diabetes management system 2390 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 2900 and clinician 2902 to exchange information.

The diabetes manager 2904 can receive glucose readings from one or more sources (e.g., from the CGM 2910). The CGM 2910 continuously monitors the glucose level of the patient 2900. The CGM 2910 periodically communicates data to the diabetes manager 2904 from which the diabetes manager 2904 computes glucose levels of the patient. The diabetes manager 2904 and the CGM 2910 communicate wirelessly using a proprietary wireless protocol. Throughout the present disclosure, Gazell wireless protocol developed by Nordic Semiconductor, Inc. is used as an example only. Any other suitable wireless protocol can be used instead. The Gazell wireless protocol is described in nRF24LE1 Ultra-low Power Wireless System On-Chip Solution, Product Specification v1.4, which is incorporated herein by reference in its entirety.

Additionally, the diabetes manager 2904 includes a blood glucose meter (BGM) and a port that communicates with the BGM (not shown). The port can receive a blood glucose measurement strip 2936. The patient 2900 deposits a sample of blood on the blood glucose measurement strip 2936. The BGM analyzes the sample and measures the blood glucose level in the sample. The blood glucose level measured from the sample and/or the glucose level computed using data received from the CGM 2910 can be used to determine the amount of insulin to be administered to the patient 2900.

The diabetes manager 2904 communicates with the insulin pump 2912 or 2914. The insulin pump 2912 or 2914 can be configured to receive instructions from the diabetes manager 2904 to deliver a predetermined amount of insulin to the patient 2900. Additionally, the insulin pump 2912 or 2914 can receive other information including meal and/or exercise schedules of the patient 2900. The insulin pump 2912 or 2914 can determine the amount of insulin to administer based on the additional information.

The insulin pump 2912 or 2914 can also communicate data to the diabetes manager 2904. The data can include amounts of insulin delivered to the patient 2900, corresponding times of delivery, and pump status. The diabetes manager 2904 and the insulin pump 2912 or 2914 can communicate using a wireless communication protocol such as Bluetooth. Other wireless or wireline communication protocols can also be used.

In addition, the diabetes manager 2904 can communicate with the other healthcare devices 2934. For example, the other healthcare devices 2934 can include a blood pressure meter, a weight scale, a pedometer, a fingertip pulse oximeter, a thermometer, etc. The other healthcare devices 2934 obtain and communicate personal health information of the patient 2900 to the diabetes manager 2904 through wireless, USB, or other interfaces. The other healthcare devices 2934 may use communication protocols compliant with ISO/IEEE 11073 extended using guidelines from Continual® Health Alliance. The diabetes manager 2904 can communicate with the other healthcare devices 2934 using interfaces including Bluetooth, USB, etc. Further, the devices of the diabetes management system 2390 can communicate with each other via the diabetes manager 2904.

The diabetes manager 2904 can communicate with the PC 2906 using Bluetooth, USB, or other interfaces. A diabetes management software running on the PC 2906 includes an analyzer-configurator that stores configuration information of the devices of the diabetes management system 2390. The configurator has a database to store configuration information of the diabetes manager 2904 and the other devices. The configurator can communicate with users through standard web or computer screens in non-web applications. The configurator transmits user-approved configurations to the devices of the diabetes management system 2390. The analyzer retrieves data from the diabetes manager 2904, stores the data in a database, and outputs analysis results through standard web pages or computer screens in non-web based applications.

The diabetes manager 2904 can communicate with the mobile device 2932 using Bluetooth. The mobile device 2932 may include a cellular phone, a pager, or a personal digital assistant (PDA). The diabetes manager 2904 can send messages to an external network through the mobile device 2932. The mobile device 2932 can transmit messages to the external network upon receiving requests from the diabetes manager 2904.

Referring now to FIG. 82, the diabetes manager 2904 comprises a blood glucose measuring (BGM) module 3300, a communication module 3302, a user interface module 3304, user interfaces 3306, a processing module 3308, memory 3310, and a power module 3312. The user interface module 3304 and the processing module 3308 can be implemented by an application processing module 3309. The BGM module 3300 includes a blood glucose measuring engine that analyzes samples provided by the patient 2900 on the blood glucose measurement strip 2936 and that measures the amount of blood glucose in the samples. The communication module 3302 includes multiple radios that communicate with different devices of the diabetes management system 2390. The user interface module 3304 interfaces the diabetes manager 2904 to various user interfaces 3306 that the patient 2900 can use to interact with the diabetes manager 2904. For example, the user interfaces 3306 can include keys, switches, a display, a speaker, a microphone, a secure digital (SD) card port, a USB port, etc. (not shown).

The processing module 3308 processes data received from the BGM module 3300, the communication module 3302, and the user interface module 3304. The processing module 3308 uses memory 3310 for processing and storing data. The memory 3310 can include volatile and nonvolatile memory. The processing module 3308 outputs data to and receives data from the user interfaces 3306 via the user interface module 3304. The processing module 3308 outputs data to and receives data from the devices of the diabetes management system 2390 via the communication module 3302. The power module 3312 supplies power to the components of the diabetes manager 2904. The power module 3312 includes a rechargeable battery. The battery can be recharged using an adapter that plugs into a wall outlet. The battery can also be charged via the USB port of the diabetes manager 2904.

Figure 118A:
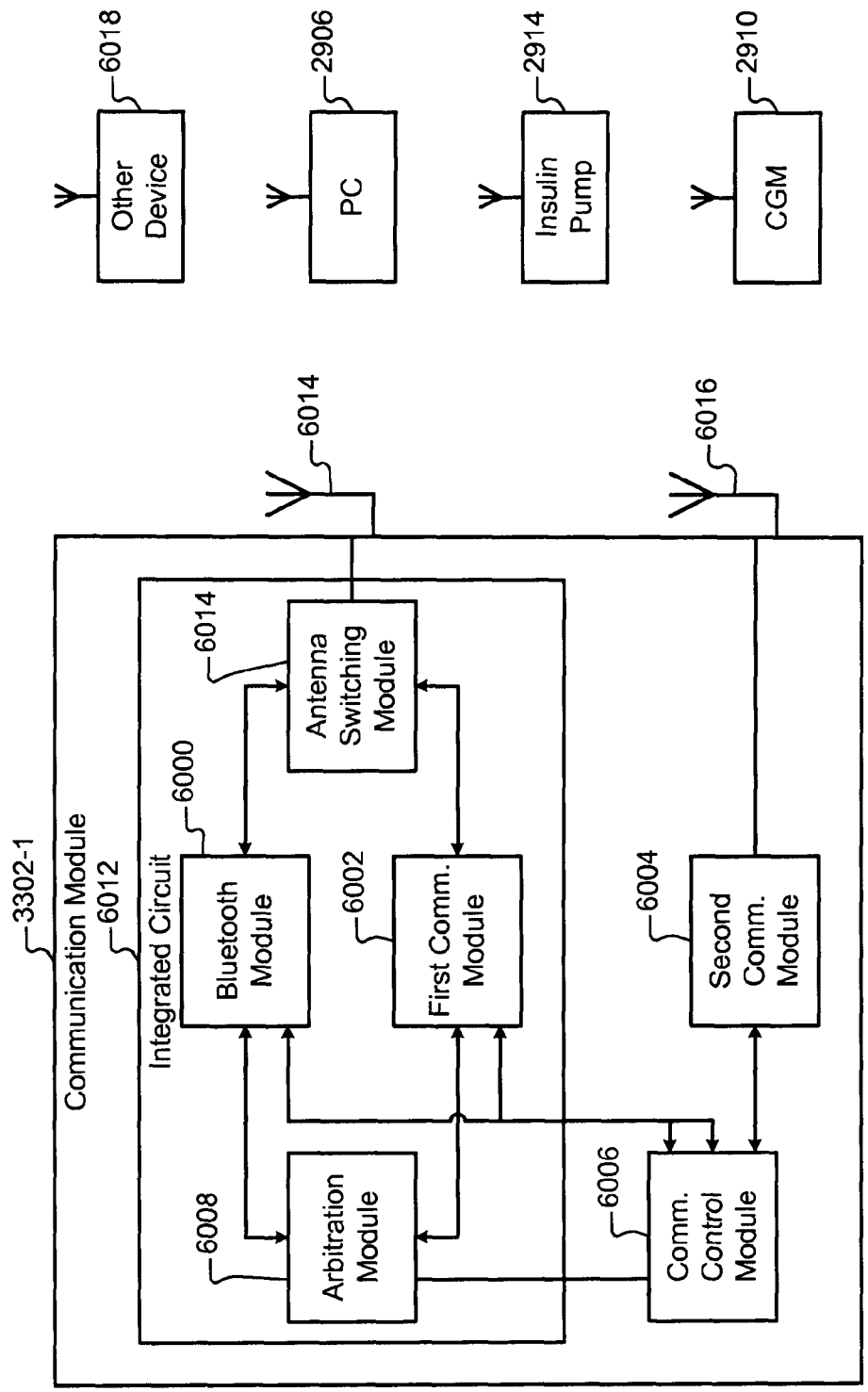
FIG. 118A is a functional block diagram of a communication module used by the diabetes manager of FIG. 82, where the communication module uses a shared antenna.
Figure 118B:
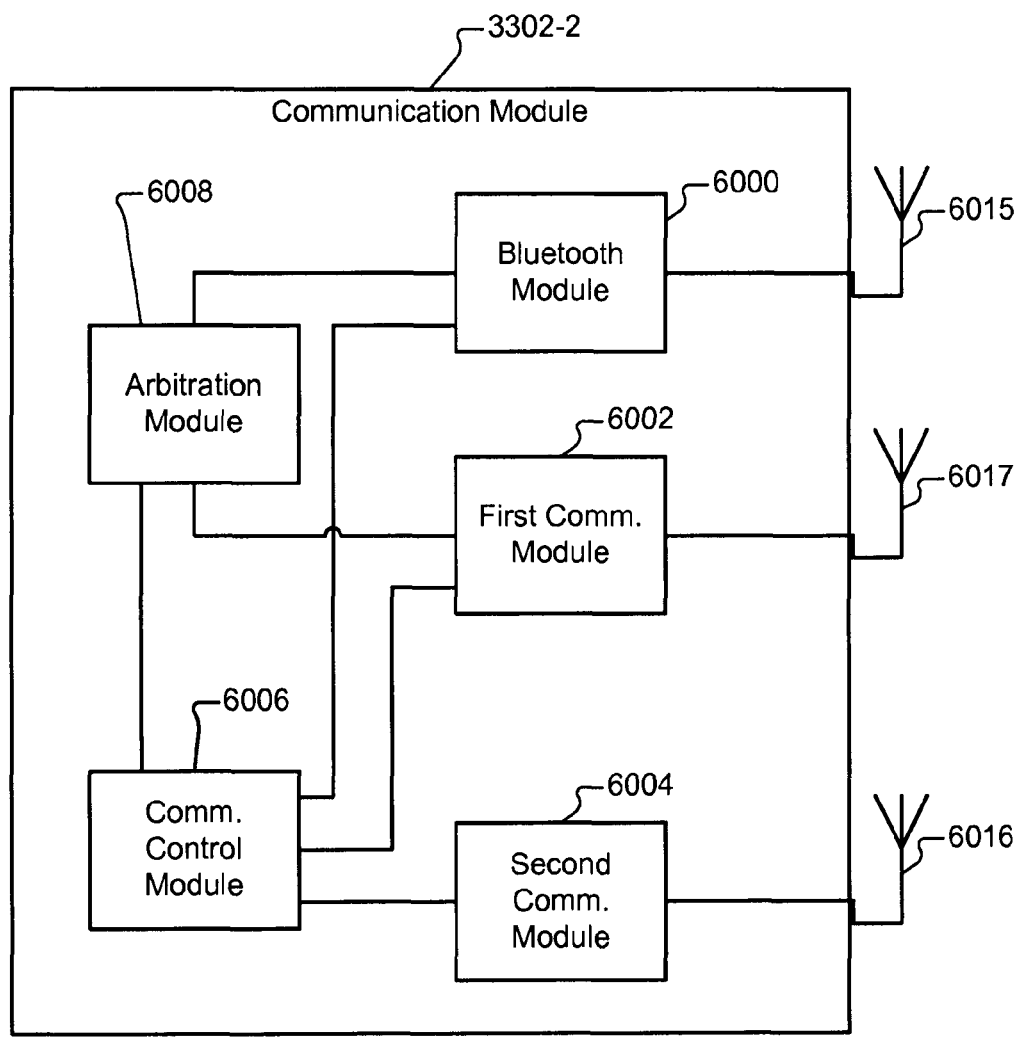
FIG. 118B is a functional block diagram of a communication module used by the diabetes manager of FIG. 82, where the communication module does not use a shared antenna.

Referring now to FIGS. 118A and 118B, different implementations of the communication module 3302 are shown. In FIG. 118A, a communication module 3302-1 comprises a Bluetooth module 6000, a first communication module 6002, a second communication module 6004, a communication control module 6006, an arbitration module 6008, and an antenna switching module 6010. The Bluetooth module 6000 and the first communication module 6002 are integrated into an integrated circuit (IC) 6012. The Bluetooth module 6000 and the first communication module 6002 communicate in a 2.4 GHz frequency band (industrial, scientific, and medical or ISM band). The Bluetooth module 6000 and the first communication module 6002 share a first antenna 6014. The second communication module 6004 may operate in the same ISM band or in a different frequency band and uses a second antenna 6016. The first and second antennas 6014 and 6016 are spatially orthogonal to reduce interference.

In FIG. 118B, a communication module 3302-2 comprises the Bluetooth module 6000, the first communication module 6002, the second communication module 6004, the communication control module 6006, and the arbitration module 6008. The Bluetooth module 6000 and the first communication module 6002 are not integrated into an IC. Additionally, the Bluetooth module 6000 and the first communication module 6002 have separate antennas 6015 and 6017, respectively. Accordingly, the antenna switching module 6010 is unnecessary. The antennas 6015, 6016, and 6017 are spatially orthogonal to reduce interference. The following discussion uses the implementation shown in FIG. 118A as an example only. The teachings disclosed below (except those related to sharing an antenna) apply equally to the implementation shown in FIG. 118B.

In FIG. 118A, the Bluetooth module 6000 communicates with the insulin pump 2914 and the PC 2906. The first communication module 6002 communicates with the CGM 2910 using the Gazell protocol. The first communication module 6002 estimates blood glucose based on the data received from the CGM 2910. The second communication module 6004 communicates with other device 6018 using a wireless communication protocol different than Bluetooth and Gazell protocols. For example, the second communication module 6004 may use a communication protocol suitable for communicating with a Medingo insulin pump. Alternatively, the second communication module 6004 may use WiFi, Machine-to-Machine cellular, Worldwide Interoperability for Microwave Access (WiMAX), or other wireless or wireline communication protocols developed by IEEE or other entities.

Throughout the present disclosure, the insulin pump 2914, the PC 2906, and the CGM 2910 are used as exemplary devices. Further, the discussion related to priorities of the insulin pump 2914, the PC 2906, and the CGM 2910 is for example only. Additionally or alternatively, the Bluetooth module 6000 and the first communication module 6002 can communicate with several other devices having different priorities.

Several techniques can be used to manage coexistence of the Bluetooth module 6000 and the first communication module 6002, which utilize the Bluetooth and Gazell protocols, respectively. For example, the techniques can include application-level control, frequency mapping, and/or hardware control of transceivers used in the Bluetooth module 6000 and the first communication module 6002. These techniques decrease probability of collisions and interference between communications performed by the Bluetooth module 6000 and the first communication module 6002. Application-level control includes utilizing the user interfaces 3306 to avoid simultaneous communication using the Bluetooth module 6000 and the first communication module 6002. For example, the patient 2900 can utilize the user interfaces 3306 to manually select one device to interact with at a time. Frequency mapping includes allocating distinct channels within the ISM band to the Bluetooth module 6000 and the first communication module 6002. The communication control module 6006 performs the frequency mapping as explained below.

Hardware control of transceivers involves using a RF coexistence interface such as BL6450 developed by Texas Instruments that provides RF coexistence signals that can be adapted for use with the Bluetooth module 6000 and the first communication module 6002. For example, Bluetooth asynchronous connectionless link (ACL) packets and Gazell protocol packets transmitted/received by the Bluetooth module 6000 and the first communication module 6002 can be interleaved in a controlled manner. The result is an application that appears as communicating via the Bluetooth module 6000 and the first communication module 6002 simultaneously. The communication control module 6006 and the arbitration module 6008 control the transceivers of the Bluetooth module 6000 and the first communication module 6002 as explained below. In addition, the arbitration module 6008 can manage the coexistence by automatically arbitrating priority between the Bluetooth module 6000 and the first communication module 6002 based on various considerations as explained below.

The communication control module 6006 controls communication of the diabetes manager 2904 with the other devices in the diabetes management system 2390 via the Bluetooth module 6000 and the first and second communication modules 6002 and 6004. The arbitration module 6008 arbitrates priority between the Bluetooth module 6000 and the first communication module 6002 when communication via the Bluetooth module 6000 and the first communication module 6002 is attempted concurrently. The antenna switching module 6010 switches the connection of the first antenna 6014 between the Bluetooth module 6000 and the first communication module 6002 depending on whether the Bluetooth module 6000 or the first communication module 6002 is granted priority.

More specifically, the Bluetooth module 6000 selectively communicates in the ISM band with the insulin pump 2914 external to the diabetes manager 2904 via the first antenna 6014 using the Bluetooth protocol. The first communication module 6002 selectively communicates in the ISM band with the CGM 2910 external to the diabetes manager 2904 via the first antenna 6014 using the Gazell protocol. To minimize interference and number of packet retries, the communication control module 6006 allocates a first channel in the ISM band to the Bluetooth module 6000 and allocates a second channel in the ISM band to the first communication module 6002. For example, the communication control module 6006 can use frequency mapping, where channels allocated to first communication module 6002 are removed from Bluetooth channel map. Further, the communication control module 6006 reduces interference using techniques including time division multiple access (TDMA), channel hopping, channel adaptation, etc.

The arbitration module 6008 arbitrates priority between the Bluetooth module 6000 and the first communication module 6002 in many ways. For example, the arbitration module 6008 typically grants permission to communicate to the Bluetooth module 6000 and denies permission to communicate to the first communication module 6002 when the Bluetooth module 6000 and the first communication module 6002 request permission to communicate concurrently. This is because the insulin pump 2914 delivers therapy (insulin) to the patient 2900 and therefore generally takes precedence over the CGM 2910, which collects diagnostic data for estimating glucose level of the patient 2900. Additionally, while the diagnostic data can be read from the CGM 2910 periodically, scheduled delivery of insulin generally cannot be delayed.

The arbitration module 6008 allocates priority differently when a device other than the insulin pump 2914 (e.g., the PC 2906) is contending with the CGM 2910 for priority to communicate with the diabetes manager 2904. For example, when the Bluetooth module 6000 requests permission to communicate with the PC 2906 and the first communication module 6002 also requests permission to communicate concurrently, the arbitration module 6008 denies permission to communicate to the Bluetooth module 6000 and grants permission to communicate to the first communication module 6002.

Occasionally, the diagnostic data may indicate that the glucose level of the patient 2900 is less than a predetermined threshold, while the insulin pump 2914 may be programmed to deliver a bolus insulin dose to the patient 2900. In such a situation, communicating the diagnostic data collected by the CGM 2910 to the diabetes manager 2904 takes precedence over communicating with the insulin pump 2914. Accordingly, the arbitration module 6008 denies permission to communicate to the Bluetooth module 6000 and grants permission to communicate to the first communication module 6002 when the Bluetooth module 6000 and the first communication module 6002 request permission to communicate concurrently.

Stated generally, a handheld medical device (e.g., the diabetes manager 2904) comprises a first communication module (e.g., the Bluetooth module 6000) that selectively communicates in a first frequency band (e.g., the ISM band) with a first device (e.g., the insulin pump 2914) external to the handheld medical device via a first antenna (e.g., 6014) using a first wireless communication protocol (e.g., Bluetooth). The first device administers a substance (e.g., insulin) to a patient (2900) by communicating with the handheld medical device via the first communication module. A second communication module (e.g., 6002) selectively communicates in the first frequency band with a second device (e.g., the CGM 2910) external to the handheld medical device via the first antenna using a second wireless communication protocol (e.g., Gazell). The second device monitors a health parameter (e.g., blood glucose level) of the patient by communicating with the handheld medical device via the second communication module. An arbitration module (e.g., 6008) grants permission to communicate to the first communication module and denies permission to communicate to the second communication module when the first and second communication modules request permission to communicate concurrently and when the first device has a higher priority than the second device based on a condition of the patient. In some implementations, the first communication module (e.g., the Bluetooth module 6000) and the second communication module (e.g., 6002) use separate antennas.

Further, the handheld medical device comprises an antenna switching module (e.g., 6010) that connects the first antenna to the first communication module when the first communication module is granted permission to communicate and that connects the first antenna to the second communication module when the second communication module is granted permission to communicate. Additionally, the handheld medical device comprises a third communication module (e.g., 6004) that selectively communicates in a second frequency band with a third device (e.g., the other device 6018) external to the handheld medical device via a second antenna (e.g., 6016) using a third wireless communication protocol (e.g., WiFi, WiMAX, etc.) that is different than the first and second wireless communication protocols.

The arbitration module 6008 can arbitrate priority based on other events, conditions, and operations of the diabetes manager 2904. For example, the arbitration module 6008 can deny priority to at least one of the Bluetooth module 6000 and the first communication module 6002 when the BGM module 3300 performs blood glucose measurements. In some implementations, the communication control module 6006 may disable communication of the Bluetooth module 6000 and the first and second communication modules 6002 and 6004 when the BGM module 3300 performs blood glucose measurements. This is because these communications can cause electrical interference in glucose sensing circuitry of the BGM module 3300, which can render the blood glucose measurements inaccurate. Additionally or alternatively, these communications can increase internal temperature of the diabetes manager 2904, which can also render the blood glucose measurements inaccurate.

Further, the CGM 2910 and/or the insulin pump 2914 may generate alarms or alerts to indicate predetermined conditions. For example, the CGM 2910 may indicate when glucose level of the patient 2900 is less than a predetermined threshold. The insulin pump 2914 may indicate when insulin supply in the insulin pump 2914 is less than a predetermined threshold, and so on. The arbitration module 6008 may grant priority to the communication module corresponding to the device generating the alarm or alert. Occasionally, the patient 2900 may press a key on the user interface 3306 to send a message via the mobile device 2932 indicating an emergency condition. Accordingly, the arbitration module 6008 may grant priority to the Bluetooth module 6000 to communicate with the mobile device 2932.

Additionally, the arbitration module 6008 may grant or deny priority based on a state of charge of the battery. For example, when the state of charge is less than a predetermined threshold, the arbitration module 6008 may grant priority to the Bluetooth module 6000 to communicate with the insulin pump 2914 and may deny priority to the first communication module 6002, which communicates with the CGM 2910.

The arbitration module 6008 can also arbitrate priority based on the direction of communication between the diabetes manager 2904 and the insulin pump 2914, the CGM 2910, and the PC 2906. For example, when the arbitration module 6008 receives signals from the Bluetooth module 6000 and the first communication module 6002 for concurrent communication, the arbitration module 6008 identifies the insulin pump 2914, the PC 2906, or the CGM 2910 as the source or destination of the signals. Depending on the operation being performed, the arbitration module 6008 determines whether the insulin pump 2914, the PC 2906, or the CGM 2910 has a higher priority and grants permission to communicate to the corresponding communication module. For example, when the diabetes manager 2904 receives configuration or other updates (e.g., firmware updates) from the PC 2906, the arbitration module 6008 grants priority to the Bluetooth module 6000 and denies priority to the first communication module 6002.

Figure 119:
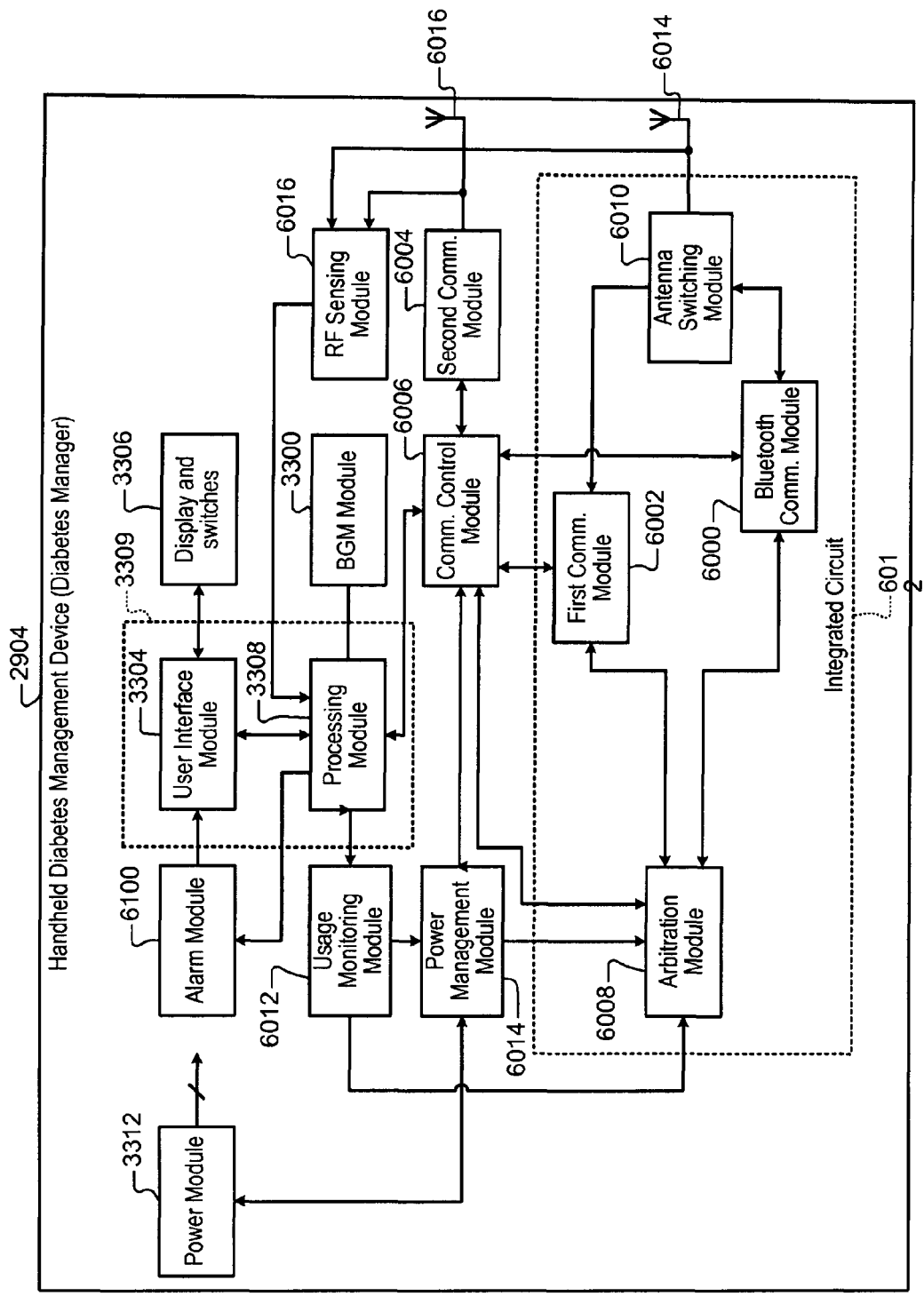
FIG. 119 is a detailed functional block diagram of the diabetes manager of FIG. 82.

Referring now to FIG. 119, a detailed functional block diagram of the diabetes manager 2904 is shown. Although the Bluetooth module 6000 and the first communication module 6002 are shown integrated and sharing the first antenna 6014, the Bluetooth module 6000 and the first communication module 6002 need to not be integrated and can have separate antennas as shown in FIG. 118B. Elements of the diabetes manager 2904 that are described above are not described again. In addition to these elements, the diabetes manager 2904 includes an alarm module 6100, a usage monitoring module 6102, a power management module 6104, and a radio frequency (RF) sensing module 6106.

The alarm module 6100 outputs alarm signals (e.g., audio, video, vibrate, and/or other signals) to the user interfaces 3306 (e.g., when blood glucose level is less than a first predetermined threshold or greater than a second predetermined threshold). The usage monitoring module 6102 monitors usage of the diabetes manager 2904. For example, the usage monitoring module 6102 detects when the diabetes manager 2904 is idle, generating an alarm, measuring blood glucose level, or communicating with the PC 2906, the insulin pump 2914, the CGM 2910, and so on.

The power management module 6104 monitors the amount of power available from the battery. Based on the usage of the diabetes manager 2904 and the power available from the battery, the power management module 6104 deactivates one or more components of the diabetes manager 2904 to save power. Deactivation of a component includes supplying no power to the component (i.e., shutting down the component) or supplying minimum power to put the component in a standby or power save mode (e.g., turning off or slowing one or more clocks used by the component).

Based on the usage and the power available, the arbitration module 6008 arbitrates priority between the Bluetooth module 6000 and the first communication module 6002. For example, when the power available is less than a predetermined threshold, the arbitration module 6008 can deny permission to the communication module that will consume more power and grant priority to the communication module that will consume less power.

When the BGM module 3300 measures blood glucose level in the blood sample, the power management module 6104 deactivates at least one or all of the Bluetooth module 6000 and the first and second communication modules 6002 and 6004. The RF sensing module 6106 senses RF signals in the proximity of the diabetes manager 2904. For example, the RF sensing module 6106 uses techniques such as clear channel assessment (CCA), which is generally used to find a best channel for transmission, to sense RF signals. Specifically, rather than using CCA to find the best channel for transmission, the RF sensing module 6106 uses CCA to detect RF emitting devices in the vicinity of the diabetes manager 2904. The processing module 3308 deactivates the BGM module 3300 when the RF sensing module 6106 senses the RF signals proximate to the diabetes manager 2904 to avoid interference with the blood glucose measurement.

In some implementations, the RF sensing module 6106 can be implemented in transceivers of the Bluetooth module 6000 and the first and second communication modules 6002 and 6004. For example, the transceivers include radio signal strength indicator (RSSI) circuitry that determines an amount of power needed to maintain a communications link with a device. The RSSI circuitry of the transceivers can be used to scan the respective frequency bands to detect RF signals proximate to the diabetes manager 2904.

Figure 120:
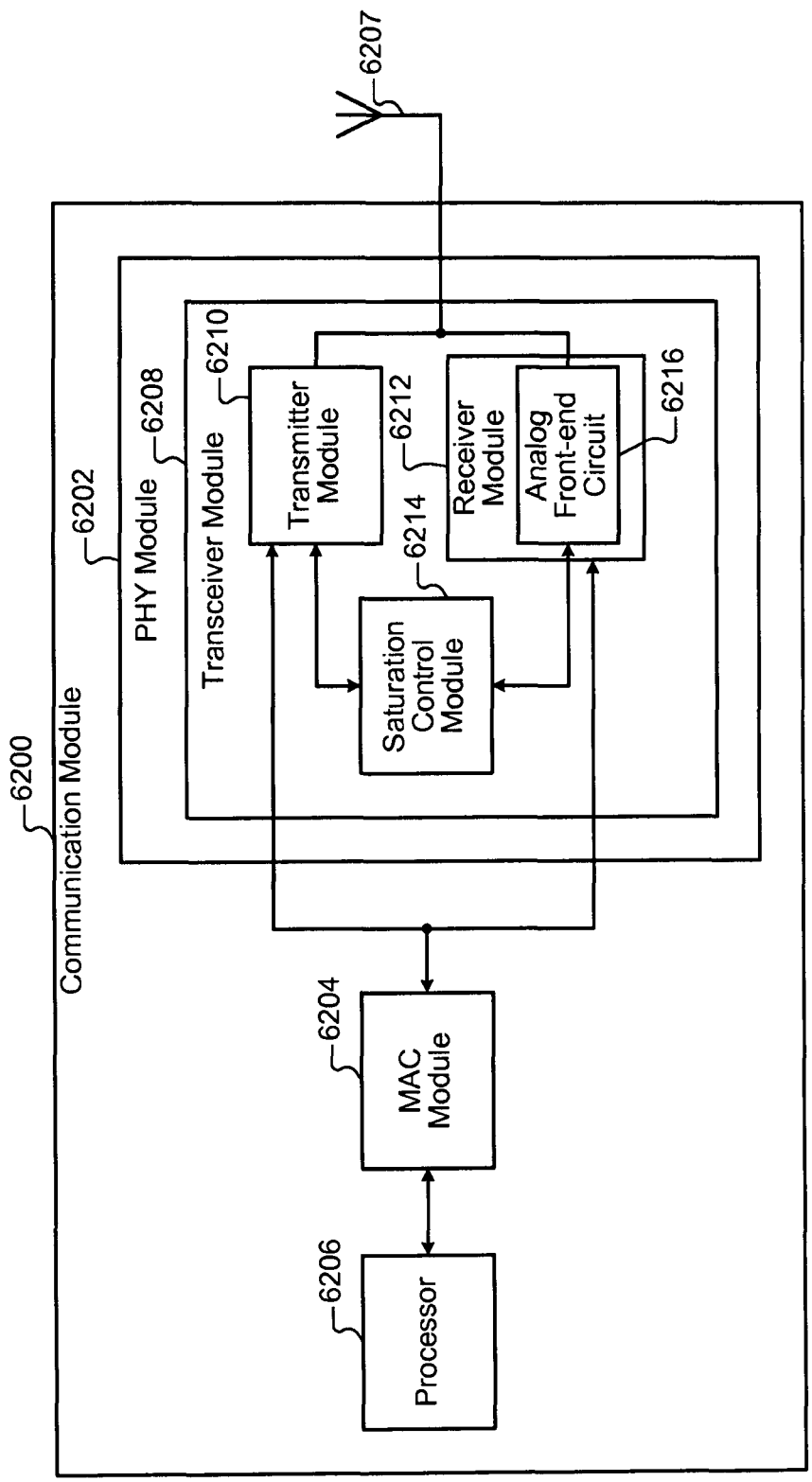
FIG. 120 is a functional block diagram of a communication module.

Referring now to FIG. 120, a functional block diagram of a communication module 6200 is shown. The communication module 6200 is representative of the Bluetooth module 6000 or the first or second communication module 6002 or 6004. The communication module 6200 comprises a physical layer (PHY) module 6202, a media access control (MAC) module 6204, a processor module 6206, and an antenna 6207. The PHY module 6202 comprises a transceiver module 6208, which includes a transmitter module 6210, a receiver module 6212, and a saturation control module 6214. The transmitter module 6210 is collocated with the receiver module 6212. The transmitter module 6210 and the receiver module 6212 transmit and receive data via the antenna 6207, respectively. For example, for the first communication module 6002, the transceiver module 6208 may include an nRF24LE1 transceiver developed by Nordic Semiconductor, Inc. described in the nRF24LE1 Ultra-low Power Wireless System On-Chip Solution, Product Specification v1.4, which is incorporated herein by reference in its entirety.

The MAC module 6204 communicates with the transmitter module 6210 and the receiver module 6212 and controls access of the communication module 6200 to the wireless medium. The processor module 6206 processes data transmitted and received by the transmitter module 6210 and the receiver module 6212, respectively. The receiver module 6212 includes a front-end circuit 6216 that performs functions including demodulation, analog-to-digital conversion (ADC), automatic gain control (AGC), etc. The saturation control module 6214 prevents saturation of the front-end circuit 6216 by the transmitter module 6210 to minimize interference. In some implementations, the AGC in the front-end circuit 6216 can prevent saturation of the front-end circuit 6216 so long as signal strengths of received signals are less than a predetermined threshold.

Figure 121:
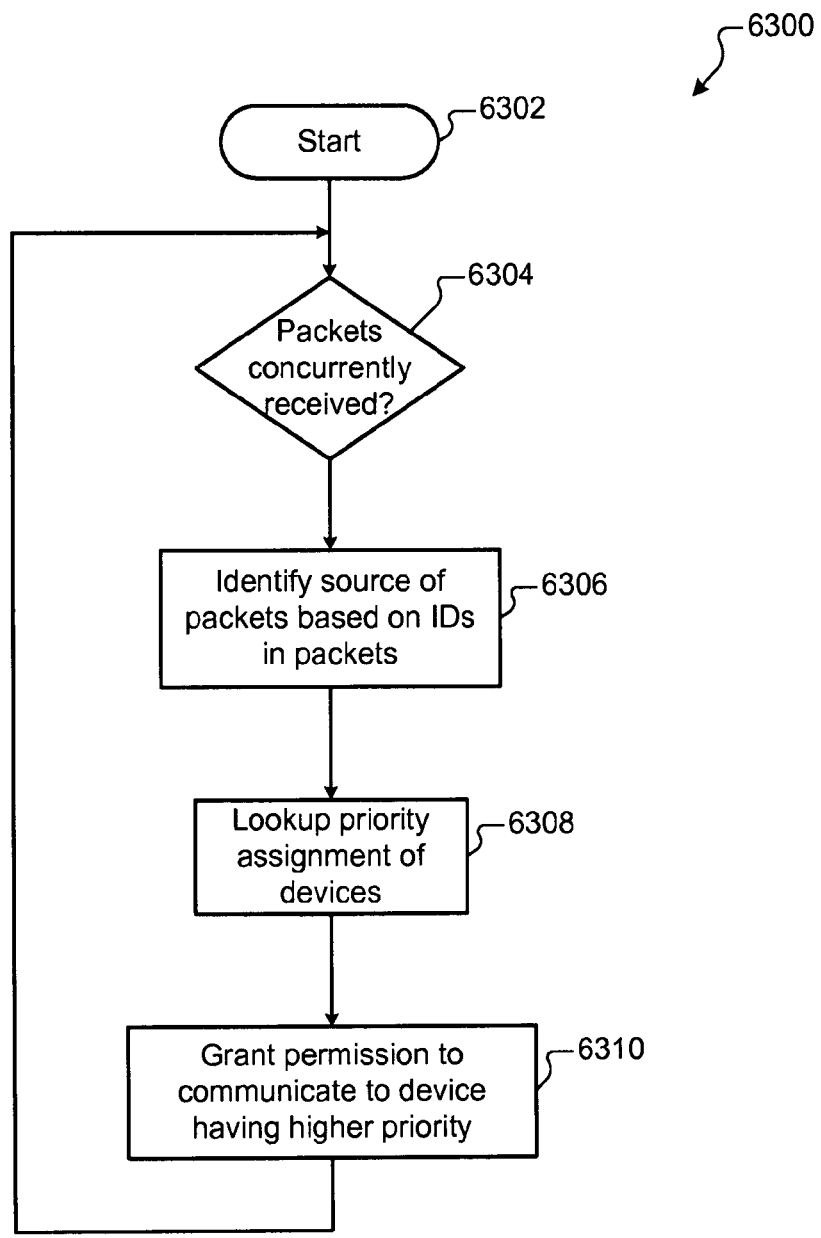
FIG. 121 is a flowchart of a method for arbitrating priority between a plurality of communication modules using a shared antenna.

Referring now to FIG. 121, in an exemplary implementation, the arbitration module 6008 performs a method 6300 for arbitrating priority between the Bluetooth module 6000 and the first communication module 6002. Control begins at 6302. At 6304, control determines if requests for simultaneous communication are received from the Bluetooth module 6000 and the first communication module 6002. For example, packets may be simultaneously received via the first and second antennas 6014 and 6016. If the result at 6304 is false, control waits. If the result at 6304 is true, at 6306, control identifies devices that originated the packets based on identifying information included in the packets.

At 6308, control looks up predetermined priorities for the identified devices. For example, the predetermined priorities may be stored in a lookup table or control registers in the arbitration module 6008. The predetermined priorities can be altered/updated dynamically based on the usage and operation of the diabetes manager 2904 and associated devices described above. At 6310, based on the priority assigned to the identified devices, control grants permission to communicate to the device having higher priority. Control returns to 6302.

In an exemplary embodiment, the arbitration module 6008 arbitrates priority between the Bluetooth module 6000 and the first communication module 6002 using coexistence signals as follows. For managing coexistence, the Bluetooth module 6000 of FIG. 5 utilizes three coexistence signals: BT_RF_ACTIVE, BT_PRIORITY, and BT_TX_CONFX. The Bluetooth module 6000 outputs BT_RF_ACTIVE to indicate transmit or receive activity of the Bluetooth module 6000. The Bluetooth module 6000 outputs BT_PRIORITY to indicate that a priority transaction is about to occur and whether the activity is transmit or receive type. BT_TX_CONFX is an input to the Bluetooth module 6000 that disables an internal power amplifier of the Bluetooth module 6000 when asserted.

The first communication module 6002 utilizing the nRF24LE1 transceiver does not inherently include hardware to implement the co-existence signals. Similar operations, however, can be performed by the first communication module 6002 using the arbitration module 6008 and/or the communication control module 6006. For example, when the first communication module 6002 is about to receive diagnostic data from the CGM 2910, the arbitration module 6008 and/or the communication control module 6006 can assert BT_TX_CONFX, check BT_RF_ACTIVE to ensure that the Bluetooth module 6000 is no longer active, and allow the first communication module 6002 to receive the diagnostic data from the CGM 2910. After the transaction between first communication module 6002 and the CGM 2910 is completed, the arbitration module 6008 and/or the communication control module 6006 can de-assert BT_TX_CONFX. An exemplary method for managing coexistence using this approach performed by the arbitration module 6008 and/or the communication control module 6006 is explained below.

Figure 122:
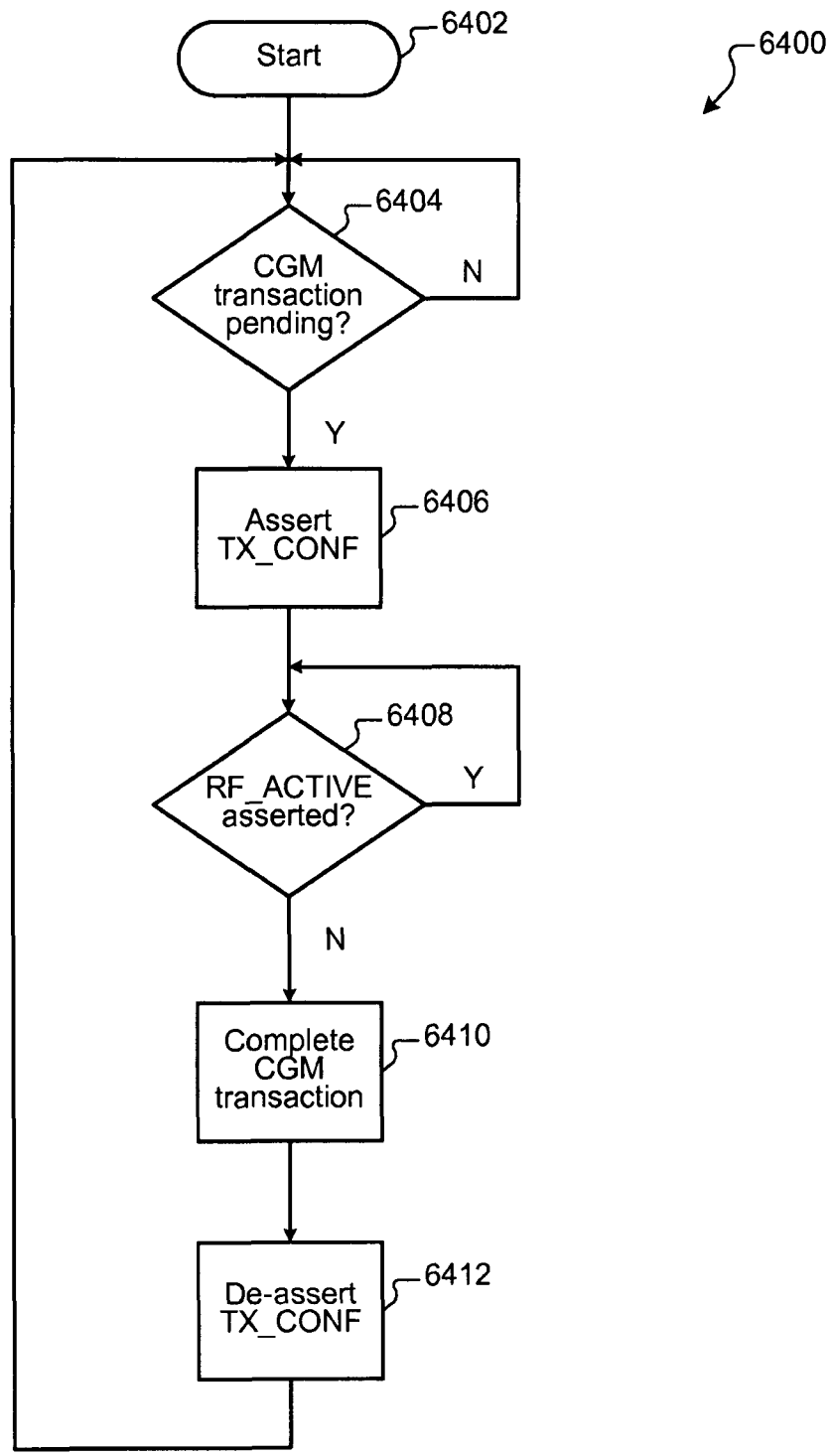
FIG. 122 is a flowchart of a method for managing coexistence of a plurality of communication modules using a shared antenna.

Referring now to FIG. 122, a flowchart of a method 6400 for managing coexistence of the Bluetooth module 6000 and the first communication module 6002 using a shared antenna is shown. Control begins at 6402. At 6404, control determines if a transaction with CGM 2910 using the first communication module 6002 is pending. Control waits if a transaction is not pending. At 6406, if a transaction is pending, control asserts BT_TX_CONF, which disables an internal power amplifier of the Bluetooth module 6000. At 6408, control determines if BT_RF_ACTIVE is asserted, which indicates transmit or receive activity of the Bluetooth module 6000. Control returns to 6408 if BT_RF_ACTIVE is asserted. At 6410, if BT_RF_ACTIVE is not asserted, which indicates no transmit or receive activity by the Bluetooth module 6000, control completes the pending transaction using the first communication module 6002. At 6412, control de-asserts BT_TX_CONF, which enables an internal power amplifier of the Bluetooth module 6000, and control returns to 6402.

When large amounts of diagnostic data are downloaded from the CGM 2910 using the first communication module 6002, the RF usage may have large gaps where the Bluetooth module 6000 can have an opportunity to send and receive packets. For example, a largest Gazell packet may be 1.316 msec long. Accordingly, even if 10 records were downloaded at a time, for example, including acknowledgements, the Bluetooth module 6000 may be disabled on the order of 15 to 30 msec depending on the number of retries and other timing parameters.

Further, when a large number of records are to be downloaded from the CGM 2910, the number of records can be divided into groups with a gap of 50 to 100 msec between the groups due to other system constraints. The quality of service (QoS) of the Bluetooth module 6000 is set to reliable so that Bluetooth packets are retried until Bluetooth link breaks down, which makes the Bluetooth interface robust. The default link timeout for the Bluetooth interface is typically 20 seconds while applications generally have a much shorter timeout such as 1 second.

A sniff interval setting of the Bluetooth module 6000 can impact this strategy. While Bluetooth is a polling-based system, the connection between the diabetes manager 2904 and the insulin pump 2914 can use sniff mode to save power. The sniff interval can be set to 16 msec, for example, which means that the slave and host devices (e.g., the insulin pump 2914 and the Bluetooth module 6000) can wake up to exchange packets every 16 msec.

In summary, if the first communication module 6002 allows the Bluetooth module 6000 to complete transactions and does not disable the Bluetooth module 6000 for an extended period of time, an RF coexistence interface such as BL6450 provided by Texas Instruments can be used to manage coexistence of the Bluetooth module 6000 and the first communication module 6002.

Handheld Medical Device as a Communications Mediator Between a Personal Computer-Based Configurator and Another Networked Medical Device, Efficient Procedure for Pairing Medical Devices for Wireless Communication with Limited User Interaction, and Diabetes Care Kit that is Preconfigured to Establish a Secure Bidirectional Communication Link Between a Blood Glucose Meter and Insulin Pump Referring now to FIG. 75, a person 2900 with diabetes and a healthcare professional 2902 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 2900 typically shares with the clinician 2902 a variety of patient data including blood glucose measurements, continuous glucose monitor data, amounts of insulin infused, amounts of food and beverages consumed, exercise schedules, and other lifestyle information. The clinician 2902 can obtain additional patient data that includes measurements of HbA1C, cholesterol levels, triglycerides, blood pressure, and weight of the patient 2900. The patient data can be recorded manually or electronically on a handheld diabetes managing device 2904, a diabetes analysis software executed on a personal computer (PC) 2906, and/or a web-based diabetes analysis site (not shown). The clinician 2902 can analyze the patient data manually or electronically using the diabetes analysis software and/or the web-based diabetes analysis site. After analyzing the patient data and reviewing adherence of the patient 2900 to previously prescribed therapy, the clinician 2902 can decide whether to modify the therapy for the patient 2900.

Referring now to FIG. 76, the patient 2900 can use a continuous glucose monitor (CGM) 2910, an ambulatory durable insulin infusion pump 2912 or an ambulatory non-durable insulin infusion pump 2914 (collectively insulin pump 2912 or 2914), and the handheld diabetes managing device 2904 (hereinafter the diabetes manager 2904). The CGM 2910 uses a subcutaneous sensor to sense and monitor the amount of glucose in the blood of the patient 2900 and communicates corresponding readings to the handheld diabetes managing device 2904.

The diabetes manager 2904 performs various tasks including measuring and recording blood glucose levels, determining an amount of insulin to be administered to the patient 2900 via the insulin pump 2912 or 2914, receiving patient data via a user interface, archiving the patient data, etc. The diabetes manager 2904 periodically receives readings from the CGM 2910 indicating insulin level in the blood of the patient 2900. The diabetes manager 2904 transmits instructions to the insulin pump 2912 or 2914, which delivers insulin to the patient 2900. Insulin can be delivered in the form of a bolus dose, which raises the amount of insulin in the blood of the patient 2900 by a predetermined amount. Additionally, insulin can be delivered in a scheduled manner in the form of a basal dose, which maintains a predetermined insulin level in the blood of the patient 2900.

Referring now to FIG. 77, a diabetes management system 2930 used by the patient 2900 and the clinician 2902 includes one or more of the following devices: the diabetes manager 2904, the continuous glucose monitor (CGM) 2910, the insulin pump 2912 or 2914, a mobile device 2932, the diabetes analysis software on the PC 2906, and other healthcare devices 2934. The diabetes manager 2904 is configured as a system hub and communicates with the devices of the diabetes management system 2930. Alternatively, the insulin pump 2914 or the mobile device 2932 can serve as the system hub. Communication between the various devices in the diabetes management system 2930 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 2900 and clinician 2902 to exchange information.

The diabetes manager 2904 can receive blood glucose readings from one or more sources (e.g., from the CGM 2910). The CGM 2910 continuously measures the blood glucose level of the patient 2900. The CGM 2910 periodically communicates the blood glucose level to the diabetes manager 2904. The diabetes manager 2904 and the CGM 2910 communicate wirelessly using a proprietary Gazell wireless protocol developed by Nordic Semiconductor, Inc.

Additionally, the diabetes manager 2904 includes a blood glucose meter (BGM) and a port that communicates with the BGM (both not shown). The port can receive a blood glucose measurement strip 2936. The patient 2900 deposits a sample of blood or other bodily fluid on the blood glucose measurement strip 2936. The BGM analyzes the sample and measures the blood glucose level in the sample. The blood glucose level measured from the sample and/or the blood glucose level read by the CGM 2910 can be used to determine the amount of insulin to be administered to the patient 2900.

The diabetes manager 2904 communicates with the insulin pump 2912 or 2914. The insulin pump 2912 or 2914 can be configured to receive instructions from the diabetes manager 2904 to deliver a predetermined amount of insulin to the patient 2900. Additionally, the insulin pump 2912 or 2914 can receive other information including meal and/or exercise schedules of the patient 2900. The insulin pump 2912 or 2914 can determine the amount of insulin to administer based on the additional information.

The insulin pump 2912 or 2914 can also communicate data to the diabetes manager 2904. The data can include amounts of insulin delivered to the patient 2900, corresponding times of delivery, and pump status. The diabetes manager 2904 and the insulin pump 2912 or 2914 can communicate using a wireless communication protocol such as Bluetooth. Other wireless or wireline communication protocols can also be used.

In addition, the diabetes manager 2904 can communicate with other healthcare devices 2934. For example, the other healthcare devices 2934 can include a blood pressure meter, a weight scale, a pedometer, a fingertip pulse oximeter, a thermometer, etc. The other healthcare devices 2934 obtain and communicate personal health information of the patient 2900 to the diabetes manager 2904 through wireless, USB, or other interfaces. The other healthcare devices 2934 use communication protocols compliant with ISO/IEEE 11073 extended using guidelines from Continual® Health Alliance. The diabetes manager 2904 can communicate with the other healthcare devices 2934 using interfaces including Bluetooth, USB, etc. Further, the devices of the diabetes management system 2930 can communicate with each other via the diabetes manager 2904.

The diabetes manager 2904 can communicate with the PC 2906 using Bluetooth, USB, or other interfaces. A diabetes management software running on the PC 2906 includes an analyzer-configurator that stores configuration information of the devices of the diabetes management system 2930. The configurator has a database to store configuration information of the diabetes manager 2904 and the other devices. The configurator can communicate with users through standard web or computer screens in non-web applications. The configurator transmits user-approved configurations to the devices of the diabetes management system 2930. The analyzer retrieves data from the diabetes manager 2904, stores the data in a database, and outputs analysis results through standard web pages or computer screens in non-web based applications.

The diabetes manager 2904 can communicate with the mobile device 2932 using Bluetooth. The mobile device 2932 can include a cellular phone, a PDA, or a pager. The diabetes manager 2904 can send messages to an external network through the mobile device 2932. The mobile device 2932 can transmit messages to the external network based on requests received from the diabetes manager 2904.

In some embodiments, the communication between the diabetes manager 2904 and the insulin pump 2912 or 2914 can be made more secure and reliable by including various security features. When the diabetes manager 2904 and the insulin pump 2912 or 2914 will communicate wirelessly, for example, the diabetes manager 2904 and the insulin pump 2912 or 2914 can be paired to establish a secure bidirectional communication link. Various exemplary methods of pairing a handheld diabetes managing device (such as diabetes manager 2904) and an insulin pump (such as insulin pump 2912 or 2914) are illustrated in FIGS. 123-129.

Figure 123:
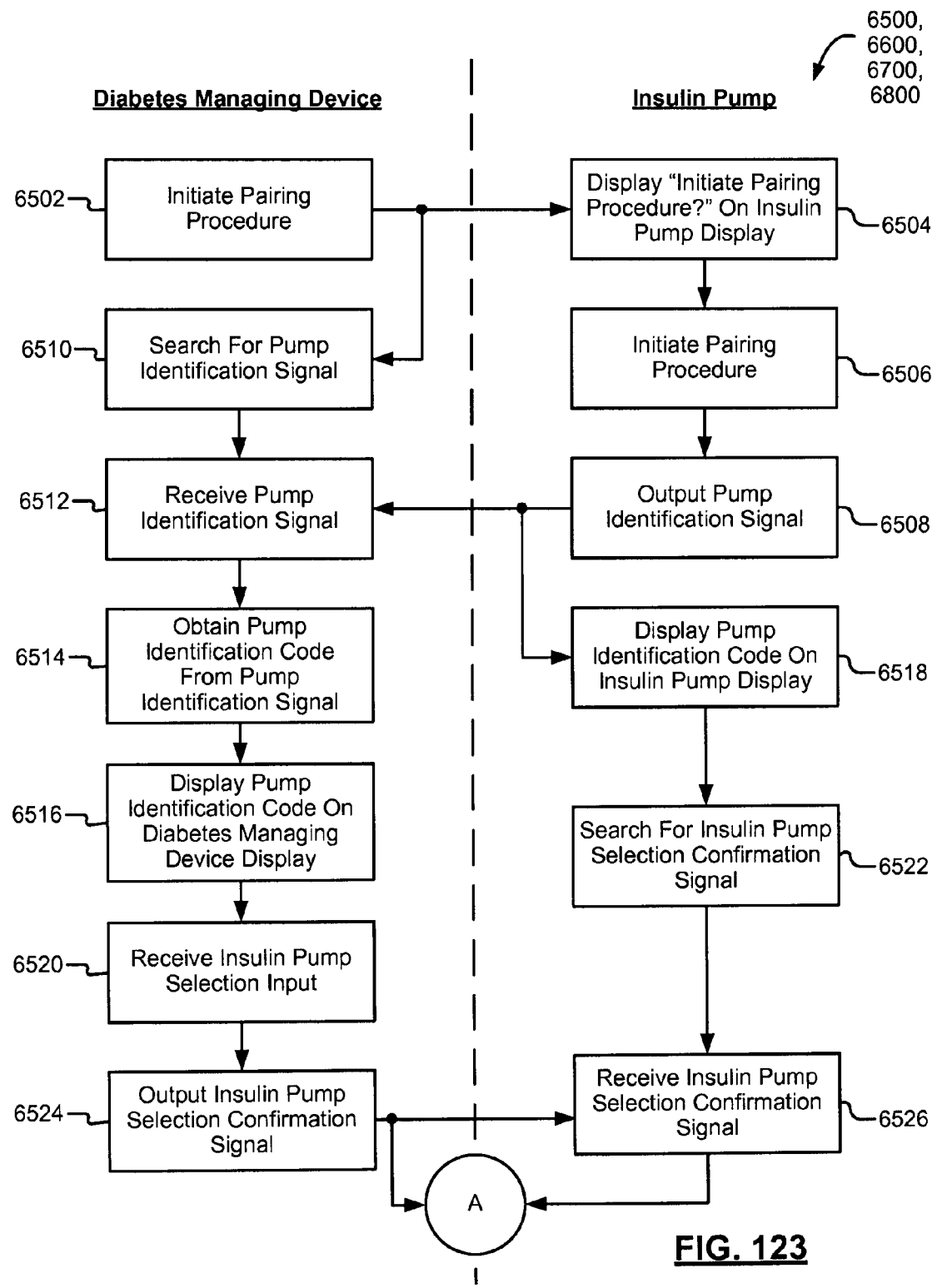
FIG. 123 shows a flow-chart illustrating a portion of an exemplary method of pairing a handheld diabetes managing device and an insulin pump according to the present disclosure.
Figure 124:
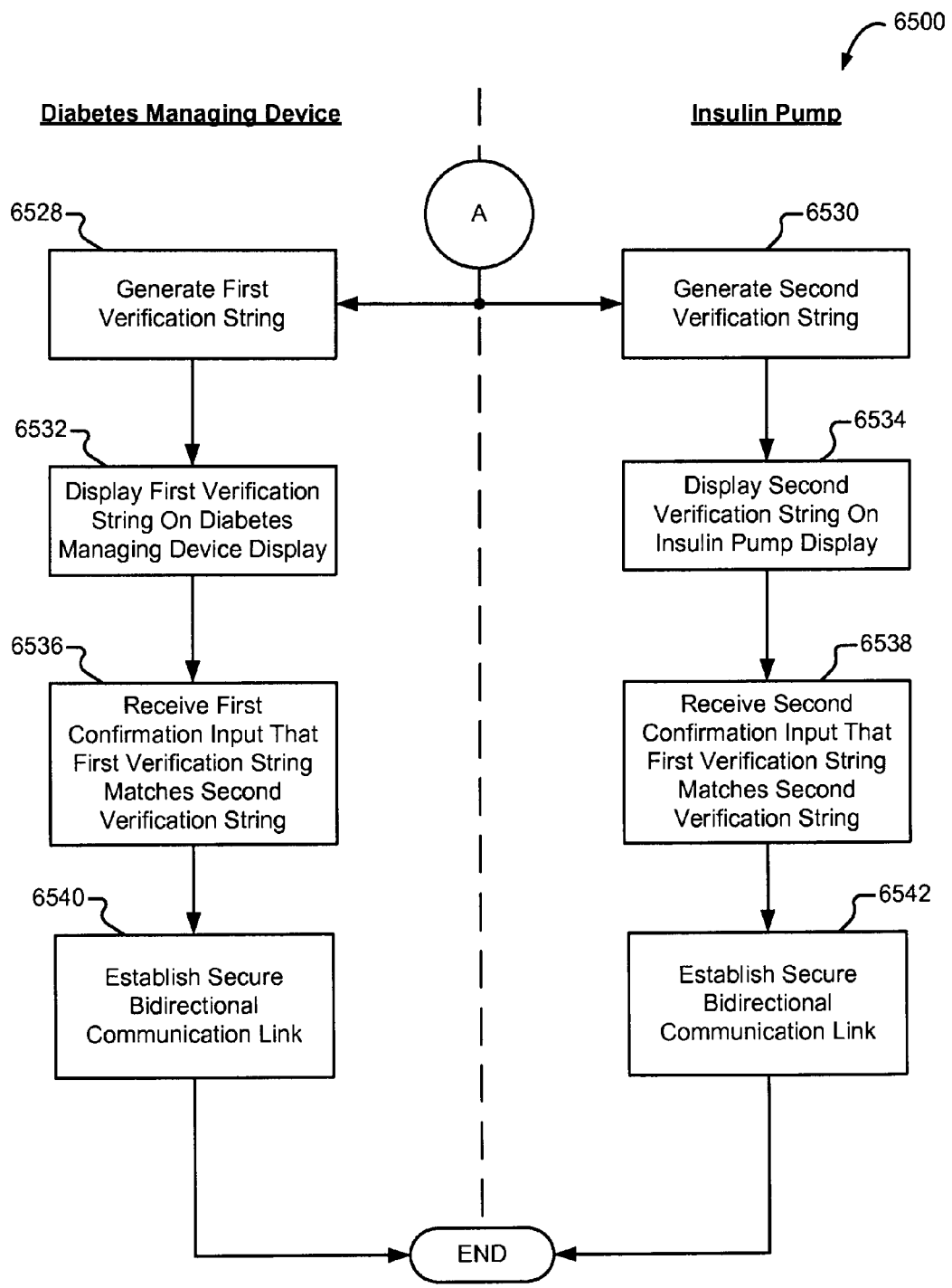

Referring now to FIGS. 123 and 124, a first exemplary method 6500 of pairing a handheld diabetes managing device and an insulin pump according to the present disclosure illustrated. While each step in the exemplary method 6500 is illustrated and will be described herein as occurring at one of the handheld diabetes managing device or the insulin pump, one skilled in the art will appreciate that each step could occur at the other one, or both, of the handheld diabetes managing device or the insulin pump. For example only, method 6500 begins at step 6502 with the pairing procedure being initiated at the diabetes managing device and proceeds to step 6504 with the insulin pump displaying "Initiate Pairing Procedure?" on an insulin pump display. One skilled in the art will recognize that the pairing procedure can instead be initiated at the insulin device and the diabetes managing device can display "Initiate Pairing Procedure?" on a diabetes managing device display.

Method 6500 begins at step 6502 with the pairing procedure being initiated at the diabetes managing device. The method proceeds to step 6504 at which the insulin pump displays "Initiate Pairing Procedure?" on an insulin pump display. At step 6506, the pairing procedure is initiated at the insulin pump. The pairing procedure can be initiated by placing the diabetes managing device and/or insulin pump in a "pairing" mode, for example, by a switch or push button. In some embodiments, a user, such as the patient 2900 or clinician 2902 described above, can initiate the pairing procedure, for example, by selecting an "Initiate Pairing Procedure?" option from a dropdown menu on the diabetes managing device and/or insulin pump or by choosing "Yes" or similar when prompted by "Initiate Pairing Procedure?" on the display. In some embodiments, the diabetes managing device display and/or the insulin pump display can be a touchscreen that allows a user to touch an appropriate location on the display to initiate the pairing procedure.

At step 6510, the diabetes managing device searches for a pump identification signal, which is output from the insulin pump at step 6508. The pump identification signal can include a pump identification code that contains information sufficient to uniquely identify the insulin pump, for example, the brand name, model and/or serial number. The diabetes managing device receives the pump identification signal at step 6512 and obtains the pump identification code from the pump identification signal at step 6514. The pump identification code can then be displayed on the diabetes managing device display (step 6516). In some embodiments, the diabetes managing device can display information (such as a pump identification code) related to any and all insulin pumps that are within the communication range of the diabetes managing device.

In order to ensure that the proper pump identification code is selected, the insulin pump can display its unique pump identification code on its display (step 6518). The user (patient 2900, clinician 2902, etc.) can then choose the pump identification code on the diabetes managing device that matches the pump identification code displayed on the insulin pump. In this manner, the proper pump identification code can be selected such that the diabetes managing device receives an insulin pump selection input at step 6520. The insulin pump can search for an insulin pump selection confirmation signal (step 6524), which is output from the diabetes managing device at step 6524. At step 6526, the insulin pump selection confirmation signal is received by the insulin pump to inform the insulin pump that it has been selected by the diabetes managing device for pairing.

The method 6500 continues, as shown in FIG. 124, to steps 6528 and 6530 at which the diabetes managing device and insulin pump generate first and second verification strings, respectively. The first verification string can be displayed on the diabetes managing device display (step 6532) and the second verification string can be displayed on the insulin pump display (step 6534). If the first and second verification strings match, the diabetes managing device can receive a first confirmation input at step 6536. Similarly, the insulin pump can receive a second confirmation input at step 6538 if the first and second verification strings match.

In some embodiments, the user (patient 2900, clinician 2902, etc.) can confirm that first and second verification strings match and input the first and second confirmation inputs into the diabetes managing device and insulin pump, respectively. The user can input the first and second confirmation inputs, for example, by actuating a switch or push button, selecting an appropriate option from a dropdown menu on the diabetes managing device and/or insulin pump or by selecting "Match" or similar option on the diabetes managing device and/or insulin pump displays. In some embodiments, the diabetes managing device display and/or the insulin pump display can be touch screens that allows a user to touch an appropriate location on the display to input the first and second confirmation inputs. For example only, the diabetes managing device (diabetes manager 2904) can have a touch screen display that displays the first verification string, a message reading "Does this code match the code on the insulin pump you are attempting to pair?" and two soft buttons—one reading "Yes" and the other "No." Similarly, the insulin pump can have a touch screen display that displays the second verification string, a message reading "Does this code match the code on the diabetes manager you are attempting to pair?" and two soft buttons—one reading "Yes" and the other "No." In this example, the user can input the first and second confirmation inputs into the diabetes managing device and insulin pump, respectively, by activating one of the soft buttons by touching the touch screen at the appropriate location.

Upon receipt of the first confirmation input at the diabetes managing device and the second confirmation input at the insulin pump, a secure bidirectional communication link is established at steps 6540 and 6542 to complete the pairing procedure, after which method 6500 ends. If the first and second verification strings do not match, however, the pairing procedure can terminate (or be terminated by the user) without pairing the diabetes managing device and insulin pump.

In order to provide further security, the first and second verification strings can be independently generated by the diabetes managing device and insulin pump, respectively. In some embodiments, further described below, the first and second verification strings can be generated by an algorithm that is performed at each of the diabetes managing device and insulin pump. An input (for example, an encryption key) can be generated at one of the diabetes managing device and insulin pump and transmitted to the other one of the diabetes managing device and insulin pump. For example only, the input can be generated by a random number generator or similar device, or the input may be selected from a list of all possible inputs, e.g., based on output of a random number generator or similar. This input can be utilized by the algorithm to generate the first and second verification strings. In this manner, the first and second verification strings are not transmitted between the diabetes managing device and the insulin pump and, thus, are not subject to being intercepted and used to pair an unauthorized device with the diabetes managing device or insulin pump.

Figure 125:
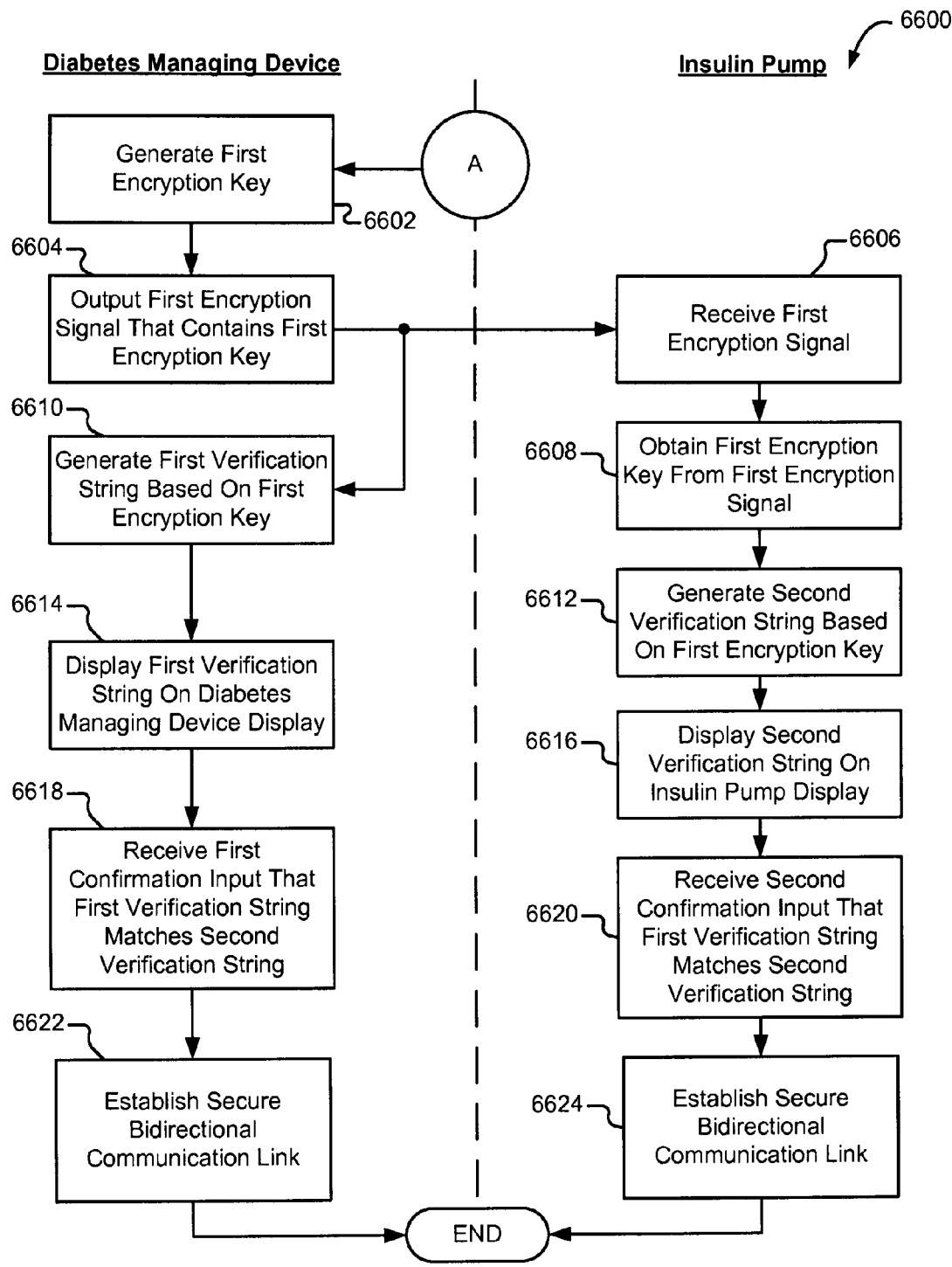

Referring now to FIGS. 123 and 125, a second exemplary method 6600 of pairing a handheld diabetes managing device and an insulin pump according to the present disclosure illustrated. Method 6600 is similar to method 6500 and can include one, more or all of steps 6502 to 6526 described above.

After the diabetes managing device outputs the insulin pump selection confirmation signal at step 6524 and the insulin pump receives the insulin pump confirmation signal at step 6526 (FIG. 123), method 6600 proceeds to step 6602 as shown in FIG. 125. At step 6602 the diabetes managing device generates a first encryption key. For example only, the first encryption key can be a public RSA key that can be used with the RSA algorithm, a well-known public-key cryptography algorithm, however, it is possible that any type of encryption key can be utilized with the present disclosure. The diabetes managing device can then output a first encryption signal that contains the first encryption key at step 6604. At step 6606, the insulin pump can receive the first encryption signal and obtain the first encryption key from the first encryption signal at step 6608.

Based on and utilizing the first encryption key, the diabetes managing device (step 6610) and the insulin pump (step 6612) can generate the first and second verification strings, respectively. As described above, the first encryption key can be input to or otherwise utilized by the algorithm stored at both the diabetes managing device and the insulin pump to independently generate the first and second verification strings. At step 6614, the first verification string can be displayed on the diabetes managing device display. Similarly, at step 6616 the second verification string can be displayed on the insulin pump display. If the first and second verification strings match, the diabetes managing device can receive a first confirmation input at step 6618 and the insulin pump can receive a second confirmation input at step 6620. In some embodiments, the user (patient 2900, clinician 2902, etc.) can confirm that first and second verification strings match and input the first and second confirmation inputs into the diabetes managing device and insulin pump, respectively.

Upon receipt of the first confirmation input at the diabetes managing device and the second confirmation input at the insulin pump, a secure bidirectional communication link is established at steps 6622 and 6624 to complete the pairing procedure, after which method 6600 ends. If the first and second verification strings do not match, however, the pairing procedure can terminate (or be terminated by the user) without pairing the diabetes managing device and insulin pump.

Figure 126A:
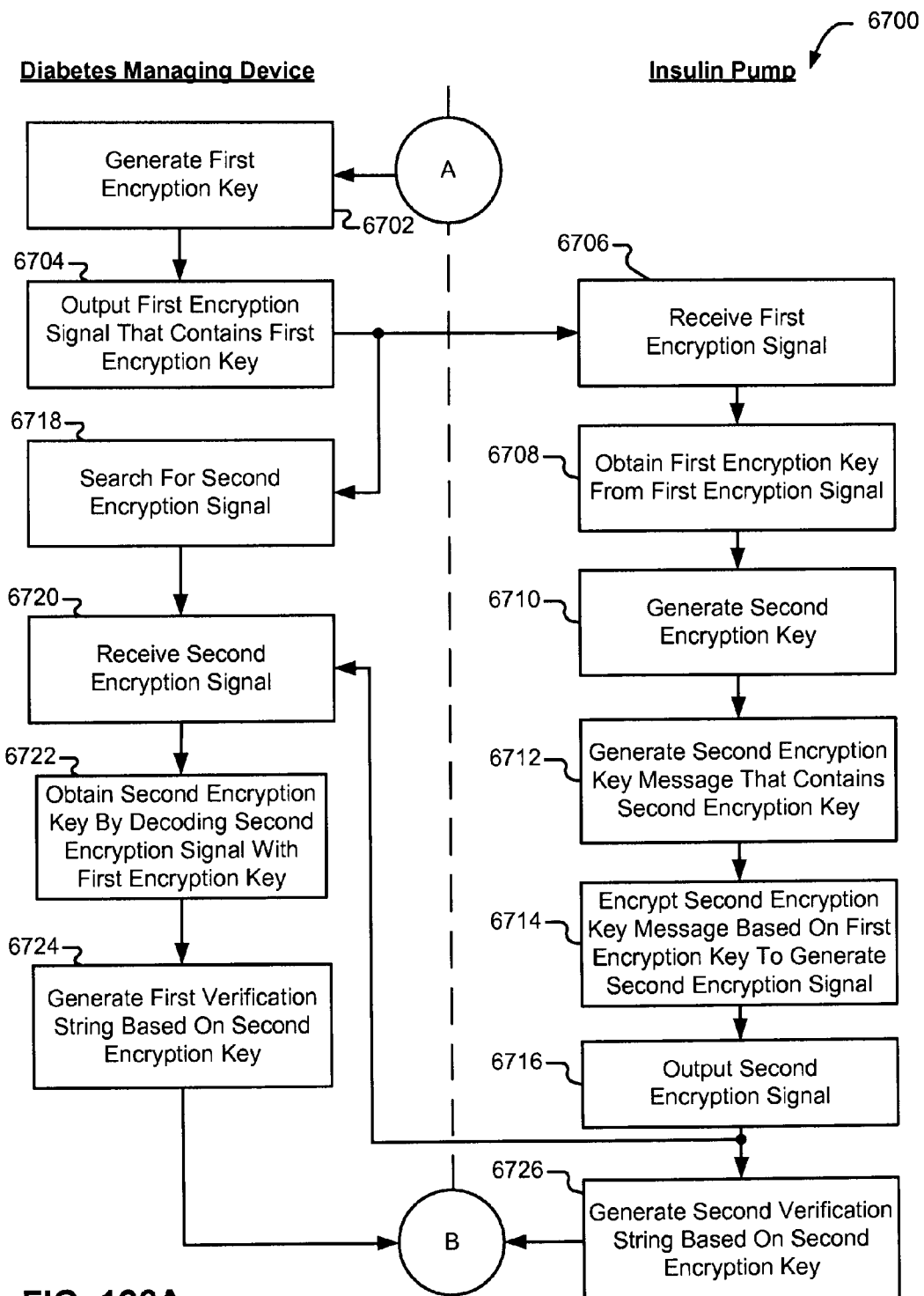
Figure 126B:
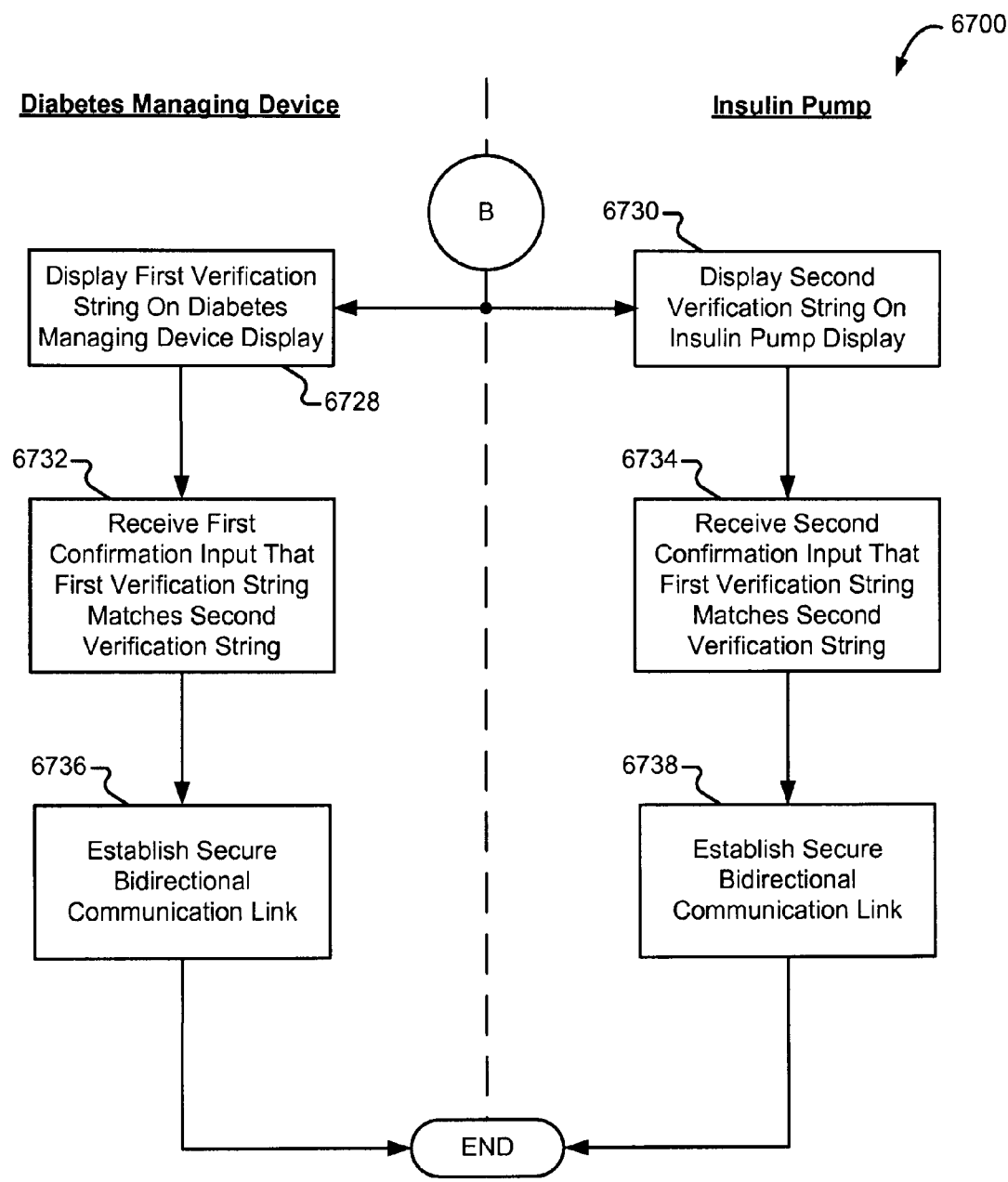

Referring now to FIGS. 123, 126A and 126B, a third exemplary method 6700 of pairing a handheld diabetes managing device and an insulin pump according to the present disclosure illustrated. Method 6700 is similar to methods 6500 and 6600 and can include one, more or all of steps 6502 to 6526 described above.

After the diabetes managing device outputs the insulin pump selection confirmation signal at step 6524 and the insulin pump receives the insulin pump confirmation signal at step 6526 (FIG. 123), method 6700 proceeds to step 6702 as shown in FIG. 126A. At step 6702 the diabetes managing device generates a first encryption key. For example only, the first encryption key can be a public RSA key that can be used with the RSA algorithm, a well-known public-key cryptography algorithm, however, it is possible that any type of encryption key can be utilized with the present disclosure. The diabetes managing device can then output a first encryption signal that contains the first encryption key at step 6704. At step 6706, the insulin pump can receive the first encryption signal and obtain the first encryption key from the first encryption signal at step 6708.

After obtaining the first encryption key at step 6708, the insulin pump can generate a second encryption key (step 6710) and generate a second encryption key message that contains the second encryption key (step 6712). For example only, the first and second encryption keys can each be a public RSA key, however, it is possible that any type of encryption key can be utilized with the present disclosure. At step 6714, the insulin pump encrypts the second encryption key message (that includes the second encryption key) based on and utilizing the first encryption key to generate a second encryption signal. The insulin pump then outputs the second encryption signal at step 6716.

After outputting the first encryption signal, the diabetes managing device can search for the second encryption signal at step 6718. The diabetes managing device can receive the second encryption signal (step 6720) and obtain the second encryption key from the second encryption signal (step 6722). In various embodiments, the diabetes managing device can obtain the second encryption key by decoding the second encryption signal with the first encryption key, which was generated at step 6702.

Based on and utilizing the second encryption key, the diabetes managing device (step 6724) and the insulin pump (step 6726) can generate the first and second verification strings, respectively. Similar to the process described above in regard to the first encryption key, the second encryption key can be input to or otherwise utilized by an algorithm stored at both the diabetes managing device and the insulin pump to independently generate the first and second verification strings. Referring now to FIG. 126B, the first verification string can be displayed on the diabetes managing device display at step 6728. Similarly, at step 6730 the second verification string can be displayed on the insulin pump display. If the first and second verification strings match, the diabetes managing device can receive a first confirmation input (step 6732) and the insulin pump can receive a second confirmation input (step 6734). In some embodiments, the user (patient 2900, clinician 2902, etc.) can confirm that first and second verification strings match and input the first and second confirmation inputs into the diabetes managing device and insulin pump, respectively.

Upon receipt of the first confirmation input at the diabetes managing device and the second confirmation input at the insulin pump, a secure bidirectional communication link is established at steps 6736 and 6738 to complete the pairing procedure, after which method 6700 ends. If the first and second verification strings do not match, however, the pairing procedure can terminate (or be terminated by the user) without pairing the diabetes managing device and insulin pump.

Figure 127A:
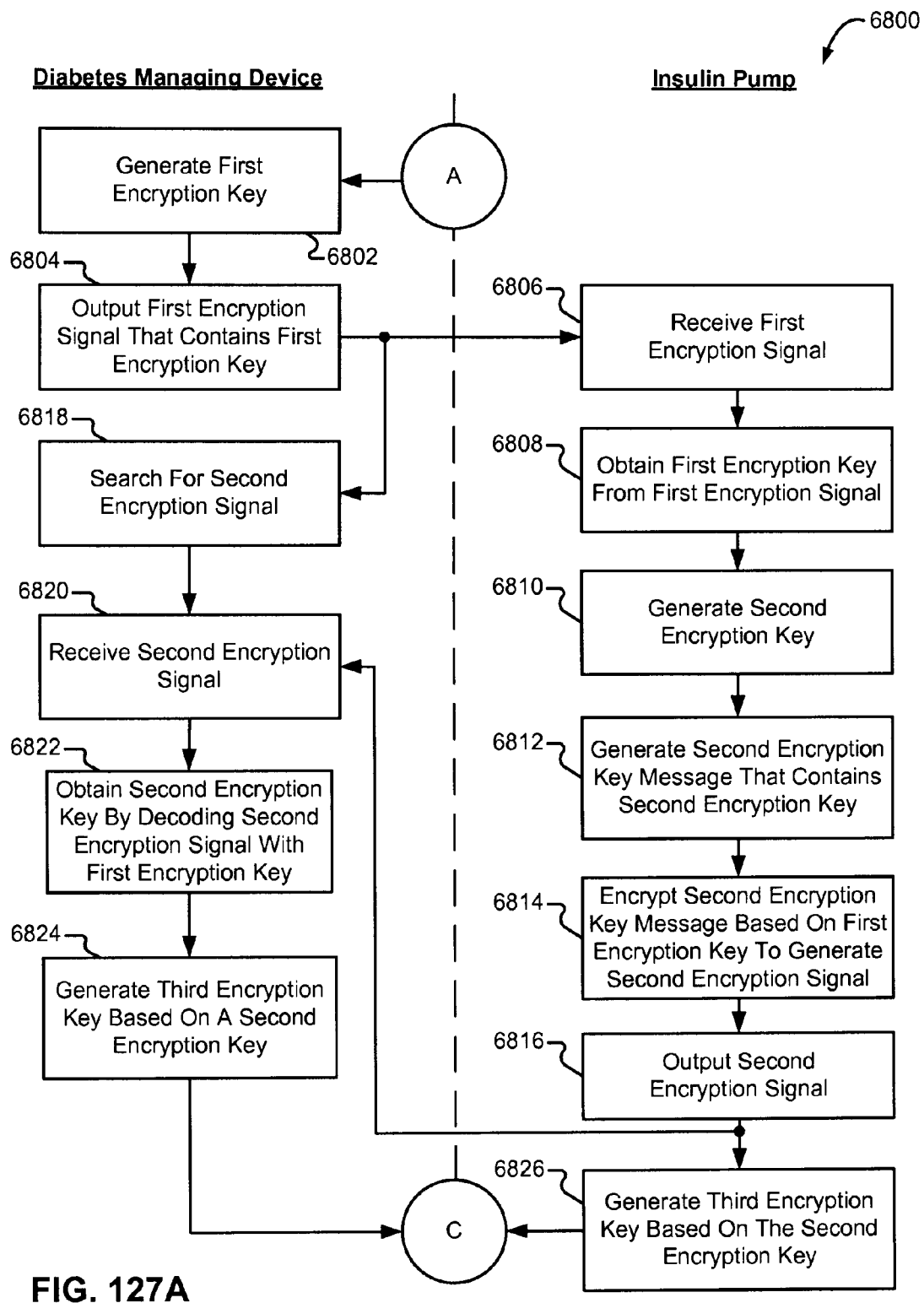
Figure 127B:
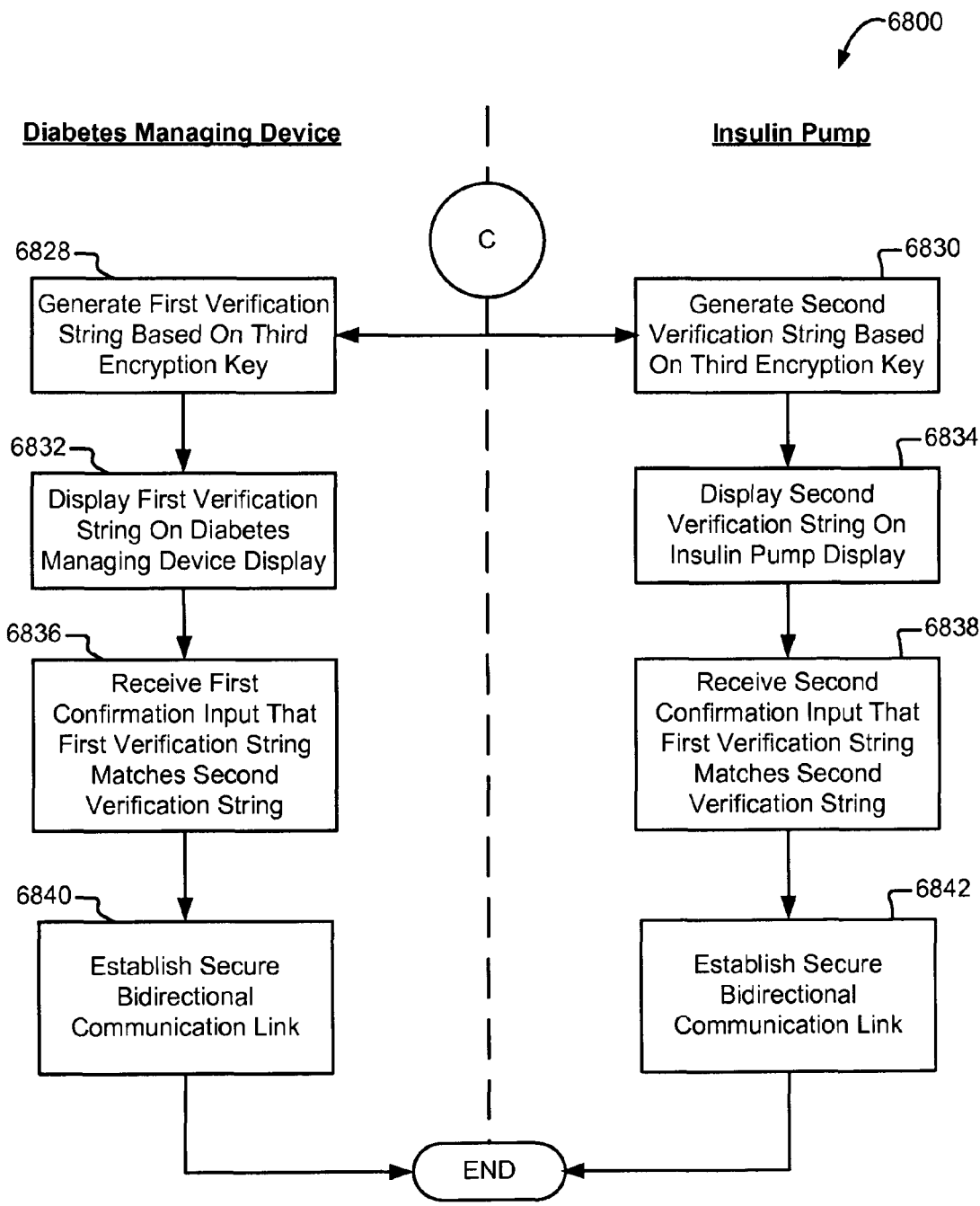

Referring now to FIGS. 123, 127A and 127B, a fourth exemplary method 6800 of pairing a handheld diabetes managing device and an insulin pump according to the present disclosure illustrated. Method 6800 is similar to methods 6500, 6600 and 6700 and can include one, more or all of steps 6502 to 6526 described above.

After the diabetes managing device outputs the insulin pump selection confirmation signal at step 6524 and the insulin pump receives the insulin pump confirmation signal at step 6526 (FIG. 123), method 6800 proceeds to step 6802 as shown in FIG. 127A. At step 6802 the diabetes managing device generates a first encryption key. For example only, the first encryption key can be a public RSA key that can be used with the RSA algorithm, a well-known public-key cryptography algorithm, however, it is possible that any type of encryption key can be utilized with the present disclosure. The diabetes managing device can then output a first encryption signal that contains the first encryption key at step 6804. At step 6806, the insulin pump can receive the first encryption signal and obtain the first encryption key from the first encryption signal at step 6808.

After obtaining the first encryption key at step 6808, the insulin pump can generate a second encryption key (step 6810) and generate a second encryption key message that contains the second encryption key (step 6812). For example only, the first and second encryption keys can each be a public RSA key, however, it is possible that any type of encryption key can be utilized with the present disclosure. At step 6814, the insulin pump encrypts the second encryption key message (that includes the second encryption key) based on and utilizing the first encryption key to generate a second encryption signal. The insulin pump then outputs the second encryption signal at step 6816.

After outputting the first encryption signal, the diabetes managing device can search for the second encryption signal at step 6818. The diabetes managing device can receive the second encryption signal (step 6820) and obtain the second encryption key from the second encryption signal (step 6822). In various embodiments, the diabetes managing device can obtain the second encryption key by decoding the second encryption signal with the first encryption key, which was generated at step 6802.

Based on and utilizing the second encryption key, both the diabetes managing device (step 6824) and the insulin pump (step 6826) can generate a third encryption key. Similar to the process described above in regard to the generation of the first and second verification strings based on the second encryption key, the second encryption can be input to or otherwise utilized by an algorithm stored at both the diabetes managing device and the insulin pump to independently generate the third encryption key. For example only, the first encryption key can be a Twofish cipher key that can be used with the Twofish algorithm, a well-known cryptography algorithm.

Referring now to FIG. 127B, based on and utilizing the third encryption key, the diabetes managing device (step 6828) and the insulin pump (step 6830) can generate the first and second verification strings, respectively. Similar to the process described above in regard to the first and second encryption keys, the third encryption can be input to or otherwise utilized by the algorithm stored at both the diabetes managing device and the insulin pump to independently generate the first and second verification strings. The first verification string can be displayed on the diabetes managing device display at step 6832. Similarly, at step 6834 the second verification string can be displayed on the insulin pump display. If the first and second verification strings match, the diabetes managing device can receive a first confirmation input (step 6836) and the insulin pump can receive a second confirmation input (step 6838). In some embodiments, the user (patient 2900, clinician 2902, etc.) can confirm that first and second verification strings match and input the first and second confirmation inputs into the diabetes managing device and insulin pump, respectively.

Upon receipt of the first confirmation input at the diabetes managing device and the second confirmation input at the insulin pump, a secure bidirectional communication link is established at steps 6840 and 6842 to complete the pairing procedure, after which method 6800 ends. If the first and second verification strings do not match, however, the pairing procedure can terminate (or be terminated by the user) without pairing the diabetes managing device and insulin pump.

Figure 128:
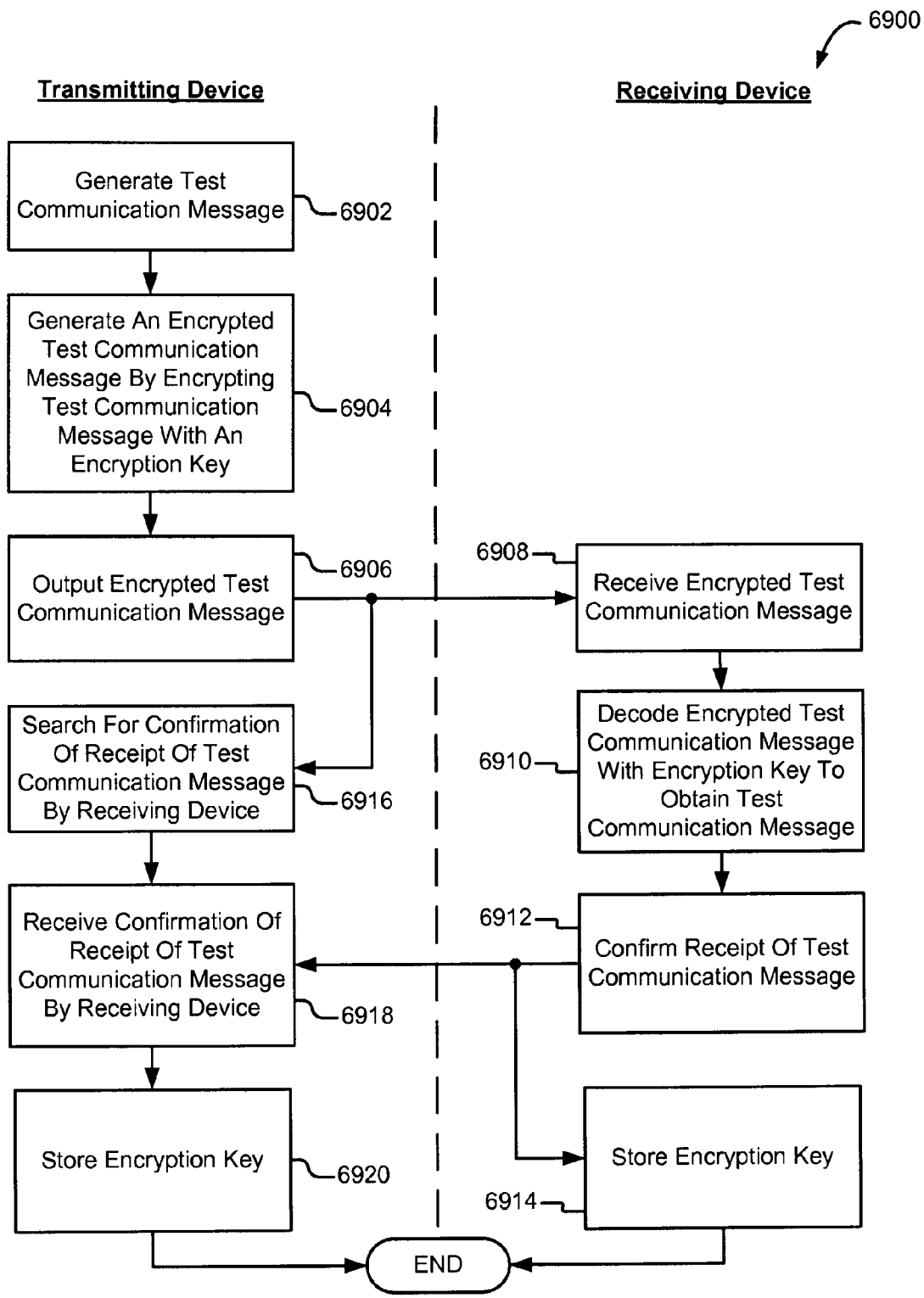

Referring now to FIG. 128, an exemplary method 6900 of establishing a secure bidirectional communication link during pairing of a handheld diabetes managing device and an insulin pump according to the present disclosure is illustrated. Method 6900 can be utilized, for example, at steps 6540, 6542, 6622, 6624, 6736, 6738, 6840 and 6842 described above. In FIG. 128, method 6900 is illustrated as taking place at a transmitting device and a receiving device. One skilled in the art will appreciate that the diabetes managing device (such as diabetes manager 2904) and insulin pump (such as insulin pump 2912 or 2914) described above can act as either one of the transmitting device or the receiving device. That is, the diabetes managing device can act as the transmitting device and the insulin pump can act as the receiving device, or the insulin pump can act as the transmitting device and the diabetes managing device can act as the receiving device.

The method 6900 begins at step 6902 at which the transmitting device generates a test communication message. At step 6904, the transmitting device then encrypts the test communication message with an encryption key to generate an encrypted test communication message. The encryption key can be any type of encryption key, including but not limited to the first, second or third encryption key described above. The encrypted test communication message is output by the transmitting device at step 6906 and received by the receiving device at step 6908. The receiving device then decodes the encrypted test communication message with the encryption key to obtain the test communication message (step 6910). In various embodiments, the test communication message can be authenticated, as described below with reference to FIG. 130. The receiving device then confirms receipt of the test communication message (step 6912) and stores the encryption key (step 6914) for future use.

After outputting the encrypted test communication message, the transmitting device searches for confirmation of receipt of the test communication message by the receiving device (step 6916). At step 6918, the transmitting device receives confirmation of receipt of the test communication message by the receiving device. The encryption key is stored at the transmitting device for future use at step 6920, after which method 6900 ends.

Figure 129:
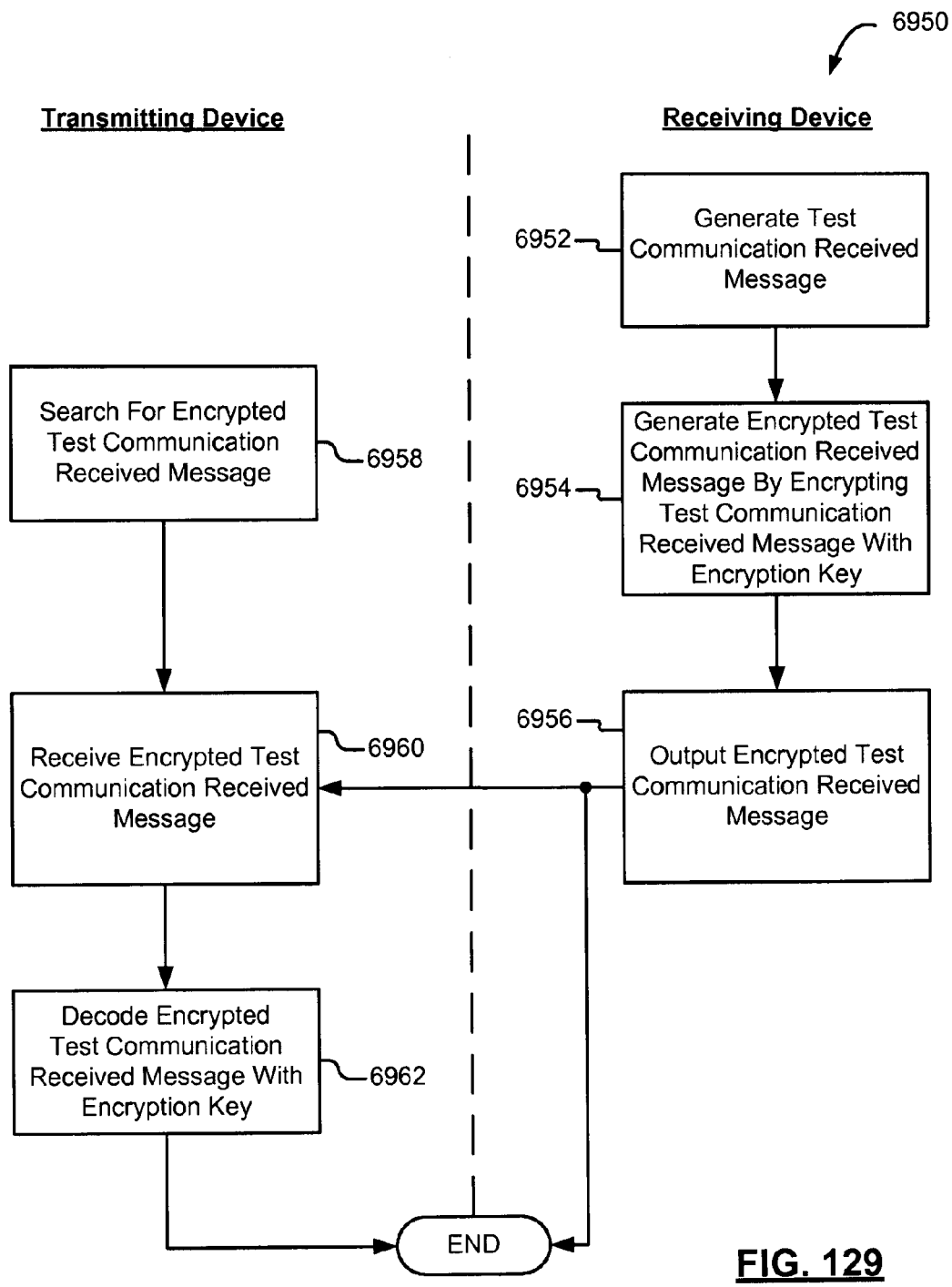

Referring now to FIG. 129, an exemplary method 6950 of confirming receipt of a test communication message by a receiving device according to the present disclosure illustrated. Method 6950 can be utilized, for example, at step 6912, 816 and 818 described above. In FIG. 129, method 6950 is illustrated as taking place at a transmitting device and a receiving device. One skilled in the art will appreciate that the diabetes managing device (such as diabetes manager 2904) and insulin pump (such as insulin pump 2912 or 2914) described above can act as either one of the transmitting device or the receiving device. That is, the diabetes managing device can act as the transmitting device and the insulin pump can act as the receiving device, or the insulin pump can act as the transmitting device and the diabetes managing device can act as the receiving device.

The method 6950 begins at step 6952 at which the receiving device generates a test communication received message. At step 6952, the receiving device then encrypts the test communication received message with an encryption key to generate an encrypted test communication received message. The encryption key can be any type of encryption key, including but not limited to the first, second or third encryption key described above. The encrypted test communication received message is output by the received device at step 6956.

At step 6958, the transmitting device searches for the encrypted test communication received message output by the receiving device at step 6956. The encrypted test communication received message is received by the transmitting device at step 6960. The transmitting device then decodes the encrypted test communication received message with the encryption key at step 6962, after which method 6950 ends. While method 6950 of FIG. 129 has been described in the context of confirming receipt of a test communication message by a receiving device, one skilled in the art will appreciate that method 6950 can be utilized to confirm receipt of any, some or all communication messages sent between the transmitting and receiving devices.

Figure 130:
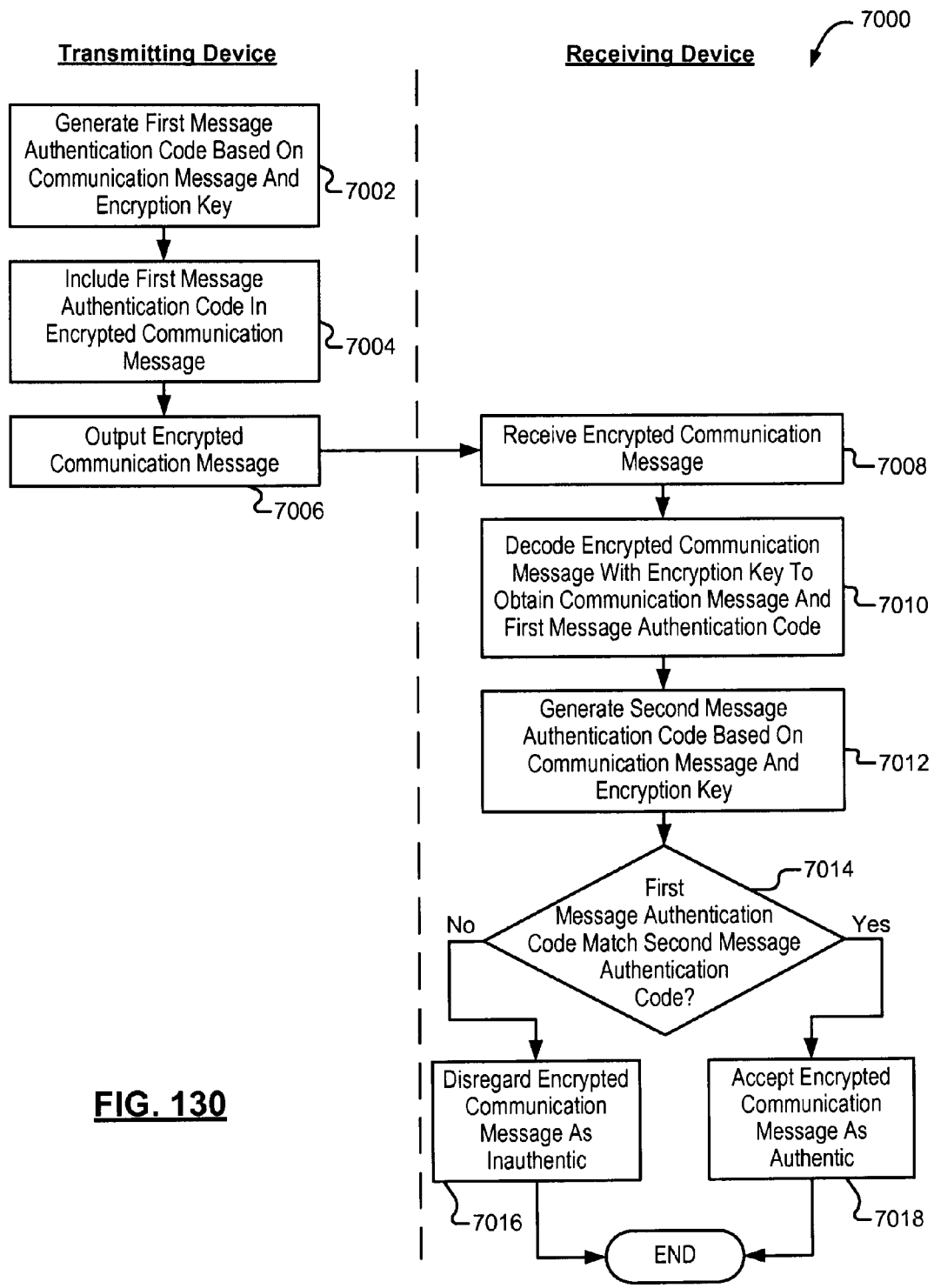

Referring now to FIG. 130, an exemplary method 7000 of authenticating a communication message sent from a transmitting device to a receiving device according to the present disclosure illustrated. Method 7000 can be utilized, for example, to authenticate the test communication message described above in relation to FIGS. 128 and 129. In various embodiments, method 7000 can be used to authenticate each and every communication message sent from the transmitting device to the receiving device.

In FIG. 130, method 7000 is illustrated as taking place at a transmitting device and a receiving device. One skilled in the art will appreciate that the diabetes managing device (such as diabetes manager 2904) and insulin pump (such as insulin pump 2912 or 2914) described above can act as either one of the transmitting device or the receiving device. That is, the diabetes managing device can act as the transmitting device and the insulin pump can act as the receiving device, or the insulin pump can act as the transmitting device and the diabetes managing device can act as the receiving device.

The method 7000 begins at step 7002 at which the transmitting device generates a first message authentication code based on the communication message and the encryption key. The first message authentication code can be generated by a process that is similar to the process described above in regard to the generation of the first and second verification strings. For example only, the first message authentication code can be generated based on inputting the communication message and the encryption key to an algorithm stored at both the diabetes managing device and the insulin pump. The encryption key can be any type of encryption key, including but not limited to the first, second or third encryption key described above. At step 7004, the transmitting device includes the first message authentication code in an encrypted communication message. The encrypted communication message can include a version of the communication message that has been encrypted with the encryption key, as well as the first message authentication code generate at step 7002. For example only, the encrypted communication message can include two separate data fields; the first data field can include the communication message that has been encrypted and the second data field can include the first message authentication code.

The transmitting device outputs the encrypted communication message at step 7006, which is received by the receiving device at step 7008. The receiving device decodes the encrypted communication message at step 7010 to obtain the communication message and the first message authentication code. At step 7012, the receiving device can generate a second message authentication code based on the communication message and encryption key. The second message authentication code can be generated by the same process used to generate the first message authentication code described above, i.e., the second message authentication code can be generated by inputting the communication message and the encryption key to the algorithm stored at both the diabetes managing device and the insulin pump. If the diabetes managing device and the insulin pump both share the same algorithm and encryption key, each communication message may be authenticated by comparing the first and second message authentication codes. Thus, the receiving device compares the first and second message authentication codes at step 7014. If the first and second message authentication codes do not match, the method 7000 proceeds to step 7016 at which the receiving device disregards the encrypted communication message as inauthentic. If, however, the first and second message authentication codes do match, the method 7000 proceeds to step 7018 at which the receiving device accepts the encrypted communication message as authentic. After either step 7016 or 7018, method 7000 ends.

Figure 131:
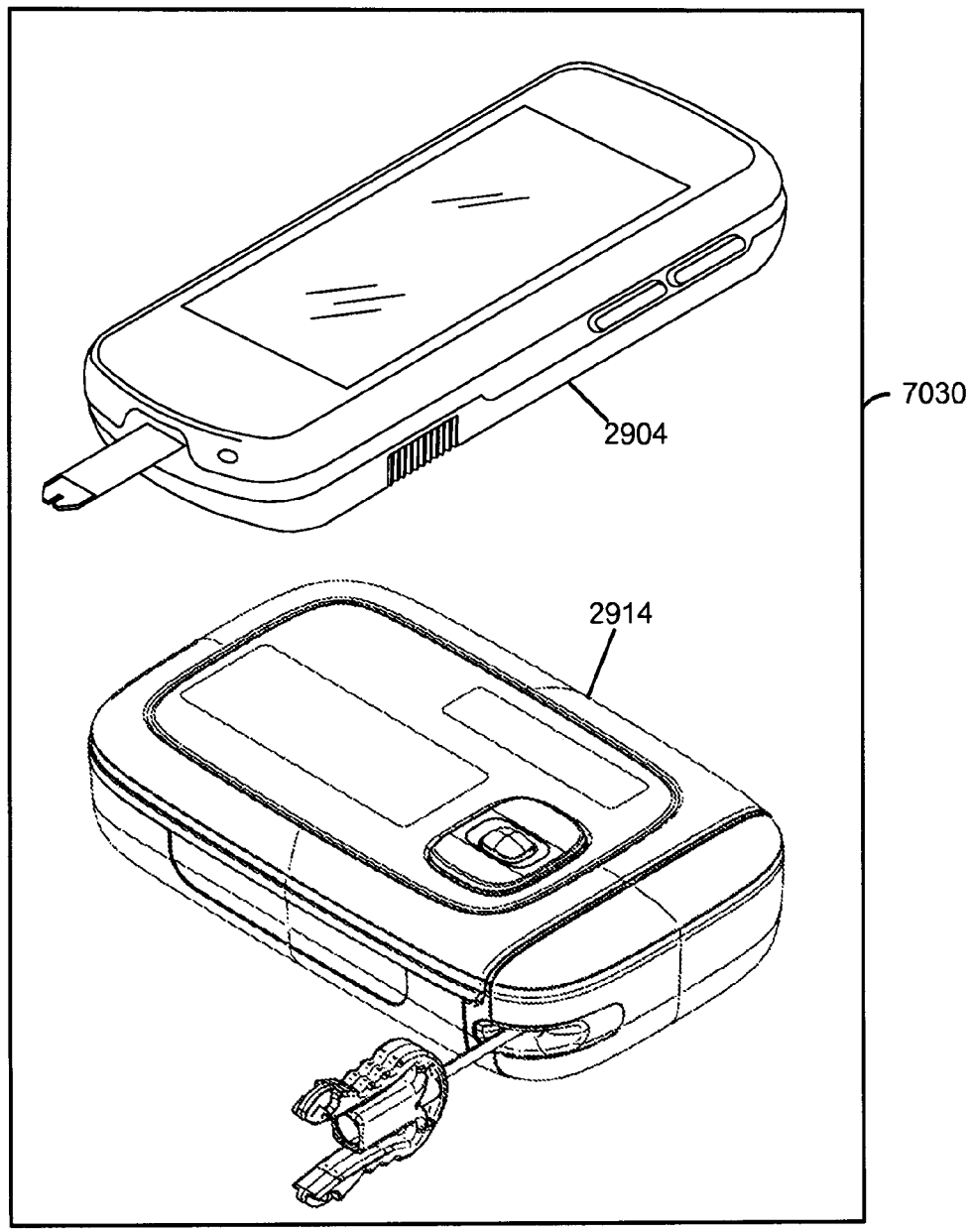
Figure 132:
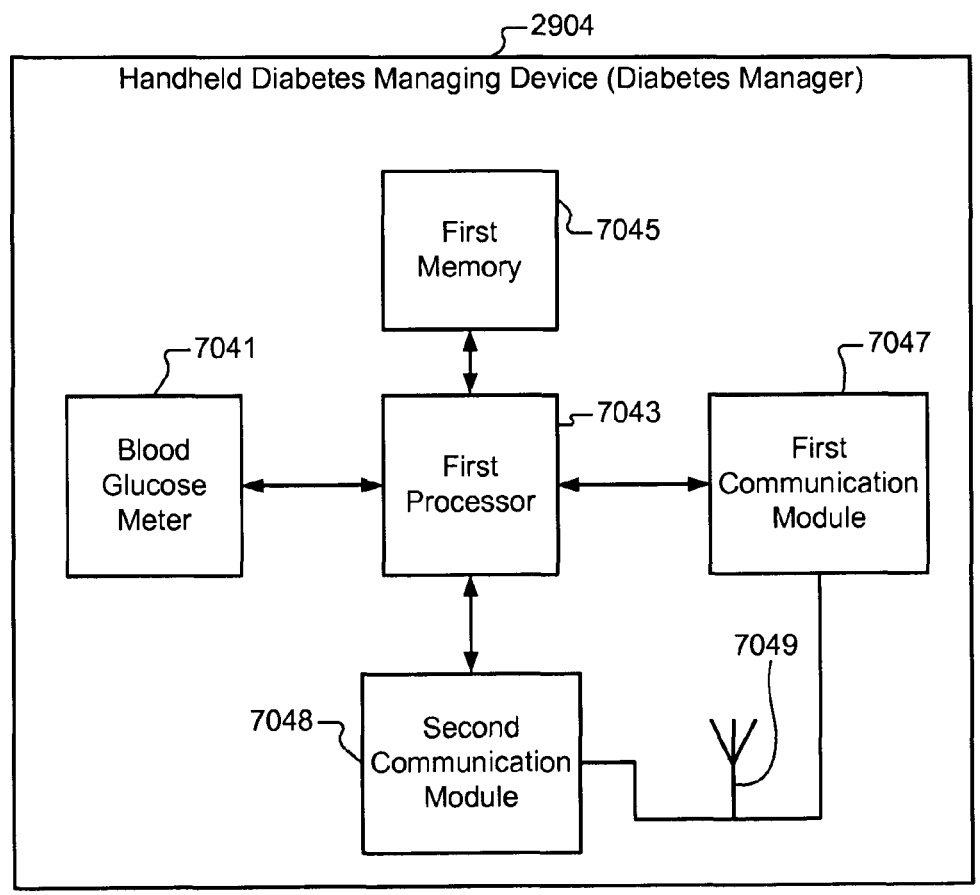
Figure 133:
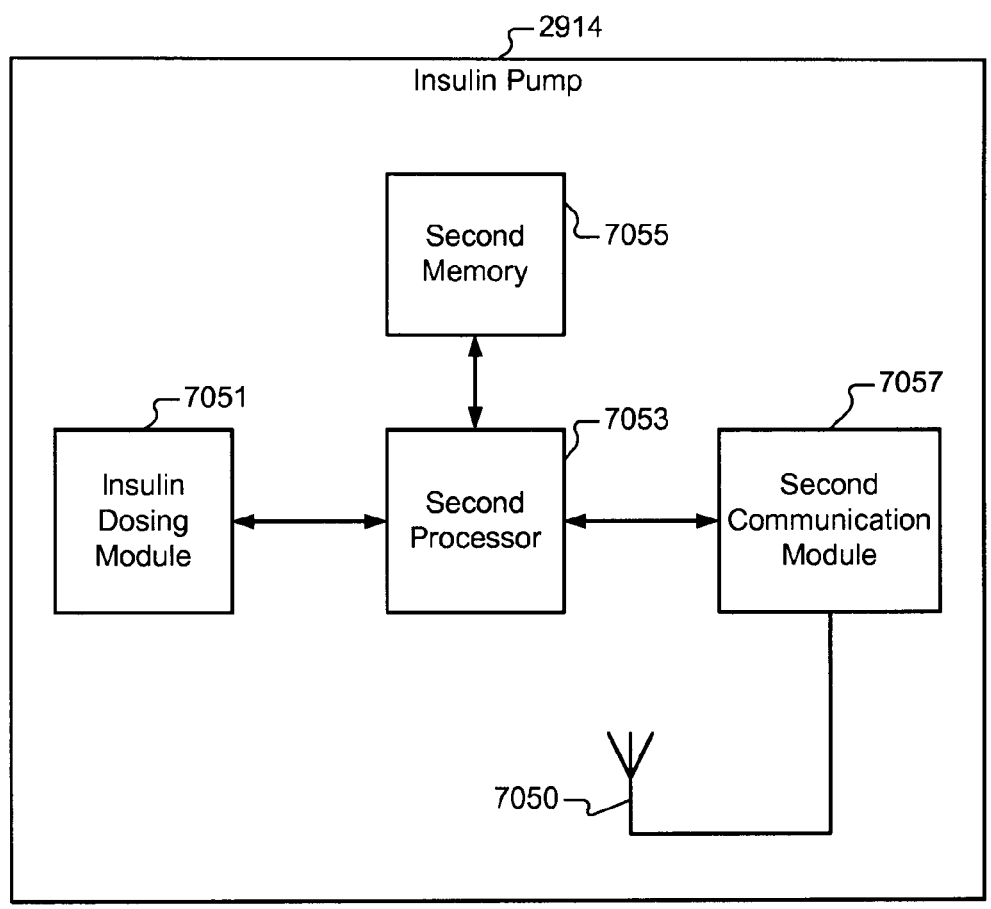

Referring now to FIGS. 131-133, a diabetes care kit 7030 for providing diagnostics and therapy according to the present disclosure is illustrated. Diabetes care kit 7030 can include a handheld diabetes managing device (such as diabetes manager 2904) and an insulin pump (such as insulin pump 2912 or 2914). Diabetes care kit 7030 can be preconfigured to reduce initial setup by a user (patient 2900, clinician 2902, etc.), for example, by establishing a paired relationship between the diabetes manager 2904 and insulin pump 2914 before providing the diabetes care kit 7030 to the user.

Referring now to FIG. 132, diabetes manager 2904 can include a blood glucose meter 7041, a first processor 7043, a first memory 7045, a first communication module 7047 and a first antenna 7049. The blood glucose meter 7041 can determine a blood glucose level of a user, for example, by measuring the blood glucose in a capillary blood sample provided by the user or obtaining a blood glucose estimate provided by a continuous glucose monitor, such as CGM 2910 described above. The blood glucose meter 7041 can be coupled to the first processor 7043 such that the first processor 7043 can receive the blood glucose level from the blood glucose meter 7041. Based on the blood glucose level, the first processor 7043 can generate an insulin pump command. The insulin pump command can be an instruction that notifies the insulin pump 2914 to provide an appropriate dose of insulin to provide to the user. The first processor 7043 can generate the insulin pump command based on an algorithm stored in the first memory 7045. In addition to the blood glucose level of the user, the insulin pump command can be based on a number of other factors, such as the weight and insulin resistance of the user, and input(s) by the user regarding whether the user will be eating a meal or exercising.

An encryption key can also be preloaded into the first memory 7045 for use by the first processor 7043 and first communication module 7047. For example only, the encryption key can be loaded into the first memory 7045 during manufacture of the diabetes manager 2904, after completion of manufacture but before the diabetes manager 2904 is packaged or otherwise included in the kit 7030, or any time before providing the kit 7030 to a user. The encryption key (such as the first, second or third encryption key described above) can be utilized to establish a secure bidirectional communication link between the diabetes manager 2904 and insulin pump 2914 as well as for other security purposes (such as authentication of messages transmitted between the diabetes manager 2904 and insulin pump 2914), as described above.

The first communication module 7047 can be coupled to the first processor 7043 and first memory 7047. The first communication module 7047 can utilize the encryption key to generate encrypted communication messages, such as an encrypted communication message based on the insulin pump command. The first antenna 7049 can be coupled to the first communication module 7047 such that encrypted communication messages can be transmitted from the first antenna 7049 to, e.g., the insulin pump 2914.

Referring now to FIG. 133, insulin pump 2914 can include an insulin dosing module 7051, a second processor 7053, a second memory 7055, a second communication module 7057 and a second antenna 7059. The insulin dosing module 7051 can dispense insulin to a user (patient 2900) based on the insulin pump command. The insulin dosing module 7051 can be coupled to the second processor 7053 such that the second processor 7043 can transmit an insulin dose command to the insulin dosing module 7051. The insulin dose command can be generated by the second processor 7053 based on the insulin pump command. An algorithm stored in the second memory 7055 can be utilized by the processor 7053 to generate the insulin dose command. In addition to the insulin pump command, the insulin dose command can be based on a number of other factors, such as a previous dose or doses provided to the user or a blood glucose estimate provided by a continuous glucose monitor, such as CGM 2910 described above.

The encryption key can also be preloaded into the second memory 7055 for use by the second processor 7053 and second communication module 7057. For example only, the encryption key can be loaded into the second memory 7055 during manufacture of the insulin pump 2914, after completion of manufacture but before the insulin pump 2914 is packaged or otherwise included in the kit 7030, or any time before providing the kit 7030 to a user. The encryption key (such as the first, second or third encryption key described above) can be utilized to establish a secure bidirectional communication link between the diabetes manager 2904 and insulin pump 2914 as well as for other security purposes (such as authentication of messages transmitted between the diabetes manager 2904 and insulin pump 2914), as described above.

The second antenna 7059 can be coupled to the second communication module 7057. The second antenna 7059 can decode encrypted communication messages sent by the diabetes manager 2904, such as the encrypted communication message based on the insulin pump command. The second communication module 7057 can be coupled to the second antenna 7059, as well as the second processor 7053 and second memory 7057. The second communication module 7057 can utilize the encryption key to decode the encrypted communication messages sent by the diabetes manager 2904. For example, the second communication module 7047 can utilize the encryption key to decode the encrypted communication message to obtain the insulin pump command generated by the diabetes manager 2904.

While the diabetes manager 2904 has been described above as generating and transmitting encrypted communication messages to the insulin pump 2914, and the insulin pump has been described as receiving and decoding encrypted communication messages from the diabetes manager 2904, one skilled in the art will appreciate that the diabetes manager 2904 can also receive and decode encrypted communication messages generated by and transmitted from the insulin pump 2914.

Furthermore, the kit 7030 and its associated diabetes manager 2904 and insulin pump 2914 can perform the methods described above in relation to FIGS. 123-130, such as, but not limited to, any or all of the methods 6500, 6600, 6700, 6800, 6950, 7000 for pairing and utilizing a secure bidirectional communication link between the diabetes manager 2904 and insulin pump 2914, any or all of the methods 6900, 6950 for establishing the secure bidirectional communication link by sending a test communication message from the diabetes manager 2904 to the insulin pump 2914 (or vice-versa) and confirming receipt of communication messages sent from the diabetes manager 2904 to the insulin pump 2914 (or vice-versa), and the method 7000 of method of authenticating a communication message sent from the diabetes manager 2904 to the insulin pump 2914 (or vice-versa). For example, the kit 7030 and its associated diabetes manager 2904 and insulin pump 2914 can perform the methods of pairing and utilizing a secure bidirectional communication link, as described above, in the event that a user replaces a component of, or adds a component (such as, CGM 2910) to, the kit 7030 after obtaining the kit 7030.

In some exemplary embodiments, the handheld diabetes managing device (diabetes manager 2904) can include a first pairing application. The first pairing application can be implemented as computer executable instructions stored on a non-transitory tangible computer readable medium at the handheld diabetes managing device, such as first memory 7045. The first pairing application can be configured to execute a pairing procedure at the handheld diabetes managing device (diabetes manager 2904) for pairing the handheld diabetes managing device (diabetes manager 2904) and the insulin pump (insulin pump 2914). Similarly, the insulin pump (insulin pump 2914) can include a second pairing application. The second pairing application can be implemented as computer executable instructions stored on a non-transitory tangible computer readable medium at the insulin pump, such as second memory 7055. The second pairing application can be configured to execute the pairing procedure at the insulin pump (insulin pump 2914). The pairing procedure can include, for example, any or all of the methods 6500, 6600, 6700, 6800, 6900, 6950, 7000 for pairing and utilizing a secure bidirectional communication link between the diabetes manager 2904 and insulin pump 2914 that are described above.

In some exemplary embodiments, the handheld diabetes managing device (diabetes manager 2904) can include a first message confirmation application. The first message confirmation application can be implemented as computer executable instructions stored on a non-transitory tangible computer readable medium at the handheld diabetes managing device, such as first memory 7045. The first message confirmation application can be configured to execute a procedure at the handheld diabetes managing device (diabetes manager 2904) for confirming receipt of a communication message at a receiving device, such as the handheld diabetes managing device (diabetes manager 2904) and/or the insulin pump (insulin pump 2914). Similarly, the insulin pump (insulin pump 2914) can include a second message confirmation application. The second message confirmation application can be implemented as computer executable instructions stored on a non-transitory tangible computer readable medium at the insulin pump, such as second memory 7055. The second message confirmation application can be configured to execute the procedure for confirming receipt of the communication message at the receiving device at the insulin pump (insulin pump 2914). The procedure can include, for example, any or all of the methods 6900, 6950 for confirming receipt of the communication message at the diabetes manager 2904 and/or insulin pump 2914 that are described above.

Finally, in various exemplary embodiments, the handheld diabetes managing device (diabetes manager 2904) can include a first message authentication application. The first message authentication application can be implemented as computer executable instructions stored on a non-transitory tangible computer readable medium at the handheld diabetes managing device, such as first memory 7045. The first message authentication application can be configured to execute a procedure at the handheld diabetes managing device (diabetes manager 2904) for authenticating a communication message received by a receiving device, such as the handheld diabetes managing device (diabetes manager 2904) and/or the insulin pump (insulin pump 2914). Similarly, the insulin pump (insulin pump 2914) can include a second message authentication application. The second message authentication application can be implemented as computer executable instructions stored on a non-transitory tangible computer readable medium at the insulin pump, such as second memory 7055. The second message authentication application can be configured to execute the procedure for authenticating a communication message received by the receiving device. The procedure can include, for example, the method 7000 for authenticating a communication message received by the diabetes manager 2904 and/or insulin pump 2914 that are described above.

Referring now to FIGS. 132 through 137, the handheld diabetes managing device (diabetes manager 2904) can act as a communication hub of the diabetes management system 2930 to provide a secure and efficient communication path between the various devices. For example only, the handheld diabetes managing device (diabetes manager 2904) can provide a secure and efficient communication path between the insulin pump (insulin pump 2912 or 2914) and an external computing device (for example, CGM 2910, mobile device 2932, personal computer 2906 and its associated diabetes analysis software, and other healthcare devices 2934 described above). Further, handheld diabetes managing device (diabetes manager 2904), insulin pump (insulin pump 2912 or 2914) and external computing device (for example, CGM 2910, mobile device 2932, personal computer 2906 and its associated diabetes analysis software, and other healthcare devices 2934 described above) can be components of a diabetes care system (such as, diabetes management system 2930).

The handheld diabetes managing device (diabetes manager 2904) can include a blood glucose meter 7041, a processor (first processor 7043), a first communication module 7047 and a second communication module 7048. As described above, the blood glucose meter 7041 can determine a blood glucose level of a user (patient 2900), for example, by measuring the blood glucose in a capillary blood sample provided by the user or obtaining a blood glucose estimate provided by a continuous glucose monitor, such as CGM 2910. The processor (first processor 7043) of the handheld diabetes managing device (diabetes manager 2904) can be coupled to the blood glucose meter (blood glucose meter 7041). The processor (first processor 7043) can generate blood glucose meter data and an insulin pump instruction based on the blood glucose level of the user. Non-limiting examples of blood glucose meter data include at least one of a plurality of blood glucose levels, an amount of food and beverage consumed and associated time of consumption, and an exercise schedule. An insulin pump instruction can include, e.g, an amount of insulin that is recommended to be delivered by the insulin pump to the patient 2900. Additionally, the insulin pump instruction can be further based on, e.g., an insulin level received from a continuous glucose monitor (CGM 2910), an expected meal, an expected exercise event, the insulin resistance of patient 2900, the weight of patient 2900 and the insulin pump data, examples of which are described below.

The first communication module 7047 can be coupled to the processor (first processor 7043). The first communication module 7047 can be configured to establish a first secure bidirectional communication link with an insulin pump (insulin pump 2912 or 2914). For example only, the first secure bidirectional communication link between the handheld diabetes managing device (diabetes manager 2904) and insulin pump (insulin pump 2912 or 2914) can be a wireless communication link, such as a Bluetooth link. The first secure bidirectional communication link can be established by any or all of the methods 6500, 6600, 6700, 6800, 6900, 6950, 7000 described above. Further, the first communication module 7047 can be configured to transmit the insulin pump instruction to the insulin pump 2912 or 2914 over the first secure bidirectional communication link.

Similar to the first communication module 7047 described above, the second communication module 7048 can also be coupled to the processor (first processor 7043) and antenna 7049. The second communication module 7048 can be configured to establish a second secure bidirectional communication link with an external computing device (CGM 2910, mobile device 2932, personal computer 2906 and its associated diabetes analysis software, or other healthcare device(s) 2934). For example only, the second secure bidirectional communication link between the handheld diabetes managing device (diabetes manager 2904) and external computing device can be a wired communication link, such as a Universal Serial Bus link. Alternatively, the second secure bidirectional communication link between the handheld diabetes managing device (diabetes manager 2904) and external computing device can be a wireless communication link, such as a Bluetooth link, that can be established by any or all of the methods 6500, 6600, 6700, 6800, 6900, 6950, 7000 described above. Further, the second communication module 7048 can be configured to transmit the blood glucose meter data to the external computing device over the second secure bidirectional communication link.

Thus, the handheld diabetes managing device (diabetes manager 2904) can be configured to pass information between all components of the diabetes management system 2930 without establishing a direct communication link or pairing relationship between the individual components. This can be accomplished by establishing a paired relationship/secure-bidirectional communication link between the handheld diabetes managing device (diabetes manager 2904) and each component. The handheld diabetes managing device (diabetes manager 2904) can be configured to deliver insulin pump data from the insulin pump (insulin pump 2912 or 2914) to the external computing device over a secure communication path without a direct communication link between the insulin pump and external computing device. Examples of insulin pump data include, but are not limited to, an amount and time of insulin delivered to patient 2900 during a previous period. The previous period can be adjusted by the user (patient 2900, clinician 2902, etc.).

In some embodiments, a method of transmitting information between an insulin pump and an external computing device without providing a direct link between the insulin pump and external computing device in a diabetes care system for providing diagnostics and therapy that includes a handheld diabetes managing device is presented. The method can include the steps of establishing a first secure bidirectional communication link between the handheld diabetes managing device and the insulin pump and establishing a second secure bidirectional communication link between the handheld diabetes managing device and the external computing device. The first and/or second secure bidirectional communication links can be established by any or all of the methods 6500, 6600, 6700, 6800, 6900, 6950, 7000 described above.

Once the first and second secure bidirectional communication links are established, information can be transmitted between the insulin pump and the external computing device over a secure communication path that includes the first secure bidirectional communication link and the second secure bidirectional communication link. In a non-limiting example, the first secure bidirectional communication link can be utilized to transmit information between the handheld diabetes managing device and the insulin pump and the second secure bidirectional communication link can be utilized to transmit the information between the handheld diabetes managing device and the external computing device.

Referring now to FIG. 135, an exemplary method 7100 of establishing a pass-through mode in a handheld diabetes managing device is illustrated. In pass-through mode, the handheld diabetes managing device (such as diabetes manager 2904) can be utilized as a communications mediator between an external computing device (such as personal computer 2906) and an insulin pump (such as insulin pump 2912 or 2914). That is, the handheld diabetes managing device can be utilized to pass messages over a secure communication path between the external computing device and the insulin pump.

At step 7105, a first secure bidirectional communication link between a handheld diabetes managing device and an external computing device can be established. This first secure bidirectional communication link can be established by any or all of the methods 6500, 6600, 6700, 6800, 6900, 6950, 7000 described above. Alternatively, the secure bidirectional communication link between the handheld diabetes managing device and external computing device can be a wired communication link, such as a Universal Serial Bus link. At step 7110, the external computing device can query the handheld diabetes managing device to determine if it is paired to an insulin pump. If the handheld diabetes managing device is not paired to an insulin pump, the method can proceed to step 7115 at which pass-through mode cannot be established.

If the handheld diabetes managing device is paired to an insulin pump, a second secure bidirectional communication link between the handheld diabetes managing device and the insulin pump can be established at step 7120. This second secure bidirectional communication link can be established by any or all of the methods 6500, 6600, 6700, 6800, 6900, 6950, 7000 described above. At step 7125, the handheld diabetes managing device can report to the external computing device that the second secure bidirectional communication link has been established. The external computing device can request that the handheld diabetes managing device enter pass-through mode at step 7130. The handheld diabetes managing device can then enter pass-through mode at step 7135. Further, handheld diabetes managing device can report to external computing device that it has entered pass-through mode (step 7140).

Referring now to FIG. 136, an exemplary method 7200 of sending a command from an external computing device (such as personal computer 2906) to an insulin pump (such as insulin pump 2912 or 2914) through a handheld diabetes managing device (such as diabetes manager 2904) in pass-through mode is illustrated. At step 7205, the external computing device can generate a command for the insulin pump. In order to transmit the command to the insulin pump, the external computing device can generate a command message based on the command at step 7210. The command message can be, for example, the command for the insulin pump that has been modified/encrypted/etc. for secure transmission over the secure bidirectional communication link between the external computing device and the handheld diabetes managing device. In some embodiments, the command message can be generated by encrypting the command with an encryption key (such as the first, second or third encryption keys) as described above. At step 7215, the command message can be transmitted to the handheld diabetes managing device. The handheld diabetes managing device can analyze the command message to determine if the command is an "End Pass-Through Mode Command" at step 7220. For example only, the handheld diabetes managing device can retrieve the command from the command message by modifying/decrypting/etc. the command message. In some embodiments, the command can be retrieved by decrypting the command message with an encryption key (such as the first, second or third encryption keys) as described above. If the command is an "End Pass-Through Mode Command," the handheld diabetes managing device can end pass-through mode at step 7220.

If the command is not an "End Pass-Through Mode Command" at step 7220, the handheld diabetes managing device can generate an insulin pump command based on the command at step 7230. The insulin pump command can be, for example, the command that has been modified/encrypted/etc. for secure transmission over the secure bidirectional communication link between the insulin pump and the handheld diabetes managing device. In some embodiments, the insulin pump command can be generated by encrypting the command with an encryption key (such as the first, second or third encryption keys) as described above. At step 7235, the insulin pump command can be transmitted to the insulin pump. The insulin pump can then retrieve the command from the insulin pump command at step 7240. For example only, the insulin pump can retrieve the command by modifying/decrypting/etc. the insulin pump command. In some embodiments, the command can be retrieved by decrypting the insulin pump command with an encryption key (such as the first, second or third encryption keys) as described above.

Referring now to FIG. 137, an exemplary method 7300 of sending a response from an insulin pump (such as insulin pump 2912 or 2914) to an external computing device (such as personal computer 2906) through a handheld diabetes managing device (such as diabetes manager 2904) in pass-through mode is illustrated. At step 7305, the insulin pump can generate a response to the external computing device. The response can include any message or data present at the insulin pump that is desired by the external computing device, such as the insulin pump data described above. The insulin pump can generate a response message based on the response at step 7310. The response message can be, for example, the response that has been modified/encrypted/etc. for secure transmission over the secure bidirectional communication link between the insulin pump and the handheld diabetes managing device. In some embodiments, the response message can be generated by encrypting the response with an encryption key (such as the first, second or third encryption keys) as described above. The response message can be transmitted to the handheld diabetes managing device at step 7315. The handheld diabetes managing device, at step 7320, can generate a pump response message based on the response message. At step 7325, the pump response message can be transmitted to the external computing device.

The pump response message can be, for example, the response that has been modified/encrypted/etc. for secure transmission over the secure bidirectional communication link between the external computing device and the handheld diabetes managing device. In some embodiments, the pump response message can be generated by encrypting the response with an encryption key (such as the first, second or third encryption keys) as described above. For example only, the handheld diabetes managing device can retrieve the response by modifying/decrypting/etc. the response message. In some embodiments, the response can be retrieved by decrypting the response message with an encryption key (such as the first, second or third encryption keys) as described above. Then, the response can be modified/encrypted/etc. for secure transmission over the secure bidirectional communication link between the handheld diabetes managing device and the external computing device.

Referring now to FIG. 138, an exemplary method 7400 of pairing an insulin pump (such as insulin pump 2912 or 2914) to an external computing device (such as personal computer 2906) through a handheld diabetes managing device (such as diabetes manager 2904) in pass-through mode is illustrated. Method 7400 can, for example, begin when the command generated by external computing device at step 7205 in method 7200 (FIG. 137) is a pairing command. For example, upon entering pass-through mode a user can initiate a secure pairing mode, e.g., by selecting a pairing option on the external computing device or by choosing yes when prompted to initiate pairing. Secure pairing mode can pair the insulin pump with the external computing device by utilizing the handheld diabetes managing device to securely transmit an encryption key (such as the first, second or third encryption keys) between the insulin pump and external computing device.

After receiving the pairing command, the insulin pump can retrieve the encryption key from its memory (for example, second memory 7055) at step 7405. The insulin pump can then generate a first encryption key message based on the encryption key at step 7410. The first encryption key message can be, for example, the encryption key that has been modified/encrypted/etc. for secure transmission over the secure bidirectional communication link between the insulin pump and the handheld diabetes managing device. In some embodiments, the first encryption key message can be generated by encrypting the encryption key with an encryption key (such as the first, second or third encryption keys) as described above. At step 7415, the first encryption key message is transmitted to the handheld diabetes managing device. The handheld diabetes managing device can then generate a second encryption key message based on the first encryption key message (step 7420). For example, the handheld diabetes managing device can retrieve the encryption key by modifying/decrypting/etc. the first encryption key message. In some embodiments, the encryption key can be retrieved by decrypting the first encryption key message with an encryption key (such as the first, second or third encryption keys) as described above. Then, the second encryption key message can be generated by, for example, modifying/encrypting/etc. the encryption key for secure transmission over the secure bidirectional communication link between the external computing device and the handheld diabetes managing device. In some embodiments, the second encryption key message can be generated by encrypting the encryption key with an encryption key (such as the first, second or third encryption keys) as described above.

The handheld diabetes managing device can then transmit the second encryption key message to the external computing device at step 7425. The external computing device, at step 7430, can retrieve the encryption key from the second encryption key message. For example, the external computing device can retrieve the encryption key by modifying/decrypting/etc. the second encryption key message. In some embodiments, the encryption key can be retrieved by decrypting the second encryption key message with an encryption key (such as the first, second or third encryption keys) as described above. Upon receipt and storage of the encryption key by the external computing device, the insulin pump and external computing device can be in a paired relationship such that they can communicate over a secure bidirectional communication link without the handheld diabetes managing device acting as a communications mediator.

Metadata Tagging System for a Diabetes
Management System of Devices

Referring now to FIG. 75, a person 2900 with diabetes and a healthcare professional 2902 are shown in a clinical environment. Persons with diabetes include persons with metabolic syndrome, pre-diabetes, type 1 diabetics, type 2 diabetes, and gestational diabetes and are collectively referred to as a patient. Healthcare providers for diabetes are diverse and include nurses, nurse practitioners, physicians, and endocrinologists and are collectively referred to as a clinician.

During a healthcare consultation, the patient 2900 typically shares with the clinician 2902 a variety of patient data including blood glucose measurements, continuous glucose monitor data, amounts of insulin infused, amounts of food and beverages consumed, exercise schedules, and other lifestyle information. The clinician 2902 may obtain additional patient data that includes measurements of HbA1C, cholesterol levels, triglycerides, blood pressure, and weight of the patient 2900. The patient data can be recorded manually or electronically on a handheld diabetes management device 2904, a diabetes analysis software executed on a personal computer (PC) 2906, and/or a web-based diabetes analysis site (not shown). The clinician 2902 can analyze the patient data manually or electronically using the diabetes analysis software and/or the web-based diabetes analysis site. After analyzing the patient data and reviewing adherence of the patient 2900 to previously prescribed therapy, the clinician 2902 can decide whether to modify the therapy for the patient 2900.

Referring now to FIG. 76, the patient 2900 can use a continuous glucose monitor (CGM) 2910, an ambulatory durable insulin infusion pump 2912 or an ambulatory non-durable insulin infusion pump 2914 (collectively insulin pump 2912 or 2914), and the handheld diabetes management device 2904 (hereinafter the diabetes manager 2904). The CGM 2910 uses a subcutaneous sensor to sense and monitor the amount of glucose in the blood of the patient 2900 and communicates corresponding readings to the handheld diabetes management device 2904.

The diabetes manager 2904 performs various tasks including measuring and recording blood glucose levels, determining an amount of insulin to be administered to the patient 2900 via the insulin pump 2912 or 2914, receiving patient data via a user interface, archiving the patient data, etc. The diabetes manager 2904 periodically receives readings from the CGM 2910 indicating insulin level in the blood of the patient 2900. The diabetes manager 2904 transmits instructions to the insulin pump 2912 or 2914, which delivers insulin to the patient 2900. Insulin can be delivered in the form of a bolus dose, which raises the amount of insulin in the blood of the patient 2900 by a predetermined amount. Additionally, insulin can be delivered in a scheduled manner in the form of a basal dose, which maintains a predetermined insulin level in the blood of the patient 2900.

Referring now to FIG. 77, a diabetes management system 2930 used by the patient 2900 and the clinician 2902 includes one or more of the following devices: the diabetes manager 2904, the continuous glucose monitor (CGM) 2910, the insulin pump 2912 or 2914, a mobile device 2932, the diabetes analysis software on the PC 2906, and other healthcare devices 2934. The diabetes manager 2904 is configured as a system hub and communicates with the devices of the diabetes management system 2930. Alternatively, the insulin pump 2914 or the mobile device 2932 can serve as the system hub. Communication between the various devices in the diabetes management system 2930 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 2900 and clinician 2902 to exchange information.

The diabetes manager 2904 can receive blood glucose readings from one or more sources (e.g., from the CGM 2910). The CGM 2910 continuously measures the blood glucose level of the patient 2900. The CGM 2910 periodically communicates the blood glucose level to the diabetes manager 2904. The diabetes manager 2904 and the CGM 2910 communicate wirelessly using a proprietary Gazell wireless protocol developed by Nordic Semiconductor, Inc.

Additionally, the diabetes manager 2904 includes a blood glucose meter (BGM) and a port that communicates with the BGM (both not shown). The port can receive a blood glucose measurement strip 2936. The patient 2900 deposits a sample of blood or other bodily fluid on the blood glucose measurement strip 2936. The BGM analyzes the sample and measures the blood glucose level in the sample. The blood glucose level measured from the sample and/or the blood glucose level read by the CGM 2910 can be used to determine the amount of insulin to be administered to the patient 2900.

The diabetes manager 2904 communicates with the insulin pump 2912 or 2914. The insulin pump 2912 or 2914 can be configured to receive instructions from the diabetes manager 2904 to deliver a predetermined amount of insulin to the patient 2900. Additionally, the insulin pump 2912 or 2914 can receive other information including meal and/or exercise schedules of the patient 2900. The insulin pump 2912 or 2914 can determine the amount of insulin to administer based on the additional information.

The insulin pump 2912 or 2914 can also communicate data to the diabetes manager 2904. The data can include amounts of insulin delivered to the patient 2900, corresponding times of delivery, and pump status. The diabetes manager 2904 and the insulin pump 2912 or 2914 can communicate using a wireless communication protocol such as Bluetooth. Other wireless or wireline communication protocols can also be used.

In addition, the diabetes manager 2904 can communicate with other healthcare devices 2934. For example, the other healthcare devices 2934 can include a blood pressure meter, a weight scale, a pedometer, a fingertip pulse oximeter, a thermometer, etc. The other healthcare devices 2934 obtain and communicate personal health information of the patient 2900 to the diabetes manager 2904 through wireless, USB, or other interfaces. The other healthcare devices 2934 use communication protocols compliant with ISO/IEEE 11073 extended using guidelines from Continual® Health Alliance. The diabetes manager 2904 can communicate with the other healthcare devices 2934 using interfaces including Bluetooth, USB, etc. Further, the devices of the diabetes management system 2930 can communicate with each other via the diabetes manager 2904.

The diabetes manager 2904 can communicate with the PC 2906 using Bluetooth, USB, or other interfaces. A diabetes management software running on the PC 2906 includes an analyzer-configurator that stores configuration information of the devices of the diabetes management system 2930. The configurator has a database to store configuration information of the diabetes manager 2904 and the other devices. The configurator can communicate with users through standard web or computer screens in non-web applications. The configurator transmits user-approved configurations to the devices of the diabetes management system 2930. The analyzer retrieves data from the diabetes manager 2904, stores the data in a database, and outputs analysis results through standard web pages or computer screens in non-web based applications.

The diabetes manager 2904 can communicate with the mobile device 2932 using Bluetooth. The mobile device 2932 may include a cellular phone, a PDA, or a pager. The diabetes manager 2904 can send messages to an external network through the mobile device 2932. The mobile device 2932 can transmit messages to the external network based on requests received from the diabetes manager 2904.

Referring now to FIG. 82, the diabetes manager 2904 comprises a blood glucose measuring (BGM) module 3300, a communication module 3302, a user interface module 3304, user interfaces 3306, a processing module 3308, memory 3310, and a power module 3312. The BGM module 3300 includes a blood glucose measuring engine that analyzes the sample provided by the patient 2900 on the blood glucose measuring strip 2936 and that measures the amount of blood glucose in the sample. The communication module 3302 includes multiple radios that communicate with different devices of the diabetes management system 2930. The user interface module 3304 interfaces the diabetes manager 2904 to various user interfaces 3306 that the patient 2900 can use to interact with the diabetes manager 2904. For example, the user interfaces 3306 can include keys, switches, a display, a speaker, a microphone, a secure digital (SD) card port, a USB port, etc. of the diabetes manager 2904 (not shown).

The processing module 3308, processes data received from the BGM module 3300, the communication module 3302, and the user interface module 3304. The processing module 3308 uses memory 3310 for processing and storing data. The memory 3310 can include volatile and nonvolatile memory. The processing module 3308 outputs data to and receives data from the user interfaces 3306 via the user interface module 3304. The processing module 3308 outputs data to and receives data from the devices of the diabetes management system 2930 via the communication module 3302. The power module 3312 supplies power to the components of the diabetes manager 2904. The power module 3312 includes a rechargeable battery. The battery can be recharged using an adapter that plugs into a wall outlet. The battery can also be charged via the USB port of the diabetes manager 2904.

FIG. 139 illustrates a diabetes manager 7500 and a plurality of devices, each device performing a different function relating to treatment of diabetes of a patient. The devices include a CGM 7540, an insulin pump 7520, and a PC 7530. It is envisioned, however, that the system can include more or less devices. The diabetes manager 7500 includes a plurality of communication interfaces 7502, 7504 and 7506, that receive data records from the plurality of devices. Depending on the transmitting device, the received data records can include a metadata tag. A metadata tag is additional data, stored with the data record, which provides additional information to a data management module 7516. A metadata item is a contiguous set of byes within a data record that gives the value for a property of the data record. The metadata tag includes a device identifier of the device which generated the data, a record identifier, and a source identifier which indicates whether the record was originated by the patient, the device, or a third party. An exemplary structure of a metadata tag with exemplary metadata items is provided below:

```
Metadata tag {
    data_record_type;
    device_identifier;
    record_identifier;
    source_identifier;
    time_stamp;
    last_modification;
    checksum;
}
```

As discussed, the diabetes manager 7500 is in communication with the plurality of devices, such that data records are transferred from the devices to the diabetes manager 7500 and to the devices from the diabetes manager 7500. The diabetes manager 7500 relies on data received from the various devices to manage the treatment of the patient's diabetes. Thus, an issue arises when data received from more than one source and the received data is inconsistent. Further, there is a need for a reliable way to resolve such inconsistencies, as medical decisions can be derived from the received data.

For example, a patient can enter, via user interface 7510, that a first amount of insulin was delivered at a specific time. The insulin pump 7520, however, may transmit a record indicating that a second amount of insulin was delivered at the same time. The diabetes manager 7500 needs to be able to determine the source of the inconsistent records as well as to know which record to base a future decision on in the future. The metadata tags discussed above provide a solution to these problems. As will be described below, each device has a metadata generator associated therewith that generates metadata to allow a data management module 7516 to manage the data records received from various sources.

An exemplary insulin pump 7520 is comprised of a pump data generator 7524, a metadata generator 7526, and a communication interface 7522. The pump data generator generates records relating to the administration of insulin to a patient and records relating to the operational state of the insulin pump 7520. The insulin pump 7520 can also have a user interface which allows a patient to enter additional data relating to the administration of the patient's insulin. Thus, the pump data generator 7524 can be further configured to generate data records pertaining to the patient entered data.

The metadata generator 7526 of the insulin pump generates metadata tags for data records that are transmitted to another device, e.g. the diabetes manager 7500. When the pump data generator 7524 generates a new pump data record, the metadata generator 7526 receives a request to generate a metadata tag. The metadata tag can be a data structure with predefined metadata items. The predefined metadata items can include the device, record, and source identifiers, as well as a time-stamp, a time of last modification, and a cyclic redundancy check or checksum. The device identifier is a static value indicating the identity of the pump. The device identifier is a bit string representing numerical values, character values, or a combination of both. In some embodiments, the device identifier is an unsigned 32-bit value that uniquely identifies the device from all other devices in the plurality of devices. Further, the device identifier can be a generic identifier of a particular type of pump, specific to the brand of pump, unique to the particular pump, or a combination thereof.

The record identifier is a value generated by the metadata generator 7526. Each time the metadata generator 7526 generates a record identifier, the value should be a new value. Thus, in some embodiments the metadata generator 7526 implements a counter that is incremented every time a new record is generated. For instance, the first record generated by the pump data generator 7524 will have a record identifier of 1. The following record will have a record identifier of 2, and so on and so forth. The record identifier can also include character values. In some embodiments, the record identifier is an unsigned 32-bit value that the device will not reproduce for any subsequent records it produces. It is envisioned that other means of generating a record identifier can also be implemented. Together, the device identifier and the record identifier constitute a unique number for the record, regardless of the device generating the data record.

The metadata generator 7526 also generates a source identifier that indicates whether the record was originated by the pump or by a human. This can be a one-bit flag, or can further indicate whether the record was generated by the patient or a third party, e.g. a clinician.

The metadata generator 7526 can further populate additional metadata items in the metadata tag, including the time stamp and the time that the record was last modified. It is appreciated that the time that a record was last modified can be initially set equal to the time stamp, and another device can change the value of the time that a record was last modified. It is noted that the time can be relative or absolute time. The metadata generator can further include a metadata item indicating of what type of record it is, e.g. insulin pump record or insulin pump error record.

The metadata generator 7526 can also calculate a checksum value using a predetermined function. The checksum is a function of the value in the data record. The validity of the data record can later be verified by applying the predetermined function to the stored data record and comparing the result to the received checksum.

Once a metadata tag is generated, the communication interface 7522 of the insulin pump 7520 can transmit the pump data record and the metadata tag to a communication interface of another device, such as the communication interface 7502 of the diabetes manager 7500.

The PC 7530 generates patient data. As mentioned above, the PC 7530 executes diabetes analysis software. This software can receive input from the patient or other devices, e.g. the diabetes manager 7500. Based on various data, the PC data generator 7534 will generate a PC data record.

When a PC data record is generated, a metadata generator 7536 of the PC 7530 will generate a metadata tag in a manner similar to that of the metadata generator 7526 of the insulin pump 7520. The metadata generator 7536 will provide the metadata items of the metadata tag, including a device indicator, i.e. a value that indicates that the PC generated the data record, a record identifier, and a source identifier. The metadata generator 7536 can implement a counter similar to the one described above. Of note, both the PC and the insulin pump (or any other device) can generate metadata tags whose record identifiers have equal values because the device identifier in each metadata tag will be different. The metadata tag can also include metadata items indicating a time-stamp, a field indicating a time of last modification, a record type indicator, and a checksum.

After a PC data record and corresponding metadata tag have been generated, the communication interface 7532 of the PC 7530 communicates the PC data record to a corresponding communication interface 7504 of the diabetes manager 7500.

Some devices do not have the requisite computational resources to generate metadata tags. For instances, a CGM 7540 may lack the resources to generate a metadata tag each time it transmits a CGM measurement. In these embodiments, the CGM 7540 monitors the patient's glucose levels and transmits the CGM measurements without any metadata. The CGM data generator 7544 generates CGM data records indicating the CGM measurements or operational conditions of the CGM and the communication interface of the CGM 7542 transmits the CGM data records to a corresponding communication interface 7506 of the diabetes manager 7500. A proxy metadata generator 7508 residing on the diabetes manager 7500, however, generates metadata tags corresponding to the CGM data records. The proxy metadata generator 7508 generates metadata tags in the manner described above. The proxy metadata generator 7508 will associate the device identifier of the CGM 7540 and will implement an independent counter for generating the record identifier for the CGM data records. As the CGM 7540 does not have a user interface, all records will be classified as being machine generated. The time stamp provided to the metadata tag can be the time that the CGM data record is received. While a lack of computational resources is cited as a reason for including a proxy metadata generator 7508, the decision does not need to be based on the computational resources of the transmitting device.

The diabetes manager 7500 also generates data records. For instance, an exemplary diabetes manager 7500 includes a user interface 7510 and a blood glucose monitor (BGM) 7512, both of which can generate data records. The BGM 7512 generates BG data records. The user interface 7510 receives patient input which is used to generate patient data records. The metadata generator 7504 of the diabetes manager receives an instruction from the user interface 7510, the BGM 7512, or any other data generating component of the diabetes manager 7500. The metadata generator 7514 generates a metadata tag having metadata items indicating a device identifier of the diabetes manager 7500, a record identifier, and a source identifier. If the data record originates from the user interface 7510 based on the input of the patient, then the source identifier can indicate that the patient data record is human-generated. If the BGM 7512 generates a data record based on an automated bG reading, then the source identifier can indicate that the BGM data record is machine generated. Additional metadata items, such as record type, time stamp, time of last modification, and checksum can also be recorded in the metadata tag.

The data management module 7516 receives the data records from the various data sources and stores them in the datastore 7518 of the diabetes manager 7500. The datastore 7518 can have one or more databases stored thereon. The data management module 7516 uses a data record and the corresponding metadata tag to generate an entry in the database or to modify an entry in the database.

The exemplary data management module 7516 is further configured to resolve conflicts between two data records. To resolve conflicts, the data management module 7516 adheres to a set of predetermined rules for resolving data conflicts. An exemplary rule is that a machine-generated record receives precedence over a human-generated value. For instance, in the example above, the patient and the insulin pump can provide two different values for an amount of insulin delivered at a specific time. In this case, the data management module 7516 will enter the machine-generated value in the database entry, unless there is an indication of an error, e.g. a checksum value in the metadata does not match a computed checksum value based on the values in the data record. Another exemplary rule is that a later modification of a record gains precedence over an earlier entered modification. For example, if a patient enters meal information indicating that he ate 500 carbohydrates at breakfast, then later changes that value to 800, the later value is stored in the database. It is envisioned that other rules can be implemented by the data management module 7516 for maintaining data consistency throughout the system of devices.

While the foregoing describes the situation where all data records are transmitted to the diabetes manager 7500, it is noted that data records can be transferred to the devices from the diabetes manager 7500 as well. For instance, the diabetes manager 7500 can communicate data records to the PC 7530. The PC 7530 can also have a data management module that ensures data records are consistent between the PC 7530 and the diabetes manager 7500.

FIG. 140 illustrates an example of data records and corresponding metadata tags being transmitted throughout the system of devices. In the example, a CGM 7600 and an insulin pump 7602, transmit CGM data records 7610 and pump records 7612, respectively, to a diabetes manager 7604. As shown, the CGM data record is initially transmitted without a metadata tag, while the pump record has a metadata tag 7614. The diabetes manager 7604 passes the CGM data record 7610 and pump record 7612 to the PC 7606. The diabetes manager 7604 has generated a metadata tag 7616 on behalf the CGM 7600 to accompany the CGM record 7610. Note that the device ID and the record ID of both the CGM data record 7610 and the pump data record 7612 are not altered when transmitted from the diabetes manager 7604 to the PC 7606. The diabetes manager 7604 has also generated a BG data record 7618 and a UI record 7622, as well as corresponding metadata 7620 and 7624 respectively. Note that both records have the same device ID, as both were generated by the diabetes manager 7600.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

APPENDIX A

Common RPC Numeric Object Attributes

| Attribute Name | Value | Qualifier |
| --- | --- | --- |
| Handle | The Handle attribute represents a reference ID for this object. Each object shall have a unique ID assigned by the agent. | M |
| Type | Defined in each of the numeric objects. | M |
| Metric-Spec-Small | mss-avail-intermittent \| mss-avail-stored-data \| mss-upd-aperiodic \| mss-msmt-aperiodic \| mssacc-agent-initiated \| mss-cat-manual. | M |
| Unit-Code | Defined in each of the numeric objects. | O |
| Attribute-Value-Map | Defined in each of the numeric objects | M |
| Absolute-Time-Stamp | AbsoluteTime as defined in ISO/IEEE 11073-20601 | M |
| Basic-Nu-Observed-Value | This attribute defines the numerical observed value of the object, without any further embedded status information, but with a smaller numerical representation compared to Simple-Nu-Observed-Value. One and only one of Simple-Nu-Observed-Value, Basic-Nu-Observed-Value or Nu-Observed-Value shall be present. | C |
| Simple-Nu-Observed-Value | This attribute defines the numerical observed value of the object, without any further embedded status information as found in Nu-Observed-Value. One and only one of Simple-Nu-Observed-Value, Basic-Nu-Observed-Value, or Nu-Observed-Value shall be present. | C |
| Nu-Observed-Value | This attribute defines the numerical observed value of the object and combines it with measurement status and unit information. It is used when status/unit are dynamic and are always provided together with the value. One and only one of Simple-Nu-Observed-Value, Basic-Nu-Observed-Value or Nu-Observed-Value shall be present. | |

Pen/Syringe Insulin ID
This object is analogous to data returned by the ICI "Send Results, from Start to End" command, field type 34.

| Attribute Name | Value | Qualifier |
| --- | --- | --- |
| Type | MDC_PART_OBJ MDC_CTXT_RPC_PENSYR_INS_ID | M |
| Attribute-Value-Map | MDC_ATTR_NU_BAL_OBS_BASIC, then MDC_ATTR_TIME_STAMP_ABS | M |
| Absolute-Time-Stamp | AbsoluteTime as defined in ISO/IEEE 11073-20601 | M |
| Basic-Nu-Observed-Value | See ISO/IEEE 11073-20601—This indicates the Insulin ID value, ranging from 1 to 255 | M |

Pen/Syringe Insulin Bolus Amount
This object is analogous to data returned by the ICI "Send Results from Start to End" command, field type 34.

| Attribute Name | Value | Qualifier |
| --- | --- | --- |
| Type | MDC_PART_OBJ MDC_CTXT_RPC_PENSYR_BOLUS_AMT | M |
| Unit-Code | MDC_DIM_X_INTL_UNIT | M |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601 | M |
| Basic-Nu-Observed-Value | See ISO/IEEE 11073-20601—This indicates a pen/syringe insulin dose in International Units (IU), ranging from 0.0 to 999.9 | M |

Insulin Bolus Recommendation

| Attribute Name | Value | Qualifier |
| --- | --- | --- |
| Type | MDC_PART_OBJ \| MDC_CTXT_RPC_BOLUS_RECOMMENDATION | M |
| Unit-Code | MDC_DIM_X_INTL_UNIT | M |
| Attribute-Value-Map | MDC_ATTR_NU_ AL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601—This indicates a pen/syringe insulin dose in International Units (IU), ranging from 0.0 to 999.9 | M |

Pump Insulin Bolus Amount
his object is analogous to data returned by the ICI "Send Results from Start to End" command, field type 35.

| Attribute Name | Value | Qualifier |
| --- | --- | --- |
| Type | MDC_PART_OBJ \| MDC_CTXT_RPC_PUMP_BOLUS_AMT | M |
| Unit-Code | MDC_DIM_X_INTL_UNIT | O |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601—This indicates a pump insulin dose in International Units (IU), ranging from 0.0 to 999.9 | M |

Pump Temporary Basal Rate
This object is analogous to data returned by the ICI "Send Results from Start to End" command, field type 35.

| Attribute Name | Value | Qualifier |
| --- | --- | --- |
| Type | MDC_PART_OBJ \| MDC_CTXT_RPC_PUMP_TEMP_BASAL_RATE | M |
| Unit-Code | MDC_DIM_X_INTL_UNIT_PER_HR \| MDC_DIM_PERCENT | O |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601—This indicates the insulin pump's temporary basal rate in International Units per hour (IU/hr), ranging from 0.0 to 999.9, or as a percentage ranging from 0.0 to 100.0 | M |

Pump Temporary Basal Duration
Insulin pump's temporary basal duration BCD Number (hhmm) 0x0000-0x9959
This object is analogous to data returned by the ICI "Send Results from Start to End" command, field type 35.

| Attribute Name | Value | Qualifier |
| --- | --- | --- |
| Type | MDC_PART_OBJ \| MDC_CTXT_RPC_PUMP_TEMP_BASAL_DURATION | M |
| Unit-Code | | O |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601—This indicates the insulin pump's temporary basal duration in hours and minutes (BDC format). | M |

Pump Wave Amount
The object is analogous to data returned by the ICI "Send Results from Start to End" command, field type 35.

| Attribute Name | Value | Qualifier |
| --- | --- | --- |
| Type | MDC_PART_OBJ \| MDC_CTXT_RPC_PUMP_WAVE_AMT | M |
| Unit-Code | MDC_DIM_X_INTL_UNIT | O |
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601—This indicates the insulin pump's wave amount in International Units (IU), ranging from 0.0 to 999.9 | M |

Pump Wave Duration
Insulin pump's wave duration BCD Number (hhmm) 0x0000-0x9959
This object is analogous to data returned by the ICI "Search Results from Start to End" command, field type 35.

| Attribute Name | Value | Qualifier |
| --- | --- | --- |
| Type | MDC_PART_OBJ \| MDC_CTXT_RPC_PUMP_WAVE_DURATION | M |
| Unit-Code | | O |

-continued

| Attribute Name | Value | Qualifier |
|---|---|---|
| Attribute-Value-Map | MDC_ATTR_NU_VAL_OBS_BASIC, then MDC_ATTR_TIME_STAMP_ABS | M |
| Absolute-Time-Stamp | AbsoluteTime as defined in ISO/IEEE 11073-20601. | M |
| Basic-Nu-Observed-Value | See ISO/IEEE 11073-20601—This indicates the insulin pump's wave duration in hours and minutes (BCD format). | M |

APPENDIX B
Common RPC Enumeration Object Attributes

| Attribute Name | Value | Qualifier |
|---|---|---|
| Handle | The Handle attribute represents a reference ID for this object. Each object shall have a unique ID assignment by the agent. | M |
| Type | Defined in each of the enumeration objects. | M |
| Metric-Spec-Small | mss-avail-intermittent | mss-avail-stored-data | mss-upd-aperiodic | mssacc-agent-initiated | mss-cat-manual. | M |
| Attribute-Value-Noa | Defined in each of the enumeration objects. | M |
| Absolute-Time-Stamp | AbsoluteTime as defined in ISO/IEEE 11072-20601 | M |
| Enum-Observed-Value-Simple-OID | The value is reported as a nomenclature code. One and only one of Enum-Observed-Value-Simple-OID, Enum-Observed-Value-Basic-Bit-Str shall be present | C |
| Enum-Observed-Value-Basic-Bit-Str | The value is reported as a bit string of 32-bits. One and only one of Enum-Observed-Value-Simple-OID, Enum-Observed-Value-Basic-Bit-Str, Enum-Observed-Value-Simple-Str shall be present. | C |
| Enum-Observed-Value-Simple-Str | The value is reported as an ASCII printable string. One and only one of Enum-Observed-Value-Simple-OID, Enum-Observed-Value-Basic-Bit-Str, Enum-Observed-Value-Simple-Str shall be present | C |

Timeblock (Meal Segment)
This object is analogous to data returned by the ICI "Send Results from Start to End" command, field type 31.

| Attribute Name | Value | Qualifier |
|---|---|---|
| Type | MDC_PART_OBJ | MDC_CTXT_RPC_MEAL_SEG_TIMEBLOCK | M |
| Attribute-Value-Map | MDC_ATTR_ENUM_OBS_VAL_SIMP_OID, then MDC_ATTR_TIME_STAMP_ABS | M |
| Absolute-Time-Stamp | AbsoluteTime as defined in ISO/IEEE 11073-20601. | M |
| Enum-Observed-Value-Simple-OID | Valid values are RPC_MEAL_SEG_TIME_NT RPC_MEAL_SEG_TIME_BB RPC_MEAL_SEG_TIME_AB RPC_MEAL_SEG_TIME_BL RPC_MEAL_SEG_TIME_AL RPC_MEAL_SEG_TIME_BD RPC_MEAL_SEG_TIME_AD RPC_MEAL_SEG_TIME_EV | M |

Structured Test Type
This object is analogous to data returned by the ICI "Send Results from Start to End" command, field type 6.

| Attribute Name | Value | Qualifier |
|---|---|---|
| Type | MDC_PART_OBJ | MDC_CTXT_RPC_ST_TYPE | M |

-continued

| Attribute Name | Value | Qualifier |
|---|---|---|
| Attribute-Value-Map | MDC_ATTR_ENUM_OBS_VAL_SIMP_OID, then MDC_ATTR_TIME_STAMP_ABS | M |
| Absolute-Time-Stamp | AbsoluteTime as defined in ISO/IEEE 11073-20601. | M |
| Enum-Observed-Value-Simple-OID | Valid values are RPC_STRUCTURED_TEST_3_DAY_SNAP \| RPC_STRUCTURED_TEST_BIT | M |

Structured Test Time Event
This object is analogous to data returned by the ICI "Send Results from Start to End" command, field type 6.

| Attribute Name | Value | Qualifier |
|---|---|---|
| Type | MDC_PART_OBJ \| MDC_CTXT_RPC_MEAL_SEG_TIME_EVENT | M |
| Attribute-Value-Map | MDC_ATTR_ENUM_OBS_VAL_SIMP_OID, then MDC_ATTR_TIME_STAMP_ABS | M |
| Absolute-Time-Stamp | AbsoluteTime as defined in ISO/IEEE 11073-20601. | M |
| Enum-Observed-Value-Simple-OID | Valid values are RPC_ST_TIME_EVENT_BB RPC_ST_TIME_EVENT_AB RPC_ST_TIME_EVENT_BL RPC_ST_TIME_EVENT_AL RPC_ST_TIME_EVENT_BD RPC_ST_TIME_EVENT_AD RPC_ST_TIME_EVENT_BT | M |

Structured Test Protocol Events

| Attribute Name | Value | Qualifier |
|---|---|---|
| Type | MDC_PART_OBJ \| MDC_CTXT_RPC_ST_PROTOCOL_EVENT | M |
| Attribute-Value-Map | MDC_ATTR_ENUM_OBS_VAL_SIMP_OID, then MDC_ATTR_TIME_STAMP_ABS | M |
| Absolute-Time-Stamp | AbsoluteTime as defined in ISO/IEEE 11073-20601. | M |
| Enum-Observed-Value-Simple-OID | Valid values are RPC_ST_MISSED_BG_ACQUISITION RPC_ST_MISSED_INSULIN_ADMINISTRATION RPC_ST_EXIT_NO_REASON RPC_ST_EXIT_TIME_LIMIT_EXCEEDED RPC_ST_EXIT_GOAL_REACHED RPC_ST_EXIT_TOO_MANY_SEVEREHYPOS RPC_ST_EXIT_TOO_MANY_HYPOS RPC_ST_EXIT_ADHERENCE RPC_ST_EXIT_PROTOCOL RPC_ST_EXIT_MAXIMUMDOSE RPC_ST_EXIT_INVALIDDATETIME RPC_ST_EXIT_INVALIDPARAM | M |

Structured Test Configuration Change

| Attribute Name | Value | Qualifier |
|---|---|---|
| Type | MDC_PART_OBJ \| MDC_CTXT_RPC_ST_CONFIG_CHANGE | M |
| Unit-Code | | O |
| Attribute-Value-Map | MDC_ATTR_ENUM_OBS_VAL_SIMP_OID, then MDC_ATTR_TIME_STAMP_ABS | M |
| Absolute-Time-Stamp | AbsoluteTime as defined in ISO/IEEE 11073-20601. | M |
| Enum-Observed-Value-Simple-OID | See section 6.1.1.19 for Structured Test Parameter definitions | M |

What is claimed is:

1. A diabetes care manager in data communication with a medical device using a communication protocol, the diabetes care manager comprising:
   a data store;
   a processing module executing instructions in the data store;
   a meter that measures the concentration of glucose in blood;
   a collection application implemented as computer executable instructions in the data store of the diabetes care manager, the collection application executes a structured collection procedure for obtaining measurement data from the meter and provides access to the measurement data, wherein the structured collection procedure having parameters including a schedule of collection events;
   a configuration application implemented as computer executable instructions in the data store of the diabetes care manager that accesses and manipulates the parameters of the structured collection procedure using a set of action commands, wherein the set of action commands are defined in compliance with the communication protocol; and
   a collection interface implemented as computer executable instructions in the data store of the diabetes care manager that receives an action command from the configuration application, executes the received action command and issues a response command in response thereto, wherein the response command is defined in compliance with the communication protocol.

2. The diabetes care manager of claim 1 wherein the communication protocol is defined in accordance with IEEE standard 11073.

3. The diabetes care manager of claim 1 wherein the diabetes care manager authenticates with the medical device using a set of authentication commands, where the set of authentication commands are defined as a private extension of the communication protocol.

4. The diabetes care manager of claim 1 wherein the parameters of the structured collection procedure are further defined as reminders for one or more collection events associated with the structured collection procedure such that the configuration application uses the set of action commands to at least one of read a reminder for a collection event or set a reminder for a collection event.

5. The diabetes care manager of claim 1 wherein the parameters of the structured collection procedure is further defined as an operational status of the structured collection procedure such that the configuration application uses the set of action commands to at least one of read the operational status or set the operational status for a collection event.

6. The diabetes care manager of claim 1 wherein the parameters of the structured collection procedure is selected from the group consisting of: a start date for the collection procedure, a pre-meal target range for measurement data from the meter, a post-meal target range for measurement data from the meter and a bedtime target ranges for measurement data from the meter.

7. The diabetes care manager of claim 1 wherein the collection application includes an instance of an object pertaining to the meter and defined in accordance with IEEE standard 11073-10417.

8. The diabetes care manager of claim 1 wherein the set of action commands are defined as a private extension of IEEE standard 11073-20601.

9. The diabetes care manager of claim 1 wherein the set of action commands are executed using the Uses Action and Event Report services as defined in 11073-20601.

10. The diabetes care manager of claim 1 wherein the configuration application resides on a computing device distinct from the collection device and communicates via a wireless communication link with the collection device.

11. A diabetes care manager in data communication with a medical device using a communication protocol, the diabetes care manager comprising:
    a memory;
    a processing module executing instructions in the memory;
    a meter that measures the concentration of glucose in blood;
    a collection application implemented as computer executable instructions in the memory of the diabetes care manager, the collection application executes a structured collection procedure for obtaining measurement data from the meter in accordance with configurable criteria and provides access to the measurement data, wherein the structured collection procedure is stored in a non-modifiable portion of the memory and the configurable criteria is stored in a modifiable portion of the memory;
    a configuration application implemented as computer executable instructions in the memory of the diabetes care manager that accesses and manipulates the criteria of the structured collection procedure using a set of action commands, wherein the set of action commands are defined in compliance with the communication protocol; and
    a collection interface implemented as computer executable instructions in the memory of the diabetes care manager that receives an action command from the configuration application, executes the received action command and issues a response command in response thereto, wherein the response command is defined in compliance with the communication protocol.

12. The diabetes care manager of claim 11 wherein the collection application begins collection of measurement data for the structured collection procedure when entry criteria for the structured collection procedure are satisfied.

13. The diabetes care manager of claim 11 wherein the collection application ends data collection for the structured collection procedure when adherence criteria or exit criteria for the structured bG test are satisfied.

14. The diabetes care manager of claim 11 wherein the collection application marks measurement data stored for the structured collection procedure as accepted when the adherence criteria for the structured bG test are satisfied.

15. The diabetes care manager of claim 11 wherein the non-modifiable portion of the memory is partitioned from other portions of the memory and marked as being non-modifiable.

16. The diabetes care manager of claim 11 wherein the configurable criteria include reminders for one or more collection events associated with the structured collection procedure such that the configuration application uses the set of action commands to at least one of read a reminder for a collection event or set a reminder for a collection event.

17. The diabetes care manager of claim 11 wherein the configurable criteria includes an operational status of the structured collection procedure such that the configuration application uses the set of action commands to at least one of read the operational status or set the operational status for a collection event.

18. The diabetes care manager of claim 11 wherein the collection application includes an instance of an object pertaining to the meter and defined in accordance with IEEE standard 11073-10417.

19. The diabetes care manager of claim 11 wherein the set of action commands are defined as a private extension of IEEE standard 11073-20601.

20. The diabetes care manager of claim 11 wherein the set of action commands are executed using the Uses Action and Event Report services as defined in 11073-20601.

* * * * *